(12) United States Patent
Djuranovic

(10) Patent No.: US 12,428,640 B2
(45) Date of Patent: Sep. 30, 2025

(54) METHODS TO MODULATE PROTEIN TRANSLATION EFFICIENCY

(71) Applicant: Washington University, St. Louis, MO (US)

(72) Inventor: Sergej Djuranovic, St. Louis, MO (US)

(73) Assignee: Washington University, St. Louis, MO (US)

( * ) Notice: Subject to any disclaimer, the term of this patent is extended or adjusted under 35 U.S.C. 154(b) by 741 days.

(21) Appl. No.: 16/534,667

(22) Filed: Aug. 7, 2019

(65) Prior Publication Data

US 2020/0048634 A1 Feb. 13, 2020

Related U.S. Application Data

(60) Provisional application No. 62/764,577, filed on Aug. 9, 2018.

(51) Int. Cl.
*C12N 15/113* (2010.01)
*C12N 15/70* (2006.01)

(52) U.S. Cl.
CPC ............ *C12N 15/113* (2013.01); *C12N 15/70* (2013.01); *C12N 2830/008* (2013.01)

(58) Field of Classification Search
CPC .................. C12N 15/113; C12N 15/70; C12N 2830/008; C12N 15/67; C12P 21/02
See application file for complete search history.

(56) References Cited

U.S. PATENT DOCUMENTS

| 4,873,316 | A | 10/1989 | Meade et al. |
| 6,566,495 | B1 | 5/2003 | Fodor et al. |
| 11,603,553 | B2 * | 3/2023 | Djuranovic .......... C12Q 1/6827 |

FOREIGN PATENT DOCUMENTS

| EP | 0264166 A1 | 4/1988 | |
| WO | WO-2016086988 A1 * | 6/2016 | ......... C12N 15/1089 |

OTHER PUBLICATIONS

Voges et al. "Analyzing and enhancing mRNA translational efficiency in an *Escherichia coli* in vitro expression system." Biochemical and biophysical research communications 318.2 (2004): 601-614 (Year: 2004).*
Koutmou et al. "Ribosomes slide on lysine-encoding homopolymeric A stretches." Elife 4 (2015): e05534 (Year: 2015).*
Amann, E. et al., "Tightly regulated tac promoter vectors useful for the expression of unfused and fused proteins in *Escherichia coli*," Gene, 1988, pp. 301-315, vol. 69, No. 2.
Arthur, L. et al., "Translational control by lysine-encoding A-rich sequences," Sci. Adv., Jul. 2015, pp. 1-11, vol. 1, e1500154.
Atomi, H. et al., "Overview of the genetic tools in the Archaea," Front. Microbiol, Oct. 2012, pp. 1-13, vol. 3, No. 337.
Baldari, C. et al., "A novel leader peptide which allows efficient secretion of a fragment of human interleukin 1beta in *Saccharomyces cerevisiae*," EMBO J., 1987, pp. 229-234, vol. 6, No. 1.
Banerji, J. et al., "A Lymphocyte-Specific Cellular Enhancer Is Located Downstream of the Joining Region in Immunoglobulin Heavy Chain Genes," Cell, Jul. 1983, pp. 729-740, vol. 33, No. 3.
Boshart, M. et al., "A Very Strong Enhancer Is Locate Upstream of an Immediate Early Gene of Human Cytomegalovirus," Cell, Jun. 1985, pp. 521-530, vol. 41.
Byrne, G. et al., "Multiplex gene regulation: A two-tiered approach to transgene regulation in transgenic mice," PNAS, Jul. 1989, pp. 5473-5477, vol. 86.
Calame, K. et al., "Transcriptional Controlling Elements in the Immunoglobulin and T Cell Receptor Loci," Adv. Immunol., 1988, pp. 235-275, vol. 43.
Camper, S. et al., "Postnatal repression of the alpha-fetoprotein gene is enhancer independent," Genes Dev., 1989, pp. 537-546, vol. 3.
Edlund, T. et al., "Cell-Specific Expression of the Rat Insulin Gene: Evidence for Role of Two Distinct 5' Flanking Elements," Sci., Nov. 1985, pp. 912-916, vol. 230, No. 4728.
Gamble, C. et al., "Adjacent Codons Act in Concert to Modulate Translation Efficiency in Yeast," Cell, Jul. 2016, pp. 679-690, vol. 166.
Goodman, D. et al. "Causes and Effects of N-Terminal Codon Bias in Bacterial Genes," Sci., Oct. 2013, pp. 475-479, vol. 342, No. 6157.
Kaufman, R. et al., "Translation efficiency of polycistronic mRNAs and their utilization to express heterologous genes in mammalian cells," EMBO J., 1987, pp. 187-193, vol. 6, No. 1.
Kessel, M. et al., "Murine Developmental Control Genes," Sci., Jul. 1990, pp. 374-379, vol. 249, No. 4967.
Kurjan, J. et al., "Structure of a Yeast Pheromone Gene (MFalpha): A Putative alpha-Factor Precursor Contains Four Tandem Copies of Mature alpha-Factor," Cell, Oct. 1982, pp. 933-943, vol. 30, No. 3.
Navon, S. et al., "Amino acid sequence repertoire of the bacterial proteome and the occurrence of untranslatable sequences," PNAS, Jun. 2016, pp. 7166-7170, vol. 113, No. 26.
O'Hare, K. et al., "Transformation of mouse fibroblasts to methotrexate resistance by a recombinant plasmid expressing a prokaryotic dihydrofolate reductase," PNAS, Mar. 1981, pp. 1527-1531, vol. 78, No. 3.
Pinkert, C. et al., "An albumin enhancer located 10 kb upstream functions along with its promoter to direct efficient, liver-specific expression in transgenic mice," Genes Dev., 1987, pp. 268-277, vol. 1.
Presnyak, V. et al., "Codon Optimality Is a Major Determinant of mRNA Stability," Cell, Mar. 2015, pp. 1111-1124, vol. 160.
Queen, C. et al., "Immunoglobulin Gene Transcription Is Activated by Downstream Sequence Elements," Cell, Jul. 1983, pp. 741-748, vol. 33, No. 3.

(Continued)

*Primary Examiner* — Fereydoun G Sajjadi
*Assistant Examiner* — Alexander W Nicol
(74) *Attorney, Agent, or Firm* — Polsinelli PC

(57) ABSTRACT

The present disclosure relates to compositions and methods to modulate the level of expression of a protein in a deliberate manner (i.e., tunable regulation of expression) with only a minimal change to the genetic sequence of the gene of interest. The present disclosure therefore also provides compositions and methods to predictably alter protein abundance.

4 Claims, 66 Drawing Sheets
(28 of 66 Drawing Sheet(s) Filed in Color)
Specification includes a Sequence Listing.

(56) References Cited

OTHER PUBLICATIONS

Rockett, J. et al., "DNA arrays: technology, options and toxicological applications," Xenobiotica, 2000, pp. 155-177, vol. 30, No. 2.
Schultz, L. et al., "Expression and secretion in yeast of a 400-kDa envelope glycoprotein derived from Epstein-Barr virus," Gene, 1987, pp. 113-123, vol. 54, No. 1.
Seed, B., "An LFA-3 cDNA encodes a phospholipid-linked membrane protein homologous to its receptor CD2," Nature, Oct. 1987, pp. 840-842, vol. 329.
Smith, D. et al., "Single-step purification of polypeptides expressed in *Escherichia coli* as fusions with glutathione S-transferase," Gene, 1988, pp. 31-40, vol. 67, No. 1.
Takebe, Y. et al., "SRalpha Promoter: an Efficient and Versatile Mammalian cDNA Expression System Composed of the Simian Virus 40 Early Promoter and the R-U5 Segment of Human T-Cell Leukemia Virus Type 1 Long Terminal Repeat," Mol. Cell. Biol., Jan. 1988, pp. 466-472, vol. 8, No. 1.
Tuller, T. et al., "An Evolutionary Conserved Mechanism for Controlling the Efficiency of Protein Translation," Cell, Apr. 2010, pp. 344-354, vol. 141.
Verma, M. et al., "Short translational ramp determines efficiency of protein synthesis," bioRxiv, Mar. 9, 2019; 26 pgs.
Winoto, A. et al., "A novel, inducible and T cell-specific enhancer located at the 3' end of the T cell receptor alpha ocus," EMBO J., 1989, pp. 729-733, vol. 8, No. 3.
Yoshioka, N. et al., "Efficient Generation of Human iPSCs by a Synthetic Self-Replicative RNA," Cell Stem Cell, Aug. 2013, pp. 246-254, vol. 13.

\* cited by examiner

XXX (position 3, 4 and 5 or the amino acid sequence) or
= 5' – NNNNNNNNN – 3' (codons 3, 4, and 5 of the coding sequence)

5' – NNNNNNNNN – 3'   Position 1
5' – NNNNNNNNN – 3'   Position 2
5' – NNNNNNNNN – 3'   Position 3
5' – NNNNNNNNN – 3'   Position 4
5' – NNNNNNNNN – 3'   Position 5
5' – NNNNNNNNN – 3'   Position 6
5' – NNNNNNNNN – 3'   Position 7
5' – NNNNNNNNN – 3'   Position 8
5' – NNNNNNNNN – 3'   Position 9
5' – NNNCTTNNN – 3'   Motif CTT at position 4

```
ATG GTG AAG TAT CAC agc aag gcg  (SEQ ID NO: 1)
Met Val Lys Tyr His Ser Lys Gly  (SEQ ID NO: 2)

ATG GTG CAA GTA TCA agc aag gcg  (SEQ ID NO: 3)
Met Val Gln Val Ser Ser Lys Gly  (SEQ ID NO: 4)

ATG GTG ACA AGT ATC agc aag gcg  (SEQ ID NO: 5)
Met Val Thr Ser Ile Ser Lys Gly  (SEQ ID NO: 6)

ATG GTG CAC AAG TAT agc aag gcg  (SEQ ID NO: 7)
Met Val His Lys Tyr Ser Lys Gly  (SEQ ID NO: 8)
```

FIG. 13

*Concentration of proteins: KFS= 48 μg/mL  SKG= 53 μg/mL

In vivo Human Dermal Fibroblasts 5' TOP sequences con　　WT　KIH　KFS　　　NCT

SEQUENCE LISTING

<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: SYNTHESIZED

```
<400> SEQUENCE: 1
atggtgaagt atcacagcaa ggcg                                              24

<210> SEQ ID NO 2
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 2

Met Val Lys Tyr His Ser Lys Gly
1               5

<210> SEQ ID NO 3
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 3
atggtgcaag tatcaagcaa ggcg                                              24

<210> SEQ ID NO 4
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 4

Met Val Gln Val Ser Ser Lys Gly
1               5

<210> SEQ ID NO 5
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 5
atggtgacaa gtatcagcaa ggcg                                              24

<210> SEQ ID NO 6
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 6

Met Val Thr Ser Ile Ser Lys Gly
1               5

<210> SEQ ID NO 7
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 7
atggtgcaca agtatagcaa ggcg                                              24
```

<210> SEQ ID NO 8
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 8

Met Val His Lys Thr Ser Lys Gly
1               5

<210> SEQ ID NO 9
<211> LENGTH: 720
<212> TYPE: DNA
<213> ORGANISM: Artificial Sequence
<220> FEATURE:
<223> OTHER INFORMATION: SYNTHESIZED

<400> SEQUENCE: 9
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggcac      420 aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa    720

<210> SEQ ID NO 10
<211> LENGTH: 239
<212> TYPE: PRT
<213> ORGANISM: Artificial Sequence
<220> FEATURE:
<223> OTHER INFORMATION: SYNTHESIZED

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 11
<211> LENGTH: 11
<212> TYPE: RNA
<213> ORGANISM: Artificial Sequence
<220> FEATURE:
<223> OTHER INFORMATION: Synthesized

<400> SEQUENCE: 11
agccaccaug g                                                              11

<210> SEQ ID NO 12
<211> LENGTH: 9
<212> TYPE: PRT
<213> ORGANISM: Artificial Sequence
<220> FEATURE:
<223> OTHER INFORMATION: Synthesized

<400> SEQUENCE: 12

Ile Gly Lys His His His His His His
1               5

<210> SEQ ID NO 13
<211> LENGTH: 9
<212> TYPE: PRT
<213> ORGANISM: Artificial Sequence
<220> FEATURE:
<223> OTHER INFORMATION: Synthesized

<400> SEQUENCE: 13

Lys Phe Ser His His His His His His
1               5

<210> SEQ ID NO 14
<211> LENGTH: 9
<212> TYPE: PRT
<213> ORGANISM: Artificial Sequence
<220> FEATURE:
<223> OTHER INFORMATION: Synthesized

<400> SEQUENCE: 14

Thr Val Gly His His His His His His
1               5

<210> SEQ ID NO 15
<211> LENGTH: 8
<212> TYPE: PRT

```
<213> ORGANISM: Artificial Sequence
<220> FEATURE:
<223> OTHER INFORMATION: Synthesized

<400> SEQUENCE: 15

His His His His His Ile Gly Lys
1               5

<210> SEQ ID NO 16
<211> LENGTH: 8
<212> TYPE: PRT
<213> ORGANISM: Artificial Sequence
<220> FEATURE:
<223> OTHER INFORMATION: Synthesized

<400> SEQUENCE: 16

His His His His His Lys Phe Ser
1               5

<210> SEQ ID NO 17
<211> LENGTH: 8
<212> TYPE: PRT
<213> ORGANISM: Artificial Sequence
<220> FEATURE:
<223> OTHER INFORMATION: Synthesized

<400> SEQUENCE: 17

His His His His His Thr Val Gly
1               5

<210> SEQ ID NO 18
<211> LENGTH: 39
<212> TYPE: DNA
<213> ORGANISM: Artificial Sequence
<220> FEATURE:
<223> OTHER INFORMATION: Synthesized

<400> SEQUENCE: 18
gggcaaccta aaacttacac acccggtaag gaaataacc                              39

<210> SEQ ID NO 19
<211> LENGTH: 9
<212> TYPE: PRT
<213> ORGANISM: Artificial Sequence
<220> FEATURE:
<223> OTHER INFORMATION: Synthesized

<400> SEQUENCE: 19

His His His His His His Thr Val Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Synthesized

<400> SEQUENCE: 20

His His His His His Lys Ile His
1               5

<210> SEQ ID NO 21
<211> LENGTH: 7
<212> TYPE: PRT
<213> ORGANISM: Artificial Sequence
<220> FEATURE:
```

```
<223> OTHER INFORMATION: Synthesized

<400> SEQUENCE: 21

Met Phe Thr Val Gly Lys Phe
1               5

<210> SEQ ID NO 22
<211> LENGTH: 7
<212> TYPE: PRT
<213> ORGANISM: Artificial Sequence
<220> FEATURE:
<223> OTHER INFORMATION: Synthesized

<400> SEQUENCE: 22

Met Phe Lys Ile His Lys Phe
1               5
```

US 12,428,640 B2

METHODS TO MODULATE PROTEIN TRANSLATION EFFICIENCY

CROSS-REFERENCE TO RELATED APPLICATIONS

This application claims the priority of U.S. provisional application Ser. No. 62/764,577, filed Aug. 9, 2018, the disclosures of which are hereby incorporated by reference in their entirety.

GOVERNMENTAL RIGHTS

This invention was made with government support under GM007067 and GM112834 awarded by the National Institutes of Health. The government has certain rights in the invention.

FIELD OF THE INVENTION

The present disclosure relates to modulation of protein expression.

REFERENCE TO TABLES SUBMITTED ON A COMPACT DISC

The present disclosure incorporates by reference the tables on the following compact discs: Disc 1 of 2 and Disc 2 of 2, which were filed with U.S. Ser. No. 62/764,577. The information recorded on the two compact discs are identical. For each compact disc: the machine format is PC; the operating system compatibility is Windows; and the files contained on the compact disc are (1) Table A.txt, 2,393 KB, created Aug. 8, 2018, (2) Table B.txt, 3,055 KG, created Aug. 8, 2018, (3) Table C.txt, 28 KB, created Aug. 8, 2018. The polynucleotide sequence in Table A, B, and C include all possible 9nt sequences except for those that encode a stop codon when the polynucleotide sequence is read in frame 1.

BACKGROUND

Across many fields of science and industry there is an interest in manipulating gene expression and optimizing the production of specific gene products. A major challenge is to model and predict translation efficiency from the sequences of genes. Gene products can be altered by manipulating gene copy numbers, using RNAi or other methods in the art to decrease protein levels, varying expression by changing promoters, optimizing coding sequences, or other factors. These approaches are generally time-consuming, organism specific, costly, can be inconsistent and do not offer the ability to tightly control the extent to which the protein level is either reduced or increased. Accordingly, there remains a need in the art for alternative methods.

SUMMARY

Among the various aspects of the disclosure is the provision of a method to modulate the level of expression of a protein. In general, the method comprises modifying the nucleic acid sequence encoding a protein of interest to produce a modified nucleic acid sequence encoding a second protein, wherein the nucleic acid sequence encoding the protein of interest and the modified nucleic acid sequence encoding the second protein have a different polynucleotide sequence at codons 3, 4, and 5. The modified nucleic acid is then expressed in a cell or in a cell-free transcription/translation system. The modified polynucleotide sequence does not encode at codons 3, 4, and 5 a stop codon recognizable by the cell or the cell-free system. The level of expression of the second can be increased or decreased, as compared to the protein of interest, depending upon the change(s) made at codons 3, 4, and 5. The change(s) made at codons 3, 4, and 5 also may or may not result in changes in the amino acid sequence of the protein of interest. As such, the second protein can have the same or a different amino acid sequence than the protein of interest.

In some embodiments, the method comprises inserting a polynucleotide sequence between the second and third codons of a nucleic acid sequence encoding a protein of interest. For example, a polynucleotide sequence selected from (i) $5'-n^1n^2n^3-3'$, (ii) $5'-n^1n^2n^3n^4n^5n^6-3'$, and (iii) $5'-n^1n^2n^3n^4n^5n^6n^7n^8n^9-3'$, may be inserted between the second and third codons of a nucleic acid sequence encoding a protein of interest, wherein $n^1$, $n^2$, $n^3$, $n^4$, $n^5$, $n^6$, $n^7$, $n^8$, and $n^9$ are each independently selected from the group consisting of adenine, thymine, uracil, guanine, and cytosine. In one example, a polynucleotide sequence selected from Table A, Table B, or Table C may be inserted between the second and third codons of a nucleic acid sequence encoding a protein of interest. In another example, a polynucleotide sequence selected from Table D may be inserted between the second and third codons of a nucleic acid sequence encoding a protein of interest. In another example, a polynucleotide sequence encoding a peptide selected from Table I may be inserted between the second and third codons of a nucleic acid sequence encoding a protein of interest.

In other embodiments, the method comprises inserting a polynucleotide sequence between the third and fourth codons of a nucleic acid sequence encoding a protein of interest. For example, a polynucleotide sequence selected from (i) $5'-n^1n^2n^3-3'$, and (ii) $5'-n^1n^2n^3n^4n^5n^6-3'$, may be inserted between the third and fourth codons of a nucleic acid sequence encoding a protein of interest, wherein $n^1$, $n^2$, $n^3$, $n^4$, $n^5$, and $n^6$ are each independently selected from the group consisting of adenine, thymine, uracil, guanine, and cytosine. In one example, the polynucleotide sequence is selected to result in a nucleic acid sequence that has at codons 3, 4, and 5 a polynucleotide sequence from Table A, Table B, or Table C. In another example, the polynucleotide sequence is selected to result in a nucleic acid sequence that has at codons 3, 4, and 5 a polynucleotide sequence from Table D. In another example, the polynucleotide sequence is selected to result in a nucleic acid sequence encoding a peptide selected from Table I.

In other embodiments, the method comprises inserting a polynucleotide sequence between the fourth and fifth codons of a nucleic acid sequence encoding a protein of interest. For example, a polynucleotide sequence that is $5'-n^1n^2n^3-3'$ may be inserted between the fourth and fifth codons of a nucleic acid sequence encoding a protein of interest, wherein $n^1$, $n^2$, and $n^3$ are each independently selected from the group consisting of adenine, thymine, uracil, guanine, and cytosine. In one example, the polynucleotide sequence is selected to result in a nucleic acid sequence that has at codons 3, 4, and 5 a polynucleotide sequence from Table A, Table B, or Table C. In another example, the polynucleotide sequence is selected to result in a nucleic acid sequence that has at codons 3, 4, and 5 a polynucleotide sequence from Table D. In another example, the polynucleotide sequence is selected to result in a nucleic acid sequence encoding a peptide selected from Table I.

In other embodiments, the method comprises changing one or more nucleotides of a nucleic acid sequence encoding a protein of interest, wherein the one or more changes are at codon three, codon four, codon five, or any combination thereof. For example, 1, 2, or 3 nucleotides changes may be made at the codon three; 1, 2, or 3 nucleotides changes may be made at codon four; or 1, 2, or 3 nucleotides changes may be made at codon five. In another example, 2, 3, 4, 5, or 6 nucleotides changes may be made at the codon three and codon four; 2, 3, 4, 5, or 6 nucleotides changes may be made at codon three and codon five; or 2, 3, 4, 5, or 6 nucleotides changes may be made at codon four and codon five. In another example, 3, 4, 5, 6, 7, 8, or 9 nucleotides changes may be made at codon three, codon four and codon five. In further examples, one or more changes may be made at codon three, codon four, codon five, or any combination thereof, to produce a modified nucleic acid sequence that has a polynucleotide sequence of Table A, Table B or Table C, at codons 3, 4 and 5. In still further examples, one or more changes may be made at codon three, codon four, codon five, or any combination thereof, to produce a modified nucleic acid sequence that has a polynucleotide sequence of Table D, at codons 3, 4 and 5. In still further examples, one or more changes may be made at codon three, codon four, codon five, or any combination thereof, to produce a modified nucleic acid sequence that has a polynucleotide sequence encoding a peptide selected from Table I.

Another aspect of the present disclosure encompasses a method to increase the level of expression of a protein. The method comprises (a) identifying a score from Table A, B, or C for a polynucleotide sequence consisting of codons 3, 4 and 5 of a nucleic acid sequence encoding a first protein of interest; (b) selecting a polynucleotide sequence from Table A, B, or C, or from Table D that has a higher score than the score from (a); (c) modifying the nucleic acid sequence encoding the first protein of interest in step (a) to the polynucleotide sequence selected in (b); and (d) expressing the modified nucleic acid sequence in a cell or in a cell-free transcription/translation system. Modifying the nucleic acid sequence in step (c) can occur by (i) inserting a polynucleotide sequence between the second and third codons of the nucleic acid sequence encoding the first protein of interest, wherein the polynucleotide sequence is selected from 5'-$n^1n^2n^3$-3', 5'-$n^1n^2n^3n^4n^5n^6$-3', and 5'-$n^2n^3n^4n^5n^6n^7n^8n^9$-3', wherein $n^1$, $n^2$, $n^3$, $n^4$, $n^5$, $n^6$, $n^7$, $n^8$ and $n^9$ are each independently selected from the group consisting of adenine, thymine, uracil, guanine, and cytosine; (ii) inserting a polynucleotide sequence between the third and fourth codons of the nucleic acid sequence encoding the first protein of interest, wherein the polynucleotide sequence is selected from 5'-$n^1n^2n^3$-3', and 5'-$n^1n^2n^3n^4n^5n^6$-3', wherein $n^1$, $n^2$, $n^3$, $n^4$, $n^5$ and $n^6$ are each independently selected from the group consisting of adenine, thymine, uracil, guanine, and cytosine; or (iii) inserting a polynucleotide sequence between the fourth and fifth codons of the nucleic acid sequence encoding the first protein of interest, wherein the polynucleotide sequence is 5'-$n^1n^2n^3$-3', wherein $n^1$, $n^2$, and $n^3$ are each independently selected from the group consisting of adenine, thymine, uracil, guanine, and cytosine; or (iv) changing one or more nucleotides of the nucleic acid sequence from step (a) at codon two, codon three, codon four, or any combination thereof, to produce a modified nucleic acid sequence that has the polynucleotide sequence from step (b) at codons three, four and five.

Another aspect of the present disclosure encompasses a method to decrease the level of expression of a protein. The method comprises (a) identifying a score from Table A, B, or C for a polynucleotide sequence consisting of codons 3, 4 and 5 of a nucleic acid sequence encoding a first protein of interest; (b) selecting a polynucleotide sequence from Table A, B, or C, or from Table D that has a lower score than the score from (a); (c) modifying the nucleic acid sequence encoding the first protein of interest in step (a) to the polynucleotide sequence selected in (b); and (d) expressing the modified nucleic acid sequence in a cell or in a cell-free transcription/translation system. Modifying the nucleic acid sequence in step (c) can occur by (i) inserting a polynucleotide sequence between the second and third codons of the nucleic acid sequence encoding the first protein of interest, wherein the polynucleotide sequence is selected from 5'-$n^1n^2n^3$-3', 5'-$n^1n^2n^3n^4n^5n^6$-3', and 5'-$n^1n^2n^3n^4n^5n^6n^7n^8n^9$-3', wherein $n^1$, $n^2$, $n^3$, $n^4$, $n^5$, $n^6$, $n^7$, $n^8$, and $n^9$ are each independently selected from the group consisting of adenine, thymine, uracil, guanine, and cytosine; (ii) inserting a polynucleotide sequence between the third and fourth codons of the nucleic acid sequence encoding the first protein of interest, wherein the polynucleotide sequence is selected from 5'-$n^1n^2n^3$-3', and 5'-$n^1n^2n^3n^4n^5n^6$-3', wherein $n^1$, $n^2$, $n^3$, $n^4$, $n^5$, and $n^6$ are each independently selected from the group consisting of adenine, thymine, uracil, guanine, and cytosine; or (iii) inserting a polynucleotide sequence between the second and third codons of the nucleic acid sequence encoding the first protein of interest, wherein the polynucleotide sequence is 5'-$n^1n^2n^3$-3', wherein $n^1$, $n^2$, and $n^3$ are each independently selected from the group consisting of adenine, thymine, uracil, guanine, and cytosine; or (iv) changing one or more nucleotides of the nucleic acid sequence from step (a) at the second codon, the third codon, the fourth codon, or any combination thereof, to produce a modified nucleic acid sequence that has the polynucleotide sequence from step (b) at codons 3, 4 and 5.

Other aspects of the present disclosure encompass vectors. A vector can comprise a promoter operably linked to a nucleic acid construct $R^1$-$R^2$-$R^3$-$R^4$ wherein $R^1$ is a start codon; $R^2$ is a polynucleotide sequence 5'-$n^1n^2n^3$-3', wherein $n^1$, $n^2$, and $n^3$ are each independently selected from the group consisting of adenine, thymine, uracil, guanine, and cytosine; $R^3$ is a polynucleotide sequence selected from Table A, Table B, Table C, or Table D, or a polynucleotide sequence encoding a peptide selected from Table E, Table F, or Table G; and $R^4$ is a multiple cloning site. Vectors may be used express a protein of interest after a nucleic acid encoding the protein of interest is cloned into the multiple cloning site. Accordingly, the vector or nucleic acid sequence may contain additional elements known in the art to facilitate the expression and/or recovering of the protein of interest. As a non-limiting example, in some embodiments a vector can comprise a promoter operably linked to a nucleic acid construct $R^1$-$R^{1.4}$-$R^2$-$R^3$-$R^4$-$R^{4.4}$ wherein $R^1$, $R^2$, $R^3$, and $R^4$ are defined as above, and $R^{1.4}$ is an optional polynucleotide sequence encoding a peptide tag or an optional polynucleotide sequence encoding a peptide tag and a cleavage sequence, and $R^{4.4}$ is an optional polynucleotide sequence encoding a peptide tag or an optional polynucleotide sequence encoding a cleavage sequence and a peptide tag.

Other aspects of the present disclosure encompass isolated, non-natural nucleic acid molecules. The nucleic acid molecule can comprise a polynucleotide sequence selected from Table A, Table B, or Table C, at codons 3, 4, and 5. The nucleic acid molecule can comprise a polynucleotide sequence selected from Table D, at codons 3, 4, and 5. The nucleic acid molecule can comprise a polynucleotide sequence encoding a peptide selected from Table I. The nucleic acid molecule can comprise $R^5$-$R^6$-$R^7$, wherein $R^5$, $R^6$, and $R^7$ are joined by phosphodiester bonds; and wherein (a) $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid; (b) $R^6$ is a polynucleotide sequence selected from Table A, Table B, or Table C, a polynucleotide sequence selected from Table D, or a polynucleotide sequence encoding a peptide selected from Table I; and (c) $R^7$ is a second fragment of a polynucleotide sequence of interest, wherein the second fragment lacks the first and second codons of the sequence of interest. The nucleic acid molecule can comprise $R^5$-$R^6$-$R^7$, wherein $R^5$, $R^6$, and $R^7$ are joined by phosphodiester bonds; and wherein (a) $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid; (b) $R^6$ is a polynucleotide sequence selected from Table A, Table B, or Table C, a polynucleotide sequence selected from Table D, or a polynucleotide sequence encoding a peptide selected from Table I, with the proviso that $R^6$ is not a polynucleotide sequence consisting of codons 3, 4, and 5 of the polynucleotide sequence of interest; and $R^7$ is a second fragment of the polynucleotide sequence of interest, the second fragment lacking the first and second codons of the sequence of interest. The isolated nucleic acid molecule may further comprise one or more regulatory element, for example a promoter, operatively-linked to the polynucleotide sequence.

Other aspects of the present disclosure encompass oligonucleotide probes and expression vectors comprising nucleic acid molecules of the present disclosure.

Other aspects of the present disclosure encompass isolated polypeptides. The isolated polypeptide can comprise a formula $R^8$-$R^9$-$R^{10}$, wherein $R^8$, $R^8$, and $R^{10}$ are joined by peptide bonds; and wherein (a) $R^8$ is a first fragment of an amino acid sequence of interest, wherein the first fragment consists of the first and second amino acids of the sequence of interest; (b) $R^9$ is a polypeptide selected from Tables E, F, G or I; and (b) $R^{10}$ is a second fragment of an amino acid sequence of interest, wherein the second fragment lacks the first and second amino acids of the sequence of interest. For the avoidance of doubt, "an amino acid sequence of interest" is the amino acid sequence of a protein of interest. The isolated polypeptide can comprise formula $R^8$-$R^9$-$R^{10}$ wherein $R^8$, $R^9$, and $R^{10}$ are joined by peptide bonds; and wherein (a) $R^8$ is a first fragment of an amino acid sequence of interest, the first fragment consisting of the first and second amino acids of the sequence of interest; $R^9$ is a polypeptide selected from Tables E, F, G or I, with the proviso that $R^6$ is not the same as amino acids 3, 4, and 5 of the amino acid sequence of interest; and $R^{10}$ is a second fragment of an amino acid sequence of interest, the second fragment lacking the first, second, third, fourth and fifth amino acids of the sequence of interest. The isolated polypeptide may further comprise one or more peptide tags associated with the N-terminus, the C-terminus, and/or an internal location of the polypeptide.

Still other aspects and iterations of the disclosure are described more thoroughly below.

BRIEF DESCRIPTION OF THE FIGURES

The application file contains at least one photograph executed in color. Copies of this patent application publication with color photographs will be provided by the Office upon request and payment of the necessary fee.

FIG. 3A depicts an EGFP reporter construct or an EGFP variant. When the drawing represents a nucleic acid sequence (e.g., an EGFP reporter construct), the blue rectangle is a random sequence of nine nucleotides (also referred to as the "9nt sequence") inserted after the second codon and before the third codon of the wild type (WT) EGFP open reading frame (ORF). When the drawing represents an amino acid sequence (e.g., an EGFP variant), the blue rectangle is a random sequence of three amino acids inserted after the second amino acid (valine) and before the next amino acid (serine) of the WT EGFP amino acid sequence. FIG. 3B is a schematic of the nomenclature used to describe the 9nt sequence and the EGFP reporter constructs. Positions 1-9 are in reference to the positioning within the 9nt sequence. The term "motif" refers to a sequence of nucleotides within the 9nt sequence without indication to positioning. The positioning of a motif within the 9nt sequence is determined by the position of the motif's first nucleotide. For example, motif CTT at position 4 would encode a leucine at amino acid 4 of an EGFP variant from the reporter system.

FIG. 4A is an image of five representative groupings of clones from the library that were separated by FACS based on relative EGFP levels (RFU) expressed (relative to non-induced cells and/or cells that do not express EGFP). FIG. 4B graphically shows the distribution of the 9nt sequences in each BIN in terms of GFP score. The graph is a smoothed histogram that includes a position for each sequence present in the library, which represents the relative occupancy of each BIN within the 230,000 unique 9nt sequences of the library (density, y-axis). The graph shows that the majority of sequences have a medium expression level score (around GFP score 3, x-axis). For reference, WT EGFP has a GFP score of about 2.1-2.3.

FIG. 5A graphically represents the number of sequencing reads from each BIN, with each dot being a 9nt sequence. In FIG. 5B, the number of reads for each unique sequence was determined and is shown graphically as the frequency (y-axis) of the total counts (i.e., reads) per sequence (log 10; x-axis). The average number of reads for each unique sequence in all sequenced BINs is 144.26. FIG. 5C graphically shows the correlation between two biological replicates. FIG. 5D graphically shows the distribution of sequence reads across BINs for all sequences without stop codons (orange line=Absent), and for all sequence reads with stop codons present in the 9nt sequence (blue line=Amber (UAG); green line=Ochre (UAA); yellow line=Opal (UGA)). FIG. 5E compares the GFP scores of Amber codons and Gln CAG codons by their sequence read distribution. The *E. coli* cells used in these experiments are DH5α cells with an AMBER suppressor (gInV44) mutation; so in these experiments, Amber codons serve as a control for CAG codon. The graph shows GFP scores on the y-axis for Amber codons and Gln CAG codons at codons 2, 3, and 4 of the EGFP variant. The comparison is made against the GFP score of the complete library without CAG and Amber codons (Absent).

FIG. 6A graphically depicts the distribution of sequences based on the average charge of the amino acids encoded by the 9 nt sequence (x-axis, pK value for amino acids). FIG. 6B graphically depicts the distribution of sequences based on the average hydrophobicity of the amino acids encoded by the 9 nt sequence (x-axis, hydrophobicity for amino acids). FIG. 6C graphically depicts the distribution of reads based on tRNA abundance index (tAI). FIG. 6D graphically depicts the distribution of reads for *E. coli* rare codons (Arg (R), Leu (L), or Ile (I)) compared with the rest of the library. FIG. 6E graphically depicts the distribution of reads for three rare Arg (R) codons compared with the rest of the library. In each of FIG. 6A-6E, the y-axis is the GFP score.

FIG. 8A, FIG. 8B, FIG. 8C, FIG. 8D, FIG. 8E, and FIG. 8F graphically depicts the amino acid frequency encoded by codons 3-5 in high-expressing EGFP variants from a first (FIG. 8A-C) and a second (FIG. 8D-F) biological replicate.

FIG. 9B and FIG. 9E show that EGFP constructs with either motif present at any position encode EGFP variants with an average GFP score that is higher than the average GFP score for the rest of the library (Absent). FIG. 9C and FIG. 9F show how the GFP score is affected by the position of the motif. The AADTAT motif shows a slight amino acid preference given that position 1 and 4 are on average higher than other positions. This analysis identifies K/N as preferred amino acids at position 3/4 of EGFP variants with high translation efficiency and Y/I as preferred amino acids at position 4/5 of EGFP variants with high translation efficiency. EGFP constructs encoding stop codons were filtered out in the analyses depicted in FIGS. 9B, 9C, 9E and 9F.

FIG. 10A graphically depicts cumulative data for the presence of K or N as amino acid 3 or 4 paired with either I or Y at amino acid 4 and 5, respectively (present) versus the rest of the library. FIG. 10B graphically depicts cumulative data for both motifs coding for amino acids 3 and 4, or 4 and 5, versus the rest of the library (absent). The middle column represents all sequences that have K or N as amino acid 3 with I or Y as amino acid 4. The last column represents all sequences that have K or N as amino acid 4 with I or Y as amino acid 5. The data suggest a position bias. FIG. 10C and FIG. 10D show the distribution of amino acids at position 3 of the EGFP variant when AADTAT (FIG. 10C) or AAVATT (FIG. 10D) are coding for amino acids at position 4 and 5 of the EGFP variant. FIG. 10C and FIG. 10D provide additional information about which amino acid sequence has the highest expression (as evidenced by the GFP score) once the motifs are moved to code for amino acids in position 4 and 5. Preferred amino acids at position 3 should be ones that have a GFP score above 4 and a narrow distribution (i.e., Q, N, K, M, H, D, E in FIG. 10C, and K, H, D, C, N, T, M, Q and E in FIG. 10D). In each of FIG. 10A-10D, the y-axis is the GFP score.

FIG. 11A graphically depicts the influence of Tyr tRNA:mRNA pairs on the distribution of GFP scores for 9nt sequences with the AADTAT motif without considering positional information. FIG. 11B graphically depicts the influence of Tyr tRNA:mRNA pairs on the distribution of GFP scores for 9nt sequences with the AADTAT motif at positions 1 or 4 of the 9nt sequence, as compared to the rest of the library (absent). The data indicate there is a small difference between TAT and TAC Tyr codons. FIG. 11C graphically depicts the influence of the Lys tRNA:mRNA and Asn tRNA:mRNA pairs on the distribution of sequences with the AADTAT motif at positions 1 or 4 of GFP scores for 9nt sequences, as compared to the rest of the library (absent).

In FIG. 12A, positional data is not shown. In FIG. 12B, positional data is shown. Overall, FIG. 12A and FIG. 12B show that there are small differences between the Ile codons, with the ATC codon resulting in a slight decrease in the GFP score.

FIG. 13 depicts the set-up for testing library results on positional and amino acid bias in in vitro and in vivo experiments. Depicted are the first 24 nucleotides of the EGFP sequence or the first 8 amino acids of the EGFP variant. Four variants are shown. In SEQ ID NO: 1, the motif AAGTAT is at position 1 and amino acids 3 and 4 are K and Y, respectively. In SEQ ID NO: 2, the motif AAGTAT is at position 2. In SEQ ID NO: 2, the motif AAGTAT is at position 3. In SEQ ID NO: 4, the motif AAGTAT is at position 4, and amino acids 4 and 5 are K and Y, respectively. The complete EGFP nucleotide and amino acid sequences are provided as SEQ ID NO: 9 and 10, respectively.

FIG. 23A is an illustration of the structure of the human G-alpha inhibitory (Gαi) protein. FIG. 23B is an image of a protein gel. Recombinant WT 6× His tagged human Gαi protein and two high expressing clones, Cl1 (insertion of the amino acid sequence "KFS" after the 2$^{nd}$ amino acid of pet15b vector) and Cl2 (insertion of KIH (motif AAVATT (KI)) between 2nd and 3rd codon of pet15b vector) were expressed in E. coli BL21 cells. Samples were obtained from 10% of the equal amount of BL21 cells 2 hours after induction with 1 mM IPTG in LB medium. Arrow indicates expected position for the Gαi protein on the gel. Control is purified Gαi protein. FIG. 23C Western blot analysis of the same gel as in FIG. 23B using anti-His antibody. FIG. 23 D western blot analysis of WT and two high expressing variants (CL1 and CL2) of human Gαi protein in in vitro NEB PURE system. 10% of the in vitro reaction was applied to protein gel in 2×SDS sample buffer. 100 ng of purified T7 promoter included PCR products was used for each variant in in vitro transcription-translation expression system. Control represents reaction without a template DNA.

In FIG. 26A, drops of the same amount of E. coli BL21 cells expressing the EGFP variants, the mCherry variants, or WT were plated on 0.2% Arabinose LB agar plates and exposed to blue light after overnight growth. In FIG. 26B, overnight cultures of mCardinal variants induced with 0.2% arabinose in LB media at the daylight indicating higher expression of high expressing variants by absorbance of the blue light from daylight spectra. FIG. 26C and FIG. 26D are images of E. coli and S. cerevisiae colonies, respectively, expressing WT EGFP or an EGFP variant with additional amino acids inserted between 2$^{nd}$ and 3$^{rd}$ amino acid in EGFP sequence. EGFP sequence variants from pet16b vector expressed in E. coli were digested using NcoI and XhoI restriction enzymes and cloned into pGAL418 vector for expression in S. cerevisiae. Clones that show higher expression in E. coli show similar trend of expression in S. cerevisiae.

FIG. 28A depicts expected Cy3 and Cy5 traces for the experiment. Briefly the Cy3-labeled small subunit of the

Figure 28A:
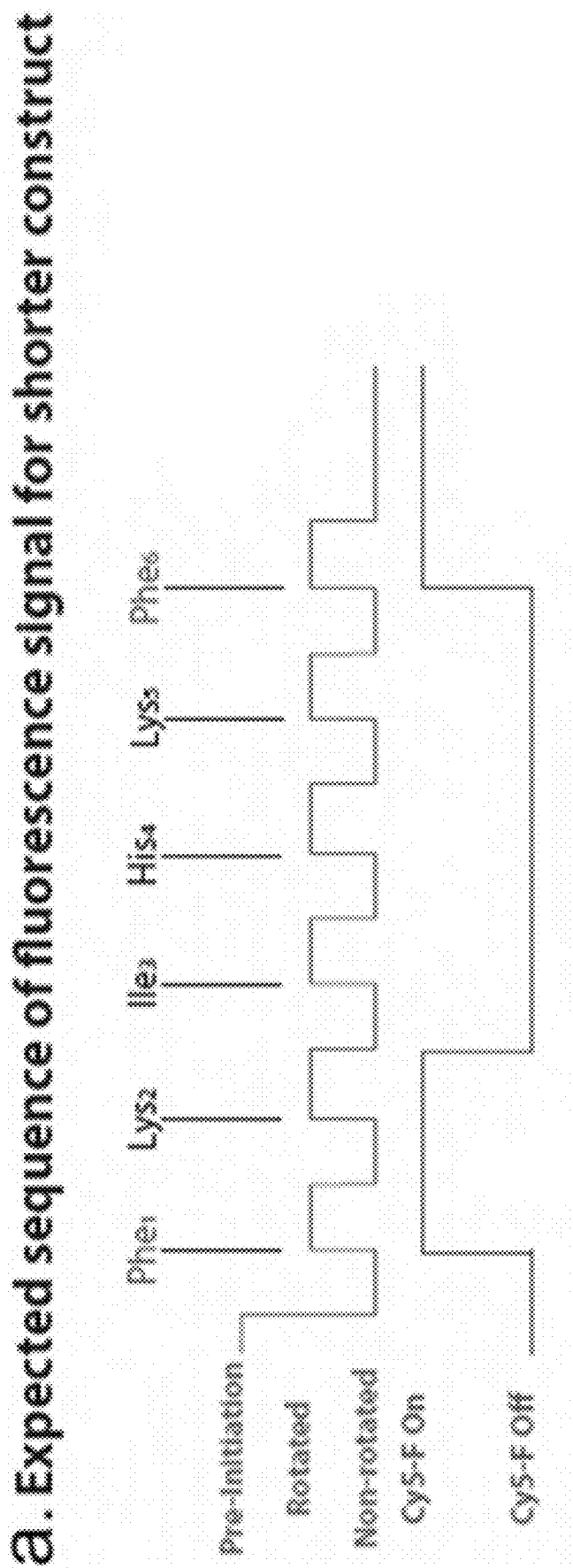
FIG. 28A, FIG. 28B, and FIG. 28C show hypothetical and experimental data from single molecule (SM) FRET experiments at zero mode using two short mRNAs encoding MFTVGKF (SEQ ID NO: 21) and MFTVGKF (SEQ ID NO: 21).
Figure 28B:
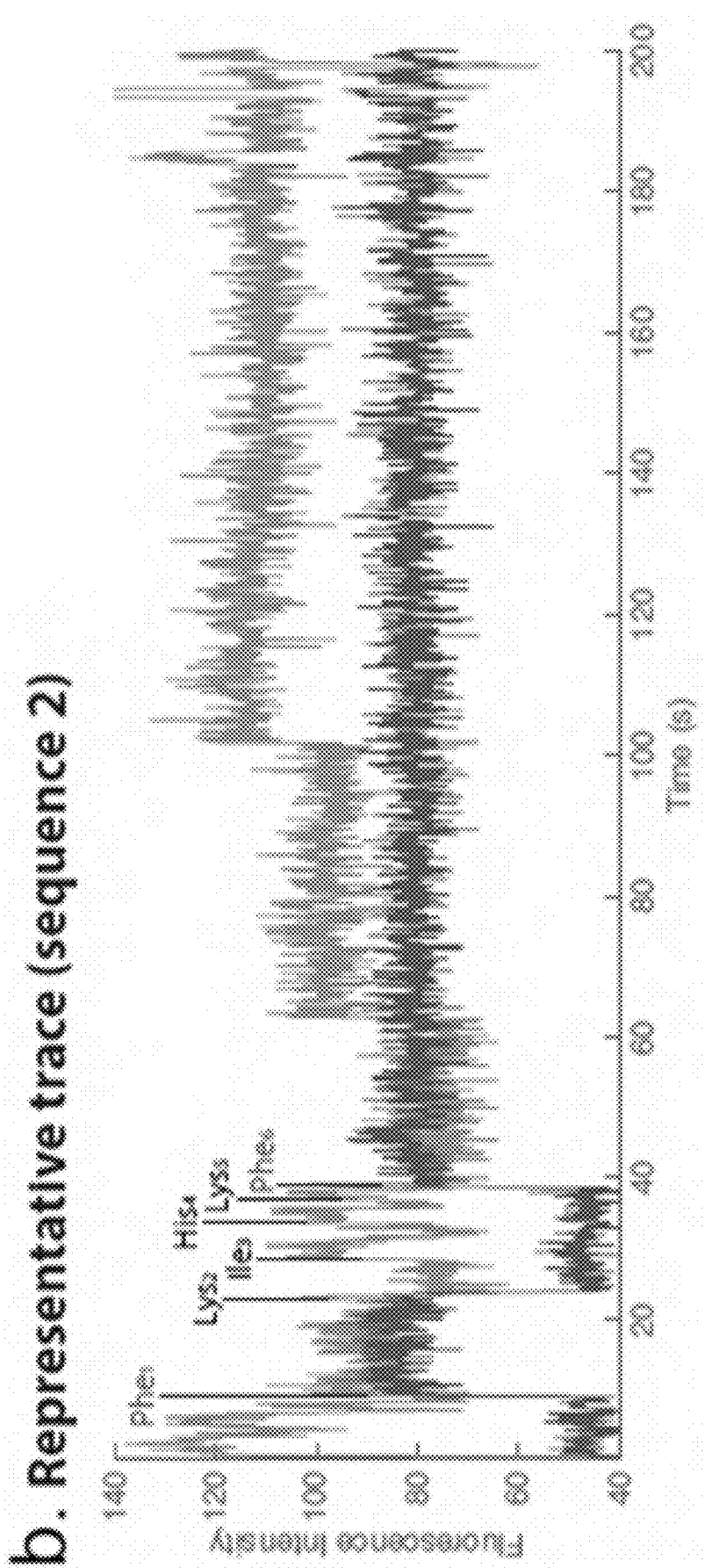
Figure 28C:
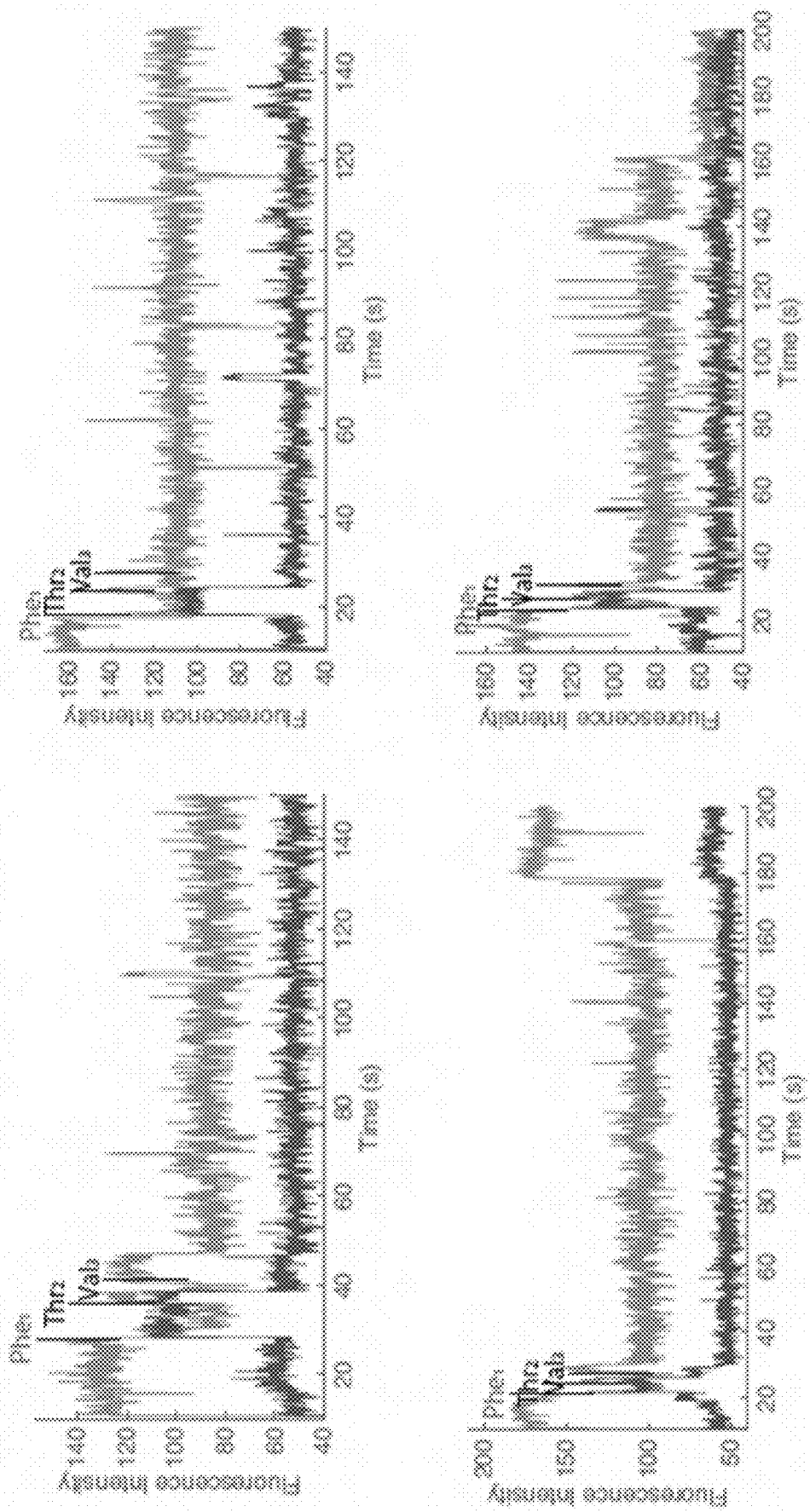

*E. coli* ribosome is expected to give a signal for the translocation of the ribosome during each peptide bond formation. Cy5-labeled Phe tRNA is expected to give a higher signal as it binds to A-site and moves to the P-site of the ribosome. The traces in FIG. 28B and FIG. 28C show that changes in ribosome processivity and a block in ribosome movement at the 3rd and 4th codon result in the reduced translational efficiency of MFTVGKF (SEQ ID NO: 21) sequence (sequence 5, FIG. 28C) compared to MFKIHKF (SEQ ID NO: 22) sequence (sequence 2, FIG. 28B).

Figure 29A:
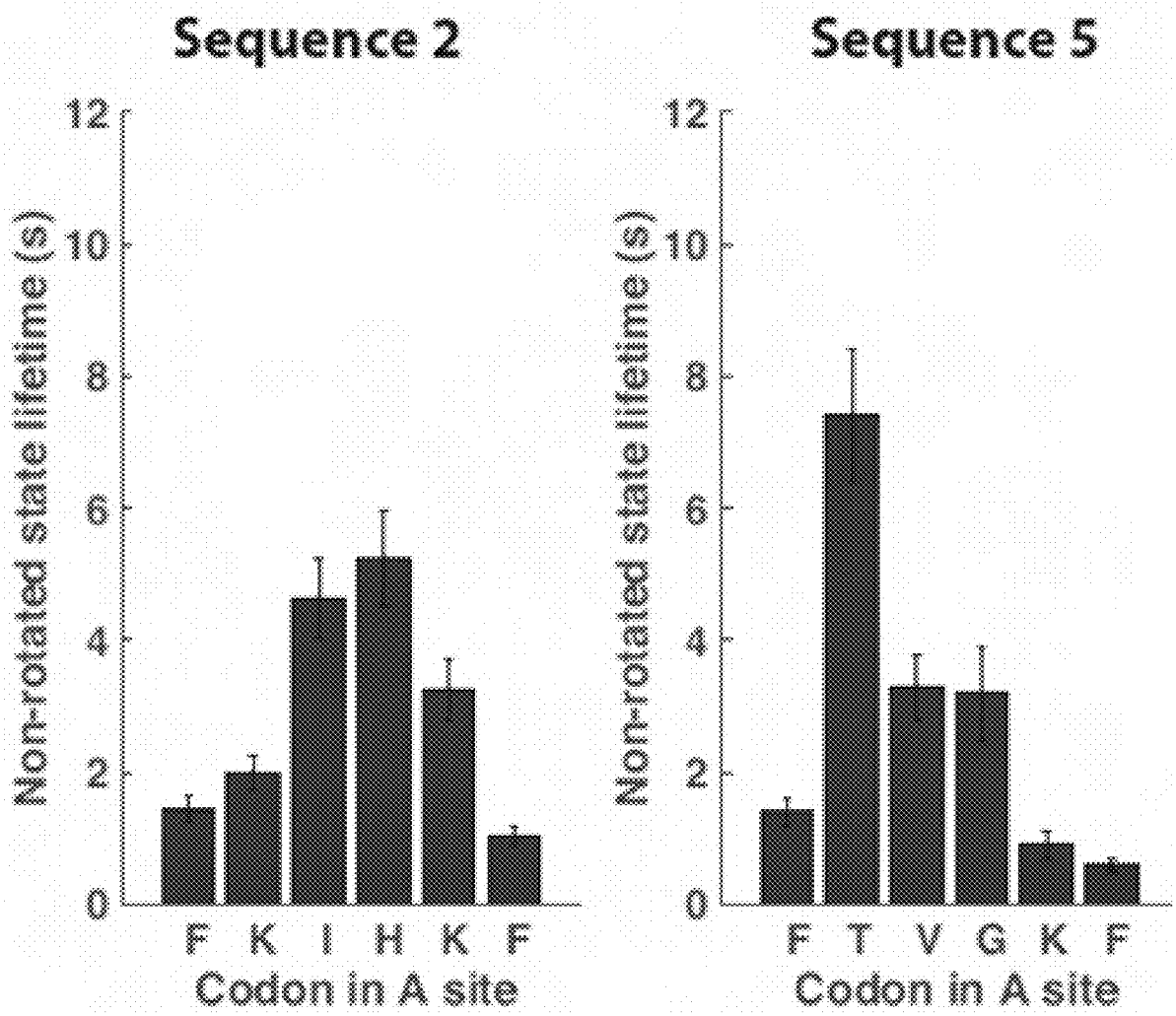
Figure 29B:
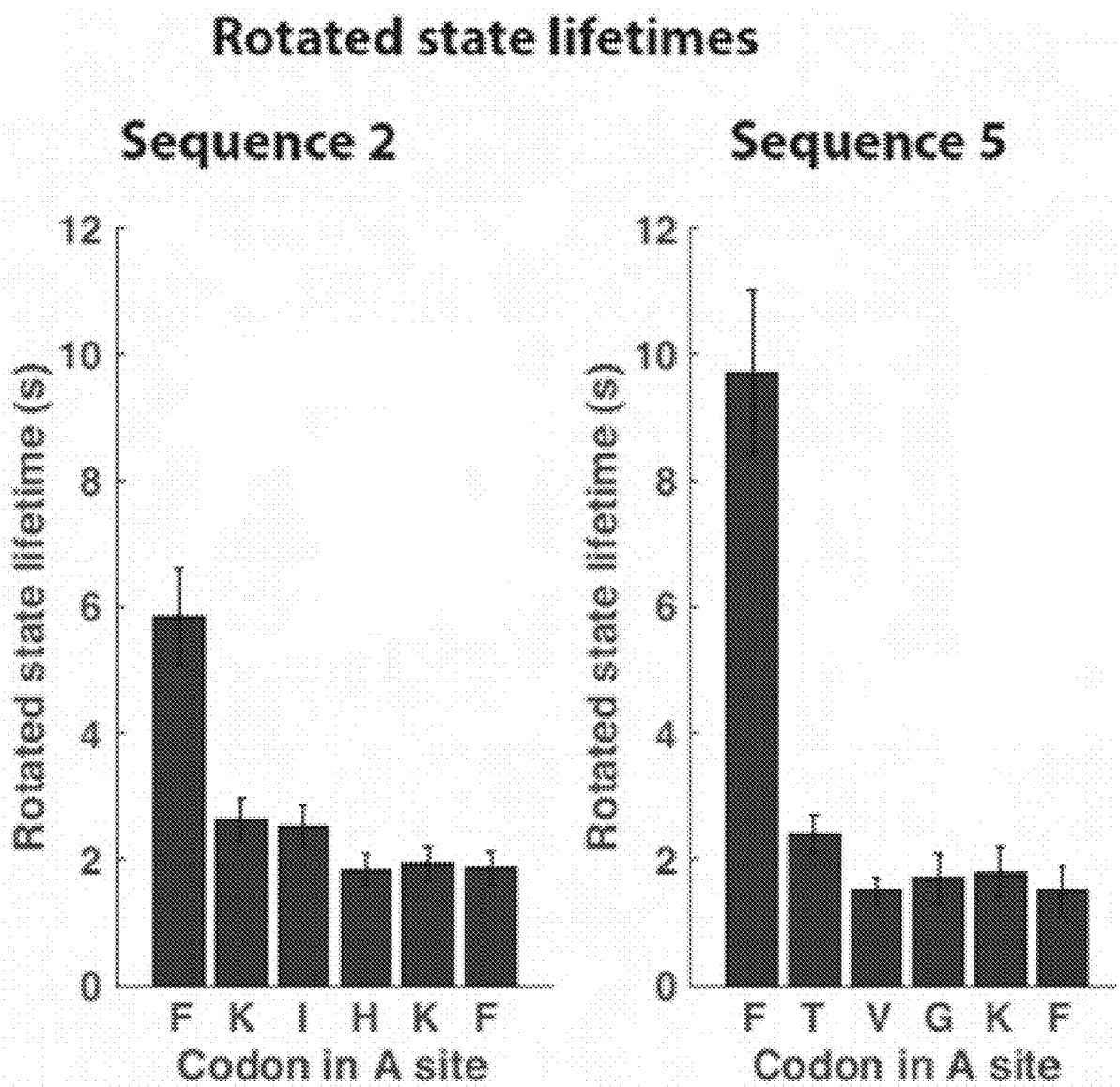
Figure 29C:
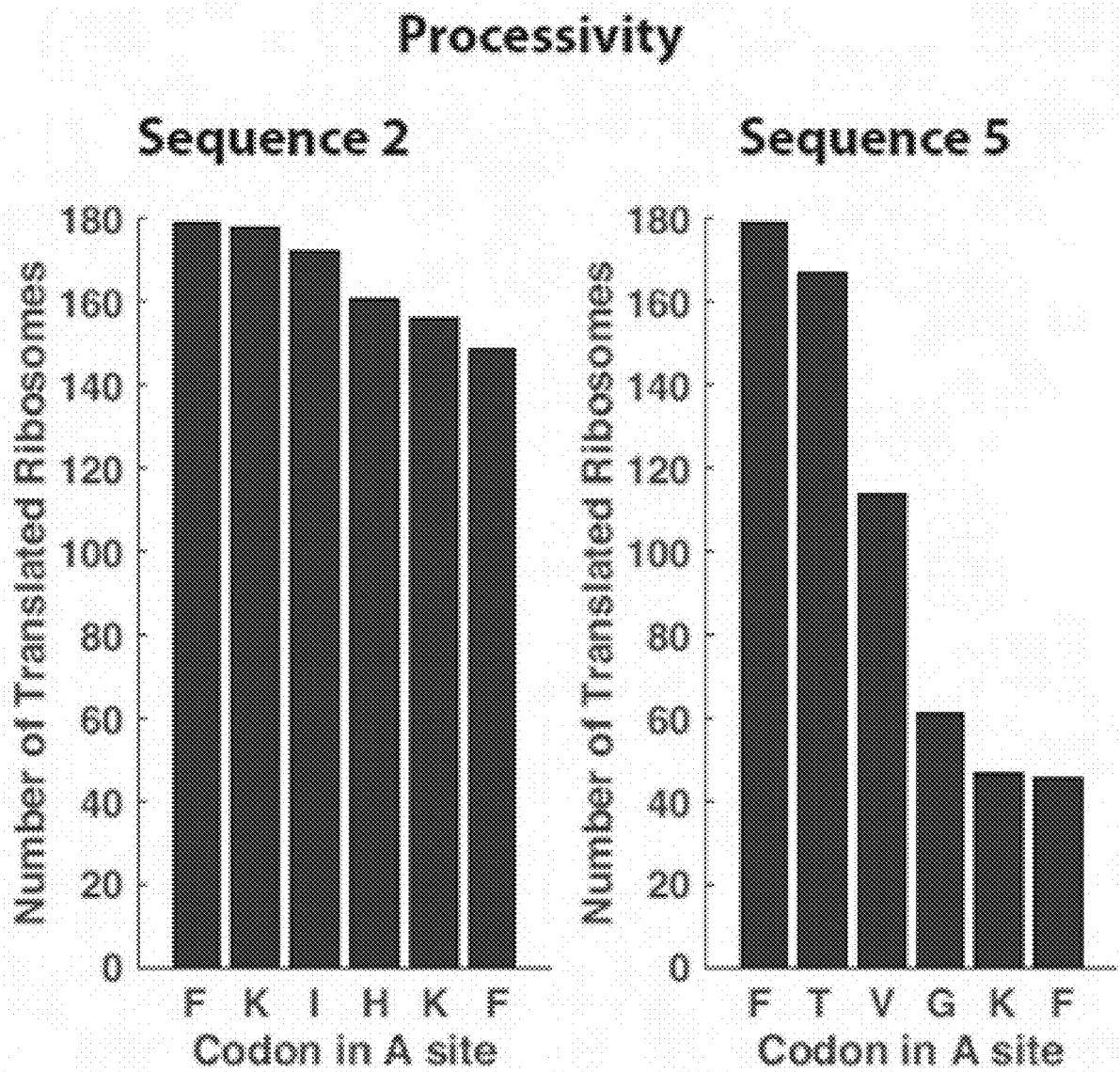

FIG. 29A, FIG. 29B, and FIG. 29C show data from single molecule (SM) FRET experiments at zero mode using two short mRNAs encoding the polypeptide MFTVGKF (SEQ ID NO: 21) ("sequence 2") or the polypeptide MFTVGKF (SEQ ID NO: 21) ("sequence 5"). FIG. 29A and FIG. 29B are graphs showing the calculated translation rates for rotated (FIG. 29A) and non-rotated (FIG. 29B) states of the two assayed sequences. These data indicate similar translation rates for both sequences. FIG. 29C is a graph showing the number of translated ribosomes per codon in the A site, which is a measure of processivity. The number of ribosomes that continuously make the MFKIHKF (SEQ ID NO: 22) peptide does not change significantly during the translation (processivity is 94% over the whole sequence). Ribosomes synthesizing MFTVGKF (SEQ ID NO: 21) peptide "pause" between codons 3 and 4 as well as between codons 4 and 5 reducing processivity of ribosome to 27% over the whole sequence. These data show that insertion of the low expressing sequence encoding TVG negatively affects processivity compared to insertion of the high expressing sequence encoding KIH.

Figure 30A:
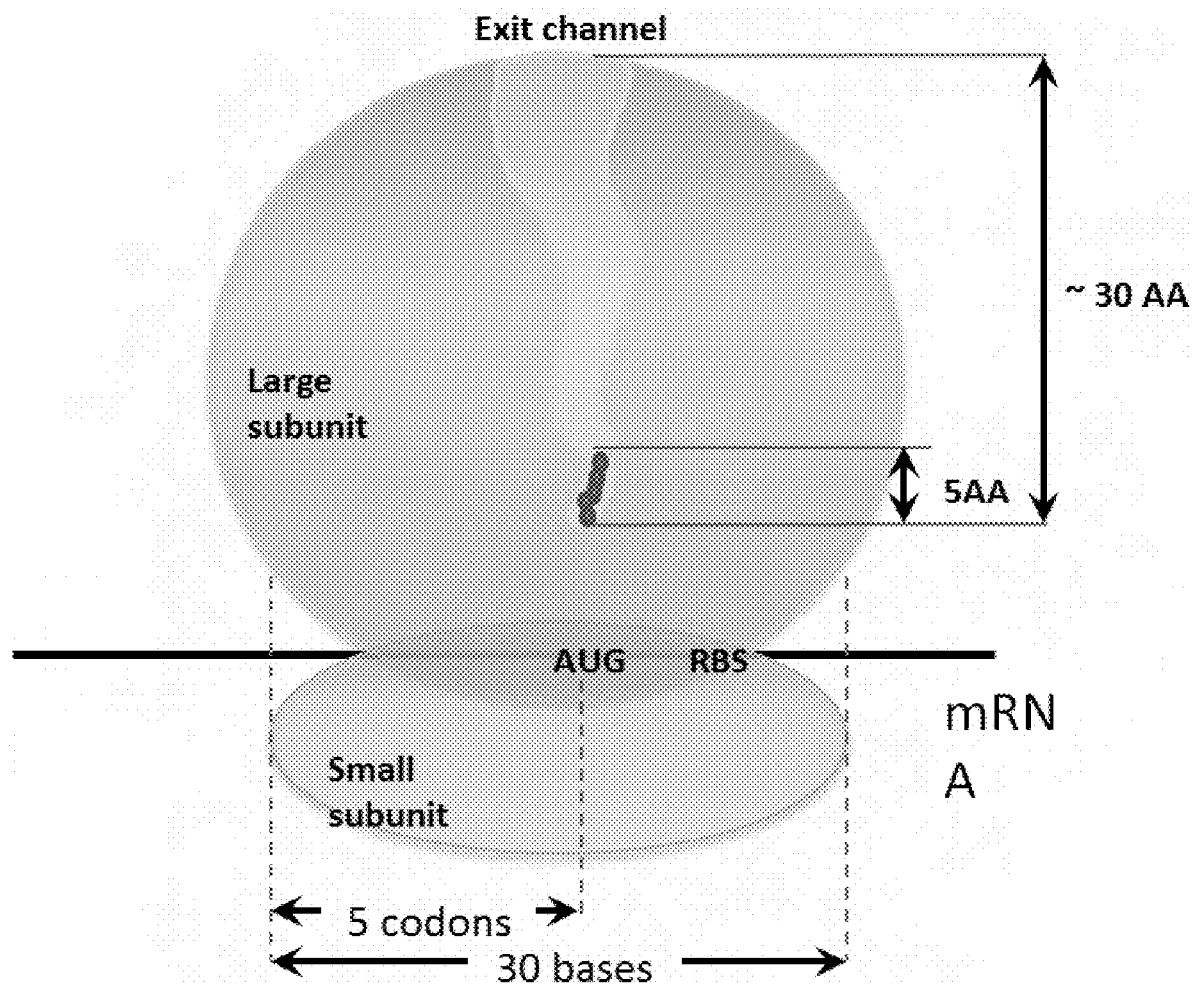
Figure 30B:
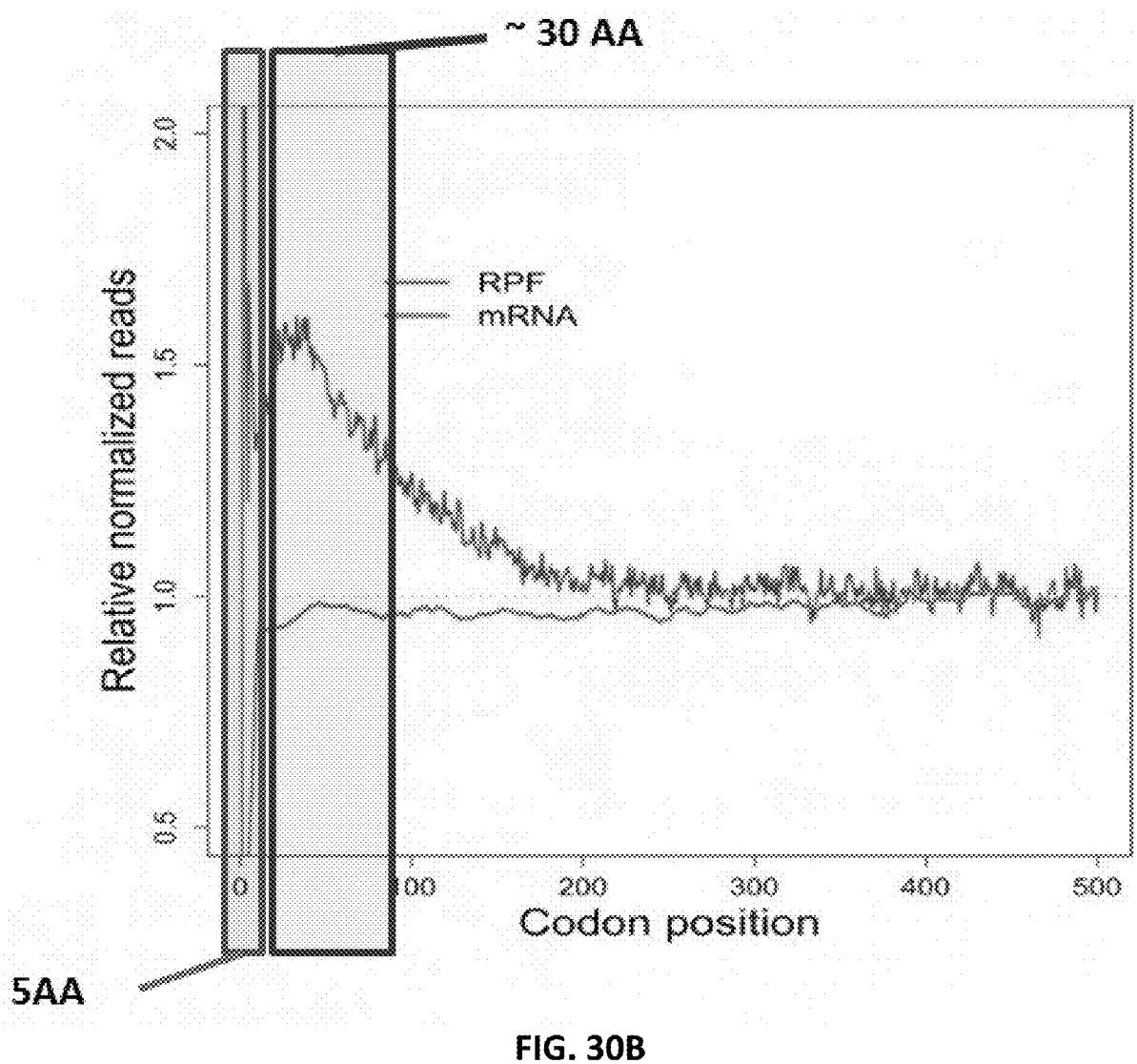

FIG. 30A and FIG. 30B model ribosome selection and the effect on translation efficiency. In FIG. 30A, a pentapeptide is shown in the ribosome exit channel and the length of the first ribosome footprint is depicted. Previous work in the field studying how the protein exit channel influences translation focused primarily on the constriction around L4 and L22, which is thirty amino acids away from the PTC. In contrast, the present disclosure has identified the entrance to the exit channel and P site as critical to translation efficiency. FIG. 30B depicts a metagene analysis of ribosome profiling data from mouse cells. The 5 amino acid barrier that is described in this disclosure, as well as the "classical" translational ramp over amino acids 30-40, is shown.

DETAILED DESCRIPTION

The present disclosure provides compositions and methods to modulate the level of expression of a protein in a deliberate manner (i.e., tunable regulation of expression) with only a minimal change to the genetic sequence of the gene of interest. The present disclosure therefore also provides compositions and methods to predictably alter protein abundance. Advantageously, the methods of the present disclosure are independent of the gene of interest, applicable to prokaryotes, archaea, and eukaryotes, and allows for both gross and fine tuning of protein abundance in an efficient and highly reproducible way.

Figure 1:
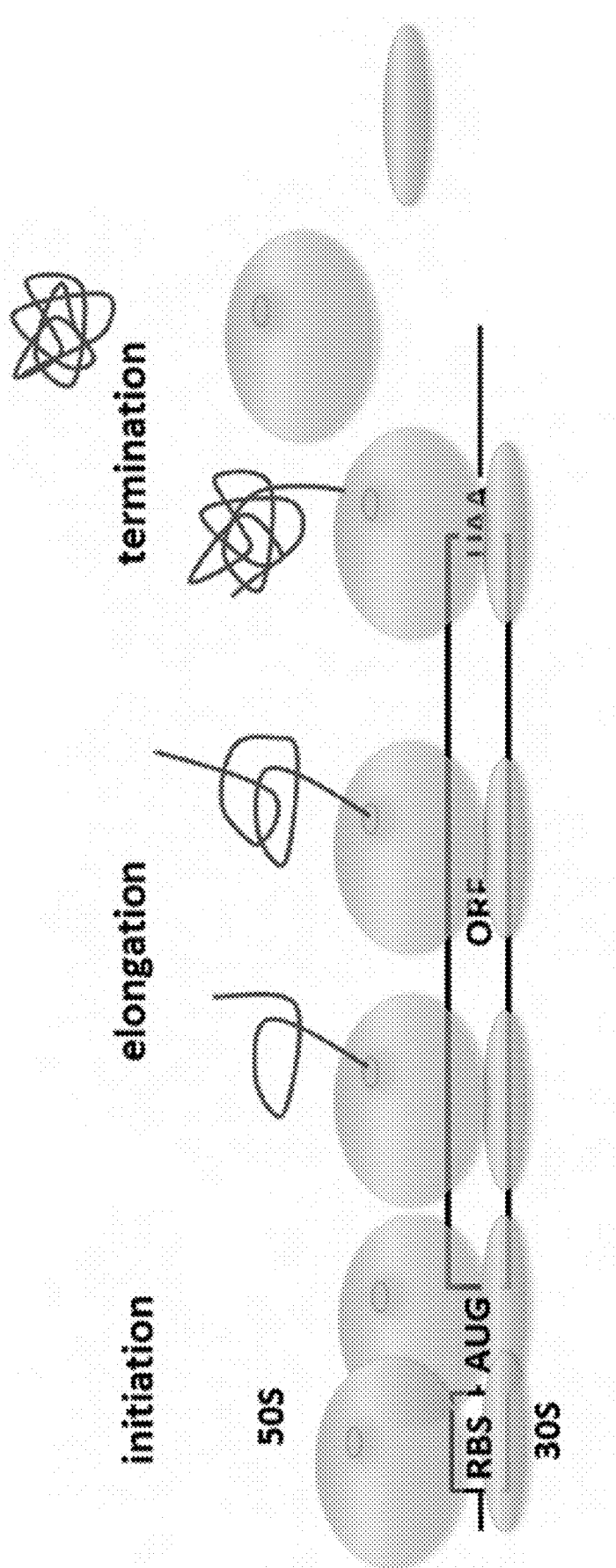
FIG. 1 is a simplified schematic of translation in prokaryotes. A common ribosomal binding site (RBS) in prokaryotic mRNA is the Shine-Dalgarno sequence (5'-AGGAGG-3').
Figure 2:
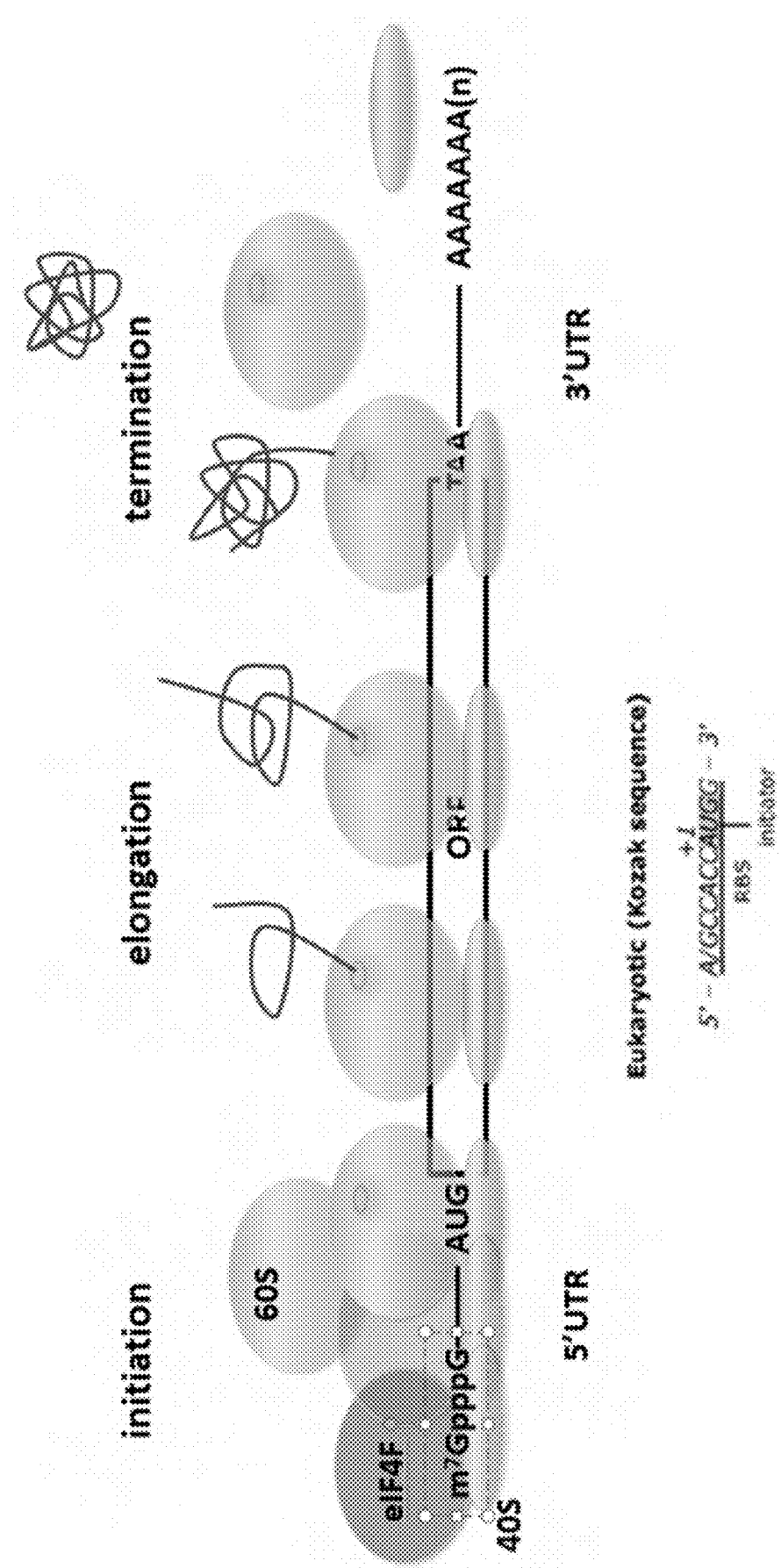
FIG. 2 is a simplified schematic of translation in eukaryotes. In this schematic, the 5' cap of the mRNA acts as the RBS. However, presence of an internal ribosome entry site allows for translation initiation in a cap-independent manner. The start codon (5'-AUG-3') is typically found within the Kozak sequence. (A/GCCACCAUGG SEQ ID NO: 11)
Figures 3A, 3B:
FIG. 3A and FIG. 3B show the set-up of a reporter system to test the influence of codons 3-5 of an mRNA sequence and the first five amino acids of a nascent peptide on translation efficiency.

Translation efficiency, as used herein, refers to the level of expression of a given protein, which is also referred to herein as protein abundance. Amino acids are polymerized into peptides in the peptidyl transferase center (PTC) within the large subunit of the ribosome. The nascent peptides then pass through a channel, referred to as the peptide exit tunnel, before they reach the extraribosomal environment where they fold into a protein. FIG. 1 and FIG. 2 are simplified schematics of the translation process in prokaryotes and eukaryotes, respectively.

It was generally assumed that translation efficiency is determined primarily by translation initiation. However, there is a growing understanding that efficiency of protein synthesis is regulated by multiple factors including, but not limited to, tRNA abundance, ribosome structure, codon composition, mRNA structure, and amino acid sequence. For example, research in the field suggests translation of the first 150 nucleotides of an mRNA, a period referred to as "early elongation" or the "5' translational ramp," is a contributor to translation efficiency. Rate of translation initiation, tRNA abundance bias, mRNA structure, ribosome structure, and the presence of retained initiation factors have all been suggested as possible mechanisms by which the 150 nucleotide length ramp affects translation efficiency. In particular, research in the field has focused on a constriction in the peptide exit channel that can accommodate about 30 amino acids away from the PTC. See, for example, Tuller T. et al., (2011). *Cell* 141(2), 344-354; Presnyak V. et al., (2015). *Cell* 160, 1111-1124; Gamble C. et al., (2016). *Cell* 166, 679-690; Goodman D. et al, (2013). *Science* 342, 475-479; Navon et al., (2016). *PNAS* 113, 7166-7170; or Arthur L. et al., (2015) *Science Advances* 1(6), e1500154.

The present disclosure is based on the discovery that translation efficiency, as measured by amount of synthesized protein or a surrogate therefor, is dependent on the early translational ramp that comprises the first 5 codons of the mRNA, which is referred to herein as the "short ramp" or "short transitional ramp". As further detailed herein, changes in the short ramp are responsible for at least a 3-4 order of magnitude difference in protein abundance. The observed difference is not dependent on tRNA abundance, efficiency of translation initiation, or overall mRNA structure. Surprisingly, it has been discovered that translation efficiency is regulated by composition of the amino acid sequence and to a much lower extent on the local mRNA structure. Single-molecule measurements of translation kinetics indicate substantial pausing of ribosome on the $4^{th}$ or $5^{th}$ amino acid for distinct amino acid compositions within the short translational ramp. Consequently, the inventors have discovered that introduction of preferred sequence motifs at certain positions (whether by insertion of a new sequence or editing the existing sequence) improves translation output for numerous recombinant proteins in the cells from *E. coli* to humans, indicating an evolutionary conserved mechanism for controlling translational efficiency.

Several definitions that apply throughout this disclosure will now be presented. As used herein, "about" refers to numeric values, including whole numbers, fractions, percentages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

The term "comprising" means "including, but not necessarily limited to"; it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

An EGFP variant, as used herein, refers to an EGFP protein encoded by a polynucleotide sequence that is different than the wild type EGFP (WT EGFP) coding sequence (SEQ ID NO: 9). An EGFP variant may or may not have a different amino acid sequence than wild type EGFP (SEQ ID NO: 10). A high-expressing EGFP variant refers to an EGFP variant that has GFP score of more than 4. A medium-expressing EGFP variant refers to an EGFP variant that has a GFP score of 2-4. A low-expressing EGFP variant refers to an EGFP variant that has GFP score of less than 2.

A "gene," as used herein, refers to a polynucleotide containing at least one open reading frame that is capable of encoding a particular protein after being transcribed and translated. As used herein, a "gene product" is the biochemical material, either RNA or protein, resulting from expression of a gene. A measurement of the amount of gene product is sometimes used to infer how active a gene is. As used herein, "gene expression" is the process by which information from a gene is used in the synthesis of a functional gene product. As used herein, a "reporter gene" refers to a gene that produces a gene product that is easily detected. Examples of reporter genes include, but are not limited to, bioluminescent, fluorescent, computed tomography (CT), magnetic resonance imaging (MRI), positron emission tomography (PET), single-photon emission computed tomography (SPECT) reporter genes, and the like. In some aspects, the reporter gene is a bioluminescent reporter gene (e.g., firefly luciferase). In some aspects, the reporter gene is a fluorescent reporter gene (e.g., a fluorescent protein (GFP, mCherry, etc.).

The term "isolated," as used herein, indicates a component (e.g., a polynucleotide, a polypeptide, an epitope binding agent, etc.) has been separated from its natural environment. In some embodiments, an isolated component may be purified to greater than 95% or 99% purity, as determined by methods known in the art.

As used herein, "modulating" broadly means to cause or facilitate a qualitative or quantitative change, alteration, or modification in a molecule, a process, pathway, or phenomenon of interest. As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a cell.

As used herein, "modulating the level of expression of a protein" refers to causing or facilitating a qualitative or quantitative change, alteration, or modification in the amount of at least one polypeptide produced in a cell as a result of translation of at least one polynucleotide sequence (e.g., mRNA) encoding such at least one polypeptide.

The term "operably linked" means that a polynucleotide sequence is linked to one or more regulatory element(s) in a manner that allows for expression of the polynucleotide sequence (e.g., in an in vitro transcription/translation system, in a host cell when a vector comprising the polynucleotide sequence operably linked to one or more regulatory elements is introduced into the host cell, in a host cell when a polynucleotide sequence operably linked to one or more regulatory elements is integrated into the host cell's genome, etc.).

The terms "polynucleotide", "polynucleotide sequence", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (sh RNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "polypeptide," "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; non-limiting examples of such modifications include disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

A "protein of interest" refers to any protein for which the tunable regulation of its expression is desired in cells. A polynucleotide sequence encoding a protein of interest may be referred to as "a polynucleotide sequence of interest."

As used herein the term "wild type" is a term of the art understood by skilled persons and means a typical form of an organism, strain, gene or characteristic as distinguished from a variant form.

The term "non-naturally occurring" indicates the involvement of the hand of man. The terms, when referring to nucleic acid molecules or polypeptides, means that the sequence of the nucleic acid molecule or the polypeptide has been deliberately changed from the sequence as found in nature.

Other aspects of the present disclosure are described in further detail below.

I. Method to Modulate the Expression of a Protein

In an aspect, the present disclosure provides a method to modulate the level of expression of a protein. Generally speaking, the method comprises modifying the nucleic acid sequence encoding a protein of interest to produce a modified nucleic acid sequence encoding a second protein, wherein the nucleic acid sequence encoding the protein of interest and the modified nucleic acid sequence encoding the second protein have a different polynucleotide sequence at codons 3, 4, and 5. The modified nucleic acid is then expressed in a cell or in a cell-free transcription/translation system. Importantly, the modified polynucleotide sequence at codons 3, 4, and 5 does not encode a stop codon recognizable by the cell or the cell-free system. The level of expression can be increased or decreased depending upon the change(s) made at codons 3, 4, and 5. The change(s) made at codons 3, 4, and 5 also may or may not result in changes in the amino acid sequence of the protein of interest. As such, the second protein can have the same as or a different amino acid sequence than the protein of interest.

As used herein, the term "protein of interest" refers to any protein for which the tunable regulation of its expression in cells is desired. In some embodiments, the protein of interest comprises a reporter protein. As used herein, the term "reporter protein" refers to a protein that has visually identifiable characteristic(s) or is capable of producing visually identifiable characteristic(s). Nom-limiting examples include enzymes (e.g., β-galactosidase, chloramphenicol acetytransferase, horseradish peroxidase, luciferase, etc.), chromoproteins, fluorescent proteins, chemiluminescent proteins. In some embodiments, the protein of interest comprises a therapeutic protein, including but not limited to an antibody, an antibody fragment, a peptide, an enzyme. In some embodiments, the protein of interest comprises a naturally occurring protein. In some embodiments, the protein of interest comprises a variant of a naturally occurring protein. In some embodiments, the protein of interest comprises a fusion protein. In some embodiments, the protein of interest is a naturally occurring viral protein or a variant thereof. In some embodiments, the protein of interest is a naturally occurring prokaryotic protein or a variant thereof. In some embodiments, the protein of interest is a naturally occurring archaeal protein or a variant thereof. In some embodiments, the protein of interest is a naturally occurring mammalian protein or a variant thereof. In some embodiments, the protein of interest comprises a human protein or a variant thereof.

A nucleic acid encoding a protein of interest comprises a polynucleotide sequence that codes for the protein of interest, which may or may not include introns. A nucleic acid encoding a protein of interest may also further comprise one or more regulatory element that is operatively-linked to the polynucleotide sequence encoding the protein of interest. The one or more regulatory elements may be selected on the basis of the host cell to be used for expression. Suitable regulatory elements are described in further detail in Section IV.

Any method known in the art can be used to modify a nucleic acid sequence at codons 3, 4 and 5, provided the change does not result in a stop codon encoded by codon 3, 4 or 5 of the modified nucleic acid sequence, or in a shift in the reading frame of the modified nucleic acid sequence at any position corresponding to codons 6 and greater in the nucleic acid sequence encoding the protein of interest. Non-limiting examples include in vitro and in vivo methods to insert into a nucleic acid sequence encoding a protein of interest a polynucleotide sequence consisting of 3, 6, or 9 nucleotides, and in vitro and in vivo methods to make on or more nucleotide changes in a nucleic acid sequence.

In some embodiments, the method comprises inserting a polynucleotide sequence between the second and third codons of a nucleic acid sequence encoding a protein of interest. For example, a polynucleotide sequence selected from (i) 5'-$n^1n^2n^3$-3', (ii) 5'-$n^1n^2n^3n^4n^5n^6$-3', and (iii) 5'-$n^1n^2n^3n^4n^5n^6n^7n^8n^9$-3', may be inserted between the second and third codons of a nucleic acid sequence encoding a protein of interest, wherein $n^1$, $n^2$, $n^3$, $n^4$, $n^5$, $n^6$, $n^7$, $n^8$, and $n^9$ are each independently selected from the group consisting of adenine, thymine, uracil, guanine, and cytosine. In another example, a polynucleotide sequence selected from Table A, Table B, or Table C may be inserted between the second and third codons of a nucleic acid sequence encoding a protein of interest. In another example, a polynucleotide sequence selected from Table D may be inserted between the second and third codons of a nucleic acid sequence encoding a protein of interest. In another example, a polynucleotide sequence encoding a peptide selected from Table I may be inserted between the second and third codons of a nucleic acid sequence encoding a protein of interest. The above modifications may be made to the nucleic acid sequence in vitro using standard molecular cloning techniques that rely on restriction endonucleases, PCR-based methods, etc., or in vivo using any number of genome-editing tools known to a skilled artisan (including, but not limited to, programmable site-specific nucleases such as zinc-finger nucleases (ZFNs), transcription activator like-effector nucleases (TALENs), and Clustered Regulatory Interspaced Short Palindromic Repeats (CRISPR)/CRISPR-associated (Cas) system, etc.).

In other embodiments, the method comprises inserting a polynucleotide sequence between the third and fourth codons of a nucleic acid sequence encoding a protein of interest. For example, a polynucleotide sequence selected from (i) 5'-$n^1n^2n^3$-3' and (ii) 5'-$n^1n^2n^3n^4n^5n^6$-3', may be inserted between the third and fourth codons of a nucleic acid sequence encoding a protein of interest, wherein $n^1$, $n^2$, $n^3$, $n^4$, $n^5$, and $n^6$ are each independently selected from the group consisting of adenine, thymine, uracil, guanine, and cytosine. The above modifications may be made to the nucleic acid sequence in vitro using standard molecular cloning techniques that rely on restriction endonucleases, PCR-based methods, etc., or in vivo using any number of genome-editing tools known to a skilled artisan (including, but not limited to, programmable site-specific nucleases such as zinc-finger nucleases (ZFNs), transcription activator like-effector nucleases (TALENs), and Clustered Regulatory Interspaced Short Palindromic Repeats (CRISPR)/CRISPR-associated (Cas) system, etc.).

In other embodiments, the method comprises inserting a polynucleotide sequence between the fourth and fifth codons of a nucleic acid sequence encoding a protein of interest. For example, a polynucleotide sequence that is 5'-$n^1n^2n^3$-3' may be inserted between the fourth and fifth codons of a nucleic acid sequence encoding a protein of interest, wherein $n^1$, $n^2$, and $n^3$ are each independently selected from the group consisting of adenine, thymine, uracil, guanine, and cytosine. The above modifications may be made to the nucleic acid sequence in vitro using standard molecular cloning techniques that rely on restriction endonucleases, PCR-based methods, etc., or in vivo using any number of genome-editing tools known to a skilled artisan (including, but not limited to, programmable site-specific nucleases such as zinc-finger nucleases (ZFNs), transcription activator like-effector nucleases (TALENs), and Clustered Regulatory Interspaced Short Palindromic Repeats (CRISPR)/CRISPR-associated (Cas) system, etc.).

In other embodiments, the method comprises changing one or more nucleotides of a nucleic acid sequence encoding a protein of interest, wherein the one or more changes are at codon three, codon four, codon five, or any combination thereof. For example, 1, 2, or 3 nucleotides changes may be made at codon three; 1, 2, or 3 nucleotides changes may be made at codon four; or 1, 2, or 3 nucleotides changes may be made at codon five. In another example, 2, 3, 4, 5, or 6 nucleotides changes may be made at codon three and codon four; 2, 3, 4, 5, or 6 nucleotides changes may be made at codon three and codon five; or 2, 3, 4, 5, or 6 nucleotides changes may be made at codon four and codon five. In another example, 3, 4, 5, 6, 7, 8, or 9 nucleotides changes may be made at codon three, codon four, and codon five. In further examples, one or more changes may be made at codon three, codon four, codon five, or any combination thereof, to produce a modified nucleic acid sequence that has a polynucleotide sequence of Table A, Table B or Table C, at codons 3, 4 and 5. In still further examples, one or more changes may be made at the second codon, the third codon, the fourth codon, or any combination thereof, to produce a modified nucleic acid sequence that has a polynucleotide sequence of Table D, at codons 3, 4 and 5. In still further examples, one or more changes may be made at the second codon, the third codon, the fourth codon, or any combination thereof, to produce a modified nucleic acid sequence encoding a peptide selected from Table I. The above modifications may be made to the nucleic acid sequence in vitro using standard molecular cloning techniques that rely on restriction endonucleases, PCR-based methods, etc., or in vivo using any number of genome-editing tools known to a skilled artisan (including, but not limited to, programmable site-specific nucleases such as zinc-finger nucleases (ZFNs), transcription activator like-effector nucleases (TALENs), and Clustered Regulatory Interspaced Short Palindromic Repeats (CRISPR)/CRISPR-associated (Cas) system, etc.).

Modifying a nucleic acid sequence encoding a protein of interest by interesting a polynucleotide sequence consisting of 3, 6, or 9 nucleotides will result in a modified nucleic acid sequence encoding a second protein that has a different amino acid sequence than the protein of interest. Modifying a nucleic acid sequence encoding a protein of interest by changing one or more nucleotides at the codon three, codon four, codon five, or any combination thereof, may or may not result in a modified nucleic acid sequence encoding a second protein that has a different amino acid sequence than the protein of interest. For example, if the polynucleotide sequence at codons 3, 4, and 5 is 5'-TACTACTAT-3', changing one nucleotide so that the sequence becomes 5'-TAT-TACTAT-3' changes the Expression Score from 2.86 to 4.57 but has no effect on the amino acid sequence.

Once a nucleic acid sequence encoding a protein of interest is modified, the modified nucleic acid is then expressed in a cell or in a cell-free transcription/translation system. Importantly, the polynucleotide sequence at codons 3, 4, and 5 of the modified nucleic acid sequence does not encode a stop codon recognizable by the cell or the cell-free system. Preferably, the polynucleotide sequence at codons 3, 4, and 5 of the modified nucleic acid sequence also does not encode a methionine. The polynucleotide sequences in Tables A-F do not encode a stop codon when inserted into a nucleic acid sequence in-frame. To express the modified nucleic acid in a cell or in a cell-free transcription/translation system, or more additional steps may need to be taken. For example, the modified nucleic acid may need to be cloned into a suitable expression vector, packaged into a viral particle for delivery into a cell, etc. A skilled artisan will appreciate that the choice of cell or cell-free transcription/translation system will be influenced in part by features of the modified nucleic acid sequence—e.g., the presence/absence of introns, the presence/absence of a 5' cap on an mRNA, choice of promoter and other regulatory elements, etc. Advantageously, the method of the present disclosure can be used with any cell type (e.g., prokaryote, archaea, eukaryote, etc.).

Compared to the protein of interest, the level of expression of the protein encoded by the modified nucleic acid may be higher or lower by up to about 3-5 orders of magnitude difference. The direction and magnitude of the change depends upon the original polynucleotide sequence at codons 3, 4, and 5 and the modified polynucleotide sequence at codons 3, 4, and 5. Advantageously, the present disclosure provides methods to modulate the level of expression of a protein of interest in a deliberate manner (i.e., tunable regulation of expression) by selecting a polynucleotide sequence from Table A, B, or C that has a higher or lower score than the score from Table A, B, or C for a polynucleotide sequence consisting of codons 3, 4 and 5 of the nucleic acid sequence encoding the protein of interest. For example, to achieve the greatest change in protein expression, the difference between the GFP score (or RFU value) for codons 3, 4 and 5 of the nucleic acid sequence encoding a protein of interest and the GFP score (or RFU value) for the selected polynucleotide sequence should be maximized. Although the correlation between RFU and protein abundance measured by quantitative western blot is not strictly linear, the RFU values can be used as an estimate of magnitude of increase or decrease if the desired goal is to not maximize the change but to achieve an intermediate level of change.

In certain embodiments, the present disclosure provides a method to increase the level of expression of a protein. The method comprises (a) identifying a score from Table A, B, or C for a polynucleotide sequence consisting of codons 3, 4 and 5 of a nucleic acid sequence encoding a protein of interest; (b) selecting a polynucleotide sequence from Table A, B, or C that has a higher score; (c) modifying the nucleic acid sequence encoding the protein of interest in step (a); and (d) expressing the modified nucleic acid sequence in a cell or in a cell-free transcription/translation system. Modifying the nucleic acid sequence in step (c) can occur by Modifying the nucleic acid sequence in step (c) can occur by (i) inserting a polynucleotide sequence between the second and third codons of the nucleic acid sequence encoding the first protein of interest, wherein the polynucleotide sequence is selected from 5'-$n^1n^2n^3$-3', 5'-$n^1n^2n^3n^4n^5n^6$-3', and 5'-$n^1n^2n^3n^4n^5n^6n^7n^8n^9$-3', wherein $n^1$, $n^2$, $n^3$, $n^4$, $n^5$, $n^6$, $n^7$, $n^8$, and $n^9$ are each independently selected from the group consisting of adenine, thymine, uracil, guanine, and cytosine; (ii) inserting a polynucleotide sequence between the third and fourth codons of the nucleic acid sequence encoding the first protein of interest, wherein the polynucleotide sequence is selected from 5'-$n^1n^2n^3$-3', and 5'-$n^1n^2n^3n^4n^5n^6$-3', wherein $n^1$, $n^2$, $n^3$, $n^4$, $n^5$, and $n^6$ are each independently selected from the group consisting of adenine, thymine, uracil, guanine, and cytosine; or (iii) inserting a polynucleotide sequence between the second and third codons of the nucleic acid sequence encoding the first protein of interest, wherein the polynucleotide sequence is 5'-$n^1n^2n^3$-3', wherein $n^1$, $n^2$, and $n^3$ are each independently selected from the group consisting of adenine, thymine, uracil, guanine, and cytosine; or (iv) changing one or more nucleotides of the nucleic acid sequence from step (a) at codon three, codon four, codon five, or any combination thereof, to produce a modified nucleic acid sequence that has the polynucleotide sequence from step (b) at codons 3, 4 and 5. In various embodiments, the inserted polynucleotide sequence is not 5'-AAA-3', 5'-AAAAAA-3', or 5'-AAAAAAAAA-3', or the change at codon three, codon four, and/or codon five of the nucleic acid sequence from step (a) does not result in an 5'-AAA-3' codon.

In certain embodiments, the present disclosure provides a method to increase the level of expression of a protein. The method comprises (a) identifying a score from Table A, B, or C for a polynucleotide sequence consisting of codons 3, 4 and 5 of a nucleic acid sequence encoding a protein of interest; (b) selecting a polynucleotide sequence from Table D that has a higher score; (c) modifying the nucleic acid sequence encoding the protein of interest in step (a); and (d)

expressing the modified nucleic acid sequence in a cell or in a cell-free transcription/translation system. Modifying the nucleic acid sequence in step (c) can occur by (i) inserting a polynucleotide sequence between the second and third codons of the nucleic acid sequence encoding the first protein of interest, wherein the polynucleotide sequence is selected from $5'-n^1n^2n^3-3'$, $5'-n^1n^2n^3n^4n^5n^6-3'$, and $5'-n^1n^2n^3n^4n^5n^6n^7n^8n^9-3'$, wherein $n^1$, $n^2$, $n^3$, $n^4$, $n^5$, $n^6$, $n^7$, $n^8$, and $n^9$ are each independently selected from the group consisting of adenine, thymine, uracil, guanine, and cytosine; (ii) inserting a polynucleotide sequence between the third and fourth codons of the nucleic acid sequence encoding the first protein of interest, wherein the polynucleotide sequence is selected from $5'-n^1n^2n^3-3'$, and $5'-n^1n^2n^3n^4n^5n^6-3'$, wherein $n^1$, $n^2$, $n^3$, $n^4$, $n^5$, and $n^6$ are each independently selected from the group consisting of adenine, thymine, uracil, guanine, and cytosine; or (iii) inserting a polynucleotide sequence between the fourth and fifth codons of the nucleic acid sequence encoding the first protein of interest, wherein the polynucleotide sequence is $5'-n^1n^2n^3-3'$, wherein $n^1$, $n^2$, and $n^3$ are each independently selected from the group consisting of adenine, thymine, uracil, guanine, and cytosine; or (iv) changing one or more nucleotides of the nucleic acid sequence from step (a) at codon three, codon four, codon five, or any combination thereof, to produce a modified nucleic acid sequence that has the polynucleotide sequence from step (b) at codons 3, 4 and 5. In various embodiments, the inserted polynucleotide sequence is not 5'-AAA-3', 5'-AAAAAA-3', or 5'-AAAAAAAAA-3', or the change at the second codon, the third codon, and/or the fourth codon of the nucleic acid sequence from step (a) does not result in an 5'-AAA-3' codon.

In certain embodiments, the present disclosure provides a method to decrease the level of expression of a protein. The method comprises (a) identifying a score from Table A, B, or C for a polynucleotide sequence consisting of codons 3, 4 and 5 of a nucleic acid sequence encoding a protein of interest; (b) selecting a polynucleotide sequence from Table A, B, or C that has a lower score; (c) modifying the nucleic acid sequence encoding the protein of interest in step (a); and (d) expressing the modified nucleic acid sequence in a cell or in a cell-free transcription/translation system. Modifying the nucleic acid sequence in step (c) can occur by Modifying the nucleic acid sequence in step (c) can occur by (i) inserting a polynucleotide sequence between the second and third codons of the nucleic acid sequence encoding the first protein of interest, wherein the polynucleotide sequence is selected from $5'-n^1n^2n^3-3'$, $5'-n^1n^2n^3n^4n^5n^6-3'$, and $5'-n^1n^2n^3n^4n^5n^6n^7n^8n^9-3'$, wherein $n^1$, $n^2$, $n^3$, $n^4$, $n^5$, $n^6$, $n^7$, $n^8$, and $n^9$ are each independently selected from the group consisting of adenine, thymine, uracil, guanine, and cytosine; (ii) inserting a polynucleotide sequence between the third and fourth codons of the nucleic acid sequence encoding the first protein of interest, wherein the polynucleotide sequence is selected from $5'-n^1n^2n^3-3'$, and $5'-n^1n^2n^3n^4n^5n^6-3'$, wherein $n^1$, $n^2$, $n^3$, $n^4$, $n^5$, and $n^6$ are each independently selected from the group consisting of adenine, thymine, uracil, guanine, and cytosine; or (iii) inserting a polynucleotide sequence between the second and third codons of the nucleic acid sequence encoding the first protein of interest, wherein the polynucleotide sequence is $5'-n^1n^2n^3-3'$, wherein $n^1$, $n^2$, and $n^3$ are each independently selected from the group consisting of adenine, thymine, uracil, guanine, and cytosine; or (iv) changing one or more nucleotides of the nucleic acid sequence from step (a) at the second codon, the third codon, the fourth codon, or any combination thereof, to produce a modified nucleic acid sequence that has the polynucleotide sequence from step (b) at codons 3, 4 and 5. In various embodiments, the inserted polynucleotide sequence is not 5'-AAA-3', 5'-AAAAAA-3', or 5'-AAAAAAAAA-3', or the change at codon three, codon four, and/or codon five of the nucleic acid sequence from step (a) does not result in an 5'-AAA-3' codon.

In certain embodiments, the present disclosure provides a method to decrease the level of expression of a protein. The method comprises (a) identifying a score from Table A, B, or C for a polynucleotide sequence consisting of codons 3, 4 and 5 of a nucleic acid sequence encoding a protein of interest; (b) selecting a polynucleotide sequence from Table D that has a lower score; (c) modifying the nucleic acid sequence encoding the protein of interest in step (a); and (d) expressing the modified nucleic acid sequence in a cell or in a cell-free transcription/translation system. Modifying the nucleic acid sequence in step (c) can occur by (i) inserting a polynucleotide sequence selected from $5'-n^1n^2n^3-3'$, $5'-n^1n^2n^3n^4n^5n^6-3'$, and $5'-n^1n^2n^3n^4n^5n^6n^7n^8n^9-3'$, into the nucleic acid sequence from step (a) between the second and third codon, wherein $n^1$, $n^2$, $n^3$, $n^4$, $n^5$, $n^6$, $n^7$, $n^8$, and $n^9$ are each independently selected from the group consisting of adenine, thymine, uracil, guanine, and cytosine, to produce a modified nucleic acid sequence that has the polynucleotide sequence from step (b) at codons 3, 4 and 5; or (ii) changing one or more nucleotides of the nucleic acid sequence from step (a) at codon three, codon four, codon five, or any combination thereof, to produce a modified nucleic acid sequence that has the polynucleotide sequence from step (b) at codons 3, 4 and 5. In various embodiments, the inserted polynucleotide sequence is not 5'-AAA-3', 5'-AAAAAA-3', or 5'-AAAAAAAAA-3', or the change at codon three, codon four, and/or codon five of the nucleic acid sequence from step (a) does not result in an 5'-AAA-3' codon.

Selection of a polynucleotide sequence from Tables A-D can be further guided by the information in Tables E, F, or G. These tables show the distribution of amino acids encoded by the polynucleotide sequences from Table A, B, and C, regardless of their codons, with their mean GFP score, range for the GFP score, and total counts in the EGFP library. When selecting a polynucleotide sequence for codons 3, 4 and 5 of the modified nucleic acid sequence, it may be preferable to select a sequence that encodes an amino acid sequence that has a narrow range for the GFP score. The range takes into account all possible codons encoding that amino acid sequence and their spread, and serves as a proxy for standard deviation. Amino acid sequences with a narrow range will have a high expression value regardless of the codon used. Alternatively, or in addition, it may be preferable to not select a sequence that codes for a methionine to avoid the creation of an alternative translation start site. Alternatively or in addition to the above, consideration of codon bias, rare codons, tRNA availability in the host cell or similar limitations of the cell-free transcription/translation system may further guide selection of a polynucleotide sequence from Tables A-D. Codon optimization programs are available as freeware or from commercial sources.

In still further embodiments, the present disclosure provides a method to increase or decrease the level of expression of a protein. The method comprises (a) identifying a score from Table A, B, or C for a polynucleotide sequence consisting of codons 3, 4 and 5 of a nucleic acid sequence encoding a protein of interest; (b) selecting an amino acid sequence from Table E, F, or G that has a higher or lower score, respectively; (c) modifying the nucleic acid sequence encoding the protein of interest in step (a) to encode the amino acid sequence selected in step (b); and (d) expressing the modified nucleic acid sequence in a cell or in a cell-free transcription/translation system. Modifying the nucleic acid sequence in step (c) can occur by (i) inserting a polynucleotide sequence selected from 5'-$n^1n^2n^3$-3', 5'-$n^1n^2n^3n^4n^5n^6$-3', and 5'-$n^1n^2n^3n^4n^5n^6n^7n^8n^9$, 3', into the nucleic acid sequence from step (a) between the second and third codon, third and fourth codon, or fourth and fifth codon (as described above), wherein $n^1$, $n^2$, $n^3n^4$, $n^5$, $n^6$, $n^7$, $n^8$, and $n^9$ are each independently selected from the group consisting of adenine, thymine, uracil, guanine, and cytosine; or (ii) changing one or more nucleotides of the nucleic acid sequence from step (a) at codon three, codon four, codon five, or any combination thereof. In various embodiments, the amino acid sequence selected from Table E, F, or G will not include a methionine and/or will have a range for its score that is about 15% or less of the score. In certain embodiments, the amino acid sequence selected from Table E, F, or G will have a range for its score that is about 5% to about 15% of the score. In other embodiments, the amino acid sequence selected from Table E, F, or G will have a range for its score that is less than about 12.5% of the score. In other embodiments, the amino acid sequence selected from Table E, F, or G will have a range for its score that is about 10% or less of the score. In other embodiments, the amino acid sequence selected from Table E, F, or G will have a range for its score that is about 7.5% or less of the score. In other embodiments, the amino acid sequence selected from Table E, F, or G will have a range for its score that is about 5% or less of the score.

II. Nucleic Acid Molecules

In another aspect, the present disclosure provides isolated, non-natural nucleic acid molecules comprising a polynucleotide sequence selected from Table A, Table B, or Table C, at codons 3, 4, and 5. The isolated nucleic acid molecule may further comprise one or more regulatory element(s) that are operatively-linked to the polynucleotide sequence. The one or more regulatory elements may be selected, at least in part, on the basis of the host cells to be used for expression. Suitable regulatory elements are described in further detail in Section IV. In various embodiments, the polynucleotide sequence selected from Table A, Table B, or Table C is not 5'-AAAAAAAAA-3'.

In another aspect, the present disclosure provides an isolated, non-natural nucleic acid molecule comprising a polynucleotide sequence selected from Table D at codons 3, 4, and 5. The isolated nucleic acid molecule may further comprise one or more regulatory element that is operatively-linked to the polynucleotide sequence. The one or more regulatory elements may be selected, at least in part, on the basis of the host cells to be used for expression. Suitable regulatory elements are described in further detail in Section IV. In various embodiments, the polynucleotide sequence selected from Table A, Table B, or Table C is not 5'-AAAAAAAAA-3' and/or does not encode a methionine.

In another aspect, the present disclosure provides an isolated nucleic acid molecule comprising $R^5$-$R^6$-$R^7$, wherein $R^5$, $R^6$, and $R^7$ are joined by phosphodiester bonds. $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid; optionally the polynucleotide sequence does not encode a methionine. $R^6$ is a polynucleotide sequence selected from Table A, Table B, or Table C. $R^7$ is a second fragment of a polynucleotide sequence of interest, wherein the second fragment lacks the first and second codons of the sequence of interest. The isolated nucleic acid molecule may further comprise one or more regulatory element that is operatively-linked to $R^5$-$R^6$-$R^7$. The one or more regulatory element(s) may be selected, at least in part, on the basis of the host cells to be used for expression. Suitable regulatory elements are described in further detail in Section IV. In various embodiments, the polynucleotide sequence selected from Table A, Table B, or Table C is not 5'-AAAAAAAAA3'.

In another aspect, the present disclosure provides an isolated nucleic acid molecule comprising $R^5$-$R^6$-$R^7$, wherein $R^5$, $R^6$, and $R^7$ are joined by phosphodiester bonds. $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid. $R^6$ is a polynucleotide sequence selected from Table D. $R^7$ is a second fragment of a polynucleotide sequence of interest, wherein the second fragment lacks the first and second codons of the sequence of interest. The isolated nucleic acid molecule may further comprise one or more regulatory element that is operatively-linked to $R^5$-$R^6$-$R^7$. The one or more regulatory element may be selected, at least in part, on the basis of the host cells to be used for expression. Suitable regulatory elements are described in further detail in Section IV.

In another aspect, the present disclosure provides an isolated nucleic acid molecule comprising $R^5$-$R^6$-$R^7$, wherein $R^5$, $R^6$, and $R^7$ are joined by phosphodiester bonds. $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid. $R^6$ is a polynucleotide sequence selected from Table A, Table B, or Table C with the proviso that $R^6$ is not a polynucleotide sequence consisting of codons 3, 4, and 5 of the polynucleotide sequence of interest, and optionally codons 3, 4, and 5 do not encode a methionine. $R^7$ is a second fragment of the polynucleotide sequence of interest, the second fragment lacking the first and second codons of the sequence of interest. The isolated nucleic acid molecule may further comprise one or more regulatory element that is operatively-linked to $R^5$-$R^6$-$R^7$. The one or more regulatory elements may be selected, at least in part, on the basis of the host cells to be used for expression. Suitable regulatory elements are described in further detail in Section IV. In various embodiments, the polynucleotide sequence selected from Table A, Table B, or Table C is not 5'-AAAAAAAAA-3'.

In another aspect, the present disclosure provides an isolated nucleic acid molecule comprising $R^5$-$R^6$-$R^7$, wherein $R^5$, $R^6$, and $R^7$ are joined by phosphodiester bonds. $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid. $R^6$ is a polynucleotide sequence selected from Table D, with the proviso that $R^6$ is not a polynucleotide sequence consisting of codons 3, 4, and 5 of the polynucleotide sequence of interest. $R^7$ is a second fragment of the polynucleotide sequence of interest, the second fragment lacking the first and second codons of the sequence of interest. The isolated nucleic acid molecule may further comprise one or more regulatory element that is operatively-linked to $R^5$-$R^6$-$R^7$. The one or more regulatory elements may be selected, at least in part, on the basis of the host cells to be used for expression. Suitable regulatory elements are described in further detail in Section IV.

Isolated polynucleotides of the present disclosure may be produced by any method known in the art.

III. Isolated Oligonucleotide Probes and Array

In another aspect, the present disclosure provides an isolated oligonucleotide probe comprising a polynucleotide sequence selected from Table A, Table B, or Table C, wherein the oligonucleotide probe is detectably labeled with a fluorescent, chemiluminescent, radioactive, colorimetric, and/or resonance label. In various embodiments, the polynucleotide sequence selected from Table A, Table B, or Table C is not 5'-AAAAAAAA3'.

In another aspect, the present disclosure provides an isolated oligonucleotide probe comprising a polynucleotide sequence selected from Table D, wherein the oligonucleotide probe is detectably labeled with a fluorescent, chemiluminescent, radioactive, colorimetric, and/or resonance label. In various embodiments, the polynucleotide sequence selected from Table A, Table B, or Table C is not 5'-AAAAAAAA-3'.

In another aspect, the present disclosure provides an array comprising a substrate, wherein the substrate comprises an oligonucleotide probe as described above or an epitope binding agent. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of specifically binding to a polynucleotide sequence of Table A, B, or C. Nucleic acids may include RNA, DNA, and naturally occurring or synthetically created derivatives. In various embodiments, the polynucleotide sequence selected from Table A, Table B, or Table C is not 5'-AAAAAAAA-3'.

Several substrates suitable for the construction of arrays are known in the art, and one skilled in the art will appreciate that other substrates may become available as the art progresses. The substrate may be a material that may be modified to contain discrete individual sites appropriate for the attachment or association of an epitope binding agent and is amenable to at least one detection method. Non-limiting examples of substrate materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. In an exemplary embodiment, the substrate may allow optical detection without appreciably fluorescing.

A substrate may be planar, a substrate may be a well, e.g., a well of a plate, or alternatively, a substrate may be a bead. Additionally, the substrate may be the inner surface of a tube for flow-through sample analysis to minimize sample volume. Similarly, the substrate may be flexible, such as a flexible foam, including closed cell foams made of particular plastics.

An oligonucleotide probe or an epitope binding agent may be attached to the substrate in a wide variety of ways, as will be appreciated by those in the art. An oligonucleotide probe or epitope binding agent may either be synthesized first, with subsequent attachment to the substrate, or may be directly synthesized on the substrate. The substrate and/or the oligonucleotide probe or epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, an oligonucleotide probe or epitope binding agent may be attached using functional groups on the nucleic acid or epitope binding agent either directly or indirectly using linkers.

An oligonucleotide probe or epitope binding agent may also be attached to the substrate non-covalently. For example, a biotinylated oligonucleotide probe or epitope binding agent may be prepared, which may bind to surfaces covalently coated with streptavidin, resulting in attachment. Alternatively, an oligonucleotide probe or epitope binding agent may be synthesized on the surface using techniques such as photopolymerization and photolithography. Additional methods of attaching epitope binding agents to arrays and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

An oligonucleotide probe or epitope binding agent may be attached to the substrate at a spatially defined address of the array. Arrays may comprise from about 1 to about several hundred thousand addresses. In one embodiment, the array may be comprised of less than 10,000 addresses. In another alternative embodiment, the array may be comprised of at least 10,000 addresses. In yet another alternative embodiment, the array may be comprised of less than 5,000 addresses. In still another alternative embodiment, the array may be comprised of at least 5,000 addresses. In a further embodiment, the array may be comprised of less than 500 addresses. In yet a further embodiment, the array may be comprised of at least 500 addresses.

An oligonucleotide probe or epitope binding agent may be represented more than once on a given array. In other words, more than one address of an array may be comprised of the same oligonucleotide probe or epitope binding agent. In some embodiments, two, three, or more than three addresses of the array may be comprised of the same oligonucleotide probe or epitope binding agent. In certain embodiments, the array may comprise control oligonucleotide probes or epitope binding agents and/or control addresses. The controls may be internal controls, positive controls, negative controls, or background controls.

Arrays of the present disclosure may be utilized in several suitable applications. For example, an array may be used in a method for detecting association between an epitope binding agent and a target. As used herein, "target" refers to a nucleic acid comprising a polynucleotide sequence selected from Table A, Table B or Table C. This method typically comprises incubating a sample comprising a target with the array under conditions such that the target may associate with the epitope binding agent attached to the array. The association may then be detected, using means commonly known in the art, such as fluorescence. "Association," as used in this context, may refer to hybridization, covalent binding, or ionic binding. A skilled artisan will appreciate that conditions under which association may occur will vary depending on the epitope binding agent, the substrate, the sample, and the detection method utilized. As such, suitable conditions may have to be optimized for each individual array created.

In yet another embodiment, the array may be used as a tool in a method for determining whether a subject has a genomic mutation in a gene that results in increased or decreased expression of the protein encoded by the gene. Typically, such a method comprises incubating the array with a biological sample from the subject. If the biological sample comprises a polynucleotide sequence selected from Table A, Table B or Table C, then an association between the array and the sample may be detected, and the subject may have a genomic mutation in a gene that results in increased or decreased expression of the protein encoded by the gene.

IV. Vectors

In another aspect, the present disclosure provides vectors for the tunable expression of polypeptides of interest in cells. The presently disclosed vectors comprise a nucleic acid molecule of Section II. Vectors of the present disclosure may further comprise one more regulatory element and/or one or more cloning site.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. Suitable vectors include plasmid vectors, viral vectors, and self-replicating RNA (Yoshioka et al., Cell Stem Cell, 2013, 13:246-254). In some embodiments, the encoding nucleic acid can be present in a plasmid vector. Non-limiting examples of suitable plasmid vectors include pUC, pBR322, pET, pBluescript, and variants thereof. In other embodiments, the encoding nucleic acid can be part of a viral vector (e.g., lentiviral vectors, adeno-associated viral vectors, adenoviral vectors, and so forth). The plasmid or viral vector can comprise additional expression control sequences (e.g., enhancer sequences, Kozak sequences, polyadenylation sequences, transcriptional termination sequences, etc.), selectable marker sequences (e.g., antibiotic resistance genes), origins of replication (e.g., bacterial, yeast, mammalian, etc.), and the like. Additional information about vectors and use thereof can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, NY, 3$^{rd}$ edition, 2001.

Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the presently disclosed subject matter in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed.

In some embodiments, a vector comprises a nucleic acid molecule comprising a polynucleotide sequence selected from Table A, Table B, or Table C, at codons 3, 4, and 5 operatively linked to a regulatory element. For example, a vector may comprise a nucleic acid molecule comprising a promoter operatively linked to a polynucleotide sequence comprising (i) a translational start codon, (iii) a second codon encoding any natural or non-natural amino acid, and (iii) and a polynucleotide sequence selected from Table A, Table B, or Table C encoding codons 3, 4, and 5. In another example, a vector may comprise a nucleic acid molecule comprising a promoter operatively linked to a polynucleotide sequence consisting of a (i) a translational start codon, (iii) a second codon encoding any natural or non-natural amino acid, and (iii) and a polynucleotide sequence selected from Table A, Table B, or Table C encoding codons 3, 4, and 5. In various embodiments, the vector may further comprise a multiple cloning site proximal to, and in-frame with, the polynucleotide sequence operatively linked to the regulatory element. Alternatively, or in addition, the vector may further comprise one or more additional regulatory elements, one or more cleavage sites, one or more linkers and/or one more sequences encoding a peptide tag. Suitable peptide tags are described in further detail in Section V. The sequence encoding the peptide tag can be associated with the N-terminus, the C-terminus, and/or an internal location of the nucleic acid operatively linked to the regulatory element and may be proximal to a cleavage site. In various embodiments, the polynucleotide sequence selected from Table A, Table B, or Table C is not 5'-AAAAAAAAA-3'.

In other embodiments, a vector comprises a nucleic acid molecule comprising a polynucleotide operatively linked to a regulatory element, the polynucleotide sequence selected from Table D, at codons 3, 4, and 5 or the polynucleotide sequence encoding a peptide selected from Table I. For example, a vector may comprise a nucleic acid molecule comprising a promoter operatively linked to a polynucleotide sequence comprising (i) a translational start codon, (iii) a second codon encoding any natural or non-natural amino acid, and (iii) and a polynucleotide sequence selected from Table D encoding codons 3, 4, and 5. In another example, a vector may comprise a nucleic acid molecule comprising a promoter operatively linked to a polynucleotide sequence consisting of a (i) a translational start codon, (iii) a second codon encoding any natural or non-natural amino acid, and (iii) and a polynucleotide sequence selected from Table D encoding codons 3, 4, and 5 or a polynucleotide sequence encoding a peptide selected from Table I. In various embodiments, the vector may further comprise a multiple cloning site proximal to, and in-frame with, the polynucleotide sequence operatively linked to the regulatory element. Alternatively, or in addition, the vector may further comprise one or more additional regulatory elements, one or more linkers and/or one more sequences encoding a peptide tag. Suitable peptide tags are described in further detail in Section V. The sequence encoding the peptide tag can be associated with the N-terminus, the C-terminus, and/or an internal location of the nucleic acid operatively linked to the regulatory element and may be proximal to a cleavage site.

In other embodiments, a vector comprises a nucleic acid molecule comprising $R^5$-$R^6$-$R^7$, wherein $R^5$, $R^6$, and $R^7$ are joined by phosphodiester bonds, and (a) $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid; (b) $R^6$ is a polynucleotide sequence selected from Table A, Table B, or Table C; and (c) $R^7$ is a second fragment of a polynucleotide sequence of interest, wherein the second fragment lacks the first and second codons of the sequence of interest. In various embodiments, the vector may further comprise a multiple cloning site proximal to, and in-frame with, the polynucleotide sequence operatively linked to the regulatory element. Alternatively, or in addition, the vector may further comprise one or more additional regulatory elements and/or one more sequence encoding a peptide tag. Suitable peptide tags are described in further detail in Section V. The sequence encoding the peptide tag can be associated with the N-terminus, the C-terminus, and/or an internal location of the nucleic acid operatively linked to the regulatory element. In various embodiments, the polynucleotide sequence selected from Table A, Table B, or Table C is not 5'-AAAAAAAAA-3'.

In other embodiments, a vector comprises a nucleic acid molecule comprising $R^5$-$R^6$-$R^7$, wherein $R^5$, $R^6$, and $R^7$ are joined by phosphodiester bonds; and (a) $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid; (b) $R^6$ is a polynucleotide sequence selected from Table D or a polynucleotide sequence encoding a peptide selected from Table I; and (c) $R^7$ is a second fragment of a polynucleotide sequence of interest, wherein the second fragment lacks the first and second codons of the sequence of interest. In various embodiments, the vector may further comprise a multiple cloning site proximal to, and in-frame with, the polynucleotide sequence operatively linked to the regulatory element. Alternatively, or in addition, the vector may further comprise one or more additional regulatory elements and/or one more sequences encoding a peptide tag. Suitable peptide tags are described in further detail in Section V. The sequence encoding the peptide tag can be associated with the N-terminus, the C-terminus, and/or an internal location of the nucleic acid operatively linked to the regulatory element.

In other embodiments, a vector comprises nucleic acid molecule comprising $R^5$-$R^6$-$R^7$, wherein $R^5$, $R^6$, and $R^7$ are joined by phosphodiester bonds; and (a) $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid; (b) $R^6$ is a polynucleotide sequence selected from Table A, Table B, or Table C with the proviso that $R^6$ is not a polynucleotide sequence consisting of codons 3, 4, and 5 of the polynucleotide sequence of interest; and (c) $R^7$ is a second fragment of the polynucleotide sequence of interest, the second fragment lacking the first and second codons of the sequence of interest. In various embodiments, the vector may further comprise a multiple cloning site proximal to, and in-frame with, the polynucleotide sequence operatively linked to the regulatory element. Alternatively, or in addition, the vector may further comprise one or more additional regulatory elements and/or one more sequence encoding a peptide tag. Suitable peptide tags are described in further detail in Section V. The sequence encoding the peptide tag can be associated with the N-terminus, the C-terminus, and/or an internal location of the nucleic acid operatively linked to the regulatory element. In various embodiments, the polynucleotide sequence selected from Table A, Table B, or Table C is not 5'-AAAAAAAAA-3'.

In other embodiments, a vector comprises nucleic acid molecule comprising $R^5$-$R^6$-$R^7$, wherein $R^5$, $R^6$, and $R^7$ are joined by phosphodiester bonds; and (a) $R^5$ is (i) a first fragment of a polynucleotide sequence of interest, wherein the first fragment consists of the first and second codons of the sequence of interest, or (ii) a polynucleotide sequence consisting of a start codon and second codon encoding any natural or non-natural amino acid; (b) $R^6$ is a polynucleotide sequence selected from Table D or a polynucleotide sequence encoding a peptide selected from Table I, with the proviso that $R^6$ is not a polynucleotide sequence consisting of codons 3, 4, and 5 of the polynucleotide sequence of interest; and (c) $R^7$ is a second fragment of the polynucleotide sequence of interest, the second fragment lacking the first and second codons of the sequence of interest. In various embodiments, the vector may further comprise a multiple cloning site proximal to, and in-frame with, the polynucleotide sequence operatively linked to the regulatory element. Alternatively, or in addition, the vector may further comprise one or more additional regulatory elements and/or one more sequence encoding a peptide tag. Suitable peptide tags are described in further detail in Section V. The sequence encoding the peptide tag can be associated with the N-terminus, the C-terminus, and/or an internal location of the nucleic acid operatively linked to the regulatory element.

In other embodiments, a vector comprises a nucleic acid construct $R^1$-$R^2$-$R^3$-$R^4$, wherein $R^1$, $R^2$, $R^3$ and $R^4$ are joined by phosphodiester bonds; and (a) $R^1$ is any start codon; (b) $R^2$ is a polynucleotide sequence 5'-$n^1 n^2 n^3$-3', wherein $n^1$, $n^2$, and $n^3$ are each independently selected from the group consisting of adenine, thymine, uracil, guanine, and cytosine; (c) $R^3$ is a polynucleotide sequence selected from Table A, Table B, Table C, or Table D, or a polynucleotide sequence encoding a peptide selected from Table E, Table F, Table G, or Table I; and (e) $R^4$ is a multiple cloning site. In various embodiments, the vector may further one or more additional regulatory elements and/or one more polynucleotide sequence encoding a peptide tag. Suitable peptide tags are described in further detail in Section V. The sequence encoding the peptide tag can be associated with the N-terminus, the C-terminus, and/or an internal location of the nucleic acid operatively linked to the regulatory element.

In other embodiments, a vector comprises a nucleic acid construct $R^1$-$R^{1A}$-$R^2$-$R^3$-$R^4$-$R^{4A}$, wherein $R^1$, $R^{1A}$, $R^2$, $R^3$, $R^4$ and $R^{4A}$ are joined by phosphodiester bonds; and (a) $R^1$ is any start codon; (b) $R^{1A}$ is an optional polynucleotide sequence encoding a peptide tag and a cleavage sequence, (c) $R^2$ is a polynucleotide sequence 5'-$n^1 n^2 n^3$-3', wherein $n^1$, $n^2$, and $n^3$ are each independently selected from the group consisting of adenine, thymine, uracil, guanine, and cytosine; (d) $R^3$ is a polynucleotide sequence selected from Table A, Table B, Table C, or Table D, or a polynucleotide sequence encoding a peptide selected from Table E, Table F, Table G, or Table I; (e) $R^4$ is a multiple cloning site, and (f) $R^{4A}$ is an optional polynucleotide sequence encoding a cleavage sequence and a peptide tag. In various embodiments, the vector may further one or more additional regulatory elements and/or one more polynucleotide sequence encoding a peptide tag. Suitable peptide tags are described in further detail in Section V. The sequence encoding the peptide tag can be associated with the N-terminus, the C-terminus, and/or an internal location of the nucleic acid operatively linked to the regulatory element.

The term "regulatory element" is intended to include promoters, enhancers, internal ribosomal entry sites (IRES), and other expression control elements (e.g., transcription termination signals, such as polyadenylation signals and poly-U sequences, etc.). Such regulatory elements are described, for example, in Goeddel (1990) Gene Expression Technology: Methods in Enzymology 185, Academic Press, San Diego, Calif. Regulatory elements include those that direct constitutive expression of a nucleotide sequence in many types of host cell and those that direct expression of the nucleotide sequence only in certain host cells (e.g., tissue-specific regulatory sequences). Regulatory elements also include those that direct inducible expression in response to a specific stimulus (e.g., an inducible promoter).

A cell-specific promoter may direct expression primarily in a desired cell of interest, such as muscle cell, a neuron, a skin cell, a blood cell, an immune cell, a liver cell, a pancreatic cell, a spleen cell, etc. In some embodiments, the promoter is a tissue-specific promoter that is active in specific tissues. In some embodiments, the promoter is a tumor-specific promoter that is active specifically in tumor cells. Regulatory elements may also direct expression in a temporal-dependent manner, such as in a cell-cycle dependent or developmental stage-dependent manner, which may or may not also be tissue or cell-type specific.

In some embodiments, a vector comprises one or more pol III promoters, one or more pol II promoters, one or more pol I promoters, or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (e.g., Boshart et al. (1985) Cell 41:521-530), the SV40 promoter, the dihydrofolate reductase promoter, the β-actin promoter, the phosphoglycerol kinase (PGK) promoter, and the EF1α promoter.

Also encompassed by the term "regulatory element" are enhancer elements, such as WPRE; CMV enhancers; the R-U5' segment in LTR of HTLV-I (Takebe et al. (1988) Mol. Cell. Biol. 8:466-472); SV40 enhancer; and the intron sequence between exons 2 and 3 of rabbit β-globin (O'Hare et al. (1981) Proc. Natl. Acad. Sci. USA. 78(3):1527-31). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). Advantageous vectors include lentiviruses and adeno-associated viruses, and types of such vectors can also be selected for targeting particular types of cells.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins.

Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson (1988) Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A. respectively, to the target recombinant protein.

Examples of suitable inducible non-fusion *E. coli* expression vectors include pTrc (Amrann et al. (1988) Gene 69:301-315) and pET 11d (Studier et al. (1990) Gene Expression Technology: Methods in Enzymology 185, Academic Press, San Diego, Calif.).

In some embodiments, a vector is an archaeal expression vector. Suitable archaeal expression vectors are known in the art. See, for example, Atomi et al., *Front. Microbiol,* 2012, 3:337.

In some embodiments, a vector is a yeast expression vector. Examples of vectors for expression in yeast Saccharomyces cerevisiae include pYepSec1 (Baldari, et al. (1987) EMBO J. 6: 229-234), pMFa (Kuijan and Herskowitz (1982) Cell 30: 933-943), pJRY88 (Schultz et al. (1987) Gene 54: 113-123), pYES2 (Invitrogen Corporation, San Diego, Calif.), and picZ (InVitrogen Corp, San Diego, Calif.).

In some embodiments, a vector is an insect expression vector. A non-limiting example of an insect expression vector is an insect baculovirus expression vector.

In some embodiments, a vector is capable of driving expression of one or more sequences in mammalian cells using a mammalian expression vector. Examples of mammalian expression vectors include pCDM8 (Seed (1987) Nature 329: 840) and pMT2PC (Kaufman et al. (1987) EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook et al. (1989) Molecular Cloning: A Laboratory Manual. 2nd ed., Cold Spring Harbor Laboratory, Cold Spring Harbor Laboratory Press, Cold Spring Harbor, N.Y.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1: 268-277), lymphoid-specific promoters (Calame and Eaton (1988) Adv. Immunol. 43: 235-275), in particular promoters of T cell receptors (Winoto and Baltimore (1989) EMBO J.8: 729-733) and immunoglobulins (Baneiji et al. (1983) Cell 33: 729-740; Queen and Baltimore (1983) Cell 33: 741-748), neuron-specific promoters (e.g., the neurofilament promoter; Byrne and Ruddle (1989) Proc. Natl. Acad. Sci. USA 86: 5473-5477), pancreas-specific promoters (Edlund et al. (1985) Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) Science 249: 374-379) and the α-fetoprotein promoter (Campes and Tilghman (1989) Genes Dev. 3: 537-546).

V. Recombinant Polypeptides

In another aspect, the present disclosure provides an isolated polypeptide comprising formula $R^8$-$R^9$-$R^{10}$, wherein $R^8$, $R^9$, and $R^{10}$ are joined by peptide bonds. $R^8$ is a first fragment of an amino acid sequence of interest, wherein the first fragment consists of the first and second amino acids of the sequence of interest. $R^9$ is a polypeptide selected from Tables E, F, or G. $R^{10}$ is a second fragment of an amino acid sequence of interest, wherein the second fragment lacks the first and second amino acids of the sequence of interest. For the avoidance of doubt, "an amino acid sequence of interest" is the amino acid sequence of a protein of interest. In various embodiments, the amino acid sequence selected from Table E, F, or G will not include a methionine and/or will have a range for its score that is about that is about 15% or less of the score. In certain embodiments, the amino acid sequence selected from Table E, F, or G will have a range for its score that is about 5% to about 15% of the score. In other embodiments, the amino acid sequence selected from Table E, F, or G will have a range for its score that is less than about 12.5% of the score. In other embodiments, the amino acid sequence selected from Table E, F, or G will have a range for its score that is about 10% or less of the score. In other embodiments, the amino acid sequence selected from Table E, F, or G will have a range for its score that is about 7.5% or less of the score. In other embodiments, the amino acid sequence selected from Table E, F, or G will have a range for its score that is about 5% or less of the score.

In another aspect, the present disclosure provides an isolated polypeptide comprising formula $R^8$-$R^9$-$R^{10}$ wherein $R^8$, $R^9$, and $R^{10}$ are joined by peptide bonds. $R^8$ is a first fragment of an amino acid sequence of interest, the first fragment consisting of the first and second amino acids of the sequence of interest. $R^9$ is a polypeptide selected from Tables E, F, or G with the proviso that $R^6$ is not the same as amino acids 3, 4, and 5 of the amino acid sequence of interest. $R^{10}$ is a second fragment of an amino acid sequence of interest, the second fragment lacking the first, second, third, fourth and fifth amino acids of the sequence of interest. In various embodiments, the amino acid sequence selected from Table E, F, or G will not include a methionine and/or will have a range for its score that is about that is about 15% or less of the score. In certain embodiments, the amino acid sequence selected from Table E, F, or G will have a range for its score that is about 5% to about 15% of the score. In other embodiments, the amino acid sequence selected from Table E, F, or G will have a range for its score that is less than about 12.5% of the score. In other embodiments, the amino acid sequence selected from Table E, F, or G will have a range for its score that is about 10% or less of the score. In other embodiments, the amino acid sequence selected from Table E, F, or G will have a range for its score that is about 7.5% or less of the score. In other embodiments, the amino acid sequence selected from Table E, F, or G will have a range for its score that is about 5% or less of the score.

Isolated polypeptide described above may further comprise one or more peptide tag associated with the N-terminus, the C-terminus, and/or an internal location of the polypeptide. A peptide tag can be an affinity tag, a purification tag, a solubility tag, a stability tag, or a detection tag. A peptide tag may have more than one utility—e.g. a peptide tag may be both an affinity tag and a purification tag. Suitable affinity tags, purification tags, solubility tags, stability tags, or detection tags are well known in the art and commercially available. A non-limiting list of suitable peptide tags is provided in Table H. The functions attributed to each tag in the table are not limiting.

Isolated polypeptides of the present disclosure may be produced by any method known in the art.

VI. Applications

The compositions and methods disclosed herein can be used in a variety of therapeutic, diagnostic, industrial, and research applications. In some embodiments, the present disclosure can be used to modulate transcription of any chromosomal sequence or modify/edit any chromosomal sequence of interest in a cell, animal, or plant in order to model and/or study the function of genes and/or proteins encoded thereby, study genetic or epigenetic conditions of interest, or study biochemical pathways involved in various diseases or disorders. For example, transgenic organisms can be created that model diseases or disorders, wherein the expression of one or more nucleic acid sequences associated with a disease or disorder is altered. The disease model can be used to study the effects of mutations on the organism, study the development and/or progression of the disease, study the effect of a pharmaceutically active compound on the disease, and/or assess the efficacy of a potential gene therapy strategy.

In further embodiments, the compositions and methods disclosed herein can be used for diagnostic tests to establish the presence of a disease or disorder and/or for use in determining treatment options.

In additional embodiments, the compositions and methods disclosed herein can be used to correct genetic mutations associated with a particular disease or disorder that can be remedied by an increase or decrease in expression of a particular protein. Such modifications may be made in cells ex vivo or in vivo.

In still other embodiments, the compositions and methods disclosed herein can be used to generate crop plants with improved traits or increased resistance to environmental stresses. The present disclosure can also be used to generate farm animal with improved traits or production animals. For example, pigs have many features that make them attractive as biomedical models, especially in regenerative medicine or xenotransplantation.

Table D

| High-expressing EGFP variants | | | | Med-expressing EGFP variants | | | | Low-expressing EGFP variants | | | |
|---|---|---|---|---|---|---|---|---|---|---|---|
| NT SEQ | AA SEQ | GS | RFU | NT SEQ | AA SEQ | GS | RFU | NT SEQ | AA SEQ | GS | RFU |
| AACATCTAC | NIY | 5.00 | 12000 | TGCCGGGGA | CRG | 3.02 | 0.17 | GCCCGGGGG | ARG | 1.38 | 424.47 |
| AAGTACCCA | KYP | 5.00 | 12000 | GAGGTCAGG | EVR | 3.02 | 0.27 | GAGGTGGAC | EVD | 1.37 | 325.44 |

Table D-continued

| High-expressing EGFP variants | | | | Med-expressing EGFP variants | | | | Low-expressing EGFP variants | | | |
|---|---|---|---|---|---|---|---|---|---|---|---|
| NT SEQ | AA SEQ | GS | RFU | NT SEQ | AA SEQ | GS | RFU | NT SEQ | AA SEQ | GS | RFU |
| CCATTACAT | PLH | 5.00 | 12000 | AGGAGGATA | RRI | 3.02 | 0.06 | GTGGTGGAC | VVD | 1.37 | 377.21 |
| TACTATGCA | YYA | 5.00 | 11977 | CTAGGCGGG | LGG | 3.02 | 0.38 | GGGGGCTCC | GGS | 1.37 | 368.07 |
| CGAGAAATC | REI | 4.99 | 11941 | AAAGGGAGG | KGR | 3.02 | 0.22 | GGGTGGTCC | GWS | 1.35 | 375.07 |
| AAATATCGC | KYR | 4.98 | 11883 | GCGGTTGAG | AVE | 3.02 | 0.20 | GTGGGTGCC | VGA | 1.34 | 271.28 |
| AAGTATCAC | KYH | 4.97 | 11888 | AGAGGGTGG | RGW | 3.02 | 0.22 | GGGGGCCCG | GGP | 1.34 | 399.94 |
| AAAATCTTC | KIF | 4.97 | 11803 | GTGGGGGAG | VGE | 3.02 | 0.22 | GCGGTGGGC | AVG | 1.33 | 342.30 |
| AAATACTGT | KYC | 4.95 | 11775 | GAGCGGGGA | ERG | 3.02 | 0.17 | CGGGTGAAC | RVN | 1.30 | 348.90 |
| AAATTCTAT | KFY | 4.94 | 11763 | ATTGAGATT | IEI | 2.90 | 0.25 | TTGGTGAGC | LVS | 1.29 | 140.00 |
| AAAAATGTC | KNV | 4.93 | 11701 | GGGGGCGAT | GGD | 2.90 | 0.44 | CGTGTGAAC | RVN | 1.29 | 346.32 |
| AACTGTACT | NCT | 4.93 | 11717 | GGGGGCAGT | GGS | 2.87 | 0.26 | CTTGCCGGC | LAG | 1.28 | 320.72 |
| GATACTATT | DTI | 4.92 | 11682 | AGCAAGGGG | SKG | 2.87 | 0.27 | CCGGTGGGC | PVG | 1.27 | 299.13 |
| AAACAAGTT | KQV | 4.92 | 11650 | TCGGTGGGT | SVG | 2.68 | 0.32 | CTCGCGGGG | LAG | 1.26 | 197.29 |
| AAATTCAGT | KFS | 4.90 | 11608 | GGAGTAGCA | GVA | 2.68 | 0.65 | CTATGGGTA | LWV | 1.25 | 302.20 |
| ACGAATGAC | TND | 4.90 | 11571 | GTGGCGCAT | VAH | 2.49 | 0.13 | CCGGTGTTC | PVF | 1.21 | 274.42 |
| AAAAAATAT | KKY | 4.89 | 11548 | AGTGTCGGT | SVG | 2.49 | 0.36 | GCGGTGGAC | AVD | 1.19 | 212.86 |
| AATATAACT | NIT | 4.88 | 11464 | | | | | CCGGTGAGC | PVS | 1.13 | 154.46 |
| AAAATACAC | KIH | 4.84 | 11360 | | | | | CCCTCGGGG | PSG | 1.12 | 67.30 |
| | | | | | | | | CTCGCCGGG | LAG | 1.07 | 67.40 |
| | | | | | | | | GAGTCCCCG | ESP | 1.05 | 73.01 |

NT SEQ = nucleotide sequence;
AA SEQ = amino acid sequence;
GS = GFP score;
RFU = relative fluorescence units as measured by FACS.

TABLE E

| High expressing EGFP variants | | | |
|---|---|---|---|
| AA SEQ | GFP Score Mean | Range | Total counts |
| KYY | 4.8409 | 0.2582 | 5199 |
| KHY | 4.7892 | 0.4214 | 1803 |
| KYH | 4.7581 | 0.4416 | 2796 |
| KFY | 4.7470 | 0.6225 | 2985 |
| NQY | 4.7296 | 0.2172 | 1184 |
| NHN | 4.7278 | 0.8188 | 1209 |
| KKY | 4.7243 | 0.6466 | 4512 |
| KYC | 4.7242 | 0.6580 | 4493 |
| KMH | 4.7184 | 0.1502 | 1978 |
| KNY | 4.7162 | 0.5075 | 2804 |
| NHY | 4.7092 | 0.6579 | 2017 |
| NYK | 4.7091 | 0.5381 | 2345 |
| KKH | 4.7058 | 0.6036 | 2890 |
| HQH | 4.6752 | 0.3455 | 718 |
| HMH | 4.6598 | 0.3356 | 1067 |
| KIY | 4.6441 | 0.7636 | 5127 |
| KYQ | 4.6337 | 0.7941 | 4287 |
| NMH | 4.6328 | 0.9114 | 779 |
| KNF | 4.6098 | 0.5399 | 3581 |
| NIY | 4.6092 | 0.7081 | 3220 |
| KHI | 4.6016 | 0.7590 | 2393 |
| KFC | 4.5983 | 0.5728 | 4381 |
| NYY | 4.5894 | 0.9155 | 1073 |
| NTY | 4.5882 | 1.2719 | 2515 |
| KII | 4.5862 | 0.8976 | 7265 |
| KMY | 4.5849 | 0.7873 | 3752 |
| NNI | 4.5821 | 0.5673 | 2492 |
| KHM | 4.5792 | 0.4230 | 742 |
| NMY | 4.5757 | 1.1226 | 2581 |
| KNK | 4.5746 | 0.5020 | 2967 |
| HIH | 4.5575 | 0.9543 | 1213 |
| NYN | 4.5532 | 0.7926 | 1072 |
| NIK | 4.5524 | 0.7273 | 4631 |
| KYF | 4.5518 | 1.1095 | 3779 |
| MHK | 4.5493 | 0.3708 | 901 |
| NFK | 4.5421 | 0.8384 | 3378 |
| MKY | 4.5402 | 0.7669 | 2020 |
| KHC | 4.5379 | 0.8003 | 2258 |
| NKY | 4.5358 | 0.5384 | 1831 |
| DYY | 4.5350 | 1.2355 | 3044 |
| HKY | 4.5346 | 1.3171 | 1139 |
| DIY | 4.5345 | 0.9972 | 4493 |

TABLE E-continued

High expressing EGFP variants

| AA SEQ | GFP Score Mean | GFP Score Range | Total counts |
|---|---|---|---|
| HNM | 4.5303 | 0.5105 | 756 |
| NII | 4.5279 | 0.8361 | 4370 |
| KYN | 4.5238 | 0.4072 | 3881 |
| NFY | 4.5225 | 0.8110 | 1349 |
| KHF | 4.5166 | 1.2326 | 1801 |
| NYC | 4.5136 | 0.4706 | 2374 |
| KYE | 4.5112 | 0.7264 | 3526 |
| KFF | 4.5105 | 0.9082 | 1591 |
| KNC | 4.5020 | 1.2620 | 3550 |
| KNH | 4.4996 | 1.3290 | 1401 |
| HTY | 4.4963 | 0.9779 | 2932 |
| KTY | 4.4923 | 1.6429 | 2821 |
| NHM | 4.4916 | 0.8114 | 550 |
| NPI | 4.4865 | 2.3813 | 1746 |
| NKQ | 4.4834 | 1.2928 | 1752 |
| KNN | 4.4832 | 0.6353 | 2071 |
| NNN | 4.4824 | 0.9554 | 1192 |
| KCY | 4.4822 | 1.7319 | 3355 |
| NYH | 4.4818 | 1.4590 | 1127 |
| MHF | 4.4777 | 0.5055 | 587 |
| NHI | 4.4748 | 1.3922 | 1846 |
| NKI | 4.4744 | 1.2101 | 2866 |
| QIY | 4.4738 | 0.9541 | 1892 |
| NTI | 4.4727 | 1.2015 | 2632 |
| NKH | 4.4723 | 1.1139 | 1692 |
| NCY | 4.4693 | 1.2458 | 2925 |
| MNI | 4.4657 | 0.8948 | 1062 |
| KQY | 4.4637 | 1.4101 | 3021 |
| NCI | 4.4636 | 1.2352 | 3762 |
| KNI | 4.4617 | 1.7772 | 5325 |
| IKH | 4.4562 | 1.3513 | 2819 |
| DYK | 4.4559 | 1.0629 | 3906 |
| KHT | 4.4552 | 2.5102 | 2188 |
| KCI | 4.4551 | 0.7593 | 5216 |
| KIF | 4.4544 | 1.0430 | 3044 |
| KNM | 4.4542 | 0.4696 | 1836 |
| NMK | 4.4535 | 1.0953 | 2063 |
| NYF | 4.4515 | 0.9905 | 2034 |
| KHH | 4.4508 | 1.4913 | 1114 |
| NNY | 4.4502 | 1.0575 | 2281 |
| NNH | 4.4501 | 0.7128 | 447 |
| KYM | 4.4488 | 0.8305 | 2731 |
| KCF | 4.4486 | 0.9521 | 2055 |
| NNC | 4.4472 | 1.5893 | 1329 |
| KTI | 4.4457 | 2.3520 | 4493 |
| YNH | 4.4444 | 0.5237 | 880 |
| NFH | 4.4420 | 1.6108 | 946 |
| KYS | 4.4391 | 1.7256 | 6134 |
| NNK | 4.4388 | 0.5258 | 2226 |
| KKI | 4.4376 | 1.4982 | 4552 |
| KSY | 4.4375 | 1.7026 | 7299 |
| KYW | 4.4364 | 0.4166 | 2123 |
| NKK | 4.4355 | 1.2639 | 3386 |
| YQH | 4.4350 | 1.0070 | 404 |
| KFW | 4.4319 | 0.3524 | 2276 |
| KIH | 4.4309 | 1.7232 | 3629 |
| NYT | 4.4282 | 1.1679 | 2851 |
| EYY | 4.4280 | 1.6226 | 3230 |
| IYH | 4.4256 | 1.2219 | 1695 |
| MFK | 4.4217 | 0.4430 | 2560 |
| KYK | 4.4207 | 0.7937 | 4241 |
| DKY | 4.4196 | 1.0055 | 3294 |
| EIY | 4.4194 | 1.1145 | 5041 |
| QYK | 4.4089 | 1.0561 | 1776 |
| DII | 4.4082 | 1.5043 | 5954 |
| KIN | 4.4081 | 0.8432 | 5669 |
| HYF | 4.3993 | 1.1296 | 743 |
| NIQ | 4.3993 | 0.9371 | 2308 |
| KMQ | 4.3948 | 0.7906 | 1301 |
| KHK | 4.3944 | 1.3260 | 2206 |
| MYY | 4.3939 | 1.0128 | 1043 |
| TKH | 4.3922 | 2.1875 | 1886 |
| KHW | 4.3916 | 1.3991 | 2135 |
| TYH | 4.3912 | 1.1683 | 1414 |
| KYI | 4.3900 | 1.5735 | 3350 |
| HIY | 4.3877 | 1.6252 | 1781 |
| KFI | 4.3875 | 0.9519 | 3900 |
| KTK | 4.3802 | 1.9687 | 3691 |
| KFN | 4.3794 | 1.0494 | 2154 |
| DYH | 4.3792 | 1.0817 | 1897 |
| HMK | 4.3760 | 0.4110 | 1150 |
| IKY | 4.3657 | 1.0854 | 2499 |
| QYI | 4.3648 | 2.2621 | 2369 |
| NYR | 4.3617 | 1.7862 | 7325 |
| MKK | 4.3614 | 0.6144 | 2106 |
| NHC | 4.3576 | 1.7221 | 2001 |
| MHY | 4.3568 | 0.1481 | 724 |
| EKY | 4.3564 | 0.7595 | 5286 |
| IQY | 4.3537 | 1.3482 | 2129 |
| KYL | 4.3512 | 2.2988 | 4928 |
| KTH | 4.3511 | 1.3463 | 1801 |
| MIY | 4.3489 | 0.9813 | 1996 |
| NQQ | 4.3483 | 1.4388 | 1036 |
| NKF | 4.3442 | 1.1924 | 2601 |
| NFF | 4.3439 | 1.4747 | 660 |
| KIK | 4.3328 | 0.8860 | 4994 |
| HTI | 4.3291 | 1.7829 | 1448 |
| DYF | 4.3274 | 1.3915 | 1363 |
| NSY | 4.3269 | 1.9500 | 3321 |
| QYF | 4.3208 | 1.5612 | 1542 |
| YNY | 4.3204 | 1.4803 | 1267 |
| KQI | 4.3203 | 2.4591 | 3492 |
| NFC | 4.3192 | 1.3553 | 1502 |
| NKC | 4.3169 | 2.4526 | 3513 |
| TYN | 4.3144 | 1.3157 | 2426 |
| KIQ | 4.3105 | 0.6013 | 2624 |
| NYE | 4.3094 | 1.3189 | 2270 |
| NHK | 4.3065 | 0.9934 | 1108 |
| YTF | 4.3029 | 1.7412 | 605 |
| HQY | 4.3006 | 2.8803 | 904 |
| KLY | 4.3003 | 2.4472 | 7768 |
| NYL | 4.2987 | 2.0977 | 3861 |
| NYI | 4.2985 | 2.5255 | 2675 |
| QNI | 4.2906 | 1.0866 | 1541 |
| DNM | 4.2874 | 0.4209 | 1804 |
| KTF | 4.2869 | 2.0256 | 3165 |
| NTF | 4.2854 | 1.6585 | 2197 |
| NTN | 4.2846 | 2.1714 | 1739 |
| HTN | 4.2845 | 2.7745 | 805 |
| KMK | 4.2724 | 1.0743 | 2623 |
| EYM | 4.2695 | 0.7027 | 1983 |
| DFI | 4.2682 | 1.5358 | 2115 |
| KLH | 4.2659 | 2.7746 | 6610 |
| NIH | 4.2642 | 1.5783 | 3055 |
| EII | 4.2638 | 0.9982 | 6397 |
| YTY | 4.2617 | 2.8137 | 2924 |
| HHI | 4.2607 | 1.7752 | 266 |
| KHS | 4.2604 | 1.7811 | 3216 |
| NFT | 4.2602 | 2.4433 | 1886 |
| QYN | 4.2560 | 1.3204 | 771 |
| KYR | 4.2553 | 2.2848 | 11534 |
| KIW | 4.2541 | 0.7004 | 3720 |
| HYQ | 4.2504 | 2.6115 | 766 |
| QNY | 4.2496 | 2.1318 | 1251 |
| HYC | 4.2485 | 2.5279 | 2533 |
| HTH | 4.2476 | 2.6989 | 882 |
| KFK | 4.2471 | 2.1283 | 5434 |
| NLY | 4.2445 | 2.7161 | 5878 |
| HNK | 4.2444 | 1.2123 | 1325 |
| QYY | 4.2430 | 2.2685 | 2380 |
| EYC | 4.2430 | 1.2563 | 3726 |
| NYM | 4.2394 | 0.7871 | 753 |
| KIC | 4.2375 | 1.6490 | 6178 |
| HHF | 4.2370 | 1.5617 | 566 |
| KPI | 4.2352 | 2.0639 | 3151 |
| NNF | 4.2342 | 1.6171 | 1132 |
| IQH | 4.2340 | 2.2262 | 939 |
| NLH | 4.2336 | 2.4140 | 3763 |

TABLE E-continued

High expressing EGFP variants

| AA SEQ | GFP Score Mean | GFP Score Range | Total counts |
|---|---|---|---|
| KSI | 4.2300 | 2.2368 | 11897 |
| HNF | 4.2287 | 1.3172 | 507 |
| KKQ | 4.2284 | 1.4890 | 1654 |
| TYY | 4.2266 | 2.1691 | 2181 |
| KIL | 4.2253 | 1.9341 | 7166 |
| MNY | 4.2234 | 1.6426 | 913 |
| NQK | 4.2230 | 1.5610 | 2658 |
| NKN | 4.2220 | 1.5787 | 1264 |
| HHC | 4.2214 | 1.5895 | 710 |
| KFH | 4.2210 | 2.0275 | 1999 |
| ITH | 4.2205 | 1.4801 | 2606 |
| KYT | 4.2204 | 1.9119 | 2216 |
| IMK | 4.2193 | 1.3199 | 2303 |
| NKA | 4.2180 | 1.3396 | 2546 |
| NYV | 4.2160 | 2.8145 | 4998 |
| KIE | 4.2141 | 0.6482 | 3786 |
| HHY | 4.2125 | 1.9486 | 417 |
| NHW | 4.2101 | 0.8950 | 1488 |
| YTH | 4.2084 | 2.2879 | 1332 |
| KIR | 4.2079 | 2.1938 | 14911 |
| KHN | 4.2023 | 1.6478 | 1629 |
| KQF | 4.2019 | 1.9729 | 1311 |
| ENI | 4.2018 | 1.0962 | 3869 |
| YHH | 4.2000 | 2.0743 | 478 |
| KFT | 4.1981 | 1.5846 | 3044 |
| KFV | 4.1977 | 2.2964 | 6575 |
| KIM | 4.1953 | 1.5486 | 2083 |
| KNL | 4.1942 | 2.0660 | 4425 |
| KNR | 4.1893 | 1.9642 | 7690 |
| KNQ | 4.1887 | 2.6276 | 1706 |
| QHH | 4.1881 | 1.0077 | 269 |
| KLI | 4.1842 | 2.6235 | 11778 |
| NFI | 4.1832 | 1.0126 | 1938 |
| KKF | 4.1829 | 1.8841 | 2172 |
| HIM | 4.1823 | 0.9778 | 518 |
| KYA | 4.1817 | 2.6157 | 3863 |
| INY | 4.1797 | 1.6536 | 1508 |
| NIR | 4.1773 | 2.2146 | 8964 |
| NIM | 4.1765 | 0.4527 | 1401 |
| QIK | 4.1734 | 1.1574 | 3262 |
| DFK | 4.1712 | 1.0744 | 2124 |
| KKK | 4.1696 | 0.5870 | 3268 |
| KFM | 4.1695 | 0.5060 | 1117 |
| HFF | 4.1691 | 1.4727 | 423 |
| TKY | 4.1680 | 1.8493 | 3224 |
| NNR | 4.1675 | 2.0971 | 3258 |
| PYN | 4.1641 | 2.0526 | 346 |
| EFN | 4.1547 | 1.1395 | 1878 |
| HYN | 4.1539 | 1.6360 | 709 |
| IHK | 4.1532 | 2.3231 | 1616 |
| YMH | 4.1511 | 0.7497 | 688 |
| NLK | 4.1498 | 2.3961 | 6889 |
| NTH | 4.1486 | 1.7948 | 869 |
| YNI | 4.1468 | 1.7840 | 1360 |
| NTK | 4.1454 | 1.9751 | 2856 |
| EFY | 4.1449 | 1.2214 | 2432 |
| IKK | 4.1443 | 1.7294 | 3281 |
| IYK | 4.1442 | 1.4009 | 2268 |
| INH | 4.1427 | 2.1863 | 1144 |
| TQY | 4.1421 | 2.3684 | 1641 |
| YYH | 4.1385 | 2.3393 | 609 |
| NIN | 4.1380 | 1.5873 | 1812 |
| DYC | 4.1370 | 1.5058 | 3028 |
| NQF | 4.1347 | 2.4408 | 970 |
| NVK | 4.1344 | 2.1686 | 7758 |
| EKF | 4.1338 | 1.7846 | 2606 |
| KLK | 4.1324 | 2.3124 | 7477 |
| NNQ | 4.1310 | 2.5238 | 955 |
| DIH | 4.1256 | 2.0132 | 2292 |
| QIF | 4.1236 | 1.8002 | 1720 |
| NFV | 4.1229 | 2.4528 | 3174 |
| EYK | 4.1215 | 0.9525 | 3926 |
| KKN | 4.1211 | 1.4035 | 3285 |
| NQI | 4.1153 | 2.0181 | 1744 |
| IFH | 4.1139 | 2.8805 | 2059 |
| DYN | 4.1129 | 1.3904 | 1020 |
| MMQ | 4.1128 | 1.0211 | 800 |
| NNV | 4.1115 | 1.9839 | 4708 |
| EKH | 4.1113 | 1.3498 | 2898 |
| MYK | 4.1109 | 1.5312 | 721 |
| ENM | 4.1091 | 0.7522 | 1482 |
| KNV | 4.1091 | 2.2138 | 6383 |
| NTP | 4.1073 | 2.0229 | 719 |
| KYV | 4.1055 | 2.1557 | 7544 |
| KQH | 4.1054 | 2.0868 | 1380 |
| CHY | 4.1042 | 2.4027 | 920 |
| EKI | 4.1036 | 1.7167 | 5769 |
| KIV | 4.1034 | 2.3758 | 10092 |
| QFH | 4.1025 | 1.3064 | 882 |
| INK | 4.1020 | 1.4128 | 3237 |
| YQQ | 4.1010 | 2.8226 | 638 |
| ENY | 4.1008 | 1.0449 | 2160 |
| ITY | 4.0989 | 2.2927 | 2464 |
| KFL | 4.0980 | 2.1611 | 3851 |
| QII | 4.0979 | 2.3852 | 3516 |
| NSI | 4.0961 | 2.3324 | 5487 |
| NKR | 4.0960 | 2.5298 | 6543 |
| HNI | 4.0956 | 2.3404 | 1333 |
| NKT | 4.0927 | 1.7918 | 1792 |
| DIC | 4.0926 | 2.3412 | 4791 |
| NYS | 4.0926 | 2.3068 | 2831 |
| KYD | 4.0923 | 1.0615 | 2057 |
| SNY | 4.0904 | 3.0717 | 2941 |
| EMH | 4.0904 | 1.9676 | 2702 |
| YMY | 4.0885 | 1.2503 | 760 |
| NIF | 4.0882 | 2.4088 | 1843 |
| DKK | 4.0878 | 0.8763 | 3569 |
| HFY | 4.0864 | 2.5619 | 1287 |
| QMQ | 4.0864 | 1.6542 | 385 |
| KIS | 4.0843 | 2.0845 | 7201 |
| NKM | 4.0843 | 0.8144 | 973 |
| FYH | 4.0823 | 2.1176 | 330 |
| NQH | 4.0815 | 2.5023 | 1285 |
| IHC | 4.0808 | 1.9870 | 2058 |
| KKC | 4.0802 | 1.2175 | 3123 |
| NFN | 4.0798 | 1.8018 | 1073 |
| NVI | 4.0779 | 2.2191 | 7585 |
| NIV | 4.0774 | 2.2650 | 8172 |
| QNC | 4.0774 | 1.0783 | 1318 |
| NNT | 4.0769 | 2.2179 | 1715 |
| KIA | 4.0765 | 2.2446 | 5721 |
| MKN | 4.0752 | 1.3779 | 628 |
| KLC | 4.0747 | 2.4180 | 8823 |
| KFQ | 4.0745 | 2.2312 | 2286 |
| KHL | 4.0741 | 2.6572 | 3492 |
| KTN | 4.0732 | 2.1735 | 2647 |
| TIY | 4.0727 | 1.8767 | 2336 |
| THY | 4.0725 | 2.3569 | 1241 |
| KNW | 4.0703 | 0.8970 | 1512 |
| HNC | 4.0675 | 2.4205 | 1524 |
| MNK | 4.0673 | 0.5517 | 856 |
| TNI | 4.0668 | 2.3397 | 2051 |
| DHK | 4.0659 | 2.1446 | 1681 |
| DNI | 4.0586 | 1.5377 | 2749 |
| KMC | 4.0568 | 0.4296 | 1689 |
| NHV | 4.0565 | 2.5273 | 3805 |
| KNS | 4.0561 | 1.6908 | 4058 |
| KAY | 4.0551 | 2.2498 | 3547 |
| KLN | 4.0542 | 2.6707 | 4501 |
| KFA | 4.0536 | 2.7043 | 3947 |
| NCN | 4.0533 | 1.8268 | 1319 |
| NDK | 4.0525 | 0.9006 | 1812 |
| NFW | 4.0520 | 0.8116 | 659 |
| QKF | 4.0513 | 2.3519 | 872 |
| YKH | 4.0498 | 1.7788 | 609 |
| DYQ | 4.0486 | 2.1603 | 869 |
| MCK | 4.0485 | 0.6146 | 1880 |
| MCY | 4.0482 | 1.8864 | 1916 |

TABLE E-continued

High expressing EGFP variants

| AA SEQ | GFP Score Mean | Range | Total counts |
|---|---|---|---|
| YKI | 4.0480 | 1.8624 | 2131 |
| NHQ | 4.0465 | 2.2225 | 832 |
| DKI | 4.0459 | 1.9486 | 3262 |
| KNT | 4.0456 | 2.7453 | 2876 |
| MQN | 4.0452 | 1.5362 | 744 |
| KSH | 4.0436 | 2.4662 | 4666 |
| HLH | 4.0431 | 2.9704 | 1981 |
| EYF | 4.0375 | 2.1479 | 1597 |
| SKY | 4.0366 | 2.5340 | 4757 |
| NNL | 4.0355 | 2.5563 | 2457 |
| NIL | 4.0353 | 2.5738 | 4742 |
| RNI | 4.0342 | 2.5072 | 5933 |
| EYI | 4.0322 | 2.0475 | 3872 |
| DYI | 4.0318 | 2.6227 | 3344 |
| KNA | 4.0316 | 2.7743 | 4476 |
| DHY | 4.0310 | 2.3077 | 1263 |
| MTY | 4.0310 | 1.6805 | 1568 |
| DIK | 4.0306 | 2.2210 | 4286 |
| HYH | 4.0305 | 2.2928 | 674 |
| NNW | 4.0297 | 0.9308 | 1770 |
| KQC | 4.0295 | 2.4439 | 2327 |
| RNY | 4.0289 | 2.6833 | 3973 |
| QKQ | 4.0287 | 2.2011 | 918 |
| NMI | 4.0279 | 2.0879 | 1316 |
| MQK | 4.0268 | 1.5787 | 948 |
| QNK | 4.0267 | 1.3510 | 1637 |
| KKL | 4.0260 | 2.1350 | 6202 |
| NLI | 4.0237 | 2.7365 | 6015 |
| KVY | 4.0236 | 2.1755 | 6012 |
| DFY | 4.0225 | 1.6446 | 1594 |
| QKI | 4.0221 | 1.4471 | 1610 |
| NYD | 4.0208 | 2.1097 | 710 |
| NQT | 4.0188 | 2.0987 | 628 |
| SIY | 4.0176 | 2.3607 | 5220 |
| HKL | 4.0145 | 2.7813 | 2741 |
| NIT | 4.0144 | 2.7172 | 3419 |
| KLQ | 4.0135 | 2.4212 | 7408 |
| HNA | 4.0124 | 2.2693 | 1087 |
| DNY | 4.0095 | 1.9538 | 1104 |
| FNH | 4.0085 | 2.4426 | 512 |
| KQW | 4.0074 | 1.2016 | 1142 |
| NIC | 4.0073 | 2.1996 | 2784 |
| HKH | 4.0063 | 2.0403 | 666 |
| MIH | 4.0055 | 1.9024 | 768 |
| HIF | 4.0048 | 2.6006 | 1088 |
| DMN | 4.0030 | 1.1770 | 455 |
| CKY | 4.0009 | 1.8068 | 2369 |
| HHK | 4.0002 | 2.3249 | 573 |

TABLE F

Medium-expressing EGFP variants

| AA SEQ | Mean | Range | Total counts |
|---|---|---|---|
| TNY | 3.9994 | 2.2940 | 2048 |
| YNT | 3.9990 | 2.6623 | 1567 |
| NVH | 3.9988 | 2.4112 | 4239 |
| EIK | 3.9983 | 1.6752 | 5055 |
| NSK | 3.9980 | 1.9405 | 4188 |
| TFK | 3.9979 | 2.6767 | 1798 |
| HYI | 3.9924 | 2.3333 | 570 |
| NAY | 3.9921 | 2.9107 | 3267 |
| CKH | 3.9914 | 2.0291 | 1183 |
| NFA | 3.9906 | 2.4833 | 1605 |
| HYD | 3.9901 | 1.7645 | 485 |
| MKF | 3.9896 | 2.0592 | 1086 |
| HNH | 3.9891 | 2.6316 | 658 |
| NTV | 3.9888 | 2.7300 | 5104 |
| NRY | 3.9886 | 2.2107 | 5404 |
| TKI | 3.9873 | 2.2149 | 3252 |
| HTF | 3.9867 | 2.6928 | 1235 |
| DYV | 3.9865 | 2.4378 | 5002 |
| DKH | 3.9864 | 1.6203 | 2235 |
| NYW | 3.9862 | 1.6822 | 804 |
| HNN | 3.9861 | 2.2632 | 539 |
| HYM | 3.9848 | 1.3232 | 531 |
| HKI | 3.9837 | 2.1177 | 1498 |
| NTT | 3.9835 | 2.0859 | 1503 |
| DYM | 3.9824 | 1.0084 | 1499 |
| TYK | 3.9806 | 2.3358 | 2206 |
| YKA | 3.9801 | 2.2625 | 2830 |
| NVY | 3.9799 | 2.5305 | 5502 |
| EFI | 3.9793 | 2.2701 | 3153 |
| EFK | 3.9765 | 1.9481 | 3125 |
| HMQ | 3.9760 | 1.1928 | 912 |
| KSM | 3.9746 | 2.0133 | 3632 |
| YHT | 3.9738 | 2.1607 | 1105 |
| LKH | 3.9735 | 2.6847 | 2538 |
| YNC | 3.9714 | 1.4146 | 1610 |
| QFK | 3.9708 | 2.6042 | 1716 |
| QKY | 3.9699 | 1.5733 | 2248 |
| KRY | 3.9685 | 2.7589 | 7875 |
| DMK | 3.9682 | 0.7250 | 1962 |
| EYN | 3.9681 | 2.3560 | 2045 |
| SNI | 3.9672 | 2.3583 | 3888 |
| TNK | 3.9671 | 1.6801 | 1827 |
| EKK | 3.9662 | 1.3618 | 3953 |
| DNK | 3.9655 | 1.3336 | 2297 |
| KSK | 3.9624 | 2.1540 | 4822 |
| MNF | 3.9622 | 1.2620 | 177 |
| INF | 3.9620 | 1.3345 | 1149 |
| YHK | 3.9617 | 2.0160 | 1020 |
| KTQ | 3.9616 | 2.6402 | 3234 |
| KFS | 3.9615 | 2.1590 | 5748 |
| DKF | 3.9612 | 1.6381 | 2192 |
| MHC | 3.9599 | 2.1815 | 738 |
| KNE | 3.9588 | 2.1705 | 1570 |
| QYL | 3.9587 | 2.6225 | 4542 |
| ENH | 3.9571 | 1.7557 | 1394 |
| EKM | 3.9567 | 0.9835 | 1860 |
| KYP | 3.9559 | 3.0000 | 1064 |
| QTK | 3.9548 | 2.5181 | 1703 |
| NEI | 3.9541 | 2.5045 | 3470 |
| KKM | 3.9538 | 1.3294 | 1689 |
| YKV | 3.9512 | 2.3326 | 3967 |
| MFC | 3.9505 | 1.8798 | 1029 |
| YAH | 3.9504 | 2.5403 | 463 |
| KKV | 3.9499 | 1.8830 | 6201 |
| YYA | 3.9498 | 2.7798 | 2290 |
| KHD | 3.9498 | 2.4074 | 1393 |
| NYQ | 3.9497 | 3.0402 | 1196 |
| HKF | 3.9491 | 2.5996 | 1021 |
| KQK | 3.9487 | 1.4935 | 2038 |
| IKQ | 3.9482 | 2.4747 | 2354 |
| MKQ | 3.9445 | 1.4049 | 982 |
| NDI | 3.9430 | 2.0805 | 2090 |
| CNI | 3.9430 | 2.5290 | 2733 |
| YNK | 3.9425 | 1.5775 | 1388 |
| NVN | 3.9408 | 1.8530 | 4753 |
| YNN | 3.9402 | 1.3471 | 1372 |
| HCY | 3.9394 | 2.2560 | 1099 |
| FNN | 3.9389 | 0.9744 | 642 |
| EMK | 3.9379 | 1.3385 | 2376 |
| KLF | 3.9367 | 2.6667 | 4279 |
| QIM | 3.9298 | 1.3849 | 1417 |
| QYT | 3.9285 | 2.7098 | 2308 |
| MQF | 3.9285 | 2.0280 | 668 |
| KAI | 3.9284 | 2.8118 | 6085 |
| EHI | 3.9266 | 1.9096 | 2155 |
| QTI | 3.9266 | 2.7715 | 1769 |
| NCK | 3.9254 | 2.0213 | 2991 |
| NHH | 3.9251 | 2.9979 | 467 |
| NEH | 3.9246 | 2.1202 | 1010 |
| IHY | 3.9238 | 2.5695 | 877 |

TABLE F-continued

Medium-expressing EGFP variants

| AA SEQ | Mean | Range | Total counts |
|---|---|---|---|
| EFF | 3.9195 | 1.5691 | 968 |
| QMY | 3.9194 | 2.1225 | 1039 |
| KRI | 3.9192 | 2.4937 | 7758 |
| KIT | 3.9188 | 2.8797 | 4541 |
| KSN | 3.9180 | 2.9522 | 4254 |
| KSF | 3.9174 | 2.6702 | 3507 |
| HIN | 3.9161 | 2.3779 | 1620 |
| NFL | 3.9124 | 2.9073 | 2422 |
| MSI | 3.9119 | 1.8317 | 4105 |
| NYA | 3.9099 | 2.7763 | 2831 |
| TYF | 3.9094 | 2.3191 | 1581 |
| KMI | 3.9090 | 1.4522 | 2460 |
| QTF | 3.9089 | 1.9938 | 1780 |
| HYK | 3.9089 | 1.5635 | 1003 |
| HKQ | 3.9087 | 0.8840 | 963 |
| NYP | 3.9083 | 1.9709 | 584 |
| KCC | 3.9082 | 1.4305 | 2742 |
| FKH | 3.9081 | 2.1678 | 813 |
| NMN | 3.9079 | 1.4308 | 963 |
| FHY | 3.9078 | 2.5810 | 747 |
| DTF | 3.9073 | 1.7226 | 1392 |
| YNS | 3.9067 | 2.1105 | 2288 |
| KKW | 3.9048 | 0.5560 | 1799 |
| HNY | 3.9041 | 2.2191 | 843 |
| NEY | 3.9037 | 1.6797 | 1397 |
| NHF | 3.9020 | 1.6522 | 984 |
| YNA | 3.9006 | 2.5698 | 1663 |
| HKC | 3.9000 | 2.3840 | 1431 |
| KFR | 3.9000 | 2.5835 | 7024 |
| NKL | 3.8992 | 2.2050 | 3587 |
| KML | 3.8991 | 2.0011 | 3410 |
| NKS | 3.8972 | 2.3410 | 4049 |
| RKY | 3.8967 | 2.5252 | 4903 |
| HYY | 3.8964 | 2.5571 | 845 |
| KCK | 3.8958 | 2.2773 | 3639 |
| YKY | 3.8958 | 1.4382 | 876 |
| DKL | 3.8951 | 2.3525 | 5160 |
| QHK | 3.8942 | 2.2183 | 977 |
| EKQ | 3.8937 | 1.5452 | 2931 |
| QHY | 3.8935 | 1.8021 | 875 |
| DKM | 3.8913 | 1.6830 | 1128 |
| DNF | 3.8912 | 1.7062 | 1000 |
| DYW | 3.8912 | 0.6477 | 1657 |
| INC | 3.8896 | 1.8334 | 2548 |
| DTY | 3.8863 | 2.4785 | 3262 |
| MKC | 3.8858 | 1.8019 | 2222 |
| ENF | 3.8857 | 1.1514 | 932 |
| RYY | 3.8856 | 2.6117 | 3750 |
| NFR | 3.8837 | 2.0213 | 4624 |
| QHF | 3.8825 | 2.2569 | 743 |
| MKI | 3.8821 | 1.8706 | 1677 |
| KMM | 3.8802 | 0.6586 | 945 |
| NQR | 3.8784 | 2.6106 | 4251 |
| EMY | 3.8784 | 1.9165 | 2569 |
| KMF | 3.8783 | 2.0455 | 2258 |
| NNA | 3.8779 | 2.4819 | 1694 |
| TNN | 3.8776 | 2.4708 | 1170 |
| EHY | 3.8770 | 2.1012 | 1322 |
| HCP | 3.8765 | 1.3720 | 37 |
| HFK | 3.8743 | 2.0961 | 1495 |
| NMR | 3.8737 | 2.0633 | 3141 |
| KVI | 3.8731 | 2.4889 | 7188 |
| MNH | 3.8728 | 2.1458 | 987 |
| NQC | 3.8708 | 2.4470 | 1740 |
| YDI | 3.8705 | 2.4490 | 1429 |
| AYY | 3.8703 | 2.3458 | 2276 |
| MCF | 3.8701 | 0.7832 | 1009 |
| DNC | 3.8697 | 1.4881 | 1618 |
| YYY | 3.8689 | 1.7127 | 718 |
| HNL | 3.8682 | 2.3229 | 1673 |
| HYT | 3.8679 | 2.4643 | 1235 |
| NFM | 3.8657 | 0.3797 | 1538 |
| YHM | 3.8654 | 2.3411 | 518 |
| KTM | 3.8645 | 2.4524 | 1585 |
| TSY | 3.8639 | 2.6745 | 4429 |
| MIF | 3.8629 | 0.9113 | 830 |
| YKK | 3.8628 | 1.1737 | 1337 |
| MMK | 3.8626 | 1.8192 | 830 |
| KRN | 3.8625 | 2.1460 | 6213 |
| HYV | 3.8616 | 2.4031 | 2432 |
| KKP | 3.8614 | 2.6892 | 625 |
| MTF | 3.8605 | 1.6201 | 933 |
| NIE | 3.8600 | 1.9741 | 2455 |
| TNF | 3.8600 | 2.6096 | 1184 |
| NKV | 3.8589 | 2.5122 | 5178 |
| TMF | 3.8588 | 1.7817 | 1005 |
| KST | 3.8584 | 2.7863 | 6815 |
| TKQ | 3.8574 | 2.3489 | 2096 |
| ICK | 3.8572 | 2.1333 | 3149 |
| SYY | 3.8570 | 2.8477 | 2049 |
| KLL | 3.8562 | 3.0992 | 12503 |
| YTN | 3.8556 | 1.7286 | 1509 |
| WYY | 3.8552 | 1.0548 | 908 |
| KHQ | 3.8536 | 2.1336 | 888 |
| IHN | 3.8528 | 2.3213 | 954 |
| HIL | 3.8526 | 2.7692 | 2897 |
| NRI | 3.8515 | 2.3844 | 5531 |
| DMQ | 3.8510 | 1.5735 | 715 |
| IKR | 3.8503 | 2.4706 | 9689 |
| IRY | 3.8500 | 2.4715 | 6469 |
| NNP | 3.8483 | 2.5195 | 473 |
| QYQ | 3.8480 | 2.4663 | 1118 |
| KTL | 3.8478 | 3.1638 | 4716 |
| NHT | 3.8475 | 2.9028 | 587 |
| HKN | 3.8466 | 1.6016 | 666 |
| NNM | 3.8457 | 0.9602 | 546 |
| EHN | 3.8454 | 2.2530 | 1583 |
| TKN | 3.8440 | 1.9884 | 1674 |
| KQQ | 3.8437 | 2.0076 | 1162 |
| CTY | 3.8418 | 2.5698 | 1881 |
| IHF | 3.8401 | 2.1271 | 1215 |
| MKR | 3.8400 | 1.9999 | 4081 |
| YHN | 3.8387 | 2.6491 | 565 |
| NTL | 3.8386 | 3.0000 | 2357 |
| MIC | 3.8380 | 0.9193 | 1930 |
| SHY | 3.8376 | 2.8667 | 1915 |
| HYS | 3.8376 | 2.7804 | 1785 |
| HKK | 3.8368 | 1.6726 | 1356 |
| NTC | 3.8362 | 2.7558 | 1648 |
| NSF | 3.8348 | 2.2664 | 1406 |
| KKR | 3.8342 | 2.0752 | 8704 |
| EYL | 3.8336 | 2.4735 | 6408 |
| MIK | 3.8330 | 1.2190 | 2486 |
| DIV | 3.8329 | 2.1520 | 8185 |
| NIS | 3.8325 | 2.3725 | 4829 |
| QYM | 3.8320 | 0.1418 | 742 |
| KVK | 3.8310 | 2.1437 | 8269 |
| NLL | 3.8308 | 2.7250 | 7401 |
| KTT | 3.8304 | 2.7293 | 2635 |
| MHS | 3.8300 | 2.0735 | 1576 |
| SNF | 3.8296 | 2.2598 | 2113 |
| DYL | 3.8295 | 2.4273 | 4590 |
| MYH | 3.8281 | 2.1136 | 904 |
| KQM | 3.8269 | 2.1461 | 949 |
| KNP | 3.8267 | 2.2680 | 388 |
| HSF | 3.8253 | 2.7019 | 1435 |
| ISK | 3.8252 | 3.0444 | 5689 |
| EIH | 3.8248 | 1.6770 | 2629 |
| NVF | 3.8246 | 2.6284 | 4418 |
| NNS | 3.8236 | 3.0284 | 4077 |
| YTI | 3.8225 | 2.5205 | 1960 |
| HII | 3.8218 | 2.2173 | 1443 |
| QQY | 3.8209 | 2.6055 | 578 |
| QIN | 3.8203 | 2.1614 | 1958 |
| MYN | 3.8201 | 1.7131 | 683 |
| RKI | 3.8187 | 2.1519 | 7430 |
| KCM | 3.8180 | 1.4530 | 2148 |
| HSY | 3.8179 | 2.3417 | 1685 |
| CNH | 3.8174 | 1.6204 | 634 |
| NCF | 3.8170 | 2.2763 | 1320 |

TABLE F-continued

Medium-expressing EGFP variants

| AA SEQ | Mean | Range | Total counts |
|---|---|---|---|
| CNY | 3.8169 | 2.2692 | 998 |
| KKE | 3.8163 | 2.0929 | 2689 |
| YMK | 3.8151 | 2.1936 | 1875 |
| HIC | 3.8149 | 2.8348 | 879 |
| EIM | 3.8142 | 1.8028 | 3488 |
| KKT | 3.8142 | 2.0501 | 2299 |
| HQD | 3.8140 | 1.6713 | 178 |
| KSV | 3.8133 | 2.4040 | 11337 |
| KMR | 3.8121 | 2.2664 | 5792 |
| NPT | 3.8115 | 2.8621 | 759 |
| QNQ | 3.8114 | 2.2803 | 914 |
| IFK | 3.8097 | 2.3823 | 2203 |
| KCT | 3.8087 | 2.2906 | 3560 |
| QYC | 3.8077 | 2.3221 | 980 |
| QCY | 3.8071 | 2.3691 | 1573 |
| ILK | 3.8065 | 2.5781 | 6831 |
| TFY | 3.8060 | 2.5882 | 1660 |
| KTC | 3.8048 | 2.6670 | 2909 |
| HTK | 3.8043 | 2.3859 | 890 |
| EKC | 3.8034 | 1.7099 | 3221 |
| SNH | 3.8031 | 2.3482 | 1469 |
| NDY | 3.8022 | 2.3251 | 997 |
| MKH | 3.8019 | 1.6628 | 313 |
| DFH | 3.8017 | 1.8858 | 868 |
| NIA | 3.8006 | 2.5445 | 5442 |
| PCP | 3.8000 | 0.0000 | 15 |
| HIR | 3.7996 | 2.3093 | 3362 |
| NEK | 3.7991 | 1.2118 | 1990 |
| CKF | 3.7978 | 2.3969 | 1832 |
| TYT | 3.7968 | 2.8804 | 1978 |
| IKC | 3.7960 | 2.2260 | 2535 |
| KVF | 3.7953 | 2.4480 | 5085 |
| THF | 3.7948 | 2.6549 | 479 |
| NKP | 3.7938 | 2.5102 | 791 |
| KLM | 3.7913 | 1.8962 | 3430 |
| KTV | 3.7909 | 2.8168 | 6603 |
| NQL | 3.7907 | 2.3773 | 1927 |
| EIN | 3.7903 | 1.5926 | 2594 |
| MNT | 3.7882 | 2.5752 | 1271 |
| IMH | 3.7880 | 1.5117 | 861 |
| DHI | 3.7871 | 2.4747 | 1644 |
| MTK | 3.7868 | 2.4301 | 934 |
| EIF | 3.7867 | 2.3849 | 2407 |
| YQK | 3.7867 | 1.7806 | 1243 |
| NPH | 3.7862 | 1.9091 | 234 |
| KPH | 3.7853 | 2.3879 | 804 |
| DIN | 3.7852 | 2.2430 | 2379 |
| NSH | 3.7850 | 2.8573 | 1299 |
| QYH | 3.7847 | 2.3326 | 1410 |
| ENC | 3.7843 | 1.7909 | 2104 |
| DKC | 3.7839 | 2.4033 | 3199 |
| KCN | 3.7835 | 2.3007 | 1914 |
| TYC | 3.7828 | 2.8247 | 2137 |
| NNE | 3.7821 | 1.4339 | 1392 |
| HLY | 3.7812 | 2.7848 | 2887 |
| HNR | 3.7811 | 2.1408 | 1945 |
| TTY | 3.7791 | 2.8929 | 1580 |
| KLR | 3.7788 | 3.1876 | 20361 |
| KHR | 3.7769 | 2.8229 | 4008 |
| KHV | 3.7754 | 2.4618 | 4793 |
| HIK | 3.7750 | 1.8818 | 1458 |
| NHL | 3.7749 | 2.5820 | 2375 |
| QIQ | 3.7744 | 2.5971 | 1256 |
| QYV | 3.7744 | 2.3647 | 4133 |
| KPK | 3.7727 | 2.5399 | 1912 |
| KEH | 3.7718 | 2.1958 | 1403 |
| NRN | 3.7703 | 2.2449 | 2676 |
| TQF | 3.7696 | 3.3044 | 926 |
| NFQ | 3.7696 | 2.3237 | 801 |
| MFY | 3.7690 | 2.0448 | 1004 |
| NSN | 3.7681 | 3.0750 | 2576 |
| YHY | 3.7666 | 1.7042 | 547 |
| STY | 3.7662 | 2.8546 | 4447 |
| QFY | 3.7662 | 3.0901 | 1338 |
| HSI | 3.7661 | 2.8750 | 2192 |
| HHA | 3.7650 | 2.0556 | 623 |
| KKA | 3.7639 | 3.0813 | 3572 |
| NPN | 3.7638 | 2.2595 | 338 |
| INR | 3.7630 | 3.1441 | 7055 |
| IQC | 3.7630 | 2.1998 | 2024 |
| YKC | 3.7605 | 1.8919 | 1409 |
| YVH | 3.7603 | 2.4558 | 3409 |
| MQI | 3.7597 | 2.1080 | 1048 |
| DNN | 3.7590 | 2.1505 | 838 |
| EKL | 3.7583 | 2.3662 | 5750 |
| DYT | 3.7580 | 2.7491 | 2330 |
| INA | 3.7577 | 2.7160 | 2177 |
| KQL | 3.7550 | 2.6592 | 3958 |
| MNN | 3.7545 | 1.4077 | 441 |
| HFH | 3.7543 | 2.8040 | 538 |
| TNH | 3.7540 | 2.2747 | 660 |
| QTY | 3.7534 | 2.9176 | 1399 |
| NPY | 3.7522 | 2.4062 | 1038 |
| TKK | 3.7517 | 1.7658 | 2342 |
| QHI | 3.7497 | 2.1792 | 942 |
| PTN | 3.7495 | 2.8451 | 486 |
| YCK | 3.7494 | 1.5156 | 2206 |
| SHF | 3.7488 | 2.2967 | 1034 |
| HTT | 3.7487 | 2.6985 | 1491 |
| FMH | 3.7472 | 2.5436 | 532 |
| ENN | 3.7471 | 1.4623 | 1649 |
| YQN | 3.7463 | 2.7500 | 640 |
| QVY | 3.7462 | 2.4021 | 4115 |
| NLC | 3.7461 | 2.7126 | 4933 |
| KQN | 3.7458 | 1.7179 | 1457 |
| CNV | 3.7457 | 2.1083 | 3960 |
| QMH | 3.7441 | 2.3227 | 735 |
| NLF | 3.7432 | 2.4566 | 2882 |
| YEH | 3.7427 | 2.6732 | 1112 |
| ETY | 3.7413 | 2.5547 | 3215 |
| CKN | 3.7408 | 1.8410 | 1345 |
| NND | 3.7405 | 1.4138 | 656 |
| INN | 3.7389 | 1.3552 | 1264 |
| DYE | 3.7369 | 1.6891 | 1828 |
| MFF | 3.7368 | 1.3945 | 818 |
| HNV | 3.7361 | 2.2081 | 1995 |
| MSY | 3.7360 | 2.4092 | 2544 |
| YWK | 3.7360 | 1.2176 | 582 |
| THH | 3.7359 | 2.7474 | 777 |
| IEH | 3.7358 | 2.1038 | 1047 |
| QFF | 3.7353 | 2.1189 | 731 |
| KQV | 3.7353 | 2.7129 | 4847 |
| DHC | 3.7346 | 2.0925 | 1373 |
| NHD | 3.7330 | 1.6035 | 218 |
| HYL | 3.7326 | 2.7474 | 1424 |
| NMF | 3.7322 | 2.1460 | 1094 |
| EYH | 3.7316 | 2.8646 | 2047 |
| HQI | 3.7315 | 3.3831 | 912 |
| PMF | 3.7315 | 2.8993 | 223 |
| PNK | 3.7313 | 2.2378 | 967 |
| ESY | 3.7307 | 2.5414 | 4330 |
| TYL | 3.7299 | 2.8940 | 4539 |
| LYH | 3.7293 | 2.6530 | 2268 |
| DCI | 3.7275 | 2.2101 | 2824 |
| HLI | 3.7270 | 3.0499 | 2798 |
| YHL | 3.7267 | 2.6071 | 1925 |
| HMN | 3.7255 | 1.5220 | 490 |
| CYA | 3.7240 | 2.6263 | 2038 |
| RKF | 3.7237 | 2.6281 | 3922 |
| HNS | 3.7227 | 2.1103 | 2316 |
| KEY | 3.7215 | 2.4688 | 2691 |
| NIW | 3.7213 | 2.3266 | 1761 |
| NLT | 3.7198 | 2.9825 | 3398 |
| EMM | 3.7188 | 0.5971 | 633 |
| CKI | 3.7175 | 2.0536 | 1951 |
| ITK | 3.7175 | 2.5502 | 2775 |
| DIF | 3.7158 | 1.8919 | 1640 |
| QLI | 3.7154 | 2.5401 | 4146 |
| INS | 3.7154 | 2.8507 | 3979 |
| KRF | 3.7150 | 2.3818 | 3855 |

TABLE F-continued

Medium-expressing EGFP variants

| AA SEQ | Mean | Range | Total counts |
|---|---|---|---|
| KEI | 3.7149 | 1.9484 | 2946 |
| YCY | 3.7133 | 2.4143 | 1421 |
| NTS | 3.7114 | 2.4515 | 3038 |
| QIH | 3.7108 | 1.9799 | 1376 |
| MIT | 3.7068 | 2.3833 | 2048 |
| QHN | 3.7062 | 2.0600 | 591 |
| NLQ | 3.7060 | 2.4309 | 2495 |
| HIT | 3.7044 | 2.6404 | 1343 |
| YEY | 3.7027 | 1.7926 | 1004 |
| QLY | 3.7024 | 2.8084 | 3222 |
| YTQ | 3.7016 | 2.9653 | 1494 |
| RIY | 3.7010 | 3.0000 | 6010 |
| MNC | 3.7007 | 1.0768 | 510 |
| KMN | 3.7004 | 1.3838 | 826 |
| YIH | 3.7001 | 2.2833 | 1056 |
| YQY | 3.6997 | 1.7155 | 636 |
| IPQ | 3.6991 | 2.8006 | 866 |
| NQP | 3.6987 | 2.1851 | 547 |
| IQK | 3.6984 | 2.5011 | 1513 |
| MHM | 3.6982 | 0.0435 | 59 |
| TKL | 3.6981 | 2.5487 | 4278 |
| KPN | 3.6965 | 2.3319 | 1550 |
| KLS | 3.6956 | 2.6693 | 11682 |
| HNQ | 3.6951 | 2.4663 | 347 |
| YSN | 3.6945 | 2.4066 | 2703 |
| HYW | 3.6938 | 0.8042 | 98 |
| QSI | 3.6934 | 2.7267 | 3780 |
| NLR | 3.6926 | 2.9348 | 11406 |
| FYK | 3.6923 | 2.0759 | 598 |
| NTR | 3.6920 | 2.8854 | 3836 |
| EMQ | 3.6908 | 1.7431 | 1077 |
| EFC | 3.6890 | 1.3537 | 2737 |
| YKM | 3.6887 | 1.6503 | 439 |
| NDF | 3.6887 | 1.7566 | 659 |
| KDY | 3.6881 | 2.0002 | 2239 |
| HFT | 3.6880 | 2.7368 | 921 |
| CTI | 3.6876 | 2.7640 | 2456 |
| YPI | 3.6874 | 2.9082 | 1081 |
| DMI | 3.6871 | 2.0305 | 1988 |
| KFE | 3.6869 | 2.0421 | 3071 |
| NDH | 3.6844 | 2.7292 | 517 |
| TMK | 3.6843 | 1.8782 | 1155 |
| CQY | 3.6840 | 2.5912 | 825 |
| IKN | 3.6832 | 1.6034 | 1241 |
| MMI | 3.6827 | 0.9013 | 694 |
| NQM | 3.6827 | 1.7133 | 535 |
| NTM | 3.6824 | 1.7437 | 601 |
| DFT | 3.6822 | 2.3088 | 1189 |
| MIR | 3.6818 | 2.2480 | 5048 |
| NCM | 3.6816 | 1.4300 | 802 |
| NEQ | 3.6814 | 2.2704 | 700 |
| YNL | 3.6812 | 1.9477 | 2593 |
| DQY | 3.6809 | 2.0714 | 1464 |
| RNF | 3.6800 | 3.4558 | 2644 |
| YIY | 3.6791 | 1.6460 | 1037 |
| TMQ | 3.6787 | 1.8470 | 1471 |
| EFM | 3.6775 | 0.7335 | 1190 |
| DNL | 3.6768 | 2.2213 | 3056 |
| HVI | 3.6764 | 2.7551 | 3201 |
| TNV | 3.6758 | 2.7808 | 3919 |
| ELK | 3.6756 | 2.0857 | 9202 |
| YQT | 3.6749 | 2.5667 | 492 |
| YQF | 3.6746 | 1.8000 | 377 |
| KKS | 3.6743 | 2.4025 | 5106 |
| MNL | 3.6743 | 1.8570 | 1237 |
| YYF | 3.6736 | 1.8853 | 582 |
| DTI | 3.6732 | 2.6147 | 7987 |
| QPP | 3.6731 | 0.3462 | 29 |
| LYY | 3.6728 | 2.4061 | 2079 |
| FQY | 3.6724 | 1.5052 | 406 |
| KTS | 3.6724 | 2.8427 | 5153 |
| QKH | 3.6714 | 1.5065 | 1440 |
| NLN | 3.6708 | 2.0065 | 1911 |
| YQI | 3.6700 | 2.9397 | 1269 |
| YSY | 3.6698 | 3.0618 | 2960 |
| DYS | 3.6689 | 2.3433 | 2807 |
| CYN | 3.6685 | 2.1819 | 855 |
| HLF | 3.6665 | 2.6823 | 1652 |
| MYC | 3.6642 | 2.4273 | 1309 |
| KPT | 3.6641 | 2.6389 | 944 |
| ENK | 3.6640 | 0.6204 | 2458 |
| KCV | 3.6639 | 2.2484 | 6099 |
| TKF | 3.6637 | 2.4084 | 1794 |
| TYI | 3.6636 | 2.4132 | 1999 |
| PDP | 3.6635 | 0.5349 | 121 |
| EYE | 3.6629 | 1.9200 | 2587 |
| ELY | 3.6622 | 2.8554 | 6148 |
| YNM | 3.6620 | 1.7750 | 741 |
| DVY | 3.6616 | 1.8372 | 4935 |
| QIV | 3.6607 | 2.6341 | 5016 |
| KLV | 3.6604 | 2.7709 | 13437 |
| NAH | 3.6598 | 2.4529 | 1699 |
| DKV | 3.6593 | 2.2829 | 6584 |
| MYS | 3.6593 | 2.1904 | 2120 |
| DTK | 3.6590 | 2.4561 | 2808 |
| DLH | 3.6586 | 2.4081 | 1647 |
| PHP | 3.6585 | 1.0000 | 72 |
| YSH | 3.6582 | 3.0529 | 2112 |
| NID | 3.6577 | 2.3823 | 1580 |
| DKR | 3.6574 | 2.2705 | 6207 |
| HYR | 3.6569 | 2.8542 | 1910 |
| FYY | 3.6567 | 1.9537 | 520 |
| FKY | 3.6563 | 2.6239 | 743 |
| MQH | 3.6561 | 2.1605 | 290 |
| DIT | 3.6554 | 2.6596 | 3122 |
| DKN | 3.6554 | 1.4678 | 1682 |
| SKI | 3.6526 | 2.4549 | 5270 |
| DIQ | 3.6523 | 2.1601 | 2340 |
| DIS | 3.6523 | 2.2254 | 4290 |
| KLT | 3.6521 | 2.9947 | 6012 |
| YYK | 3.6517 | 1.6929 | 1000 |
| NMQ | 3.6497 | 1.9593 | 1284 |
| YPN | 3.6493 | 2.7568 | 927 |
| MNV | 3.6491 | 1.9090 | 1771 |
| TTI | 3.6478 | 2.8588 | 1731 |
| KIP | 3.6478 | 3.0000 | 1723 |
| EYR | 3.6478 | 2.4397 | 6592 |
| QNN | 3.6475 | 1.4091 | 1026 |
| HHL | 3.6474 | 2.5287 | 661 |
| YKL | 3.6470 | 2.3502 | 2272 |
| CYH | 3.6462 | 2.2354 | 875 |
| NQN | 3.6456 | 2.6575 | 1092 |
| PFN | 3.6452 | 2.7752 | 532 |
| TIQ | 3.6438 | 2.5161 | 1849 |
| HKT | 3.6432 | 2.5083 | 586 |
| NAI | 3.6429 | 2.9224 | 2961 |
| QYS | 3.6418 | 3.1028 | 2088 |
| TQI | 3.6415 | 2.4518 | 1806 |
| KPF | 3.6414 | 2.2500 | 636 |
| KPS | 3.6410 | 2.7083 | 2162 |
| MIQ | 3.6402 | 2.1756 | 1021 |
| LHP | 3.6391 | 1.9728 | 376 |
| MHI | 3.6387 | 2.1179 | 858 |
| KCS | 3.6380 | 2.2516 | 5271 |
| HVY | 3.6362 | 2.0583 | 1874 |
| QQK | 3.6353 | 2.5637 | 811 |
| QYR | 3.6345 | 2.4994 | 4008 |
| QNT | 3.6344 | 2.2803 | 990 |
| IMY | 3.6340 | 2.6917 | 2122 |
| DVK | 3.6338 | 1.8521 | 5175 |
| SYC | 3.6337 | 2.3868 | 3362 |
| QSY | 3.6336 | 2.8221 | 3232 |
| YQM | 3.6336 | 2.1427 | 761 |
| IYQ | 3.6335 | 2.6188 | 1518 |
| NHR | 3.6331 | 2.5969 | 2830 |
| DMY | 3.6330 | 1.7741 | 1082 |
| ITN | 3.6326 | 2.5582 | 1108 |
| YNV | 3.6324 | 2.9407 | 3393 |
| CHF | 3.6318 | 1.6600 | 650 |
| DIL | 3.6318 | 3.1203 | 5190 |

TABLE F-continued

Medium-expressing EGFP variants

| AA SEQ | Mean | Range | Total counts |
|---|---|---|---|
| QNL | 3.6314 | 2.5072 | 1491 |
| MFA | 3.6312 | 1.7385 | 1475 |
| NSM | 3.6304 | 2.3376 | 1044 |
| QKL | 3.6295 | 2.3882 | 2288 |
| EHK | 3.6295 | 2.5779 | 1194 |
| DFN | 3.6291 | 2.1521 | 1134 |
| SYI | 3.6287 | 2.5220 | 3315 |
| HHN | 3.6281 | 1.5324 | 259 |
| NWY | 3.6274 | 1.2971 | 845 |
| KCH | 3.6266 | 2.6317 | 1330 |
| DVI | 3.6257 | 2.3615 | 8316 |
| YAP | 3.6257 | 1.9545 | 236 |
| EKN | 3.6249 | 1.8476 | 1473 |
| KDI | 3.6241 | 2.3458 | 3321 |
| MKS | 3.6239 | 2.1037 | 3242 |
| SKK | 3.6226 | 2.2701 | 4468 |
| KTP | 3.6221 | 2.9087 | 529 |
| YYT | 3.6220 | 2.8061 | 1181 |
| KRK | 3.6217 | 2.4479 | 7048 |
| QMI | 3.6201 | 1.9679 | 815 |
| MTI | 3.6197 | 2.1358 | 1587 |
| FQC | 3.6196 | 1.5772 | 441 |
| NIP | 3.6189 | 2.2886 | 724 |
| KQS | 3.6187 | 2.3586 | 3963 |
| DSK | 3.6178 | 2.2365 | 4315 |
| HSM | 3.6177 | 2.4700 | 1388 |
| MKV | 3.6166 | 1.8953 | 2706 |
| SKN | 3.6166 | 2.4459 | 2478 |
| QIL | 3.6164 | 2.6571 | 3630 |
| IPH | 3.6161 | 1.8945 | 324 |
| EFH | 3.6142 | 2.0601 | 1548 |
| ENL | 3.6139 | 2.1025 | 4035 |
| NRK | 3.6135 | 2.3213 | 3405 |
| MHN | 3.6130 | 2.1176 | 435 |
| INT | 3.6125 | 2.2783 | 1796 |
| LKY | 3.6119 | 2.7734 | 2825 |
| IQN | 3.6117 | 2.5143 | 1217 |
| ENR | 3.6110 | 2.5763 | 6783 |
| LHH | 3.6104 | 2.6368 | 1079 |
| HQN | 3.6100 | 0.2851 | 185 |
| KDF | 3.6100 | 2.4085 | 1186 |
| DYR | 3.6094 | 2.4656 | 4374 |
| NRF | 3.6093 | 2.5102 | 3155 |
| PMK | 3.6090 | 1.8324 | 691 |
| KPY | 3.6087 | 2.5273 | 793 |
| EYQ | 3.6084 | 2.2749 | 1751 |
| KSC | 3.6082 | 2.5251 | 4673 |
| ESK | 3.6075 | 2.1412 | 6801 |
| TPI | 3.6071 | 3.1860 | 1192 |
| DKQ | 3.6057 | 2.0450 | 1458 |
| KIG | 3.6052 | 2.2643 | 9956 |
| MHT | 3.6052 | 2.6189 | 1107 |
| NQA | 3.6049 | 3.0641 | 1204 |
| NVC | 3.6045 | 2.2268 | 3919 |
| NDT | 3.6042 | 2.4687 | 1085 |
| NHS | 3.6041 | 2.7316 | 780 |
| EMI | 3.6027 | 2.0910 | 1984 |
| MSK | 3.6026 | 2.0195 | 2408 |
| NKW | 3.6019 | 1.7167 | 1650 |
| KQR | 3.6004 | 2.3790 | 4160 |
| KCQ | 3.6003 | 2.5988 | 1378 |
| KQP | 3.6000 | 2.9533 | 721 |
| QFC | 3.5999 | 2.2558 | 1522 |
| NMS | 3.5998 | 1.7870 | 1325 |
| EQM | 3.5997 | 1.1744 | 916 |
| IHQ | 3.5994 | 2.5119 | 1029 |
| RIH | 3.5984 | 2.8958 | 3343 |
| QQI | 3.5977 | 2.3235 | 755 |
| LHN | 3.5973 | 2.8304 | 955 |
| DLI | 3.5961 | 2.8491 | 5534 |
| AKY | 3.5959 | 2.8071 | 2461 |
| NVT | 3.5958 | 3.0614 | 3814 |
| MCH | 3.5953 | 1.6812 | 336 |
| TQH | 3.5952 | 3.1791 | 858 |
| HVF | 3.5945 | 2.5111 | 1566 |
| NCC | 3.5940 | 2.4659 | 1546 |
| EYS | 3.5940 | 2.5607 | 4924 |
| KSA | 3.5935 | 2.6021 | 6845 |
| PYY | 3.5932 | 3.0000 | 669 |
| NKE | 3.5927 | 1.6065 | 1721 |
| KDH | 3.5919 | 1.3910 | 555 |
| KFD | 3.5915 | 2.5013 | 1491 |
| FNY | 3.5915 | 1.2857 | 421 |
| QTM | 3.5897 | 2.5385 | 433 |
| QKK | 3.5896 | 1.0319 | 1095 |
| YSM | 3.5888 | 2.1864 | 1475 |
| NVL | 3.5887 | 2.7722 | 9382 |
| IIH | 3.5885 | 2.5121 | 1254 |
| HIQ | 3.5884 | 2.6796 | 960 |
| HPP | 3.5882 | 0.0000 | 17 |
| KID | 3.5872 | 2.1896 | 2845 |
| DLK | 3.5869 | 2.7370 | 5705 |
| FAM | 3.5865 | 1.7230 | 448 |
| MQR | 3.5860 | 2.3446 | 1947 |
| MQY | 3.5859 | 2.1616 | 1363 |
| KKD | 3.5853 | 1.8237 | 2306 |
| EQH | 3.5848 | 1.6387 | 461 |
| NNG | 3.5846 | 1.8572 | 3584 |
| PFF | 3.5837 | 2.5887 | 308 |
| HCK | 3.5830 | 2.0521 | 1340 |
| MSH | 3.5800 | 2.8039 | 864 |
| NML | 3.5798 | 2.1753 | 2127 |
| KYG | 3.5798 | 2.3043 | 6061 |
| TIC | 3.5786 | 2.5084 | 2755 |
| CKL | 3.5778 | 2.5898 | 3964 |
| ELI | 3.5777 | 2.4001 | 7886 |
| HQF | 3.5777 | 2.4199 | 452 |
| QIT | 3.5775 | 2.8136 | 1473 |
| TIK | 3.5773 | 2.2946 | 3046 |
| LYK | 3.5763 | 2.4973 | 2560 |
| IAH | 3.5761 | 2.7250 | 531 |
| INI | 3.5753 | 1.7778 | 1567 |
| MPD | 3.5753 | 0.8120 | 378 |
| ANI | 3.5753 | 2.0948 | 2239 |
| YQC | 3.5742 | 2.2099 | 1395 |
| QFQ | 3.5739 | 2.2947 | 784 |
| DQH | 3.5732 | 2.5462 | 733 |
| SYN | 3.5709 | 2.9589 | 1852 |
| SIF | 3.5690 | 2.3566 | 3052 |
| YYE | 3.5681 | 2.3052 | 1109 |
| QNF | 3.5678 | 2.4031 | 1178 |
| KQE | 3.5674 | 1.8744 | 1878 |
| YTA | 3.5670 | 2.5997 | 2573 |
| TKA | 3.5667 | 2.5476 | 3222 |
| YLH | 3.5667 | 2.4209 | 2005 |
| ECN | 3.5662 | 1.9985 | 1781 |
| PHY | 3.5658 | 2.8182 | 469 |
| WIY | 3.5654 | 2.1027 | 1605 |
| YCA | 3.5639 | 1.8974 | 2268 |
| CNL | 3.5638 | 2.8488 | 2582 |
| EIT | 3.5629 | 2.5947 | 4160 |
| YQP | 3.5628 | 2.7450 | 320 |
| ETK | 3.5624 | 2.2408 | 2215 |
| CYK | 3.5623 | 2.2962 | 1004 |
| TLN | 3.5617 | 2.2030 | 3102 |
| DQK | 3.5615 | 2.5129 | 1213 |
| HSK | 3.5607 | 2.4173 | 1901 |
| TYV | 3.5601 | 2.3876 | 3482 |
| HGP | 3.5597 | 2.4041 | 633 |
| PPS | 3.5596 | 2.7562 | 538 |
| KSS | 3.5596 | 2.6491 | 7531 |
| FNP | 3.5595 | 1.8442 | 196 |
| MYI | 3.5595 | 1.3907 | 766 |
| SIH | 3.5591 | 2.7091 | 2239 |
| TKC | 3.5589 | 2.3577 | 2060 |
| MKL | 3.5584 | 2.5481 | 2869 |
| YIA | 3.5583 | 2.5497 | 2489 |
| RHY | 3.5577 | 2.7625 | 1780 |
| CIH | 3.5577 | 2.5078 | 1182 |
| WEY | 3.5570 | 0.4210 | 1013 |

TABLE F-continued

Medium-expressing EGFP variants

| AA SEQ | Mean | Range | Total counts |
|---|---|---|---|
| TQN | 3.5566 | 1.6145 | 225 |
| ISY | 3.5560 | 2.7003 | 4015 |
| KSQ | 3.5553 | 3.0729 | 2310 |
| TNL | 3.5552 | 2.9000 | 1539 |
| NVR | 3.5549 | 2.5639 | 14405 |
| DNH | 3.5544 | 2.2611 | 766 |
| HFA | 3.5534 | 2.7752 | 1501 |
| SYF | 3.5531 | 2.1748 | 1331 |
| IYR | 3.5526 | 2.6497 | 4983 |
| IHS | 3.5519 | 2.9429 | 2212 |
| TFF | 3.5507 | 2.8462 | 788 |
| SKF | 3.5505 | 2.6354 | 2715 |
| DQI | 3.5503 | 2.0906 | 1624 |
| ESI | 3.5501 | 2.5533 | 6032 |
| EKV | 3.5490 | 2.2209 | 8317 |
| QNR | 3.5472 | 2.3382 | 2229 |
| QMN | 3.5462 | 1.9510 | 682 |
| NTQ | 3.5460 | 3.2740 | 1415 |
| NPS | 3.5457 | 2.3895 | 1071 |
| FNK | 3.5456 | 2.4147 | 767 |
| HFN | 3.5455 | 1.8582 | 599 |
| DQL | 3.5453 | 2.7018 | 2240 |
| YPQ | 3.5453 | 2.4255 | 295 |
| CNF | 3.5452 | 1.7764 | 783 |
| PHQ | 3.5449 | 2.8232 | 122 |
| TKR | 3.5449 | 2.6462 | 6645 |
| SQY | 3.5446 | 2.7666 | 2312 |
| QYW | 3.5445 | 0.4622 | 279 |
| QYD | 3.5445 | 2.6533 | 476 |
| QCK | 3.5442 | 2.2000 | 1463 |
| VKY | 3.5441 | 2.3271 | 2521 |
| NDM | 3.5438 | 0.8285 | 614 |
| NYG | 3.5418 | 1.8282 | 3084 |
| WPY | 3.5417 | 0.7157 | 311 |
| PTI | 3.5410 | 3.0000 | 965 |
| KVH | 3.5407 | 2.6277 | 4446 |
| DFF | 3.5400 | 1.6819 | 687 |
| TIF | 3.5398 | 2.2566 | 1791 |
| IHI | 3.5395 | 2.2180 | 831 |
| QFI | 3.5394 | 2.5190 | 1565 |
| QHL | 3.5393 | 2.8814 | 1517 |
| KLA | 3.5392 | 2.5459 | 9763 |
| INQ | 3.5384 | 1.9626 | 1150 |
| IIK | 3.5380 | 2.2723 | 2802 |
| DYA | 3.5378 | 2.7003 | 4440 |
| QFR | 3.5377 | 2.7086 | 2644 |
| KRV | 3.5376 | 2.3106 | 12344 |
| KAM | 3.5373 | 2.1618 | 1161 |
| CYQ | 3.5356 | 2.1725 | 830 |
| HFL | 3.5349 | 2.3359 | 1440 |
| DSY | 3.5334 | 2.6456 | 3341 |
| SFY | 3.5329 | 2.4507 | 1462 |
| QLK | 3.5328 | 2.8461 | 3145 |
| YIR | 3.5327 | 2.7791 | 4300 |
| DMH | 3.5320 | 2.4051 | 1517 |
| PPC | 3.5299 | 0.8846 | 168 |
| SMY | 3.5293 | 2.5330 | 2254 |
| HQS | 3.5289 | 2.6426 | 981 |
| DTN | 3.5286 | 2.3769 | 1382 |
| EYW | 3.5285 | 1.3607 | 1943 |
| TSK | 3.5282 | 3.1154 | 4451 |
| DLY | 3.5277 | 2.6881 | 3455 |
| YIK | 3.5275 | 1.6189 | 1514 |
| HTQ | 3.5267 | 2.8506 | 1314 |
| TTK | 3.5263 | 2.7667 | 2763 |
| NSV | 3.5262 | 3.0732 | 6131 |
| SKL | 3.5260 | 2.7214 | 5480 |
| QFM | 3.5257 | 1.5821 | 640 |
| RYN | 3.5252 | 2.6079 | 2909 |
| RNN | 3.5251 | 2.2623 | 2472 |
| TMH | 3.5240 | 2.6261 | 687 |
| YPT | 3.5229 | 2.3136 | 495 |
| WKF | 3.5228 | 1.2848 | 688 |
| CIY | 3.5228 | 2.3370 | 1859 |
| EIC | 3.5227 | 2.0519 | 3869 |
| KEK | 3.5225 | 1.3876 | 2196 |
| HVK | 3.5223 | 2.4049 | 3048 |
| NSA | 3.5223 | 2.6272 | 2853 |
| MHH | 3.5221 | 1.3529 | 321 |
| KAF | 3.5216 | 2.5000 | 1847 |
| ETI | 3.5212 | 1.8381 | 2894 |
| QHC | 3.5210 | 2.4708 | 712 |
| KTE | 3.5208 | 2.2782 | 2348 |
| HND | 3.5206 | 1.5429 | 535 |
| NLS | 3.5202 | 2.8549 | 7784 |
| CYY | 3.5198 | 2.4966 | 910 |
| KWY | 3.5193 | 1.6371 | 1756 |
| FPN | 3.5188 | 1.9000 | 146 |
| NPL | 3.5186 | 3.0541 | 1516 |
| HNT | 3.5175 | 2.5073 | 479 |
| KLD | 3.5175 | 1.6217 | 4147 |
| MFN | 3.5174 | 1.2033 | 1041 |
| IYC | 3.5164 | 2.2885 | 1503 |
| QIC | 3.5158 | 1.6075 | 2500 |
| DIR | 3.5155 | 2.0955 | 7664 |
| YQL | 3.5153 | 2.6672 | 2016 |
| QFS | 3.5149 | 2.2254 | 1706 |
| HMR | 3.5147 | 2.1514 | 1288 |
| IKA | 3.5144 | 2.7249 | 3006 |
| KVN | 3.5138 | 2.3655 | 4683 |
| HFW | 3.5137 | 0.7100 | 212 |
| NQV | 3.5129 | 2.6938 | 3430 |
| MLY | 3.5123 | 2.6481 | 2090 |
| AKH | 3.5105 | 2.6935 | 1529 |
| NWH | 3.5103 | 1.5139 | 650 |
| NMC | 3.5101 | 2.2534 | 1141 |
| IMQ | 3.5100 | 1.8387 | 943 |
| YHE | 3.5094 | 2.2446 | 771 |
| LNY | 3.5087 | 2.6950 | 1891 |
| QFN | 3.5087 | 2.3652 | 681 |
| QVF | 3.5085 | 2.4027 | 1898 |
| NHA | 3.5080 | 3.0185 | 1533 |
| YYM | 3.5078 | 1.9864 | 479 |
| QLL | 3.5075 | 2.9777 | 6153 |
| MVY | 3.5073 | 1.6996 | 1597 |
| YDK | 3.5068 | 1.5241 | 1208 |
| THI | 3.5067 | 2.2824 | 1254 |
| HLQ | 3.5057 | 3.2235 | 1257 |
| TSH | 3.5056 | 3.0143 | 1412 |
| QLH | 3.5052 | 2.7905 | 1648 |
| QLF | 3.5048 | 2.5429 | 1777 |
| SKH | 3.5043 | 2.4839 | 3785 |
| MWH | 3.5040 | 0.1921 | 327 |
| CMF | 3.5040 | 0.8927 | 647 |
| QTT | 3.5034 | 2.7586 | 1197 |
| EYT | 3.5028 | 2.4618 | 3408 |
| NLV | 3.5022 | 2.6603 | 7629 |
| MPP | 3.5019 | 1.0581 | 257 |
| NEN | 3.5016 | 1.6389 | 801 |
| YIQ | 3.5015 | 2.3058 | 1339 |
| NLP | 3.5006 | 3.5295 | 1232 |
| KAK | 3.4999 | 2.5287 | 3339 |
| CNN | 3.4996 | 1.6099 | 948 |
| FWF | 3.4996 | 1.0620 | 357 |
| KCA | 3.4995 | 2.6246 | 3780 |
| WKC | 3.4989 | 2.3548 | 1465 |
| YSK | 3.4987 | 2.7180 | 2869 |
| QCN | 3.4986 | 2.2997 | 1134 |
| MWP | 3.4985 | 0.4263 | 232 |
| QMR | 3.4984 | 2.4805 | 2032 |
| NQS | 3.4982 | 2.9254 | 1893 |
| MQT | 3.4981 | 1.7159 | 399 |
| QYA | 3.4976 | 2.7361 | 1974 |
| TIN | 3.4973 | 2.6277 | 1699 |
| IQT | 3.4973 | 2.5623 | 1151 |
| TTH | 3.4969 | 2.8930 | 1143 |
| YKQ | 3.4959 | 2.2449 | 1057 |
| KAH | 3.4956 | 2.2881 | 1601 |
| YHI | 3.4945 | 2.5701 | 685 |
| SQF | 3.4944 | 2.1462 | 1573 |

TABLE F-continued

Medium-expressing EGFP variants

| AA SEQ | Mean | Range | Total counts |
|---|---|---|---|
| KHE | 3.4941 | 1.9208 | 776 |
| CNC | 3.4934 | 1.5671 | 1118 |
| HMI | 3.4931 | 2.2782 | 513 |
| WGY | 3.4931 | 0.8393 | 2823 |
| ETF | 3.4928 | 2.2409 | 1649 |
| YDM | 3.4924 | 1.5324 | 853 |
| SQI | 3.4914 | 2.4836 | 2405 |
| TYR | 3.4913 | 2.8438 | 5216 |
| IHR | 3.4910 | 2.8503 | 3505 |
| PDF | 3.4909 | 2.1180 | 333 |
| YDY | 3.4908 | 2.5088 | 702 |
| STK | 3.4905 | 2.5602 | 3535 |
| ECY | 3.4898 | 1.9502 | 2481 |
| HQR | 3.4895 | 2.5134 | 1284 |
| MCI | 3.4894 | 1.2899 | 1277 |
| CMD | 3.4893 | 1.0690 | 554 |
| YFN | 3.4892 | 1.5494 | 844 |
| EFQ | 3.4885 | 2.2928 | 1226 |
| THT | 3.4883 | 3.0000 | 610 |
| MST | 3.4876 | 2.7655 | 3104 |
| DNV | 3.4871 | 2.3698 | 3986 |
| PWP | 3.4866 | 1.0000 | 153 |
| KTD | 3.4865 | 2.4812 | 1062 |
| MNQ | 3.4862 | 2.3405 | 658 |
| MLH | 3.4856 | 2.6971 | 1806 |
| KDM | 3.4856 | 0.6085 | 1294 |
| RYT | 3.4851 | 3.0149 | 4837 |
| NAK | 3.4850 | 2.3956 | 2405 |
| YYN | 3.4845 | 2.4267 | 683 |
| TYS | 3.4845 | 2.7774 | 3458 |
| YEI | 3.4838 | 1.8279 | 1729 |
| QIR | 3.4836 | 3.3497 | 3910 |
| YDH | 3.4834 | 1.2212 | 317 |
| YKN | 3.4832 | 1.4805 | 1233 |
| YCM | 3.4832 | 1.2871 | 907 |
| TSF | 3.4830 | 2.5543 | 1450 |
| RMI | 3.4828 | 2.2838 | 2853 |
| NFE | 3.4820 | 1.8241 | 1243 |
| YCH | 3.4816 | 2.7673 | 601 |
| IYS | 3.4812 | 2.5355 | 3085 |
| QVI | 3.4805 | 2.7663 | 3209 |
| WNN | 3.4802 | 1.3646 | 774 |
| NSC | 3.4800 | 2.2244 | 2275 |
| DLM | 3.4796 | 2.4663 | 2005 |
| HSQ | 3.4792 | 3.5338 | 1091 |
| WKI | 3.4792 | 1.5818 | 1853 |
| TNS | 3.4790 | 2.9375 | 1752 |
| MYM | 3.4789 | 0.8472 | 240 |
| HLM | 3.4780 | 2.0909 | 820 |
| NPM | 3.4779 | 2.6634 | 323 |
| RYC | 3.4779 | 2.2517 | 4223 |
| SII | 3.4777 | 2.6935 | 6150 |
| MKA | 3.4769 | 2.2939 | 1913 |
| WPF | 3.4768 | 0.7327 | 494 |
| HWP | 3.4765 | 0.8769 | 165 |
| MQA | 3.4763 | 2.2494 | 1159 |
| WNK | 3.4763 | 2.0071 | 629 |
| PTP | 3.4749 | 2.3636 | 203 |
| HIV | 3.4740 | 2.8292 | 2745 |
| MLF | 3.4737 | 2.3715 | 1671 |
| EIL | 3.4730 | 2.7701 | 6077 |
| HHW | 3.4723 | 0.2754 | 181 |
| NVA | 3.4716 | 2.3685 | 4233 |
| QNS | 3.4714 | 2.7478 | 1592 |
| RKH | 3.4705 | 2.8273 | 3901 |
| MMR | 3.4704 | 2.2429 | 2564 |
| QCP | 3.4700 | 1.1832 | 428 |
| RTI | 3.4695 | 2.8505 | 5175 |
| DKT | 3.4695 | 2.4038 | 1707 |
| QPE | 3.4694 | 1.6352 | 701 |
| SIN | 3.4692 | 2.6357 | 3688 |
| ELH | 3.4687 | 2.8828 | 4143 |
| IMR | 3.4687 | 1.9213 | 4323 |
| NCQ | 3.4683 | 2.6443 | 1091 |
| ISH | 3.4680 | 2.6429 | 2201 |
| THN | 3.4677 | 2.2143 | 424 |
| NSP | 3.4659 | 1.8315 | 384 |
| MAY | 3.4656 | 1.4424 | 519 |
| MQP | 3.4651 | 1.7265 | 377 |
| NRM | 3.4650 | 2.0335 | 1713 |
| HMY | 3.4647 | 2.9980 | 430 |
| DVH | 3.4640 | 2.4967 | 2869 |
| ECI | 3.4638 | 2.5197 | 3167 |
| TFQ | 3.4636 | 2.1057 | 675 |
| KFG | 3.4632 | 1.7382 | 5356 |
| YTK | 3.4631 | 2.4901 | 2479 |
| YSI | 3.4629 | 2.4282 | 2708 |
| YHR | 3.4628 | 2.7172 | 1507 |
| HTM | 3.4626 | 2.3313 | 255 |
| VMP | 3.4626 | 1.2667 | 1048 |
| KQA | 3.4622 | 2.6340 | 1604 |
| KLE | 3.4618 | 2.1906 | 5406 |
| NFS | 3.4618 | 3.1635 | 2027 |
| PPD | 3.4602 | 1.2308 | 254 |
| MML | 3.4598 | 1.5064 | 961 |
| CMH | 3.4598 | 1.6955 | 578 |
| KQT | 3.4598 | 2.4620 | 1337 |
| DNQ | 3.4594 | 2.9268 | 933 |
| TYA | 3.4587 | 2.8387 | 2401 |
| WDH | 3.4586 | 0.2333 | 326 |
| MNR | 3.4583 | 1.6466 | 2067 |
| MYF | 3.4579 | 0.4956 | 874 |
| STF | 3.4573 | 2.9717 | 2855 |
| IRK | 3.4571 | 2.5347 | 5532 |
| KND | 3.4566 | 1.7661 | 1135 |
| YCQ | 3.4559 | 2.3314 | 990 |
| RIK | 3.4555 | 2.4844 | 6896 |
| WGF | 3.4553 | 0.5506 | 2363 |
| TIH | 3.4549 | 2.6699 | 1523 |
| NLA | 3.4549 | 3.0311 | 4204 |
| RFK | 3.4548 | 2.6102 | 4647 |
| TKT | 3.4546 | 2.7046 | 1914 |
| KEC | 3.4545 | 1.7861 | 2313 |
| DCK | 3.4545 | 1.8481 | 2619 |
| HLV | 3.4543 | 3.2545 | 4531 |
| FKC | 3.4542 | 2.1962 | 1298 |
| MGH | 3.4540 | 0.8148 | 1300 |
| MHV | 3.4537 | 1.9868 | 833 |
| KEV | 3.4533 | 1.7559 | 5139 |
| RTY | 3.4528 | 2.8613 | 3402 |
| DFV | 3.4527 | 2.2427 | 3612 |
| KVL | 3.4525 | 2.4045 | 10911 |
| KDK | 3.4514 | 1.4612 | 1955 |
| GWM | 3.4513 | 0.6830 | 2407 |
| QHS | 3.4512 | 2.9420 | 671 |
| CIK | 3.4495 | 2.5057 | 2548 |
| CWW | 3.4494 | 0.1025 | 1198 |
| IKS | 3.4494 | 2.3356 | 4952 |
| FNQ | 3.4494 | 2.5918 | 458 |
| WDQ | 3.4493 | 1.1185 | 596 |
| HKV | 3.4491 | 2.3607 | 2344 |
| FRP | 3.4490 | 1.6842 | 328 |
| CHI | 3.4488 | 3.2293 | 889 |
| YTV | 3.4481 | 2.6631 | 3725 |
| QTR | 3.4474 | 2.6200 | 3626 |
| YHS | 3.4461 | 2.6885 | 1802 |
| QSK | 3.4458 | 2.7595 | 2910 |
| RPI | 3.4456 | 2.9630 | 2945 |
| HNE | 3.4455 | 2.4948 | 740 |
| ENS | 3.4453 | 2.1004 | 3716 |
| HKM | 3.4451 | 2.1682 | 421 |
| PQN | 3.4447 | 2.1865 | 455 |
| QKC | 3.4441 | 2.0846 | 1013 |
| ADD | 3.4438 | 0.5490 | 969 |
| MGQ | 3.4436 | 0.4728 | 1755 |
| DLV | 3.4433 | 2.6443 | 9247 |
| ISN | 3.4431 | 2.3661 | 3494 |
| YTM | 3.4425 | 2.1787 | 538 |
| PLP | 3.4406 | 3.5333 | 387 |
| QQN | 3.4405 | 1.9946 | 414 |

TABLE F-continued

Medium-expressing EGFP variants

| AA SEQ | Mean | Range | Total counts |
|---|---|---|---|
| IWD | 3.4401 | 0.3363 | 524 |
| HPI | 3.4394 | 2.5962 | 736 |
| NEF | 3.4389 | 2.3492 | 1657 |
| CVY | 3.4387 | 2.4689 | 3786 |
| STN | 3.4385 | 2.7216 | 2090 |
| QKN | 3.4381 | 0.7917 | 653 |
| EHQ | 3.4381 | 2.3434 | 717 |
| DHN | 3.4365 | 2.7937 | 788 |
| NET | 3.4364 | 2.0881 | 1148 |
| CPF | 3.4362 | 1.4589 | 420 |
| TSI | 3.4358 | 3.3486 | 4405 |
| YNR | 3.4357 | 2.1969 | 2869 |
| NPF | 3.4357 | 1.6894 | 157 |
| SYV | 3.4354 | 2.5002 | 6997 |
| LNN | 3.4353 | 2.3289 | 1840 |
| KWH | 3.4348 | 1.0348 | 949 |
| HHQ | 3.4346 | 2.5501 | 437 |
| NES | 3.4345 | 2.2189 | 3307 |
| FHH | 3.4337 | 2.1842 | 217 |
| RFY | 3.4334 | 2.6848 | 2820 |
| WEM | 3.4329 | 0.3428 | 978 |
| QKT | 3.4324 | 1.3665 | 767 |
| QIA | 3.4321 | 2.4297 | 1869 |
| NCL | 3.4319 | 2.5590 | 2810 |
| YHV | 3.4317 | 2.2682 | 1534 |
| QNH | 3.4314 | 1.9766 | 568 |
| YHA | 3.4310 | 2.6819 | 515 |
| DNT | 3.4309 | 2.5066 | 1357 |
| TKV | 3.4306 | 2.5563 | 4368 |
| CMK | 3.4299 | 1.7620 | 1144 |
| IAK | 3.4295 | 2.5421 | 2339 |
| TLK | 3.4288 | 2.6275 | 4177 |
| QLM | 3.4288 | 2.7285 | 1433 |
| EHH | 3.4287 | 1.6981 | 463 |
| EKS | 3.4280 | 1.9364 | 5719 |
| TII | 3.4280 | 2.4606 | 2761 |
| MIE | 3.4276 | 1.2393 | 1388 |
| NWN | 3.4274 | 1.6267 | 495 |
| EHF | 3.4270 | 1.8800 | 585 |
| YKT | 3.4267 | 1.9066 | 1118 |
| AKI | 3.4267 | 2.1430 | 3240 |
| FMY | 3.4263 | 1.4416 | 318 |
| QNV | 3.4262 | 2.5092 | 1949 |
| FWE | 3.4261 | 0.7090 | 587 |
| NPK | 3.4258 | 2.3317 | 670 |
| RNW | 3.4254 | 1.7987 | 2058 |
| PYF | 3.4250 | 2.3897 | 409 |
| KEF | 3.4250 | 1.4801 | 1391 |
| WTW | 3.4249 | 0.1956 | 1292 |
| QPM | 3.4244 | 1.7521 | 385 |
| STI | 3.4238 | 3.6356 | 4743 |
| MLP | 3.4236 | 2.3407 | 727 |
| APM | 3.4230 | 1.6667 | 618 |
| NSL | 3.4227 | 2.7035 | 4799 |
| YIP | 3.4226 | 2.5613 | 634 |
| HRY | 3.4222 | 2.5786 | 1747 |
| NVV | 3.4217 | 2.3556 | 7121 |
| INL | 3.4215 | 2.2500 | 2032 |
| CKM | 3.4212 | 2.2537 | 635 |
| YKR | 3.4208 | 2.6365 | 3610 |
| EQK | 3.4202 | 1.0428 | 1173 |
| FSY | 3.4201 | 1.9641 | 825 |
| DTC | 3.4199 | 2.4844 | 1835 |
| SLY | 3.4198 | 2.9437 | 7590 |
| AYH | 3.4195 | 2.1145 | 1446 |
| KCP | 3.4192 | 1.9955 | 554 |
| KDN | 3.4192 | 1.8698 | 1229 |
| CTF | 3.4190 | 3.0462 | 1039 |
| RKL | 3.4186 | 2.8386 | 8201 |
| RHF | 3.4184 | 2.6456 | 2336 |
| NMD | 3.4184 | 0.1498 | 164 |
| PCY | 3.4181 | 1.5818 | 396 |
| REY | 3.4181 | 2.4021 | 4072 |
| KFP | 3.4177 | 2.5845 | 737 |
| YQR | 3.4174 | 2.6234 | 2595 |
| TLF | 3.4170 | 2.8371 | 2417 |
| MII | 3.4165 | 1.6470 | 936 |
| TRP | 3.4161 | 1.8980 | 1025 |
| QHD | 3.4158 | 2.1359 | 426 |
| DQF | 3.4154 | 2.5045 | 748 |
| KVQ | 3.4153 | 2.3004 | 3996 |
| YNQ | 3.4152 | 2.2307 | 488 |
| RYV | 3.4150 | 2.5896 | 9128 |
| CKR | 3.4148 | 2.3311 | 4855 |
| KDC | 3.4147 | 1.5521 | 1596 |
| QKW | 3.4144 | 0.5666 | 481 |
| IKI | 3.4138 | 1.2630 | 1911 |
| ITI | 3.4135 | 1.9548 | 1042 |
| KTA | 3.4133 | 2.7709 | 2427 |
| RIF | 3.4131 | 2.6565 | 4267 |
| HCM | 3.4131 | 2.4404 | 638 |
| CAH | 3.4130 | 1.6806 | 914 |
| WNI | 3.4123 | 1.8160 | 1155 |
| QKR | 3.4123 | 2.4988 | 3448 |
| SYS | 3.4120 | 2.9415 | 5649 |
| SQP | 3.4110 | 2.6733 | 440 |
| SIK | 3.4098 | 2.7000 | 5106 |
| MYR | 3.4094 | 2.2376 | 3277 |
| PWH | 3.4093 | 0.8931 | 125 |
| CSY | 3.4091 | 2.9005 | 2885 |
| FMD | 3.4088 | 0.6077 | 481 |
| YYQ | 3.4087 | 1.7338 | 648 |
| YLK | 3.4087 | 2.3336 | 2144 |
| DTL | 3.4084 | 2.8018 | 3831 |
| IEK | 3.4077 | 2.2532 | 2047 |
| RII | 3.4077 | 2.4833 | 7825 |
| FWD | 3.4076 | 0.3152 | 317 |
| NCP | 3.4069 | 1.6098 | 151 |
| HIW | 3.4064 | 1.7013 | 262 |
| QPL | 3.4062 | 2.7949 | 968 |
| KWD | 3.4061 | 0.6747 | 895 |
| NTD | 3.4061 | 2.4289 | 734 |
| MGC | 3.4056 | 0.6010 | 3057 |
| MLQ | 3.4055 | 2.0601 | 1576 |
| KCL | 3.4050 | 2.5526 | 3881 |
| QPK | 3.4048 | 2.6390 | 523 |
| KSL | 3.4045 | 2.6954 | 8970 |
| WEI | 3.4040 | 0.4476 | 1518 |
| QLR | 3.4037 | 3.3636 | 5102 |
| LNH | 3.4034 | 2.6148 | 1549 |
| MDP | 3.4034 | 0.7542 | 79 |
| QRF | 3.4031 | 2.6141 | 2678 |
| PDM | 3.4028 | 1.9947 | 278 |
| WDF | 3.4026 | 0.7797 | 521 |
| HKR | 3.4025 | 2.7121 | 2016 |
| MYV | 3.4022 | 1.5197 | 1579 |
| NSS | 3.4021 | 3.6611 | 4657 |
| IVK | 3.4011 | 2.0585 | 5011 |
| VDC | 3.4011 | 1.1348 | 3039 |
| CWM | 3.4008 | 0.1297 | 329 |
| SNK | 3.4008 | 2.4587 | 3537 |
| NQD | 3.4003 | 2.5376 | 506 |
| WGI | 3.4002 | 0.7682 | 4421 |
| DDP | 3.4000 | 1.8500 | 398 |
| DNR | 3.4000 | 2.7214 | 3925 |
| SHK | 3.3997 | 2.8768 | 2152 |
| QVK | 3.3994 | 2.0331 | 3128 |
| QHM | 3.3993 | 1.9354 | 524 |
| NTA | 3.3991 | 2.7110 | 1589 |
| HFC | 3.3991 | 2.7600 | 1430 |
| KDW | 3.3990 | 0.5834 | 1042 |
| CWG | 3.3982 | 0.4755 | 5712 |
| CEY | 3.3980 | 1.7681 | 1470 |
| NEL | 3.3978 | 2.3587 | 2308 |
| RFH | 3.3978 | 2.7708 | 2450 |
| PAM | 3.3978 | 1.6512 | 475 |
| CNT | 3.3978 | 2.7630 | 1303 |
| NAC | 3.3975 | 2.6435 | 2469 |
| VHP | 3.3974 | 1.8636 | 712 |
| TMV | 3.3968 | 1.8274 | 2134 |

TABLE F-continued

Medium-expressing EGFP variants

| AA SEQ | Mean | Range | Total counts |
|---|---|---|---|
| DQT | 3.3966 | 2.4175 | 782 |
| ERI | 3.3966 | 2.3433 | 8641 |
| YFK | 3.3964 | 2.1075 | 838 |
| SHN | 3.3964 | 2.5606 | 804 |
| QLQ | 3.3963 | 2.5298 | 1326 |
| CYF | 3.3960 | 0.7757 | 642 |
| WPP | 3.3953 | 1.8929 | 303 |
| MAT | 3.3950 | 2.5429 | 1101 |
| DQQ | 3.3947 | 1.0422 | 401 |
| RNK | 3.3941 | 2.6780 | 2872 |
| TML | 3.3933 | 2.6747 | 2244 |
| QTW | 3.3930 | 1.3926 | 484 |
| PFY | 3.3922 | 2.2507 | 767 |
| MFS | 3.3922 | 2.1776 | 1242 |
| MWL | 3.3917 | 0.7670 | 1029 |
| RVY | 3.3915 | 2.6043 | 8178 |
| TQK | 3.3913 | 2.8054 | 1336 |
| NQW | 3.3898 | 2.1948 | 738 |
| VWF | 3.3893 | 0.7028 | 1510 |
| ILH | 3.3891 | 2.8404 | 2931 |
| SYT | 3.3890 | 3.0128 | 2003 |
| RYF | 3.3888 | 2.6957 | 2962 |
| HAE | 3.3884 | 1.1683 | 548 |
| ACF | 3.3879 | 2.2840 | 862 |
| EIV | 3.3878 | 2.1200 | 6817 |
| CTN | 3.3866 | 2.5775 | 1120 |
| IKT | 3.3865 | 2.5833 | 1054 |
| HHS | 3.3865 | 2.8354 | 963 |
| KDA | 3.3863 | 2.0104 | 1522 |
| HSN | 3.3862 | 2.5437 | 1569 |
| MFI | 3.3857 | 0.8963 | 902 |
| VYK | 3.3857 | 2.2492 | 3433 |
| LQF | 3.3854 | 2.4081 | 1386 |
| RDW | 3.3854 | 1.1265 | 3125 |
| SNL | 3.3853 | 3.1080 | 3845 |
| KMT | 3.3853 | 1.0377 | 623 |
| DSI | 3.3851 | 2.4676 | 4429 |
| KHP | 3.3847 | 3.0436 | 780 |
| QIS | 3.3845 | 2.6346 | 2587 |
| HFM | 3.3843 | 1.3270 | 288 |
| EMP | 3.3840 | 0.9686 | 663 |
| MQM | 3.3831 | 0.2926 | 55 |
| HAW | 3.3831 | 1.5059 | 338 |
| KSR | 3.3831 | 2.8774 | 12486 |
| QTP | 3.3826 | 1.8616 | 302 |
| QVW | 3.3824 | 0.9051 | 1598 |
| VHY | 3.3821 | 2.6606 | 1654 |
| KTR | 3.3820 | 3.0380 | 6608 |
| SNC | 3.3818 | 2.7972 | 2718 |
| HVM | 3.3817 | 2.3146 | 853 |
| SMH | 3.3817 | 2.2282 | 957 |
| VNP | 3.3814 | 2.5431 | 798 |
| WAI | 3.3814 | 0.6647 | 1597 |
| PYQ | 3.3813 | 2.5261 | 271 |
| III | 3.3813 | 1.3492 | 1600 |
| FTH | 3.3811 | 2.6853 | 832 |
| MSF | 3.3809 | 1.7414 | 1624 |
| KWA | 3.3808 | 0.8356 | 1544 |
| SPF | 3.3808 | 2.9490 | 470 |
| SYL | 3.3804 | 2.8015 | 4032 |
| KEL | 3.3802 | 2.6435 | 4693 |
| DWW | 3.3800 | 0.4768 | 1420 |
| WWM | 3.3799 | 0.0000 | 987 |
| EIR | 3.3797 | 2.5459 | 9960 |
| ICY | 3.3790 | 2.5419 | 1786 |
| YKP | 3.3789 | 2.9619 | 510 |
| CYT | 3.3787 | 2.4399 | 1423 |
| WVI | 3.3787 | 1.0278 | 2585 |
| MIA | 3.3786 | 2.9234 | 2219 |
| PME | 3.3785 | 1.1836 | 314 |
| SCP | 3.3780 | 1.4400 | 1116 |
| YYR | 3.3779 | 2.5921 | 2899 |
| WFD | 3.3769 | 0.7932 | 596 |
| NCV | 3.3768 | 2.2399 | 2854 |
| YLP | 3.3765 | 2.4924 | 823 |
| HDY | 3.3752 | 2.2154 | 601 |
| YAN | 3.3752 | 1.9929 | 1040 |
| SMF | 3.3750 | 2.0164 | 1454 |
| LRP | 3.3750 | 2.2103 | 2445 |
| SHI | 3.3750 | 3.4524 | 2194 |
| QYE | 3.3749 | 2.0291 | 1389 |
| NSR | 3.3748 | 2.9944 | 7090 |
| NVQ | 3.3747 | 2.0608 | 2809 |
| HLR | 3.3745 | 3.2910 | 4472 |
| HKA | 3.3744 | 2.6009 | 1033 |
| DRI | 3.3741 | 3.3143 | 6472 |
| HTL | 3.3739 | 3.7487 | 1727 |
| IYT | 3.3737 | 2.2316 | 1547 |
| MPL | 3.3730 | 1.9498 | 543 |
| QHA | 3.3729 | 1.9378 | 708 |
| MVM | 3.3726 | 0.5875 | 831 |
| QLT | 3.3726 | 3.1476 | 2809 |
| MYE | 3.3726 | 1.5688 | 759 |
| EQI | 3.3723 | 1.6484 | 1683 |
| RAC | 3.3717 | 1.2917 | 5881 |
| MTL | 3.3714 | 2.5341 | 1466 |
| WEW | 3.3713 | 0.1951 | 2586 |
| WGV | 3.3713 | 0.6204 | 14723 |
| HRI | 3.3713 | 2.8772 | 1598 |
| IKF | 3.3711 | 2.1613 | 1601 |
| IKL | 3.3711 | 2.4103 | 2921 |
| TSP | 3.3710 | 2.3250 | 1018 |
| HKW | 3.3707 | 0.7199 | 311 |
| CWF | 3.3706 | 0.4641 | 652 |
| QMW | 3.3704 | 0.1669 | 256 |
| NRV | 3.3703 | 2.5667 | 8669 |
| KMV | 3.3700 | 2.0146 | 2499 |
| TNR | 3.3698 | 2.7982 | 3663 |
| YCT | 3.3694 | 2.6474 | 1032 |
| KRH | 3.3693 | 2.5253 | 2834 |
| ITT | 3.3691 | 2.8141 | 1396 |
| QAW | 3.3690 | 0.8762 | 1152 |
| MYT | 3.3690 | 2.2112 | 1190 |
| HRW | 3.3689 | 1.1439 | 1433 |
| WWC | 3.3689 | 0.0190 | 1518 |
| NCT | 3.3687 | 2.8205 | 1253 |
| PYL | 3.3686 | 2.7766 | 1091 |
| IDH | 3.3683 | 1.3125 | 335 |
| NWK | 3.3682 | 1.1241 | 1505 |
| HTS | 3.3680 | 2.8254 | 2067 |
| VWW | 3.3678 | 0.3859 | 3509 |
| ITP | 3.3672 | 3.6023 | 756 |
| KHA | 3.3671 | 2.6269 | 1450 |
| EVI | 3.3669 | 2.0027 | 7429 |
| LQW | 3.3666 | 1.2548 | 1133 |
| DTH | 3.3664 | 2.2515 | 1466 |
| EWA | 3.3659 | 0.7887 | 3445 |
| VDD | 3.3658 | 1.0630 | 2260 |
| EQF | 3.3657 | 1.8264 | 1016 |
| GRW | 3.3652 | 1.5774 | 16947 |
| RYW | 3.3650 | 2.5416 | 2023 |
| NIG | 3.3649 | 2.2369 | 4859 |
| TKS | 3.3649 | 3.1548 | 4318 |
| IQF | 3.3647 | 2.1481 | 619 |
| MTT | 3.3647 | 2.8874 | 665 |
| YPH | 3.3642 | 2.7007 | 590 |
| SYH | 3.3641 | 2.8751 | 1075 |
| SMI | 3.3641 | 2.2089 | 2166 |
| PSE | 3.3639 | 2.0709 | 1852 |
| RDF | 3.3638 | 1.7443 | 1872 |
| LHY | 3.3633 | 2.5150 | 1228 |
| WWL | 3.3632 | 0.4458 | 2488 |
| YVK | 3.3621 | 2.2791 | 3524 |
| MIM | 3.3620 | 0.7750 | 194 |
| AHL | 3.3618 | 2.5616 | 1482 |
| KRA | 3.3616 | 2.5095 | 8583 |
| EYA | 3.3615 | 2.1779 | 3804 |
| WHI | 3.3613 | 1.6603 | 860 |
| AYK | 3.3612 | 2.6741 | 2147 |
| PHW | 3.3607 | 0.7376 | 137 |

TABLE F-continued

Medium-expressing EGFP variants

| AA SEQ | Mean | Range | Total counts |
|---|---|---|---|
| FLH | 3.3603 | 2.9817 | 929 |
| HSH | 3.3602 | 2.4564 | 784 |
| VDF | 3.3601 | 1.5708 | 1796 |
| SSF | 3.3595 | 2.6190 | 2508 |
| TVK | 3.3595 | 2.5415 | 4566 |
| YQV | 3.3593 | 2.5985 | 2199 |
| QFV | 3.3592 | 2.4024 | 1649 |
| YSF | 3.3591 | 2.3280 | 1447 |
| QSW | 3.3591 | 0.8584 | 873 |
| WAK | 3.3590 | 0.2403 | 1819 |
| HCW | 3.3588 | 0.6724 | 584 |
| PHF | 3.3588 | 2.4970 | 405 |
| PTW | 3.3585 | 1.5472 | 594 |
| PFD | 3.3584 | 1.6158 | 302 |
| HQL | 3.3578 | 2.8298 | 1165 |
| ESM | 3.3572 | 2.2689 | 2604 |
| KEA | 3.3570 | 2.2102 | 2535 |
| CWD | 3.3567 | 0.4129 | 674 |
| NSQ | 3.3563 | 2.3866 | 1775 |
| YMR | 3.3558 | 2.5743 | 1891 |
| DSF | 3.3555 | 2.2540 | 2348 |
| RPF | 3.3554 | 2.7276 | 1136 |
| PIF | 3.3553 | 1.9031 | 728 |
| TPA | 3.3549 | 2.3993 | 887 |
| QTH | 3.3548 | 3.1373 | 802 |
| MQL | 3.3548 | 2.1821 | 1175 |
| ERY | 3.3545 | 2.7294 | 4861 |
| TTN | 3.3542 | 2.6771 | 1097 |
| LWM | 3.3541 | 0.6990 | 836 |
| YIF | 3.3539 | 2.3249 | 839 |
| THQ | 3.3538 | 2.3337 | 427 |
| TLH | 3.3538 | 3.1626 | 1768 |
| SRY | 3.3538 | 3.7066 | 6137 |
| RKN | 3.3533 | 2.0369 | 2682 |
| CAY | 3.3527 | 2.4630 | 1664 |
| HLK | 3.3521 | 2.5485 | 2376 |
| WDW | 3.3519 | 0.0884 | 1058 |
| KDL | 3.3518 | 2.1339 | 2509 |
| TNT | 3.3516 | 2.6842 | 1190 |
| TEK | 3.3515 | 2.1047 | 2709 |
| VVV | 3.3514 | 1.1964 | 21747 |
| DGM | 3.3511 | 0.7744 | 2646 |
| KPV | 3.3508 | 2.8365 | 2569 |
| IKP | 3.3506 | 2.5609 | 1133 |
| VDW | 3.3504 | 1.0389 | 2517 |
| WGH | 3.3504 | 0.6465 | 2265 |
| ENW | 3.3504 | 0.9116 | 888 |
| MEE | 3.3499 | 0.4252 | 859 |
| QFL | 3.3494 | 2.3401 | 1459 |
| RMY | 3.3494 | 1.9833 | 2132 |
| IHH | 3.3493 | 2.3404 | 820 |
| DFQ | 3.3492 | 1.8060 | 919 |
| VQH | 3.3489 | 1.5810 | 1155 |
| RMN | 3.3488 | 1.5094 | 1479 |
| DLF | 3.3487 | 2.4439 | 2292 |
| PIW | 3.3487 | 1.0844 | 629 |
| WEE | 3.3484 | 0.3557 | 2407 |
| WEC | 3.3482 | 0.3738 | 1857 |
| QEG | 3.3476 | 0.9291 | 4685 |
| TNA | 3.3475 | 2.9020 | 1661 |
| RNT | 3.3474 | 3.1052 | 3568 |
| IRP | 3.3474 | 1.9333 | 1232 |
| NEM | 3.3473 | 0.4484 | 466 |
| NSW | 3.3472 | 1.8934 | 1333 |
| KVT | 3.3468 | 2.4407 | 5447 |
| QQQ | 3.3465 | 2.2328 | 750 |
| DML | 3.3462 | 2.2968 | 1766 |
| TIV | 3.3460 | 2.5064 | 4510 |
| RMW | 3.3459 | 0.8252 | 2047 |
| DHA | 3.3459 | 2.3075 | 781 |
| QEY | 3.3454 | 1.7441 | 975 |
| QRI | 3.3453 | 2.7011 | 2749 |
| FMW | 3.3451 | 0.3258 | 499 |
| KRL | 3.3450 | 2.7242 | 8103 |
| THC | 3.3447 | 2.7593 | 941 |
| QPI | 3.3446 | 2.0986 | 453 |
| RVF | 3.3444 | 2.1799 | 7640 |
| HDI | 3.3444 | 2.3959 | 632 |
| FNS | 3.3442 | 2.0380 | 1362 |
| DWA | 3.3434 | 0.7036 | 1611 |
| MGL | 3.3433 | 1.0062 | 5892 |
| VWC | 3.3432 | 0.4173 | 3514 |
| EVY | 3.3432 | 2.4627 | 5663 |
| EKA | 3.3431 | 2.3788 | 3721 |
| CAW | 3.3430 | 0.8651 | 1972 |
| SLI | 3.3427 | 2.9895 | 7240 |
| THA | 3.3426 | 2.6982 | 1008 |
| IPK | 3.3420 | 2.4802 | 711 |
| YET | 3.3418 | 2.2704 | 1044 |
| MQC | 3.3412 | 1.1761 | 713 |
| MWN | 3.3409 | 0.6091 | 577 |
| FCG | 3.3407 | 1.0481 | 2628 |
| HIP | 3.3405 | 2.8811 | 899 |
| WEL | 3.3404 | 0.5056 | 3115 |
| HIA | 3.3403 | 3.0826 | 1975 |
| TMN | 3.3400 | 1.3500 | 281 |
| QPY | 3.3397 | 2.4744 | 458 |
| WHF | 3.3395 | 0.6622 | 447 |
| QQG | 3.3395 | 1.6519 | 2429 |
| ENV | 3.3392 | 1.8088 | 2996 |
| NST | 3.3392 | 3.0227 | 1751 |
| QHR | 3.3390 | 2.6691 | 1214 |
| RIW | 3.3387 | 1.6367 | 4216 |
| FKE | 3.3386 | 0.9335 | 846 |
| TIA | 3.3385 | 3.7704 | 3359 |
| FEH | 3.3384 | 2.2038 | 545 |
| PML | 3.3384 | 2.5823 | 627 |
| WVP | 3.3382 | 0.8772 | 1971 |
| AKN | 3.3382 | 1.9336 | 1327 |
| HHG | 3.3381 | 1.2237 | 792 |
| QTV | 3.3380 | 2.2470 | 3230 |
| WAE | 3.3380 | 0.6553 | 2391 |
| CNQ | 3.3380 | 2.4571 | 495 |
| YEL | 3.3380 | 1.8179 | 2030 |
| NRH | 3.3376 | 3.4003 | 1460 |
| FAK | 3.3375 | 1.4640 | 820 |
| FAD | 3.3369 | 0.9323 | 763 |
| AYN | 3.3369 | 3.1033 | 1535 |
| VPH | 3.3367 | 1.7043 | 1284 |
| TNC | 3.3365 | 2.0092 | 1081 |
| WEV | 3.3364 | 0.3719 | 4519 |
| EQY | 3.3362 | 1.6153 | 750 |
| ELM | 3.3359 | 1.7229 | 3314 |
| VDE | 3.3358 | 1.2467 | 3843 |
| LRW | 3.3355 | 1.9430 | 5833 |
| WEF | 3.3351 | 0.5961 | 1017 |
| ADQ | 3.3350 | 0.9923 | 1167 |
| HWE | 3.3349 | 0.5032 | 433 |
| TFN | 3.3349 | 2.3095 | 981 |
| LQH | 3.3349 | 2.0733 | 774 |
| MYA | 3.3348 | 2.1286 | 1362 |
| EIS | 3.3345 | 3.0263 | 5592 |
| HEY | 3.3343 | 2.6620 | 1023 |
| RLH | 3.3341 | 3.3467 | 6900 |
| DFM | 3.3340 | 1.8155 | 735 |
| TEI | 3.3340 | 2.5266 | 2806 |
| MLK | 3.3337 | 2.1818 | 2137 |
| VWS | 3.3336 | 0.7072 | 5786 |
| LWF | 3.3335 | 0.8366 | 1115 |
| KVE | 3.3334 | 2.0127 | 5197 |
| WPH | 3.3334 | 0.6863 | 247 |
| MIN | 3.3331 | 1.8298 | 778 |
| EMN | 3.3331 | 0.9102 | 882 |
| DVF | 3.3330 | 1.5050 | 3064 |
| WTC | 3.3330 | 0.7809 | 1246 |
| RYK | 3.3329 | 2.6843 | 3603 |
| WMN | 3.3329 | 0.1700 | 305 |
| HLL | 3.3327 | 2.7596 | 3453 |
| TWP | 3.3326 | 1.4348 | 407 |
| YHC | 3.3325 | 2.0923 | 844 |

TABLE F-continued

Medium-expressing EGFP variants

| AA SEQ | Mean | Range | Total counts |
|---|---|---|---|
| SQC | 3.3319 | 2.4833 | 2133 |
| WDS | 3.3318 | 0.8287 | 1946 |
| NKD | 3.3313 | 2.0287 | 846 |
| TDP | 3.3312 | 1.1710 | 412 |
| MMN | 3.3311 | 0.5084 | 119 |
| WHC | 3.3310 | 1.6465 | 608 |
| PYK | 3.3310 | 2.9687 | 730 |
| YQS | 3.3307 | 2.6946 | 2682 |
| TPL | 3.3304 | 2.3446 | 1340 |
| YEN | 3.3303 | 1.9966 | 1118 |
| DKS | 3.3302 | 2.0092 | 3040 |
| ISA | 3.3297 | 2.6484 | 4974 |
| MGV | 3.3297 | 1.0968 | 6837 |
| KPR | 3.3293 | 2.5609 | 2738 |
| QNW | 3.3292 | 0.9210 | 321 |
| SNQ | 3.3291 | 2.6628 | 1177 |
| NHP | 3.3285 | 2.2294 | 455 |
| TTF | 3.3285 | 2.7453 | 2133 |
| QPN | 3.3281 | 1.4864 | 305 |
| TQV | 3.3280 | 2.4734 | 2399 |
| AEF | 3.3279 | 0.7733 | 1712 |
| VGH | 3.3275 | 1.3728 | 6102 |
| IPN | 3.3272 | 2.7000 | 550 |
| STH | 3.3271 | 2.6835 | 1648 |
| NWP | 3.3267 | 1.7600 | 186 |
| DLL | 3.3265 | 3.2621 | 7124 |
| YPY | 3.3264 | 2.1022 | 334 |
| QLN | 3.3262 | 2.5212 | 1349 |
| NWF | 3.3258 | 0.8937 | 514 |
| LTY | 3.3257 | 3.0786 | 2613 |
| RAI | 3.3256 | 2.2453 | 5528 |
| CWL | 3.3256 | 0.8125 | 2385 |
| QRH | 3.3252 | 2.0440 | 1238 |
| MGF | 3.3249 | 0.7406 | 1481 |
| DHW | 3.3246 | 1.3104 | 704 |
| VDG | 3.3244 | 0.7401 | 12782 |
| IAP | 3.3241 | 1.2000 | 206 |
| NEA | 3.3241 | 2.3125 | 1936 |
| YQA | 3.3241 | 1.5526 | 873 |
| DDV | 3.3239 | 0.8850 | 2289 |
| WYK | 3.3237 | 1.4829 | 884 |
| KSE | 3.3236 | 2.8053 | 4634 |
| QTN | 3.3235 | 2.0429 | 566 |
| HML | 3.3234 | 2.4056 | 983 |
| KRT | 3.3234 | 2.9603 | 5187 |
| YEF | 3.3234 | 1.1712 | 825 |
| KWG | 3.3233 | 0.3662 | 4463 |
| QLP | 3.3233 | 2.9583 | 1653 |
| QAD | 3.3232 | 0.7686 | 1069 |
| EFL | 3.3226 | 2.3846 | 2301 |
| NLM | 3.3226 | 2.4058 | 1611 |
| MRY | 3.3222 | 2.5901 | 2713 |
| GQW | 3.3218 | 1.2933 | 3505 |
| VAC | 3.3218 | 3.1023 | 5664 |
| LQY | 3.3217 | 2.7926 | 975 |
| VFP | 3.3213 | 2.0819 | 897 |
| CMY | 3.3213 | 2.2020 | 834 |
| CTQ | 3.3212 | 2.1809 | 1010 |
| GHD | 3.3211 | 0.9283 | 1216 |
| ACI | 3.3210 | 2.1326 | 1732 |
| KER | 3.3209 | 2.3490 | 5840 |
| SSY | 3.3209 | 2.8500 | 3771 |
| IST | 3.3208 | 2.8889 | 3421 |
| NAF | 3.3207 | 2.6908 | 1847 |
| VDY | 3.3207 | 1.9710 | 1887 |
| SVY | 3.3202 | 2.9874 | 7425 |
| DWV | 3.3202 | 0.4202 | 2722 |
| IYY | 3.3199 | 2.0971 | 815 |
| NAL | 3.3198 | 2.9259 | 3161 |
| THL | 3.3196 | 3.6170 | 1877 |
| AVW | 3.3188 | 0.9253 | 5839 |
| NVS | 3.3187 | 2.6798 | 6061 |
| ANK | 3.3185 | 2.5489 | 2130 |
| QWW | 3.3185 | 0.5042 | 952 |
| VWM | 3.3184 | 0.4784 | 1714 |
| DPL | 3.3183 | 3.2827 | 1168 |
| SLH | 3.3182 | 2.6030 | 3940 |
| AWQ | 3.3177 | 1.2773 | 808 |
| GMF | 3.3175 | 1.3190 | 1433 |
| RLI | 3.3169 | 2.4425 | 10857 |
| LWI | 3.3166 | 0.8034 | 1767 |
| LHR | 3.3166 | 2.5564 | 3271 |
| QKS | 3.3164 | 2.6557 | 1728 |
| FIP | 3.3164 | 2.5000 | 417 |
| TIL | 3.3163 | 2.8243 | 3324 |
| WGL | 3.3160 | 0.7179 | 9441 |
| DFC | 3.3159 | 1.5174 | 1424 |
| HPL | 3.3159 | 2.5926 | 467 |
| CHH | 3.3157 | 2.3967 | 788 |
| VEW | 3.3157 | 0.2722 | 4989 |
| STT | 3.3156 | 2.8310 | 1943 |
| EHL | 3.3156 | 2.0015 | 1659 |
| TCF | 3.3154 | 2.1590 | 1184 |
| KET | 3.3154 | 2.4673 | 1762 |
| WER | 3.3153 | 1.0698 | 6079 |
| AGM | 3.3151 | 1.1063 | 4173 |
| RMH | 3.3149 | 2.7095 | 836 |
| SKC | 3.3149 | 2.4628 | 4408 |
| KLP | 3.3148 | 2.9231 | 1684 |
| ACN | 3.3145 | 1.8667 | 890 |
| KVC | 3.3141 | 2.3908 | 5061 |
| TLI | 3.3138 | 2.9979 | 3975 |
| WKN | 3.3136 | 1.1233 | 653 |
| DIM | 3.3134 | 1.8603 | 1288 |
| CPW | 3.3133 | 0.5875 | 327 |
| WVV | 3.3133 | 0.8898 | 8058 |
| PFW | 3.3132 | 1.2455 | 370 |
| PCK | 3.3130 | 1.6588 | 331 |
| HYE | 3.3127 | 2.7803 | 1145 |
| VWN | 3.3126 | 0.9236 | 1726 |
| KEM | 3.3125 | 0.2610 | 1105 |
| RTN | 3.3124 | 2.5639 | 3160 |
| TFA | 3.3122 | 2.5333 | 1833 |
| VPF | 3.3122 | 1.8524 | 1108 |
| IWM | 3.3121 | 0.6211 | 448 |
| RSY | 3.3119 | 2.9053 | 6193 |
| ILR | 3.3119 | 2.6236 | 11637 |
| DQC | 3.3113 | 2.9388 | 1713 |
| YIN | 3.3113 | 1.9631 | 1351 |
| RYH | 3.3113 | 3.2276 | 2504 |
| WDI | 3.3108 | 1.1103 | 838 |
| GMD | 3.3108 | 1.4767 | 2523 |
| SLF | 3.3108 | 2.7500 | 3512 |
| KEW | 3.3108 | 0.5706 | 2040 |
| FWG | 3.3104 | 0.5591 | 2479 |
| TLC | 3.3101 | 2.5454 | 3775 |
| SKR | 3.3101 | 2.6623 | 10734 |
| YNG | 3.3100 | 2.1008 | 2275 |
| YSA | 3.3093 | 2.8788 | 3706 |
| CNK | 3.3093 | 2.1646 | 1141 |
| ESF | 3.3091 | 2.8533 | 3185 |
| RMK | 3.3090 | 1.4991 | 2450 |
| WVY | 3.3087 | 0.6029 | 2339 |
| DWG | 3.3086 | 0.6556 | 4647 |
| CGW | 3.3086 | 0.2513 | 5540 |
| TVH | 3.3084 | 2.4830 | 2402 |
| IQA | 3.3083 | 2.4343 | 1458 |
| IYA | 3.3080 | 2.7294 | 2020 |
| REI | 3.3077 | 2.6337 | 6978 |
| IYP | 3.3076 | 1.6083 | 437 |
| LQC | 3.3073 | 2.1928 | 1606 |
| MHL | 3.3073 | 2.5759 | 1458 |
| SQH | 3.3070 | 2.8413 | 1402 |
| PDI | 3.3070 | 1.5931 | 698 |
| AGF | 3.3069 | 2.1644 | 4542 |
| CYS | 3.3069 | 2.4044 | 2903 |
| WVR | 3.3067 | 0.6519 | 12695 |
| MGY | 3.3066 | 0.9315 | 1078 |
| FNM | 3.3066 | 2.3974 | 241 |
| HFQ | 3.3065 | 2.0169 | 418 |

TABLE F-continued

Medium-expressing EGFP variants

| AA SEQ | Mean | Range | Total counts |
|---|---|---|---|
| FDG | 3.3064 | 1.0255 | 2220 |
| CVQ | 3.3063 | 2.0362 | 2188 |
| LHC | 3.3063 | 2.5811 | 1823 |
| DCY | 3.3062 | 2.1222 | 1239 |
| WNS | 3.3061 | 1.8214 | 1426 |
| WPC | 3.3060 | 1.2968 | 678 |
| HCG | 3.3059 | 1.0288 | 1647 |
| MFR | 3.3059 | 2.3870 | 2499 |
| RQH | 3.3059 | 2.7367 | 1450 |
| PHN | 3.3058 | 1.7195 | 334 |
| KDE | 3.3057 | 1.8538 | 1241 |
| MGR | 3.3056 | 1.2811 | 9369 |
| NHE | 3.3056 | 2.4954 | 806 |
| IEQ | 3.3056 | 1.8238 | 1074 |
| LCA | 3.3051 | 2.3600 | 3400 |
| VPD | 3.3051 | 2.0116 | 1837 |
| QQR | 3.3047 | 2.1612 | 2064 |
| HRN | 3.3047 | 2.5030 | 1347 |
| MEW | 3.3047 | 0.0601 | 1214 |
| NMA | 3.3045 | 1.9708 | 894 |
| VGL | 3.3044 | 1.8803 | 24905 |
| EYV | 3.3044 | 2.4417 | 5641 |
| HIS | 3.3040 | 2.8681 | 2325 |
| KPQ | 3.3040 | 2.6452 | 881 |
| AYV | 3.3039 | 2.5977 | 3673 |
| EML | 3.3037 | 1.6495 | 3057 |
| DFD | 3.3035 | 1.7443 | 758 |
| DNS | 3.3035 | 2.9136 | 2537 |
| PGL | 3.3031 | 1.7762 | 4776 |
| WWA | 3.3031 | 0.4440 | 2477 |
| PMP | 3.3030 | 1.0909 | 56 |
| QDF | 3.3025 | 2.0235 | 742 |
| KAS | 3.3025 | 3.2894 | 5354 |
| RQF | 3.3023 | 2.7634 | 2157 |
| LWR | 3.3022 | 1.4472 | 6412 |
| RLY | 3.3021 | 2.6969 | 7245 |
| QLA | 3.3018 | 2.9245 | 3217 |
| NRL | 3.3017 | 2.7021 | 5089 |
| WNL | 3.3013 | 1.7353 | 1442 |
| QGP | 3.3010 | 1.6154 | 1259 |
| PQC | 3.3009 | 2.3816 | 500 |
| IIM | 3.3008 | 0.8562 | 481 |
| WDM | 3.3008 | 0.1016 | 428 |
| SNN | 3.3007 | 2.4845 | 2108 |
| RAK | 3.3007 | 1.9627 | 5006 |
| FQL | 3.3006 | 2.6037 | 730 |
| GPY | 3.3005 | 1.3941 | 1231 |
| GGH | 3.3002 | 1.0606 | 8023 |
| TIS | 3.3001 | 2.7696 | 3670 |
| DLA | 3.3001 | 2.5920 | 4260 |
| SYE | 3.2998 | 2.8230 | 2324 |
| RAF | 3.2998 | 2.0053 | 2523 |
| NMT | 3.2998 | 1.7830 | 321 |
| WWE | 3.2996 | 0.1822 | 2375 |
| MEM | 3.2994 | 0.1338 | 331 |
| DNA | 3.2994 | 2.1056 | 2000 |
| ITF | 3.2993 | 2.8333 | 856 |
| FNA | 3.2984 | 2.4506 | 1172 |
| SIR | 3.2983 | 2.9577 | 11028 |
| KMS | 3.2981 | 2.5231 | 1943 |
| VAF | 3.2979 | 1.3929 | 2857 |
| GQM | 3.2975 | 0.6902 | 1855 |
| DLC | 3.2973 | 2.7616 | 3880 |
| YWG | 3.2971 | 0.5239 | 3019 |
| EGP | 3.2970 | 1.9526 | 3895 |
| TTP | 3.2969 | 1.6810 | 272 |
| VKF | 3.2966 | 2.0570 | 2312 |
| WEG | 3.2964 | 0.3888 | 9490 |
| VNY | 3.2962 | 2.3936 | 2454 |
| AGC | 3.2962 | 1.7420 | 9473 |
| WAL | 3.2962 | 1.1148 | 3606 |
| MDW | 3.2956 | 0.4911 | 557 |
| WWF | 3.2955 | 0.2081 | 716 |
| PQE | 3.2955 | 1.7905 | 449 |
| CWI | 3.2952 | 0.9181 | 751 |
| ENQ | 3.2951 | 2.2478 | 1770 |
| RTK | 3.2945 | 3.0244 | 4149 |
| MKP | 3.2943 | 1.3116 | 303 |
| RTW | 3.2943 | 1.9872 | 2538 |
| YHQ | 3.2942 | 2.6429 | 195 |
| YMD | 3.2937 | 1.0503 | 208 |
| FWA | 3.2936 | 1.1576 | 672 |
| VDV | 3.2935 | 1.4327 | 7221 |
| CKQ | 3.2934 | 2.4254 | 971 |
| EFV | 3.2934 | 2.2730 | 4825 |
| ELV | 3.2931 | 2.2534 | 12913 |
| DQV | 3.2929 | 2.2094 | 2180 |
| FHA | 3.2929 | 1.8617 | 459 |
| WMW | 3.2928 | 0.0000 | 881 |
| HNW | 3.2926 | 0.2969 | 314 |
| LCM | 3.2926 | 1.4789 | 1715 |
| WVK | 3.2925 | 0.8471 | 2608 |
| VCG | 3.2925 | 0.8793 | 15034 |
| QGC | 3.2921 | 1.1768 | 3919 |
| RIQ | 3.2921 | 2.6944 | 3223 |
| YCS | 3.2919 | 2.3627 | 2384 |
| NLW | 3.2917 | 1.7162 | 2018 |
| HSR | 3.2916 | 2.9310 | 3594 |
| DFL | 3.2913 | 2.1846 | 1313 |
| MGA | 3.2913 | 1.0396 | 4651 |
| DGH | 3.2912 | 0.9913 | 1927 |
| GMA | 3.2909 | 0.9725 | 4068 |
| NVW | 3.2902 | 1.8762 | 2878 |
| VWI | 3.2901 | 1.0621 | 2510 |
| WDV | 3.2900 | 1.3288 | 2977 |
| AVT | 3.2900 | 3.6648 | 4483 |
| CVH | 3.2899 | 2.6921 | 2767 |
| KEN | 3.2896 | 1.6303 | 1623 |
| MSA | 3.2894 | 2.7082 | 3388 |
| YDT | 3.2892 | 2.7538 | 5492 |
| QHT | 3.2891 | 2.3945 | 1114 |
| PCW | 3.2891 | 2.0500 | 473 |
| ADC | 3.2890 | 1.7603 | 1809 |
| VVF | 3.2890 | 1.2558 | 5683 |
| CKA | 3.2887 | 2.6214 | 3025 |
| IHT | 3.2886 | 2.6599 | 943 |
| IVH | 3.2882 | 3.0570 | 3219 |
| FTW | 3.2882 | 1.6795 | 528 |
| AQI | 3.2880 | 2.2570 | 1517 |
| YSF | 3.2878 | 2.8163 | 5488 |
| NWV | 3.2878 | 0.5707 | 1803 |
| NWI | 3.2878 | 1.4100 | 1271 |
| RPY | 3.2875 | 2.2306 | 1217 |
| ADT | 3.2875 | 1.8000 | 1915 |
| LKL | 3.2875 | 2.8457 | 5308 |
| MKM | 3.2873 | 0.3811 | 268 |
| YWP | 3.2872 | 1.0889 | 146 |
| SFC | 3.2871 | 2.0084 | 1880 |
| WGW | 3.2871 | 0.0803 | 6592 |
| DPC | 3.2870 | 1.8838 | 473 |
| WKA | 3.2869 | 1.6775 | 2110 |
| CIR | 3.2869 | 2.0078 | 5858 |
| DFR | 3.2868 | 2.0765 | 3076 |
| NGH | 3.2866 | 2.2178 | 9879 |
| EWG | 3.2865 | 0.3217 | 10065 |
| ITR | 3.2864 | 2.8274 | 4700 |
| IYE | 3.2864 | 2.0410 | 2006 |
| VEG | 3.2863 | 0.7646 | 23246 |
| SKV | 3.2860 | 2.6186 | 9155 |
| TTT | 3.2859 | 3.5775 | 1373 |
| VDL | 3.2859 | 2.1463 | 4789 |
| NVM | 3.2853 | 2.1606 | 1622 |
| WAW | 3.2852 | 0.3317 | 2142 |
| WGC | 3.2851 | 0.4456 | 5548 |
| MKE | 3.2850 | 1.6300 | 699 |
| LAH | 3.2849 | 2.7992 | 1137 |
| TSN | 3.2848 | 3.1667 | 2268 |
| LCH | 3.2847 | 2.6006 | 1376 |
| VPM | 3.2847 | 2.1492 | 820 |
| FAF | 3.2846 | 2.1754 | 538 |

TABLE F-continued

Medium-expressing EGFP variants

| AA SEQ | Mean | Range | Total counts |
|---|---|---|---|
| EPF | 3.2846 | 1.9593 | 353 |
| VME | 3.2844 | 0.5542 | 2104 |
| LWL | 3.2843 | 1.3932 | 3756 |
| FLP | 3.2841 | 2.2819 | 621 |
| QMP | 3.2840 | 0.8717 | 411 |
| VMD | 3.2840 | 1.0094 | 1491 |
| RDY | 3.2840 | 2.3192 | 2453 |
| MDV | 3.2840 | 1.1180 | 1407 |
| PSY | 3.2839 | 3.1476 | 1135 |
| SMN | 3.2839 | 2.1203 | 1015 |
| AMI | 3.2838 | 1.4777 | 1328 |
| MEG | 3.2836 | 0.5251 | 4687 |
| AIY | 3.2836 | 2.3137 | 2388 |
| WNY | 3.2835 | 0.8014 | 862 |
| KHG | 3.2834 | 1.7862 | 2063 |
| FGV | 3.2828 | 1.5344 | 6141 |
| LQM | 3.2827 | 1.4988 | 1267 |
| RNM | 3.2826 | 2.1842 | 1927 |
| QRW | 3.2825 | 0.8941 | 1957 |
| FGP | 3.2824 | 2.0000 | 946 |
| VCF | 3.2822 | 0.8170 | 1679 |
| REF | 3.2822 | 2.6111 | 3550 |
| WGK | 3.2822 | 0.4439 | 3466 |
| YRP | 3.2817 | 1.7000 | 600 |
| EGG | 3.2811 | 0.9846 | 44206 |
| LWS | 3.2809 | 2.1512 | 4118 |
| WDE | 3.2808 | 0.4120 | 1545 |
| MDM | 3.2804 | 0.5609 | 366 |
| MLC | 3.2804 | 1.9637 | 2964 |
| QND | 3.2801 | 1.4917 | 385 |
| HWG | 3.2800 | 0.8197 | 1876 |
| IFN | 3.2797 | 1.8866 | 1136 |
| EAY | 3.2794 | 2.3783 | 2629 |
| KWE | 3.2794 | 0.5238 | 1183 |
| PTM | 3.2792 | 0.7069 | 99 |
| KGI | 3.2790 | 2.0469 | 5790 |
| LKQ | 3.2789 | 3.6592 | 1989 |
| KCE | 3.2784 | 1.4560 | 1823 |
| AWI | 3.2780 | 0.5713 | 1046 |
| QQW | 3.2780 | 0.6452 | 319 |
| LHL | 3.2779 | 2.5579 | 2111 |
| YNP | 3.2778 | 3.0036 | 491 |
| PCL | 3.2775 | 3.3492 | 944 |
| PVA | 3.2774 | 2.7283 | 3004 |
| WAN | 3.2773 | 1.1734 | 693 |
| TIT | 3.2771 | 2.7606 | 1992 |
| AGW | 3.2771 | 0.8123 | 10382 |
| ETL | 3.2766 | 2.2991 | 3801 |
| WQK | 3.2766 | 1.5033 | 780 |
| ACD | 3.2765 | 1.2222 | 876 |
| ATW | 3.2764 | 1.2014 | 1864 |
| HWA | 3.2764 | 1.1719 | 452 |
| GWH | 3.2764 | 1.1896 | 1570 |
| SKT | 3.2763 | 2.6242 | 3645 |
| YWV | 3.2763 | 0.8354 | 1567 |
| WWW | 3.2762 | 0.0000 | 1434 |
| VVE | 3.2760 | 0.9598 | 12196 |
| ANM | 3.2760 | 1.5765 | 946 |
| SVI | 3.2758 | 2.5769 | 10832 |
| ADV | 3.2754 | 1.8907 | 3696 |
| YIC | 3.2749 | 1.7639 | 1805 |
| CWV | 3.2748 | 0.7008 | 2621 |
| DSC | 3.2747 | 2.3360 | 2522 |
| KMP | 3.2746 | 1.1073 | 546 |
| HIE | 3.2745 | 2.2462 | 1381 |
| QMK | 3.2744 | 0.5723 | 773 |
| QEM | 3.2744 | 1.8006 | 617 |
| RFC | 3.2743 | 2.7523 | 3356 |
| TTL | 3.2743 | 2.7173 | 1657 |
| AWF | 3.2741 | 0.7900 | 953 |
| VMA | 3.2741 | 0.8949 | 2506 |
| RQI | 3.2738 | 2.9450 | 3357 |
| APL | 3.2737 | 3.2457 | 1653 |
| SNV | 3.2734 | 2.3808 | 5527 |
| MPF | 3.2733 | 1.1805 | 255 |
| DLR | 3.2731 | 2.8202 | 8920 |
| AYI | 3.2727 | 2.4591 | 1601 |
| MGS | 3.2727 | 1.5548 | 4723 |
| QKV | 3.2726 | 1.8970 | 2544 |
| LNP | 3.2724 | 2.5602 | 527 |
| FMT | 3.2721 | 2.4630 | 581 |
| RYQ | 3.2719 | 2.9577 | 2353 |
| DGL | 3.2716 | 1.6559 | 8802 |
| VDP | 3.2714 | 1.9057 | 1152 |
| QML | 3.2711 | 1.7918 | 1358 |
| SLK | 3.2710 | 2.3752 | 6852 |
| VDS | 3.2709 | 2.2333 | 5429 |
| HSL | 3.2708 | 2.8791 | 2237 |
| SYA | 3.2708 | 3.0209 | 3582 |
| LAK | 3.2707 | 3.0857 | 3162 |
| CHR | 3.2704 | 2.3322 | 1798 |
| VWY | 3.2704 | 0.6044 | 1581 |
| FTY | 3.2703 | 3.0250 | 814 |
| YTS | 3.2702 | 3.1058 | 2568 |
| ERP | 3.2700 | 2.0714 | 3080 |
| KDV | 3.2698 | 1.7552 | 2097 |
| RYL | 3.2698 | 3.5237 | 7318 |
| YGK | 3.2697 | 1.8581 | 2493 |
| YEC | 3.2695 | 1.9158 | 1726 |
| TQL | 3.2695 | 3.8636 | 1843 |
| VGC | 3.2692 | 1.0868 | 15234 |
| YCI | 3.2691 | 2.0835 | 1313 |
| LQD | 3.2689 | 1.9600 | 889 |
| KAN | 3.2685 | 2.4598 | 2502 |
| MWG | 3.2682 | 0.2996 | 2974 |
| HQG | 3.2682 | 1.7197 | 1303 |
| LWQ | 3.2681 | 1.1244 | 1446 |
| RFW | 3.2681 | 0.9361 | 2862 |
| DLN | 3.2680 | 2.5759 | 2981 |
| TVY | 3.2679 | 2.7208 | 3734 |
| DGW | 3.2679 | 1.2769 | 4723 |
| WDR | 3.2675 | 0.6114 | 3786 |
| MHR | 3.2673 | 2.4667 | 1441 |
| GCC | 3.2673 | 1.2791 | 4816 |
| WVF | 3.2671 | 1.1930 | 1858 |
| GRG | 3.2670 | 1.6549 | 89055 |
| TDI | 3.2669 | 3.1519 | 1935 |
| YPL | 3.2664 | 2.4265 | 1482 |
| CKT | 3.2664 | 3.1853 | 1060 |
| GGF | 3.2663 | 1.2149 | 9003 |
| GWC | 3.2663 | 0.8429 | 5931 |
| VVS | 3.2661 | 2.4037 | 19818 |
| MCP | 3.2655 | 0.9569 | 185 |
| GQS | 3.2650 | 1.2904 | 5362 |
| QWH | 3.2650 | 1.0816 | 120 |
| WDK | 3.2650 | 0.6591 | 816 |
| YDQ | 3.2645 | 1.1503 | 437 |
| PYH | 3.2644 | 2.1429 | 211 |
| RTF | 3.2643 | 2.8901 | 3193 |
| PAV | 3.2640 | 2.4356 | 2265 |
| DHL | 3.2638 | 2.5289 | 1543 |
| PCC | 3.2638 | 2.5000 | 480 |
| LHF | 3.2636 | 2.6239 | 711 |
| VEE | 3.2636 | 0.7237 | 6065 |
| YNF | 3.2636 | 1.7864 | 488 |
| FAY | 3.2627 | 2.3716 | 450 |
| ANN | 3.2624 | 2.1178 | 1586 |
| AYT | 3.2624 | 2.5776 | 1585 |
| CGH | 3.2623 | 1.1124 | 1883 |
| WKY | 3.2622 | 1.5578 | 897 |
| QVN | 3.2618 | 2.7121 | 1999 |
| KCW | 3.2616 | 1.8357 | 2403 |
| RAY | 3.2615 | 2.1794 | 3311 |
| IGP | 3.2614 | 1.1310 | 1736 |
| CQI | 3.2613 | 1.8542 | 1078 |
| FGG | 3.2612 | 1.5189 | 12661 |
| MWS | 3.2611 | 1.0529 | 1429 |
| YCE | 3.2611 | 1.4700 | 1076 |
| TFM | 3.2610 | 1.8184 | 625 |
| KPP | 3.2610 | 1.5333 | 146 |

TABLE F-continued

Medium-expressing EGFP variants

| AA SEQ | Mean | Range | Total counts |
|---|---|---|---|
| PEP | 3.2609 | 1.7714 | 293 |
| WGG | 3.2609 | 0.5827 | 32405 |
| HPR | 3.2609 | 3.0341 | 1048 |
| AYF | 3.2608 | 2.2326 | 914 |
| CMN | 3.2607 | 1.5241 | 508 |
| DRY | 3.2607 | 2.3542 | 6007 |
| QCW | 3.2606 | 0.4240 | 953 |
| ADN | 3.2604 | 1.7111 | 736 |
| SIC | 3.2603 | 2.5861 | 4733 |
| CGQ | 3.2602 | 2.4069 | 2932 |
| EFW | 3.2601 | 1.7087 | 1310 |
| EFS | 3.2599 | 1.9817 | 3422 |
| NRS | 3.2598 | 2.3556 | 6018 |
| PYE | 3.2597 | 2.2882 | 592 |
| ECP | 3.2596 | 1.2100 | 881 |
| GGW | 3.2595 | 0.6626 | 26862 |
| NTE | 3.2595 | 2.2549 | 1552 |
| MGD | 3.2594 | 0.6351 | 2406 |
| RNL | 3.2593 | 3.4722 | 5467 |
| VDR | 3.2593 | 1.6336 | 8783 |
| QVH | 3.2586 | 1.9222 | 1271 |
| HAA | 3.2586 | 1.8462 | 924 |
| YFI | 3.2585 | 1.5119 | 730 |
| MKT | 3.2585 | 2.8452 | 1354 |
| QIP | 3.2583 | 2.6393 | 449 |
| CKK | 3.2581 | 1.9211 | 2038 |
| TMC | 3.2580 | 2.2008 | 843 |
| TIR | 3.2580 | 2.7258 | 6857 |
| KPM | 3.2580 | 1.8545 | 499 |
| VHT | 3.2580 | 3.2557 | 1258 |
| KRP | 3.2580 | 2.0069 | 1095 |
| CQH | 3.2579 | 2.4105 | 644 |
| HMF | 3.2578 | 1.3399 | 379 |
| FDT | 3.2578 | 1.7515 | 639 |
| EGV | 3.2577 | 1.0089 | 20540 |
| QRY | 3.2577 | 2.6036 | 2517 |
| YKS | 3.2574 | 2.3695 | 2642 |
| DMV | 3.2570 | 1.2945 | 1987 |
| QWG | 3.2568 | 0.6089 | 2671 |
| VCE | 3.2567 | 1.0548 | 3495 |
| RAN | 3.2565 | 2.5123 | 2827 |
| AWY | 3.2563 | 0.9548 | 1071 |
| SFV | 3.2563 | 2.4426 | 4459 |
| KTW | 3.2562 | 1.6524 | 1758 |
| YTR | 3.2561 | 2.7279 | 4538 |
| IAN | 3.2561 | 2.5590 | 933 |
| CMA | 3.2560 | 1.3603 | 927 |
| MWD | 3.2559 | 0.3031 | 406 |
| LNS | 3.2554 | 2.8485 | 4249 |
| HPG | 3.2552 | 1.8694 | 1253 |
| MWF | 3.2551 | 0.1307 | 293 |
| EFR | 3.2551 | 2.5513 | 7062 |
| QFE | 3.2550 | 2.4479 | 961 |
| REH | 3.2549 | 2.5491 | 2788 |
| RAE | 3.2547 | 2.5494 | 6948 |
| QPV | 3.2545 | 3.3048 | 1792 |
| FME | 3.2545 | 0.4355 | 435 |
| VQC | 3.2545 | 2.5087 | 2890 |
| GRV | 3.2544 | 1.4562 | 39036 |
| PVM | 3.2542 | 1.7418 | 1222 |
| YWE | 3.2539 | 1.0690 | 965 |
| WPG | 3.2539 | 0.7154 | 4242 |
| RSH | 3.2538 | 2.9201 | 4288 |
| EVK | 3.2538 | 2.0976 | 8702 |
| ELF | 3.2538 | 1.9465 | 3440 |
| DVA | 3.2537 | 1.8996 | 5325 |
| HWD | 3.2536 | 0.6504 | 485 |
| DAG | 3.2536 | 1.3205 | 8324 |
| EWD | 3.2535 | 0.1480 | 1375 |
| VAG | 3.2535 | 1.9872 | 26847 |
| PAL | 3.2534 | 3.4966 | 1506 |
| IWA | 3.2531 | 1.1727 | 1326 |
| YER | 3.2530 | 2.0498 | 4813 |
| QDD | 3.2529 | 1.3626 | 546 |
| IWI | 3.2529 | 0.4375 | 1007 |
| YTT | 3.2526 | 2.7349 | 1315 |
| TMA | 3.2522 | 1.9890 | 1027 |
| EPM | 3.2521 | 2.1963 | 654 |
| QST | 3.2519 | 2.7692 | 2127 |
| GHL | 3.2519 | 1.5532 | 2888 |
| CDG | 3.2516 | 1.2886 | 3984 |
| LCW | 3.2514 | 1.0477 | 2048 |
| GHA | 3.2513 | 1.9748 | 2390 |
| QQS | 3.2513 | 2.2101 | 1012 |
| CWA | 3.2513 | 0.4371 | 1808 |
| FHS | 3.2510 | 2.4725 | 935 |
| RHQ | 3.2509 | 1.8598 | 754 |
| DPI | 3.2509 | 2.7351 | 1469 |
| DWP | 3.2508 | 1.3817 | 477 |
| DKA | 3.2508 | 2.3250 | 2317 |
| LRY | 3.2507 | 2.6649 | 4428 |
| TVF | 3.2502 | 2.5553 | 3858 |
| LKI | 3.2497 | 2.3718 | 2627 |
| LYR | 3.2495 | 2.8595 | 6509 |
| VGE | 3.2495 | 1.1744 | 18089 |
| DFS | 3.2494 | 2.5529 | 2113 |
| RYI | 3.2494 | 2.8049 | 4503 |
| LAF | 3.2494 | 1.8778 | 1675 |
| HFR | 3.2493 | 2.3480 | 1682 |
| MKW | 3.2492 | 1.1461 | 943 |
| KVR | 3.2492 | 2.6583 | 17060 |
| KDR | 3.2490 | 2.2657 | 3992 |
| VMW | 3.2490 | 0.1607 | 2252 |
| WPR | 3.2488 | 1.5845 | 2032 |
| MYP | 3.2487 | 2.3111 | 500 |
| KCR | 3.2486 | 2.6028 | 7006 |
| HAF | 3.2486 | 1.5455 | 237 |
| TLY | 3.2486 | 3.3381 | 3847 |
| VQY | 3.2485 | 2.4167 | 1801 |
| TSV | 3.2483 | 3.5000 | 6947 |
| RGY | 3.2480 | 2.6374 | 8500 |
| HGH | 3.2479 | 1.9559 | 555 |
| AES | 3.2478 | 1.7991 | 5725 |
| PNW | 3.2477 | 1.1945 | 482 |
| KDQ | 3.2475 | 2.1139 | 1251 |
| MMH | 3.2474 | 1.6487 | 761 |
| KAQ | 3.2473 | 2.4644 | 2260 |
| LHA | 3.2473 | 3.3168 | 1565 |
| MAD | 3.2473 | 1.2801 | 737 |
| ELP | 3.2472 | 1.7922 | 1859 |
| HLP | 3.2470 | 3.2904 | 1207 |
| DDG | 3.2468 | 0.5453 | 3635 |
| QPF | 3.2468 | 1.5029 | 212 |
| KVM | 3.2466 | 1.5713 | 3425 |
| VVW | 3.2465 | 0.9167 | 8806 |
| GGM | 3.2465 | 1.5320 | 10965 |
| PFP | 3.2462 | 3.1379 | 220 |
| QCG | 3.2461 | 0.9998 | 3150 |
| GQG | 3.2458 | 1.4494 | 15292 |
| GRQ | 3.2457 | 2.2174 | 8771 |
| MWA | 3.2456 | 0.6106 | 1080 |
| DGG | 3.2455 | 1.1316 | 23750 |
| DCH | 3.2455 | 0.8641 | 330 |
| HTR | 3.2453 | 2.4749 | 2256 |
| IAW | 3.2451 | 0.6937 | 1438 |
| WKQ | 3.2451 | 1.7585 | 606 |
| RQY | 3.2451 | 2.6793 | 3492 |
| TEF | 3.2451 | 1.8566 | 1243 |
| IWP | 3.2449 | 2.0029 | 455 |
| LKM | 3.2448 | 1.9154 | 1682 |
| QQP | 3.2447 | 1.4778 | 185 |
| QQM | 3.2447 | 2.4272 | 652 |
| ISQ | 3.2446 | 2.9900 | 2527 |
| EPY | 3.2445 | 2.1869 | 843 |
| SMK | 3.2445 | 2.1849 | 1781 |
| GWQ | 3.2444 | 0.8239 | 3123 |
| CIS | 3.2444 | 2.4122 | 3205 |
| QPW | 3.2443 | 0.9475 | 242 |
| IFR | 3.2443 | 2.5897 | 3573 |
| TRY | 3.2441 | 2.8024 | 3740 |

TABLE F-continued

Medium-expressing EGFP variants

| AA SEQ | Mean | Range | Total counts |
|---|---|---|---|
| DGD | 3.2439 | 0.8358 | 4251 |
| SML | 3.2439 | 2.4039 | 3290 |
| IWW | 3.2438 | 0.2323 | 1240 |
| HPF | 3.2437 | 3.1273 | 237 |
| HVH | 3.2437 | 2.6476 | 1255 |
| QPT | 3.2434 | 1.6765 | 351 |
| IQR | 3.2431 | 2.5636 | 3943 |
| VCV | 3.2430 | 1.5982 | 6766 |
| FQH | 3.2429 | 2.3718 | 251 |
| KGK | 3.2426 | 1.8793 | 4693 |
| LYW | 3.2423 | 1.1803 | 1814 |
| KAA | 3.2422 | 2.5805 | 2732 |
| VMF | 3.2421 | 1.4477 | 1203 |
| MAW | 3.2421 | 0.2918 | 761 |
| GHF | 3.2420 | 1.3288 | 853 |
| WTE | 3.2419 | 0.6918 | 1162 |
| WCY | 3.2417 | 1.2442 | 717 |
| WGA | 3.2415 | 1.1256 | 9157 |
| LNW | 3.2415 | 1.8712 | 1262 |
| ETA | 3.2412 | 2.2980 | 2234 |
| VIP | 3.2411 | 2.8726 | 1688 |
| QNM | 3.2411 | 1.0806 | 513 |
| EGD | 3.2411 | 0.6445 | 7075 |
| ALY | 3.2411 | 2.8655 | 3875 |
| MSC | 3.2410 | 1.6863 | 2361 |
| QTQ | 3.2409 | 2.4211 | 770 |
| QGT | 3.2407 | 2.0511 | 3009 |
| VGG | 3.2407 | 1.3112 | 79467 |
| PCD | 3.2406 | 2.0000 | 551 |
| LRF | 3.2405 | 2.5034 | 4648 |
| GHT | 3.2404 | 1.8275 | 1412 |
| MGG | 3.2404 | 0.5198 | 13694 |
| RCY | 3.2403 | 2.2797 | 2340 |
| RKK | 3.2403 | 2.1333 | 3630 |
| MYD | 3.2403 | 1.3510 | 465 |
| GRY | 3.2402 | 2.1145 | 9581 |
| PRV | 3.2399 | 2.0953 | 4599 |
| DTT | 3.2398 | 2.5000 | 1406 |
| GMR | 3.2396 | 1.3194 | 8596 |
| ADE | 3.2395 | 1.6936 | 1552 |
| PWN | 3.2395 | 2.4764 | 366 |
| TPQ | 3.2395 | 1.8636 | 503 |
| SGW | 3.2395 | 1.2171 | 9815 |
| EMF | 3.2394 | 1.1204 | 747 |
| TEY | 3.2392 | 2.5492 | 1673 |
| CFE | 3.2391 | 1.2028 | 1108 |
| PCV | 3.2390 | 2.4023 | 984 |
| AHD | 3.2387 | 1.4500 | 714 |
| KAC | 3.2386 | 2.3667 | 3156 |
| LGY | 3.2386 | 2.1848 | 5425 |
| HWV | 3.2386 | 2.1518 | 803 |
| HWW | 3.2378 | 1.0864 | 399 |
| VPG | 3.2377 | 2.0036 | 9019 |
| KVS | 3.2377 | 2.9474 | 9836 |
| PDW | 3.2374 | 0.6333 | 486 |
| FAA | 3.2373 | 2.0000 | 1183 |
| HQV | 3.2373 | 2.9368 | 1279 |
| AKS | 3.2372 | 2.3231 | 3529 |
| RCE | 3.2371 | 1.6918 | 4239 |
| WAG | 3.2370 | 0.5671 | 11283 |
| WGD | 3.2366 | 0.6336 | 4646 |
| TYQ | 3.2366 | 2.4667 | 802 |
| KRS | 3.2365 | 2.3143 | 8155 |
| KMG | 3.2365 | 0.8647 | 2533 |
| MCQ | 3.2364 | 2.1972 | 692 |
| VED | 3.2363 | 1.6117 | 3768 |
| EPI | 3.2363 | 2.3764 | 2062 |
| RSW | 3.2361 | 2.5043 | 6581 |
| IMD | 3.2361 | 1.4317 | 422 |
| KAL | 3.2358 | 2.7189 | 4628 |
| FDV | 3.2357 | 1.3788 | 1383 |
| TQA | 3.2355 | 2.3676 | 1623 |
| RIL | 3.2355 | 2.9628 | 9638 |
| AHK | 3.2355 | 2.3363 | 1140 |
| LQL | 3.2354 | 2.6285 | 2644 |
| VAY | 3.2352 | 1.5816 | 3301 |
| PYW | 3.2349 | 1.0135 | 435 |
| WNT | 3.2348 | 2.2778 | 923 |
| RTA | 3.2348 | 2.7723 | 4738 |
| NRP | 3.2348 | 1.8071 | 553 |
| MSV | 3.2346 | 2.4704 | 4961 |
| QIW | 3.2346 | 1.3178 | 691 |
| PQH | 3.2344 | 2.2355 | 242 |
| NAP | 3.2343 | 2.4056 | 318 |
| RHI | 3.2342 | 2.9341 | 2333 |
| FHF | 3.2341 | 2.6348 | 325 |
| NSD | 3.2337 | 1.7057 | 1256 |
| TKE | 3.2337 | 2.1086 | 1390 |
| PYR | 3.2337 | 3.3368 | 1486 |
| EDV | 3.2336 | 1.8467 | 3820 |
| DPM | 3.2335 | 1.4715 | 554 |
| CIA | 3.2335 | 2.7736 | 3444 |
| YEK | 3.2334 | 1.7022 | 1955 |
| EFP | 3.2332 | 1.5762 | 683 |
| VSG | 3.2331 | 1.9514 | 26911 |
| SYK | 3.2331 | 2.5656 | 2963 |
| DAW | 3.2330 | 1.2256 | 1592 |
| QSN | 3.2329 | 2.8502 | 1556 |
| AMY | 3.2328 | 1.4962 | 1156 |
| GHC | 3.2328 | 1.0863 | 1869 |
| TCP | 3.2327 | 1.5364 | 308 |
| DGP | 3.2327 | 2.3896 | 2582 |
| MIS | 3.2326 | 2.1784 | 2300 |
| AEG | 3.2326 | 1.0491 | 13063 |
| STV | 3.2326 | 3.7300 | 7082 |
| YVR | 3.2325 | 2.3802 | 10959 |
| PCS | 3.2323 | 2.7129 | 869 |
| MPN | 3.2323 | 2.1667 | 155 |
| QGA | 3.2322 | 1.5466 | 5166 |
| QQL | 3.2322 | 2.7990 | 1492 |
| HWY | 3.2321 | 2.4303 | 324 |
| LNT | 3.2321 | 2.8281 | 1769 |
| CTP | 3.2320 | 2.0216 | 497 |
| AKK | 3.2320 | 1.9513 | 2299 |
| NCS | 3.2319 | 2.4896 | 1654 |
| ELL | 3.2319 | 3.2885 | 9878 |
| QLS | 3.2318 | 3.1809 | 4151 |
| HLN | 3.2317 | 3.1898 | 1081 |
| RTH | 3.2317 | 3.2500 | 1499 |
| FEW | 3.2316 | 0.4193 | 1014 |
| EDE | 3.2315 | 0.5997 | 1876 |
| WTP | 3.2315 | 1.1975 | 370 |
| ITA | 3.2313 | 2.7419 | 3123 |
| PSW | 3.2311 | 1.4452 | 894 |
| WEH | 3.2311 | 0.7250 | 618 |
| PAS | 3.2311 | 2.5556 | 1698 |
| TFR | 3.2310 | 2.6955 | 3979 |
| YLY | 3.2310 | 3.4499 | 2376 |
| IQI | 3.2309 | 1.3649 | 924 |
| FNC | 3.2309 | 2.4188 | 867 |
| QQV | 3.2309 | 2.6586 | 1568 |
| TMI | 3.2308 | 2.2223 | 1267 |
| WGN | 3.2307 | 0.9227 | 2693 |
| GRD | 3.2306 | 2.0932 | 12695 |
| MMG | 3.2305 | 0.3174 | 1358 |
| VPC | 3.2304 | 2.4087 | 2050 |
| VPA | 3.2304 | 2.6520 | 3804 |
| LMN | 3.2304 | 0.6862 | 560 |
| QSF | 3.2303 | 2.7167 | 1365 |
| MRP | 3.2303 | 2.8358 | 675 |
| MIP | 3.2303 | 2.3434 | 603 |
| GRC | 3.2302 | 1.4374 | 14325 |
| RVK | 3.2302 | 2.1875 | 11037 |
| QPG | 3.2302 | 2.4037 | 1849 |
| QWY | 3.2298 | 1.2056 | 643 |
| KVW | 3.2298 | 1.3971 | 3751 |
| YPS | 3.2297 | 3.6795 | 1753 |
| CKS | 3.2295 | 2.0054 | 2793 |
| NWG | 3.2294 | 0.5135 | 2651 |
| HCR | 3.2290 | 2.3538 | 1848 |

TABLE F-continued

Medium-expressing EGFP variants

| AA SEQ | Mean | Range | Total counts |
|---|---|---|---|
| AWH | 3.2290 | 1.8125 | 463 |
| WPL | 3.2290 | 1.0514 | 791 |
| VGQ | 3.2288 | 1.2555 | 8362 |
| VGF | 3.2286 | 1.0039 | 7447 |
| PQP | 3.2284 | 2.0000 | 113 |
| TFL | 3.2284 | 3.0962 | 1980 |
| DWE | 3.2283 | 0.5501 | 1159 |
| CGG | 3.2283 | 1.0473 | 25754 |
| LQV | 3.2282 | 2.2269 | 3301 |
| NVP | 3.2282 | 2.7337 | 987 |
| TPP | 3.2282 | 1.7797 | 377 |
| VFH | 3.2281 | 2.6167 | 937 |
| YKF | 3.2279 | 1.8876 | 700 |
| HTW | 3.2277 | 1.1062 | 250 |
| MWC | 3.2275 | 0.3199 | 419 |
| SIV | 3.2274 | 2.9475 | 9462 |
| QPD | 3.2273 | 1.4000 | 250 |
| IFA | 3.2273 | 2.8452 | 1608 |
| VFV | 3.2273 | 1.2834 | 4338 |
| PVH | 3.2273 | 2.8036 | 824 |
| QGN | 3.2272 | 1.4114 | 1550 |
| GRM | 3.2270 | 1.5577 | 6659 |
| GWF | 3.2269 | 0.8564 | 2069 |
| GDC | 3.2269 | 1.3308 | 3831 |
| CPY | 3.2268 | 1.7866 | 539 |
| EIQ | 3.2268 | 2.0146 | 2532 |
| ECT | 3.2267 | 2.2667 | 2629 |
| CGD | 3.2266 | 1.1101 | 4304 |
| MRT | 3.2266 | 2.3459 | 1793 |
| TPD | 3.2265 | 1.8487 | 454 |
| DRP | 3.2265 | 2.6190 | 1260 |
| ADS | 3.2264 | 1.7604 | 2869 |
| CME | 3.2263 | 0.4423 | 870 |
| WLA | 3.2263 | 1.4205 | 3378 |
| VRD | 3.2263 | 1.9623 | 8090 |
| TMD | 3.2262 | 0.9643 | 596 |
| MGW | 3.2262 | 0.2441 | 3122 |
| DRV | 3.2260 | 2.4927 | 9391 |
| GGV | 3.2259 | 1.4170 | 54486 |
| GTW | 3.2258 | 0.4928 | 4271 |
| GQV | 3.2257 | 1.1319 | 8106 |
| CLY | 3.2257 | 2.8256 | 2815 |
| QEI | 3.2255 | 1.4734 | 1571 |
| DFA | 3.2254 | 2.4385 | 1484 |
| ADG | 3.2254 | 1.6040 | 7486 |
| FYE | 3.2253 | 1.9082 | 382 |
| ADL | 3.2251 | 2.3291 | 2578 |
| KEQ | 3.2251 | 2.3460 | 947 |
| LSY | 3.2249 | 3.6984 | 5173 |
| ENT | 3.2244 | 2.3954 | 1779 |
| CEP | 3.2244 | 2.6422 | 523 |
| GPW | 3.2243 | 1.7886 | 2964 |
| LFH | 3.2242 | 2.9583 | 1363 |
| VTL | 3.2241 | 2.0727 | 5703 |
| LTW | 3.2241 | 1.6071 | 1687 |
| CHK | 3.2241 | 2.7747 | 581 |
| MSN | 3.2239 | 1.9321 | 1401 |
| PAY | 3.2238 | 1.9296 | 724 |
| MGE | 3.2237 | 0.9986 | 3634 |
| MKG | 3.2236 | 1.8586 | 3191 |
| VFA | 3.2235 | 1.7981 | 2695 |
| KWL | 3.2234 | 1.3989 | 2104 |
| RPD | 3.2234 | 2.2233 | 1520 |
| WWH | 3.2233 | 0.1697 | 591 |
| NWM | 3.2231 | 0.7082 | 330 |
| WDG | 3.2231 | 0.5295 | 6225 |
| GPA | 3.2231 | 3.2228 | 6200 |
| WVM | 3.2229 | 0.5504 | 2306 |
| YVQ | 3.2229 | 2.3584 | 2426 |
| QQF | 3.2228 | 2.5564 | 571 |
| HSV | 3.2227 | 3.5425 | 3336 |
| SVH | 3.2226 | 2.8100 | 4176 |
| FAE | 3.2226 | 1.1726 | 851 |
| VEF | 3.2226 | 0.8498 | 2619 |
| PNY | 3.2225 | 2.6914 | 363 |
| AGR | 3.2224 | 2.0307 | 32630 |
| QCR | 3.2222 | 2.4759 | 2695 |
| FWM | 3.2220 | 0.3092 | 166 |
| NAN | 3.2220 | 2.2592 | 1673 |
| MPA | 3.2220 | 2.1260 | 482 |
| LGH | 3.2220 | 2.8229 | 3277 |
| TKD | 3.2219 | 2.0014 | 1450 |
| EAQ | 3.2219 | 1.1743 | 1569 |
| APH | 3.2218 | 1.8235 | 481 |
| INP | 3.2218 | 2.5019 | 780 |
| AQD | 3.2217 | 1.7374 | 1008 |
| YTP | 3.2217 | 2.4212 | 283 |
| IRH | 3.2216 | 2.6763 | 2476 |
| LHV | 3.2214 | 2.4637 | 2264 |
| WYV | 3.2214 | 2.2721 | 2784 |
| FTK | 3.2211 | 3.3650 | 560 |
| REW | 3.2211 | 0.7887 | 5690 |
| EGF | 3.2208 | 1.1346 | 3630 |
| VQM | 3.2207 | 0.9439 | 1343 |
| PAT | 3.2207 | 1.4499 | 501 |
| ADW | 3.2207 | 0.8003 | 1972 |
| GRF | 3.2207 | 1.4804 | 6394 |
| VQF | 3.2206 | 2.2363 | 1720 |
| PFA | 3.2205 | 2.5028 | 527 |
| QSD | 3.2204 | 2.6551 | 935 |
| IEY | 3.2204 | 1.9250 | 1329 |
| NWA | 3.2204 | 1.0575 | 931 |
| QWF | 3.2201 | 0.5573 | 510 |
| GPF | 3.2197 | 1.7500 | 1111 |
| QGE | 3.2196 | 0.6828 | 3924 |
| WGT | 3.2193 | 1.0287 | 4466 |
| TRF | 3.2191 | 2.9635 | 3255 |
| NCR | 3.2191 | 2.6239 | 3094 |
| TIM | 3.2190 | 2.0992 | 1424 |
| AFA | 3.2189 | 1.8514 | 920 |
| PPM | 3.2188 | 1.4928 | 183 |
| DPY | 3.2187 | 1.5022 | 222 |
| SHV | 3.2187 | 3.7084 | 2737 |
| HPM | 3.2186 | 1.2418 | 60 |
| VWA | 3.2186 | 0.9013 | 5095 |
| RCP | 3.2185 | 2.3043 | 1087 |
| VAE | 3.2184 | 2.3556 | 5896 |
| NDQ | 3.2184 | 1.9795 | 336 |
| SIL | 3.2182 | 2.9235 | 7253 |
| PTE | 3.2181 | 1.6538 | 682 |
| WES | 3.2180 | 1.1741 | 3503 |
| YAM | 3.2178 | 2.3458 | 467 |
| SDD | 3.2177 | 2.1719 | 978 |
| RHH | 3.2177 | 2.6658 | 1310 |
| CPE | 3.2175 | 2.1955 | 486 |
| IVA | 3.2173 | 2.2333 | 5976 |
| VES | 3.2171 | 2.0943 | 8673 |
| IHA | 3.2171 | 2.6907 | 947 |
| AYP | 3.2169 | 2.5992 | 359 |
| GDR | 3.2168 | 2.0139 | 12999 |
| GDW | 3.2167 | 0.7571 | 3676 |
| VRG | 3.2167 | 1.9437 | 50461 |
| SCY | 3.2166 | 2.6989 | 1797 |
| PII | 3.2166 | 2.3421 | 1195 |
| QDI | 3.2162 | 2.1274 | 1118 |
| GHH | 3.2161 | 1.5882 | 867 |
| DEP | 3.2161 | 1.5791 | 606 |
| VRL | 3.2160 | 2.6995 | 17450 |
| MLL | 3.2160 | 2.4405 | 3496 |
| FKK | 3.2159 | 1.9899 | 677 |
| QWM | 3.2155 | 0.0936 | 304 |
| WAC | 3.2155 | 0.7466 | 1994 |
| WMG | 3.2154 | 0.2401 | 3204 |
| PSN | 3.2153 | 3.0198 | 988 |
| VVI | 3.2152 | 1.4867 | 8448 |
| QSM | 3.2151 | 2.8443 | 1237 |
| PGR | 3.2150 | 2.7346 | 10304 |
| WAH | 3.2150 | 1.7181 | 715 |
| MLN | 3.2149 | 1.4529 | 986 |
| HKE | 3.2149 | 1.7736 | 570 |

TABLE F-continued

Medium-expressing EGFP variants

| AA SEQ | Mean | Range | Total counts |
|---|---|---|---|
| FWC | 3.2148 | 0.6905 | 727 |
| DTV | 3.2148 | 2.4992 | 5860 |
| MFM | 3.2145 | 0.6109 | 271 |
| WPV | 3.2145 | 1.2897 | 1841 |
| PFV | 3.2144 | 2.4299 | 1173 |
| FGH | 3.2144 | 1.4167 | 905 |
| YNE | 3.2144 | 2.0160 | 1055 |
| GRT | 3.2143 | 1.9836 | 11213 |
| GMQ | 3.2143 | 1.5348 | 1790 |
| ATY | 3.2141 | 2.6106 | 1467 |
| GAM | 3.2140 | 0.8407 | 3553 |
| GGC | 3.2139 | 1.2185 | 23038 |
| VRW | 3.2139 | 0.9760 | 10630 |
| VGR | 3.2138 | 2.0847 | 50346 |
| IYI | 3.2137 | 2.0509 | 1128 |
| APC | 3.2137 | 3.7059 | 972 |
| WGS | 3.2136 | 1.5219 | 10227 |
| NMV | 3.2134 | 2.0021 | 1743 |
| THK | 3.2134 | 2.6707 | 1120 |
| CGR | 3.2132 | 1.3180 | 16648 |
| DGA | 3.2131 | 1.2784 | 7688 |
| KNG | 3.2131 | 1.8627 | 2716 |
| AGL | 3.2130 | 2.6818 | 15000 |
| ILQ | 3.2129 | 2.6477 | 3154 |
| VGV | 3.2128 | 1.6204 | 35707 |
| WSW | 3.2126 | 0.6786 | 2061 |
| VWR | 3.2126 | 0.8936 | 10776 |
| AGI | 3.2123 | 2.3563 | 6832 |
| VAH | 3.2120 | 1.8832 | 1796 |
| HDH | 3.2120 | 0.8830 | 236 |
| YVA | 3.2119 | 2.2773 | 4538 |
| QEF | 3.2118 | 1.7754 | 853 |
| PGQ | 3.2116 | 1.9003 | 1598 |
| KMA | 3.2116 | 2.0011 | 866 |
| VWQ | 3.2114 | 0.8964 | 1797 |
| CRW | 3.2114 | 1.3846 | 3277 |
| QME | 3.2113 | 0.9654 | 463 |
| DQR | 3.2111 | 2.4604 | 3084 |
| ISR | 3.2111 | 2.7500 | 9100 |
| PGI | 3.2110 | 1.6518 | 2424 |
| GML | 3.2109 | 1.3013 | 4531 |
| YRY | 3.2108 | 2.3148 | 2563 |
| VEV | 3.2108 | 1.4180 | 11905 |
| FNT | 3.2107 | 2.3926 | 547 |
| DHV | 3.2107 | 2.4654 | 1861 |
| WQF | 3.2106 | 1.6131 | 541 |
| YHF | 3.2104 | 2.2487 | 411 |
| HKP | 3.2103 | 2.1717 | 171 |
| RLF | 3.2101 | 3.6564 | 5946 |
| RGG | 3.2100 | 1.3109 | 81654 |
| TDL | 3.2100 | 2.2579 | 1904 |
| ANY | 3.2098 | 2.4905 | 1569 |
| PDH | 3.2095 | 1.8354 | 152 |
| NDA | 3.2095 | 2.2033 | 1388 |
| AVL | 3.2094 | 2.6423 | 9988 |
| AAC | 3.2094 | 2.5435 | 3135 |
| WMD | 3.2091 | 0.5145 | 603 |
| PFM | 3.2091 | 1.1728 | 268 |
| HST | 3.2089 | 3.0176 | 1220 |
| NRC | 3.2087 | 1.9547 | 2252 |
| AAV | 3.2087 | 2.2962 | 7836 |
| QSR | 3.2087 | 3.4000 | 5309 |
| HRG | 3.2087 | 1.8452 | 5541 |
| PRD | 3.2087 | 2.0806 | 1213 |
| HRF | 3.2086 | 2.8138 | 1170 |
| GMK | 3.2085 | 0.6880 | 2271 |
| CCS | 3.2085 | 1.8600 | 1930 |
| VTW | 3.2084 | 1.0610 | 2456 |
| KRD | 3.2084 | 2.1221 | 4055 |
| MPC | 3.2083 | 0.6923 | 125 |
| CWC | 3.2082 | 0.2123 | 964 |
| VGW | 3.2082 | 0.7981 | 15018 |
| LIH | 3.2082 | 2.1533 | 2318 |
| MLD | 3.2082 | 1.4951 | 1537 |
| AIK | 3.2079 | 2.6601 | 3224 |
| GEV | 3.2079 | 0.9343 | 17224 |
| PDA | 3.2078 | 2.6439 | 808 |
| WAF | 3.2077 | 1.1966 | 797 |
| RGW | 3.2077 | 1.0638 | 18188 |
| RPS | 3.2074 | 3.7789 | 3849 |
| VRF | 3.2073 | 1.9499 | 5485 |
| AVC | 3.2072 | 1.8518 | 5812 |
| VRT | 3.2071 | 1.8684 | 7374 |
| GGG | 3.2070 | 1.1551 | 129976 |
| NLD | 3.2070 | 2.3528 | 1232 |
| DPD | 3.2068 | 1.4069 | 506 |
| RPW | 3.2067 | 2.3336 | 1580 |
| VDK | 3.2067 | 1.1755 | 2262 |
| AYQ | 3.2066 | 2.5755 | 1613 |
| AII | 3.2066 | 2.7039 | 3374 |
| FSM | 3.2066 | 2.0385 | 929 |
| SYR | 3.2065 | 3.2929 | 6476 |
| QVQ | 3.2064 | 2.3179 | 1961 |
| KES | 3.2062 | 2.0292 | 3958 |
| DTM | 3.2061 | 1.6312 | 515 |
| MAC | 3.2061 | 0.8615 | 706 |
| PRP | 3.2060 | 2.2941 | 826 |
| CLP | 3.2059 | 2.2222 | 1346 |
| QLV | 3.2058 | 3.2889 | 6221 |
| PAW | 3.2057 | 1.6912 | 1194 |
| ACR | 3.2057 | 2.3333 | 5964 |
| CGE | 3.2056 | 0.6179 | 5433 |
| HAG | 3.2056 | 1.6433 | 2620 |
| KPL | 3.2054 | 3.1416 | 1883 |
| LLH | 3.2054 | 3.4140 | 3688 |
| HVN | 3.2054 | 2.4343 | 1370 |
| WVH | 3.2054 | 0.7655 | 947 |
| WAS | 3.2053 | 2.3427 | 4130 |
| LHS | 3.2053 | 3.1389 | 2291 |
| TLQ | 3.2051 | 3.7380 | 3582 |
| LYA | 3.2051 | 2.4127 | 2769 |
| VAA | 3.2050 | 2.7738 | 8208 |
| RDI | 3.2050 | 2.6426 | 3390 |
| WNR | 3.2047 | 2.1983 | 2229 |
| AGQ | 3.2046 | 2.5627 | 6189 |
| FDQ | 3.2046 | 1.0424 | 213 |
| SQK | 3.2044 | 2.4420 | 2249 |
| QGV | 3.2044 | 1.1791 | 7458 |
| VSW | 3.2044 | 1.3696 | 5257 |
| CQQ | 3.2043 | 2.2735 | 662 |
| DVL | 3.2043 | 3.1356 | 7354 |
| MPE | 3.2041 | 1.4552 | 410 |
| EDP | 3.2041 | 1.3030 | 647 |
| DAS | 3.2038 | 1.6400 | 3334 |
| EIA | 3.2037 | 2.3756 | 4068 |
| QHW | 3.2036 | 0.8400 | 178 |
| VPQ | 3.2036 | 2.3433 | 1092 |
| VMV | 3.2036 | 1.3214 | 4673 |
| DGV | 3.2035 | 1.2931 | 11886 |
| RIN | 3.2032 | 2.5368 | 3903 |
| DSN | 3.2032 | 2.4044 | 1898 |
| SEK | 3.2031 | 1.9499 | 3950 |
| FFI | 3.2031 | 0.9825 | 180 |
| AEI | 3.2030 | 1.9742 | 2567 |
| VRV | 3.2027 | 1.4601 | 25052 |
| AGV | 3.2027 | 1.7826 | 21756 |
| RLA | 3.2024 | 3.4169 | 12775 |
| NCW | 3.2024 | 1.6395 | 884 |
| VRA | 3.2023 | 2.2063 | 15098 |
| SEF | 3.2022 | 2.5771 | 2436 |
| GMW | 3.2021 | 0.5704 | 2663 |
| LQS | 3.2021 | 2.5960 | 3048 |
| FWI | 3.2020 | 0.6619 | 426 |
| NER | 3.2019 | 2.6498 | 3708 |
| MMC | 3.2018 | 1.4905 | 707 |
| KGN | 3.2017 | 1.7649 | 3072 |
| VFL | 3.2017 | 3.0492 | 2844 |
| RYG | 3.2016 | 2.3455 | 9409 |
| NPR | 3.2016 | 2.4029 | 1537 |
| TPG | 3.2015 | 2.3622 | 3177 |

TABLE F-continued

Medium-expressing EGFP variants

| AA SEQ | Mean | Range | Total counts |
|---|---|---|---|
| MLA | 3.2015 | 2.3097 | 2336 |
| GRE | 3.2014 | 1.0822 | 22325 |
| ETP | 3.2014 | 1.9913 | 937 |
| WAV | 3.2014 | 0.7640 | 4778 |
| SNR | 3.2011 | 2.7976 | 6144 |
| FNI | 3.2010 | 2.9750 | 358 |
| IIY | 3.2009 | 2.1645 | 1440 |
| AYL | 3.2009 | 2.8558 | 2757 |
| WGE | 3.2008 | 0.3059 | 7354 |
| YAI | 3.2005 | 2.7343 | 1858 |
| HRA | 3.2002 | 2.6279 | 1428 |
| LMW | 3.2000 | 0.7325 | 1089 |
| TKP | 3.1998 | 2.5605 | 697 |
| YMF | 3.1997 | 1.5747 | 346 |
| LLP | 3.1996 | 4.0000 | 2232 |
| VHM | 3.1992 | 1.0337 | 749 |
| EDD | 3.1992 | 1.1582 | 1262 |
| GGI | 3.1992 | 1.1621 | 14845 |
| QWP | 3.1992 | 2.1037 | 453 |
| GQE | 3.1992 | 0.6474 | 4251 |
| DPG | 3.1991 | 1.8747 | 3029 |
| SWI | 3.1989 | 0.9984 | 1822 |
| VAW | 3.1989 | 1.2490 | 5791 |
| YPK | 3.1989 | 2.9167 | 1170 |
| NAS | 3.1988 | 2.7351 | 2825 |
| PRE | 3.1988 | 2.4884 | 2320 |
| GEG | 3.1985 | 0.9119 | 39335 |
| LMQ | 3.1985 | 1.9217 | 1272 |
| CGC | 3.1984 | 0.7391 | 4526 |
| KWV | 3.1984 | 1.0072 | 2554 |
| WCW | 3.1983 | 0.3590 | 1149 |
| VAM | 3.1983 | 1.3759 | 2018 |
| CLW | 3.1982 | 0.9972 | 1981 |
| GEM | 3.1980 | 0.7704 | 3367 |
| MNG | 3.1980 | 1.3222 | 1916 |
| PDV | 3.1979 | 2.4526 | 1497 |
| FYA | 3.1979 | 1.4128 | 710 |
| HSP | 3.1979 | 3.2340 | 554 |
| WGR | 3.1978 | 0.9451 | 19119 |
| ITS | 3.1976 | 3.3006 | 3817 |
| CQR | 3.1974 | 2.2532 | 2693 |
| EAT | 3.1973 | 2.7569 | 2046 |
| SCQ | 3.1972 | 2.1029 | 1269 |
| ALF | 3.1972 | 2.3221 | 2430 |
| WVG | 3.1972 | 1.5221 | 15513 |
| GES | 3.1970 | 1.1306 | 12615 |
| GQN | 3.1969 | 1.1992 | 1277 |
| PKF | 3.1967 | 2.5089 | 708 |
| MGK | 3.1967 | 1.1245 | 2333 |
| MWW | 3.1966 | 0.0000 | 656 |
| CMP | 3.1966 | 1.5359 | 466 |
| AQC | 3.1966 | 1.9191 | 1157 |
| VVC | 3.1965 | 2.0910 | 9202 |
| LLA | 3.1965 | 3.7716 | 6466 |
| MWE | 3.1965 | 0.3356 | 898 |
| FVG | 3.1963 | 1.8860 | 7729 |
| WEA | 3.1963 | 0.9091 | 2576 |
| DRF | 3.1961 | 1.6186 | 2024 |
| QPS | 3.1957 | 3.2079 | 912 |
| TGV | 3.1956 | 1.9002 | 11606 |
| KPE | 3.1955 | 1.4530 | 948 |
| LNK | 3.1955 | 2.0926 | 1664 |
| FPL | 3.1953 | 3.2051 | 958 |
| MAA | 3.1949 | 1.9450 | 1248 |
| SWC | 3.1948 | 0.8153 | 2285 |
| RWP | 3.1948 | 1.6733 | 1605 |
| ARY | 3.1948 | 2.7000 | 2725 |
| SCF | 3.1947 | 1.9238 | 1388 |
| HKS | 3.1946 | 2.6980 | 1719 |
| CKC | 3.1945 | 1.9320 | 2223 |
| APN | 3.1944 | 2.0275 | 492 |
| WAR | 3.1944 | 1.0016 | 5711 |
| VAQ | 3.1943 | 2.5631 | 2385 |
| SIS | 3.1942 | 2.7977 | 7181 |
| DYD | 3.1939 | 1.7921 | 1025 |
| SKQ | 3.1938 | 2.6233 | 1989 |
| MWM | 3.1937 | 0.0000 | 475 |
| TLS | 3.1936 | 3.0459 | 5758 |
| YTL | 3.1935 | 3.0077 | 2389 |
| RVW | 3.1934 | 2.0880 | 11009 |
| LPY | 3.1930 | 3.1798 | 840 |
| LRE | 3.1930 | 2.7910 | 7985 |
| MPI | 3.1928 | 1.5691 | 649 |
| RWK | 3.1928 | 0.9289 | 3269 |
| LWC | 3.1926 | 0.9825 | 1757 |
| IKV | 3.1926 | 2.0173 | 3284 |
| VCA | 3.1925 | 1.4722 | 4217 |
| FVE | 3.1925 | 1.1808 | 2166 |
| HLA | 3.1925 | 3.8750 | 1559 |
| QDK | 3.1925 | 1.7900 | 1038 |
| SIA | 3.1923 | 3.4051 | 4710 |
| EGE | 3.1922 | 0.5612 | 11208 |
| WDY | 3.1921 | 0.5947 | 408 |
| MAM | 3.1921 | 0.4690 | 519 |
| AKD | 3.1918 | 1.6673 | 1548 |
| DRD | 3.1918 | 2.0477 | 2769 |
| GQA | 3.1917 | 1.5498 | 5601 |
| QAG | 3.1915 | 1.1349 | 4950 |
| LPL | 3.1914 | 3.3057 | 2580 |
| GTL | 3.1914 | 3.0560 | 7212 |
| HMA | 3.1914 | 1.4065 | 331 |
| SQL | 3.1913 | 2.8373 | 3189 |
| LPN | 3.1913 | 2.2009 | 1107 |
| AFP | 3.1912 | 2.5741 | 605 |
| AGT | 3.1912 | 2.2779 | 7277 |
| IMP | 3.1912 | 2.2498 | 620 |
| CRN | 3.1912 | 1.8569 | 2680 |
| RSF | 3.1910 | 2.4774 | 4507 |
| WEK | 3.1909 | 0.4643 | 1379 |
| RAS | 3.1909 | 3.6286 | 10064 |
| RLK | 3.1908 | 2.7786 | 9917 |
| NVE | 3.1907 | 2.1669 | 3975 |
| SPW | 3.1906 | 2.5200 | 743 |
| FAR | 3.1905 | 2.5909 | 2226 |
| ATN | 3.1901 | 1.9399 | 1208 |
| AAM | 3.1901 | 1.3204 | 1722 |
| PFR | 3.1899 | 2.1890 | 1187 |
| HHH | 3.1899 | 2.5588 | 250 |
| MNA | 3.1899 | 2.2317 | 973 |
| WFQ | 3.1897 | 1.1422 | 484 |
| MLS | 3.1897 | 2.7594 | 4286 |
| STL | 3.1896 | 3.6141 | 4722 |
| WDA | 3.1895 | 0.9072 | 1705 |
| WHK | 3.1894 | 2.0518 | 359 |
| VWH | 3.1893 | 0.9999 | 1142 |
| QVR | 3.1891 | 2.6554 | 9653 |
| PLA | 3.1891 | 3.7556 | 1627 |
| NRQ | 3.1888 | 2.8454 | 2129 |
| KVV | 3.1886 | 2.3630 | 10825 |
| AAT | 3.1885 | 2.8416 | 2374 |
| QGF | 3.1885 | 1.2950 | 1758 |
| VPT | 3.1885 | 2.4914 | 1427 |
| GDE | 3.1884 | 1.0217 | 4469 |
| SNT | 3.1881 | 2.6462 | 1495 |
| GDA | 3.1880 | 2.2037 | 6600 |
| FRY | 3.1879 | 2.1867 | 1286 |
| IPT | 3.1878 | 2.8537 | 1006 |
| SKE | 3.1878 | 2.1424 | 3245 |
| HWR | 3.1876 | 1.4234 | 1164 |
| DLQ | 3.1875 | 2.6262 | 1819 |
| RGF | 3.1875 | 1.5395 | 7623 |
| QAH | 3.1873 | 3.2081 | 351 |
| NPV | 3.1872 | 3.0217 | 1107 |
| SPQ | 3.1871 | 2.4076 | 365 |
| EGC | 3.1870 | 1.1828 | 8682 |
| LCG | 3.1869 | 2.4068 | 8660 |
| VWG | 3.1867 | 0.5731 | 15982 |
| IWL | 3.1865 | 1.3337 | 1731 |
| RAG | 3.1865 | 1.7628 | 29997 |
| ACM | 3.1863 | 0.9944 | 983 |

TABLE F-continued

Medium-expressing EGFP variants

| AA SEQ | Mean | Range | Total counts |
|---|---|---|---|
| RAL | 3.1861 | 3.0012 | 8100 |
| TTS | 3.1861 | 2.8903 | 2508 |
| PQT | 3.1861 | 2.3856 | 366 |
| RNR | 3.1860 | 2.5574 | 8109 |
| RKM | 3.1859 | 2.0836 | 2110 |
| VNK | 3.1859 | 2.1637 | 2516 |
| INW | 3.1858 | 1.9961 | 650 |
| ESP | 3.1858 | 3.8235 | 1750 |
| DVP | 3.1857 | 1.9757 | 1467 |
| NGQ | 3.1857 | 1.5033 | 1685 |
| WRQ | 3.1856 | 1.2132 | 2281 |
| DHH | 3.1856 | 2.2035 | 801 |
| RYS | 3.1855 | 2.7522 | 8130 |
| CAG | 3.1855 | 1.7614 | 9180 |
| EPP | 3.1855 | 2.0524 | 322 |
| AVF | 3.1854 | 1.8350 | 3421 |
| FPF | 3.1853 | 1.0999 | 255 |
| EGA | 3.1853 | 1.0415 | 12759 |
| RMD | 3.1853 | 1.2682 | 1490 |
| GLF | 3.1850 | 1.7888 | 4196 |
| RAQ | 3.1848 | 3.1878 | 2959 |
| YAG | 3.1848 | 1.8862 | 4858 |
| VRC | 3.1847 | 1.6079 | 9838 |
| MMF | 3.1844 | 0.8688 | 188 |
| RQL | 3.1844 | 2.9519 | 6279 |
| DGR | 3.1843 | 1.6813 | 15988 |
| FAV | 3.1842 | 2.7469 | 2239 |
| FSH | 3.1842 | 3.1810 | 647 |
| LFW | 3.1841 | 1.3272 | 1059 |
| WCC | 3.1841 | 0.2308 | 1260 |
| EMA | 3.1840 | 1.5936 | 1666 |
| YWA | 3.1839 | 1.3263 | 830 |
| VDT | 3.1838 | 1.9508 | 2061 |
| CCG | 3.1835 | 0.8474 | 4092 |
| MTA | 3.1834 | 2.9686 | 1202 |
| DLS | 3.1829 | 2.4973 | 6369 |
| FGW | 3.1826 | 0.3225 | 2500 |
| EPT | 3.1825 | 1.7429 | 539 |
| FCP | 3.1825 | 0.6576 | 107 |
| LRR | 3.1823 | 2.6894 | 19935 |
| QGI | 3.1821 | 1.3767 | 3061 |
| PGA | 3.1818 | 2.7674 | 4475 |
| WTG | 3.1817 | 1.1631 | 4656 |
| TAY | 3.1816 | 2.9869 | 1105 |
| WVS | 3.1815 | 2.3610 | 6381 |
| KVA | 3.1815 | 3.0583 | 6168 |
| SNS | 3.1815 | 3.4871 | 4035 |
| GGE | 3.1815 | 1.2087 | 30529 |
| EGL | 3.1814 | 1.3291 | 12957 |
| HWM | 3.1813 | 1.6703 | 208 |
| DQS | 3.1813 | 2.3518 | 1568 |
| FWV | 3.1813 | 1.1133 | 1211 |
| AHV | 3.1809 | 2.6342 | 1700 |
| CDQ | 3.1808 | 1.3800 | 874 |
| WQY | 3.1808 | 2.3893 | 884 |
| IAM | 3.1808 | 0.9054 | 613 |
| CIF | 3.1807 | 2.2953 | 1313 |
| IYM | 3.1805 | 1.0248 | 350 |
| KDS | 3.1805 | 2.3617 | 2663 |
| GDD | 3.1805 | 2.0676 | 3218 |
| AKT | 3.1804 | 2.2917 | 1363 |
| ELC | 3.1804 | 2.5252 | 5728 |
| TLL | 3.1802 | 3.4597 | 6342 |
| GQI | 3.1802 | 1.2435 | 2250 |
| LGF | 3.1801 | 1.8538 | 5261 |
| QFA | 3.1801 | 3.6023 | 901 |
| CWS | 3.1801 | 0.9478 | 2625 |
| TFT | 3.1800 | 2.8225 | 1267 |
| PVW | 3.1799 | 1.0557 | 2053 |
| RHN | 3.1797 | 3.3583 | 1505 |
| IQS | 3.1795 | 2.4564 | 2776 |
| GHE | 3.1795 | 0.9548 | 1853 |
| DGE | 3.1795 | 0.8836 | 5755 |
| WTF | 3.1792 | 2.0772 | 984 |
| VCD | 3.1791 | 0.9770 | 2174 |
| QWD | 3.1790 | 1.1029 | 679 |
| RGL | 3.1789 | 1.9982 | 23774 |
| GNA | 3.1788 | 1.8938 | 3311 |
| WPA | 3.1788 | 1.3915 | 1022 |
| EEN | 3.1787 | 1.3114 | 1682 |
| HAY | 3.1784 | 1.5286 | 417 |
| RAT | 3.1784 | 2.8587 | 4570 |
| FAW | 3.1784 | 1.8159 | 896 |
| CCY | 3.1783 | 1.6536 | 610 |
| PEW | 3.1782 | 1.3657 | 898 |
| CAM | 3.1781 | 1.3436 | 778 |
| EHA | 3.1780 | 1.5789 | 1358 |
| VRQ | 3.1779 | 1.4919 | 5979 |
| VTG | 3.1777 | 2.1362 | 12262 |
| HSD | 3.1774 | 1.5000 | 825 |
| GTG | 3.1774 | 1.4453 | 22117 |
| CEI | 3.1772 | 1.7414 | 2640 |
| TFS | 3.1772 | 2.6311 | 2526 |
| LTM | 3.1772 | 2.2863 | 1050 |
| ACL | 3.1771 | 2.8235 | 2924 |
| ACW | 3.1770 | 0.9770 | 1378 |
| GAV | 3.1769 | 1.6714 | 20646 |
| CRD | 3.1769 | 1.4586 | 1990 |
| LKW | 3.1768 | 1.2104 | 1484 |
| PEL | 3.1766 | 3.6429 | 1979 |
| LEE | 3.1766 | 1.3070 | 3853 |
| VHG | 3.1764 | 1.8708 | 4678 |
| GVV | 3.1764 | 1.5693 | 33937 |
| SAW | 3.1764 | 1.7791 | 2908 |
| SMR | 3.1763 | 2.7213 | 4655 |
| LNR | 3.1763 | 3.2330 | 4933 |
| MDS | 3.1762 | 1.6532 | 1128 |
| VDM | 3.1761 | 1.0922 | 2083 |
| RGH | 3.1761 | 1.9181 | 5140 |
| PGF | 3.1760 | 1.5015 | 1294 |
| VEA | 3.1760 | 1.0024 | 7252 |
| SIT | 3.1758 | 3.5877 | 4190 |
| SPD | 3.1758 | 3.0000 | 803 |
| NGW | 3.1757 | 0.8633 | 3440 |
| WRR | 3.1752 | 1.8941 | 10465 |
| VVT | 3.1752 | 1.9059 | 6953 |
| CWY | 3.1751 | 0.8978 | 648 |
| SGP | 3.1750 | 2.1628 | 4158 |
| YSS | 3.1749 | 2.7885 | 3644 |
| MLR | 3.1748 | 2.4614 | 6671 |
| LKN | 3.1748 | 1.6688 | 1325 |
| GAF | 3.1746 | 1.5767 | 3152 |
| YMN | 3.1746 | 1.7230 | 312 |
| CYV | 3.1744 | 2.3018 | 2952 |
| HDM | 3.1744 | 1.7766 | 326 |
| KKG | 3.1744 | 2.1209 | 5217 |
| LHK | 3.1743 | 2.4505 | 1476 |
| DDD | 3.1743 | 0.8580 | 773 |
| SLC | 3.1743 | 2.9170 | 5926 |
| FDP | 3.1742 | 1.0606 | 66 |
| WWR | 3.1742 | 0.5115 | 4964 |
| GDF | 3.1741 | 1.2482 | 1558 |
| YTE | 3.1741 | 2.5661 | 1249 |
| QCH | 3.1739 | 2.1201 | 727 |
| PFC | 3.1739 | 2.2241 | 666 |
| RAH | 3.1735 | 2.6363 | 2501 |
| TTM | 3.1734 | 2.1117 | 753 |
| PEC | 3.1733 | 1.2093 | 799 |
| CDA | 3.1733 | 1.6961 | 1500 |
| CWR | 3.1732 | 0.9539 | 3710 |
| DST | 3.1731 | 3.3971 | 2658 |
| LSW | 3.1731 | 1.6136 | 3514 |
| KAT | 3.1731 | 2.6100 | 1666 |
| VVL | 3.1731 | 2.4423 | 15236 |
| EDG | 3.1730 | 0.6474 | 6634 |
| MPH | 3.1729 | 2.1170 | 522 |
| QGG | 3.1728 | 2.0108 | 17152 |
| TIP | 3.1727 | 2.5191 | 449 |
| SVA | 3.1727 | 2.7661 | 9340 |
| YSL | 3.1726 | 2.7188 | 3877 |

TABLE F-continued

Medium-expressing EGFP variants

| AA SEQ | Mean | Range | Total counts |
|---|---|---|---|
| VQQ | 3.1725 | 2.4932 | 1437 |
| FDA | 3.1723 | 2.2584 | 765 |
| DRN | 3.1723 | 2.3961 | 3400 |
| GAW | 3.1722 | 1.0527 | 8536 |
| ARL | 3.1722 | 3.3083 | 9425 |
| MTN | 3.1720 | 2.0233 | 697 |
| FGR | 3.1720 | 2.0239 | 6957 |
| QMA | 3.1720 | 1.1074 | 613 |
| GRL | 3.1719 | 2.1766 | 23445 |
| DRL | 3.1719 | 2.8544 | 5848 |
| LCQ | 3.1718 | 3.1629 | 1432 |
| QDN | 3.1718 | 1.9197 | 401 |
| ASD | 3.1717 | 2.0951 | 2378 |
| YEW | 3.1717 | 0.2353 | 1086 |
| YWD | 3.1717 | 1.0602 | 571 |
| SGG | 3.1716 | 2.5084 | 43656 |
| VMI | 3.1715 | 1.3160 | 1686 |
| YML | 3.1715 | 2.1805 | 1428 |
| QTG | 3.1713 | 1.8925 | 2523 |
| RGA | 3.1712 | 2.3842 | 27151 |
| IDT | 3.1711 | 2.8450 | 1060 |
| GEC | 3.1710 | 0.9967 | 7036 |
| EHS | 3.1709 | 2.1488 | 2051 |
| GPM | 3.1708 | 1.0618 | 1663 |
| WLW | 3.1705 | 0.6247 | 2823 |
| APY | 3.1703 | 2.7578 | 674 |
| TRH | 3.1703 | 2.8702 | 1865 |
| WED | 3.1702 | 0.3914 | 1549 |
| GKY | 3.1700 | 1.6801 | 2893 |
| FAN | 3.1700 | 2.0563 | 315 |
| MHW | 3.1699 | 1.8289 | 469 |
| RAR | 3.1698 | 3.0862 | 17609 |
| RNV | 3.1696 | 3.2544 | 8353 |
| GVM | 3.1693 | 0.8127 | 6959 |
| GGR | 3.1692 | 1.4442 | 83902 |
| GNY | 3.1691 | 2.2927 | 2027 |
| APV | 3.1691 | 2.8475 | 2087 |
| VQG | 3.1690 | 1.2481 | 9226 |
| YST | 3.1690 | 3.4667 | 2009 |
| HDW | 3.1689 | 0.6358 | 408 |
| SCL | 3.1689 | 2.5250 | 4034 |
| LTL | 3.1689 | 2.9420 | 4093 |
| PVP | 3.1689 | 3.4026 | 1005 |
| QKA | 3.1689 | 1.9603 | 764 |
| GLM | 3.1687 | 1.6266 | 4930 |
| LGR | 3.1687 | 2.1520 | 30785 |
| SLL | 3.1686 | 3.6447 | 8641 |
| GDV | 3.1686 | 1.6311 | 8858 |
| RDV | 3.1685 | 1.8472 | 7428 |
| EYD | 3.1685 | 2.0739 | 1532 |
| AWW | 3.1684 | 1.0413 | 2235 |
| RWI | 3.1683 | 1.2841 | 2772 |
| CTK | 3.1683 | 2.4251 | 1338 |
| WTY | 3.1683 | 1.4436 | 881 |
| DQP | 3.1679 | 2.5408 | 437 |
| VVG | 3.1675 | 1.9921 | 43916 |
| EKT | 3.1674 | 2.5582 | 1977 |
| WPM | 3.1674 | 0.8274 | 252 |
| IAF | 3.1672 | 2.0264 | 927 |
| WPE | 3.1672 | 0.7509 | 994 |
| GDG | 3.1670 | 1.3261 | 18808 |
| RFF | 3.1670 | 2.3995 | 1720 |
| CMW | 3.1669 | 0.3274 | 557 |
| WCV | 3.1668 | 0.6498 | 3888 |
| WVA | 3.1668 | 1.1852 | 5959 |
| ATL | 3.1667 | 3.5535 | 3429 |
| VCC | 3.1666 | 1.2444 | 2739 |
| AVY | 3.1665 | 1.7334 | 3659 |
| YLN | 3.1665 | 2.3910 | 2748 |
| EKR | 3.1664 | 2.3849 | 8207 |
| GDY | 3.1663 | 1.2755 | 1507 |
| VSA | 3.1663 | 3.0605 | 9138 |
| CHS | 3.1662 | 2.5431 | 1136 |
| LLW | 3.1661 | 1.7126 | 3333 |
| FFL | 3.1661 | 2.2173 | 333 |
| FHC | 3.1660 | 2.9092 | 516 |
| GAG | 3.1660 | 1.3892 | 46713 |
| MYW | 3.1659 | 0.4807 | 635 |
| LMS | 3.1658 | 2.3411 | 2472 |
| ACY | 3.1657 | 2.1244 | 1195 |
| IFM | 3.1656 | 1.1192 | 272 |
| HEN | 3.1656 | 2.1358 | 324 |
| QSL | 3.1656 | 2.7688 | 3701 |
| LIW | 3.1656 | 1.5983 | 1496 |
| AVE | 3.1655 | 1.2382 | 7005 |
| FAS | 3.1654 | 2.4848 | 1305 |
| PGT | 3.1654 | 3.3341 | 2496 |
| MWY | 3.1653 | 0.2586 | 446 |
| QRV | 3.1653 | 2.5247 | 6119 |
| RRD | 3.1652 | 2.3069 | 8205 |
| DSL | 3.1651 | 2.5188 | 4482 |
| QAS | 3.1651 | 1.8532 | 2588 |
| EHP | 3.1651 | 1.1857 | 246 |
| GGT | 3.1650 | 2.0262 | 17441 |
| MRH | 3.1648 | 2.1264 | 1350 |
| MGN | 3.1647 | 1.3300 | 1369 |
| CVN | 3.1647 | 2.5722 | 2718 |
| VGM | 3.1647 | 2.1912 | 6318 |
| PKI | 3.1646 | 2.3005 | 670 |
| THW | 3.1646 | 2.4565 | 710 |
| GTR | 3.1646 | 2.0404 | 12966 |
| LNF | 3.1646 | 2.7344 | 993 |
| ADP | 3.1643 | 2.7827 | 693 |
| AQP | 3.1640 | 2.0526 | 560 |
| GGL | 3.1640 | 1.8501 | 34303 |
| SVP | 3.1639 | 2.6190 | 2952 |
| DDS | 3.1639 | 1.3066 | 2008 |
| PLL | 3.1639 | 3.7532 | 3101 |
| VCL | 3.1639 | 2.1991 | 5470 |
| RAV | 3.1639 | 2.4431 | 13034 |
| HPS | 3.1637 | 3.6087 | 722 |
| ENA | 3.1637 | 2.1032 | 2279 |
| QVM | 3.1636 | 1.3974 | 2069 |
| ADR | 3.1636 | 2.1411 | 5318 |
| DAN | 3.1635 | 2.8019 | 1005 |
| RFQ | 3.1633 | 3.0637 | 2480 |
| LDE | 3.1632 | 2.7629 | 1865 |
| KSP | 3.1632 | 3.4686 | 751 |
| RGQ | 3.1632 | 2.1478 | 9233 |
| LKS | 3.1631 | 2.8383 | 5161 |
| VCH | 3.1629 | 1.1716 | 1289 |
| LEW | 3.1629 | 1.4563 | 2785 |
| PGV | 3.1629 | 2.3606 | 7201 |
| LKK | 3.1628 | 1.7834 | 2984 |
| ADA | 3.1627 | 2.5819 | 1801 |
| LKP | 3.1626 | 2.9881 | 964 |
| VRE | 3.1626 | 1.5875 | 12730 |
| VAV | 3.1624 | 2.5000 | 11947 |
| WSP | 3.1623 | 1.3828 | 761 |
| FAL | 3.1622 | 2.6061 | 1396 |
| EKP | 3.1622 | 2.0842 | 972 |
| LRT | 3.1622 | 3.2461 | 4924 |
| RIS | 3.1621 | 2.6429 | 11493 |
| TNE | 3.1619 | 2.1975 | 1007 |
| CSH | 3.1619 | 2.3073 | 914 |
| WCF | 3.1615 | 0.6124 | 578 |
| NGP | 3.1614 | 3.5852 | 1044 |
| VFG | 3.1613 | 1.2644 | 8224 |
| QKG | 3.1613 | 1.3316 | 2809 |
| VTV | 3.1611 | 2.3583 | 7434 |
| SVF | 3.1611 | 2.8598 | 4998 |
| PTR | 3.1610 | 3.5518 | 1355 |
| RGI | 3.1610 | 2.1744 | 12357 |
| QSV | 3.1609 | 2.8597 | 5462 |
| GWW | 3.1609 | 1.0314 | 6001 |
| GRR | 3.1609 | 2.4097 | 52133 |
| VKG | 3.1609 | 1.2253 | 10688 |
| LPI | 3.1608 | 3.1400 | 1322 |
| EWW | 3.1608 | 0.1237 | 1812 |
| VAI | 3.1608 | 2.8974 | 3686 |

TABLE F-continued

Medium-expressing EGFP variants

| AA SEQ | Mean | Range | Total counts |
|---|---|---|---|
| EDF | 3.1605 | 1.0999 | 633 |
| ALN | 3.1604 | 2.6866 | 2791 |
| SFF | 3.1604 | 2.2513 | 994 |
| GRA | 3.1604 | 2.2129 | 25652 |
| QEH | 3.1603 | 2.1953 | 1104 |
| GCQ | 3.1601 | 1.0340 | 3053 |
| VGD | 3.1600 | 1.8844 | 11926 |
| EAH | 3.1600 | 1.6165 | 1213 |
| VRS | 3.1598 | 3.0776 | 18727 |
| CWE | 3.1596 | 0.4490 | 1679 |
| PVK | 3.1596 | 2.4362 | 1837 |
| GMV | 3.1596 | 1.2302 | 6262 |
| CTV | 3.1594 | 2.7075 | 3175 |
| KTG | 3.1594 | 1.9604 | 5288 |
| KWF | 3.1592 | 1.1879 | 928 |
| NAQ | 3.1591 | 2.4226 | 1201 |
| AFW | 3.1591 | 1.0376 | 1246 |
| EQT | 3.1590 | 2.2362 | 1054 |
| TEN | 3.1588 | 1.6215 | 1106 |
| DIW | 3.1588 | 1.3588 | 1344 |
| HQM | 3.1587 | 1.4771 | 423 |
| HDV | 3.1583 | 1.8628 | 1016 |
| PVR | 3.1583 | 2.3839 | 5731 |
| LRV | 3.1582 | 3.0805 | 16095 |
| SSM | 3.1582 | 1.9307 | 2011 |
| NFG | 3.1581 | 2.2907 | 2745 |
| RDA | 3.1581 | 1.9542 | 4776 |
| RNQ | 3.1581 | 3.1543 | 2710 |
| RTL | 3.1580 | 3.3790 | 6604 |
| SSI | 3.1579 | 2.9617 | 5195 |
| CWH | 3.1579 | 0.6935 | 409 |
| LQA | 3.1578 | 3.4012 | 5217 |
| AFT | 3.1578 | 3.4997 | 1248 |
| RWA | 3.1578 | 1.9158 | 6282 |
| CRF | 3.1576 | 2.3401 | 2750 |
| AAA | 3.1575 | 2.4240 | 5165 |
| YGF | 3.1574 | 1.4483 | 1984 |
| CAP | 3.1574 | 2.2889 | 609 |
| QCI | 3.1573 | 2.7358 | 1600 |
| IQM | 3.1573 | 0.6994 | 259 |
| LGK | 3.1573 | 2.5413 | 7883 |
| GLW | 3.1572 | 1.1695 | 9443 |
| KGT | 3.1571 | 1.7861 | 4395 |
| CQF | 3.1570 | 2.0990 | 581 |
| TNM | 3.1570 | 2.1867 | 594 |
| SPN | 3.1569 | 2.0221 | 583 |
| DVN | 3.1569 | 2.4296 | 2643 |
| VTF | 3.1569 | 1.3154 | 2010 |
| DHP | 3.1566 | 1.3492 | 86 |
| FPD | 3.1566 | 1.7656 | 257 |
| VMT | 3.1565 | 2.8935 | 1156 |
| AEL | 3.1563 | 1.8446 | 4606 |
| INV | 3.1563 | 2.1291 | 2855 |
| QMM | 3.1562 | 0.3679 | 402 |
| PEH | 3.1562 | 1.6345 | 246 |
| CAL | 3.1562 | 2.4356 | 3519 |
| GEW | 3.1561 | 0.8184 | 7027 |
| TVP | 3.1561 | 2.8947 | 1290 |
| RVI | 3.1560 | 2.3287 | 10790 |
| GCH | 3.1560 | 1.1670 | 1911 |
| PCI | 3.1560 | 2.3267 | 450 |
| EVD | 3.1560 | 2.3114 | 4999 |
| PDE | 3.1559 | 1.5600 | 559 |
| AGE | 3.1558 | 1.5321 | 11206 |
| SEN | 3.1558 | 1.9906 | 2243 |
| NGI | 3.1557 | 2.0703 | 3773 |
| WWG | 3.1556 | 0.4138 | 7559 |
| GPC | 3.1556 | 2.2864 | 2976 |
| AVV | 3.1554 | 1.5113 | 13568 |
| VYH | 3.1553 | 2.0569 | 1057 |
| IIL | 3.1553 | 3.2169 | 2120 |
| ECK | 3.1552 | 1.9958 | 3244 |
| QRP | 3.1552 | 2.3507 | 758 |
| SKS | 3.1552 | 3.0771 | 6193 |
| RKA | 3.1551 | 3.2539 | 5837 |
| MRK | 3.1549 | 1.6933 | 2329 |
| SWP | 3.1548 | 1.6500 | 682 |
| MCL | 3.1548 | 1.7971 | 1756 |
| CNS | 3.1547 | 2.6342 | 2084 |
| WDC | 3.1547 | 0.5601 | 1362 |
| PSV | 3.1545 | 3.8284 | 2700 |
| RKQ | 3.1545 | 2.4188 | 3149 |
| EAA | 3.1545 | 2.0590 | 4534 |
| VHA | 3.1543 | 1.4464 | 1895 |
| IIA | 3.1540 | 2.5763 | 3124 |
| WLG | 3.1540 | 1.1265 | 11996 |
| CYR | 3.1539 | 2.3447 | 3718 |
| TPR | 3.1538 | 3.2004 | 1753 |
| IMN | 3.1534 | 1.4057 | 775 |
| TAG | 3.1534 | 1.4515 | 8213 |
| MAG | 3.1534 | 1.1001 | 3991 |
| WEP | 3.1534 | 0.8667 | 882 |
| MIV | 3.1533 | 1.7367 | 1765 |
| AMS | 3.1533 | 2.1785 | 2259 |
| GIG | 3.1532 | 1.0639 | 18224 |
| RKC | 3.1531 | 2.3438 | 5440 |
| DIA | 3.1531 | 2.9346 | 3186 |
| MQV | 3.1529 | 2.4175 | 1587 |
| RLC | 3.1528 | 2.9122 | 10900 |
| CRP | 3.1528 | 2.7857 | 1092 |
| VTA | 3.1527 | 2.4922 | 4372 |
| NPA | 3.1526 | 2.8166 | 887 |
| TMR | 3.1526 | 2.6443 | 3142 |
| REG | 3.1525 | 1.2935 | 26799 |
| CWP | 3.1524 | 1.3926 | 409 |
| PAC | 3.1524 | 2.7598 | 929 |
| VHQ | 3.1522 | 2.5143 | 653 |
| FWP | 3.1522 | 0.9455 | 175 |
| IRQ | 3.1522 | 2.9043 | 2994 |
| KGH | 3.1519 | 1.1041 | 1580 |
| VHR | 3.1518 | 1.6558 | 4618 |
| WAA | 3.1517 | 1.6583 | 3862 |
| GSV | 3.1516 | 2.1770 | 21301 |
| RGV | 3.1515 | 1.4484 | 36496 |
| HPD | 3.1515 | 2.6161 | 139 |
| GKG | 3.1514 | 0.9282 | 20279 |
| CDV | 3.1514 | 1.3804 | 2447 |
| TSL | 3.1514 | 3.1063 | 5303 |
| SDH | 3.1513 | 2.2811 | 627 |
| EWE | 3.1513 | 0.4722 | 2379 |
| HHR | 3.1513 | 2.2944 | 733 |
| TPM | 3.1511 | 0.6270 | 297 |
| PMC | 3.1511 | 1.2083 | 330 |
| RGE | 3.1510 | 1.5625 | 19753 |
| AKA | 3.1510 | 2.9076 | 2719 |
| RRP | 3.1510 | 3.7536 | 3212 |
| DMF | 3.1509 | 1.5419 | 541 |
| RMQ | 3.1507 | 2.4965 | 2440 |
| ELS | 3.1506 | 2.1090 | 9169 |
| LRG | 3.1506 | 2.6834 | 29214 |
| RNS | 3.1504 | 3.2984 | 5720 |
| TLR | 3.1503 | 3.1815 | 8562 |
| AVS | 3.1503 | 2.8541 | 10861 |
| LKC | 3.1502 | 2.9313 | 4370 |
| FRE | 3.1501 | 1.6810 | 2483 |
| ASI | 3.1498 | 2.4342 | 3693 |
| RDP | 3.1498 | 1.7733 | 1293 |
| EES | 3.1497 | 1.6381 | 5003 |
| WQG | 3.1497 | 0.9244 | 2653 |
| VDQ | 3.1495 | 1.4970 | 1316 |
| YRH | 3.1493 | 2.8214 | 1550 |
| CQG | 3.1493 | 0.9575 | 3351 |
| GPL | 3.1491 | 2.1479 | 5022 |
| ANF | 3.1491 | 2.0373 | 1052 |
| LEC | 3.1490 | 2.3592 | 4044 |
| ATP | 3.1489 | 2.8319 | 664 |
| GVT | 3.1487 | 1.9698 | 10214 |
| VSV | 3.1487 | 2.2808 | 14023 |
| WPI | 3.1487 | 1.1013 | 453 |
| YMA | 3.1487 | 1.5966 | 542 |

TABLE F-continued

Medium-expressing EGFP variants

| AA SEQ | Mean | Range | Total counts |
|---|---|---|---|
| SWL | 3.1487 | 2.7391 | 3591 |
| HRR | 3.1486 | 2.3993 | 3404 |
| TQS | 3.1486 | 2.1935 | 1512 |
| PGY | 3.1486 | 1.9143 | 1473 |
| TWN | 3.1485 | 1.7757 | 402 |
| WRG | 3.1485 | 0.9440 | 18765 |
| EWQ | 3.1484 | 0.1010 | 1208 |
| VKS | 3.1482 | 2.2382 | 6049 |
| TMY | 3.1482 | 1.6715 | 513 |
| LMK | 3.1479 | 2.0326 | 1455 |
| LRA | 3.1479 | 3.4056 | 10547 |
| CKV | 3.1478 | 2.3585 | 4120 |
| QPA | 3.1478 | 2.7831 | 671 |
| PWS | 3.1477 | 1.9333 | 764 |
| VLP | 3.1477 | 2.5849 | 3014 |
| CIN | 3.1477 | 1.9758 | 1946 |
| PTL | 3.1476 | 3.5364 | 1129 |
| LTC | 3.1475 | 2.2750 | 1878 |
| EQC | 3.1474 | 1.5018 | 1272 |
| ATH | 3.1473 | 2.2392 | 951 |
| RML | 3.1472 | 2.2426 | 4530 |
| GCF | 3.1471 | 1.3034 | 1741 |
| SGT | 3.1470 | 2.1942 | 6941 |
| LKA | 3.1468 | 2.9672 | 4718 |
| FTS | 3.1468 | 3.3464 | 1629 |
| VQS | 3.1467 | 2.6972 | 4294 |
| SVV | 3.1466 | 1.9436 | 16791 |
| YFY | 3.1465 | 1.6012 | 723 |
| AKF | 3.1465 | 2.3552 | 1333 |
| RCF | 3.1465 | 2.0488 | 2107 |
| RDG | 3.1464 | 1.4845 | 14031 |
| VMS | 3.1464 | 1.4582 | 3236 |
| EHM | 3.1462 | 2.2095 | 465 |
| QKP | 3.1462 | 1.9099 | 341 |
| ANV | 3.1461 | 2.8106 | 3074 |
| RWD | 3.1460 | 1.4633 | 2856 |
| FWL | 3.1460 | 1.2689 | 952 |
| QWA | 3.1458 | 1.5360 | 838 |
| FED | 3.1458 | 1.2429 | 943 |
| PPA | 3.1458 | 2.2667 | 713 |
| CGL | 3.1457 | 1.7339 | 8893 |
| RDQ | 3.1457 | 1.3478 | 1982 |
| YES | 3.1456 | 2.2878 | 2300 |
| GDH | 3.1456 | 1.0013 | 1150 |
| SAP | 3.1456 | 2.9240 | 957 |
| AVI | 3.1454 | 1.7859 | 5645 |
| SLT | 3.1454 | 3.0203 | 4987 |
| LPV | 3.1454 | 3.0693 | 2685 |
| IWG | 3.1452 | 1.0983 | 3865 |
| LWD | 3.1450 | 1.2603 | 2087 |
| FMK | 3.1449 | 1.8220 | 476 |
| EHV | 3.1449 | 2.4458 | 2558 |
| RPA | 3.1448 | 2.5675 | 3494 |
| FSN | 3.1447 | 2.1952 | 854 |
| PSC | 3.1446 | 2.0000 | 1503 |
| HSW | 3.1444 | 1.5314 | 576 |
| SQA | 3.1442 | 2.7443 | 2913 |
| EAG | 3.1442 | 1.0688 | 13623 |
| WAM | 3.1442 | 1.9558 | 838 |
| MYL | 3.1441 | 2.0123 | 1383 |
| AEE | 3.1441 | 1.1194 | 3554 |
| TND | 3.1440 | 2.7510 | 3742 |
| DGY | 3.1440 | 2.1124 | 2711 |
| PNI | 3.1438 | 2.7211 | 732 |
| CGF | 3.1438 | 1.6957 | 2557 |
| YCR | 3.1437 | 2.8356 | 2944 |
| ATI | 3.1437 | 2.5208 | 2674 |
| KRQ | 3.1435 | 2.6239 | 2929 |
| FKS | 3.1435 | 2.1881 | 1612 |
| QFT | 3.1434 | 3.0688 | 874 |
| FSP | 3.1434 | 1.6356 | 553 |
| HRS | 3.1434 | 2.3785 | 3423 |
| PNS | 3.1433 | 2.7000 | 883 |
| FGE | 3.1433 | 1.2891 | 3325 |
| ARE | 3.1432 | 1.6523 | 7410 |
| VRR | 3.1432 | 2.2527 | 31286 |
| THP | 3.1431 | 1.6315 | 293 |
| HMW | 3.1431 | 0.0101 | 266 |
| YYL | 3.1427 | 2.8651 | 1349 |
| MGP | 3.1426 | 1.5718 | 1144 |
| GTV | 3.1426 | 1.8044 | 10090 |
| NSG | 3.1425 | 2.6171 | 5407 |
| QRA | 3.1425 | 2.7636 | 4341 |
| HAV | 3.1424 | 1.6032 | 1022 |
| QEP | 3.1424 | 1.7859 | 387 |
| QQT | 3.1424 | 2.9315 | 428 |
| DQM | 3.1423 | 1.9728 | 564 |
| TNP | 3.1423 | 1.1667 | 311 |
| TLP | 3.1423 | 2.6402 | 1288 |
| LKT | 3.1422 | 2.6163 | 2212 |
| LSF | 3.1420 | 2.6800 | 2792 |
| EPC | 3.1419 | 1.6154 | 833 |
| CHC | 3.1418 | 1.3982 | 899 |
| IFP | 3.1416 | 2.5434 | 536 |
| LLR | 3.1416 | 3.3613 | 14542 |
| VNH | 3.1415 | 2.6597 | 1268 |
| VCS | 3.1414 | 1.9288 | 5343 |
| PNR | 3.1413 | 3.3307 | 1849 |
| HHM | 3.1412 | 2.1820 | 326 |
| LNC | 3.1411 | 2.2537 | 2138 |
| AKE | 3.1409 | 1.4100 | 2199 |
| VSR | 3.1408 | 2.5462 | 17294 |
| VGT | 3.1408 | 1.8142 | 10384 |
| VEP | 3.1407 | 1.4952 | 2142 |
| SSK | 3.1406 | 2.7852 | 4607 |
| DAL | 3.1406 | 3.0234 | 3046 |
| WCQ | 3.1405 | 0.4146 | 741 |
| DVS | 3.1404 | 2.6209 | 6630 |
| QFD | 3.1404 | 2.2611 | 513 |
| ACV | 3.1403 | 1.9806 | 3204 |
| MSS | 3.1402 | 2.9337 | 3092 |
| VLW | 3.1402 | 1.7033 | 6090 |
| GTD | 3.1402 | 1.3237 | 2986 |
| ESS | 3.1401 | 2.0580 | 6993 |
| CNR | 3.1401 | 3.6395 | 3159 |
| NGK | 3.1400 | 1.6133 | 2752 |
| HKD | 3.1399 | 0.4959 | 541 |
| MHP | 3.1399 | 0.6434 | 50 |
| EAV | 3.1398 | 1.6469 | 6404 |
| RAM | 3.1398 | 2.7398 | 3025 |
| WRL | 3.1395 | 1.4210 | 6646 |
| LQR | 3.1395 | 2.6231 | 5538 |
| EAD | 3.1394 | 1.1898 | 2370 |
| ILM | 3.1394 | 1.5360 | 956 |
| VWL | 3.1394 | 1.5025 | 5619 |
| EWF | 3.1394 | 0.5534 | 900 |
| SSN | 3.1393 | 3.5714 | 3087 |
| SKA | 3.1393 | 2.6523 | 3568 |
| DQA | 3.1393 | 2.6961 | 1589 |
| QKD | 3.1392 | 1.0455 | 533 |
| RDH | 3.1391 | 2.6975 | 1057 |
| IER | 3.1389 | 2.5912 | 7545 |
| VFW | 3.1388 | 0.6060 | 1666 |
| EHT | 3.1387 | 2.3139 | 1072 |
| GTH | 3.1387 | 1.5707 | 1644 |
| RVL | 3.1387 | 2.9095 | 17419 |
| TYD | 3.1386 | 2.6607 | 852 |
| PRS | 3.1385 | 3.0471 | 2932 |
| KWP | 3.1384 | 1.5778 | 507 |
| HVC | 3.1383 | 2.5132 | 2038 |
| QGH | 3.1383 | 1.5018 | 957 |
| SSH | 3.1382 | 2.8026 | 1818 |
| AQV | 3.1380 | 2.8430 | 3274 |
| ACS | 3.1379 | 2.4231 | 3643 |
| VQV | 3.1379 | 1.5232 | 5084 |
| AFH | 3.1379 | 2.3663 | 713 |
| QNE | 3.1379 | 1.8061 | 591 |
| TWR | 3.1378 | 1.1959 | 3103 |
| AEV | 3.1376 | 1.3296 | 7131 |
| VDA | 3.1375 | 2.6332 | 3582 |

TABLE F-continued

Medium-expressing EGFP variants

| AA SEQ | Mean | Range | Total counts |
|---|---|---|---|
| NLE | 3.1374 | 2.0503 | 2478 |
| DHF | 3.1374 | 1.3296 | 506 |
| IRN | 3.1373 | 2.7047 | 3173 |
| CGM | 3.1373 | 0.8384 | 2566 |
| LAT | 3.1372 | 3.4768 | 4380 |
| AGG | 3.1371 | 2.2028 | 49795 |
| NRT | 3.1370 | 3.5570 | 2726 |
| SGA | 3.1370 | 2.2800 | 14508 |
| RRY | 3.1370 | 2.9324 | 8720 |
| LAD | 3.1369 | 2.5974 | 2275 |
| DCG | 3.1368 | 0.8835 | 4025 |
| GGA | 3.1367 | 2.2017 | 38426 |
| RYR | 3.1367 | 2.8664 | 11282 |
| GME | 3.1367 | 0.4711 | 3643 |
| TWL | 3.1367 | 2.3305 | 1957 |
| DGC | 3.1367 | 0.8004 | 5310 |
| DMD | 3.1367 | 1.1158 | 698 |
| FKP | 3.1367 | 2.5476 | 113 |
| IRF | 3.1366 | 1.9273 | 3145 |
| FFG | 3.1366 | 1.5420 | 1221 |
| IDQ | 3.1365 | 2.3167 | 768 |
| DRK | 3.1365 | 1.9026 | 4250 |
| RCV | 3.1364 | 2.3072 | 8705 |
| IQL | 3.1364 | 2.5212 | 1971 |
| YTD | 3.1362 | 2.4352 | 991 |
| GCG | 3.1362 | 1.8006 | 23130 |
| SGL | 3.1362 | 2.6525 | 14749 |
| HQT | 3.1361 | 2.7615 | 739 |
| VEQ | 3.1361 | 1.1852 | 3235 |
| MDA | 3.1361 | 0.9041 | 655 |
| RAA | 3.1361 | 2.8722 | 8425 |
| TTC | 3.1361 | 2.8165 | 1647 |
| RIR | 3.1360 | 2.8627 | 15391 |
| YYS | 3.1359 | 2.6588 | 1785 |
| GGQ | 3.1359 | 1.2889 | 13450 |
| WYG | 3.1359 | 0.8054 | 2821 |
| VAD | 3.1359 | 1.9399 | 4153 |
| ERF | 3.1358 | 2.2295 | 3041 |
| YLA | 3.1357 | 3.1898 | 2787 |
| PLF | 3.1357 | 2.7454 | 1150 |
| VGA | 3.1356 | 2.3244 | 22640 |
| SLQ | 3.1355 | 2.6702 | 2800 |
| VWD | 3.1355 | 1.0309 | 2563 |
| KPA | 3.1354 | 2.9913 | 842 |
| MWV | 3.1353 | 0.3854 | 1708 |
| QDE | 3.1352 | 0.8026 | 774 |
| DHQ | 3.1351 | 2.2919 | 457 |
| GRI | 3.1348 | 2.4081 | 10792 |
| DTQ | 3.1348 | 2.3230 | 784 |
| VYG | 3.1346 | 1.2469 | 6698 |
| YGP | 3.1345 | 2.1234 | 1254 |
| QHV | 3.1345 | 2.5629 | 949 |
| KPW | 3.1345 | 2.1017 | 457 |
| AAG | 3.1343 | 2.5715 | 17415 |
| QAE | 3.1343 | 1.0403 | 976 |
| ATQ | 3.1341 | 2.8792 | 1371 |
| IPA | 3.1341 | 2.8998 | 892 |
| GGY | 3.1339 | 1.2695 | 8753 |
| GCA | 3.1338 | 1.7104 | 6735 |
| LMD | 3.1337 | 1.5852 | 814 |
| CIM | 3.1336 | 1.0285 | 901 |
| IYN | 3.1336 | 1.9335 | 1061 |
| ADF | 3.1335 | 1.5074 | 720 |
| VFM | 3.1335 | 1.0010 | 1118 |
| PAH | 3.1334 | 3.8082 | 500 |
| RNA | 3.1334 | 2.8070 | 3451 |
| RMP | 3.1333 | 2.4052 | 890 |
| FVK | 3.1333 | 2.1109 | 1928 |
| KSD | 3.1332 | 2.5781 | 3341 |
| GVF | 3.1332 | 1.4615 | 5176 |
| LKR | 3.1329 | 2.6753 | 8389 |
| VDI | 3.1328 | 1.2576 | 2553 |
| RGP | 3.1328 | 2.6872 | 7711 |
| DSR | 3.1328 | 2.7689 | 8457 |
| TGL | 3.1327 | 1.9474 | 8768 |
| WIV | 3.1327 | 1.8367 | 3468 |
| AQM | 3.1325 | 1.4196 | 663 |
| QQD | 3.1323 | 2.1182 | 316 |
| GQR | 3.1323 | 1.8571 | 11202 |
| SAY | 3.1323 | 3.0549 | 3051 |
| IFI | 3.1322 | 2.0623 | 924 |
| VDN | 3.1322 | 1.3352 | 1513 |
| WMP | 3.1321 | 0.6584 | 315 |
| HSS | 3.1321 | 3.2953 | 2046 |
| GEF | 3.1320 | 1.1653 | 3524 |
| GQC | 3.1320 | 1.1264 | 3420 |
| YAS | 3.1319 | 2.9668 | 2900 |
| WNF | 3.1319 | 1.4963 | 544 |
| RSL | 3.1319 | 3.6843 | 12429 |
| DYP | 3.1318 | 2.3526 | 365 |
| VVR | 3.1318 | 2.5536 | 31327 |
| PAI | 3.1317 | 1.4500 | 409 |
| NWQ | 3.1312 | 1.6507 | 777 |
| EGW | 3.1311 | 1.0402 | 8676 |
| GRS | 3.1311 | 2.7235 | 27417 |
| EAC | 3.1310 | 1.0616 | 2406 |
| QGD | 3.1310 | 1.2518 | 2295 |
| SQN | 3.1310 | 2.3077 | 1566 |
| WDD | 3.1309 | 0.5772 | 804 |
| VDH | 3.1309 | 1.3536 | 773 |
| CCP | 3.1307 | 2.4870 | 353 |
| QTL | 3.1307 | 2.7984 | 1594 |
| VTR | 3.1306 | 2.3636 | 8397 |
| QSH | 3.1305 | 2.1597 | 840 |
| WLF | 3.1305 | 1.2381 | 1438 |
| VEY | 3.1305 | 1.9475 | 2837 |
| WKL | 3.1303 | 2.0310 | 3246 |
| VCR | 3.1302 | 1.4113 | 8782 |
| EQV | 3.1301 | 2.2457 | 3411 |
| DVM | 3.1300 | 1.0176 | 2405 |
| WRD | 3.1298 | 1.1507 | 2364 |
| EDA | 3.1297 | 0.9488 | 2075 |
| WRW | 3.1296 | 0.6100 | 3701 |
| HFV | 3.1295 | 1.6875 | 1348 |
| WRF | 3.1293 | 1.0917 | 1825 |
| PLI | 3.1293 | 2.9571 | 1266 |
| YRK | 3.1292 | 2.2914 | 3008 |
| TTV | 3.1291 | 3.1250 | 3310 |
| WWI | 3.1290 | 0.6818 | 837 |
| IPM | 3.1290 | 2.8767 | 240 |
| VPN | 3.1290 | 2.7127 | 1500 |
| ARF | 3.1288 | 2.4290 | 2596 |
| VRH | 3.1288 | 1.8522 | 3690 |
| PLN | 3.1287 | 3.0409 | 718 |
| RHL | 3.1287 | 3.0370 | 3880 |
| GPN | 3.1287 | 2.2358 | 1661 |
| RCL | 3.1287 | 2.3612 | 5933 |
| MFV | 3.1285 | 1.7778 | 1567 |
| WWD | 3.1284 | 0.4098 | 1040 |
| RAD | 3.1284 | 2.8461 | 4976 |
| ESL | 3.1283 | 2.5619 | 7015 |
| RCG | 3.1279 | 2.4044 | 16051 |
| PAR | 3.1279 | 2.8182 | 3440 |
| DSM | 3.1279 | 2.4438 | 1903 |
| YDF | 3.1279 | 1.6457 | 584 |
| AVR | 3.1277 | 2.5838 | 16298 |
| GTM | 3.1277 | 0.8788 | 1795 |
| DCM | 3.1276 | 1.5433 | 1049 |
| CYM | 3.1275 | 2.1546 | 917 |
| RWG | 3.1274 | 1.6622 | 17751 |
| LYP | 3.1273 | 2.6947 | 665 |
| EAI | 3.1273 | 2.4612 | 3651 |
| DDE | 3.1271 | 0.9080 | 1011 |
| RAW | 3.1271 | 1.7217 | 5140 |
| TCV | 3.1270 | 2.4791 | 2575 |
| EVH | 3.1269 | 2.3077 | 2937 |
| NWE | 3.1269 | 0.3405 | 838 |
| PPI | 3.1268 | 3.5200 | 374 |
| VGI | 3.1267 | 2.0892 | 11004 |
| KPC | 3.1267 | 3.0333 | 719 |

TABLE F-continued

Medium-expressing EGFP variants

| AA SEQ | Mean | Range | Total counts |
|---|---|---|---|
| GHM | 3.1266 | 1.5392 | 778 |
| VRM | 3.1266 | 1.0312 | 4785 |
| AEY | 3.1265 | 2.0620 | 1924 |
| QGS | 3.1264 | 2.1000 | 5709 |
| KGP | 3.1264 | 1.6503 | 1838 |
| GAY | 3.1264 | 1.4501 | 3790 |
| CML | 3.1263 | 1.8755 | 2047 |
| DDW | 3.1262 | 0.5009 | 1035 |
| DWC | 3.1262 | 0.3792 | 1068 |
| VEL | 3.1261 | 2.2424 | 7979 |
| WAT | 3.1261 | 1.6685 | 1428 |
| RNH | 3.1260 | 2.2671 | 1796 |
| YGG | 3.1260 | 1.3321 | 13490 |
| VTS | 3.1260 | 2.1174 | 5497 |
| FQR | 3.1259 | 2.5569 | 1167 |
| GSG | 3.1259 | 2.3112 | 42545 |
| CPG | 3.1259 | 2.3068 | 3369 |
| ASF | 3.1256 | 2.7381 | 1729 |
| QDP | 3.1255 | 1.4141 | 452 |
| RQP | 3.1254 | 2.7817 | 1332 |
| YRV | 3.1252 | 2.3713 | 5953 |
| MPY | 3.1252 | 1.8755 | 296 |
| AMH | 3.1251 | 1.4545 | 371 |
| ATF | 3.1251 | 2.5654 | 1150 |
| AHY | 3.1244 | 2.8359 | 1148 |
| MTP | 3.1243 | 1.1917 | 274 |
| SHQ | 3.1242 | 2.6657 | 1087 |
| RKT | 3.1242 | 3.2168 | 3263 |
| DQN | 3.1241 | 1.5175 | 860 |
| AKL | 3.1241 | 3.0208 | 4526 |
| LWY | 3.1240 | 1.3401 | 1292 |
| PCN | 3.1240 | 3.4029 | 161 |
| PEA | 3.1239 | 1.9318 | 1575 |
| PQA | 3.1239 | 1.9123 | 579 |
| GGN | 3.1239 | 1.3125 | 8714 |
| SLV | 3.1238 | 2.9905 | 12797 |
| PGP | 3.1237 | 3.0000 | 1082 |
| GQY | 3.1236 | 1.9027 | 1444 |
| NQE | 3.1233 | 1.9382 | 538 |
| DRH | 3.1233 | 2.5127 | 1612 |
| CVF | 3.1232 | 2.1746 | 2437 |
| ESR | 3.1232 | 2.7867 | 16276 |
| SGV | 3.1230 | 2.4505 | 23504 |
| SFN | 3.1230 | 2.5591 | 1369 |
| RDC | 3.1229 | 2.1786 | 3381 |
| NLG | 3.1228 | 2.1267 | 6063 |
| NPD | 3.1228 | 1.7000 | 344 |
| YPM | 3.1228 | 2.2593 | 585 |
| WWK | 3.1228 | 0.1560 | 666 |
| CFP | 3.1227 | 1.1905 | 476 |
| GIA | 3.1227 | 1.9953 | 5802 |
| VVA | 3.1226 | 2.4459 | 12194 |
| RFS | 3.1226 | 2.6881 | 5198 |
| ATS | 3.1224 | 2.2268 | 3174 |
| CDL | 3.1223 | 2.8339 | 2181 |
| MCN | 3.1223 | 1.9544 | 932 |
| FPP | 3.1222 | 1.3667 | 36 |
| NAA | 3.1220 | 2.2021 | 1636 |
| IKE | 3.1220 | 1.7818 | 2028 |
| EGQ | 3.1219 | 1.1839 | 4627 |
| PEI | 3.1218 | 2.5113 | 709 |
| TCI | 3.1218 | 2.4278 | 1949 |
| QCS | 3.1214 | 1.9043 | 1400 |
| FGF | 3.1214 | 1.2624 | 1620 |
| TGW | 3.1212 | 1.1484 | 5428 |
| PEY | 3.1210 | 1.9552 | 887 |
| KDG | 3.1209 | 1.7167 | 3636 |
| GPQ | 3.1209 | 2.2449 | 1314 |
| VIW | 3.1205 | 0.7389 | 2135 |
| GMT | 3.1204 | 2.3778 | 1929 |
| AQL | 3.1203 | 2.2988 | 2465 |
| ASN | 3.1203 | 1.9825 | 2328 |
| AEQ | 3.1203 | 1.3297 | 1233 |
| MLG | 3.1201 | 1.9839 | 7011 |
| GCL | 3.1200 | 2.0536 | 6344 |
| MGT | 3.1200 | 1.8311 | 2153 |
| HDL | 3.1200 | 2.8416 | 674 |
| LLK | 3.1198 | 3.4543 | 4444 |
| HVV | 3.1198 | 2.8886 | 3613 |
| VCI | 3.1198 | 1.2876 | 2961 |
| SPA | 3.1197 | 2.8000 | 1565 |
| CTE | 3.1197 | 2.3103 | 1537 |
| FGD | 3.1197 | 1.7669 | 1927 |
| LTT | 3.1197 | 3.3523 | 1640 |
| ESC | 3.1196 | 2.1692 | 4278 |
| FYN | 3.1195 | 1.7817 | 225 |
| GMM | 3.1194 | 0.6234 | 1412 |
| DTS | 3.1193 | 2.4993 | 2703 |
| RYD | 3.1193 | 2.3900 | 1961 |
| QDH | 3.1192 | 1.8277 | 233 |
| TGC | 3.1191 | 1.7895 | 5048 |
| QRN | 3.1191 | 1.7664 | 1577 |
| LPK | 3.1190 | 3.0111 | 1431 |
| VSL | 3.1190 | 2.7895 | 9927 |
| TYM | 3.1190 | 2.2532 | 686 |
| SGC | 3.1189 | 1.4021 | 9566 |
| RLN | 3.1188 | 3.5172 | 6396 |
| CAF | 3.1186 | 1.7906 | 1148 |
| AGK | 3.1186 | 1.2804 | 6947 |
| IAE | 3.1186 | 2.5433 | 2056 |
| REK | 3.1185 | 2.0218 | 4357 |
| AHG | 3.1184 | 1.8142 | 2510 |
| CMI | 3.1184 | 1.1624 | 927 |
| SHL | 3.1183 | 3.4609 | 2590 |
| HPK | 3.1182 | 3.2290 | 823 |
| CSS | 3.1181 | 2.4920 | 4159 |
| GID | 3.1181 | 1.7823 | 3066 |
| RLL | 3.1180 | 3.7321 | 15839 |
| EMS | 3.1180 | 1.1431 | 2465 |
| GSM | 3.1180 | 1.1351 | 3778 |
| IEN | 3.1180 | 1.7734 | 1264 |
| VQA | 3.1179 | 2.6227 | 3102 |
| FGL | 3.1178 | 2.2691 | 4407 |
| SPL | 3.1178 | 3.5134 | 1732 |
| ACH | 3.1177 | 1.3653 | 692 |
| RDL | 3.1176 | 2.2943 | 4518 |
| YVS | 3.1175 | 2.2085 | 5217 |
| GLD | 3.1175 | 2.1980 | 7224 |
| WQT | 3.1175 | 1.8374 | 934 |
| HGQ | 3.1174 | 1.8955 | 1184 |
| FVV | 3.1174 | 1.2428 | 4482 |
| GLA | 3.1173 | 2.6587 | 14570 |
| LPS | 3.1173 | 2.9079 | 2084 |
| QRT | 3.1173 | 3.0303 | 2348 |
| AAI | 3.1172 | 1.8801 | 2633 |
| NGF | 3.1172 | 1.2442 | 2144 |
| ALS | 3.1171 | 3.6949 | 6981 |
| QPR | 3.1169 | 1.6056 | 1389 |
| DAD | 3.1168 | 1.6152 | 1084 |
| AKC | 3.1168 | 2.3066 | 1771 |
| LKF | 3.1168 | 2.2550 | 1856 |
| MVA | 3.1166 | 1.6250 | 3634 |
| ANH | 3.1165 | 1.2495 | 551 |
| EMR | 3.1165 | 1.7195 | 4158 |
| GWT | 3.1164 | 0.9991 | 3177 |
| GHR | 3.1162 | 3.1460 | 6688 |
| SSA | 3.1162 | 2.7757 | 6047 |
| RGC | 3.1162 | 1.4953 | 16431 |
| FKL | 3.1161 | 1.9438 | 1300 |
| VIF | 3.1160 | 1.6329 | 1699 |
| NPE | 3.1160 | 2.6975 | 850 |
| PKY | 3.1159 | 2.7132 | 655 |
| YGH | 3.1157 | 1.8846 | 1264 |
| GVW | 3.1156 | 1.4397 | 13719 |
| VIL | 3.1155 | 1.6440 | 5198 |
| AQK | 3.1155 | 1.6033 | 1490 |
| TRV | 3.1154 | 2.6429 | 7331 |
| CVV | 3.1154 | 2.6375 | 8837 |
| RHR | 3.1154 | 2.5110 | 5584 |
| AMW | 3.1154 | 0.6536 | 968 |

TABLE F-continued

Medium-expressing EGFP variants

| AA SEQ | Mean | Range | Total counts |
|---|---|---|---|
| GEE | 3.1153 | 1.1818 | 10018 |
| VLM | 3.1153 | 1.7944 | 3256 |
| VLT | 3.1153 | 2.5217 | 4465 |
| PYP | 3.1152 | 0.6706 | 138 |
| REN | 3.1152 | 1.9138 | 2927 |
| SEP | 3.1150 | 1.9436 | 1001 |
| PNT | 3.1150 | 3.2125 | 598 |
| EGR | 3.1150 | 1.1461 | 26510 |
| PSI | 3.1148 | 2.4530 | 1077 |
| EMD | 3.1148 | 1.1577 | 624 |
| PGS | 3.1148 | 2.8667 | 6420 |
| QLC | 3.1147 | 2.9665 | 2339 |
| YEV | 3.1147 | 1.6705 | 3640 |
| GIY | 3.1146 | 1.7737 | 3170 |
| PFH | 3.1146 | 1.8336 | 352 |
| AFR | 3.1145 | 2.2464 | 3883 |
| QCT | 3.1140 | 2.7426 | 736 |
| HYP | 3.1140 | 3.4457 | 444 |
| LPR | 3.1140 | 3.5507 | 3016 |
| DES | 3.1139 | 1.3416 | 2572 |
| RVA | 3.1139 | 2.7472 | 15973 |
| YRM | 3.1138 | 1.9965 | 1495 |
| SFM | 3.1137 | 1.0617 | 733 |
| PYI | 3.1135 | 2.8575 | 386 |
| TFV | 3.1133 | 2.7509 | 1901 |
| PMY | 3.1132 | 2.0463 | 240 |
| TWS | 3.1132 | 2.2500 | 1481 |
| RRV | 3.1132 | 2.1761 | 25389 |
| RHC | 3.1131 | 2.3817 | 2145 |
| VSD | 3.1130 | 1.5312 | 4778 |
| AQF | 3.1130 | 2.7005 | 689 |
| TLW | 3.1128 | 1.6493 | 2159 |
| RQM | 3.1128 | 2.1581 | 1200 |
| AMF | 3.1127 | 0.9620 | 622 |
| PGE | 3.1126 | 1.9624 | 3528 |
| CLS | 3.1126 | 2.9394 | 6171 |
| EQQ | 3.1125 | 1.5777 | 803 |
| AMA | 3.1125 | 1.7996 | 1239 |
| PCR | 3.1124 | 1.4451 | 1207 |
| VHS | 3.1123 | 2.3545 | 3164 |
| PGN | 3.1122 | 2.2721 | 1469 |
| TDV | 3.1122 | 1.6996 | 1927 |
| GMS | 3.1122 | 1.6955 | 4699 |
| API | 3.1121 | 2.6091 | 890 |
| LWK | 3.1121 | 1.0529 | 1597 |
| HGV | 3.1119 | 1.5515 | 3569 |
| PKE | 3.1116 | 1.7289 | 556 |
| QAV | 3.1116 | 1.5859 | 2509 |
| TQR | 3.1116 | 2.5373 | 2311 |
| AFD | 3.1115 | 1.2182 | 999 |
| GDM | 3.1115 | 1.0094 | 1958 |
| LAY | 3.1115 | 2.2238 | 1871 |
| GTC | 3.1114 | 1.3146 | 4390 |
| GTA | 3.1113 | 2.5869 | 5440 |
| VQT | 3.1112 | 2.1923 | 1272 |
| PEE | 3.1111 | 1.3452 | 1063 |
| AMM | 3.1111 | 1.6119 | 443 |
| EGS | 3.1111 | 2.2022 | 14131 |
| QQE | 3.1110 | 1.4507 | 582 |
| LCT | 3.1109 | 2.4688 | 2336 |
| HHD | 3.1109 | 2.0285 | 386 |
| YIT | 3.1108 | 2.3897 | 1877 |
| GND | 3.1108 | 1.7395 | 2064 |
| ICP | 3.1106 | 2.0000 | 406 |
| YLR | 3.1106 | 3.1822 | 6100 |
| ERM | 3.1106 | 1.7160 | 4025 |
| ATM | 3.1104 | 1.7765 | 710 |
| HAS | 3.1104 | 1.8565 | 1188 |
| SWW | 3.1104 | 1.7604 | 2542 |
| VIG | 3.1103 | 1.3233 | 12084 |
| VPV | 3.1103 | 2.2830 | 5105 |
| TVV | 3.1100 | 2.1853 | 8638 |
| DET | 3.1100 | 2.2789 | 1258 |
| TDH | 3.1100 | 1.8990 | 400 |
| GQD | 3.1100 | 1.5411 | 2264 |
| CGS | 3.1100 | 2.3133 | 9325 |
| RSP | 3.1100 | 3.0767 | 2189 |
| VEC | 3.1099 | 1.4770 | 4819 |
| HRE | 3.1099 | 1.7721 | 1494 |
| GWI | 3.1097 | 1.0634 | 3778 |
| MDL | 3.1097 | 1.4312 | 1016 |
| RKD | 3.1096 | 2.5424 | 2561 |
| YIS | 3.1096 | 2.7308 | 2807 |
| WTS | 3.1096 | 1.7110 | 1788 |
| QED | 3.1095 | 1.1299 | 664 |
| IPC | 3.1095 | 1.8222 | 506 |
| YTG | 3.1093 | 2.4162 | 3694 |
| VCW | 3.1093 | 0.8774 | 2623 |
| VPE | 3.1092 | 2.4420 | 2238 |
| IPE | 3.1092 | 2.5390 | 1192 |
| VML | 3.1091 | 1.4262 | 3975 |
| ARV | 3.1091 | 2.4863 | 14022 |
| VAS | 3.1091 | 3.1055 | 8596 |
| SHT | 3.1090 | 3.5375 | 1643 |
| RWE | 3.1090 | 0.8342 | 4551 |
| LCP | 3.1090 | 2.8758 | 697 |
| DWD | 3.1090 | 0.5479 | 577 |
| RRW | 3.1089 | 1.6435 | 9298 |
| MAV | 3.1088 | 1.7362 | 2776 |
| GAD | 3.1087 | 1.8839 | 6813 |
| GNG | 3.1086 | 0.8761 | 9504 |
| QRL | 3.1085 | 2.9189 | 4807 |
| RPV | 3.1084 | 3.3337 | 6119 |
| PRT | 3.1084 | 2.8409 | 1029 |
| AIQ | 3.1084 | 2.6172 | 1917 |
| LCR | 3.1083 | 2.4474 | 7237 |
| RQC | 3.1082 | 2.1613 | 3536 |
| YMP | 3.1081 | 2.8496 | 282 |
| QGK | 3.1081 | 1.9947 | 3296 |
| FCW | 3.1081 | 0.5552 | 375 |
| FDH | 3.1080 | 1.4978 | 278 |
| TPV | 3.1079 | 3.2662 | 1746 |
| SCS | 3.1079 | 2.6496 | 3252 |
| IPS | 3.1078 | 2.7488 | 1212 |
| EPG | 3.1077 | 1.8264 | 4819 |
| YIE | 3.1076 | 2.0912 | 1301 |
| VSY | 3.1072 | 2.3337 | 5008 |
| ERH | 3.1071 | 1.5469 | 2279 |
| DIE | 3.1071 | 1.7656 | 1990 |
| IDK | 3.1069 | 1.6360 | 1217 |
| DDT | 3.1069 | 1.7593 | 1092 |
| TCW | 3.1069 | 1.0459 | 844 |
| NEC | 3.1068 | 2.3916 | 1333 |
| FRG | 3.1065 | 1.3067 | 7469 |
| DEI | 3.1064 | 1.3754 | 1943 |
| YQD | 3.1064 | 1.7916 | 486 |
| IMI | 3.1063 | 1.8651 | 885 |
| SCW | 3.1062 | 1.1885 | 1843 |
| WFG | 3.1062 | 0.8196 | 3205 |
| SKD | 3.1060 | 2.6692 | 2097 |
| SPT | 3.1060 | 2.9127 | 1062 |
| REA | 3.1059 | 2.3020 | 8129 |
| TVL | 3.1058 | 2.4832 | 7714 |
| HLS | 3.1056 | 2.7864 | 2576 |
| CRH | 3.1056 | 2.4274 | 1103 |
| MTV | 3.1056 | 2.1850 | 2344 |
| AIN | 3.1056 | 2.4108 | 1488 |
| VVY | 3.1055 | 1.7749 | 5191 |
| LTG | 3.1055 | 2.1468 | 7902 |
| AKG | 3.1053 | 1.3712 | 6827 |
| TAT | 3.1053 | 2.2540 | 1259 |
| ADH | 3.1051 | 1.5000 | 614 |
| EWT | 3.1050 | 1.3241 | 1342 |
| GDL | 3.1049 | 2.6066 | 5977 |
| MMV | 3.1049 | 1.3244 | 1181 |
| LGC | 3.1049 | 1.7761 | 9546 |
| ELN | 3.1048 | 2.2941 | 3598 |
| SRP | 3.1048 | 2.5529 | 1655 |
| SQD | 3.1048 | 1.3954 | 1144 |
| HER | 3.1046 | 2.8363 | 2463 |

TABLE F-continued

Medium-expressing EGFP variants

| AA SEQ | Mean | Range | Total counts |
|---|---|---|---|
| GVH | 3.1046 | 1.5242 | 4381 |
| QFW | 3.1045 | 0.7880 | 197 |
| KGF | 3.1045 | 1.5110 | 2692 |
| LII | 3.1045 | 2.0667 | 2301 |
| EGH | 3.1045 | 1.8713 | 2824 |
| FRD | 3.1044 | 1.6300 | 1545 |
| CAA | 3.1042 | 2.1675 | 2463 |
| YGL | 3.1040 | 2.2237 | 5885 |
| SWR | 3.1039 | 1.4431 | 5619 |
| GAA | 3.1039 | 2.2069 | 12669 |
| RTC | 3.1037 | 2.6883 | 3742 |
| HSA | 3.1037 | 3.0826 | 2117 |
| CCH | 3.1036 | 2.0589 | 460 |
| WVQ | 3.1036 | 0.6855 | 1656 |
| TAV | 3.1035 | 2.1541 | 3784 |
| PNV | 3.1031 | 2.2718 | 1079 |
| HEC | 3.1031 | 2.3547 | 736 |
| AMV | 3.1031 | 1.2401 | 2432 |
| VYV | 3.1030 | 1.3238 | 4689 |
| EAP | 3.1029 | 2.1714 | 1128 |
| DWK | 3.1029 | 2.0762 | 1018 |
| ANP | 3.1028 | 3.2075 | 486 |
| QSS | 3.1025 | 2.4714 | 3222 |
| TGS | 3.1024 | 2.2209 | 9498 |
| PGH | 3.1024 | 3.2505 | 1113 |
| ALR | 3.1023 | 3.1574 | 10289 |
| WVT | 3.1023 | 1.2431 | 2562 |
| QVL | 3.1021 | 2.6228 | 4988 |
| ATA | 3.1020 | 2.7902 | 2201 |
| YWS | 3.1020 | 1.5889 | 1471 |
| VNG | 3.1020 | 1.0304 | 5949 |
| YGY | 3.1018 | 2.9760 | 2013 |
| ASM | 3.1015 | 1.9918 | 1998 |
| IIN | 3.1015 | 1.4889 | 1315 |
| IMS | 3.1013 | 1.5667 | 2105 |
| AQY | 3.1013 | 3.1973 | 1457 |
| RQW | 3.1013 | 1.1194 | 2626 |
| LQK | 3.1012 | 2.8286 | 1365 |
| LDC | 3.1012 | 1.8491 | 1899 |
| RDM | 3.1012 | 0.9916 | 2007 |
| FVW | 3.1011 | 1.1431 | 1753 |
| GPG | 3.1011 | 2.2624 | 17147 |
| WEN | 3.1011 | 0.5491 | 1008 |
| NRE | 3.1009 | 2.7545 | 3276 |
| LQE | 3.1009 | 2.2368 | 1374 |
| VHE | 3.1008 | 1.3288 | 1391 |
| KGS | 3.1007 | 1.6500 | 8881 |
| GKS | 3.1006 | 1.6032 | 8298 |
| ARD | 3.1005 | 2.4773 | 4106 |
| LEP | 3.1005 | 2.0417 | 1093 |
| GSF | 3.1003 | 1.9440 | 3812 |
| WFW | 3.1000 | 0.1048 | 572 |
| HPE | 3.1000 | 1.8785 | 360 |
| RKE | 3.0998 | 2.2567 | 4489 |
| AHS | 3.0998 | 2.5328 | 2268 |
| PAK | 3.0998 | 1.8897 | 872 |
| VQL | 3.0997 | 3.1714 | 3456 |
| CMS | 3.0997 | 0.6434 | 1425 |
| GRH | 3.0997 | 2.0899 | 5348 |
| YRN | 3.0994 | 2.2888 | 1395 |
| YVN | 3.0994 | 1.7941 | 1854 |
| RET | 3.0992 | 2.4378 | 3565 |
| EYG | 3.0992 | 1.0852 | 4978 |
| DGT | 3.0992 | 1.5433 | 3164 |
| HPV | 3.0992 | 2.6538 | 713 |
| RLS | 3.0992 | 3.6039 | 18253 |
| PDN | 3.0991 | 1.3167 | 247 |
| GAK | 3.0989 | 1.1460 | 5392 |
| SVL | 3.0989 | 3.2543 | 12866 |
| TGP | 3.0988 | 2.5677 | 1612 |
| WRC | 3.0988 | 0.9220 | 3831 |
| EVA | 3.0988 | 1.9336 | 7262 |
| GDS | 3.0987 | 2.1855 | 6933 |
| EAS | 3.0987 | 1.7290 | 4842 |
| AYG | 3.0987 | 1.6338 | 4576 |
| FES | 3.0985 | 1.9506 | 1668 |
| ETN | 3.0985 | 2.5414 | 1531 |
| MIL | 3.0985 | 2.4328 | 2015 |
| MEV | 3.0984 | 0.8589 | 2374 |
| YAL | 3.0984 | 2.2148 | 2141 |
| DSH | 3.0984 | 2.5841 | 1297 |
| GHV | 3.0984 | 1.6451 | 4677 |
| HCT | 3.0983 | 2.5076 | 751 |
| VIA | 3.0983 | 2.6753 | 5212 |
| FCY | 3.0983 | 1.0000 | 354 |
| GMN | 3.0982 | 1.1727 | 1411 |
| QDR | 3.0981 | 1.8112 | 2838 |
| TGH | 3.0981 | 3.0567 | 1726 |
| RVV | 3.0979 | 2.0086 | 23567 |
| AEP | 3.0979 | 2.2348 | 1310 |
| PHE | 3.0978 | 1.2095 | 94 |
| HEI | 3.0976 | 2.2210 | 1004 |
| VCQ | 3.0976 | 1.5921 | 1573 |
| KED | 3.0976 | 0.9225 | 1479 |
| FQT | 3.0976 | 2.7143 | 298 |
| SCI | 3.0975 | 2.0279 | 2635 |
| AVM | 3.0973 | 1.2048 | 2833 |
| EQG | 3.0972 | 1.1931 | 5349 |
| VKP | 3.0972 | 2.7007 | 1354 |
| QGQ | 3.0972 | 1.1812 | 1886 |
| RRF | 3.0972 | 2.6243 | 5178 |
| ECH | 3.0971 | 1.4908 | 1217 |
| EAW | 3.0971 | 0.6589 | 2688 |
| YSP | 3.0968 | 1.6619 | 631 |
| QNG | 3.0968 | 1.1943 | 1420 |
| THV | 3.0967 | 3.2424 | 1396 |
| LVY | 3.0967 | 3.7990 | 4286 |
| WQE | 3.0966 | 0.5704 | 929 |
| ITC | 3.0965 | 2.7161 | 1625 |
| YSR | 3.0965 | 2.7813 | 5723 |
| DRS | 3.0963 | 3.3598 | 7657 |
| CPR | 3.0963 | 1.8400 | 2058 |
| HPN | 3.0962 | 2.6469 | 198 |
| WYF | 3.0961 | 1.0446 | 376 |
| IYF | 3.0959 | 2.1007 | 601 |
| GLG | 3.0959 | 1.8059 | 45977 |
| GGK | 3.0959 | 0.9089 | 16113 |
| HQA | 3.0958 | 3.1579 | 396 |
| LPF | 3.0957 | 1.5667 | 709 |
| CRA | 3.0957 | 2.5618 | 5627 |
| QQH | 3.0957 | 2.0366 | 302 |
| VSC | 3.0956 | 1.4439 | 5540 |
| CHN | 3.0955 | 2.1364 | 274 |
| VIS | 3.0955 | 1.9035 | 6765 |
| WWP | 3.0954 | 0.7524 | 745 |
| WNQ | 3.0952 | 1.0117 | 222 |
| PSS | 3.0952 | 3.0000 | 2497 |
| CLH | 3.0952 | 2.5379 | 1659 |
| HGL | 3.0952 | 1.7664 | 2228 |
| CRG | 3.0952 | 1.2907 | 16004 |
| SAG | 3.0951 | 2.5290 | 16079 |
| VGN | 3.0950 | 1.8650 | 7042 |
| WNP | 3.0950 | 2.3436 | 279 |
| PKR | 3.0949 | 2.6728 | 1505 |
| YVC | 3.0949 | 1.9163 | 3087 |
| ERL | 3.0948 | 2.3578 | 9744 |
| GEA | 3.0948 | 1.1377 | 11216 |
| RQR | 3.0948 | 3.0556 | 7690 |
| HVS | 3.0945 | 2.1765 | 3670 |
| DAP | 3.0945 | 2.1563 | 583 |
| LKV | 3.0944 | 2.2413 | 6865 |
| RKS | 3.0942 | 2.6161 | 7352 |
| GVR | 3.0942 | 1.6661 | 45033 |
| RWC | 3.0941 | 1.4705 | 4326 |
| PQV | 3.0940 | 2.4409 | 871 |
| DKD | 3.0940 | 1.4017 | 976 |
| PRL | 3.0940 | 3.1429 | 3294 |
| MWT | 3.0939 | 1.1126 | 394 |
| DEG | 3.0939 | 0.8592 | 6806 |
| AAD | 3.0939 | 2.4351 | 2647 |

TABLE F-continued

Medium-expressing EGFP variants

| AA SEQ | Mean | Range | Total counts |
|---|---|---|---|
| KGW | 3.0936 | 0.5162 | 5049 |
| RVG | 3.0932 | 2.1789 | 46271 |
| YDL | 3.0932 | 3.0409 | 2019 |
| GDI | 3.0932 | 1.1100 | 3856 |
| VIV | 3.0931 | 1.5242 | 6571 |
| WLK | 3.0929 | 1.7029 | 2396 |
| CDD | 3.0929 | 1.0315 | 690 |
| TRA | 3.0928 | 2.8197 | 5897 |
| PGM | 3.0928 | 1.2576 | 1625 |
| LPA | 3.0927 | 3.2583 | 1449 |
| DDF | 3.0927 | 0.7418 | 667 |
| GVL | 3.0927 | 3.2486 | 21952 |
| PSF | 3.0927 | 3.4458 | 714 |
| IGN | 3.0927 | 1.9568 | 3650 |
| STP | 3.0926 | 1.1455 | 388 |
| KVD | 3.0926 | 2.5974 | 3264 |
| EGN | 3.0925 | 1.1860 | 4280 |
| LSH | 3.0924 | 3.7324 | 2760 |
| MPK | 3.0924 | 1.5238 | 477 |
| RFR | 3.0924 | 2.3378 | 9075 |
| LEL | 3.0923 | 2.3902 | 5782 |
| KGQ | 3.0922 | 2.2313 | 2501 |
| HAC | 3.0922 | 1.2182 | 488 |
| PIP | 3.0922 | 1.8214 | 424 |
| IHV | 3.0920 | 2.7004 | 2591 |
| ALI | 3.0920 | 2.5610 | 4524 |
| LCV | 3.0918 | 1.7205 | 4650 |
| ELA | 3.0918 | 2.1969 | 5943 |
| SLS | 3.0918 | 3.4019 | 9452 |
| GAC | 3.0917 | 1.5170 | 7551 |
| PMT | 3.0916 | 1.3714 | 489 |
| AAR | 3.0916 | 2.7466 | 9475 |
| GSE | 3.0916 | 2.0697 | 11063 |
| MDG | 3.0915 | 0.6078 | 2622 |
| FRV | 3.0913 | 1.9454 | 4366 |
| YAK | 3.0912 | 2.4264 | 2275 |
| DVR | 3.0912 | 1.9275 | 12086 |
| SET | 3.0912 | 2.6684 | 2363 |
| PVE | 3.0911 | 2.0102 | 2074 |
| FGS | 3.0910 | 2.8182 | 4794 |
| LRD | 3.0910 | 2.6884 | 5279 |
| VCT | 3.0910 | 1.8513 | 2763 |
| LYQ | 3.0910 | 3.5069 | 1285 |
| QRS | 3.0909 | 3.4778 | 5047 |
| KAD | 3.0908 | 1.5959 | 1670 |
| RGN | 3.0908 | 2.1832 | 7510 |
| QGL | 3.0907 | 1.7235 | 5744 |
| MNS | 3.0907 | 2.2493 | 1429 |
| WQL | 3.0907 | 1.3975 | 1574 |
| FAC | 3.0907 | 1.1660 | 731 |
| DRR | 3.0906 | 2.1871 | 11326 |
| HQQ | 3.0905 | 2.3367 | 434 |
| RIC | 3.0904 | 2.6565 | 5534 |
| RWH | 3.0903 | 1.6243 | 1542 |
| EED | 3.0902 | 0.9437 | 2315 |
| WHG | 3.0902 | 0.9603 | 1686 |
| DPH | 3.0901 | 2.5876 | 462 |
| VPS | 3.0901 | 2.9341 | 6297 |
| IVV | 3.0898 | 1.5748 | 7162 |
| LYE | 3.0898 | 2.7389 | 2468 |
| EWC | 3.0898 | 0.6700 | 2015 |
| QWR | 3.0898 | 1.2713 | 2241 |
| RLG | 3.0897 | 3.2576 | 33423 |
| ITQ | 3.0896 | 2.5554 | 1067 |
| EKD | 3.0896 | 1.2070 | 1737 |
| RGS | 3.0896 | 3.0248 | 28105 |
| AWN | 3.0895 | 0.6029 | 862 |
| AHQ | 3.0895 | 3.3423 | 965 |
| FIK | 3.0895 | 2.6522 | 689 |
| WPT | 3.0894 | 1.9563 | 517 |
| DMR | 3.0893 | 1.5097 | 2914 |
| LYN | 3.0893 | 2.6492 | 1523 |
| CAV | 3.0891 | 1.6414 | 4859 |
| VLG | 3.0891 | 2.5985 | 26895 |
| LYS | 3.0890 | 2.3423 | 4820 |
| VAN | 3.0889 | 1.9601 | 2404 |
| IWC | 3.0887 | 0.5664 | 1192 |
| RDS | 3.0886 | 2.3078 | 6590 |
| GPR | 3.0884 | 2.4213 | 9998 |
| TVN | 3.0883 | 2.8777 | 2777 |
| YYD | 3.0883 | 1.7973 | 640 |
| VVM | 3.0881 | 0.9258 | 5179 |
| RGM | 3.0879 | 1.6596 | 6598 |
| DPT | 3.0878 | 2.8020 | 422 |
| GHI | 3.0878 | 2.1065 | 1815 |
| LGN | 3.0878 | 2.3588 | 4812 |
| GST | 3.0877 | 2.3028 | 6989 |
| IAG | 3.0877 | 1.2632 | 6031 |
| QLW | 3.0877 | 1.1044 | 1227 |
| EWL | 3.0877 | 1.2451 | 3107 |
| AEW | 3.0875 | 0.8226 | 2896 |
| FPS | 3.0875 | 2.7912 | 860 |
| LFK | 3.0873 | 2.6713 | 2162 |
| GGD | 3.0873 | 2.3033 | 16445 |
| LCS | 3.0871 | 3.0000 | 4603 |
| RPK | 3.0869 | 3.3858 | 2038 |
| QGY | 3.0869 | 1.6484 | 1998 |
| STS | 3.0869 | 2.9222 | 4031 |
| RSC | 3.0868 | 2.5658 | 8274 |
| SGR | 3.0867 | 2.8591 | 28102 |
| GLE | 3.0867 | 1.4512 | 11760 |
| GHQ | 3.0865 | 1.8879 | 779 |
| IDV | 3.0865 | 1.4825 | 2497 |
| GEL | 3.0864 | 1.7829 | 10127 |
| GFW | 3.0864 | 0.9586 | 2303 |
| WTA | 3.0863 | 0.9671 | 1703 |
| RPT | 3.0863 | 3.1816 | 1449 |
| WCG | 3.0862 | 0.7359 | 5969 |
| GWR | 3.0862 | 1.5510 | 17950 |
| MGI | 3.0861 | 1.8307 | 2168 |
| PMH | 3.0861 | 1.1764 | 568 |
| SSL | 3.0861 | 3.8085 | 7144 |
| TVR | 3.0861 | 3.2352 | 12732 |
| GIF | 3.0861 | 1.5361 | 2395 |
| EPL | 3.0861 | 2.0583 | 1861 |
| QRQ | 3.0860 | 2.3264 | 1240 |
| GLI | 3.0859 | 2.2088 | 8353 |
| GSL | 3.0858 | 2.2909 | 13337 |
| DHS | 3.0858 | 2.0128 | 949 |
| LRL | 3.0857 | 2.8010 | 10840 |
| IDG | 3.0856 | 1.6828 | 4384 |
| HTA | 3.0856 | 2.7016 | 1243 |
| RMA | 3.0855 | 2.2267 | 2072 |
| SDA | 3.0855 | 1.7227 | 2384 |
| CEQ | 3.0854 | 2.2185 | 958 |
| EQA | 3.0854 | 1.5219 | 1437 |
| FLE | 3.0853 | 1.5058 | 1202 |
| AED | 3.0848 | 1.5793 | 2036 |
| HEW | 3.0848 | 0.6236 | 360 |
| AEA | 3.0848 | 2.1394 | 3984 |
| WDT | 3.0847 | 1.1686 | 700 |
| KLW | 3.0844 | 1.9963 | 3442 |
| STD | 3.0843 | 2.5747 | 1672 |
| CGA | 3.0842 | 1.3106 | 8223 |
| WAY | 3.0842 | 0.9164 | 1023 |
| IWE | 3.0840 | 0.4437 | 1538 |
| LGL | 3.0840 | 2.8429 | 16399 |
| VER | 3.0840 | 1.3979 | 15390 |
| HMC | 3.0837 | 1.9679 | 520 |
| MLT | 3.0837 | 3.0158 | 1464 |
| ARR | 3.0835 | 2.9211 | 17345 |
| CKD | 3.0834 | 1.3036 | 756 |
| LCC | 3.0833 | 1.5462 | 2606 |
| PVV | 3.0833 | 2.6231 | 4704 |
| EHC | 3.0833 | 1.2001 | 1057 |
| RFG | 3.0833 | 1.9810 | 10664 |
| GDT | 3.0831 | 2.2946 | 3450 |
| NPQ | 3.0831 | 2.8343 | 642 |
| MTS | 3.0831 | 2.3147 | 1812 |
| CKE | 3.0830 | 1.4984 | 1547 |

TABLE F-continued

Medium-expressing EGFP variants

| AA SEQ | Mean | Range | Total counts |
|---|---|---|---|
| NGE | 3.0828 | 0.8733 | 3707 |
| SFK | 3.0828 | 2.8047 | 1698 |
| RTG | 3.0828 | 2.7844 | 13366 |
| GED | 3.0827 | 1.3327 | 5228 |
| TPE | 3.0827 | 1.7898 | 824 |
| HIG | 3.0826 | 2.0431 | 1770 |
| WMM | 3.0825 | 0.0000 | 206 |
| RRG | 3.0825 | 2.3359 | 53579 |
| EEG | 3.0825 | 1.2904 | 12811 |
| RQS | 3.0824 | 3.2379 | 5705 |
| AHR | 3.0822 | 2.2305 | 2330 |
| RDN | 3.0822 | 1.6648 | 1857 |
| NRD | 3.0821 | 2.3052 | 2256 |
| LCD | 3.0821 | 1.4997 | 1908 |
| PQF | 3.0820 | 1.4500 | 283 |
| ERE | 3.0820 | 1.1555 | 7609 |
| LSV | 3.0820 | 2.7988 | 10952 |
| QLG | 3.0819 | 2.5768 | 5408 |
| LLQ | 3.0818 | 2.6009 | 3165 |
| LTS | 3.0817 | 3.6479 | 4235 |
| GVI | 3.0816 | 1.2027 | 10527 |
| GFR | 3.0816 | 1.5555 | 8356 |
| DRA | 3.0816 | 2.2912 | 4935 |
| FGC | 3.0815 | 1.3625 | 2894 |
| NCH | 3.0815 | 2.6532 | 697 |
| VLH | 3.0815 | 3.5963 | 3424 |
| DPW | 3.0814 | 0.9211 | 547 |
| EAM | 3.0813 | 1.2148 | 1470 |
| DEN | 3.0813 | 1.9616 | 907 |
| VTM | 3.0813 | 0.9873 | 1244 |
| FEG | 3.0813 | 1.1211 | 3322 |
| RLP | 3.0813 | 3.1286 | 4474 |
| FDE | 3.0812 | 1.3106 | 505 |
| QMG | 3.0812 | 1.3453 | 1599 |
| PIR | 3.0812 | 3.3370 | 2537 |
| ETQ | 3.0811 | 2.0254 | 779 |
| HVA | 3.0809 | 3.8921 | 1938 |
| TGG | 3.0807 | 1.5334 | 23456 |
| REP | 3.0807 | 2.7361 | 1947 |
| RRS | 3.0805 | 2.3720 | 17846 |
| AGS | 3.0802 | 2.8216 | 16165 |
| EVP | 3.0802 | 2.1538 | 2552 |
| PCM | 3.0802 | 1.1082 | 324 |
| RVM | 3.0802 | 1.3337 | 6522 |
| GLC | 3.0801 | 1.6618 | 10754 |
| NAG | 3.0801 | 1.4516 | 4104 |
| SQT | 3.0799 | 3.0790 | 1213 |
| LSA | 3.0799 | 3.6907 | 6100 |
| GRK | 3.0798 | 1.3956 | 11885 |
| FWS | 3.0797 | 1.0612 | 856 |
| ETH | 3.0797 | 3.2381 | 1212 |
| STQ | 3.0797 | 2.7373 | 1840 |
| SGQ | 3.0795 | 2.7698 | 5832 |
| PDC | 3.0795 | 2.1250 | 451 |
| RLT | 3.0795 | 3.5260 | 6646 |
| RGD | 3.0795 | 2.0227 | 11771 |
| CVK | 3.0794 | 2.3795 | 4288 |
| ANC | 3.0794 | 2.0099 | 1278 |
| CAE | 3.0794 | 1.4668 | 2416 |
| GPE | 3.0793 | 2.0556 | 3645 |
| LTA | 3.0793 | 3.2032 | 2474 |
| ICA | 3.0791 | 2.4740 | 2041 |
| CPA | 3.0791 | 2.9242 | 1032 |
| AAE | 3.0790 | 2.0230 | 5022 |
| GRN | 3.0790 | 1.4381 | 7080 |
| ETT | 3.0789 | 2.5967 | 1563 |
| FVN | 3.0788 | 1.7344 | 947 |
| GER | 3.0788 | 1.0840 | 22680 |
| LTV | 3.0787 | 2.0328 | 4628 |
| HTV | 3.0787 | 3.5173 | 1982 |
| RWF | 3.0786 | 1.2755 | 2205 |
| GDQ | 3.0786 | 1.1127 | 1889 |
| IPD | 3.0786 | 2.0545 | 491 |
| HGG | 3.0786 | 1.4176 | 7749 |
| RPC | 3.0785 | 2.5455 | 1729 |
| ATD | 3.0782 | 1.6647 | 1457 |
| VEM | 3.0780 | 0.5567 | 2229 |
| RSG | 3.0780 | 2.6112 | 31250 |
| PLH | 3.0779 | 3.0000 | 644 |
| QNP | 3.0779 | 1.8190 | 366 |
| IRA | 3.0778 | 2.5332 | 7643 |
| GWG | 3.0777 | 1.2075 | 27867 |
| SLP | 3.0776 | 3.0250 | 1978 |
| MPW | 3.0776 | 0.9022 | 377 |
| GWA | 3.0775 | 1.4717 | 8500 |
| ASV | 3.0775 | 3.1356 | 8210 |
| TID | 3.0775 | 2.1026 | 1084 |
| SVK | 3.0774 | 2.5200 | 7489 |
| SGM | 3.0774 | 1.9335 | 4424 |
| GWY | 3.0773 | 0.9532 | 2517 |
| CCE | 3.0773 | 1.0178 | 1161 |
| YDV | 3.0772 | 1.2792 | 2060 |
| MLM | 3.0772 | 1.0985 | 624 |
| CGT | 3.0772 | 2.5260 | 3928 |
| RHE | 3.0771 | 2.1694 | 1351 |
| VLS | 3.0771 | 3.3065 | 11020 |
| YGR | 3.0771 | 1.4749 | 9452 |
| ALV | 3.0770 | 3.0609 | 7518 |
| FPW | 3.0769 | 2.1685 | 198 |
| VVK | 3.0769 | 1.6157 | 7856 |
| LMH | 3.0769 | 2.1339 | 1236 |
| HEF | 3.0768 | 2.2611 | 700 |
| SWQ | 3.0765 | 1.9522 | 1120 |
| AAL | 3.0764 | 2.2770 | 4996 |
| IIR | 3.0764 | 2.7100 | 6227 |
| RQK | 3.0763 | 2.1050 | 2295 |
| RQG | 3.0761 | 1.6987 | 9247 |
| LHW | 3.0761 | 1.4020 | 611 |
| TQC | 3.0759 | 3.1257 | 1641 |
| FHE | 3.0759 | 0.9674 | 208 |
| QQA | 3.0758 | 1.8926 | 910 |
| IIP | 3.0758 | 2.4880 | 1099 |
| IPF | 3.0757 | 1.8696 | 465 |
| FPY | 3.0756 | 2.2833 | 507 |
| YAC | 3.0755 | 1.5736 | 1137 |
| WQP | 3.0755 | 1.3027 | 329 |
| VKI | 3.0755 | 1.8880 | 3355 |
| VLV | 3.0755 | 2.6000 | 15157 |
| ADM | 3.0754 | 0.8795 | 466 |
| DCS | 3.0753 | 2.6238 | 2222 |
| GAI | 3.0751 | 2.0613 | 6149 |
| AFF | 3.0748 | 1.2427 | 620 |
| CRV | 3.0748 | 2.0570 | 7602 |
| LQI | 3.0748 | 1.7864 | 5156 |
| PTH | 3.0748 | 2.7016 | 317 |
| TLD | 3.0747 | 3.0367 | 2181 |
| RVH | 3.0745 | 2.9461 | 4665 |
| GNF | 3.0744 | 1.5346 | 1474 |
| RVQ | 3.0744 | 2.7210 | 7376 |
| AGN | 3.0743 | 2.0592 | 4378 |
| RLQ | 3.0743 | 3.2436 | 6122 |
| AIA | 3.0743 | 2.9001 | 2139 |
| KAR | 3.0743 | 3.0577 | 6600 |
| KRC | 3.0741 | 2.6635 | 5181 |
| WSM | 3.0741 | 1.1672 | 1157 |
| RDT | 3.0741 | 2.0160 | 3318 |
| KAV | 3.0740 | 2.4092 | 4697 |
| RIT | 3.0740 | 2.6651 | 5375 |
| SPS | 3.0739 | 3.0568 | 1652 |
| LDL | 3.0739 | 3.4003 | 3660 |
| TKM | 3.0738 | 1.4435 | 927 |
| VVQ | 3.0737 | 2.2604 | 5394 |
| GPI | 3.0737 | 1.8000 | 2327 |
| RSV | 3.0737 | 2.9306 | 18003 |
| LGW | 3.0736 | 1.3217 | 9466 |
| LSG | 3.0736 | 3.1201 | 18126 |
| CTC | 3.0735 | 1.9613 | 1198 |
| NDL | 3.0734 | 2.4922 | 2320 |
| KGG | 3.0734 | 1.1300 | 19212 |
| KEP | 3.0733 | 1.7859 | 776 |

TABLE F-continued

Medium-expressing EGFP variants

| AA SEQ | Mean | Range | Total counts |
|---|---|---|---|
| PHK | 3.0733 | 1.9013 | 333 |
| ATG | 3.0733 | 1.5769 | 7354 |
| LYC | 3.0732 | 2.6506 | 2587 |
| APE | 3.0731 | 2.8286 | 1004 |
| ANG | 3.0730 | 1.4049 | 4488 |
| EMG | 3.0730 | 0.8305 | 4119 |
| KRE | 3.0729 | 2.9811 | 6226 |
| MFH | 3.0727 | 0.3945 | 418 |
| SGY | 3.0727 | 1.8440 | 5269 |
| GSD | 3.0726 | 2.4573 | 6699 |
| TGK | 3.0724 | 2.3168 | 5003 |
| GFG | 3.0723 | 1.3128 | 12760 |
| AIV | 3.0723 | 1.7509 | 5674 |
| CCW | 3.0723 | 0.7474 | 802 |
| GVC | 3.0722 | 2.0377 | 12397 |
| RVR | 3.0722 | 2.3495 | 34025 |
| HPC | 3.0722 | 0.8683 | 152 |
| SWT | 3.0722 | 1.5000 | 1625 |
| IWV | 3.0722 | 1.5402 | 2878 |
| CQS | 3.0721 | 2.4586 | 1798 |
| WLS | 3.0721 | 1.4669 | 5004 |
| SQG | 3.0721 | 2.1094 | 6141 |
| HLG | 3.0720 | 2.4182 | 3423 |
| SCG | 3.0719 | 2.2228 | 8253 |
| VLN | 3.0719 | 2.1769 | 3979 |
| RKW | 3.0719 | 1.1053 | 3198 |
| AGH | 3.0718 | 1.9160 | 2949 |
| CFC | 3.0718 | 1.2643 | 543 |
| SDG | 3.0718 | 1.3134 | 6216 |
| DRT | 3.0717 | 2.2659 | 2789 |
| GVG | 3.0717 | 2.0042 | 65494 |
| WRP | 3.0716 | 2.0628 | 1151 |
| PVY | 3.0715 | 3.7136 | 1536 |
| YPA | 3.0715 | 2.9082 | 1041 |
| QCE | 3.0715 | 1.0773 | 944 |
| NRA | 3.0714 | 2.8093 | 3462 |
| WYE | 3.0714 | 0.6695 | 892 |
| GEH | 3.0714 | 1.8734 | 2181 |
| KQD | 3.0712 | 2.1547 | 716 |
| FTC | 3.0712 | 2.7810 | 531 |
| VPL | 3.0712 | 2.3158 | 3337 |
| SDY | 3.0711 | 2.3574 | 1446 |
| AHF | 3.0709 | 1.5566 | 543 |
| HWC | 3.0709 | 0.7361 | 319 |
| LIR | 3.0708 | 2.8017 | 9883 |
| GHS | 3.0707 | 2.8030 | 3038 |
| NDV | 3.0704 | 2.1942 | 1938 |
| QFP | 3.0702 | 2.5455 | 397 |
| GCT | 3.0702 | 2.4076 | 3358 |
| WCA | 3.0701 | 0.9021 | 2084 |
| ANA | 3.0701 | 2.2047 | 1121 |
| DPA | 3.0700 | 1.9293 | 561 |
| YPW | 3.0700 | 1.3437 | 161 |
| VHV | 3.0700 | 1.7582 | 2724 |
| TYG | 3.0699 | 2.1834 | 3199 |
| AAQ | 3.0699 | 2.6553 | 1892 |
| ELD | 3.0699 | 1.2875 | 2785 |
| VII | 3.0699 | 2.0095 | 2770 |
| ELR | 3.0698 | 2.8328 | 14681 |
| PWR | 3.0698 | 1.6975 | 1644 |
| TFH | 3.0697 | 2.7765 | 967 |
| LAQ | 3.0697 | 3.2144 | 2300 |
| YLG | 3.0696 | 2.2415 | 6566 |
| LMC | 3.0695 | 1.0396 | 1397 |
| APF | 3.0694 | 2.3811 | 628 |
| FAG | 3.0693 | 2.4138 | 4147 |
| PFL | 3.0692 | 2.7647 | 878 |
| RCT | 3.0691 | 2.3719 | 3217 |
| LHQ | 3.0691 | 2.7438 | 1248 |
| VGY | 3.0690 | 1.7960 | 6730 |
| LSK | 3.0689 | 2.6143 | 4890 |
| FTL | 3.0688 | 2.1012 | 1380 |
| LCY | 3.0688 | 2.0074 | 1798 |
| LIA | 3.0688 | 2.4833 | 4090 |
| EDS | 3.0687 | 1.2232 | 2564 |
| QMF | 3.0686 | 1.6952 | 359 |
| GVE | 3.0686 | 1.2101 | 15164 |
| ASR | 3.0685 | 2.6680 | 10366 |
| ARC | 3.0685 | 2.6499 | 4764 |
| RPN | 3.0685 | 3.3125 | 1241 |
| TQD | 3.0683 | 1.4224 | 704 |
| MCG | 3.0682 | 0.9863 | 3129 |
| CSW | 3.0681 | 1.4505 | 1631 |
| FLD | 3.0678 | 1.8513 | 824 |
| MCD | 3.0678 | 0.7960 | 744 |
| ICT | 3.0676 | 2.4429 | 1628 |
| SRV | 3.0675 | 2.9239 | 14282 |
| VWE | 3.0674 | 0.6354 | 4222 |
| WWY | 3.0674 | 0.1263 | 758 |
| RCA | 3.0673 | 1.9246 | 4393 |
| ADI | 3.0673 | 2.3667 | 1553 |
| MAR | 3.0672 | 1.3946 | 2592 |
| ARG | 3.0671 | 2.8463 | 29413 |
| EFT | 3.0671 | 2.3918 | 1628 |
| TWA | 3.0667 | 1.3534 | 1741 |
| VGS | 3.0667 | 2.2905 | 26856 |
| IPI | 3.0666 | 2.6818 | 1031 |
| LKD | 3.0665 | 2.0782 | 1662 |
| DVV | 3.0665 | 1.9938 | 9049 |
| WGQ | 3.0663 | 0.9021 | 2740 |
| AWR | 3.0662 | 1.6263 | 5321 |
| EVV | 3.0661 | 1.4484 | 12624 |
| PTK | 3.0659 | 2.3987 | 935 |
| SLR | 3.0659 | 3.1257 | 14677 |
| FSG | 3.0657 | 1.8737 | 4515 |
| LAV | 3.0657 | 2.9706 | 7590 |
| EEY | 3.0657 | 2.4304 | 1946 |
| RFL | 3.0656 | 3.0696 | 4511 |
| VLD | 3.0655 | 1.6578 | 4524 |
| GVA | 3.0655 | 2.2188 | 18531 |
| TLV | 3.0654 | 3.5826 | 7026 |
| GHY | 3.0652 | 1.8601 | 1038 |
| FVF | 3.0651 | 1.0565 | 1027 |
| TEM | 3.0650 | 0.9558 | 818 |
| NGY | 3.0650 | 2.1854 | 2194 |
| CGV | 3.0649 | 1.4832 | 11809 |
| ALH | 3.0647 | 3.1566 | 1894 |
| WLD | 3.0647 | 1.9184 | 1693 |
| GFA | 3.0647 | 1.4752 | 3497 |
| EPD | 3.0647 | 1.5809 | 794 |
| EEA | 3.0646 | 1.4115 | 4092 |
| AWL | 3.0646 | 2.4591 | 3355 |
| LSR | 3.0645 | 3.3277 | 12962 |
| CWQ | 3.0645 | 0.7004 | 347 |
| HRL | 3.0645 | 2.9294 | 3025 |
| YDA | 3.0645 | 2.0238 | 1351 |
| PIY | 3.0644 | 2.4182 | 547 |
| RES | 3.0644 | 2.1431 | 10500 |
| LEY | 3.0644 | 2.2576 | 2273 |
| SRG | 3.0643 | 2.2468 | 29010 |
| TGI | 3.0638 | 2.1518 | 5657 |
| EPV | 3.0637 | 2.4178 | 2701 |
| HPA | 3.0637 | 2.5435 | 421 |
| MDE | 3.0637 | 1.1177 | 551 |
| AYA | 3.0636 | 3.0060 | 1625 |
| GQT | 3.0636 | 2.1685 | 2311 |
| EWS | 3.0636 | 0.9047 | 3267 |
| EVF | 3.0636 | 1.8050 | 2903 |
| FVS | 3.0635 | 1.9436 | 2943 |
| WME | 3.0635 | 0.0765 | 611 |
| RWS | 3.0635 | 2.3308 | 7556 |
| TTE | 3.0635 | 2.3500 | 1303 |
| MLV | 3.0635 | 2.8218 | 3954 |
| EVS | 3.0634 | 3.0502 | 11132 |
| CVI | 3.0634 | 2.1245 | 4317 |
| AAS | 3.0634 | 3.3327 | 5814 |
| GAR | 3.0633 | 1.8633 | 24796 |
| AQS | 3.0632 | 3.3861 | 2816 |
| YKE | 3.0632 | 1.5126 | 1019 |
| KDP | 3.0632 | 1.8772 | 431 |

TABLE F-continued

Medium-expressing EGFP variants

| AA SEQ | Mean | Range | Total counts |
|---|---|---|---|
| QVT | 3.0631 | 2.7079 | 2820 |
| IVI | 3.0631 | 1.1208 | 3443 |
| LMV | 3.0631 | 2.3640 | 3082 |
| PKC | 3.0631 | 1.8727 | 665 |
| SAC | 3.0630 | 1.8554 | 3233 |
| SPI | 3.0630 | 2.6180 | 1065 |
| YVY | 3.0630 | 3.0748 | 1765 |
| EPS | 3.0629 | 2.0185 | 1654 |
| VNA | 3.0629 | 1.8473 | 2343 |
| DSS | 3.0627 | 3.0406 | 4167 |
| TAE | 3.0627 | 1.7722 | 2708 |
| RRR | 3.0626 | 2.7106 | 30483 |
| ECL | 3.0626 | 2.1306 | 4016 |
| ETM | 3.0624 | 1.9160 | 772 |
| TWW | 3.0624 | 0.5184 | 829 |
| QRG | 3.0623 | 1.6545 | 9624 |
| LEF | 3.0622 | 1.5469 | 1818 |
| DPS | 3.0621 | 2.5189 | 1102 |
| TSR | 3.0621 | 3.1444 | 7862 |
| ISS | 3.0619 | 2.4366 | 6024 |
| GHK | 3.0619 | 1.7797 | 1544 |
| IPL | 3.0617 | 2.6541 | 1407 |
| ATE | 3.0615 | 2.6537 | 2187 |
| SPP | 3.0615 | 3.0000 | 376 |
| DTR | 3.0615 | 2.5281 | 5153 |
| GSA | 3.0614 | 2.2236 | 11861 |
| VQK | 3.0614 | 1.7768 | 1956 |
| AAN | 3.0613 | 2.9116 | 1372 |
| SFS | 3.0613 | 3.6330 | 3130 |
| YLD | 3.0613 | 2.1911 | 1346 |
| LNI | 3.0613 | 2.4676 | 2669 |
| CQL | 3.0613 | 2.5581 | 2322 |
| AMC | 3.0612 | 1.0409 | 1101 |
| RDD | 3.0611 | 1.5217 | 2537 |
| VGK | 3.0611 | 1.5024 | 9542 |
| TSM | 3.0611 | 2.0769 | 1385 |
| DIP | 3.0610 | 2.4616 | 1018 |
| AFS | 3.0610 | 2.2438 | 2768 |
| GLS | 3.0610 | 2.4571 | 16032 |
| SHD | 3.0609 | 1.8469 | 885 |
| NCA | 3.0609 | 2.5579 | 1292 |
| GIW | 3.0608 | 0.7637 | 3495 |
| RQQ | 3.0607 | 2.6715 | 1769 |
| YEM | 3.0606 | 1.2723 | 646 |
| DWL | 3.0604 | 1.5003 | 1511 |
| WLE | 3.0603 | 0.9030 | 3726 |
| VQW | 3.0603 | 1.0998 | 2075 |
| ESN | 3.0603 | 2.4938 | 3320 |
| SGS | 3.0603 | 3.1982 | 17643 |
| VID | 3.0602 | 1.6093 | 2454 |
| KGL | 3.0602 | 2.3155 | 8446 |
| KSW | 3.0602 | 1.8340 | 2690 |
| RDR | 3.0601 | 2.5168 | 9984 |
| LMA | 3.0600 | 1.7977 | 1965 |
| GCR | 3.0599 | 1.9214 | 14751 |
| CEG | 3.0597 | 1.0134 | 7171 |
| ERV | 3.0597 | 2.0736 | 13551 |
| MDR | 3.0596 | 1.0071 | 1815 |
| AER | 3.0595 | 2.2824 | 8121 |
| LDG | 3.0595 | 1.8568 | 7486 |
| SEV | 3.0595 | 2.6190 | 8383 |
| SDR | 3.0594 | 1.8042 | 5762 |
| IEV | 3.0592 | 1.7430 | 4555 |
| YFQ | 3.0592 | 2.4280 | 454 |
| YYC | 3.0592 | 2.2692 | 896 |
| YGW | 3.0592 | 0.9085 | 2814 |
| MWQ | 3.0591 | 0.2664 | 418 |
| TFC | 3.0590 | 2.6978 | 1210 |
| TRK | 3.0590 | 2.9992 | 3636 |
| RGR | 3.0589 | 2.3760 | 51454 |
| TPH | 3.0589 | 1.7912 | 360 |
| ERA | 3.0589 | 2.0630 | 10014 |
| IML | 3.0589 | 2.4180 | 1206 |
| EVL | 3.0586 | 1.9711 | 9249 |
| ATT | 3.0586 | 3.1726 | 1520 |
| DVC | 3.0586 | 2.0024 | 4172 |
| VTC | 3.0585 | 1.6679 | 2640 |
| VVN | 3.0584 | 2.2894 | 4763 |
| VAT | 3.0583 | 2.8549 | 2676 |
| SEL | 3.0583 | 2.6071 | 6729 |
| REL | 3.0582 | 2.3588 | 10120 |
| GAN | 3.0582 | 1.3134 | 3326 |
| VPK | 3.0581 | 1.6520 | 1611 |
| FKI | 3.0581 | 1.8583 | 493 |
| RPL | 3.0580 | 3.6054 | 3334 |
| FPG | 3.0579 | 1.8331 | 1754 |
| WYH | 3.0578 | 0.3874 | 482 |
| SHS | 3.0578 | 2.7610 | 2589 |
| QEA | 3.0575 | 2.2057 | 1415 |
| LEM | 3.0574 | 1.2524 | 1503 |
| SQR | 3.0571 | 2.7922 | 5343 |
| GAH | 3.0571 | 1.6425 | 2453 |
| VVP | 3.0571 | 3.0256 | 4207 |
| ECV | 3.0570 | 1.4793 | 5513 |
| ELE | 3.0570 | 1.8378 | 5357 |
| FEP | 3.0569 | 1.7745 | 196 |
| ASC | 3.0569 | 2.5404 | 2862 |
| FKF | 3.0569 | 1.1617 | 344 |
| RWL | 3.0568 | 2.1954 | 7014 |
| KGD | 3.0567 | 1.1656 | 3534 |
| VVD | 3.0566 | 2.4701 | 7219 |
| NGT | 3.0562 | 2.0799 | 2316 |
| SDV | 3.0560 | 2.3145 | 4109 |
| CDE | 3.0560 | 1.3338 | 860 |
| YVF | 3.0559 | 1.8917 | 1987 |
| GNM | 3.0558 | 0.9942 | 1598 |
| VQR | 3.0556 | 2.5543 | 6349 |
| RYE | 3.0555 | 2.1602 | 3076 |
| VTN | 3.0554 | 2.0614 | 1900 |
| QAA | 3.0554 | 1.8043 | 1372 |
| TSA | 3.0554 | 2.5784 | 3711 |
| WNV | 3.0554 | 1.1624 | 1896 |
| NAR | 3.0554 | 2.8004 | 4212 |
| DAF | 3.0550 | 2.6682 | 1343 |
| SQQ | 3.0550 | 2.9048 | 1032 |
| TRG | 3.0548 | 2.5682 | 14464 |
| MQE | 3.0548 | 1.4459 | 385 |
| AHI | 3.0547 | 3.3718 | 1368 |
| SGF | 3.0545 | 2.0715 | 4852 |
| AYS | 3.0545 | 3.6029 | 2894 |
| WLH | 3.0545 | 1.7799 | 1481 |
| VET | 3.0544 | 1.9859 | 2740 |
| FLG | 3.0544 | 1.7407 | 4676 |
| HSC | 3.0543 | 2.5163 | 974 |
| RTR | 3.0542 | 3.3527 | 9273 |
| GCE | 3.0542 | 1.3815 | 5259 |
| LGV | 3.0542 | 2.5611 | 22415 |
| CIE | 3.0541 | 1.6396 | 1458 |
| ASH | 3.0541 | 1.8689 | 1452 |
| YGI | 3.0540 | 2.4155 | 3495 |
| ATR | 3.0539 | 3.2163 | 4386 |
| STC | 3.0538 | 2.2645 | 2022 |
| YCG | 3.0538 | 1.1563 | 2546 |
| RSR | 3.0538 | 3.6212 | 20379 |
| CCL | 3.0538 | 2.0729 | 1864 |
| PPV | 3.0537 | 2.2581 | 1189 |
| RSS | 3.0536 | 3.6343 | 13484 |
| GTY | 3.0536 | 2.0946 | 2551 |
| LNQ | 3.0536 | 2.6657 | 1250 |
| VSE | 3.0535 | 2.9454 | 6955 |
| EGY | 3.0534 | 1.1750 | 4260 |
| RTP | 3.0534 | 2.1138 | 1254 |
| FKT | 3.0532 | 2.4959 | 715 |
| CVS | 3.0532 | 1.7862 | 6875 |
| IQQ | 3.0531 | 2.8831 | 538 |
| FEV | 3.0530 | 1.3613 | 2547 |
| DCN | 3.0529 | 2.3945 | 1126 |
| GNI | 3.0529 | 2.1981 | 2909 |
| LPE | 3.0528 | 2.6875 | 1254 |
| IGW | 3.0528 | 1.0919 | 4458 |

TABLE F-continued

Medium-expressing EGFP variants

| AA SEQ | Mean | Range | Total counts |
|---|---|---|---|
| EQS | 3.0525 | 1.8925 | 1915 |
| ILI | 3.0525 | 2.0076 | 2494 |
| EFE | 3.0524 | 1.8645 | 2462 |
| RLW | 3.0523 | 2.1492 | 7135 |
| TLT | 3.0523 | 3.1518 | 2538 |
| ASG | 3.0523 | 2.0789 | 16212 |
| HPY | 3.0521 | 2.9400 | 327 |
| GCW | 3.0521 | 0.7214 | 4402 |
| SRL | 3.0519 | 2.4673 | 10953 |
| FWR | 3.0519 | 1.6097 | 1459 |
| VKH | 3.0519 | 2.5192 | 2010 |
| NRR | 3.0518 | 2.9003 | 7801 |
| VSM | 3.0515 | 1.3082 | 3294 |
| ART | 3.0514 | 2.6566 | 3921 |
| IMM | 3.0513 | 0.2563 | 375 |
| FQS | 3.0513 | 1.8188 | 1167 |
| IIQ | 3.0512 | 2.3957 | 1328 |
| KWQ | 3.0510 | 1.8030 | 659 |
| FQI | 3.0510 | 2.7149 | 2016 |
| GSC | 3.0510 | 2.4022 | 7640 |
| GWS | 3.0509 | 2.3361 | 9080 |
| IGV | 3.0509 | 1.5304 | 10939 |
| FNV | 3.0507 | 1.8720 | 1368 |
| AHN | 3.0507 | 1.8466 | 637 |
| IWF | 3.0506 | 0.8863 | 569 |
| GLV | 3.0506 | 2.2776 | 20979 |
| AYR | 3.0506 | 2.0727 | 6196 |
| EWP | 3.0505 | 1.3562 | 994 |
| TGR | 3.0505 | 2.3839 | 14098 |
| WND | 3.0504 | 1.1207 | 571 |
| SFH | 3.0503 | 3.2110 | 779 |
| SVW | 3.0502 | 1.1290 | 5963 |
| FEK | 3.0502 | 2.3833 | 731 |
| WFA | 3.0501 | 2.1266 | 1283 |
| MEQ | 3.0500 | 0.7452 | 497 |
| RFT | 3.0500 | 2.8203 | 3203 |
| VMC | 3.0500 | 1.0745 | 1782 |
| LYM | 3.0499 | 1.5129 | 1349 |
| GFS | 3.0498 | 2.1703 | 4235 |
| CSA | 3.0491 | 2.4027 | 3195 |
| LVH | 3.0489 | 2.5556 | 2724 |
| RQV | 3.0488 | 2.6569 | 5624 |
| NGR | 3.0488 | 1.1102 | 8185 |
| WCS | 3.0487 | 1.5872 | 1924 |
| VQE | 3.0486 | 1.5354 | 2138 |
| CQT | 3.0486 | 2.8563 | 1089 |
| FMR | 3.0486 | 1.6293 | 1371 |
| QVA | 3.0485 | 2.7719 | 3775 |
| ERT | 3.0485 | 2.6155 | 5089 |
| MEN | 3.0484 | 0.9567 | 476 |
| PVL | 3.0484 | 3.5918 | 3151 |
| LPT | 3.0484 | 3.4000 | 1069 |
| WSG | 3.0483 | 0.7350 | 10454 |
| GTS | 3.0482 | 2.4000 | 7785 |
| WFK | 3.0482 | 1.0669 | 999 |
| IIE | 3.0481 | 2.2256 | 2077 |
| LRC | 3.0478 | 1.8529 | 7219 |
| EMC | 3.0478 | 0.7321 | 1330 |
| VLA | 3.0478 | 2.9800 | 9383 |
| GPV | 3.0478 | 2.7572 | 7330 |
| LLY | 3.0478 | 2.5361 | 4029 |
| MEH | 3.0477 | 0.5758 | 351 |
| ASL | 3.0477 | 3.4192 | 5671 |
| GYY | 3.0477 | 1.5342 | 1831 |
| DGQ | 3.0476 | 1.1979 | 2779 |
| ERR | 3.0476 | 2.0307 | 18299 |
| RSN | 3.0475 | 3.5023 | 4670 |
| FGQ | 3.0473 | 1.5648 | 1342 |
| EEV | 3.0473 | 1.4311 | 6400 |
| EYP | 3.0470 | 2.3071 | 478 |
| QPC | 3.0470 | 1.4840 | 294 |
| AGD | 3.0469 | 2.2206 | 7067 |
| KSG | 3.0469 | 2.0782 | 9621 |
| PKW | 3.0469 | 1.9520 | 378 |
| GAE | 3.0469 | 1.7379 | 10354 |
| VAK | 3.0469 | 2.2000 | 3792 |
| LRI | 3.0468 | 2.4200 | 6402 |
| WHT | 3.0468 | 1.7231 | 634 |
| ALK | 3.0468 | 3.3148 | 4706 |
| DRG | 3.0468 | 1.5623 | 15176 |
| RRI | 3.0467 | 2.6104 | 10067 |
| YEA | 3.0467 | 2.7481 | 2169 |
| HLC | 3.0467 | 3.1933 | 1839 |
| ALD | 3.0466 | 2.1212 | 2505 |
| SAS | 3.0466 | 2.1830 | 6698 |
| RTT | 3.0466 | 3.4468 | 3511 |
| HVR | 3.0465 | 3.1282 | 4269 |
| TVD | 3.0465 | 2.6520 | 3258 |
| FGA | 3.0463 | 1.2899 | 3684 |
| SCT | 3.0463 | 3.4324 | 1863 |
| FYS | 3.0463 | 2.3431 | 944 |
| SWF | 3.0462 | 1.0349 | 1165 |
| TLA | 3.0462 | 3.8108 | 3306 |
| LLS | 3.0462 | 3.0923 | 9397 |
| WKD | 3.0462 | 1.4012 | 793 |
| PLC | 3.0461 | 2.7107 | 1701 |
| VND | 3.0461 | 1.9592 | 1262 |
| HRV | 3.0461 | 2.9599 | 3668 |
| DTA | 3.0460 | 2.2797 | 1789 |
| VFQ | 3.0460 | 1.1010 | 1228 |
| CTL | 3.0458 | 3.0544 | 2314 |
| AVP | 3.0457 | 2.8393 | 2414 |
| GCY | 3.0457 | 1.8495 | 1895 |
| MGM | 3.0456 | 1.8103 | 1509 |
| TFI | 3.0455 | 2.0639 | 1073 |
| HVW | 3.0454 | 1.0453 | 865 |
| QMC | 3.0454 | 1.4726 | 623 |
| WFL | 3.0453 | 1.8079 | 1275 |
| QSG | 3.0452 | 1.7279 | 5371 |
| VSS | 3.0451 | 2.9481 | 11125 |
| GTE | 3.0450 | 1.6154 | 5059 |
| WGP | 3.0449 | 1.5427 | 2430 |
| FNR | 3.0448 | 2.8224 | 1289 |
| YGA | 3.0447 | 1.6172 | 5383 |
| QES | 3.0446 | 1.3576 | 1880 |
| ARN | 3.0446 | 2.1350 | 2981 |
| IAI | 3.0446 | 2.3879 | 1730 |
| AAY | 3.0446 | 2.1412 | 1290 |
| RDK | 3.0445 | 2.2620 | 2702 |
| VFE | 3.0445 | 1.2534 | 2364 |
| SAQ | 3.0445 | 3.3587 | 2439 |
| PAN | 3.0445 | 2.6905 | 837 |
| WKV | 3.0444 | 1.5485 | 2418 |
| DWH | 3.0441 | 0.5531 | 517 |
| FPA | 3.0441 | 2.1528 | 507 |
| ITL | 3.0440 | 2.9848 | 2823 |
| TMW | 3.0439 | 0.5257 | 521 |
| FTN | 3.0438 | 2.5455 | 572 |
| NEV | 3.0437 | 1.7794 | 3665 |
| VKA | 3.0435 | 1.5100 | 4156 |
| DGF | 3.0434 | 1.3471 | 2446 |
| GWE | 3.0434 | 0.9639 | 6690 |
| FKD | 3.0434 | 1.3275 | 440 |
| CSG | 3.0434 | 2.5744 | 9035 |
| CVD | 3.0433 | 1.9908 | 3051 |
| REM | 3.0433 | 1.8945 | 2622 |
| FQG | 3.0433 | 1.6333 | 1407 |
| WTQ | 3.0432 | 1.5002 | 448 |
| LAS | 3.0430 | 2.9545 | 6107 |
| MFT | 3.0430 | 1.6372 | 626 |
| GQQ | 3.0429 | 1.6556 | 1917 |
| SKG | 3.0429 | 2.6179 | 11756 |
| TTR | 3.0428 | 3.9157 | 3730 |
| AST | 3.0428 | 2.7872 | 2988 |
| GMC | 3.0427 | 1.0268 | 2477 |
| FPC | 3.0425 | 1.8024 | 476 |
| EGK | 3.0425 | 0.7036 | 6345 |
| HHE | 3.0425 | 2.4263 | 273 |
| GFT | 3.0424 | 1.5869 | 2762 |
| PQL | 3.0424 | 3.6404 | 1034 |

TABLE F-continued

Medium-expressing EGFP variants

| AA SEQ | Mean | Range | Total counts |
|---|---|---|---|
| LRM | 3.0423 | 1.7652 | 3065 |
| CMR | 3.0422 | 1.6477 | 2005 |
| AEC | 3.0421 | 1.1142 | 2787 |
| YGN | 3.0421 | 2.4917 | 2000 |
| NGV | 3.0421 | 1.4743 | 6552 |
| YPP | 3.0419 | 1.8000 | 140 |
| YIL | 3.0418 | 2.6888 | 1754 |
| ERS | 3.0418 | 1.9409 | 10281 |
| EVN | 3.0418 | 2.4601 | 2993 |
| FSC | 3.0417 | 1.8243 | 1284 |
| CVE | 3.0417 | 1.0770 | 3580 |
| RRL | 3.0416 | 3.0987 | 17586 |
| MCS | 3.0416 | 1.7893 | 1435 |
| VKD | 3.0415 | 1.4673 | 2163 |
| PGK | 3.0414 | 1.9572 | 2113 |
| DRC | 3.0414 | 2.0736 | 3788 |
| LKG | 3.0414 | 1.6434 | 7862 |
| WRA | 3.0413 | 1.3814 | 6233 |
| APW | 3.0413 | 2.1364 | 687 |
| HSG | 3.0413 | 2.9597 | 3502 |
| DGI | 3.0411 | 1.5354 | 3926 |
| HGA | 3.0410 | 1.5617 | 2420 |
| LWT | 3.0410 | 2.3983 | 1304 |
| LPQ | 3.0410 | 3.2277 | 828 |
| INE | 3.0410 | 1.5053 | 1332 |
| YPG | 3.0410 | 3.1286 | 1520 |
| TCK | 3.0409 | 2.7920 | 1984 |
| ERW | 3.0409 | 1.0180 | 5520 |
| TLG | 3.0408 | 3.3501 | 10283 |
| PPE | 3.0408 | 1.8125 | 383 |
| VIR | 3.0408 | 2.6289 | 11262 |
| CII | 3.0407 | 2.2920 | 1592 |
| PRI | 3.0406 | 2.3943 | 2005 |
| IET | 3.0406 | 2.7063 | 1636 |
| IAT | 3.0405 | 3.3183 | 1267 |
| FDI | 3.0405 | 2.3523 | 608 |
| PMV | 3.0404 | 1.7037 | 388 |
| HVL | 3.0404 | 3.1036 | 3289 |
| WVE | 3.0403 | 0.6011 | 4462 |
| NGD | 3.0402 | 1.2820 | 1949 |
| AFN | 3.0401 | 1.4917 | 1070 |
| PSK | 3.0401 | 2.7148 | 1069 |
| MEA | 3.0401 | 1.8953 | 1103 |
| YGE | 3.0401 | 1.3867 | 2962 |
| LKE | 3.0400 | 2.4436 | 2506 |
| GFM | 3.0399 | 1.1360 | 1300 |
| HME | 3.0399 | 0.8645 | 309 |
| LNM | 3.0397 | 1.6476 | 778 |
| FQE | 3.0397 | 1.0905 | 547 |
| VRY | 3.0396 | 2.5384 | 5965 |
| LRS | 3.0395 | 2.7417 | 11686 |
| WCL | 3.0395 | 1.1917 | 2202 |
| IWS | 3.0395 | 1.4456 | 1650 |
| FTD | 3.0394 | 2.4925 | 502 |
| NFD | 3.0393 | 1.6905 | 284 |
| EQL | 3.0392 | 2.7147 | 2496 |
| IPG | 3.0392 | 2.4923 | 2789 |
| LEV | 3.0390 | 1.6039 | 6931 |
| CLT | 3.0389 | 2.7634 | 2156 |
| YFR | 3.0389 | 1.9487 | 2124 |
| RMG | 3.0388 | 2.1770 | 8917 |
| PIN | 3.0388 | 2.4003 | 582 |
| KGV | 3.0387 | 1.7493 | 9821 |
| WSS | 3.0386 | 2.1000 | 4637 |
| AFC | 3.0385 | 2.1266 | 1505 |
| SAA | 3.0384 | 2.8440 | 4765 |
| GTT | 3.0383 | 2.4335 | 2775 |
| WLT | 3.0380 | 1.2820 | 1944 |
| SPV | 3.0380 | 3.6410 | 2464 |
| CIT | 3.0380 | 1.8304 | 1878 |
| CSP | 3.0380 | 1.0000 | 530 |
| QYG | 3.0380 | 0.9181 | 1755 |
| HGS | 3.0378 | 2.3884 | 2649 |
| ISM | 3.0378 | 1.5189 | 1636 |
| RHW | 3.0377 | 1.6989 | 1653 |
| DWR | 3.0376 | 0.8839 | 3117 |
| EPN | 3.0376 | 2.0723 | 599 |
| VFI | 3.0375 | 1.9378 | 1855 |
| TGY | 3.0375 | 2.3069 | 3477 |
| CPK | 3.0374 | 1.4557 | 690 |
| FWK | 3.0372 | 0.8550 | 283 |
| CFH | 3.0372 | 2.5262 | 464 |
| QVS | 3.0372 | 2.4590 | 5473 |
| CVP | 3.0371 | 1.4287 | 1455 |
| APD | 3.0370 | 2.5769 | 953 |
| PDK | 3.0370 | 2.4531 | 818 |
| IVD | 3.0369 | 2.0909 | 2715 |
| LAA | 3.0367 | 3.5238 | 4544 |
| QCL | 3.0367 | 2.3588 | 2406 |
| PHL | 3.0366 | 2.0588 | 646 |
| MDK | 3.0365 | 0.1435 | 593 |
| YMC | 3.0364 | 1.0118 | 595 |
| DVG | 3.0364 | 2.1112 | 12489 |
| GLQ | 3.0364 | 2.1713 | 5280 |
| FFE | 3.0362 | 1.5263 | 450 |
| VTT | 3.0361 | 2.5139 | 1904 |
| LEI | 3.0358 | 1.6741 | 2709 |
| RHS | 3.0358 | 2.6232 | 3728 |
| GLR | 3.0358 | 2.5823 | 26678 |
| VYA | 3.0357 | 2.0198 | 2558 |
| VRI | 3.0356 | 1.6475 | 8356 |
| RNC | 3.0356 | 2.8316 | 2273 |
| VHW | 3.0356 | 1.0513 | 1034 |
| AFY | 3.0354 | 2.2206 | 1165 |
| LRK | 3.0354 | 2.6490 | 5257 |
| VVH | 3.0354 | 2.5986 | 3178 |
| GCD | 3.0353 | 1.7064 | 3031 |
| YCV | 3.0353 | 1.9289 | 2379 |
| VPR | 3.0352 | 2.8597 | 6507 |
| GKV | 3.0352 | 1.3911 | 10791 |
| ARW | 3.0351 | 2.2969 | 5912 |
| SLN | 3.0350 | 3.5047 | 4080 |
| ASE | 3.0349 | 2.6635 | 4261 |
| LGI | 3.0348 | 2.1617 | 6792 |
| VLC | 3.0348 | 2.2979 | 7071 |
| RHV | 3.0348 | 2.8639 | 3500 |
| PLM | 3.0347 | 1.9893 | 808 |
| RYA | 3.0347 | 2.7076 | 3574 |
| SQV | 3.0347 | 2.7880 | 4601 |
| GCM | 3.0346 | 1.0373 | 2017 |
| FEY | 3.0344 | 1.8530 | 978 |
| QIE | 3.0343 | 1.9464 | 1180 |
| GII | 3.0343 | 1.5500 | 4424 |
| DAI | 3.0343 | 1.9938 | 2167 |
| RTD | 3.0341 | 2.1000 | 2731 |
| MAF | 3.0341 | 1.6274 | 644 |
| ESH | 3.0340 | 2.1584 | 1878 |
| SAF | 3.0339 | 2.9000 | 2293 |
| GDN | 3.0339 | 1.4466 | 2010 |
| IGG | 3.0337 | 1.0661 | 18483 |
| WSL | 3.0336 | 1.6168 | 3977 |
| AFQ | 3.0335 | 2.4667 | 710 |
| CLG | 3.0335 | 1.8030 | 10636 |
| RWW | 3.0334 | 1.0768 | 3948 |
| NPW | 3.0333 | 2.1280 | 306 |
| CAI | 3.0333 | 2.5602 | 2039 |
| ANS | 3.0333 | 2.6206 | 2342 |
| LHI | 3.0330 | 2.2144 | 896 |
| ALQ | 3.0330 | 3.0657 | 2351 |
| YQE | 3.0329 | 1.5817 | 515 |
| IGD | 3.0329 | 1.1484 | 3685 |
| VFR | 3.0328 | 1.6270 | 5819 |
| GLH | 3.0328 | 1.9485 | 3684 |
| RWN | 3.0328 | 2.0806 | 1879 |
| EGI | 3.0327 | 1.9062 | 5883 |
| ERK | 3.0326 | 2.6758 | 6300 |
| KDT | 3.0324 | 2.7187 | 1672 |
| SCR | 3.0324 | 2.6127 | 5574 |
| ARA | 3.0324 | 2.3714 | 6963 |
| TCL | 3.0324 | 2.6234 | 2241 |

TABLE F-continued

Medium-expressing EGFP variants

| AA SEQ | Mean | Range | Total counts |
|---|---|---|---|
| AIP | 3.0323 | 2.7960 | 1108 |
| GSW | 3.0322 | 1.4704 | 9090 |
| RLD | 3.0321 | 2.5912 | 6112 |
| VMM | 3.0321 | 0.7677 | 730 |
| AIF | 3.0320 | 1.6810 | 1563 |
| ECS | 3.0320 | 2.3601 | 3762 |
| GVQ | 3.0319 | 1.7148 | 7661 |
| VSH | 3.0319 | 2.1265 | 1953 |
| RSQ | 3.0317 | 2.9341 | 4777 |
| THG | 3.0316 | 3.0085 | 1423 |
| IAR | 3.0315 | 3.2414 | 5487 |
| PTF | 3.0314 | 2.1538 | 484 |
| VMY | 3.0314 | 1.3242 | 1091 |
| HVT | 3.0313 | 2.9168 | 1134 |
| DKE | 3.0313 | 1.7222 | 1260 |
| CAD | 3.0312 | 0.9494 | 1358 |
| YTW | 3.0312 | 1.9450 | 755 |
| PRM | 3.0310 | 1.9271 | 839 |
| AME | 3.0309 | 1.7858 | 1304 |
| LGG | 3.0306 | 2.2711 | 43657 |
| IPY | 3.0306 | 1.5183 | 481 |
| FYR | 3.0305 | 2.0551 | 1378 |
| WSH | 3.0305 | 2.7371 | 1297 |
| FRA | 3.0305 | 2.8800 | 2615 |
| RCI | 3.0305 | 3.1111 | 4103 |
| ALP | 3.0304 | 2.7000 | 1593 |
| RPE | 3.0303 | 2.4545 | 2599 |
| VNV | 3.0303 | 1.3721 | 3730 |
| HFE | 3.0303 | 2.0883 | 434 |
| MWR | 3.0302 | 0.8769 | 1960 |
| EEK | 3.0301 | 1.4477 | 3013 |
| PHR | 3.0301 | 1.8019 | 1065 |
| GNP | 3.0299 | 2.1923 | 1473 |
| GIS | 3.0298 | 2.0956 | 8528 |
| HGD | 3.0296 | 1.8107 | 1259 |
| CAR | 3.0296 | 1.8678 | 5264 |
| SEI | 3.0294 | 1.6862 | 3948 |
| GMI | 3.0294 | 1.2923 | 2231 |
| AVQ | 3.0294 | 1.6305 | 3107 |
| LGA | 3.0294 | 2.2661 | 15391 |
| DCP | 3.0293 | 1.8571 | 346 |
| AFL | 3.0291 | 2.9118 | 1938 |
| IKM | 3.0290 | 0.7825 | 541 |
| FSS | 3.0289 | 2.7376 | 2093 |
| NHG | 3.0289 | 2.7273 | 836 |
| PIL | 3.0289 | 3.5665 | 1710 |
| TST | 3.0289 | 2.6445 | 2135 |
| WIL | 3.0289 | 2.7071 | 2144 |
| CSC | 3.0288 | 1.5811 | 2081 |
| RMT | 3.0286 | 1.4259 | 1398 |
| LDV | 3.0286 | 1.9858 | 3831 |
| AGY | 3.0285 | 1.5044 | 4913 |
| TRC | 3.0283 | 1.9748 | 4314 |
| RSD | 3.0282 | 1.7118 | 4785 |
| ALW | 3.0281 | 2.4813 | 2805 |
| TVS | 3.0279 | 2.7029 | 8011 |
| TPS | 3.0279 | 3.0364 | 894 |
| DQD | 3.0279 | 1.6040 | 486 |
| EEL | 3.0279 | 2.1159 | 4785 |
| MRM | 3.0278 | 0.7456 | 950 |
| WDL | 3.0277 | 1.8365 | 2030 |
| CCQ | 3.0276 | 1.4127 | 560 |
| RER | 3.0276 | 3.0928 | 17524 |
| AVH | 3.0275 | 2.5891 | 1567 |
| IPP | 3.0275 | 2.2587 | 256 |
| RLE | 3.0274 | 2.6964 | 9890 |
| PCT | 3.0273 | 3.0556 | 464 |
| TWM | 3.0273 | 1.4712 | 469 |
| TGD | 3.0273 | 2.5097 | 3351 |
| QMS | 3.0271 | 1.8400 | 1006 |
| CDR | 3.0270 | 2.0139 | 3982 |
| TQM | 3.0269 | 1.8346 | 629 |
| GPT | 3.0268 | 2.9816 | 2163 |
| GIR | 3.0267 | 1.5824 | 14130 |
| WWQ | 3.0266 | 0.3858 | 920 |
| SQS | 3.0265 | 2.7147 | 3682 |
| VYP | 3.0265 | 2.7903 | 924 |
| SSQ | 3.0265 | 3.6364 | 2675 |
| YMQ | 3.0264 | 1.6067 | 310 |
| LLG | 3.0263 | 3.1257 | 16555 |
| WID | 3.0262 | 0.8852 | 820 |
| PEM | 3.0261 | 1.5417 | 319 |
| LRH | 3.0261 | 3.2167 | 3636 |
| LER | 3.0261 | 2.6827 | 10064 |
| IDN | 3.0260 | 2.5533 | 1044 |
| TVA | 3.0260 | 3.0110 | 4872 |
| FDR | 3.0260 | 1.6501 | 1465 |
| WFS | 3.0260 | 1.5398 | 1638 |
| GFQ | 3.0259 | 1.3556 | 1801 |
| CTW | 3.0258 | 1.2065 | 943 |
| VLI | 3.0258 | 2.1566 | 5507 |
| HDR | 3.0257 | 2.1414 | 1335 |
| FKV | 3.0256 | 2.0316 | 2027 |
| GMY | 3.0255 | 1.4885 | 1363 |
| LRN | 3.0254 | 2.4409 | 3520 |
| RQT | 3.0253 | 2.7195 | 2590 |
| FLW | 3.0252 | 0.7586 | 909 |
| REE | 3.0251 | 1.1151 | 6605 |
| CCR | 3.0251 | 1.6989 | 3125 |
| AML | 3.0251 | 1.5225 | 1810 |
| SGN | 3.0251 | 2.4422 | 4550 |
| RMR | 3.0251 | 2.4024 | 6788 |
| ANQ | 3.0250 | 2.1557 | 925 |
| SVQ | 3.0249 | 2.7742 | 4516 |
| MET | 3.0249 | 0.7421 | 593 |
| MPG | 3.0248 | 2.0257 | 1930 |
| IKG | 3.0248 | 1.9862 | 5615 |
| QCD | 3.0247 | 1.8889 | 367 |
| ATC | 3.0247 | 1.9810 | 2018 |
| ILP | 3.0245 | 3.5064 | 2126 |
| IVL | 3.0245 | 2.4719 | 5485 |
| LTP | 3.0245 | 3.7780 | 1011 |
| NGG | 3.0244 | 1.3996 | 10347 |
| PAE | 3.0244 | 2.6151 | 1026 |
| EAL | 3.0244 | 2.1082 | 4211 |
| HLW | 3.0243 | 1.4118 | 1029 |
| QVV | 3.0242 | 2.5261 | 5167 |
| FIR | 3.0241 | 2.7719 | 2342 |
| KGR | 3.0238 | 1.7128 | 14768 |
| HVP | 3.0238 | 1.8604 | 705 |
| SVS | 3.0238 | 3.5500 | 13464 |
| PWY | 3.0238 | 2.2225 | 276 |
| NDR | 3.0238 | 2.3257 | 2648 |
| GGS | 3.0237 | 2.7808 | 37640 |
| PES | 3.0237 | 1.6649 | 1550 |
| LPM | 3.0236 | 2.3143 | 338 |
| REQ | 3.0234 | 1.9166 | 3024 |
| THD | 3.0233 | 1.7449 | 142 |
| VSF | 3.0233 | 2.1856 | 2900 |
| LST | 3.0232 | 3.4231 | 4270 |
| ARI | 3.0232 | 2.6062 | 5414 |
| GPD | 3.0232 | 2.1391 | 2374 |
| LGM | 3.0232 | 2.3998 | 4564 |
| NPG | 3.0231 | 1.8268 | 1643 |
| MTH | 3.0231 | 2.5094 | 611 |
| HCH | 3.0231 | 2.5139 | 421 |
| LEG | 3.0230 | 2.3981 | 14026 |
| PVI | 3.0229 | 3.0588 | 1978 |
| TRL | 3.0229 | 3.0321 | 5822 |
| RSI | 3.0228 | 3.2056 | 9609 |
| PCQ | 3.0228 | 1.6807 | 461 |
| LDT | 3.0227 | 2.4534 | 1814 |
| RQA | 3.0227 | 2.3292 | 3010 |
| SYQ | 3.0227 | 2.2752 | 1008 |
| FAH | 3.0226 | 1.5082 | 180 |
| QDA | 3.0223 | 1.2535 | 1182 |
| WAQ | 3.0223 | 1.2054 | 978 |
| PRA | 3.0223 | 2.7585 | 2929 |
| FQD | 3.0222 | 1.9935 | 261 |
| GPS | 3.0222 | 3.0541 | 5015 |

TABLE F-continued

Medium-expressing EGFP variants

| AA SEQ | Mean | Range | Total counts |
|---|---|---|---|
| CDY | 3.0218 | 1.2132 | 1001 |
| AIR | 3.0217 | 2.4326 | 7200 |
| GMP | 3.0217 | 1.7334 | 1309 |
| APK | 3.0216 | 2.5284 | 1402 |
| IDR | 3.0216 | 1.9100 | 3678 |
| GFE | 3.0216 | 1.3997 | 2699 |
| DDC | 3.0216 | 0.9217 | 817 |
| GNS | 3.0215 | 1.6765 | 4406 |
| GEI | 3.0214 | 1.0513 | 5414 |
| MVD | 3.0214 | 1.3156 | 1161 |
| FPR | 3.0213 | 2.5548 | 997 |
| LNA | 3.0210 | 3.3857 | 2667 |
| GLT | 3.0209 | 2.1179 | 7280 |
| LTN | 3.0209 | 2.7759 | 1602 |
| FCE | 3.0208 | 1.6500 | 776 |
| TCG | 3.0208 | 2.3901 | 3928 |
| MVH | 3.0207 | 1.1179 | 679 |
| PIT | 3.0207 | 3.0857 | 799 |
| LSP | 3.0206 | 4.0000 | 1398 |
| RCK | 3.0205 | 2.1257 | 3583 |
| GSR | 3.0205 | 3.3216 | 25952 |
| MAQ | 3.0203 | 1.3172 | 501 |
| GSK | 3.0201 | 1.7776 | 7129 |
| MVP | 3.0201 | 1.8182 | 1194 |
| EQN | 3.0201 | 1.2781 | 778 |
| QHP | 3.0199 | 1.1601 | 118 |
| DSV | 3.0199 | 2.7149 | 5737 |
| HMS | 3.0199 | 2.0614 | 554 |
| SYD | 3.0198 | 2.5767 | 2543 |
| MES | 3.0198 | 1.6000 | 1899 |
| PSA | 3.0198 | 2.5390 | 1238 |
| TAD | 3.0197 | 1.9385 | 1482 |
| SRS | 3.0196 | 2.6093 | 11337 |
| YFP | 3.0194 | 1.9398 | 319 |
| LGS | 3.0192 | 3.0424 | 17910 |
| MTC | 3.0192 | 2.5006 | 936 |
| SWM | 3.0191 | 1.9392 | 1040 |
| WTL | 3.0191 | 1.7412 | 1866 |
| FPV | 3.0190 | 2.8125 | 1242 |
| FVT | 3.0189 | 1.7865 | 1501 |
| LDD | 3.0188 | 1.8534 | 1293 |
| ISC | 3.0187 | 2.4692 | 2865 |
| RLR | 3.0186 | 3.4387 | 26358 |
| TQG | 3.0186 | 1.6553 | 2922 |
| CCD | 3.0186 | 1.1480 | 731 |
| VAR | 3.0185 | 2.4167 | 15733 |
| QGR | 3.0185 | 2.4600 | 10594 |
| IIV | 3.0185 | 1.6402 | 3074 |
| IAD | 3.0184 | 1.4451 | 1411 |
| PFI | 3.0184 | 3.5413 | 636 |
| VST | 3.0183 | 2.3352 | 4167 |
| KLG | 3.0183 | 2.3950 | 12492 |
| HQW | 3.0183 | 0.1915 | 296 |
| FRL | 3.0183 | 1.9091 | 2625 |
| KRR | 3.0182 | 2.5043 | 13428 |
| IFQ | 3.0181 | 2.3571 | 1074 |
| LFR | 3.0181 | 3.0764 | 6130 |
| GHP | 3.0180 | 2.7102 | 1212 |
| ACT | 3.0180 | 2.7763 | 1235 |
| WCM | 3.0180 | 0.3366 | 518 |
| LDH | 3.0180 | 1.7870 | 696 |
| RWY | 3.0180 | 1.5948 | 1884 |
| SLW | 3.0179 | 1.5373 | 4137 |
| QRD | 3.0178 | 1.7748 | 2333 |
| GIP | 3.0178 | 2.0462 | 1774 |
| LLL | 3.0177 | 3.5128 | 7674 |
| FTQ | 3.0175 | 1.6721 | 706 |
| AAF | 3.0174 | 2.1538 | 1631 |
| YLV | 3.0173 | 3.2109 | 4113 |
| AQT | 3.0173 | 2.5816 | 937 |
| FCC | 3.0172 | 1.4197 | 638 |
| LEA | 3.0169 | 1.6783 | 4783 |
| IHP | 3.0168 | 1.8565 | 259 |
| RLM | 3.0168 | 2.5875 | 4394 |
| ERN | 3.0167 | 2.2017 | 4386 |
| WWS | 3.0166 | 0.7379 | 2147 |
| CNG | 3.0166 | 1.3725 | 2766 |
| KGY | 3.0166 | 2.2451 | 3246 |
| YPD | 3.0165 | 1.6364 | 336 |
| GHG | 3.0165 | 2.0490 | 8452 |
| CSI | 3.0163 | 2.2923 | 2673 |
| TEV | 3.0162 | 2.3694 | 3694 |
| DPF | 3.0162 | 1.5180 | 460 |
| PSD | 3.0162 | 2.5625 | 875 |
| GEY | 3.0160 | 1.0565 | 3538 |
| QAR | 3.0160 | 2.3061 | 3858 |
| PHS | 3.0157 | 1.8462 | 660 |
| IVR | 3.0157 | 3.5234 | 15335 |
| ACG | 3.0156 | 1.3486 | 6734 |
| VLF | 3.0156 | 2.4940 | 3745 |
| ITE | 3.0153 | 2.6778 | 2132 |
| SDM | 3.0153 | 0.8949 | 798 |
| YRI | 3.0153 | 2.6259 | 3045 |
| RGK | 3.0153 | 2.1858 | 12684 |
| LTR | 3.0152 | 3.2259 | 6302 |
| ETS | 3.0150 | 2.0657 | 3616 |
| NGL | 3.0149 | 2.3161 | 4640 |
| CQP | 3.0149 | 1.0765 | 297 |
| WGM | 3.0148 | 0.9886 | 3004 |
| IFV | 3.0147 | 1.7672 | 1351 |
| WTR | 3.0147 | 1.4155 | 2802 |
| CLF | 3.0146 | 2.3494 | 2107 |
| DCA | 3.0146 | 1.6387 | 1657 |
| IDS | 3.0144 | 1.9965 | 2247 |
| QSQ | 3.0144 | 2.9384 | 1217 |
| LSC | 3.0144 | 3.5619 | 5343 |
| QIG | 3.0143 | 1.8236 | 2972 |
| IEL | 3.0143 | 2.6877 | 3556 |
| CKG | 3.0142 | 1.1589 | 4437 |
| VKL | 3.0142 | 2.4028 | 5384 |
| FDC | 3.0141 | 1.4632 | 674 |
| CHP | 3.0138 | 1.8387 | 228 |
| HGC | 3.0138 | 1.6526 | 1411 |
| PKL | 3.0138 | 2.4200 | 1443 |
| SCK | 3.0138 | 2.3947 | 2492 |
| HKG | 3.0137 | 1.4890 | 1839 |
| AIS | 3.0136 | 2.6745 | 4496 |
| CMQ | 3.0136 | 1.6191 | 443 |
| EKE | 3.0135 | 1.2970 | 2829 |
| CGP | 3.0135 | 1.7393 | 2250 |
| PDQ | 3.0135 | 1.4086 | 248 |
| ARS | 3.0134 | 3.0177 | 9880 |
| VCM | 3.0132 | 0.9145 | 1213 |
| SAH | 3.0132 | 2.7038 | 946 |
| PAA | 3.0132 | 2.4227 | 2045 |
| MRN | 3.0132 | 2.2315 | 1278 |
| ELQ | 3.0130 | 2.8535 | 3215 |
| WSC | 3.0129 | 0.9234 | 1810 |
| TRE | 3.0129 | 2.4778 | 4126 |
| THM | 3.0129 | 1.3683 | 288 |
| RFV | 3.0128 | 3.0165 | 7710 |
| PLT | 3.0127 | 2.2857 | 844 |
| TQE | 3.0126 | 1.9076 | 1102 |
| GFL | 3.0125 | 2.6524 | 3336 |
| FVI | 3.0125 | 2.0280 | 1353 |
| CRI | 3.0125 | 2.0839 | 3926 |
| TGT | 3.0124 | 3.3203 | 4074 |
| EGT | 3.0124 | 1.5096 | 5875 |
| CRE | 3.0123 | 1.3299 | 4711 |
| CND | 3.0123 | 1.1346 | 865 |
| SDI | 3.0123 | 2.5181 | 2333 |
| NEW | 3.0122 | 1.6650 | 1143 |
| LHE | 3.0122 | 3.0405 | 973 |
| RQE | 3.0122 | 2.5364 | 3323 |
| LSM | 3.0121 | 2.5066 | 1954 |
| FTA | 3.0121 | 2.4619 | 1318 |
| VEI | 3.0120 | 1.1961 | 3895 |
| FVA | 3.0117 | 1.4167 | 2412 |
| EAR | 3.0117 | 2.5306 | 9179 |
| LFY | 3.0116 | 2.4420 | 1232 |

TABLE F-continued

Medium-expressing EGFP variants

| AA SEQ | Mean | Range | Total counts |
|---|---|---|---|
| MQS | 3.0115 | 1.9613 | 923 |
| GIL | 3.0114 | 1.9986 | 6833 |
| GFV | 3.0114 | 1.1425 | 6487 |
| MVV | 3.0114 | 1.2384 | 4709 |
| TYW | 3.0112 | 2.6984 | 844 |
| YMS | 3.0112 | 1.9291 | 1220 |
| FDK | 3.0110 | 1.9184 | 414 |
| RPG | 3.0109 | 3.0573 | 10322 |
| ASW | 3.0106 | 1.9435 | 3235 |
| CCF | 3.0104 | 1.3596 | 598 |
| FWW | 3.0104 | 0.6571 | 511 |
| DAH | 3.0104 | 3.0657 | 669 |
| SSD | 3.0104 | 3.4208 | 2713 |
| VRN | 3.0103 | 1.7243 | 5434 |
| RKV | 3.0102 | 2.4408 | 10698 |
| QGM | 3.0102 | 1.1427 | 1319 |
| GAT | 3.0100 | 2.1218 | 5575 |
| MAN | 3.0100 | 1.6956 | 341 |
| IRG | 3.0100 | 2.3380 | 15144 |
| QID | 3.0099 | 1.5885 | 1001 |
| EQR | 3.0099 | 1.8310 | 4075 |
| FYD | 3.0099 | 1.6779 | 210 |
| EHE | 3.0097 | 1.3280 | 881 |
| LSL | 3.0096 | 3.8000 | 7552 |
| MRL | 3.0096 | 1.8747 | 3949 |
| NDN | 3.0094 | 1.4205 | 674 |
| DRW | 3.0092 | 0.9101 | 3082 |
| MRE | 3.0090 | 1.5133 | 2355 |
| AKV | 3.0090 | 3.1076 | 4251 |
| FFH | 3.0087 | 1.2511 | 137 |
| SCH | 3.0086 | 1.7387 | 960 |
| SLA | 3.0086 | 3.0638 | 6830 |
| HEH | 3.0086 | 2.5128 | 710 |
| RYM | 3.0086 | 2.9559 | 1747 |
| EVR | 3.0085 | 1.8838 | 17979 |
| NGN | 3.0085 | 2.1809 | 1989 |
| WAP | 3.0084 | 2.5250 | 790 |
| VTD | 3.0084 | 1.9234 | 1864 |
| DSA | 3.0083 | 2.5926 | 3884 |
| GDK | 3.0082 | 1.1781 | 3223 |
| LDM | 3.0082 | 1.2250 | 1172 |
| KEG | 3.0082 | 1.0530 | 5854 |
| PIK | 3.0082 | 1.9802 | 670 |
| MRW | 3.0082 | 1.1465 | 2597 |
| IFL | 3.0081 | 1.9725 | 1315 |
| VMQ | 3.0081 | 1.5339 | 1466 |
| WDP | 3.0080 | 1.3333 | 550 |
| RKG | 3.0080 | 1.6574 | 12183 |
| IYL | 3.0080 | 2.2261 | 1588 |
| MSR | 3.0080 | 2.8072 | 5497 |
| IAA | 3.0079 | 2.4971 | 2575 |
| RVS | 3.0079 | 2.5826 | 20330 |
| IFS | 3.0076 | 2.1636 | 2330 |
| ASQ | 3.0075 | 2.9203 | 2012 |
| AGA | 3.0074 | 2.1524 | 12653 |
| FKG | 3.0074 | 1.4520 | 2456 |
| GVS | 3.0073 | 2.3620 | 23215 |
| PFE | 3.0071 | 2.7647 | 605 |
| CLV | 3.0071 | 2.6987 | 6218 |
| NWD | 3.0070 | 0.4863 | 387 |
| SMD | 3.0068 | 1.8418 | 902 |
| LGP | 3.0068 | 2.9333 | 4286 |
| ECG | 3.0068 | 0.7906 | 8234 |
| SAD | 3.0066 | 2.3459 | 2400 |
| SHG | 3.0066 | 2.3061 | 2598 |
| VYD | 3.0066 | 1.0000 | 1456 |
| VSN | 3.0065 | 2.5508 | 3865 |
| LQQ | 3.0065 | 2.9096 | 950 |
| GVY | 3.0064 | 1.2526 | 6473 |
| DHG | 3.0064 | 1.7713 | 1276 |
| IGM | 3.0064 | 0.6077 | 2119 |
| RCR | 3.0063 | 1.9714 | 11049 |
| LGT | 3.0063 | 2.9476 | 6215 |
| PRR | 3.0063 | 3.0000 | 5995 |
| LQN | 3.0062 | 2.0287 | 753 |
| LAM | 3.0060 | 2.7600 | 1195 |
| ERG | 3.0059 | 1.0785 | 25152 |
| IES | 3.0057 | 2.2542 | 3700 |
| WHV | 3.0056 | 1.3544 | 1015 |
| RHT | 3.0056 | 2.8550 | 2438 |
| IRE | 3.0055 | 2.4071 | 4853 |
| NPP | 3.0055 | 1.8947 | 139 |
| TAA | 3.0051 | 2.9412 | 2525 |
| FHQ | 3.0051 | 0.9691 | 151 |
| MRS | 3.0050 | 1.8123 | 4961 |
| VTY | 3.0049 | 2.4891 | 2497 |
| VWP | 3.0049 | 1.9644 | 1748 |
| QWV | 3.0046 | 1.5927 | 1559 |
| MRD | 3.0046 | 1.1598 | 1767 |
| GKL | 3.0045 | 1.4635 | 6887 |
| WRV | 3.0045 | 1.6561 | 9189 |
| NGA | 3.0044 | 1.7622 | 3857 |
| SFR | 3.0044 | 3.9775 | ☐☐☐☐ |
| IDY | 3.0044 | 1.9225 | 891 |
| RRE | 3.0044 | 2.3972 | 14191 |
| MVF | 3.0043 | 1.5961 | 1670 |
| DMA | 3.0042 | 0.8403 | 858 |
| VTH | 3.0042 | 2.4343 | 1206 |
| TGA | 3.0042 | 2.2555 | 6536 |
| SDP | 3.0041 | 2.6000 | 564 |
| ARK | 3.0039 | 2.6711 | 4609 |
| PPP | 3.0039 | 1.1484 | 66 |
| SVM | 3.0038 | 1.1673 | 2850 |
| VYL | 3.0037 | 1.2236 | 2743 |
| LSE | 3.0037 | 1.8892 | 4981 |
| MRA | 3.0036 | 2.1668 | 4221 |
| MSL | 3.0034 | 2.7493 | 3798 |
| ASA | 3.0034 | 2.9902 | 4358 |
| LVE | 3.0033 | 2.2725 | 7639 |
| CRS | 3.0033 | 2.6494 | 6118 |
| SRF | 3.0033 | 3.2363 | 3926 |
| MRF | 3.0030 | 2.2358 | 2352 |
| GVK | 3.0029 | 0.9454 | 9885 |
| KQG | 3.0029 | 1.8165 | 3128 |
| EEE | 3.0026 | 0.8434 | 3511 |
| WCT | 3.0024 | 1.4304 | 941 |
| IQE | 3.0024 | 1.9935 | 1007 |
| MCV | 3.0021 | 1.4815 | 2009 |
| IHL | 3.0021 | 2.6679 | 1339 |
| HAR | 3.0020 | 2.6379 | 1610 |
| SPG | 3.0020 | 2.5338 | 4916 |
| LPP | 3.0020 | 3.0000 | 453 |
| MSG | 3.0018 | 1.9824 | 5469 |
| SGD | 3.0018 | 3.0185 | 6911 |
| GCV | 3.0017 | 1.9780 | 10494 |
| LWH | 3.0016 | 1.4076 | 803 |
| CGI | 3.0015 | 1.3074 | 4641 |
| RRN | 3.0014 | 3.2335 | 5495 |
| QAC | 3.0013 | 1.6333 | 926 |
| EFD | 3.0013 | 1.8541 | 1122 |
| AAH | 3.0011 | 2.6667 | 1408 |
| YAF | 3.0010 | 1.9327 | 678 |
| GTN | 3.0009 | 2.6727 | 2038 |
| TRD | 3.0007 | 3.2652 | 2690 |
| RQD | 3.0006 | 1.8261 | 1498 |
| ISP | 3.0006 | 2.7737 | 583 |
| LLM | 3.0006 | 2.2891 | 2123 |
| QRE | 3.0005 | 1.7289 | 2760 |
| TMM | 3.0004 | 0.7570 | 315 |
| LDR | 3.0003 | 2.5585 | 6025 |
| NVG | 3.0001 | 2.5404 | 8288 |
| RDE | 3.0001 | 1.2760 | 3479 |
| WVL | 3.0000 | 1.8422 | 5604 |
| ACC | 2.9997 | 1.1401 | 1454 |
| SVN | 2.9997 | 2.6845 | 4373 |
| CAS | 2.9996 | 2.1681 | 2989 |
| DAA | 2.9996 | 2.1811 | 2242 |
| SDQ | 2.9995 | 1.6788 | 917 |
| NDD | 2.9995 | 1.3730 | 412 |
| PLS | 2.9994 | 4.0000 | 2835 |

TABLE F-continued

Medium-expressing EGFP variants

| AA SEQ | Mean | Range | Total counts |
|---|---|---|---|
| YWH | 2.9994 | 2.0399 | 506 |
| PEQ | 2.9994 | 2.2253 | 269 |
| HAT | 2.9993 | 2.8477 | 319 |
| CPS | 2.9991 | 2.7313 | 1048 |
| GVD | 2.9990 | 2.1729 | 9535 |
| CER | 2.9989 | 1.2982 | 5129 |
| HVD | 2.9989 | 1.5433 | 1023 |
| IAS | 2.9988 | 2.8065 | 2930 |
| EDW | 2.9988 | 0.1867 | 1457 |
| SAR | 2.9986 | 3.7885 | 8631 |
| FET | 2.9986 | 1.7583 | 798 |
| GLN | 2.9986 | 2.2925 | 5190 |
| WRY | 2.9985 | 1.5218 | 2230 |
| TAW | 2.9983 | 1.2490 | 1449 |
| PWL | 2.9982 | 2.8051 | 964 |
| NFP | 2.9982 | 2.8707 | 780 |
| RQN | 2.9982 | 1.7474 | 1593 |
| DHT | 2.9980 | 2.8034 | 577 |
| GQK | 2.9978 | 1.2747 | 2434 |
| PLD | 2.9976 | 2.1053 | 958 |
| CFS | 2.9975 | 1.9292 | 1471 |
| GSN | 2.9974 | 2.4547 | 5628 |
| CRY | 2.9974 | 2.4710 | 2565 |
| CRL | 2.9973 | 2.9143 | 6061 |
| YCN | 2.9971 | 2.1929 | 967 |
| HAI | 2.9970 | 2.5120 | 590 |
| FRW | 2.9970 | 1.2980 | 1710 |
| LGD | 2.9968 | 2.9189 | 6830 |
| DED | 2.9968 | 0.9333 | 981 |
| RTQ | 2.9966 | 2.8141 | 2249 |
| QVG | 2.9966 | 2.1840 | 9132 |
| DAE | 2.9965 | 1.1573 | 2484 |
| ISF | 2.9965 | 3.1855 | 1652 |
| MAE | 2.9963 | 1.5135 | 1467 |
| HDN | 2.9963 | 2.3612 | 452 |
| EVC | 2.9962 | 1.2843 | 5697 |
| SST | 2.9962 | 3.7143 | 2825 |
| YAR | 2.9959 | 2.2875 | 3788 |
| FYC | 2.9959 | 1.8280 | 537 |
| HFS | 2.9958 | 2.6638 | 903 |
| QRK | 2.9958 | 2.3610 | 2384 |
| DPK | 2.9957 | 2.7927 | 861 |
| WFE | 2.9954 | 0.5898 | 811 |
| VNN | 2.9951 | 2.0735 | 1926 |
| YGD | 2.9950 | 1.2617 | 2064 |
| WPD | 2.9950 | 1.4500 | 464 |
| EEF | 2.9949 | 0.7980 | 1780 |
| EEP | 2.9947 | 1.9944 | 1065 |
| SCD | 2.9947 | 2.3716 | 1271 |
| CSM | 2.9946 | 1.6504 | 859 |
| WLP | 2.9946 | 1.6212 | 1133 |
| ERD | 2.9946 | 0.9298 | 5193 |
| WPN | 2.9944 | 1.2197 | 391 |
| TDG | 2.9944 | 1.9151 | 3651 |
| HFD | 2.9944 | 2.4553 | 437 |
| CTA | 2.9942 | 2.9186 | 1388 |
| WLC | 2.9940 | 1.1240 | 2448 |
| DEF | 2.9940 | 1.1020 | 1029 |
| VFD | 2.9938 | 1.6333 | 1546 |
| YFA | 2.9938 | 2.5480 | 1214 |
| FKQ | 2.9938 | 2.3594 | 485 |
| CSV | 2.9938 | 1.9864 | 5518 |
| CLA | 2.9938 | 3.4575 | 3585 |
| TCA | 2.9938 | 3.2904 | 1374 |
| QDG | 2.9937 | 1.3230 | 2929 |
| DPV | 2.9936 | 1.9210 | 1562 |
| VNS | 2.9936 | 2.5651 | 3939 |
| YVD | 2.9935 | 1.3685 | 1812 |
| FMN | 2.9935 | 0.1082 | 54 |
| SMV | 2.9935 | 1.2135 | 3351 |
| YKD | 2.9934 | 1.0547 | 693 |
| YAW | 2.9933 | 0.8511 | 1077 |
| PIS | 2.9933 | 2.5862 | 1598 |
| ENP | 2.9932 | 1.7894 | 414 |
| SEY | 2.9932 | 2.1121 | 2400 |
| DLT | 2.9931 | 2.5379 | 2428 |
| GWK | 2.9931 | 0.8466 | 3676 |
| WFI | 2.9931 | 1.0609 | 874 |
| CED | 2.9931 | 1.4153 | 997 |
| IAY | 2.9931 | 2.4571 | 1861 |
| QNA | 2.9930 | 2.2866 | 1044 |
| PRF | 2.9930 | 2.5714 | 958 |
| SSV | 2.9928 | 3.3517 | 10271 |
| GIC | 2.9928 | 1.9751 | 4062 |
| TPK | 2.9928 | 2.4000 | 753 |
| GWL | 2.9928 | 1.7839 | 8938 |
| WET | 2.9927 | 1.5663 | 1271 |
| VFF | 2.9927 | 2.6808 | 1045 |
| DMW | 2.9926 | 0.6964 | 625 |
| EDL | 2.9925 | 1.2824 | 2900 |
| SNE | 2.9925 | 1.7273 | 1559 |
| FQQ | 2.9924 | 2.3141 | 395 |
| MMS | 2.9924 | 1.3180 | 587 |
| GKW | 2.9924 | 0.9655 | 4318 |
| KEE | 2.9923 | 0.9207 | 2008 |
| AFK | 2.9919 | 2.7102 | 1227 |
| GFD | 2.9919 | 1.1411 | 1837 |
| QPQ | 2.9918 | 1.6566 | 223 |
| DDR | 2.9917 | 1.4146 | 2928 |
| STW | 2.9917 | 1.9175 | 1296 |
| GFH | 2.9915 | 1.6281 | 989 |
| DLP | 2.9914 | 3.0725 | 907 |
| KAE | 2.9914 | 2.1204 | 2397 |
| RPR | 2.9914 | 3.3739 | 6450 |
| TGN | 2.9914 | 1.7645 | 2791 |
| FFM | 2.9913 | 1.3064 | 152 |
| LVV | 2.9913 | 2.5378 | 14355 |
| YFT | 2.9913 | 1.8065 | 556 |
| FMS | 2.9913 | 1.4495 | 1095 |
| WRS | 2.9913 | 1.6368 | 6163 |
| SFI | 2.9912 | 3.1188 | 2050 |
| GKR | 2.9912 | 1.5635 | 13044 |
| RHG | 2.9912 | 2.6007 | 4919 |
| TGF | 2.9910 | 2.0121 | 3531 |
| FRQ | 2.9910 | 2.2868 | 1196 |
| PMM | 2.9909 | 0.4357 | 115 |
| REV | 2.9908 | 1.3923 | 13422 |
| WSE | 2.9908 | 1.0795 | 2738 |
| NVD | 2.9908 | 2.0276 | 2111 |
| SGH | 2.9906 | 2.5443 | 2781 |
| EME | 2.9905 | 0.1074 | 1198 |
| PRN | 2.9905 | 3.0229 | 1435 |
| HVG | 2.9904 | 1.8781 | 4743 |
| DCR | 2.9904 | 1.5958 | 3681 |
| CAC | 2.9904 | 1.4634 | 2324 |
| VTP | 2.9904 | 2.7692 | 947 |
| FYP | 2.9903 | 1.9643 | 305 |
| DSW | 2.9903 | 1.3015 | 2329 |
| IVM | 2.9902 | 1.0515 | 1636 |
| WIK | 2.9902 | 1.3509 | 1261 |
| WQD | 2.9902 | 0.6246 | 512 |
| IRM | 2.9902 | 1.9926 | 1527 |
| GQL | 2.9900 | 2.4654 | 5458 |
| WMS | 2.9897 | 1.3277 | 1304 |
| STR | 2.9895 | 2.8541 | 7123 |
| CQC | 2.9895 | 2.2562 | 1167 |
| GNH | 2.9893 | 1.8710 | 1231 |
| MRQ | 2.9893 | 1.8206 | 1967 |
| RRQ | 2.9893 | 2.9356 | 6574 |
| VPW | 2.9892 | 2.1273 | 1848 |
| RRA | 2.9890 | 2.8750 | 17026 |
| RTS | 2.9889 | 3.2942 | 6778 |
| GNL | 2.9889 | 2.0987 | 4039 |
| VRP | 2.9888 | 2.8909 | 3409 |
| PTC | 2.9888 | 2.8669 | 485 |
| WSY | 2.9887 | 1.9576 | 1469 |
| KGC | 2.9887 | 0.9678 | 4331 |
| VQD | 2.9887 | 1.5768 | 1619 |
| LMG | 2.9886 | 2.6199 | 5374 |
| MCT | 2.9885 | 1.8098 | 849 |

TABLE F-continued

Medium-expressing EGFP variants

| AA SEQ | Mean | Range | Total counts |
|---|---|---|---|
| PKH | 2.9885 | 2.0580 | 201 |
| GSQ | 2.9885 | 2.0979 | 4936 |
| CVC | 2.9885 | 1.1620 | 3283 |
| YGS | 2.9884 | 2.2222 | 5122 |
| DCD | 2.9884 | 1.1175 | 847 |
| NSE | 2.9883 | 2.2312 | 1840 |
| CNP | 2.9883 | 2.1725 | 282 |
| FTG | 2.9882 | 1.6757 | 2527 |
| SVR | 2.9882 | 3.2833 | 21929 |
| IAV | 2.9882 | 2.2481 | 3412 |
| ITV | 2.9881 | 1.7585 | 2878 |
| IRV | 2.9879 | 2.3557 | 8249 |
| SGE | 2.9877 | 2.4397 | 10727 |
| RMV | 2.9876 | 깨 팀 | 5479 |
| PCH | 2.9876 | 1.4085 | 232 |
| SRQ | 2.9876 | 2.1125 | 3930 |
| TDK | 2.9874 | 2.0203 | 1587 |
| PQS | 2.9873 | 1.9231 | 1018 |
| PLR | 2.9872 | 3.2180 | 3400 |
| AYC | 2.9872 | 2.3654 | 1391 |
| PLY | 2.9871 | 2.6231 | 1088 |
| LSQ | 2.9871 | 2.6821 | 3062 |
| FLA | 2.9870 | 2.8468 | 1700 |
| MVK | 2.9870 | 1.7039 | 1701 |
| AVA | 2.9869 | 2.1504 | 6093 |
| EHR | 2.9866 | 2.4701 | 2941 |
| RLV | 2.9865 | 3.5361 | 21238 |
| QEL | 2.9865 | 1.4760 | 2232 |
| EWN | 2.9864 | 1.3438 | 1343 |
| QFG | 2.9864 | 1.3376 | 1735 |
| LYD | 2.9861 | 2.4604 | 1569 |
| RCC | 2.9861 | 1.8503 | 2877 |
| GNW | 2.9859 | 1.1153 | 1797 |
| VCP | 2.9857 | 2.6250 | 1412 |
| MSP | 2.9855 | 1.7628 | 526 |
| VAL | 2.9854 | 2.9813 | 8062 |
| HWS | 2.9854 | 1.3383 | 1049 |
| WYW | 2.9854 | 0.4540 | 855 |
| ELT | 2.9852 | 3.1949 | 4882 |
| PFK | 2.9852 | 3.0227 | 576 |
| SRI | 2.9852 | 2.6905 | 6755 |
| EFA | 2.9851 | 2.4338 | 2807 |
| TRN | 2.9851 | 3.1000 | 2555 |
| LYT | 2.9850 | 3.0269 | 2334 |
| TED | 2.9847 | 1.5833 | 979 |
| LME | 2.9846 | 0.8645 | 1192 |
| CCC | 2.9845 | 1.2185 | 948 |
| YSC | 2.9844 | 1.7455 | 2043 |
| VEN | 2.9843 | 1.0098 | 1931 |
| VFT | 2.9843 | 2.1297 | 1585 |
| SSG | 2.9841 | 3.2141 | 16397 |
| YVP | 2.9841 | 3.4117 | 1405 |
| DQG | 2.9841 | 1.1927 | 3236 |
| RWR | 2.9839 | 1.6907 | 11630 |
| FSL | 2.9839 | 2.8951 | 1754 |
| TQP | 2.9838 | 1.6182 | 187 |
| WDN | 2.9838 | 0.8037 | 374 |
| RSE | 2.9838 | 2.3097 | 9476 |
| KDD | 2.9838 | 1.9804 | 577 |
| LEN | 2.9836 | 2.3835 | 1906 |
| GIM | 2.9836 | 1.1827 | 2246 |
| WMA | 2.9835 | 0.9514 | 1014 |
| LLC | 2.9834 | 2.2891 | 5328 |
| WIS | 2.9832 | 2.2942 | 2244 |
| VMK | 2.9832 | 2.1219 | 2489 |
| EPQ | 2.9832 | 2.1137 | 803 |
| ELW | 2.9832 | 1.7090 | 3783 |
| LED | 2.9831 | 2.1563 | 1994 |
| ECF | 2.9830 | 1.1538 | 1109 |
| HRK | 2.9830 | 3.4186 | 1222 |
| VMR | 2.9829 | 2.7581 | 5090 |
| FCR | 2.9828 | 1.5414 | 1363 |
| EDN | 2.9828 | 0.8835 | 830 |
| DRE | 2.9827 | 1.5570 | 3916 |
| WQA | 2.9827 | 1.1947 | 1307 |
| RMM | 2.9825 | 0.7309 | 1002 |
| AIT | 2.9825 | 2.4206 | 2154 |
| LNV | 2.9824 | 2.8272 | 3140 |
| ITM | 2.9824 | 1.2976 | 586 |
| RHP | 2.9823 | 2.3795 | 859 |
| TQT | 2.9822 | 1.7244 | 993 |
| HDG | 2.9821 | 1.5411 | 997 |
| FGY | 2.9820 | 0.9252 | 1610 |
| PFT | 2.9820 | 3.0051 | 590 |
| FSA | 2.9819 | 3.5693 | 1754 |
| HLD | 2.9819 | 2.1212 | 619 |
| SSE | 2.9818 | 2.3658 | 3793 |
| RIV | 2.9817 | 2.6983 | 10670 |
| LLE | 2.9817 | 3.1786 | 4620 |
| ICC | 2.9816 | 1.7022 | 1467 |
| HGR | 2.9816 | 2.2383 | 4928 |
| TDR | 2.9815 | 2.3716 | 2808 |
| LDN | 2.9814 | 1.7735 | 1492 |
| VYS | 2.9810 | 1.7052 | 4360 |
| LMR | 2.9810 | 3.1991 | 4719 |
| EAE | 2.9806 | 1.5098 | 3894 |
| CKP | 2.9806 | 2.5021 | 495 |
| YVE | 2.9806 | 2.4969 | 2719 |
| IPR | 2.9805 | 2.9103 | 2538 |
| CPC | 2.9803 | 1.7281 | 425 |
| HRP | 2.9803 | 3.0000 | 290 |
| QEE | 2.9802 | 0.8730 | 986 |
| LES | 2.9802 | 2.0409 | 5432 |
| YFV | 2.9801 | 1.9453 | 1578 |
| QRC | 2.9800 | 2.4115 | 1995 |
| YRE | 2.9799 | 2.2312 | 3494 |
| SAL | 2.9799 | 2.7358 | 4603 |
| SWG | 2.9799 | 1.7569 | 10352 |
| CPM | 2.9797 | 1.4983 | 571 |
| GPH | 2.9797 | 2.1846 | 978 |
| YYV | 2.9797 | 1.6094 | 2144 |
| WNC | 2.9795 | 1.9065 | 557 |
| LAI | 2.9794 | 2.1334 | 2717 |
| QWS | 2.9794 | 1.9602 | 1281 |
| GIV | 2.9793 | 1.5100 | 10502 |
| IQP | 2.9793 | 1.2455 | 303 |
| ELG | 2.9792 | 1.6616 | 17003 |
| PKD | 2.9790 | 1.8524 | 608 |
| MVT | 2.9789 | 1.7949 | 1483 |
| TME | 2.9789 | 0.7798 | 692 |
| PQI | 2.9789 | 2.4724 | 561 |
| IPV | 2.9789 | 3.2643 | 2308 |
| EPR | 2.9789 | 2.5567 | 2748 |
| SAM | 2.9788 | 1.1231 | 1652 |
| VLY | 2.9788 | 2.1710 | 4679 |
| GYH | 2.9786 | 1.5119 | 1089 |
| RCS | 2.9780 | 2.8214 | 5761 |
| ETV | 2.9779 | 2.0137 | 4553 |
| KWI | 2.9779 | 1.4447 | 1152 |
| KAG | 2.9779 | 1.4053 | 7510 |
| DPE | 2.9778 | 0.8746 | 904 |
| CTH | 2.9778 | 2.4803 | 785 |
| VLL | 2.9778 | 3.1639 | 11821 |
| PRK | 2.9777 | 2.4077 | 1464 |
| IGK | 2.9777 | 2.3915 | 5573 |
| KGA | 2.9777 | 1.5106 | 5971 |
| PLW | 2.9776 | 2.7498 | 1129 |
| GNV | 2.9775 | 1.7217 | 5656 |
| MSM | 2.9775 | 0.7401 | 468 |
| YDC | 2.9775 | 1.9484 | 947 |
| EEH | 2.9774 | 1.5380 | 1218 |
| VTE | 2.9773 | 2.7780 | 3411 |
| AWM | 2.9772 | 1.0733 | 1013 |
| IEC | 2.9771 | 2.2793 | 2149 |
| RRC | 2.9771 | 1.9415 | 10479 |
| FWQ | 2.9771 | 0.9655 | 343 |
| WTD | 2.9770 | 1.0152 | 634 |
| ARQ | 2.9770 | 2.5650 | 2219 |
| TIG | 2.9769 | 2.4593 | 6434 |
| RNG | 2.9768 | 1.8598 | 7327 |

TABLE F-continued

Medium-expressing EGFP variants

| AA SEQ | Mean | Range | Total counts |
|---|---|---|---|
| NQG | 2.9765 | 1.5360 | 2140 |
| PTA | 2.9764 | 2.7823 | 542 |
| RVP | 2.9764 | 2.1908 | 4426 |
| AQE | 2.9764 | 2.2091 | 1403 |
| AVK | 2.9761 | 1.5538 | 4260 |
| WCH | 2.9760 | 0.8264 | 464 |
| EDM | 2.9759 | 0.3902 | 790 |
| RSA | 2.9758 | 3.4818 | 8866 |
| AKQ | 2.9758 | 2.3061 | 1315 |
| IGL | 2.9757 | 1.8703 | 8309 |
| TMG | 2.9756 | 1.8555 | 2032 |
| RVT | 2.9754 | 2.6989 | 8142 |
| CRC | 2.9753 | 1.4003 | 3400 |
| PDL | 2.9753 | 2.3889 | 1088 |
| EIP | 2.9752 | 2.6823 | 1093 |
| REC | 2.9751 | 2.5623 | 5421 |
| LGE | 2.9750 | 2.1547 | 11120 |
| WNA | 2.9749 | 1.3817 | 949 |
| YLQ | 2.9747 | 2.8566 | 1041 |
| ALA | 2.9746 | 2.9552 | 4233 |
| RCH | 2.9745 | 1.8333 | 1498 |
| WQR | 2.9744 | 0.9688 | 2598 |
| ILN | 2.9744 | 2.1788 | 2806 |
| LEH | 2.9743 | 1.7649 | 1401 |
| SWS | 2.9743 | 2.5877 | 3879 |
| TSW | 2.9743 | 1.9299 | 2019 |
| GMH | 2.9742 | 1.8256 | 953 |
| VPI | 2.9742 | 1.8691 | 1592 |
| GKN | 2.9740 | 1.2185 | 2084 |
| FTT | 2.9739 | 2.4091 | 469 |
| RCN | 2.9739 | 2.2771 | 2277 |
| RMS | 2.9738 | 2.0171 | 3716 |
| SRC | 2.9737 | 2.3514 | 7060 |
| YLW | 2.9737 | 1.2839 | 1617 |
| PEF | 2.9737 | 1.1044 | 588 |
| SFT | 2.9736 | 2.6990 | 1310 |
| IGA | 2.9734 | 2.3803 | 6888 |
| FGM | 2.9734 | 0.4705 | 1393 |
| SCM | 2.9733 | 1.2888 | 904 |
| DDK | 2.9732 | 1.3765 | 980 |
| PSR | 2.9732 | 3.8563 | 3391 |
| MAL | 2.9731 | 1.6517 | 1645 |
| CRR | 2.9731 | 1.8362 | 8415 |
| WEQ | 2.9731 | 0.7328 | 838 |
| MTM | 2.9731 | 0.9002 | 246 |
| CTS | 2.9729 | 3.7987 | 2207 |
| MPQ | 2.9728 | 1.2161 | 58 |
| LGQ | 2.9727 | 2.8760 | 5004 |
| IGS | 2.9727 | 2.0459 | 8461 |
| WQS | 2.9726 | 0.7743 | 1358 |
| SRT | 2.9726 | 3.0977 | 4780 |
| AVD | 2.9726 | 2.4782 | 4519 |
| CVR | 2.9726 | 2.2046 | 11023 |
| RRM | 2.9726 | 2.7511 | 5136 |
| CLC | 2.9726 | 1.7422 | 2844 |
| LWN | 2.9724 | 1.2297 | 977 |
| GKI | 2.9723 | 1.4563 | 3998 |
| SEM | 2.9721 | 1.4499 | 1512 |
| SGI | 2.9721 | 1.9557 | 8403 |
| APQ | 2.9721 | 3.1945 | 636 |
| RIG | 2.9720 | 2.6305 | 17426 |
| SRE | 2.9720 | 1.9426 | 8552 |
| EQD | 2.9719 | 1.3277 | 871 |
| PSL | 2.9718 | 3.1929 | 1885 |
| WYL | 2.9716 | 2.6775 | 1281 |
| GVN | 2.9714 | 1.9642 | 6663 |
| NCD | 2.9714 | 1.8545 | 662 |
| THS | 2.9713 | 2.0833 | 1532 |
| DLW | 2.9712 | 1.4289 | 2104 |
| YWQ | 2.9712 | 1.2993 | 584 |
| NAV | 2.9712 | 2.1108 | 2747 |
| IIF | 2.9711 | 1.5092 | 924 |
| MIG | 2.9710 | 2.1110 | 3644 |
| RPM | 2.9709 | 1.6014 | 877 |
| DTD | 2.9708 | 1.4000 | 865 |
| DGS | 2.9708 | 2.0853 | 8396 |
| LPD | 2.9708 | 2.4025 | 946 |
| QTS | 2.9708 | 2.8841 | 2354 |
| PGC | 2.9708 | 2.4928 | 3469 |
| CAT | 2.9706 | 2.4095 | 1102 |
| RGT | 2.9706 | 1.7329 | 11449 |
| MRV | 2.9706 | 1.7404 | 5521 |
| GKA | 2.9706 | 1.6594 | 6365 |
| EVQ | 2.9704 | 2.3473 | 3453 |
| VWT | 2.9703 | 1.7106 | 2507 |
| SRN | 2.9702 | 2.9010 | 3860 |
| VFS | 2.9702 | 2.4000 | 3308 |
| KPG | 2.9702 | 1.4628 | 2493 |
| TLE | 2.9701 | 2.3679 | 3283 |
| SRW | 2.9700 | 1.7263 | 5570 |
| MHG | 2.9700 | 1.4668 | 861 |
| DAY | 2.9699 | 2.1636 | 1156 |
| PRQ | 2.9699 | 2.2727 | 1066 |
| GFP | 2.9699 | 1.9167 | 1081 |
| WTV | 2.9699 | 1.5303 | 2608 |
| WLY | 2.9696 | 1.4794 | 2177 |
| FMV | 2.9696 | 0.8944 | 959 |
| GVP | 2.9694 | 2.6000 | 5792 |
| WIR | 2.9694 | 1.5215 | 3967 |
| SPE | 2.9694 | 2.8000 | 1451 |
| LSS | 2.9693 | 2.9496 | 8392 |
| ICS | 2.9693 | 2.9328 | 3445 |
| VFN | 2.9693 | 1.0063 | 1501 |
| YKG | 2.9691 | 2.4856 | 2599 |
| SWH | 2.9690 | 1.7276 | 563 |
| EPA | 2.9689 | 2.3469 | 1275 |
| GSY | 2.9689 | 2.1982 | 4756 |
| QAL | 2.9687 | 2.4000 | 1529 |
| GIN | 2.9686 | 1.6821 | 3025 |
| WYQ | 2.9686 | 1.2015 | 605 |
| GTQ | 2.9685 | 2.3930 | 2559 |
| IVQ | 2.9684 | 1.6981 | 2624 |
| WLV | 2.9684 | 1.3127 | 6344 |
| LVP | 2.9683 | 3.7895 | 3473 |
| VKV | 2.9682 | 1.9211 | 6206 |
| CEL | 2.9681 | 2.3520 | 2879 |
| SCV | 2.9680 | 2.7161 | 4897 |
| RHD | 2.9680 | 2.5436 | 1226 |
| IGR | 2.9680 | 2.8846 | 12463 |
| LDI | 2.9679 | 2.2913 | 2495 |
| NME | 2.9678 | 0.4428 | 390 |
| SRA | 2.9677 | 3.0962 | 9560 |
| VFC | 2.9677 | 1.0971 | 1655 |
| DIG | 2.9676 | 2.3434 | 4807 |
| ANR | 2.9676 | 3.0157 | 5180 |
| RHM | 2.9675 | 1.7405 | 711 |
| HEG | 2.9674 | 2.4136 | 2819 |
| IVG | 2.9673 | 1.9286 | 13040 |
| WAD | 2.9672 | 2.1551 | 1781 |
| LAL | 2.9671 | 3.0000 | 5336 |
| SVT | 2.9669 | 3.2016 | 5803 |
| VSP | 2.9668 | 2.7883 | 2518 |
| RIE | 2.9667 | 3.2482 | 5430 |
| HNG | 2.9665 | 1.8133 | 963 |
| LPC | 2.9665 | 1.8829 | 907 |
| WSV | 2.9662 | 1.4227 | 5555 |
| RTV | 2.9662 | 3.2020 | 8422 |
| DTG | 2.9661 | 1.9503 | 4516 |
| PAD | 2.9661 | 3.7890 | 776 |
| GIK | 2.9660 | 1.8583 | 4675 |
| DLE | 2.9659 | 1.8604 | 3716 |
| RRT | 2.9659 | 3.4248 | 8157 |
| WHA | 2.9658 | 1.1431 | 469 |
| RFN | 2.9657 | 2.5031 | 2492 |
| PYA | 2.9655 | 2.7739 | 1324 |
| YDN | 2.9653 | 2.5658 | 479 |
| CDC | 2.9653 | 1.7765 | 1121 |
| RMF | 2.9651 | 2.8910 | 1481 |
| TEA | 2.9651 | 2.9394 | 2753 |
| QPH | 2.9650 | 2.6400 | 351 |

TABLE F-continued

Medium-expressing EGFP variants

| AA SEQ | Mean | Range | Total counts |
|---|---|---|---|
| TWT | 2.9648 | 1.8352 | 957 |
| LVL | 2.9646 | 3.1424 | 10565 |
| TPW | 2.9644 | 1.9042 | 521 |
| TSD | 2.9642 | 1.7350 | 1639 |
| VHN | 2.9640 | 2.8789 | 1207 |
| DAC | 2.9640 | 1.6982 | 1701 |
| WLL | 2.9639 | 2.5326 | 4282 |
| LTK | 2.9635 | 3.3768 | 2042 |
| QDY | 2.9635 | 0.9181 | 460 |
| VKK | 2.9634 | 1.7793 | 3815 |
| TAF | 2.9632 | 1.9184 | 1315 |
| PRC | 2.9631 | 2.4315 | 1768 |
| SIP | 2.9631 | 2.3780 | 961 |
| IGF | 2.9631 | 1.1329 | 3021 |
| ICR | 2.9630 | 2.8524 | 4638 |
| GFI | 2.9630 | 1.6063 | 2753 |
| TCD | 2.9629 | 1.8125 | 652 |
| QDL | 2.9628 | 1.6527 | 1239 |
| TTG | 2.9627 | 2.1931 | 4390 |
| EAK | 2.9626 | 2.3717 | 2965 |
| RFM | 2.9624 | 2.0598 | 1730 |
| WRE | 2.9623 | 0.9259 | 4581 |
| WCD | 2.9623 | 0.8686 | 1167 |
| QRR | 2.9622 | 2.3220 | 6141 |
| LPH | 2.9622 | 3.2202 | 469 |
| YAV | 2.9621 | 2.0990 | 3357 |
| FQN | 2.9619 | 2.1444 | 335 |
| LHD | 2.9618 | 2.5370 | 844 |
| VSK | 2.9617 | 2.6296 | 6191 |
| CPN | 2.9615 | 1.1859 | 421 |
| GLL | 2.9615 | 3.0000 | 14211 |
| IQV | 2.9614 | 2.6389 | 1644 |
| RCW | 2.9612 | 1.1558 | 3493 |
| KRM | 2.9611 | 2.3923 | 2852 |
| VLK | 2.9610 | 2.2349 | 6436 |
| EDI | 2.9610 | 1.2246 | 1574 |
| FYF | 2.9609 | 1.2333 | 191 |
| VPY | 2.9608 | 2.8719 | 936 |
| RSK | 2.9607 | 2.6995 | 7360 |
| AVG | 2.9606 | 2.4807 | 25878 |
| CTR | 2.9605 | 2.8304 | 3466 |
| TVI | 2.9604 | 2.5263 | 5040 |
| SWN | 2.9604 | 2.1238 | 1079 |
| DEY | 2.9599 | 1.5003 | 1666 |
| WQV | 2.9598 | 1.5514 | 1589 |
| GKF | 2.9598 | 1.1810 | 2080 |
| AWC | 2.9596 | 1.7526 | 2179 |
| YGQ | 2.9595 | 2.8061 | 1429 |
| WHN | 2.9595 | 0.5210 | 178 |
| ERC | 2.9593 | 1.5138 | 5397 |
| AHE | 2.9590 | 1.4872 | 706 |
| SIE | 2.9590 | 2.4957 | 3220 |
| TSS | 2.9590 | 3.8364 | 4239 |
| DVQ | 2.9589 | 2.1950 | 3177 |
| SMA | 2.9587 | 1.9500 | 1411 |
| VYY | 2.9586 | 1.8337 | 1468 |
| MVL | 2.9585 | 1.7132 | 3605 |
| PDG | 2.9585 | 2.5568 | 2631 |
| SFL | 2.9584 | 3.1866 | 1890 |
| HRD | 2.9583 | 1.6129 | 1019 |
| EKG | 2.9582 | 1.0377 | 7121 |
| MIW | 2.9581 | 0.4260 | 683 |
| FEC | 2.9580 | 1.2424 | 847 |
| DDA | 2.9579 | 2.2537 | 982 |
| RPH | 2.9578 | 2.7100 | 603 |
| AHH | 2.9578 | 1.4627 | 257 |
| QAQ | 2.9577 | 1.8571 | 516 |
| WVN | 2.9577 | 1.3506 | 1707 |
| CFL | 2.9576 | 1.9095 | 1539 |
| PKV | 2.9576 | 2.8027 | 1164 |
| VLR | 2.9576 | 3.3753 | 18490 |
| AQW | 2.9576 | 2.0461 | 1113 |
| IVW | 2.9576 | 1.4800 | 2625 |
| QRM | 2.9574 | 1.3729 | 1268 |
| KWN | 2.9573 | 1.1248 | 521 |
| SSW | 2.9573 | 2.0728 | 3554 |
| MFL | 2.9573 | 1.4236 | 1230 |
| GHW | 2.9572 | 0.7296 | 1805 |
| SPH | 2.9572 | 2.7500 | 556 |
| VNW | 2.9571 | 0.7741 | 1668 |
| WSD | 2.9570 | 1.6795 | 1657 |
| SES | 2.9568 | 2.3750 | 5296 |
| RKP | 2.9567 | 2.9231 | 1663 |
| SSR | 2.9565 | 3.4807 | 12120 |
| WML | 2.9564 | 0.9944 | 1463 |
| SWA | 2.9561 | 1.7967 | 2861 |
| DDI | 2.9558 | 0.9776 | 1041 |
| ALL | 2.9557 | 3.0177 | 6290 |
| GLY | 2.9555 | 2.0649 | 5148 |
| WQI | 2.9554 | 1.7628 | 524 |
| FVQ | 2.9554 | 2.2144 | 897 |
| LVK | 2.9554 | 3.1970 | 5120 |
| CPL | 2.9553 | 3.3316 | 1112 |
| IGQ | 2.9552 | 2.1421 | 3143 |
| WRN | 2.9551 | 1.2347 | 1679 |
| SLG | 2.9551 | 2.5642 | 17765 |
| YGV | 2.9549 | 1.5330 | 6198 |
| WTM | 2.9549 | 0.4722 | 544 |
| IEF | 2.9548 | 1.7334 | 1248 |
| LDP | 2.9548 | 2.8093 | 502 |
| GSS | 2.9547 | 2.4115 | 15159 |
| GKM | 2.9547 | 0.9041 | 1866 |
| SSP | 2.9546 | 3.0909 | 898 |
| AEM | 2.9546 | 0.7741 | 1282 |
| MTE | 2.9546 | 2.1775 | 1150 |
| KVG | 2.9544 | 1.6146 | 13778 |
| VWK | 2.9543 | 0.7267 | 1826 |
| DPR | 2.9543 | 1.6506 | 2236 |
| HGK | 2.9541 | 2.2386 | 1263 |
| GTF | 2.9541 | 1.8329 | 2070 |
| LTI | 2.9539 | 2.8861 | 2144 |
| MID | 2.9539 | 2.2851 | 674 |
| CPD | 2.9538 | 2.4000 | 302 |
| TGE | 2.9537 | 1.5392 | 5670 |
| SAV | 2.9536 | 2.0879 | 7468 |
| YQG | 2.9534 | 2.0501 | 1886 |
| SEG | 2.9534 | 1.4666 | 14676 |
| IRR | 2.9533 | 2.3002 | 12050 |
| WKG | 2.9533 | 1.0115 | 4101 |
| ESW | 2.9530 | 2.0911 | 3794 |
| RYP | 2.9529 | 2.1724 | 1302 |
| TDT | 2.9528 | 2.3664 | 721 |
| DKG | 2.9527 | 1.0985 | 4219 |
| SIQ | 2.9527 | 2.9687 | 2106 |
| EET | 2.9527 | 2.0878 | 1821 |
| QHE | 2.9527 | 0.9957 | 469 |
| DSD | 2.9525 | 2.7277 | 1763 |
| SNA | 2.9524 | 2.5585 | 2557 |
| YCL | 2.9524 | 1.7906 | 2039 |
| LMF | 2.9523 | 1.5110 | 1008 |
| PLQ | 2.9523 | 2.8524 | 677 |
| WKS | 2.9522 | 1.3368 | 1960 |
| SDS | 2.9522 | 2.3804 | 4028 |
| SHH | 2.9521 | 2.7684 | 690 |
| LQG | 2.9519 | 2.1939 | 5213 |
| YGC | 2.9518 | 1.1920 | 2454 |
| WKR | 2.9517 | 1.6566 | 3000 |
| IGH | 2.9517 | 2.2303 | 2058 |
| VKN | 2.9516 | 1.0032 | 1246 |
| IGY | 2.9515 | 1.6690 | 3282 |
| IRS | 2.9515 | 2.8860 | 7553 |
| TIE | 2.9515 | 2.2320 | 2182 |
| PED | 2.9514 | 2.5333 | 522 |
| VQN | 2.9513 | 2.1016 | 1105 |
| YRF | 2.9512 | 2.8827 | 2333 |
| EDR | 2.9511 | 1.2054 | 4671 |
| WSA | 2.9510 | 1.8621 | 3236 |
| TEL | 2.9510 | 2.4318 | 3069 |
| DTE | 2.9509 | 1.9146 | 1151 |
| PYV | 2.9508 | 2.7244 | 1725 |

TABLE F-continued

Medium-expressing EGFP variants

| AA SEQ | Mean | Range | Total counts |
|---|---|---|---|
| GKD | 2.9508 | 1.2075 | 3618 |
| QAM | 2.9508 | 1.0721 | 490 |
| PHV | 2.9507 | 3.8544 | 717 |
| ASY | 2.9507 | 2.8395 | 2706 |
| FCS | 2.9505 | 2.2974 | 1003 |
| SCC | 2.9504 | 1.8908 | 1967 |
| VLE | 2.9502 | 2.6703 | 7752 |
| LDY | 2.9502 | 2.1150 | 1185 |
| PLV | 2.9501 | 2.5000 | 3229 |
| STA | 2.9501 | 3.7590 | 3384 |
| HID | 2.9501 | 1.7167 | 372 |
| EIE | 2.9500 | 1.0780 | 3214 |
| IEG | 2.9500 | 1.4714 | 7288 |
| SKM | 2.9498 | 1.7568 | 1510 |
| MVR | 2.9496 | 1.3572 | 6660 |
| EQE | 2.9493 | 0.9916 | 1209 |
| CQV | 2.9493 | 2.0510 | 2254 |
| AIL | 2.9493 | 2.6738 | 4335 |
| NWR | 2.9492 | 1.1712 | 1846 |
| FVR | 2.9492 | 2.7684 | 5992 |
| LLD | 2.9491 | 2.6219 | 2963 |
| GCN | 2.9491 | 1.3956 | 1886 |
| GKK | 2.9491 | 1.7413 | 2986 |
| LCF | 2.9491 | 1.5366 | 1579 |
| QCA | 2.9490 | 1.8429 | 1640 |
| NMW | 2.9489 | 0.1022 | 395 |
| CAK | 2.9487 | 2.3570 | 1494 |
| RMC | 2.9484 | 1.6246 | 2330 |
| CRT | 2.9483 | 3.0625 | 2896 |
| IVP | 2.9483 | 2.9550 | 1619 |
| LSN | 2.9483 | 2.4178 | 3402 |
| TWQ | 2.9481 | 1.2589 | 675 |
| ILG | 2.9480 | 2.4504 | 10120 |
| GNT | 2.9480 | 2.4345 | 3308 |
| ALT | 2.9478 | 2.7147 | 2908 |
| DWM | 2.9477 | 0.0233 | 641 |
| FGT | 2.9476 | 2.4142 | 1972 |
| QWE | 2.9476 | 1.1330 | 673 |
| SVC | 2.9474 | 2.3438 | 6683 |
| LAE | 2.9472 | 2.4547 | 3364 |
| ACE | 2.9472 | 1.4487 | 1355 |
| YSG | 2.9470 | 2.5294 | 5661 |
| HGM | 2.9469 | 1.2577 | 772 |
| FHT | 2.9467 | 2.4079 | 315 |
| QDW | 2.9466 | 0.7798 | 235 |
| CTT | 2.9464 | 2.2000 | 901 |
| PHC | 2.9463 | 2.1905 | 231 |
| YTC | 2.9462 | 2.4097 | 695 |
| CDP | 2.9462 | 2.0625 | 366 |
| CHL | 2.9461 | 2.1228 | 1011 |
| AFG | 2.9461 | 2.1093 | 4759 |
| IDI | 2.9459 | 2.4707 | 1532 |
| TEG | 2.9458 | 1.2851 | 7630 |
| MSQ | 2.9458 | 2.5780 | 808 |
| EEI | 2.9455 | 1.2806 | 2825 |
| ATK | 2.9452 | 2.4838 | 2285 |
| LHT | 2.9452 | 2.6985 | 951 |
| ESV | 2.9451 | 2.1000 | 10223 |
| NAT | 2.9451 | 3.2941 | 1414 |
| DSG | 2.9450 | 1.6914 | 8206 |
| FTR | 2.9448 | 2.2477 | 2301 |
| QWC | 2.9448 | 0.8865 | 463 |
| FAI | 2.9446 | 2.0452 | 365 |
| ANT | 2.9446 | 2.5341 | 980 |
| SLD | 2.9445 | 1.8707 | 3935 |
| DAM | 2.9443 | 1.6562 | 1223 |
| HYA | 2.9443 | 2.6429 | 283 |
| LFP | 2.9442 | 2.1724 | 741 |
| HTE | 2.9442 | 1.8385 | 698 |
| VNT | 2.9442 | 2.9192 | 1427 |
| ASK | 2.9441 | 2.3501 | 4014 |
| CPH | 2.9439 | 1.6538 | 204 |
| YED | 2.9438 | 0.9021 | 1134 |
| MVG | 2.9438 | 1.2953 | 7590 |
| CLK | 2.9437 | 2.4635 | 2788 |
| QKM | 2.9436 | 0.3592 | 418 |
| WIH | 2.9435 | 0.9254 | 773 |
| CLL | 2.9435 | 2.0114 | 4531 |
| TAQ | 2.9435 | 1.7649 | 933 |
| TEP | 2.9434 | 1.5671 | 289 |
| PER | 2.9433 | 2.7547 | 3275 |
| GFC | 2.9430 | 1.0592 | 2264 |
| LWA | 2.9429 | 1.9973 | 3489 |
| AMT | 2.9429 | 1.9667 | 527 |
| YEP | 2.9428 | 2.5423 | 546 |
| FKA | 2.9428 | 3.0000 | 1185 |
| CVA | 2.9428 | 1.5660 | 5280 |
| FDL | 2.9426 | 1.6563 | 527 |
| SYW | 2.9426 | 2.0311 | 1665 |
| KCD | 2.9426 | 2.2252 | 1549 |
| KRG | 2.9422 | 2.0189 | 14510 |
| RNE | 2.9422 | 1.9430 | 2675 |
| QLD | 2.9421 | 2.4986 | 1442 |
| DAT | 2.9420 | 1.5692 | 1369 |
| YMW | 2.9419 | 0.1972 | 291 |
| FVC | 2.9419 | 1.3030 | 1861 |
| LDK | 2.9419 | 2.2394 | 2118 |
| RKR | 2.9418 | 2.2258 | 9549 |
| DAR | 2.9418 | 1.9513 | 4876 |
| ILA | 2.9417 | 2.3120 | 4439 |
| SCA | 2.9414 | 2.8570 | 2397 |
| YMI | 2.9413 | 1.4833 | 831 |
| PRG | 2.9412 | 2.9048 | 7326 |
| GFY | 2.9412 | 1.1973 | 1032 |
| LVF | 2.9411 | 3.0000 | 3519 |
| CNA | 2.9410 | 2.5671 | 1347 |
| DLG | 2.9410 | 1.4606 | 8657 |
| LAC | 2.9407 | 2.7059 | 2587 |
| CGN | 2.9406 | 1.5102 | 2548 |
| HEL | 2.9406 | 2.2533 | 1407 |
| KAP | 2.9406 | 2.8152 | 342 |
| FSE | 2.9404 | 3.2140 | 1032 |
| GIE | 2.9401 | 1.4353 | 5206 |
| WYD | 2.9401 | 0.8032 | 506 |
| LIK | 2.9401 | 1.9137 | 3756 |
| DCV | 2.9398 | 1.4884 | 2690 |
| EPK | 2.9398 | 3.2072 | 1671 |
| FCA | 2.9396 | 1.0212 | 1246 |
| PLE | 2.9395 | 2.6852 | 1703 |
| TVQ | 2.9394 | 2.5016 | 2662 |
| TSE | 2.9393 | 2.3321 | 2631 |
| EFG | 2.9393 | 1.6670 | 5338 |
| ILL | 2.9392 | 2.0902 | 4442 |
| HGE | 2.9391 | 1.6583 | 1664 |
| AEH | 2.9391 | 1.3690 | 1092 |
| TKG | 2.9386 | 2.2404 | 4953 |
| TVG | 2.9385 | 2.5173 | 13426 |
| LCE | 2.9384 | 1.9102 | 2691 |
| FSI | 2.9383 | 2.1296 | 1373 |
| IVF | 2.9383 | 1.4055 | 2066 |
| GSH | 2.9379 | 2.3616 | 3236 |
| EGM | 2.9376 | 1.0090 | 3630 |
| LET | 2.9376 | 3.1565 | 2453 |
| PAQ | 2.9376 | 1.5737 | 551 |
| FTE | 2.9375 | 1.2657 | 557 |
| YLF | 2.9375 | 1.8917 | 1439 |
| YYI | 2.9374 | 1.2206 | 709 |
| ETC | 2.9373 | 1.6265 | 1567 |
| FTI | 2.9372 | 2.4181 | 745 |
| DME | 2.9370 | 0.8617 | 859 |
| CWT | 2.9369 | 1.8645 | 612 |
| MRC | 2.9366 | 2.2027 | 2583 |
| CDI | 2.9365 | 1.6823 | 1613 |
| NDG | 2.9364 | 1.4490 | 2070 |
| DAV | 2.9363 | 1.2545 | 4194 |
| LYF | 2.9363 | 2.0005 | 1042 |
| DGN | 2.9362 | 1.1189 | 2714 |
| NAW | 2.9360 | 1.1929 | 884 |
| ESA | 2.9360 | 2.3009 | 5212 |
| CTD | 2.9359 | 1.2591 | 834 |

TABLE F-continued

Medium-expressing EGFP variants

| AA SEQ | Mean | Range | Total counts |
|---|---|---|---|
| PWQ | 2.9359 | 0.9501 | 301 |
| PPW | 2.9359 | 2.9063 | 370 |
| MLE | 2.9358 | 1.7537 | 2127 |
| NCG | 2.9358 | 1.3146 | 2253 |
| TVC | 2.9357 | 2.1592 | 4182 |
| AHP | 2.9357 | 2.5000 | 372 |
| YRL | 2.9356 | 3.1756 | 4477 |
| GKT | 2.9355 | 1.8550 | 3254 |
| ETR | 2.9354 | 2.1284 | 5438 |
| TPN | 2.9354 | 1.2595 | 312 |
| VSQ | 2.9350 | 2.1636 | 3501 |
| PKN | 2.9350 | 1.4852 | 304 |
| VTK | 2.9350 | 2.3382 | 2950 |
| EST | 2.9349 | 3.0410 | 4211 |
| TPY | 2.9349 | 1.6207 | 225 |
| NAE | 2.9349 | 1.3128 | 1156 |
| GLP | 2.9348 | 2.9312 | 4460 |
| THR | 2.9348 | 2.9707 | 1406 |
| AFM | 2.9346 | 1.3977 | 559 |
| RIM | 2.9345 | 1.9510 | 2649 |
| QVC | 2.9345 | 2.1412 | 2704 |
| IRL | 2.9344 | 2.4177 | 7235 |
| DDQ | 2.9343 | 1.6689 | 528 |
| WRH | 2.9342 | 1.4251 | 1533 |
| QVP | 2.9341 | 1.4888 | 1066 |
| VRK | 2.9340 | 1.2035 | 7920 |
| YII | 2.9340 | 1.2866 | 1210 |
| TGQ | 2.9337 | 2.8986 | 3155 |
| APT | 2.9337 | 2.2311 | 701 |
| GSI | 2.9337 | 1.8353 | 7374 |
| MDQ | 2.9337 | 0.7843 | 325 |
| PWI | 2.9335 | 2.6136 | 303 |
| DWQ | 2.9335 | 1.0971 | 465 |
| YDE | 2.9335 | 1.5926 | 578 |
| IHE | 2.9334 | 2.2000 | 808 |
| GYA | 2.9334 | 2.2273 | 4034 |
| TMP | 2.9334 | 1.4800 | 256 |
| WSR | 2.9333 | 1.6198 | 6175 |
| WIW | 2.9332 | 0.1687 | 752 |
| FRR | 2.9331 | 2.6075 | 5179 |
| FML | 2.9331 | 2.7154 | 622 |
| DEV | 2.9330 | 1.3625 | 4657 |
| SRR | 2.9329 | 2.9570 | 18342 |
| AIH | 2.9329 | 2.1433 | 1101 |
| YCW | 2.9328 | 0.6279 | 621 |
| TCR | 2.9325 | 2.7756 | 3221 |
| FEN | 2.9324 | 1.4125 | 374 |
| LFE | 2.9324 | 1.8546 | 1609 |
| VKT | 2.9323 | 2.7332 | 1748 |
| PKK | 2.9322 | 1.9705 | 884 |
| CAN | 2.9321 | 3.0972 | 925 |
| ALC | 2.9320 | 3.6120 | 3971 |
| SMS | 2.9319 | 2.1778 | 2489 |
| CEV | 2.9319 | 1.5002 | 4995 |
| ASS | 2.9318 | 3.1029 | 6433 |
| FSF | 2.9317 | 2.9474 | 643 |
| LTE | 2.9316 | 2.6032 | 2491 |
| FDF | 2.9316 | 2.0875 | 321 |
| NAD | 2.9315 | 2.2722 | 1064 |
| CYI | 2.9312 | 1.8133 | 1218 |
| AVN | 2.9312 | 3.1552 | 2975 |
| WMV | 2.9312 | 0.6676 | 1783 |
| GPK | 2.9311 | 2.4746 | 2302 |
| WYS | 2.9309 | 2.6047 | 1619 |
| VGP | 2.9308 | 2.5266 | 8743 |
| YVI | 2.9306 | 1.8750 | 2459 |
| TKW | 2.9306 | 1.6530 | 1486 |
| TMS | 2.9305 | 2.6353 | 1244 |
| MQG | 2.9304 | 0.9324 | 1774 |
| MHA | 2.9303 | 2.5581 | 775 |
| TER | 2.9303 | 1.9474 | 5977 |
| AFI | 2.9302 | 2.4409 | 1423 |
| PGW | 2.9302 | 1.3470 | 3190 |
| SFG | 2.9300 | 2.5286 | 6231 |
| PNM | 2.9298 | 1.3488 | 460 |
| DND | 2.9297 | 1.6298 | 759 |
| CSL | 2.9296 | 2.6765 | 3986 |
| ITD | 2.9296 | 1.3366 | 856 |
| MVI | 2.9294 | 1.3718 | 2383 |
| TWI | 2.9293 | 1.3167 | 1024 |
| TDY | 2.9293 | 2.3833 | 886 |
| YRS | 2.9291 | 3.6466 | 4255 |
| GCS | 2.9290 | 2.5395 | 7356 |
| LDW | 2.9289 | 1.4535 | 1394 |
| VEH | 2.9287 | 1.4643 | 1360 |
| DSP | 2.9286 | 1.9188 | 562 |
| ERQ | 2.9286 | 1.4821 | 2719 |
| CFG | 2.9285 | 1.3046 | 3007 |
| QER | 2.9284 | 1.8028 | 2985 |
| MWI | 2.9284 | 0.8154 | 741 |
| EDY | 2.9281 | 1.4316 | 1060 |
| WWV | 2.9280 | 0.6149 | 3387 |
| LNG | 2.9278 | 1.5023 | 4130 |
| YVT | 2.9278 | 2.1803 | 2750 |
| ILW | 2.9278 | 1.1782 | 2143 |
| EVG | 2.9278 | 1.3309 | 22555 |
| FVM | 2.9276 | 1.0187 | 998 |
| RWM | 2.9276 | 1.1188 | 1580 |
| CHQ | 2.9274 | 2.2293 | 261 |
| QDV | 2.9273 | 0.5939 | 1517 |
| ALG | 2.9273 | 2.6551 | 14406 |
| VSI | 2.9272 | 2.2095 | 5408 |
| FST | 2.9270 | 3.0179 | 1015 |
| CVW | 2.9269 | 0.8605 | 3246 |
| SHP | 2.9268 | 1.6903 | 327 |
| LTQ | 2.9268 | 1.9286 | 1174 |
| LVR | 2.9267 | 3.5126 | 19690 |
| LML | 2.9267 | 2.3175 | 2236 |
| VLQ | 2.9267 | 2.9616 | 4101 |
| ADY | 2.9266 | 2.0238 | 757 |
| SME | 2.9261 | 1.5365 | 1464 |
| RHK | 2.9261 | 2.0461 | 1768 |
| VHD | 2.9260 | 1.2042 | 914 |
| MLW | 2.9260 | 1.2724 | 1182 |
| IHW | 2.9260 | 1.4330 | 752 |
| HDE | 2.9259 | 0.6632 | 350 |
| YRG | 2.9258 | 1.6296 | 8147 |
| YLT | 2.9258 | 2.5583 | 1916 |
| CTG | 2.9256 | 1.8121 | 3983 |
| SHR | 2.9255 | 2.9694 | 3045 |
| RVE | 2.9255 | 1.5952 | 12051 |
| HEE | 2.9255 | 1.3504 | 710 |
| NGM | 2.9255 | 1.0901 | 1285 |
| PDS | 2.9254 | 2.9302 | 1257 |
| LPG | 2.9252 | 2.9254 | 4987 |
| DFG | 2.9252 | 1.4068 | 2997 |
| HCD | 2.9251 | 1.2057 | 287 |
| ITG | 2.9250 | 3.0219 | 4954 |
| MYQ | 2.9248 | 1.3199 | 224 |
| MRG | 2.9247 | 1.7050 | 9503 |
| MEC | 2.9246 | 0.6761 | 990 |
| SAT | 2.9246 | 2.7415 | 2602 |
| GYF | 2.9245 | 1.4568 | 1209 |
| LSD | 2.9245 | 1.9185 | 3013 |
| AYW | 2.9244 | 1.3558 | 1068 |
| SND | 2.9244 | 2.5217 | 1396 |
| HFG | 2.9243 | 2.0057 | 854 |
| YWW | 2.9243 | 0.3834 | 620 |
| IDL | 2.9242 | 2.2634 | 1601 |
| EWH | 2.9240 | 0.6702 | 685 |
| FVD | 2.9240 | 1.7656 | 1300 |
| YDR | 2.9239 | 2.1246 | 1868 |
| YAY | 2.9239 | 1.6761 | 880 |
| QAF | 2.9238 | 1.0954 | 664 |
| NTG | 2.9235 | 3.1818 | 3278 |
| GLK | 2.9233 | 1.8609 | 8342 |
| YAT | 2.9231 | 2.2446 | 713 |
| TNQ | 2.9228 | 3.3356 | 775 |
| LVM | 2.9228 | 1.9091 | 3094 |
| CFY | 2.9227 | 1.9677 | 486 |

TABLE F-continued

Medium-expressing EGFP variants

| AA SEQ | Mean | Range | Total counts |
|---|---|---|---|
| HWF | 2.9226 | 1.0451 | 268 |
| CES | 2.9226 | 1.2188 | 3274 |
| DNW | 2.9223 | 1.1281 | 805 |
| IRC | 2.9223 | 1.9618 | 5131 |
| QDS | 2.9222 | 2.1054 | 1364 |
| HLT | 2.9220 | 2.9667 | 1418 |
| LCN | 2.9219 | 1.5232 | 1660 |
| PMD | 2.9219 | 2.5263 | 132 |
| KCG | 2.9219 | 1.3064 | 4591 |
| CIV | 2.9218 | 2.1417 | 3202 |
| NGS | 2.9218 | 1.9543 | 4758 |
| EKW | 2.9215 | 0.4931 | 1437 |
| AHT | 2.9215 | 2.6089 | 675 |
| MAH | 2.9215 | 0.9739 | 172 |
| STG | 2.9215 | 2.3518 | 8178 |
| ESQ | 2.9214 | 2.0915 | 2556 |
| FYQ | 2.9211 | 2.7462 | 284 |
| PCF | 2.9209 | 0.7487 | 256 |
| FLR | 2.9208 | 3.6609 | 3317 |
| AMR | 2.9207 | 1.5760 | 2469 |
| PYG | 2.9204 | 3.2892 | 1537 |
| GET | 2.9204 | 1.9942 | 4522 |
| RVN | 2.9203 | 3.0225 | 6397 |
| SNG | 2.9203 | 1.7744 | 5343 |
| MHD | 2.9203 | 0.2485 | 291 |
| CRQ | 2.9203 | 1.6767 | 1645 |
| ETD | 2.9202 | 1.5654 | 1451 |
| AQG | 2.9201 | 2.2719 | 5904 |
| LIL | 2.9199 | 2.4286 | 3963 |
| WCP | 2.9199 | 0.9286 | 491 |
| MNM | 2.9199 | 0.6603 | 199 |
| LHM | 2.9198 | 1.2064 | 361 |
| EIW | 2.9197 | 1.4106 | 1997 |
| AMD | 2.9196 | 1.2080 | 719 |
| HQK | 2.9195 | 1.0172 | 291 |
| GFN | 2.9193 | 2.3077 | 1352 |
| FQP | 2.9192 | 2.2869 | 213 |
| TYE | 2.9191 | 2.2411 | 1064 |
| RVC | 2.9190 | 2.3042 | 11456 |
| WPQ | 2.9189 | 0.9779 | 324 |
| GWD | 2.9188 | 1.8854 | 3407 |
| CEE | 2.9187 | 0.8120 | 1910 |
| TDW | 2.9186 | 1.5467 | 997 |
| QKE | 2.9186 | 1.0362 | 1142 |
| VMG | 2.9185 | 2.2233 | 8200 |
| RTE | 2.9185 | 2.1959 | 4087 |
| LDQ | 2.9185 | 2.9091 | 922 |
| RME | 2.9184 | 1.4565 | 1840 |
| ARP | 2.9184 | 2.8750 | 1725 |
| WQH | 2.9182 | 1.6540 | 281 |
| HED | 2.9180 | 1.7951 | 458 |
| SDC | 2.9179 | 1.6489 | 1908 |
| CLQ | 2.9176 | 2.3598 | 1894 |
| SPC | 2.9175 | 2.3333 | 544 |
| WLR | 2.9174 | 1.6336 | 7557 |
| QAI | 2.9174 | 2.2828 | 1118 |
| TFW | 2.9173 | 1.8149 | 705 |
| GAL | 2.9170 | 2.3751 | 11439 |
| KME | 2.9169 | 0.4344 | 777 |
| EWR | 2.9168 | 1.4426 | 6022 |
| GEP | 2.9168 | 2.4368 | 2685 |
| PMI | 2.9167 | 2.5659 | 488 |
| GEN | 2.9165 | 1.0075 | 2709 |
| CFR | 2.9165 | 2.3944 | 2531 |
| SGK | 2.9164 | 1.5715 | 7155 |
| IRT | 2.9164 | 2.7625 | 3711 |
| NPC | 2.9164 | 1.5143 | 492 |
| TWF | 2.9163 | 0.6075 | 470 |
| ACQ | 2.9161 | 1.9201 | 1077 |
| DVE | 2.9161 | 1.2168 | 3901 |
| SEW | 2.9160 | 1.2360 | 3543 |
| YEQ | 2.9160 | 1.6987 | 500 |
| SQM | 2.9159 | 1.6080 | 731 |
| TAM | 2.9159 | 1.4018 | 731 |
| ECM | 2.9158 | 1.7216 | 1750 |
| RFE | 2.9156 | 2.6530 | 3900 |
| YGM | 2.9154 | 0.8590 | 1373 |
| DEK | 2.9150 | 1.9185 | 1677 |
| RPQ | 2.9150 | 2.2051 | 1041 |
| IMC | 2.9149 | 1.0828 | 1205 |
| EAN | 2.9147 | 1.4813 | 1554 |
| MAI | 2.9147 | 1.7784 | 1080 |
| MMA | 2.9144 | 1.2139 | 478 |
| CVT | 2.9144 | 2.3294 | 3543 |
| TGM | 2.9144 | 1.5469 | 1552 |
| YLS | 2.9143 | 2.5184 | 4398 |
| APA | 2.9142 | 2.6156 | 1646 |
| PTT | 2.9141 | 3.6726 | 749 |
| SDL | 2.9141 | 2.2300 | 2827 |
| ETG | 2.9140 | 1.4337 | 5169 |
| RFI | 2.9137 | 2.5509 | 2844 |
| NWS | 2.9136 | 1.3138 | 1416 |
| SDN | 2.9136 | 2.3237 | 1299 |
| GQF | 2.9136 | 1.5611 | 1655 |
| CCT | 2.9136 | 1.0594 | 1003 |
| SAE | 2.9133 | 1.9990 | 4038 |
| IAC | 2.9133 | 1.8340 | 1717 |
| FPQ | 2.9132 | 3.2036 | 605 |
| YWM | 2.9131 | 0.0238 | 161 |
| VIK | 2.9130 | 1.7012 | 3417 |
| PMW | 2.9129 | 1.1804 | 300 |
| ISG | 2.9128 | 2.4239 | 8554 |
| DEQ | 2.9124 | 1.2707 | 1106 |
| PDT | 2.9123 | 2.3095 | 285 |
| PPY | 2.9123 | 3.4545 | 233 |
| DRM | 2.9121 | 1.4416 | 2016 |
| WCE | 2.9120 | 0.4792 | 1196 |
| TAC | 2.9119 | 1.6223 | 1293 |
| CFQ | 2.9119 | 1.4777 | 421 |
| GAS | 2.9119 | 2.6113 | 13376 |
| WHM | 2.9118 | 0.1094 | 314 |
| SRK | 2.9117 | 2.4129 | 6454 |
| IKW | 2.9117 | 0.9803 | 1072 |
| DEA | 2.9117 | 1.2994 | 2047 |
| HTP | 2.9117 | 1.0890 | 191 |
| GKP | 2.9116 | 2.1012 | 1359 |
| LFG | 2.9116 | 1.8255 | 5875 |
| RNP | 2.9114 | 2.7587 | 1093 |
| QCV | 2.9114 | 1.8241 | 1741 |
| CLN | 2.9113 | 2.1458 | 1559 |
| GGP | 2.9111 | 2.4299 | 11870 |
| AMK | 2.9110 | 1.5617 | 919 |
| WPS | 2.9110 | 2.4487 | 1322 |
| CNW | 2.9110 | 0.9599 | 597 |
| GCK | 2.9108 | 0.8713 | 3727 |
| SSS | 2.9104 | 3.1667 | 6427 |
| LLN | 2.9103 | 1.9630 | 3384 |
| ICN | 2.9102 | 1.9070 | 1047 |
| LVQ | 2.9102 | 3.1441 | 3664 |
| YCC | 2.9101 | 2.0804 | 719 |
| VKQ | 2.9100 | 1.6510 | 2030 |
| ING | 2.9098 | 2.1143 | 3160 |
| RRH | 2.9098 | 3.3020 | 4003 |
| ESG | 2.9097 | 1.4358 | 14725 |
| HLE | 2.9097 | 1.7963 | 1608 |
| CSK | 2.9096 | 2.2143 | 2070 |
| DCC | 2.9094 | 0.9686 | 1399 |
| CSD | 2.9093 | 1.5687 | 1435 |
| SEQ | 2.9092 | 1.2826 | 1117 |
| HTC | 2.9091 | 2.2832 | 742 |
| TSG | 2.9091 | 2.1949 | 8845 |
| SYP | 2.9090 | 3.2778 | 571 |
| YRR | 2.9090 | 2.9535 | 6150 |
| PMR | 2.9090 | 3.4721 | 706 |
| PRW | 2.9089 | 2.7155 | 2100 |
| IDC | 2.9082 | 0.8137 | 1436 |
| LNL | 2.9081 | 2.9396 | 2935 |
| HAK | 2.9081 | 1.0736 | 493 |
| PVS | 2.9080 | 2.8718 | 3725 |
| LTD | 2.9080 | 1.8077 | 1858 |

TABLE F-continued

Medium-expressing EGFP variants

| AA SEQ | Mean | Range | Total counts |
|---|---|---|---|
| ARM | 2.9080 | 1.3614 | 2589 |
| IAQ | 2.9079 | 2.1911 | 1227 |
| VNL | 2.9078 | 1.3471 | 2970 |
| HRT | 2.9078 | 3.9773 | 1620 |
| FMM | 2.9078 | 0.1097 | 209 |
| SMP | 2.9077 | 1.9792 | 489 |
| PFQ | 2.9075 | 2.2623 | 364 |
| DTP | 2.9074 | 2.9357 | 507 |
| FFQ | 2.9074 | 1.9528 | 210 |
| GYL | 2.9074 | 1.6951 | 4314 |
| TSC | 2.9073 | 2.5913 | 2667 |
| ICV | 2.9073 | 1.7788 | 3132 |
| GNE | 2.9072 | 1.2053 | 2789 |
| QEW | 2.9070 | 1.7102 | 960 |
| CSR | 2.9068 | 2.0016 | 6100 |
| PPL | 2.9067 | 2.7406 | 450 |
| NAM | 2.9066 | 1.6210 | 497 |
| QTC | 2.9066 | 2.6989 | 770 |
| WLN | 2.9066 | 1.2410 | 1497 |
| DWF | 2.9065 | 1.0009 | 558 |
| PQR | 2.9063 | 3.2984 | 1471 |
| IDW | 2.9062 | 0.9886 | 947 |
| GNN | 2.9062 | 1.7681 | 1882 |
| FSW | 2.9062 | 1.3442 | 1010 |
| VHL | 2.9062 | 2.8249 | 2323 |
| MKD | 2.9060 | 0.5999 | 428 |
| FDD | 2.9059 | 2.3177 | 365 |
| IRD | 2.9058 | 2.2125 | 2824 |
| GFF | 2.9058 | 1.1745 | 749 |
| LVN | 2.9057 | 2.1212 | 3213 |
| CFF | 2.9053 | 1.5553 | 460 |
| YLL | 2.9052 | 3.4307 | 3510 |
| ATV | 2.9051 | 2.5133 | 3593 |
| NRG | 2.9050 | 2.8106 | 8852 |
| CEF | 2.9049 | 1.1010 | 993 |
| CEN | 2.9049 | 1.1792 | 618 |
| YRC | 2.9046 | 1.9610 | 2184 |
| WTT | 2.9043 | 1.7321 | 500 |
| AQQ | 2.9041 | 2.1877 | 619 |
| RFA | 2.9040 | 3.1347 | 3596 |
| KGE | 2.9038 | 0.9580 | 5115 |
| CVG | 2.9035 | 1.2626 | 14596 |
| CMV | 2.9033 | 1.3304 | 1427 |
| ISV | 2.9032 | 2.5679 | 6065 |
| RWV | 2.9032 | 1.6608 | 9818 |
| CST | 2.9030 | 2.9021 | 1977 |
| SCE | 2.9028 | 1.9743 | 2147 |
| LTH | 2.9027 | 3.5652 | 1085 |
| YCP | 2.9026 | 2.0000 | 286 |
| MAS | 2.9026 | 1.8068 | 1844 |
| YCF | 2.9026 | 1.9208 | 605 |
| HAD | 2.9025 | 1.5921 | 461 |
| QSC | 2.9022 | 2.2899 | 1796 |
| EEC | 2.9021 | 0.8984 | 2701 |
| LLT | 2.9020 | 3.4545 | 3352 |
| AID | 2.9020 | 1.2159 | 1338 |
| IFY | 2.9019 | 2.3989 | 743 |
| VTQ | 2.9019 | 1.6076 | 1592 |
| ACA | 2.9017 | 2.5958 | 1883 |
| EMT | 2.9016 | 0.8747 | 787 |
| ESD | 2.9015 | 2.3594 | 2536 |
| GWN | 2.9013 | 1.8624 | 2032 |
| WMI | 2.9012 | 0.9573 | 506 |
| GTP | 2.9011 | 2.8054 | 1548 |
| CDH | 2.9008 | 1.6008 | 375 |
| QEK | 2.9007 | 1.6616 | 1158 |
| ILF | 2.9006 | 2.0515 | 1432 |
| SRD | 2.9006 | 1.8980 | 4932 |
| DLD | 2.9004 | 1.4875 | 1821 |
| WLM | 2.9003 | 0.8362 | 1263 |
| EVT | 2.9003 | 2.0545 | 4657 |
| LVS | 2.9003 | 3.2010 | 12145 |
| AEN | 2.9001 | 1.1558 | 1163 |
| AWS | 2.9000 | 2.4853 | 3402 |
| TAN | 2.8999 | 2.4542 | 1051 |
| IYD | 2.8999 | 2.0000 | 729 |
| LCL | 2.8998 | 3.1875 | 3946 |
| LAN | 2.8998 | 2.0053 | 1510 |
| PCA | 2.8997 | 3.3506 | 803 |
| IVS | 2.8996 | 2.3885 | 7078 |
| YAA | 2.8996 | 2.0350 | 1610 |
| GFK | 2.8996 | 1.7927 | 2460 |
| IMW | 2.8995 | 0.2502 | 470 |
| CYG | 2.8995 | 1.2345 | 2122 |
| YAQ | 2.8994 | 2.8673 | 598 |
| LLV | 2.8993 | 3.8280 | 9963 |
| TRM | 2.8993 | 1.8500 | 1287 |
| FQV | 2.8992 | 1.4101 | 1037 |
| LMP | 2.8991 | 2.0328 | 426 |
| ALE | 2.8990 | 2.6684 | 4036 |
| YLI | 2.8990 | 2.3899 | 1847 |
| VMN | 2.8988 | 1.1735 | 927 |
| TAK | 2.8984 | 2.7043 | 2090 |
| FCD | 2.8982 | 1.2386 | 521 |
| FIA | 2.8981 | 2.8908 | 1134 |
| YVG | 2.8979 | 2.0879 | 8291 |
| AMP | 2.8978 | 2.6046 | 582 |
| LRQ | 2.8977 | 3.6417 | 4117 |
| IDF | 2.8975 | 1.3922 | 557 |
| WKM | 2.8974 | 0.6133 | 668 |
| HEM | 2.8972 | 1.5735 | 343 |
| QVE | 2.8971 | 1.4371 | 2418 |
| HDT | 2.8970 | 3.0727 | 725 |
| DCE | 2.8970 | 1.1836 | 1224 |
| MNW | 2.8970 | 0.6334 | 198 |
| HHP | 2.8970 | 1.4697 | 170 |
| DGK | 2.8967 | 1.2116 | 3867 |
| VHI | 2.8967 | 1.5306 | 1727 |
| ILD | 2.8964 | 2.3232 | 2225 |
| FIF | 2.8963 | 1.0542 | 424 |
| VQP | 2.8962 | 2.6667 | 1201 |
| KGM | 2.8961 | 1.0043 | 1946 |
| QCM | 2.8961 | 1.5126 | 1017 |
| YFM | 2.8961 | 1.3733 | 384 |
| QHQ | 2.8959 | 2.1121 | 469 |
| LMY | 2.8959 | 1.9822 | 984 |
| ALM | 2.8956 | 2.0909 | 1444 |
| FNG | 2.8956 | 1.3817 | 1642 |
| LWE | 2.8955 | 1.3576 | 2399 |
| APG | 2.8954 | 2.6840 | 5260 |
| WMK | 2.8951 | 0.4383 | 681 |
| FLV | 2.8950 | 2.3333 | 2840 |
| FCF | 2.8949 | 1.3289 | 185 |
| CEC | 2.8948 | 0.9446 | 1698 |
| LVD | 2.8947 | 2.7628 | 4797 |
| MCM | 2.8946 | 0.2779 | 504 |
| YRD | 2.8944 | 1.5422 | 1711 |
| AYD | 2.8942 | 1.4571 | 561 |
| PAG | 2.8941 | 2.6296 | 5915 |
| LVA | 2.8937 | 3.3704 | 8036 |
| YYG | 2.8937 | 1.6367 | 1679 |
| QWL | 2.8932 | 1.4846 | 1373 |
| TAS | 2.8932 | 2.7391 | 2807 |
| IGT | 2.8930 | 2.2568 | 4590 |
| MSD | 2.8929 | 1.3241 | 1132 |
| PNP | 2.8929 | 0.7540 | 125 |
| CSE | 2.8929 | 1.7887 | 2069 |
| IWR | 2.8927 | 1.3037 | 2492 |
| NDS | 2.8927 | 2.2094 | 1844 |
| MQD | 2.8927 | 0.8801 | 268 |
| TRI | 2.8925 | 2.2380 | 4250 |
| AIG | 2.8924 | 1.6930 | 7659 |
| CDK | 2.8922 | 1.0920 | 849 |
| SVD | 2.8920 | 2.2747 | 4538 |
| GIT | 2.8919 | 2.4671 | 3909 |
| PVT | 2.8917 | 3.0674 | 1379 |
| IAL | 2.8917 | 2.5833 | 2620 |
| HFI | 2.8917 | 1.9672 | 443 |
| PKT | 2.8915 | 1.8000 | 232 |
| MNE | 2.8912 | 1.4718 | 462 |

TABLE F-continued

Medium-expressing EGFP variants

| AA SEQ | Mean | Range | Total counts |
|---|---|---|---|
| VCN | 2.8910 | 1.1628 | 1998 |
| LDA | 2.8909 | 3.0143 | 2861 |
| RND | 2.8909 | 2.4086 | 1899 |
| IEP | 2.8908 | 2.1691 | 632 |
| FDW | 2.8908 | 0.4208 | 379 |
| YFH | 2.8906 | 2.6447 | 466 |
| IIS | 2.8905 | 2.2519 | 3149 |
| GKE | 2.8903 | 1.3481 | 4400 |
| CSQ | 2.8903 | 2.5551 | 1479 |
| LYV | 2.8903 | 2.0383 | 4490 |
| LEK | 2.8903 | 1.4333 | 1940 |
| PNH | 2.8903 | 2.1667 | 227 |
| VYT | 2.8903 | 2.0571 | 1636 |
| LIN | 2.8902 | 2.6247 | 2045 |
| QDM | 2.8900 | 0.3435 | 444 |
| VTI | 2.8899 | 2.6136 | 2161 |
| CYD | 2.8899 | 1.5503 | 350 |
| YPR | 2.8897 | 3.6464 | 1812 |
| GEK | 2.8896 | 0.8091 | 5067 |
| VYI | 2.8896 | 0.9444 | 1498 |
| WRM | 2.8894 | 0.4252 | 1919 |
| LVC | 2.8889 | 2.6502 | 6720 |
| SMC | 2.8888 | 1.4640 | 1695 |
| ARH | 2.8885 | 2.5883 | 1960 |
| WLI | 2.8885 | 1.4864 | 2055 |
| VYQ | 2.8884 | 1.6951 | 1357 |
| DPN | 2.8881 | 2.0901 | 425 |
| IQD | 2.8880 | 1.5541 | 764 |
| AKW | 2.8876 | 1.0641 | 1794 |
| HCC | 2.8875 | 1.3056 | 660 |
| PIC | 2.8875 | 2.2050 | 894 |
| FVP | 2.8873 | 2.5952 | 543 |
| IGE | 2.8873 | 1.5570 | 4675 |
| WSF | 2.8871 | 1.6483 | 1326 |
| TVW | 2.8867 | 1.6067 | 3305 |
| LVI | 2.8867 | 2.9259 | 5438 |
| AQR | 2.8864 | 2.4792 | 2927 |
| GKC | 2.8864 | 1.3562 | 3740 |
| FVL | 2.8863 | 2.8274 | 3103 |
| NDC | 2.8862 | 1.8116 | 881 |
| TWC | 2.8862 | 1.8190 | 730 |
| WCN | 2.8859 | 0.5925 | 519 |
| YID | 2.8858 | 2.1686 | 1066 |
| APS | 2.8858 | 2.7273 | 1725 |
| SPR | 2.8857 | 2.8000 | 2770 |
| HCI | 2.8857 | 1.6075 | 805 |
| TVE | 2.8857 | 1.5802 | 3472 |
| VNI | 2.8855 | 1.4049 | 2133 |
| EEM | 2.8855 | 0.6672 | 1105 |
| CIC | 2.8855 | 1.5636 | 1308 |
| FEL | 2.8855 | 1.9346 | 1329 |
| FTF | 2.8853 | 2.9824 | 334 |
| SMW | 2.8853 | 1.0655 | 986 |
| PWK | 2.8852 | 1.2819 | 338 |
| ICG | 2.8851 | 1.5234 | 4843 |
| FQA | 2.8849 | 3.3854 | 573 |
| YAD | 2.8848 | 2.1394 | 861 |
| GQH | 2.8846 | 1.7498 | 1452 |
| SEA | 2.8842 | 2.8151 | 4608 |
| VHC | 2.8840 | 1.8497 | 1586 |
| AKR | 2.8839 | 2.5206 | 5806 |
| IYV | 2.8839 | 1.9587 | 1566 |
| SVG | 2.8839 | 2.2489 | 27624 |
| FPE | 2.8838 | 1.7725 | 401 |
| SMQ | 2.8835 | 3.2698 | 956 |
| FIW | 2.8833 | 0.7841 | 386 |
| SHW | 2.8831 | 1.7429 | 933 |
| FKN | 2.8831 | 1.9593 | 513 |
| HRH | 2.8827 | 1.9412 | 409 |
| SKW | 2.8825 | 1.0040 | 2027 |
| DEH | 2.8824 | 0.9135 | 636 |
| GCI | 2.8819 | 1.7919 | 3292 |
| AWK | 2.8819 | 1.3596 | 1382 |
| MPV | 2.8818 | 1.4221 | 724 |
| RIA | 2.8817 | 2.4937 | 5899 |
| WSQ | 2.8816 | 1.4524 | 1033 |
| IHM | 2.8816 | 0.5583 | 177 |
| FFP | 2.8814 | 1.5134 | 230 |
| DCT | 2.8814 | 1.4610 | 1210 |
| FCL | 2.8813 | 2.0106 | 1133 |
| AWP | 2.8812 | 2.7613 | 702 |
| CIP | 2.8812 | 3.3229 | 866 |
| WHL | 2.8812 | 1.6993 | 1068 |
| IND | 2.8811 | 1.8897 | 857 |
| HAQ | 2.8811 | 2.0212 | 282 |
| CHA | 2.8809 | 1.9487 | 813 |
| TWY | 2.8807 | 0.8627 | 439 |
| SEH | 2.8805 | 2.2519 | 768 |
| FII | 2.8805 | 1.8710 | 586 |
| IFE | 2.8802 | 1.4061 | 1333 |
| PEV | 2.8802 | 1.6416 | 1817 |
| QWI | 2.8801 | 1.6252 | 591 |
| CPQ | 2.8800 | 1.9662 | 276 |
| YLC | 2.8800 | 2.2186 | 2397 |
| QMV | 2.8800 | 0.8333 | 1045 |
| CEA | 2.8800 | 2.2133 | 2142 |
| TEE | 2.8798 | 1.5653 | 1864 |
| DCL | 2.8797 | 1.5931 | 2298 |
| VHK | 2.8796 | 1.8616 | 1342 |
| RIP | 2.8796 | 3.7833 | 2033 |
| HCL | 2.8795 | 2.0000 | 973 |
| QAP | 2.8793 | 2.5385 | 337 |
| HAH | 2.8792 | 1.6290 | 438 |
| DSQ | 2.8792 | 2.6048 | 2204 |
| SFP | 2.8790 | 2.6606 | 553 |
| LLF | 2.8788 | 2.3089 | 2801 |
| GTI | 2.8788 | 2.0959 | 4117 |
| LVT | 2.8788 | 3.0258 | 5474 |
| RFD | 2.8788 | 1.6436 | 2068 |
| EPW | 2.8786 | 1.2419 | 637 |
| TRS | 2.8786 | 3.2363 | 6557 |
| EWY | 2.8784 | 0.3807 | 1444 |
| PNA | 2.8779 | 3.1020 | 315 |
| GNK | 2.8776 | 1.4186 | 2189 |
| CNM | 2.8776 | 1.2791 | 392 |
| RVD | 2.8774 | 2.6320 | 7431 |
| TNG | 2.8773 | 1.8992 | 2839 |
| DDL | 2.8771 | 1.5714 | 1323 |
| EPE | 2.8771 | 2.1507 | 1498 |
| PIQ | 2.8771 | 2.7061 | 287 |
| PPR | 2.8768 | 3.0000 | 1057 |
| DWS | 2.8767 | 2.1535 | 1641 |
| LIP | 2.8766 | 2.7770 | 1228 |
| ISL | 2.8766 | 3.0346 | 4136 |
| CSN | 2.8765 | 1.5831 | 1562 |
| FVY | 2.8763 | 1.6923 | 1028 |
| ILC | 2.8763 | 2.1884 | 4049 |
| DHR | 2.8756 | 2.2190 | 1259 |
| SED | 2.8755 | 2.2436 | 2272 |
| GQP | 2.8754 | 2.6328 | 1573 |
| KPD | 2.8753 | 2.1048 | 607 |
| MVS | 2.8753 | 2.4953 | 3719 |
| CHE | 2.8753 | 1.4607 | 604 |
| HDF | 2.8751 | 1.3097 | 376 |
| ICH | 2.8751 | 2.0336 | 809 |
| HTD | 2.8751 | 2.4125 | 713 |
| CVL | 2.8751 | 2.0386 | 6938 |
| QCC | 2.8751 | 1.4726 | 1007 |
| FRT | 2.8750 | 2.1634 | 1079 |
| QHG | 2.8749 | 2.2171 | 1287 |
| MQQ | 2.8748 | 0.7588 | 327 |
| IWT | 2.8744 | 1.2754 | 593 |
| YVM | 2.8741 | 1.1428 | 1159 |
| TPC | 2.8734 | 2.7333 | 371 |
| WIC | 2.8734 | 1.0382 | 955 |
| TRQ | 2.8731 | 2.9813 | 2266 |
| YGT | 2.8730 | 2.3285 | 2339 |
| MCA | 2.8730 | 1.3420 | 1100 |
| SRM | 2.8729 | 1.5393 | 3012 |
| IDE | 2.8729 | 1.3842 | 915 |

TABLE F-continued

Medium-expressing EGFP variants

| AA SEQ | Mean | Range | Total counts |
|---|---|---|---|
| TVT | 2.8729 | 2.8146 | 3176 |
| SDK | 2.8729 | 1.9234 | 2215 |
| QEN | 2.8728 | 2.4762 | 487 |
| TPF | 2.8727 | 2.7222 | 201 |
| PQQ | 2.8727 | 2.2940 | 118 |
| DVD | 2.8726 | 1.0874 | 2178 |
| PST | 2.8726 | 3.8182 | 790 |
| DMS | 2.8726 | 1.9860 | 1251 |
| HDS | 2.8724 | 1.8916 | 784 |
| CFA | 2.8720 | 2.0760 | 1075 |
| MEK | 2.8720 | 1.6856 | 818 |
| KVP | 2.8718 | 3.0192 | 1333 |
| LQT | 2.8717 | 2.0667 | 957 |
| WHW | 2.8715 | 0.0879 | 417 |
| MLI | 2.8714 | 2.3512 | 2051 |
| FVH | 2.8714 | 2.4516 | 1047 |
| SMM | 2.8713 | 0.6461 | 595 |
| CQD | 2.8711 | 1.2451 | 688 |
| HTG | 2.8709 | 1.7677 | 1531 |
| TAR | 2.8709 | 2.8919 | 4530 |
| AGP | 2.8709 | 2.7348 | 4773 |
| ADK | 2.8708 | 1.2843 | 963 |
| PQM | 2.8707 | 1.3757 | 207 |
| CIL | 2.8706 | 2.4436 | 2772 |
| AIC | 2.8705 | 2.0046 | 2125 |
| SPY | 2.8705 | 1.7588 | 220 |
| MNP | 2.8702 | 1.0621 | 168 |
| SSC | 2.8702 | 2.5419 | 4013 |
| LDS | 2.8701 | 3.4103 | 3782 |
| SAI | 2.8699 | 2.8124 | 3845 |
| YME | 2.8696 | 0.4595 | 521 |
| WRT | 2.8695 | 1.7802 | 2660 |
| QCF | 2.8694 | 1.4358 | 674 |
| PNQ | 2.8693 | 2.5286 | 549 |
| PET | 2.8692 | 2.3994 | 768 |
| LIY | 2.8691 | 2.7557 | 2183 |
| FFA | 2.8690 | 1.7755 | 549 |
| DNG | 2.8690 | 0.9078 | 2441 |
| VNE | 2.8690 | 1.3073 | 1795 |
| EDH | 2.8689 | 1.0923 | 588 |
| AAW | 2.8689 | 2.2901 | 3186 |
| FEF | 2.8688 | 0.9591 | 436 |
| AYE | 2.8686 | 1.6110 | 1580 |
| TTQ | 2.8686 | 2.8486 | 836 |
| PVF | 2.8686 | 2.7868 | 1309 |
| AFV | 2.8684 | 2.5278 | 2532 |
| NKG | 2.8684 | 2.0191 | 2821 |
| WHS | 2.8683 | 1.7522 | 923 |
| SYG | 2.8681 | 1.6865 | 5533 |
| QEV | 2.8680 | 1.5186 | 2771 |
| IVT | 2.8680 | 2.5518 | 3024 |
| SRH | 2.8679 | 2.3917 | 2240 |
| WIN | 2.8679 | 1.0293 | 929 |
| MER | 2.8678 | 0.6929 | 2496 |
| FTP | 2.8672 | 2.8000 | 145 |
| LPW | 2.8671 | 2.4624 | 756 |
| EDC | 2.8670 | 0.9178 | 1341 |
| RTM | 2.8669 | 1.5537 | 1208 |
| GYI | 2.8669 | 1.5110 | 2549 |
| HCA | 2.8668 | 2.5660 | 533 |
| SEE | 2.8667 | 1.8491 | 3498 |
| TAP | 2.8664 | 3.0000 | 795 |
| FIE | 2.8662 | 1.6399 | 651 |
| YPV | 2.8661 | 2.4990 | 1392 |
| MRI | 2.8661 | 2.3569 | 2344 |
| IQG | 2.8659 | 2.0413 | 3137 |
| FFD | 2.8654 | 1.3500 | 285 |
| WMC | 2.8654 | 0.2436 | 702 |
| SKP | 2.8652 | 3.6970 | 700 |
| HEK | 2.8652 | 2.1803 | 828 |
| MRR | 2.8652 | 1.6584 | 5927 |
| PDR | 2.8650 | 2.7397 | 1398 |
| GAQ | 2.8649 | 1.8943 | 4335 |
| NGC | 2.8649 | 1.2741 | 2465 |
| SHE | 2.8646 | 2.1948 | 1029 |
| ILY | 2.8646 | 2.7335 | 2388 |
| LWP | 2.8646 | 3.0000 | 924 |
| FIH | 2.8644 | 2.0118 | 445 |
| FCQ | 2.8644 | 1.9355 | 326 |
| AQA | 2.8642 | 2.5165 | 1183 |
| CCA | 2.8641 | 1.3497 | 1301 |
| RRK | 2.8641 | 2.3951 | 9101 |
| VEK | 2.8639 | 1.5031 | 3721 |
| GHN | 2.8638 | 2.1910 | 858 |
| ECA | 2.8638 | 1.9425 | 2548 |
| HGI | 2.8631 | 1.4921 | 1145 |
| VIT | 2.8630 | 1.8053 | 2689 |
| AYM | 2.8630 | 3.4530 | 1366 |
| QTA | 2.8629 | 2.5402 | 1459 |
| RCD | 2.8629 | 2.1600 | 2982 |
| YDS | 2.8628 | 1.8570 | 1221 |
| WFR | 2.8628 | 0.9043 | 2339 |
| AET | 2.8627 | 2.7905 | 2314 |
| CLR | 2.8627 | 2.7820 | 6638 |
| PNN | 2.8626 | 2.0457 | 152 |
| SDT | 2.8625 | 2.0821 | 1510 |
| QSA | 2.8623 | 3.2867 | 2918 |
| ACP | 2.8622 | 3.2061 | 563 |
| GYS | 2.8620 | 2.6905 | 5016 |
| FFW | 2.8619 | 1.2373 | 159 |
| FIL | 2.8619 | 2.3793 | 851 |
| EAF | 2.8619 | 1.1468 | 944 |
| ENE | 2.8618 | 0.8671 | 1634 |
| YFD | 2.8615 | 1.3668 | 324 |
| NEE | 2.8615 | 1.9080 | 1055 |
| LHG | 2.8614 | 2.7622 | 3010 |
| VIQ | 2.8612 | 1.6317 | 2181 |
| STE | 2.8610 | 2.8218 | 3109 |
| MDH | 2.8608 | 0.7524 | 297 |
| PSM | 2.8605 | 2.5411 | 584 |
| DFE | 2.8602 | 1.6314 | 985 |
| LTF | 2.8601 | 2.5385 | 1426 |
| WPK | 2.8599 | 1.7762 | 554 |
| MFE | 2.8598 | 0.2365 | 734 |
| FHV | 2.8598 | 2.6267 | 485 |
| EHG | 2.8597 | 0.9745 | 2312 |
| IGC | 2.8594 | 1.2008 | 4520 |
| TRR | 2.8592 | 2.7892 | 10754 |
| FKR | 2.8588 | 2.1014 | 1809 |
| YSQ | 2.8587 | 2.5788 | 1106 |
| MEL | 2.8587 | 1.7458 | 2133 |
| DYG | 2.8586 | 1.2292 | 3956 |
| PKA | 2.8584 | 2.4521 | 922 |
| HSE | 2.8583 | 2.6013 | 1035 |
| RCQ | 2.8583 | 1.6859 | 2130 |
| NED | 2.8579 | 1.0283 | 845 |
| HWL | 2.8578 | 1.0624 | 810 |
| LSI | 2.8576 | 3.4805 | 4534 |
| FRF | 2.8576 | 2.3845 | 1139 |
| PFS | 2.8574 | 1.6130 | 752 |
| GYT | 2.8573 | 2.6844 | 2254 |
| NWL | 2.8572 | 1.5840 | 964 |
| PKM | 2.8571 | 1.0823 | 238 |
| RCM | 2.8571 | 1.3755 | 1649 |
| VQI | 2.8569 | 2.3662 | 1891 |
| FFR | 2.8569 | 1.3089 | 864 |
| PTQ | 2.8569 | 2.0556 | 308 |
| ILV | 2.8568 | 2.4604 | 5517 |
| CEW | 2.8567 | 0.3527 | 1219 |
| CDT | 2.8566 | 2.5044 | 841 |
| LYI | 2.8565 | 1.6428 | 1248 |
| VYR | 2.8561 | 2.0021 | 5979 |
| YFS | 2.8560 | 2.1580 | 1115 |
| AQN | 2.8558 | 2.3200 | 748 |
| MED | 2.8557 | 0.8498 | 482 |
| PQW | 2.8556 | 1.5094 | 541 |
| WMF | 2.8556 | 0.5423 | 296 |
| VIN | 2.8555 | 1.2739 | 2765 |
| PND | 2.8552 | 1.2450 | 276 |
| YWL | 2.8550 | 1.7823 | 1359 |

TABLE F-continued

Medium-expressing EGFP variants

| AA SEQ | Mean | Range | Total counts |
|---|---|---|---|
| LLI | 2.8550 | 2.4041 | 3958 |
| RWQ | 2.8547 | 1.5365 | 2222 |
| YLE | 2.8544 | 1.9454 | 2104 |
| LIG | 2.8542 | 1.7660 | 7364 |
| ISI | 2.8541 | 3.1818 | 3018 |
| AIE | 2.8541 | 2.0685 | 2101 |
| EDT | 2.8541 | 1.5385 | 1397 |
| HGF | 2.8540 | 2.2745 | 898 |
| TDM | 2.8540 | 1.0152 | 617 |
| PVQ | 2.8540 | 2.4037 | 1085 |
| CWN | 2.8539 | 1.0355 | 399 |
| FFK | 2.8539 | 1.3571 | 208 |
| FEE | 2.8539 | 0.9719 | 952 |
| DAK | 2.8538 | 3.0000 | 2144 |
| DPQ | 2.8537 | 1.4638 | 458 |
| GWV | 2.8535 | 1.5049 | 12420 |
| SPM | 2.8534 | 1.7262 | 493 |
| FTM | 2.8532 | 2.2386 | 259 |
| MMD | 2.8530 | 0.5776 | 461 |
| MDF | 2.8528 | 0.7591 | 346 |
| DAQ | 2.8528 | 1.7650 | 769 |
| WMR | 2.8526 | 0.7265 | 2127 |
| HEV | 2.8524 | 1.6882 | 1943 |
| FAP | 2.8522 | 2.0269 | 176 |
| AKM | 2.8521 | 1.8127 | 884 |
| CHM | 2.8519 | 1.0501 | 356 |
| ANL | 2.8518 | 3.1206 | 2057 |
| CCV | 2.8516 | 1.5915 | 2851 |
| HCV | 2.8516 | 1.4309 | 1185 |
| IYG | 2.8514 | 1.5688 | 3275 |
| GKH | 2.8511 | 1.4812 | 1800 |
| GIQ | 2.8510 | 1.9792 | 2604 |
| YRT | 2.8509 | 3.0104 | 2228 |
| CIQ | 2.8506 | 2.9718 | 744 |
| RHA | 2.8504 | 1.8008 | 1664 |
| YWT | 2.8502 | 1.5413 | 491 |
| WRI | 2.8501 | 1.1209 | 2330 |
| QAT | 2.8499 | 2.4211 | 364 |
| TDC | 2.8495 | 1.4626 | 878 |
| IHG | 2.8494 | 2.6777 | 1556 |
| QDT | 2.8493 | 0.9261 | 574 |
| VFY | 2.8492 | 1.2171 | 1300 |
| GNR | 2.8486 | 1.8850 | 7876 |
| FCH | 2.8486 | 1.9611 | 91 |
| WCI | 2.8483 | 0.5591 | 1280 |
| IRI | 2.8483 | 1.8426 | 3354 |
| CPI | 2.8480 | 3.0281 | 664 |
| WQW | 2.8479 | 0.5552 | 733 |
| FSR | 2.8476 | 3.1208 | 2646 |
| FFV | 2.8469 | 1.7740 | 652 |
| INM | 2.8468 | 0.8125 | 423 |
| IWK | 2.8468 | 1.7325 | 1391 |
| PAF | 2.8467 | 3.0435 | 522 |
| PAP | 2.8466 | 3.0417 | 253 |
| WIE | 2.8466 | 1.3334 | 1443 |
| ACK | 2.8464 | 1.5219 | 1815 |
| YVL | 2.8463 | 2.9791 | 4500 |
| DER | 2.8463 | 1.2588 | 4338 |
| RST | 2.8462 | 2.7364 | 5295 |
| TDA | 2.8460 | 2.3954 | 1104 |
| DEW | 2.8459 | 0.6837 | 1408 |
| CHD | 2.8458 | 0.4268 | 346 |
| RED | 2.8458 | 2.4251 | 3799 |
| LAP | 2.8455 | 3.0000 | 1111 |
| LFS | 2.8455 | 2.1541 | 2796 |
| CFN | 2.8453 | 1.2344 | 481 |
| HWI | 2.8452 | 1.3112 | 338 |
| CPV | 2.8451 | 2.0889 | 1100 |
| YFE | 2.8450 | 1.7220 | 591 |
| WYA | 2.8447 | 0.8924 | 1082 |
| ENG | 2.8444 | 1.0925 | 4336 |
| TCN | 2.8442 | 1.4536 | 618 |
| EEW | 2.8441 | 0.5349 | 2369 |
| MTG | 2.8441 | 1.4160 | 2497 |
| PVN | 2.8439 | 2.9491 | 1341 |
| QQC | 2.8438 | 1.6045 | 553 |
| LFI | 2.8435 | 1.0707 | 1683 |
| ICE | 2.8435 | 1.1942 | 1381 |
| YIG | 2.8434 | 2.2546 | 3960 |
| RID | 2.8431 | 2.4870 | 3917 |
| PPQ | 2.8428 | 2.4510 | 153 |
| LAR | 2.8427 | 3.2936 | 7818 |
| FNL | 2.8426 | 2.6891 | 966 |
| LAG | 2.8424 | 2.9381 | 14125 |
| YIV | 2.8421 | 1.9245 | 2888 |
| LCI | 2.8418 | 1.8173 | 2750 |
| YDG | 2.8414 | 0.9973 | 2158 |
| TET | 2.8414 | 1.7572 | 1220 |
| FRS | 2.8414 | 2.3356 | 2880 |
| TCS | 2.8410 | 2.0964 | 1830 |
| TES | 2.8409 | 2.1678 | 3012 |
| SIG | 2.8407 | 1.6900 | 9629 |
| LIQ | 2.8404 | 2.8461 | 1871 |
| LFV | 2.8400 | 2.5934 | 3016 |
| AFE | 2.8400 | 1.2291 | 1402 |
| WIG | 2.8398 | 0.6534 | 4582 |
| VYW | 2.8396 | 0.4850 | 1532 |
| GMG | 2.8393 | 1.9076 | 13745 |
| EHD | 2.8391 | 1.2959 | 478 |
| MFG | 2.8390 | 1.8938 | 2177 |
| GYC | 2.8389 | 0.6715 | 2796 |
| CID | 2.8387 | 1.2534 | 936 |
| LIM | 2.8386 | 1.3380 | 1062 |
| VFK | 2.8385 | 2.0949 | 1854 |
| QDQ | 2.8381 | 1.7315 | 373 |
| QTE | 2.8373 | 2.1479 | 1173 |
| PMQ | 2.8372 | 0.3429 | 103 |
| PSP | 2.8371 | 2.7145 | 443 |
| LIV | 2.8371 | 2.1837 | 4760 |
| AQH | 2.8371 | 2.1818 | 345 |
| EQW | 2.8369 | 0.9010 | 1057 |
| ITW | 2.8368 | 1.1241 | 1059 |
| VMH | 2.8367 | 0.8393 | 1175 |
| ECD | 2.8366 | 1.0677 | 971 |
| IVN | 2.8362 | 1.6906 | 2626 |
| IIT | 2.8355 | 1.7424 | 1245 |
| CLM | 2.8352 | 1.6936 | 1552 |
| ASP | 2.8350 | 3.5641 | 1515 |
| NTW | 2.8349 | 1.9561 | 558 |
| WTI | 2.8342 | 1.9069 | 1317 |
| WFM | 2.8338 | 0.3602 | 349 |
| CLE | 2.8338 | 1.9167 | 2477 |
| TDS | 2.8334 | 1.5257 | 2133 |
| HHT | 2.8333 | 3.1961 | 156 |
| LFD | 2.8333 | 2.1643 | 1287 |
| YSE | 2.8333 | 1.7832 | 2089 |
| VKC | 2.8332 | 1.1823 | 3359 |
| TWK | 2.8321 | 2.1909 | 1026 |
| FHW | 2.8320 | 0.8640 | 413 |
| IGI | 2.8317 | 1.5518 | 4112 |
| ISD | 2.8312 | 2.0202 | 1899 |
| CLD | 2.8312 | 2.2907 | 1866 |
| FGK | 2.8311 | 1.5602 | 1966 |
| DEL | 2.8311 | 1.7596 | 2820 |
| MPR | 2.8309 | 1.4451 | 1248 |
| FEA | 2.8307 | 1.6190 | 1318 |
| CQK | 2.8307 | 1.9449 | 637 |
| SEC | 2.8307 | 2.0306 | 3068 |
| CIW | 2.8307 | 0.3233 | 1317 |
| CEH | 2.8306 | 1.8409 | 957 |
| PRH | 2.8305 | 3.1514 | 1367 |
| FER | 2.8305 | 1.9630 | 2270 |
| IEM | 2.8305 | 0.5286 | 814 |
| APR | 2.8304 | 2.6603 | 2507 |
| FSQ | 2.8303 | 2.5965 | 826 |
| DCF | 2.8301 | 1.6153 | 738 |
| WSI | 2.8300 | 1.5430 | 2233 |
| FSD | 2.8293 | 1.7783 | 875 |
| AMG | 2.8292 | 1.8929 | 4803 |
| DVT | 2.8291 | 1.9481 | 2664 |

TABLE F-continued

Medium-expressing EGFP variants

| AA SEQ | Mean | Range | Total counts |
|---|---|---|---|
| PPF | 2.8286 | 2.0588 | 176 |
| AEK | 2.8285 | 1.5263 | 2353 |
| FRC | 2.8284 | 1.5238 | 1845 |
| YHD | 2.8283 | 1.8605 | 276 |
| LCK | 2.8280 | 2.6336 | 2071 |
| TCH | 2.8280 | 2.2184 | 453 |
| WSK | 2.8280 | 1.6064 | 1912 |
| TAL | 2.8279 | 2.6302 | 2294 |
| LMT | 2.8269 | 1.3574 | 697 |
| NRW | 2.8269 | 1.5239 | 2167 |
| QSE | 2.8269 | 2.0389 | 2041 |
| TCQ | 2.8269 | 2.9191 | 795 |
| CYE | 2.8267 | 1.8493 | 773 |
| MWK | 2.8267 | 0.8017 | 644 |
| HVE | 2.8265 | 1.3195 | 1523 |
| WHE | 2.8262 | 0.7713 | 336 |
| GDP | 2.8262 | 2.7310 | 1852 |
| PSQ | 2.8258 | 2.8019 | 942 |
| MPS | 2.8257 | 2.7857 | 885 |
| IVY | 2.8254 | 1.9954 | 3724 |
| AND | 2.8252 | 1.2706 | 543 |
| PRY | 2.8248 | 2.2884 | 1047 |
| VYN | 2.8248 | 1.0394 | 1625 |
| QTD | 2.8246 | 2.4028 | 604 |
| CQA | 2.8243 | 1.5566 | 912 |
| WIA | 2.8241 | 1.3133 | 1722 |
| CFD | 2.8239 | 1.4324 | 594 |
| CGY | 2.8238 | 0.9615 | 2523 |
| YRW | 2.8235 | 1.2144 | 2245 |
| RFP | 2.8234 | 3.2185 | 730 |
| VKE | 2.8232 | 1.1303 | 3469 |
| WRK | 2.8232 | 1.0895 | 2957 |
| WKW | 2.8231 | 0.3254 | 815 |
| MEP | 2.8231 | 1.7125 | 455 |
| YAE | 2.8226 | 1.3120 | 1052 |
| HEP | 2.8217 | 1.8848 | 312 |
| SFW | 2.8216 | 2.4199 | 1255 |
| HAL | 2.8216 | 2.6127 | 764 |
| MVW | 2.8215 | 0.6599 | 1838 |
| WQN | 2.8213 | 0.5888 | 364 |
| YND | 2.8213 | 1.1100 | 358 |
| QMT | 2.8212 | 1.0283 | 660 |
| PQG | 2.8209 | 2.5245 | 1382 |
| TTW | 2.8209 | 1.5275 | 1050 |
| HDD | 2.8207 | 0.9416 | 332 |
| CLI | 2.8207 | 1.6062 | 3134 |
| LYG | 2.8204 | 2.6460 | 4655 |
| SER | 2.8204 | 2.4483 | 9883 |
| IRW | 2.8203 | 1.2915 | 3346 |
| IMV | 2.8202 | 0.6858 | 1320 |
| FIG | 2.8202 | 1.3085 | 2873 |
| CFW | 2.8202 | 0.8101 | 617 |
| GRP | 2.8202 | 2.9057 | 5848 |
| TFD | 2.8199 | 1.7428 | 975 |
| DNE | 2.8199 | 0.8448 | 1009 |
| FSV | 2.8197 | 2.4706 | 2562 |
| SMT | 2.8189 | 1.5762 | 1135 |
| FLQ | 2.8187 | 2.7854 | 837 |
| MSE | 2.8186 | 0.9196 | 1754 |
| YPC | 2.8186 | 2.1404 | 439 |
| AAK | 2.8184 | 1.8485 | 2104 |
| AKP | 2.8183 | 2.8261 | 586 |
| TWE | 2.8177 | 1.5139 | 1330 |
| SWE | 2.8177 | 1.4602 | 2175 |
| VHF | 2.8175 | 1.3916 | 1083 |
| AMN | 2.8174 | 1.6750 | 560 |
| FYG | 2.8173 | 2.0715 | 949 |
| WFY | 2.8173 | 0.3401 | 667 |
| QEC | 2.8172 | 0.8220 | 1299 |
| LFF | 2.8170 | 2.2285 | 784 |
| EWM | 2.8169 | 0.3473 | 859 |
| RPP | 2.8168 | 3.6364 | 639 |
| DWN | 2.8163 | 0.8445 | 657 |
| WQC | 2.8163 | 0.6328 | 823 |
| YFG | 2.8158 | 1.8807 | 1681 |
| PMS | 2.8157 | 1.9908 | 515 |
| VNR | 2.8155 | 2.3344 | 5979 |
| HGN | 2.8152 | 2.1390 | 689 |
| EQP | 2.8151 | 1.7143 | 571 |
| VNQ | 2.8151 | 1.9157 | 1145 |
| VCY | 2.8149 | 1.0951 | 1544 |
| DDM | 2.8147 | 0.9121 | 701 |
| FMI | 2.8147 | 0.8333 | 287 |
| CYL | 2.8147 | 2.5404 | 1427 |
| SLE | 2.8145 | 2.8750 | 5533 |
| CSF | 2.8144 | 3.0445 | 1525 |
| MDC | 2.8142 | 0.3992 | 314 |
| DSE | 2.8136 | 1.8240 | 2299 |
| CDS | 2.8136 | 1.5974 | 1596 |
| IFT | 2.8134 | 2.3800 | 1188 |
| DWT | 2.8134 | 2.5175 | 751 |
| WCR | 2.8132 | 1.0427 | 4063 |
| FYI | 2.8127 | 1.1482 | 478 |
| KWS | 2.8120 | 1.3280 | 2075 |
| YSW | 2.8119 | 1.7220 | 1333 |
| SQW | 2.8118 | 1.1383 | 1593 |
| IDA | 2.8118 | 1.6842 | 1765 |
| CFT | 2.8115 | 1.3073 | 779 |
| TFG | 2.8114 | 2.1196 | 2792 |
| GEQ | 2.8112 | 1.6424 | 3568 |
| LFQ | 2.8109 | 2.1368 | 1162 |
| WFT | 2.8108 | 1.4342 | 665 |
| YDD | 2.8108 | 1.8501 | 472 |
| LFA | 2.8107 | 2.5513 | 2171 |
| DEE | 2.8104 | 0.7878 | 2027 |
| VIC | 2.8103 | 1.2288 | 3254 |
| HQC | 2.8101 | 2.3560 | 603 |
| WHP | 2.8100 | 1.3115 | 141 |
| LIC | 2.8098 | 2.3948 | 3438 |
| FQM | 2.8095 | 0.6830 | 290 |
| YEE | 2.8092 | 1.5399 | 1701 |
| FDS | 2.8090 | 2.3833 | 1018 |
| HVQ | 2.8087 | 2.3892 | 936 |
| YYP | 2.8086 | 2.7272 | 345 |
| IIC | 2.8086 | 2.2217 | 2003 |
| FTV | 2.8085 | 2.2920 | 1931 |
| HRC | 2.8084 | 2.6062 | 1295 |
| PTS | 2.8084 | 3.1089 | 1079 |
| MSW | 2.8080 | 1.4639 | 995 |
| CQM | 2.8080 | 1.6071 | 416 |
| TEQ | 2.8078 | 1.8184 | 1252 |
| LVG | 2.8076 | 2.6881 | 25051 |
| WHR | 2.8076 | 1.3462 | 1548 |
| SDE | 2.8071 | 2.4045 | 2130 |
| CAQ | 2.8070 | 2.9464 | 571 |
| WIF | 2.8065 | 0.8718 | 818 |
| WNW | 2.8063 | 0.0746 | 450 |
| CCN | 2.8060 | 1.3793 | 586 |
| ECE | 2.8060 | 1.2324 | 1640 |
| HGY | 2.8060 | 2.9139 | 949 |
| FQF | 2.8057 | 0.9615 | 199 |
| FNF | 2.8057 | 1.1250 | 171 |
| DKP | 2.8055 | 2.6855 | 433 |
| GYM | 2.8053 | 0.8520 | 1493 |
| WFV | 2.8052 | 0.8615 | 2016 |
| IKD | 2.8046 | 1.2225 | 1330 |
| VIE | 2.8044 | 1.3777 | 3579 |
| NEP | 2.8041 | 1.3712 | 286 |
| YPF | 2.8032 | 1.9158 | 171 |
| PYC | 2.8032 | 1.2800 | 451 |
| FRH | 2.8031 | 1.7315 | 732 |
| PQK | 2.8029 | 1.6000 | 257 |
| SDF | 2.8027 | 2.0034 | 1478 |
| TDQ | 2.8027 | 2.5214 | 614 |
| MVC | 2.8027 | 1.1412 | 1835 |
| PID | 2.8026 | 2.0389 | 640 |
| NMM | 2.8025 | 0.0087 | 560 |
| ICF | 2.8025 | 1.4212 | 754 |
| LIF | 2.8025 | 1.3237 | 1285 |
| VNC | 2.8024 | 1.3567 | 1978 |

TABLE F-continued

Medium-expressing EGFP variants

| AA SEQ | Mean | Range | Total counts |
|---|---|---|---|
| MCW | 2.8022 | 0.2602 | 634 |
| CFK | 2.8019 | 1.9409 | 1071 |
| FCV | 2.8019 | 1.4727 | 1306 |
| FAT | 2.8017 | 2.3191 | 415 |
| WLQ | 2.8011 | 1.8154 | 1152 |
| QWN | 2.8007 | 1.1320 | 655 |
| EMV | 2.8006 | 0.9651 | 3260 |
| SIM | 2.8005 | 1.4217 | 1306 |
| CDW | 2.8005 | 0.9926 | 510 |
| NWT | 2.8004 | 0.8441 | 379 |
| FLS | 2.8003 | 2.3571 | 2522 |
| YCD | 2.8003 | 2.3026 | 626 |
| TSQ | 2.8002 | 2.0943 | 1715 |
| MTR | 2.8002 | 2.4120 | 1499 |
| SQE | 2.8000 | 2.4286 | 1737 |
| DEM | 2.8000 | 0.4104 | 876 |
| ETE | 2.8000 | 2.0547 | 1631 |
| FDM | 2.7999 | 1.2534 | 279 |
| IIW | 2.7999 | 1.2152 | 938 |
| SFA | 2.7998 | 3.1787 | 1884 |
| LIE | 2.7990 | 1.8279 | 2784 |
| TFP | 2.7990 | 1.9286 | 907 |
| CHG | 2.7990 | 2.2555 | 1290 |
| QAN | 2.7990 | 1.0931 | 371 |
| LVW | 2.7990 | 2.4040 | 5947 |
| KWT | 2.7989 | 1.5848 | 738 |
| DDH | 2.7987 | 1.8997 | 240 |
| FLK | 2.7986 | 1.7850 | 767 |
| YRA | 2.7985 | 2.0139 | 3584 |
| MEI | 2.7982 | 0.8774 | 877 |
| EVE | 2.7980 | 1.3192 | 6754 |
| YVV | 2.7980 | 1.4456 | 4959 |
| HQE | 2.7979 | 0.8750 | 498 |
| DFW | 2.7973 | 1.0854 | 579 |
| LIS | 2.7971 | 2.4583 | 5681 |
| VKR | 2.7968 | 1.9619 | 8501 |
| GYR | 2.7966 | 2.2702 | 8311 |
| FGN | 2.7962 | 1.5747 | 1567 |
| YFL | 2.7960 | 1.8649 | 1010 |
| CHV | 2.7958 | 1.7143 | 1247 |
| YWR | 2.7957 | 1.1931 | 2240 |
| ECR | 2.7956 | 3.3136 | 5971 |
| ECC | 2.7953 | 1.8850 | 1936 |
| HES | 2.7951 | 2.4544 | 1286 |
| MMP | 2.7949 | 0.0000 | 39 |
| HYG | 2.7949 | 1.2294 | 975 |
| LDF | 2.7948 | 1.7000 | 966 |
| MYG | 2.7946 | 1.6622 | 2365 |
| LEQ | 2.7946 | 2.2348 | 1692 |
| CFV | 2.7945 | 1.6034 | 1789 |
| QLE | 2.7941 | 1.9074 | 1913 |
| HDK | 2.7939 | 1.9474 | 279 |
| SNW | 2.7937 | 1.5618 | 1385 |
| WKT | 2.7935 | 1.2405 | 740 |
| WYI | 2.7935 | 0.7946 | 770 |
| SIW | 2.7932 | 1.2920 | 2026 |
| MDT | 2.7931 | 1.4714 | 263 |
| TMT | 2.7926 | 2.0000 | 464 |
| LNE | 2.7922 | 2.7066 | 1401 |
| SID | 2.7920 | 2.7705 | 2756 |
| GSP | 2.7915 | 3.1222 | 2849 |
| SFE | 2.7912 | 2.7778 | 1599 |
| FIV | 2.7907 | 1.5173 | 1916 |
| ISE | 2.7906 | 1.8645 | 2813 |
| WYN | 2.7903 | 0.7009 | 796 |
| DDY | 2.7902 | 1.4701 | 663 |
| WVD | 2.7902 | 1.8157 | 2663 |
| SWY | 2.7902 | 1.6936 | 913 |
| YWC | 2.7901 | 0.2091 | 715 |
| TWG | 2.7892 | 2.4862 | 4718 |
| SWK | 2.7879 | 1.2378 | 1571 |
| PKP | 2.7878 | 1.2291 | 150 |
| ILT | 2.7876 | 2.1374 | 2242 |
| KWC | 2.7871 | 0.4170 | 1042 |
| PVC | 2.7868 | 2.9040 | 1841 |
| GNC | 2.7866 | 1.5337 | 3026 |
| MTQ | 2.7864 | 1.2278 | 220 |
| TNW | 2.7860 | 1.6447 | 670 |
| HWN | 2.7856 | 1.5443 | 235 |
| FPK | 2.7853 | 2.0981 | 506 |
| TEW | 2.7850 | 1.0098 | 1404 |
| LQP | 2.7848 | 2.0500 | 447 |
| HCS | 2.7847 | 2.5390 | 1192 |
| KWR | 2.7847 | 1.0147 | 3510 |
| IPW | 2.7846 | 2.5197 | 538 |
| CGK | 2.7844 | 1.4835 | 3411 |
| TLM | 2.7843 | 2.5642 | 1094 |
| CPT | 2.7842 | 2.6667 | 363 |
| WNM | 2.7842 | 0.3044 | 360 |
| TIW | 2.7839 | 1.9473 | 1060 |
| TRW | 2.7829 | 1.3263 | 2950 |
| VYM | 2.7828 | 0.6129 | 894 |
| MFD | 2.7823 | 0.6429 | 833 |
| FYW | 2.7821 | 0.7957 | 222 |
| WKP | 2.7818 | 1.2694 | 407 |
| GYE | 2.7816 | 1.6645 | 2904 |
| HMV | 2.7815 | 1.2473 | 511 |
| YDW | 2.7815 | 0.6743 | 581 |
| TDN | 2.7813 | 1.7929 | 874 |
| YFW | 2.7805 | 0.2998 | 407 |
| FKW | 2.7805 | 0.8256 | 526 |
| WYT | 2.7804 | 0.8088 | 905 |
| SAK | 2.7801 | 1.9512 | 3485 |
| PKG | 2.7801 | 2.4868 | 2068 |
| PLK | 2.7800 | 1.9407 | 1220 |
| PKS | 2.7795 | 3.0822 | 1685 |
| AHM | 2.7789 | 1.1920 | 426 |
| EER | 2.7779 | 1.6781 | 7921 |
| GYN | 2.7777 | 1.4567 | 1810 |
| LAW | 2.7776 | 2.5585 | 2476 |
| PIH | 2.7774 | 2.3907 | 450 |
| CDF | 2.7772 | 1.6413 | 585 |
| AWT | 2.7767 | 2.6517 | 1239 |
| PHM | 2.7765 | 1.6830 | 128 |
| HCF | 2.7765 | 2.7894 | 427 |
| WFH | 2.7763 | 0.6165 | 246 |
| PHD | 2.7762 | 1.2084 | 155 |
| CCM | 2.7760 | 0.7775 | 744 |
| FPM | 2.7756 | 2.3179 | 267 |
| DID | 2.7756 | 0.9846 | 1180 |
| HPQ | 2.7754 | 1.1200 | 136 |
| EWV | 2.7748 | 1.2392 | 5018 |
| KMD | 2.7748 | 0.6107 | 826 |
| IWQ | 2.7747 | 1.7624 | 595 |
| NMP | 2.7747 | 1.1636 | 375 |
| PYM | 2.7746 | 1.6558 | 127 |
| IMG | 2.7744 | 2.0889 | 2226 |
| GYG | 2.7744 | 1.9405 | 10628 |
| SAN | 2.7741 | 3.0143 | 2241 |
| HPW | 2.7739 | 0.4976 | 253 |
| EPH | 2.7737 | 2.0822 | 483 |
| DMT | 2.7737 | 0.8423 | 338 |
| LFC | 2.7736 | 1.5868 | 1671 |
| RSM | 2.7734 | 2.5909 | 2974 |
| DMP | 2.7730 | 1.3921 | 407 |
| FAQ | 2.7727 | 2.1641 | 370 |
| IMT | 2.7725 | 2.1788 | 584 |
| MVE | 2.7720 | 0.8250 | 1938 |
| DQE | 2.7716 | 0.4465 | 1310 |
| MTW | 2.7715 | 0.7927 | 519 |
| IMF | 2.7712 | 1.1340 | 371 |
| ILS | 2.7708 | 2.0517 | 5784 |
| WKE | 2.7707 | 0.4047 | 1145 |
| WHY | 2.7706 | 1.0154 | 314 |
| CFM | 2.7702 | 0.9018 | 499 |
| GYW | 2.7700 | 0.6894 | 2477 |
| FHK | 2.7699 | 2.1897 | 132 |
| PCG | 2.7699 | 2.6698 | 1540 |
| YWY | 2.7698 | 1.2440 | 471 |
| ICL | 2.7698 | 1.5318 | 2332 |

TABLE F-continued

Medium-expressing EGFP variants

| AA SEQ | Mean | Range | Total counts |
|---|---|---|---|
| GYQ | 2.7697 | 1.5487 | 1814 |
| FRN | 2.7683 | 2.1595 | 1314 |
| GKQ | 2.7675 | 1.6776 | 2431 |
| ANW | 2.7670 | 1.1615 | 1068 |
| QVD | 2.7668 | 2.4686 | 1998 |
| FHR | 2.7667 | 3.0020 | 1333 |
| FCN | 2.7665 | 1.1487 | 276 |
| IYW | 2.7665 | 1.3474 | 782 |
| PLG | 2.7661 | 2.8565 | 3904 |
| VKW | 2.7660 | 0.7914 | 2623 |
| TTA | 2.7658 | 2.9958 | 1403 |
| SPK | 2.7656 | 3.3690 | 1080 |
| ETW | 2.7655 | 0.5257 | 1543 |
| PYT | 2.7647 | 2.8621 | 590 |
| CYW | 2.7644 | 0.6134 | 623 |
| CRM | 2.7644 | 0.9977 | 1664 |
| CYC | 2.7644 | 1.9913 | 950 |
| AIM | 2.7637 | 1.3537 | 1728 |
| SCN | 2.7628 | 1.9574 | 1147 |
| IDM | 2.7626 | 1.1136 | 396 |
| LIT | 2.7624 | 1.8500 | 3008 |
| RAP | 2.7622 | 3.9143 | 1943 |
| DPP | 2.7622 | 2.9722 | 250 |
| SDW | 2.7621 | 1.1157 | 1488 |
| FGI | 2.7611 | 1.4943 | 2045 |
| HCE | 2.7610 | 1.4020 | 376 |
| SLM | 2.7608 | 1.8767 | 1800 |
| FHG | 2.7606 | 2.5929 | 653 |
| GIH | 2.7602 | 1.9634 | 2049 |
| DFP | 2.7600 | 1.2341 | 280 |
| FMQ | 2.7595 | 2.2780 | 394 |
| PYS | 2.7593 | 2.9681 | 903 |
| QYP | 2.7593 | 2.3654 | 221 |
| TPT | 2.7593 | 1.5885 | 292 |
| PGD | 2.7592 | 2.3244 | 2271 |
| EVM | 2.7585 | 0.5730 | 3049 |
| CDN | 2.7583 | 1.0924 | 743 |
| QAY | 2.7581 | 1.5853 | 738 |
| PEK | 2.7571 | 1.2282 | 621 |
| VIY | 2.7562 | 1.2357 | 2231 |
| IWY | 2.7561 | 1.2026 | 503 |
| IMA | 2.7555 | 2.2356 | 596 |
| EVW | 2.7553 | 0.7473 | 4739 |
| ICW | 2.7551 | 1.1778 | 984 |
| EWI | 2.7551 | 0.6820 | 1630 |
| IID | 2.7550 | 1.3595 | 1028 |
| DMC | 2.7550 | 1.2890 | 1241 |
| MEY | 2.7545 | 0.5383 | 464 |
| HRM | 2.7545 | 1.5545 | 723 |
| DDN | 2.7544 | 0.7552 | 633 |
| PHA | 2.7536 | 1.1429 | 73 |
| AHW | 2.7536 | 1.7692 | 663 |
| DKW | 2.7526 | 0.6290 | 1345 |
| LYL | 2.7521 | 3.1337 | 2497 |
| TCY | 2.7518 | 2.4615 | 770 |
| EIG | 2.7516 | 1.1748 | 7810 |
| FWN | 2.7515 | 0.8364 | 167 |
| KAW | 2.7515 | 0.7571 | 1513 |
| PIM | 2.7514 | 1.8518 | 460 |
| GYD | 2.7514 | 1.8163 | 1681 |
| FLI | 2.7494 | 1.0937 | 666 |
| TAI | 2.7489 | 2.6916 | 1860 |
| IEI | 2.7488 | 1.7549 | 1945 |
| MFQ | 2.7482 | 1.0297 | 399 |
| IFG | 2.7482 | 1.8151 | 3394 |
| IFF | 2.7481 | 0.9404 | 411 |
| END | 2.7480 | 0.9239 | 982 |
| FDY | 2.7478 | 1.7944 | 242 |
| TFE | 2.7473 | 3.5816 | 765 |
| ICQ | 2.7469 | 1.6398 | 871 |
| FCK | 2.7468 | 1.0254 | 694 |
| CIG | 2.7465 | 1.9787 | 4449 |
| FRI | 2.7458 | 1.7805 | 1616 |
| HMD | 2.7457 | 1.3248 | 122 |
| HCN | 2.7450 | 2.0579 | 462 |
| YSD | 2.7447 | 1.6716 | 1248 |
| IVE | 2.7447 | 1.2928 | 4433 |
| WSN | 2.7445 | 1.1949 | 1375 |
| VIM | 2.7442 | 0.9396 | 1510 |
| YMV | 2.7442 | 1.1843 | 1290 |
| PYD | 2.7432 | 1.3395 | 345 |
| GTK | 2.7430 | 1.6000 | 2597 |
| CWK | 2.7429 | 0.9821 | 580 |
| VHH | 2.7429 | 3.4304 | 805 |
| FKM | 2.7413 | 0.5704 | 220 |
| MCR | 2.7412 | 1.3038 | 2247 |
| MME | 2.7405 | 0.2524 | 350 |
| FLY | 2.7403 | 2.0611 | 1063 |
| QDC | 2.7403 | 1.1795 | 767 |
| FSK | 2.7396 | 3.6988 | 1125 |
| KRW | 2.7395 | 1.8868 | 4006 |
| FLT | 2.7394 | 2.8952 | 814 |
| NDE | 2.7386 | 1.8369 | 662 |
| CMC | 2.7384 | 0.9980 | 697 |
| PWM | 2.7375 | 1.9107 | 275 |
| FMA | 2.7375 | 1.4296 | 390 |
| HGW | 2.7375 | 2.9579 | 1742 |
| SHC | 2.7375 | 1.9248 | 1096 |
| EEQ | 2.7374 | 0.5496 | 1419 |
| SWV | 2.7374 | 2.1454 | 4616 |
| CRK | 2.7371 | 1.8378 | 2603 |
| QWQ | 2.7369 | 0.8290 | 471 |
| CQE | 2.7366 | 1.3945 | 1044 |
| PNG | 2.7365 | 2.9073 | 1245 |
| PNF | 2.7360 | 1.5785 | 475 |
| SVE | 2.7358 | 2.3156 | 7577 |
| MPT | 2.7354 | 0.9222 | 244 |
| MHQ | 2.7350 | 1.6332 | 272 |
| FMP | 2.7349 | 2.4363 | 162 |
| PEG | 2.7348 | 2.4107 | 3249 |
| HPT | 2.7346 | 1.0159 | 276 |
| ISW | 2.7341 | 1.3183 | 1745 |
| SFD | 2.7338 | 2.5524 | 1280 |
| PPG | 2.7328 | 3.0879 | 1372 |
| WWN | 2.7327 | 1.0864 | 414 |
| YQW | 2.7324 | 0.8815 | 526 |
| PEN | 2.7324 | 2.7743 | 475 |
| YWF | 2.7318 | 1.0581 | 391 |
| PTG | 2.7316 | 2.7391 | 1927 |
| VNF | 2.7314 | 1.1563 | 1040 |
| DVW | 2.7312 | 1.0952 | 2885 |
| WNG | 2.7304 | 0.7638 | 2020 |
| IDD | 2.7297 | 1.1611 | 542 |
| GNQ | 2.7294 | 1.6336 | 1600 |
| VYE | 2.7291 | 1.9104 | 2026 |
| FWY | 2.7290 | 0.6273 | 353 |
| TQW | 2.7287 | 1.1790 | 891 |
| ESE | 2.7280 | 1.5334 | 4296 |
| HAM | 2.7267 | 0.8075 | 193 |
| PQD | 2.7264 | 1.3350 | 325 |
| FPI | 2.7262 | 3.4613 | 388 |
| AHA | 2.7262 | 2.3649 | 653 |
| RWT | 2.7259 | 2.4888 | 2671 |
| FIM | 2.7256 | 1.8880 | 416 |
| WYP | 2.7250 | 1.2593 | 458 |
| FRK | 2.7250 | 1.7622 | 1484 |
| SNP | 2.7241 | 2.6591 | 465 |
| ANE | 2.7233 | 1.4663 | 993 |
| YMT | 2.7232 | 1.6259 | 246 |
| AWE | 2.7230 | 1.8183 | 2659 |
| TTD | 2.7223 | 1.8250 | 703 |
| TCE | 2.7220 | 1.9031 | 1671 |
| LWG | 2.7220 | 1.4646 | 9017 |
| YHW | 2.7219 | 0.2527 | 239 |
| FEI | 2.7210 | 1.4423 | 832 |
| YWN | 2.7205 | 1.0504 | 202 |
| FFS | 2.7192 | 1.9649 | 692 |
| CQN | 2.7185 | 1.4426 | 750 |
| PNL | 2.7181 | 2.8343 | 984 |
| HRQ | 2.7174 | 2.2946 | 489 |

TABLE F-continued

Medium-expressing EGFP variants

| AA SEQ | Mean | Range | Total counts |
|---|---|---|---|
| NDP | 2.7173 | 1.5644 | 158 |
| GYP | 2.7172 | 2.4688 | 1004 |
| GYV | 2.7170 | 2.0591 | 5459 |
| WFC | 2.7167 | 0.2494 | 850 |
| TCT | 2.7160 | 2.7631 | 1103 |
| TRT | 2.7154 | 3.0664 | 2116 |
| ILE | 2.7148 | 2.4242 | 3317 |
| IEE | 2.7145 | 1.3849 | 2308 |
| PIV | 2.7142 | 3.0604 | 1610 |
| FLL | 2.7125 | 2.5357 | 1349 |
| EDK | 2.7125 | 0.7748 | 1755 |
| FLN | 2.7123 | 1.9330 | 523 |
| PWC | 2.7123 | 1.8182 | 594 |
| YWI | 2.7119 | 0.9771 | 571 |
| IVC | 2.7118 | 1.4712 | 3513 |
| FEM | 2.7110 | 0.8463 | 615 |
| HWH | 2.7108 | 0.3264 | 207 |
| PPN | 2.7106 | 1.7492 | 162 |
| IWN | 2.7100 | 0.7291 | 302 |
| VKM | 2.7100 | 1.1722 | 1174 |
| QAK | 2.7100 | 1.6176 | 1085 |
| CFI | 2.7095 | 1.0687 | 910 |
| VIH | 2.7092 | 1.9958 | 1464 |
| LFL | 2.7089 | 2.9167 | 2108 |
| CPP | 2.7088 | 1.6748 | 222 |
| PPH | 2.7087 | 3.3349 | 109 |
| FRM | 2.7067 | 1.2989 | 735 |
| WIQ | 2.7067 | 1.2420 | 814 |
| YFF | 2.7063 | 2.4784 | 262 |
| SMG | 2.7063 | 2.3974 | 5499 |
| TCC | 2.7055 | 2.3700 | 899 |
| WFP | 2.7050 | 2.1273 | 305 |
| GWP | 2.7050 | 2.1601 | 2260 |
| PNC | 2.7049 | 0.8938 | 396 |
| PTV | 2.7048 | 3.0524 | 1350 |
| WTK | 2.7048 | 1.0384 | 709 |
| YRQ | 2.7042 | 1.6982 | 1117 |
| HPH | 2.7038 | 1.5585 | 110 |
| TYP | 2.7037 | 2.7639 | 331 |
| NWC | 2.7036 | 1.1338 | 612 |
| PDY | 2.7035 | 1.3500 | 383 |
| LND | 2.7028 | 1.9472 | 1159 |
| PMG | 2.7027 | 2.4286 | 1242 |
| ICM | 2.7026 | 1.2688 | 482 |
| HET | 2.7024 | 1.7045 | 360 |
| VCK | 2.7019 | 1.3441 | 2924 |
| MAK | 2.7015 | 2.0528 | 992 |
| FYL | 2.7011 | 2.4220 | 415 |
| WYM | 2.7007 | 0.3264 | 454 |
| VYF | 2.7000 | 2.0128 | 1267 |
| WST | 2.6998 | 1.6639 | 2041 |
| CNE | 2.6996 | 0.8446 | 514 |
| STM | 2.6996 | 2.5860 | 852 |
| TDE | 2.6987 | 1.9209 | 1198 |
| YEG | 2.6983 | 1.3780 | 3868 |
| APP | 2.6981 | 3.9500 | 511 |
| IIG | 2.6977 | 2.4405 | 6014 |
| TDD | 2.6976 | 2.9751 | 857 |
| MFP | 2.6975 | 1.8495 | 202 |
| TDF | 2.6972 | 1.5066 | 712 |
| TEC | 2.6950 | 1.2724 | 1705 |
| CMM | 2.6947 | 0.3000 | 215 |
| HEA | 2.6936 | 2.0965 | 889 |
| PFG | 2.6924 | 2.6246 | 1111 |
| IED | 2.6922 | 1.2125 | 1163 |
| FCM | 2.6909 | 1.2646 | 306 |
| CMT | 2.6898 | 1.9224 | 418 |
| YHG | 2.6895 | 1.8796 | 975 |
| CCI | 2.6887 | 1.0599 | 1176 |
| WFF | 2.6885 | 1.0480 | 385 |
| DRQ | 2.6884 | 1.2229 | 1301 |
| FYT | 2.6882 | 2.0136 | 369 |
| MHE | 2.6862 | 0.7824 | 199 |
| SHA | 2.6861 | 2.4902 | 806 |
| WMT | 2.6856 | 2.2748 | 556 |
| PVD | 2.6848 | 2.5962 | 1481 |
| EWK | 2.6848 | 0.7208 | 1901 |
| HDQ | 2.6847 | 1.4131 | 232 |
| LMM | 2.6847 | 0.8473 | 448 |
| TAH | 2.6837 | 1.9573 | 667 |
| PKQ | 2.6825 | 1.8182 | 394 |
| QMD | 2.6806 | 0.6229 | 266 |
| HGT | 2.6801 | 2.7467 | 1116 |
| WMQ | 2.6800 | 0.9600 | 605 |
| PMA | 2.6797 | 1.8772 | 482 |
| WKK | 2.6789 | 1.1569 | 886 |
| LMI | 2.6788 | 1.4530 | 900 |
| FQW | 2.6779 | 0.7912 | 312 |
| LFN | 2.6775 | 2.3571 | 1154 |
| WKH | 2.6771 | 0.9024 | 419 |
| HCQ | 2.6766 | 1.3034 | 231 |
| NCE | 2.6754 | 1.3188 | 900 |
| WNE | 2.6749 | 0.4919 | 873 |
| WVW | 2.6747 | 1.9444 | 3907 |
| CYP | 2.6736 | 1.8533 | 272 |
| CEM | 2.6736 | 0.5644 | 1019 |
| ICI | 2.6726 | 1.8072 | 1156 |
| PTD | 2.6723 | 1.9100 | 335 |
| FIS | 2.6713 | 1.7939 | 1536 |
| ICD | 2.6707 | 0.9963 | 1020 |
| YPE | 2.6706 | 1.7767 | 600 |
| FNE | 2.6703 | 1.8825 | 330 |
| PWT | 2.6703 | 2.2187 | 477 |
| DEC | 2.6702 | 0.5501 | 1855 |
| QSP | 2.6692 | 1.5170 | 753 |
| WQQ | 2.6690 | 0.9152 | 316 |
| TVM | 2.6675 | 1.5734 | 1653 |
| HWQ | 2.6664 | 0.1020 | 98 |
| HDA | 2.6661 | 1.3083 | 641 |
| LFM | 2.6658 | 1.5556 | 711 |
| MMW | 2.6656 | 0.0000 | 616 |
| FFF | 2.6655 | 2.3137 | 78 |
| WIM | 2.6644 | 0.9237 | 601 |
| YVW | 2.6639 | 0.7673 | 1930 |
| YFC | 2.6627 | 2.0906 | 538 |
| CCK | 2.6627 | 2.2324 | 1172 |
| CTM | 2.6626 | 0.9025 | 313 |
| TCM | 2.6620 | 1.6677 | 651 |
| CHT | 2.6618 | 2.1384 | 653 |
| KWK | 2.6611 | 0.9398 | 1044 |
| LWW | 2.6594 | 0.9179 | 2314 |
| PTY | 2.6593 | 0.7407 | 261 |
| EMW | 2.6586 | 0.0939 | 1066 |
| IEA | 2.6576 | 1.3187 | 2661 |
| FIQ | 2.6564 | 2.5573 | 466 |
| CMG | 2.6560 | 1.9979 | 2568 |
| QET | 2.6550 | 1.8333 | 670 |
| FIN | 2.6548 | 1.2733 | 599 |
| WQM | 2.6543 | 0.1321 | 203 |
| FLC | 2.6541 | 1.8163 | 1908 |
| WIT | 2.6527 | 1.5445 | 1006 |
| FID | 2.6506 | 1.6327 | 493 |
| DCW | 2.6503 | 0.7555 | 1037 |
| VNM | 2.6484 | 1.1601 | 927 |
| CQW | 2.6482 | 1.2058 | 710 |
| FNW | 2.6480 | 0.5795 | 440 |
| DHM | 2.6477 | 1.4310 | 222 |
| FFY | 2.6476 | 1.4352 | 207 |
| ECW | 2.6475 | 0.1575 | 1916 |
| WHH | 2.6470 | 0.7562 | 129 |
| PDD | 2.6462 | 1.9288 | 458 |
| FND | 2.6458 | 0.6477 | 212 |
| SWD | 2.6453 | 2.1666 | 1394 |
| AIW | 2.6450 | 1.2522 | 1536 |
| SNM | 2.6406 | 1.1133 | 1001 |
| PSG | 2.6404 | 2.8442 | 4312 |
| TEH | 2.6391 | 1.7157 | 666 |
| FCI | 2.6386 | 1.3268 | 598 |
| NEG | 2.6383 | 0.9690 | 3141 |
| HEQ | 2.6382 | 1.8740 | 312 |

TABLE F-continued

Medium-expressing EGFP variants

| AA SEQ | Mean | Range | Total counts |
|---|---|---|---|
| MTD | 2.6377 | 1.5246 | 495 |
| LID | 2.6369 | 2.1935 | 1704 |
| AHC | 2.6366 | 2.0437 | 927 |
| FLF | 2.6365 | 1.5668 | 587 |
| YHP | 2.6361 | 1.5000 | 100 |
| IFC | 2.6359 | 1.4192 | 980 |
| PGG | 2.6358 | 2.6546 | 14052 |
| EID | 2.6355 | 1.0334 | 1674 |
| KMW | 2.6350 | 0.1493 | 480 |
| PHT | 2.6332 | 2.1452 | 132 |
| DMM | 2.6332 | 0.1574 | 160 |
| WWT | 2.6324 | 0.8030 | 824 |
| YLM | 2.6311 | 2.3178 | 777 |
| HDP | 2.6306 | 3.0000 | 135 |
| MVQ | 2.6279 | 1.3189 | 1003 |
| KWM | 2.6261 | 0.1112 | 504 |
| VWV | 2.6259 | 1.7016 | 6511 |
| MMM | 2.6243 | 0.0000 | 189 |
| TWD | 2.6230 | 2.2553 | 609 |
| DTW | 2.6221 | 1.3940 | 697 |
| HMM | 2.6218 | 0.8740 | 109 |
| WVC | 2.6213 | 1.8033 | 2999 |
| HMP | 2.6211 | 0.1285 | 141 |
| DCQ | 2.6208 | 1.4440 | 480 |
| PHG | 2.6203 | 3.0000 | 633 |
| QWK | 2.6187 | 0.1198 | 622 |
| FCT | 2.6182 | 2.4322 | 467 |
| YKW | 2.6182 | 1.5442 | 540 |
| WIP | 2.6154 | 2.2348 | 645 |
| FMC | 2.6148 | 0.7718 | 337 |
| GYK | 2.6145 | 1.0650 | 2026 |
| FYV | 2.6145 | 1.5803 | 893 |
| NWW | 2.6132 | 0.5419 | 489 |
| FLM | 2.6112 | 0.9028 | 416 |
| IME | 2.6092 | 0.5371 | 746 |
| CEK | 2.6088 | 0.5958 | 1109 |
| IEW | 2.6083 | 0.6191 | 1590 |
| MCE | 2.6082 | 0.5324 | 716 |
| WMY | 2.6074 | 0.0165 | 586 |
| VYC | 2.6064 | 1.1061 | 1971 |
| IHD | 2.6061 | 0.8867 | 481 |
| PVG | 2.6054 | 2.7429 | 6897 |
| PIG | 2.6050 | 2.4777 | 1959 |
| HMG | 2.6041 | 1.9074 | 836 |
| IFD | 2.6034 | 1.4964 | 718 |
| HNP | 2.6033 | 0.7424 | 177 |
| DHD | 2.6020 | 1.0143 | 370 |
| PIE | 2.6015 | 2.0214 | 880 |
| MND | 2.6009 | 0.6781 | 376 |
| THE | 2.5996 | 2.2832 | 586 |
| WMH | 2.5988 | 0.5387 | 264 |
| YMG | 2.5987 | 2.4088 | 1641 |
| FWT | 2.5978 | 2.2490 | 258 |
| WTH | 2.5978 | 0.7710 | 321 |
| EDQ | 2.5970 | 1.4375 | 676 |
| WTN | 2.5964 | 1.0006 | 525 |
| AWA | 2.5961 | 1.9726 | 2163 |
| TWH | 2.5939 | 1.1820 | 358 |
| QCQ | 2.5913 | 0.3303 | 609 |
| FFT | 2.5897 | 2.7991 | 215 |
| QWT | 2.5893 | 2.4827 | 295 |
| PHI | 2.5860 | 2.7274 | 415 |
| YYW | 2.5851 | 1.1667 | 298 |
| CKW | 2.5849 | 0.9608 | 1209 |
| HMT | 2.5844 | 2.5297 | 190 |
| FHL | 2.5824 | 1.7292 | 423 |
| PPT | 2.5817 | 3.4833 | 172 |
| VAP | 2.5815 | 2.8500 | 2135 |
| FPT | 2.5808 | 2.7052 | 385 |
| FHN | 2.5804 | 1.1365 | 204 |
| TQQ | 2.5797 | 1.1545 | 497 |
| WCK | 2.5790 | 0.3675 | 1117 |
| PIA | 2.5787 | 2.1030 | 567 |
| PNE | 2.5777 | 0.8648 | 360 |
| DWI | 2.5777 | 0.6431 | 1135 |
| SFQ | 2.5774 | 2.7883 | 999 |
| FIY | 2.5726 | 1.0089 | 727 |
| FQK | 2.5719 | 1.8556 | 409 |
| MCC | 2.5718 | 0.7515 | 756 |
| CET | 2.5687 | 2.1518 | 1481 |
| FHD | 2.5676 | 0.4952 | 212 |
| PSH | 2.5661 | 2.4000 | 267 |
| FDN | 2.5656 | 1.3478 | 181 |
| MQW | 2.5641 | 0.4198 | 357 |
| LFT | 2.5630 | 2.6862 | 1527 |
| GCP | 2.5626 | 2.0010 | 1815 |
| QEQ | 2.5597 | 1.5753 | 586 |
| IDP | 2.5579 | 1.4357 | 237 |
| YNW | 2.5575 | 0.2179 | 318 |
| CVM | 2.5560 | 1.0487 | 1574 |
| HWK | 2.5541 | 1.0781 | 123 |
| FMG | 2.5521 | 2.1392 | 1152 |
| QGW | 2.5473 | 1.4758 | 3063 |
| FHM | 2.5465 | 0.9070 | 72 |
| YIW | 2.5451 | 0.6995 | 805 |
| WYC | 2.5436 | 0.5128 | 931 |
| FHI | 2.5429 | 1.0000 | 325 |
| IFW | 2.5413 | 0.7274 | 399 |
| PQY | 2.5397 | 1.4328 | 266 |
| FWH | 2.5392 | 0.5012 | 205 |
| DQW | 2.5392 | 0.7934 | 631 |
| HDC | 2.5335 | 0.9187 | 402 |
| SYM | 2.5331 | 0.8369 | 960 |
| WII | 2.5330 | 0.9228 | 1072 |
| WYR | 2.5248 | 0.9478 | 2470 |
| FEQ | 2.5245 | 1.9316 | 461 |
| MMY | 2.5229 | 0.9737 | 316 |
| GAP | 2.5199 | 2.7778 | 2840 |
| FFN | 2.5190 | 0.6288 | 242 |
| DHE | 2.5125 | 2.1551 | 602 |
| ECQ | 2.5117 | 0.9238 | 1155 |
| FIT | 2.5113 | 1.4872 | 486 |
| WHD | 2.5050 | 0.3493 | 145 |
| HWT | 2.5014 | 0.3509 | 54 |
| WFN | 2.5007 | 1.3635 | 352 |
| VPP | 2.5004 | 2.8017 | 950 |
| YIM | 2.4989 | 0.6075 | 706 |
| LWV | 2.4973 | 2.7523 | 5050 |
| WNH | 2.4972 | 0.7944 | 163 |
| MDD | 2.4942 | 1.1740 | 352 |
| HQP | 2.4927 | 1.2031 | 115 |
| MDN | 2.4858 | 0.9375 | 323 |
| TWV | 2.4846 | 1.9795 | 2148 |
| NMG | 2.4814 | 2.1397 | 1297 |
| MDI | 2.4785 | 0.4859 | 451 |
| FFC | 2.4776 | 1.3258 | 241 |
| DNP | 2.4756 | 0.8083 | 217 |
| MVN | 2.4729 | 1.3785 | 1212 |
| DWY | 2.4713 | 0.7895 | 925 |
| WHQ | 2.4709 | 1.4580 | 315 |
| FIC | 2.4668 | 0.9250 | 837 |
| CHW | 2.4642 | 0.7573 | 269 |
| GPP | 2.4555 | 2.8750 | 1243 |
| IQW | 2.4533 | 0.8421 | 768 |
| YDP | 2.4503 | 1.3953 | 124 |
| FPH | 2.4471 | 1.0769 | 101 |
| AAP | 2.4393 | 2.8997 | 1180 |
| KWW | 2.4366 | 0.3090 | 1070 |
| MEF | 2.4351 | 0.6931 | 791 |
| MMT | 2.4319 | 1.4626 | 252 |
| HAN | 2.4316 | 1.6175 | 218 |
| AWG | 2.4272 | 1.8175 | 9435 |
| PWF | 2.4249 | 2.4681 | 284 |
| MFW | 2.4182 | 0.3636 | 425 |
| PPK | 2.4103 | 2.6807 | 312 |
| HHV | 2.4073 | 0.7966 | 231 |
| MDY | 2.3883 | 0.6929 | 397 |
| FMF | 2.3844 | 0.9246 | 207 |
| EHW | 2.3695 | 0.4514 | 792 |
| SHM | 2.3674 | 1.7232 | 464 |

TABLE F-continued

Medium-expressing EGFP variants

| AA SEQ | Mean | Range | Total counts |
|---|---|---|---|
| AMQ | 2.3632 | 0.3999 | 477 |
| FYM | 2.3600 | 0.6957 | 130 |
| WPW | 2.3543 | 1.9278 | 472 |
| PCE | 2.3438 | 2.5873 | 780 |
| FHP | 2.3421 | 2.6842 | 57 |
| CDM | 2.3381 | 0.1153 | 529 |
| HFP | 2.3370 | 0.7536 | 118 |
| DMG | 2.3203 | 1.9295 | 2503 |
| NDW | 2.3090 | 1.0020 | 487 |
| AWD | 2.2967 | 2.3230 | 1510 |
| YMM | 2.2800 | 0.0912 | 214 |
| MAP | 2.2551 | 2.0810 | 374 |
| PWE | 2.2514 | 1.9647 | 404 |
| IWH | 2.2217 | 0.4774 | 467 |
| AWV | 2.2083 | 2.3478 | 3443 |
| PWA | 2.2027 | 2.7857 | 989 |
| MPM | 2.1656 | 1.8176 | 190 |
| HAP | 2.0880 | 2.1101 | 160 |
| PMN | 2.0860 | 1.0511 | 108 |
| PHH | 2.0000 | 0.0000 | 27 |

TABLE G

| AA SEQ | GFP score Mean | Range | Total counts |
|---|---|---|---|
| PWV | 1.9564 | 2.2461 | 1255 |
| PWG | 1.9456 | 2.3407 | 2601 |
| PWW | 1.7967 | 0.6795 | 422 |
| PWD | 1.9246 | 1.3333 | 311 |

TABLE H

| Tag | Exemplary Function |
|---|---|
| CBP | Affinity and Purification |
| FLAG | Affinity and Purification |
| GST | Purification and Stability |
| HA | Affinity |
| HBH | Affinity and Purification |
| MBP | Solubility and Purification |
| Myc | Affinity |
| poly His (e.g. hexahistidine) | Affinity and Purification |
| S-tag | Solubility and Affinity |
| SUMO | Stability |
| TAP | Affinity and Purification |
| TRX | Solubility |
| V5 | Affinity and Purification |
| GFP and other fluorescent proteins | Detection and Purification |
| AviTag ™ | Purification |
| SBP | Purification |
| Strep | Purification |
| Polyarginine | Purification |
| Polyglutamine | Purification |

TABLE I

| HIGH | | | MEDIUM | | | LOW | | |
|---|---|---|---|---|---|---|---|---|
| AA | GFP Score | | AA | GFP Score | | AA | GFP Score | |
| Seq | Mean | Range | Seq | Mean | Range | Seq | Mean | Range |
| KYY | 4.84 | 0.26 | KKW | 3.90 | 0.56 | EHW | 2.37 | 0.45 |
| KHY | 4.79 | 0.42 | DYW | 3.89 | 0.65 | AWG | 2.43 | 1.82 |
| KYH | 4.76 | 0.44 | ENK | 3.66 | 0.62 | KWW | 2.44 | 0.31 |
| KFY | 4.75 | 0.62 | WEY | 3.56 | 0.42 | IQW | 2.45 | 0.84 |
| NQY | 4.73 | 0.22 | WGF | 3.46 | 0.55 | FIC | 2.47 | 0.92 |
| KKY | 4.72 | 0.65 | CWW | 3.45 | 0.10 | DWY | 2.47 | 0.79 |
| KYC | 4.72 | 0.66 | WTVV | 3.42 | 0.20 | WYC | 2.54 | 0.51 |
| KNY | 4.72 | 0.51 | WEI | 3.40 | 0.45 | YIW | 2.55 | 0.70 |
| NHY | 4.71 | 0.66 | KDW | 3.40 | 0.58 | DWI | 2.58 | 0.64 |
| NYK | 4.71 | 0.54 | CWG | 3.40 | 0.48 | WOK | 2.58 | 0.37 |
| KKH | 4.71 | 0.60 | VWF | 3.39 | 0.70 | QCQ | 2.59 | 0.33 |
| HQH | 4.68 | 0.35 | WAI | 3.38 | 0.66 | CEK | 2.61 | 0.60 |
| KNF | 4.61 | 0.54 | DWW | 3.38 | 0.48 | QWK | 2.62 | 0.12 |
| NIY | 4.61 | 0.71 | WGV | 3.37 | 0.62 | ECW | 2.65 | 0.16 |
| KHI | 4.60 | 0.76 | VWW | 3.37 | 0.39 | DOW | 2.65 | 0.76 |
| KFC | 4.60 | 0.57 | WWL | 3.36 | 0.45 | YVW | 2.66 | 0.77 |
| NNI | 4.58 | 0.57 | DWA | 3.34 | 0.70 | DEC | 2.67 | 0.55 |
| KNK | 4.57 | 0.50 | VWC | 3.34 | 0.42 | WNE | 2.67 | 0.49 |
| NIK | 4.55 | 0.73 | WEL | 3.34 | 0.51 | EDK | 2.71 | 0.77 |
| NKY | 4.54 | 0.54 | WAE | 3.34 | 0.66 | WFC | 2.72 | 0.25 |
| KYN | 4.52 | 0.41 | WEV | 3.34 | 0.37 | EEQ | 2.74 | 0.55 |
| NYC | 4.51 | 0.47 | WEF | 3.34 | 0.60 | DKW | 2.75 | 0.63 |
| KYE | 4.51 | 0.73 | VWS | 3.33 | 0.71 | DDN | 2.75 | 0.76 |
| KNN | 4.48 | 0.64 | KWG | 3.32 | 0.37 | EVW | 2.76 | 0.75 |
| YNH | 4.44 | 0.52 | DWV | 3.32 | 0.42 | CYW | 2.76 | 0.61 |
| NNK | 4.44 | 0.53 | CWV | 3.27 | 0.70 | GYW | 2.77 | 0.69 |
| KYW | 4.44 | 0.42 | VWY | 3.27 | 0.60 | WKE | 2.77 | 0.40 |
| KFW | 4.43 | 0.35 | GGW | 3.26 | 0.66 | DQE | 2.77 | 0.45 |
| KIY | 4.64 | 0.76 | DDG | 3.25 | 0.55 | YDW | 2.78 | 0.67 |
| | | | EGD | 3.24 | 0.64 | KWC | 2.79 | 0.42 |
| | | | EDE | 3.23 | 0.60 | YWC | 2.79 | 0.21 |
| | | | QGE | 3.22 | 0.68 | WYN | 2.79 | 0.70 |
| | | | CGE | 3.21 | 0.62 | DEE | 2.81 | 0.79 |
| | | | EGE | 3.19 | 0.56 | WOO | 2.82 | 0.63 |
| | | | EDG | 3.17 | 0.65 | WFY | 2.82 | 0.34 |
| | | | DDW | 3.13 | 0.50 | CIW | 2.83 | 0.32 |
| | | | EGK | 3.04 | 0.70 | GYC | 2.84 | 0.67 |
| | | | WVE | 3.04 | 0.60 | WIG | 2.84 | 0.65 |
| | | | | | | EEW | 2.84 | 0.53 |
| | | | | | | DEW | 2.85 | 0.68 |
| | | | | | | WCI | 2.85 | 0.56 |
| | | | | | | CEW | 2.86 | 0.35 |

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure. Those of skill in the art should, however, in light of the present disclosure, appreciate that changes may be made in the specific embodiments that are disclosed and still obtain a like or similar result without departing from the spirit and scope of the disclosure. Therefore, all matter set forth or shown in the accompanying drawings is to be interpreted as illustrative and not in a limiting sense. Further supporting details for the methods and data described in the following examples can be found in Verma et al., "Short translational ramp determines efficiency of protein synthesis," bioRxiv, March 2019, DOI: 10.1101/571059, the disclosures of which are incorporated herein by reference in their entirety.

Example 1

A reporter system was generated to test the influence of the first 5 amino acids and the mRNA sequence of the first ribosome footprint independently of other factors that may affect translation efficiency (e.g., 5'UTR, ribosomal binding site (RBS), N-terminal rule, etc.). Briefly, a plurality of a random sequences consisting of nine nucleotides were inserted into a nucleic acid sequence encoding EGFP after the second codon (GTC encoding valine) and before the third codon (AGC encoding serine), thereby producing a plurality EGFP reporter constructs. Each random sequence is referred to as a "9nt sequence," and collectively the 9nt sequences encoded all amino acids possibilities at codons 3, 4, and 5 of the EGFP variant (numbering after the insertion). The EGFP reporter constructs were cloned into a single copy plasmid under the control of an arabinose promoter (pBAD DEST49 plasmid (Invitrogen)), and the library was transformed in to E. coli DH5α cells with an AMBER suppressor (glnV44) mutation.

Figure 4A:
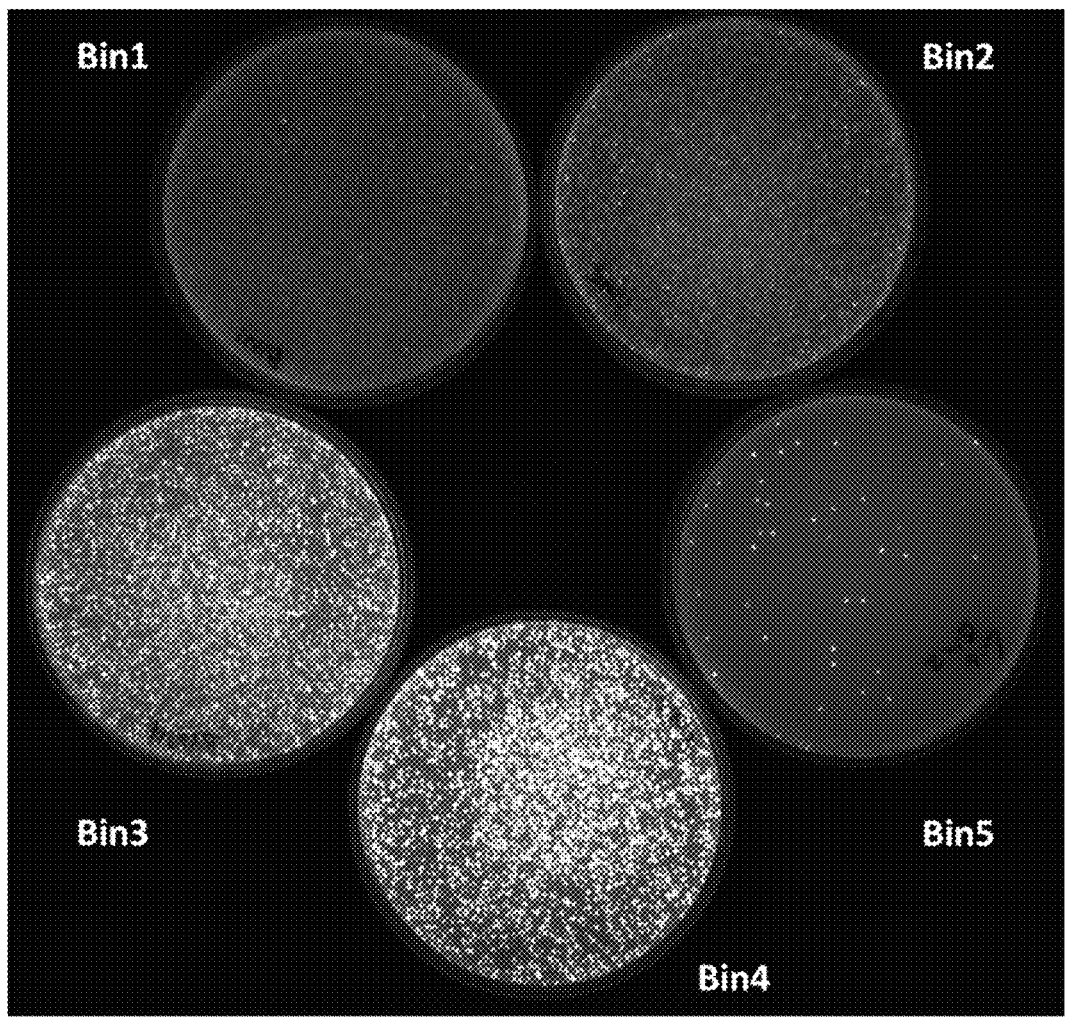
FIG. 4A and FIG. 4B show results from a reporter system to test the influence of codons 3-5 of an mRNA sequence, and the influence of the first five amino acids of a nascent peptide, on translation efficiency. A library of EGFP reporter constructs was created and then expressed in E. coli. DH5α cells with an AMBER suppressor (gInV44) mutation.
Figure 4B:
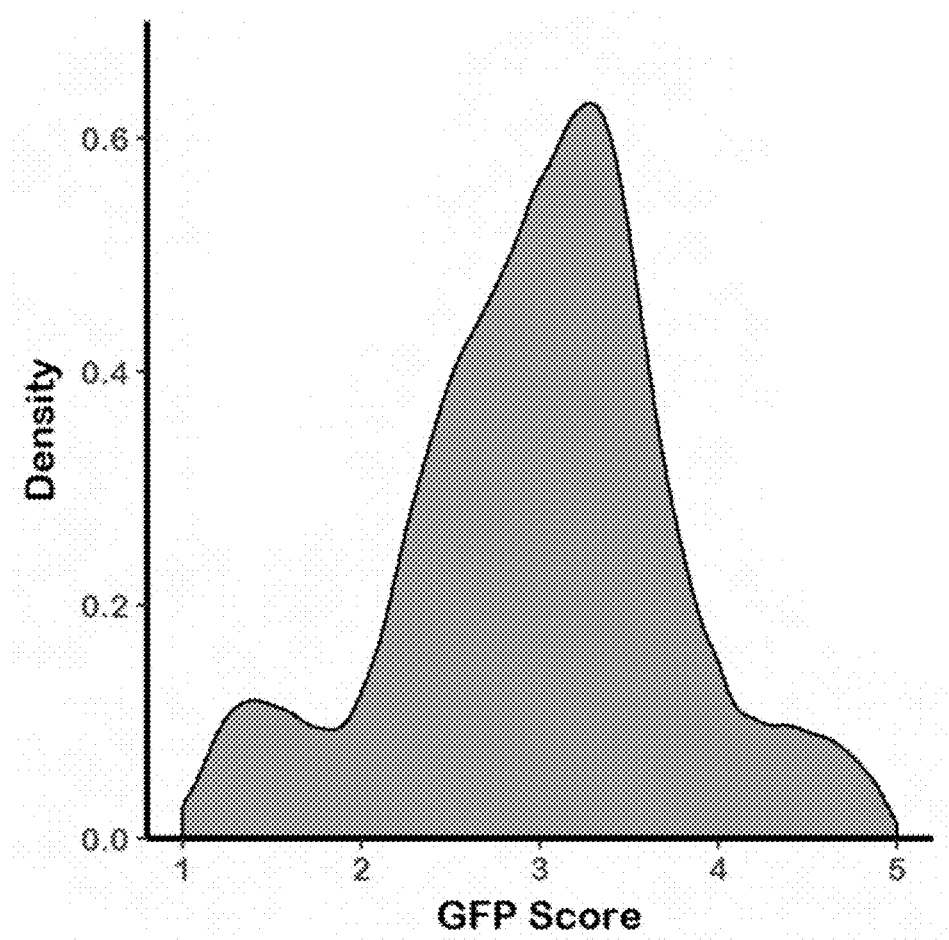
Figure 5A:
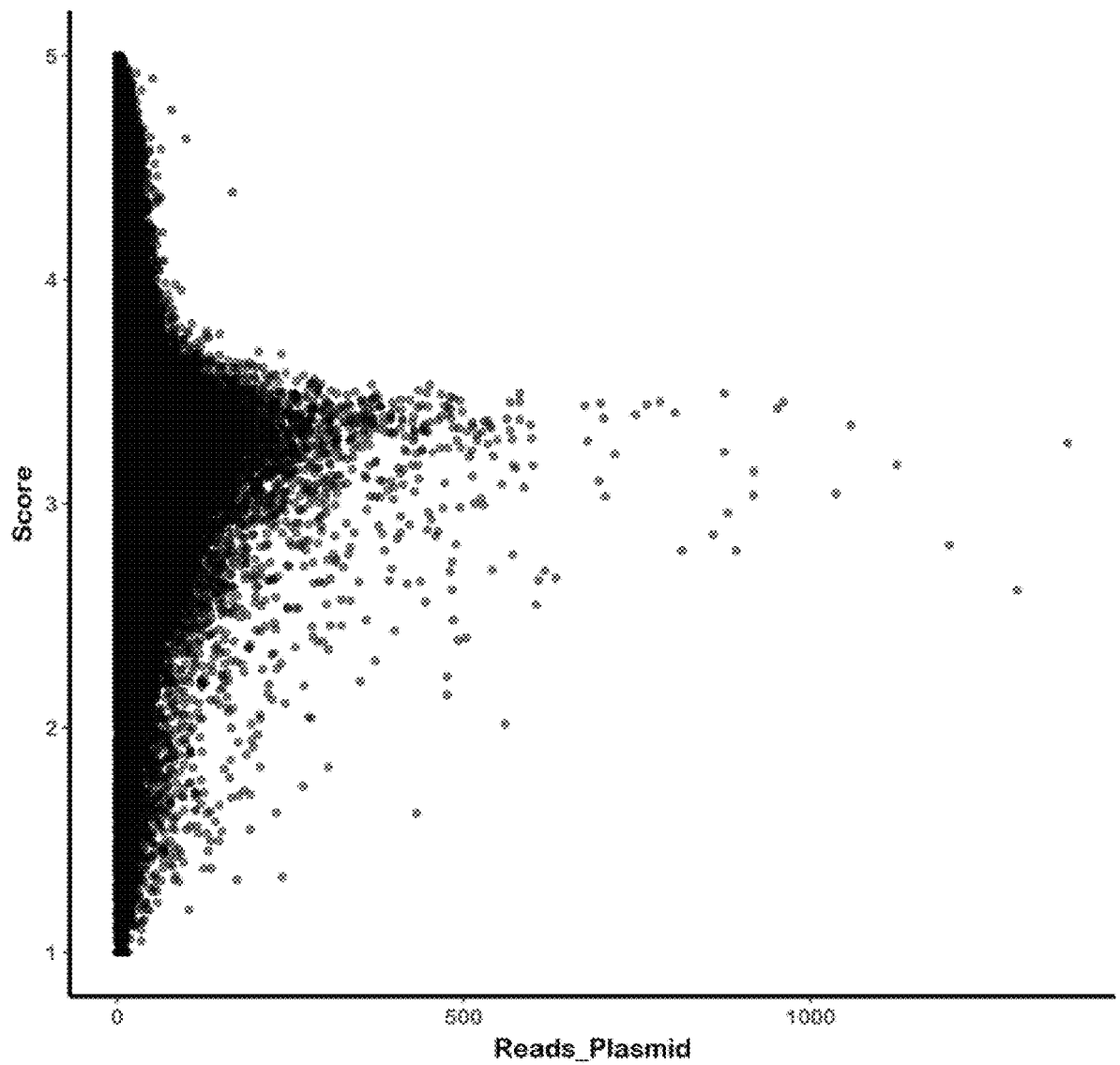
FIG. 5A, FIG. 5B, FIG. 5C, FIG. 5D, and FIG. 5E show results from a reporter system to test the influence of codons 3-5 of an mRNA sequence, and the influence of the first five amino acids of a nascent peptide, on translation efficiency.
Figure 5B:
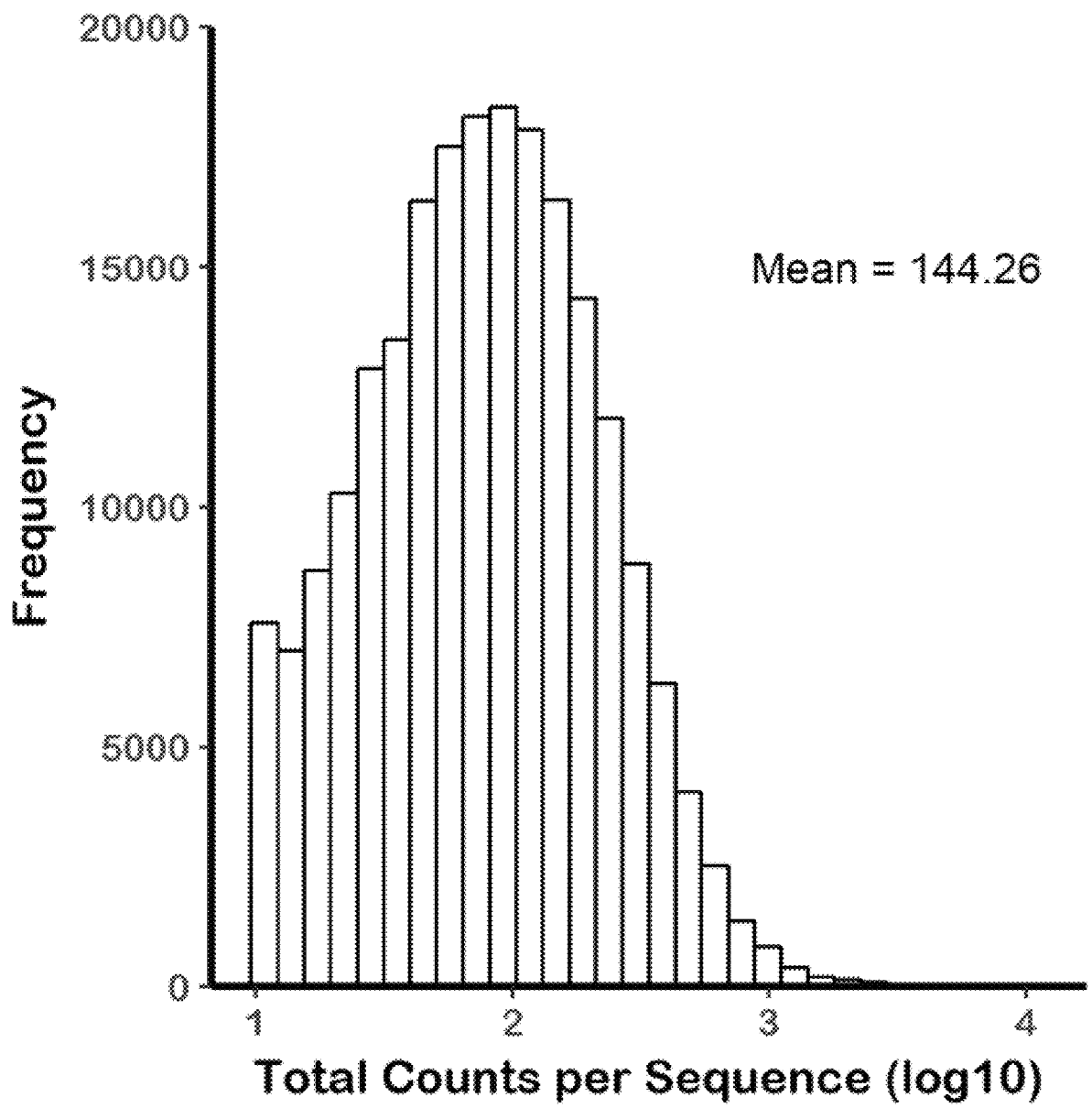
Figure 5C:
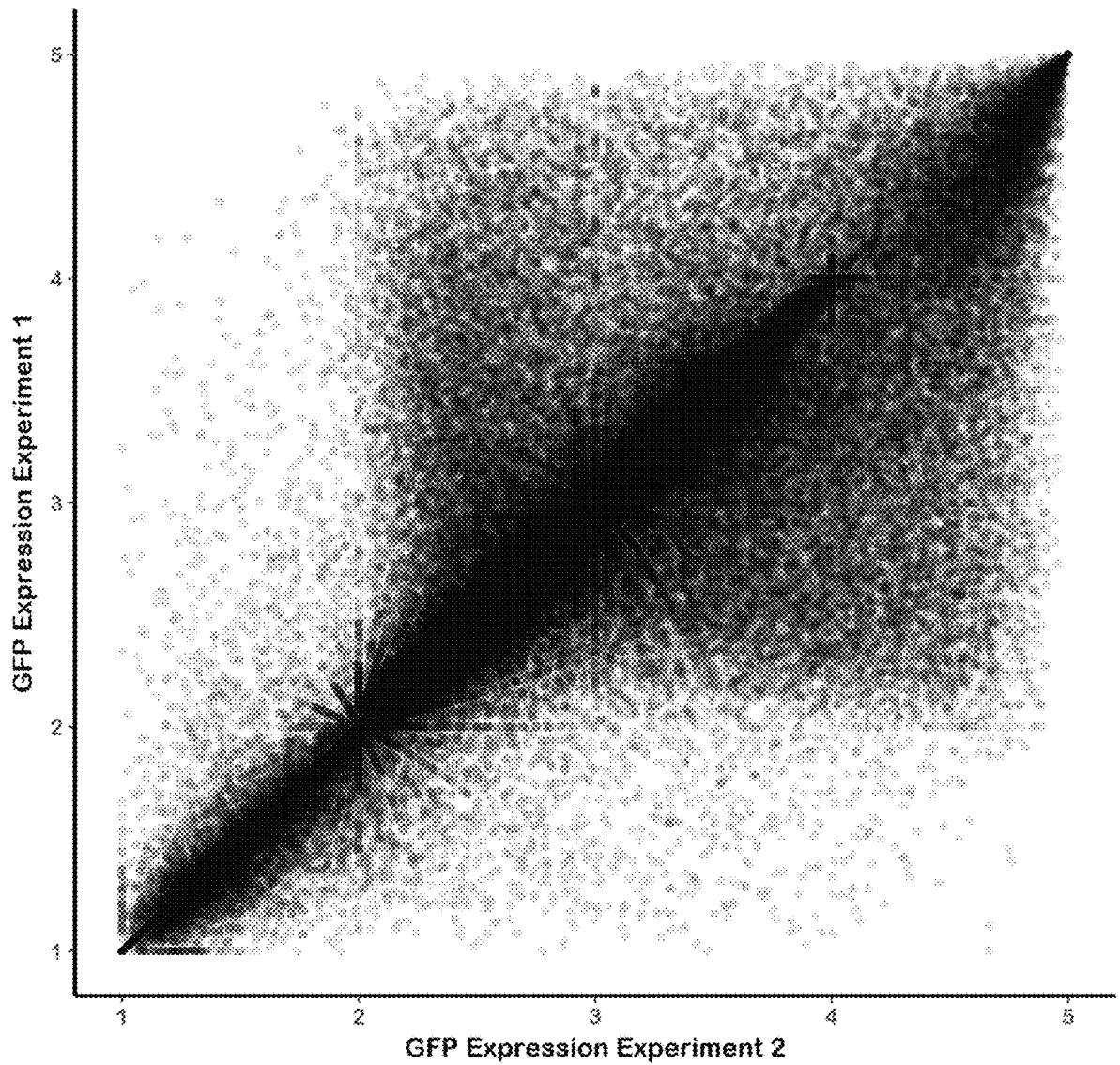
Figure 5D:
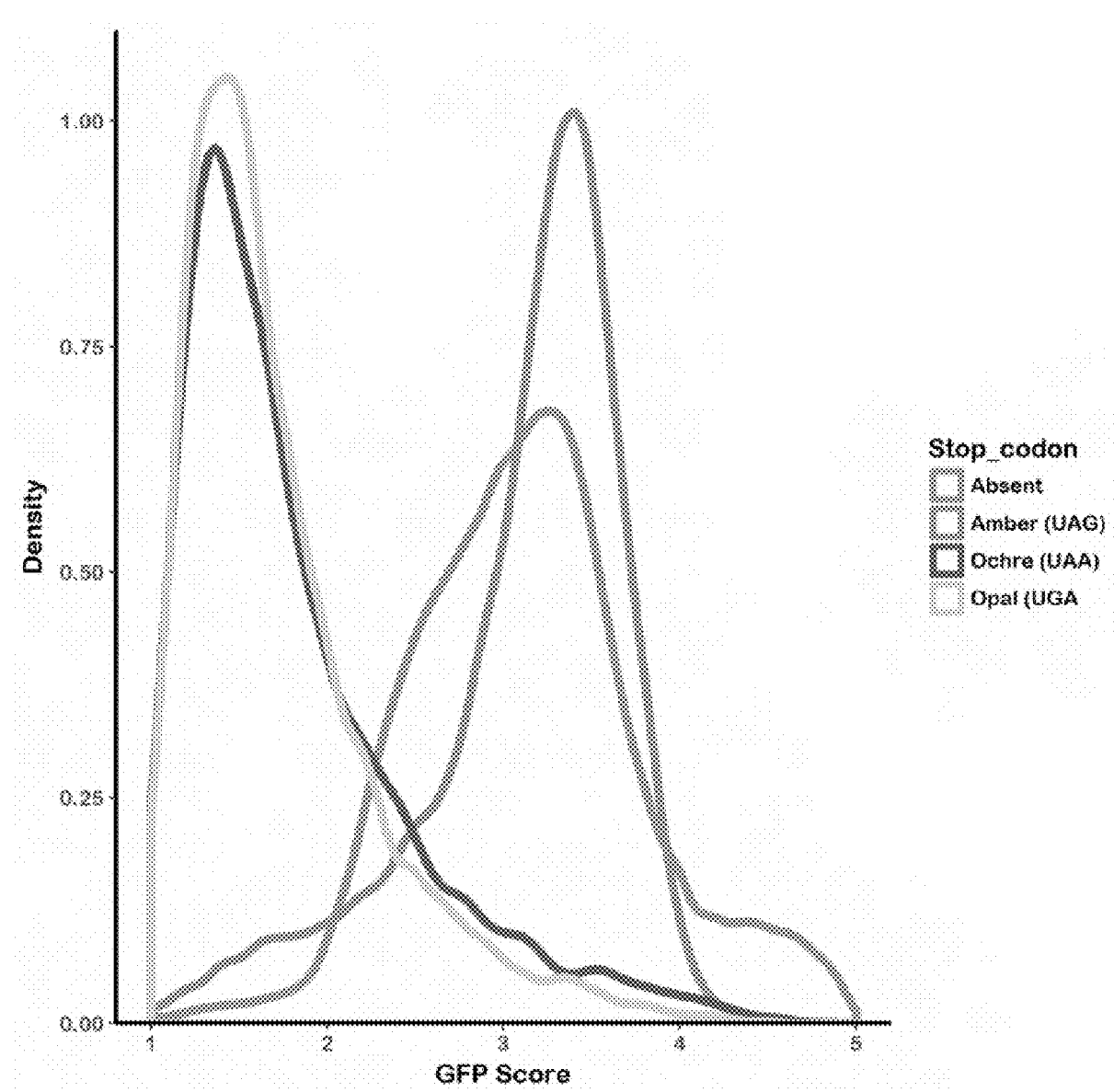
Figure 5E:
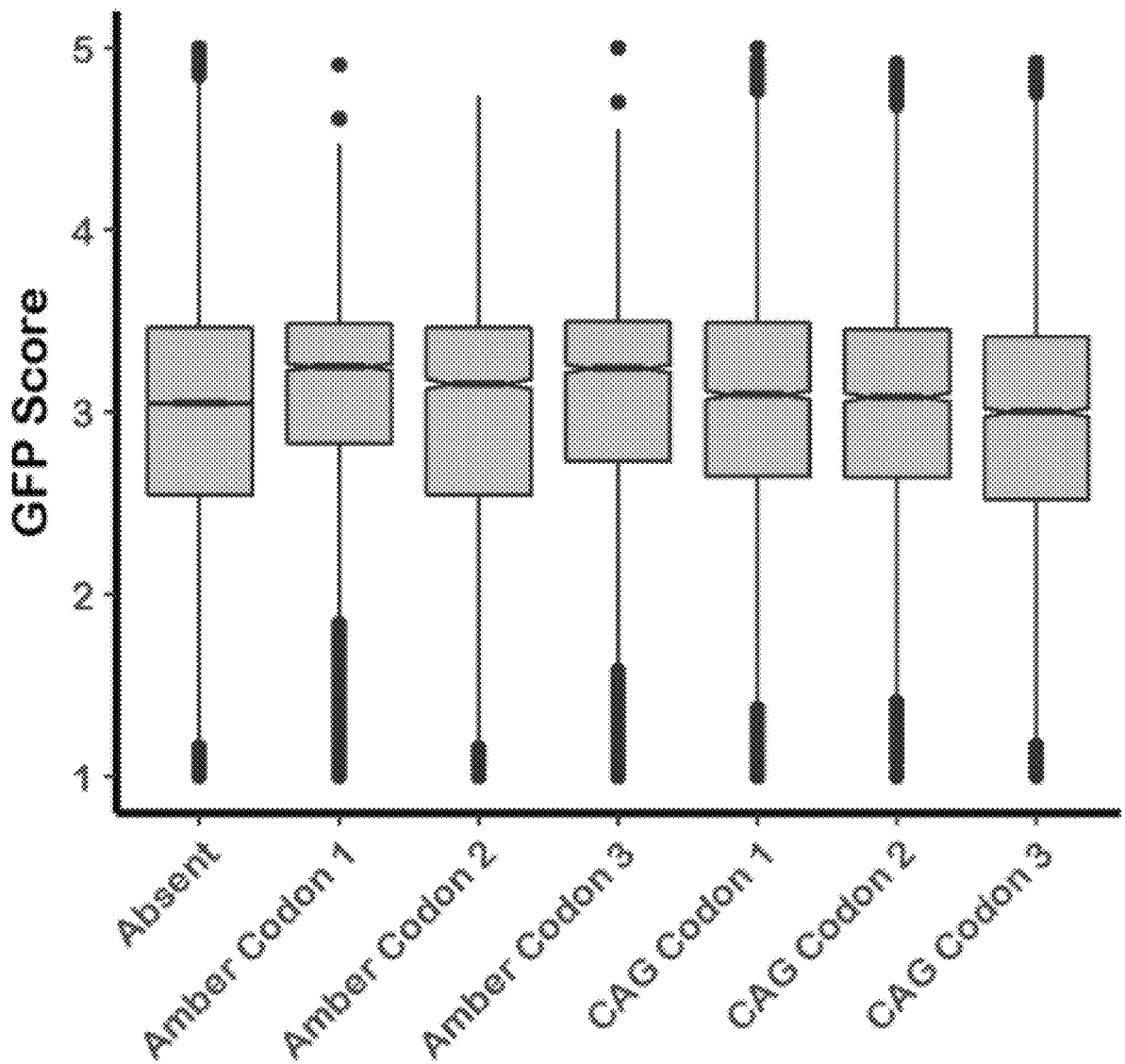
Figure 6A:
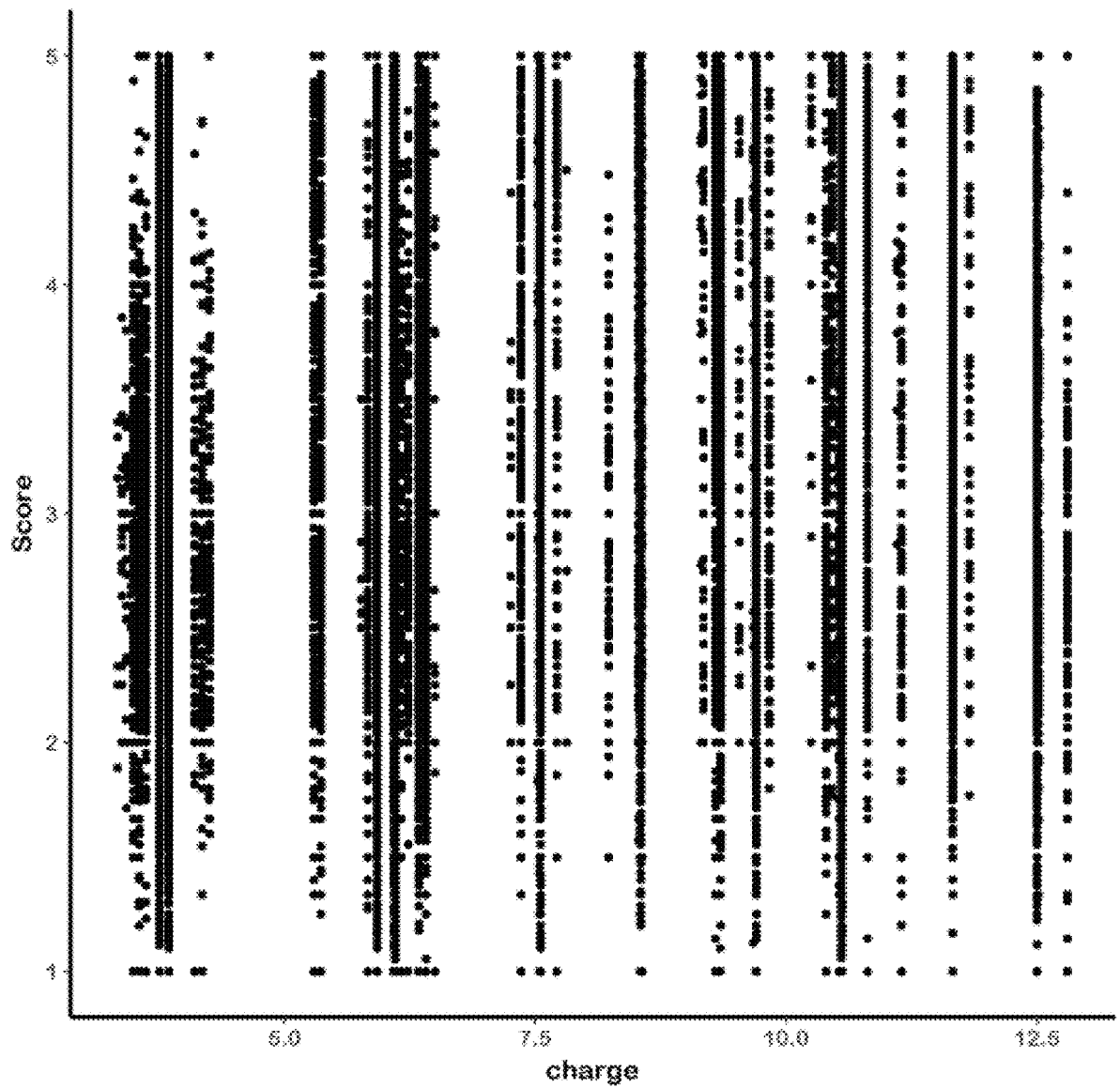
FIG. 6A, FIG. 6B, FIG. 6C, FIG. 6D, and FIG. 6E show that translation efficiency was not correlated with the amino acid charge, hydrophobicity, or tRNA abundance.
Figure 6B:
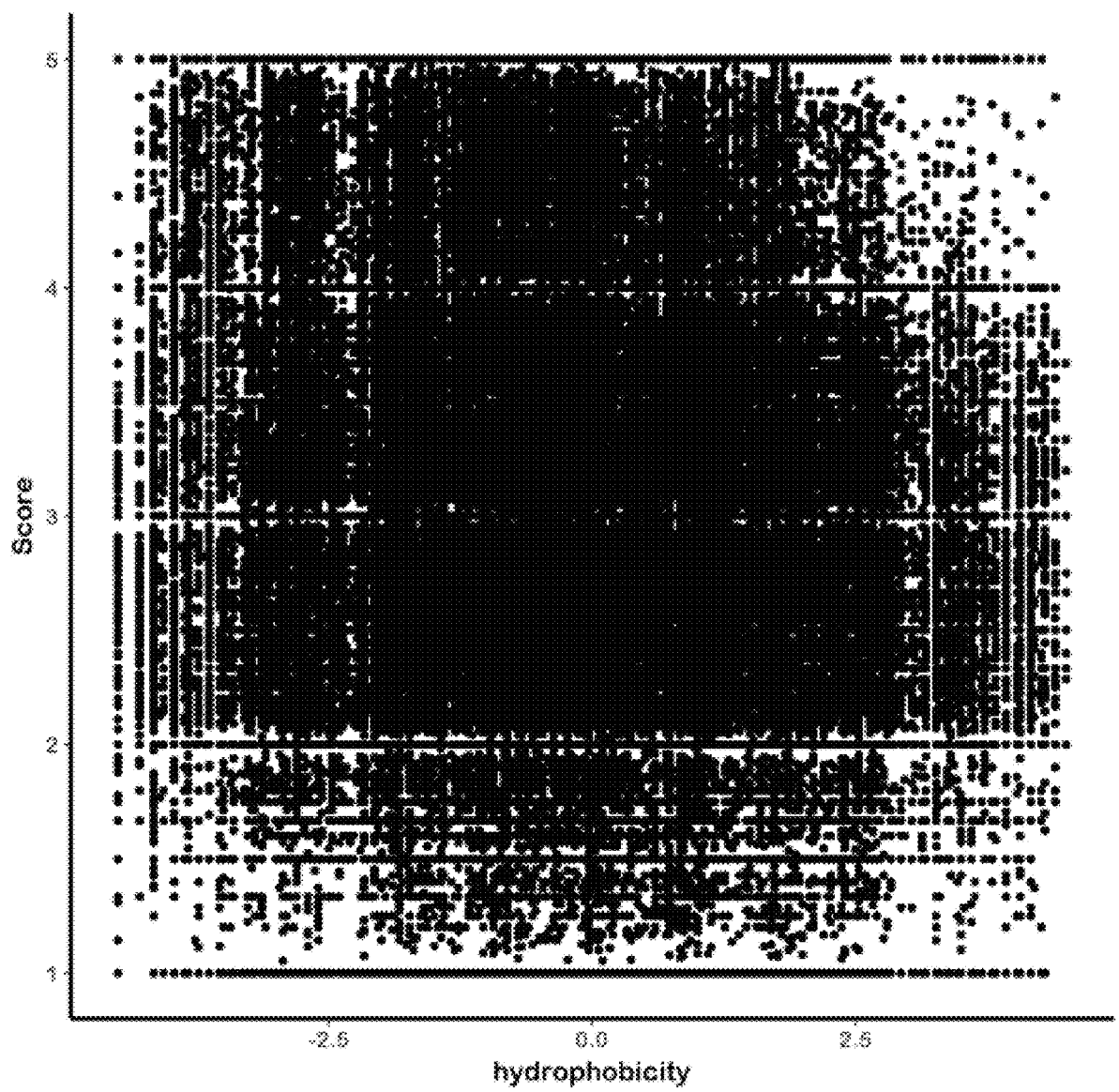
Figure 6C:
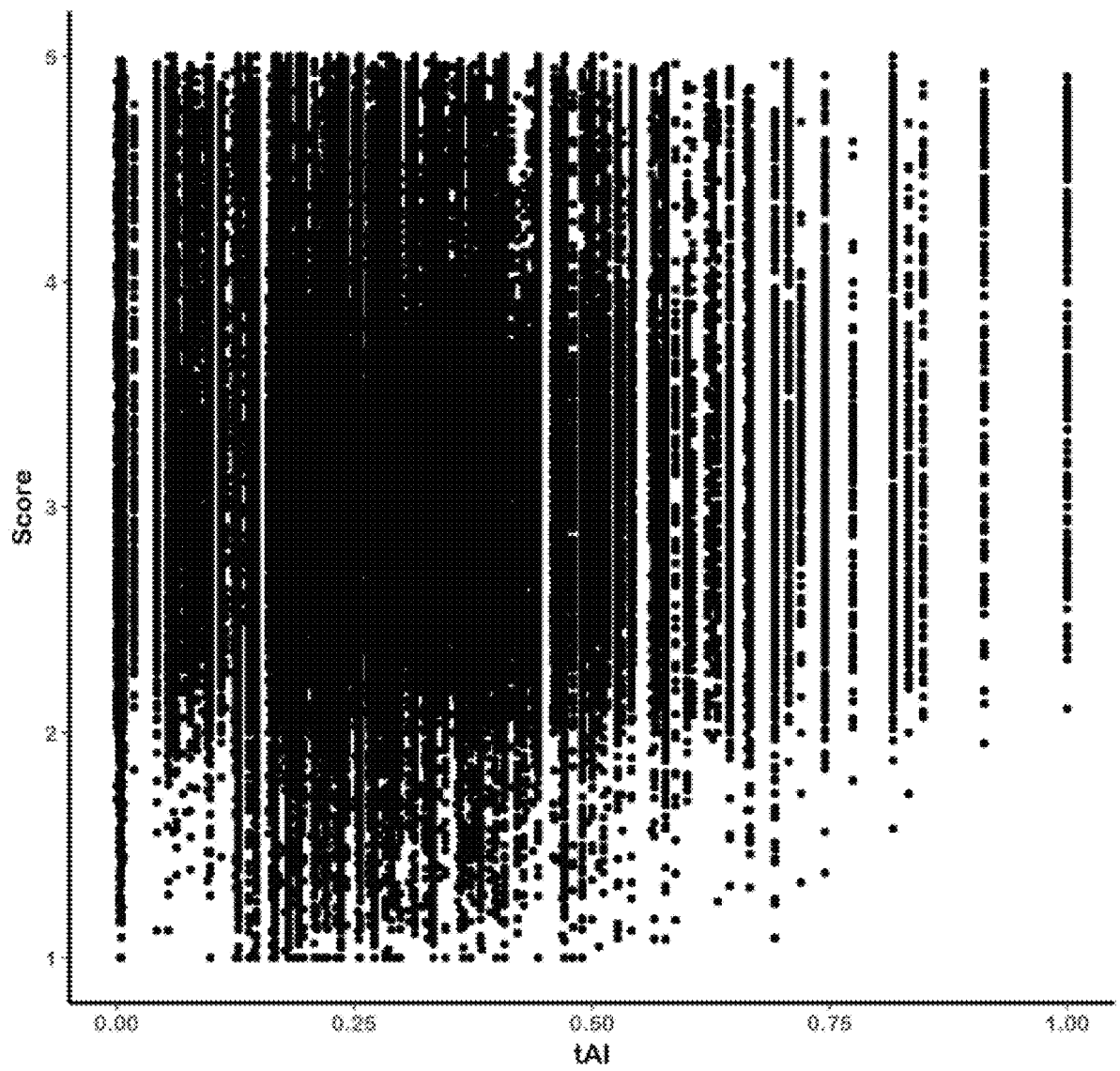
Figure 6D:
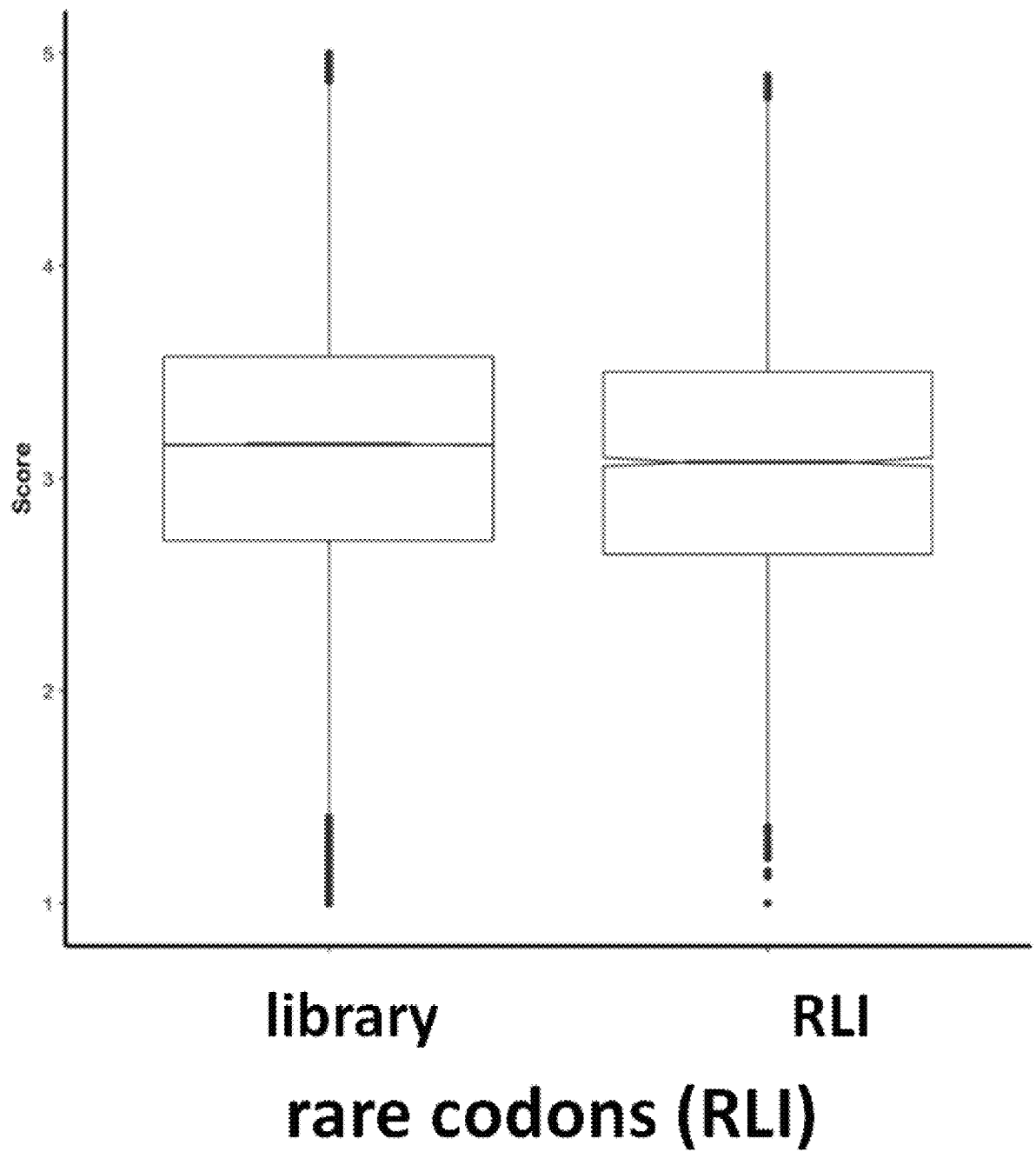
Figure 6E:
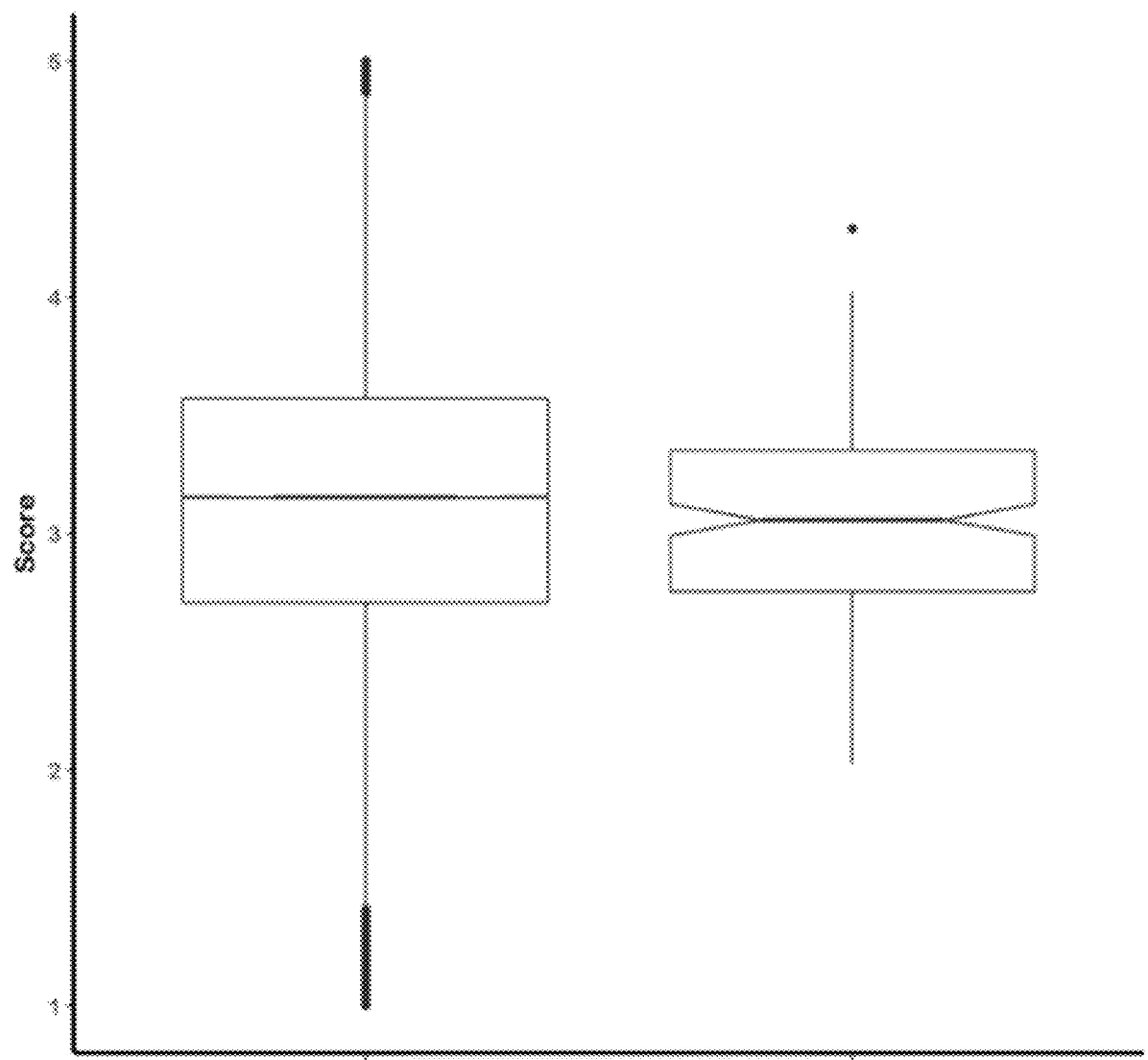
Figure 7A:
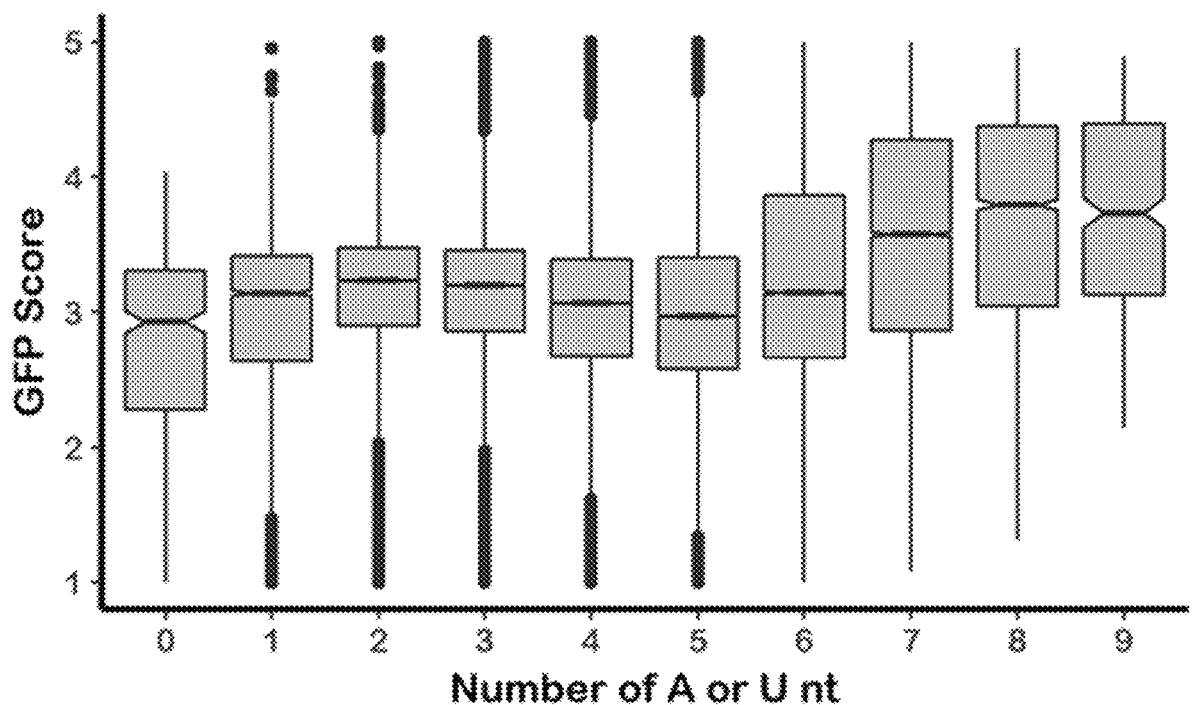
FIG. 7A and FIG. 7B show that translation efficiency was influenced by mRNA sequence and structure.
Figure 7B:
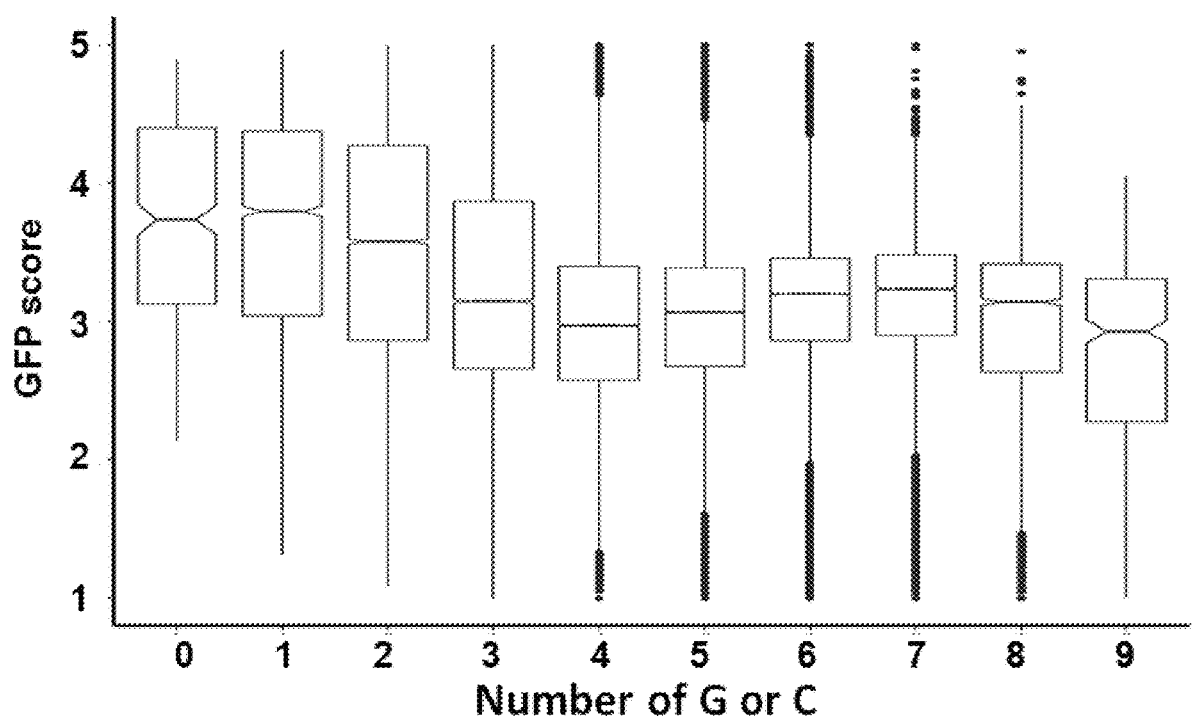
Figure 8A:
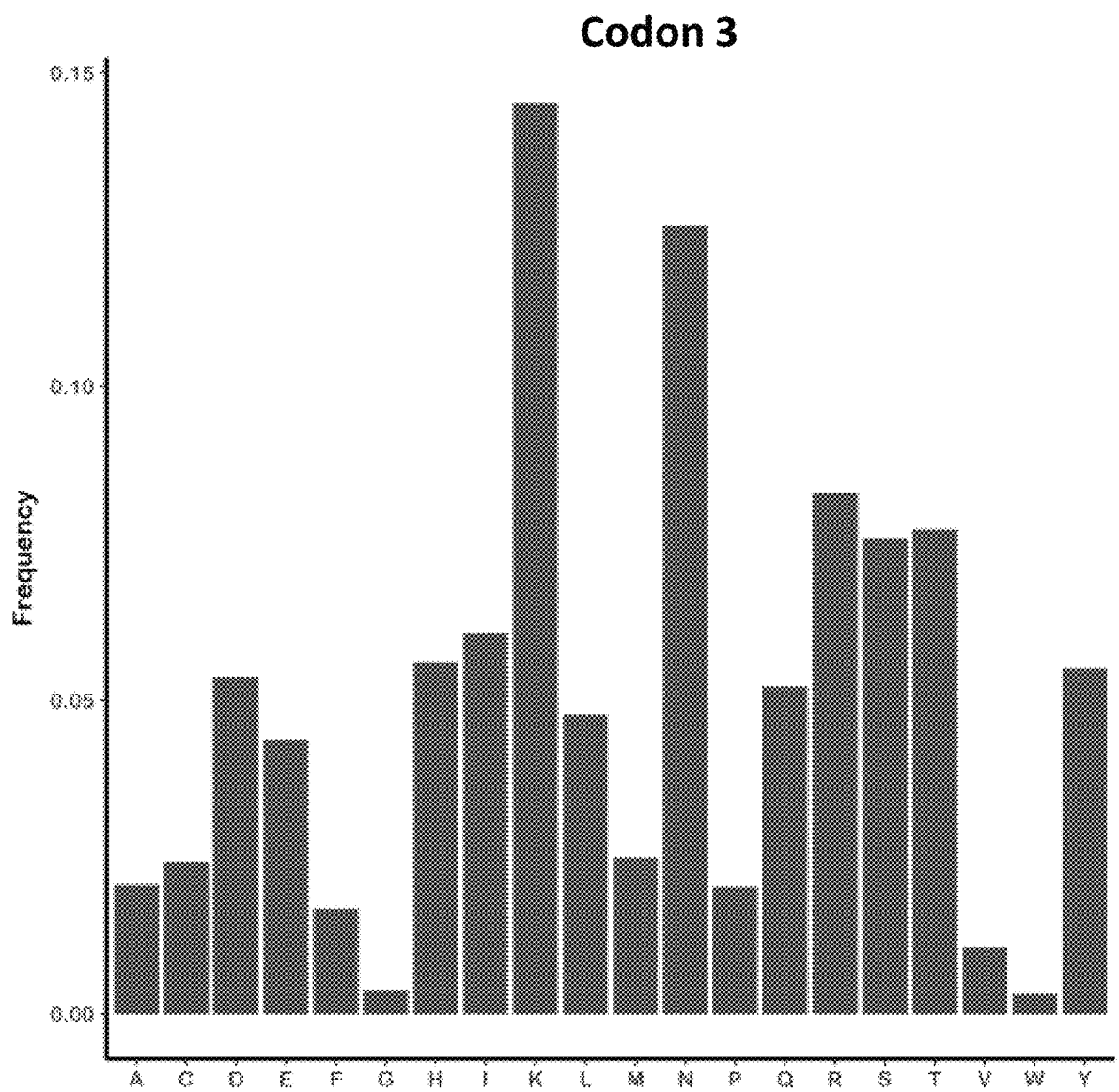
FIG. 8A graphically depicts the distribution of AU richness in the library. On the y-axis is the GFP score, and on the x-axis is the number or A or U nucleotides in a given 9nt sequence. A small shift is observed for 7, 8, and 9, which corresponds to an average GFP score shift from 3 to 3.5.
Figure 8B:
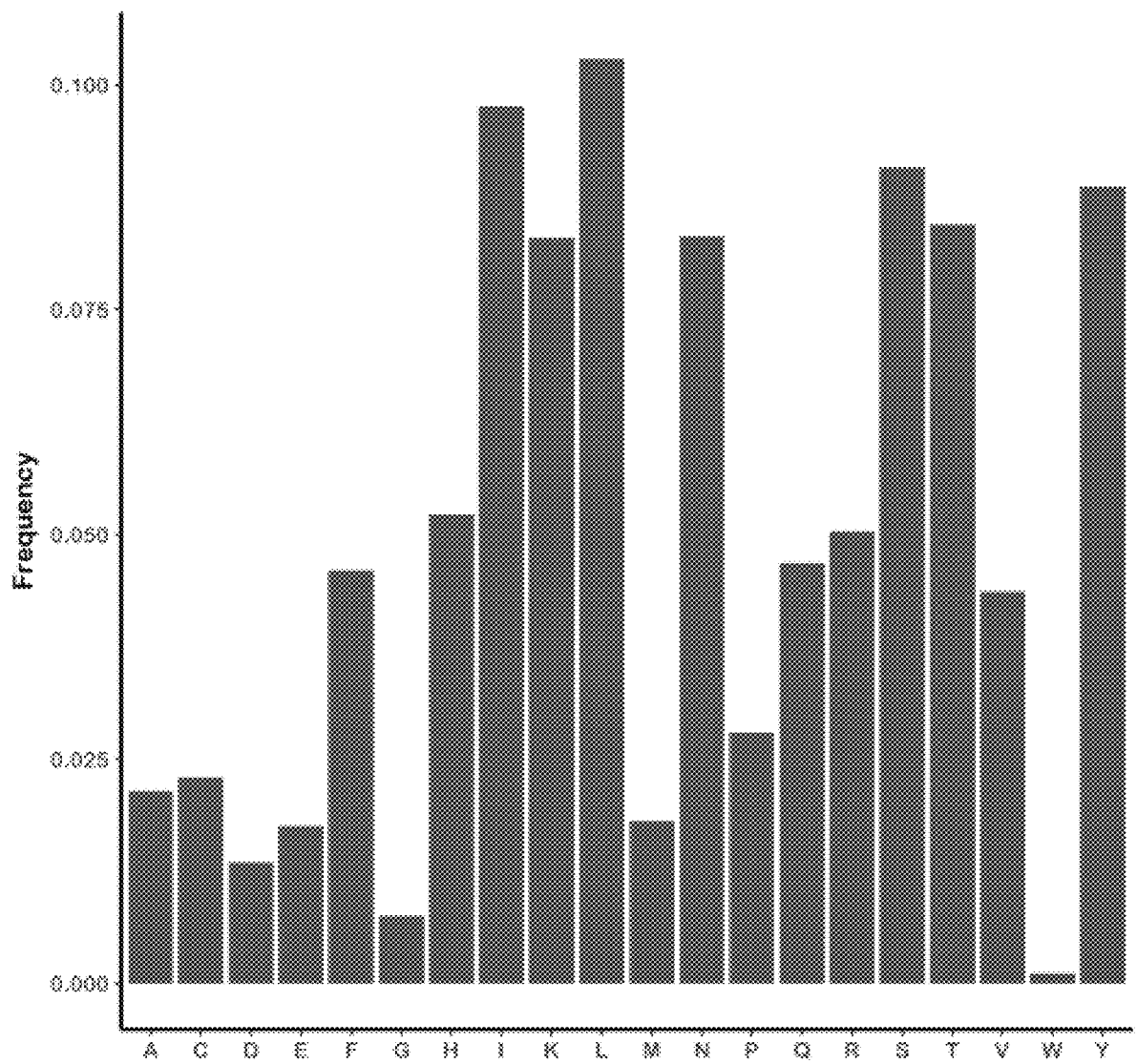
FIG. 8B graphically depicts the distribution of GC richness in the library. On the y-axis is the GFP score, and on the x-axis is the number or G or C nucleotides in a given 9nt sequence. A small shift is observed for 7, 8, and 9, which corresponds to an average GFP score shift from 3.5 to 3. The GC shift is inverted compared to the AU shift. Without wishing to be bound by theory, G:C pairs are thought to contribute more to mRNA structure than A:U because three hydrogen bonds are made in a G:C pair while two hydrogen bonds are made in an A:U pair.
Figure 8C:
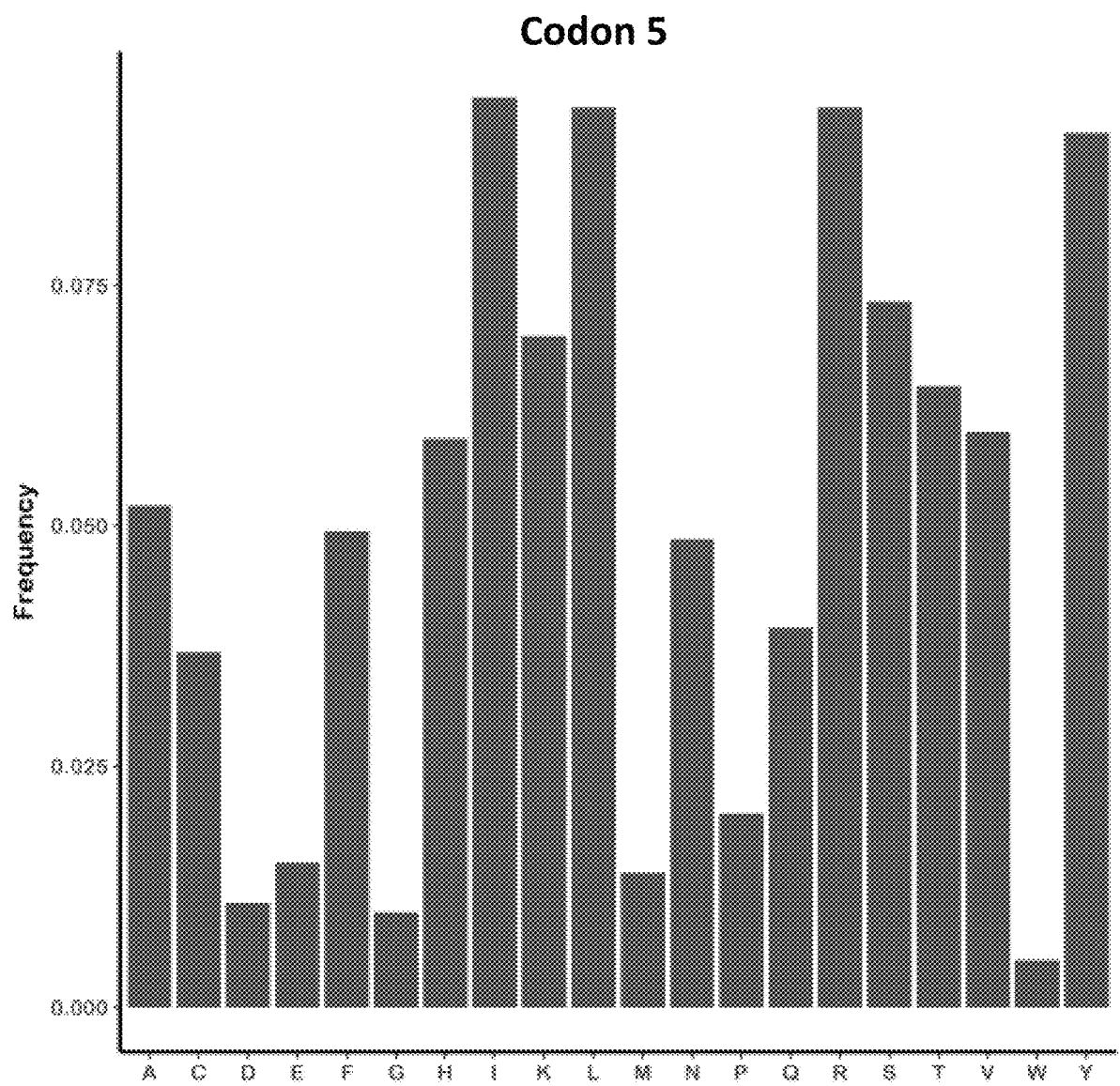
Figure 8D:
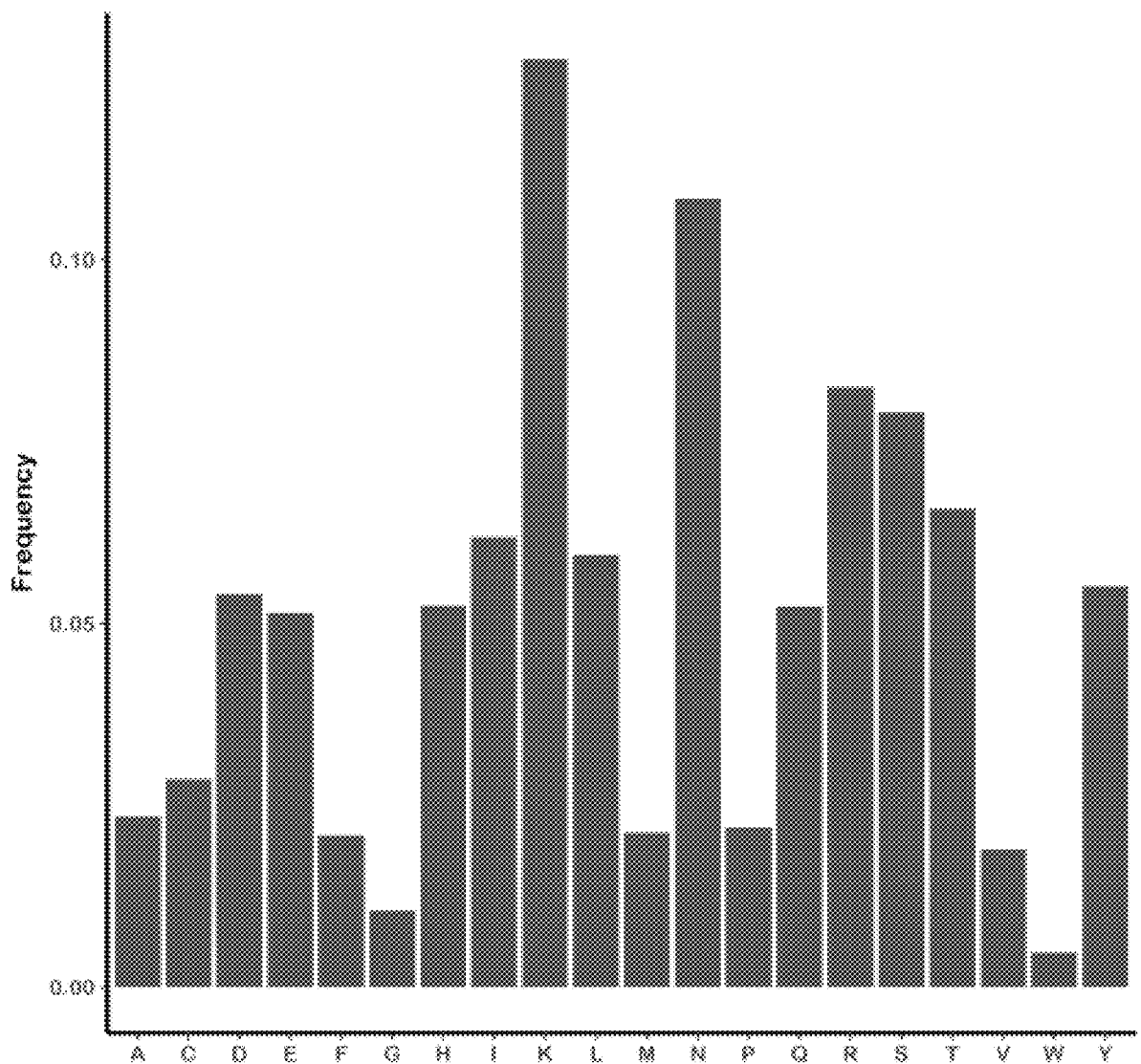
Figure 8E:
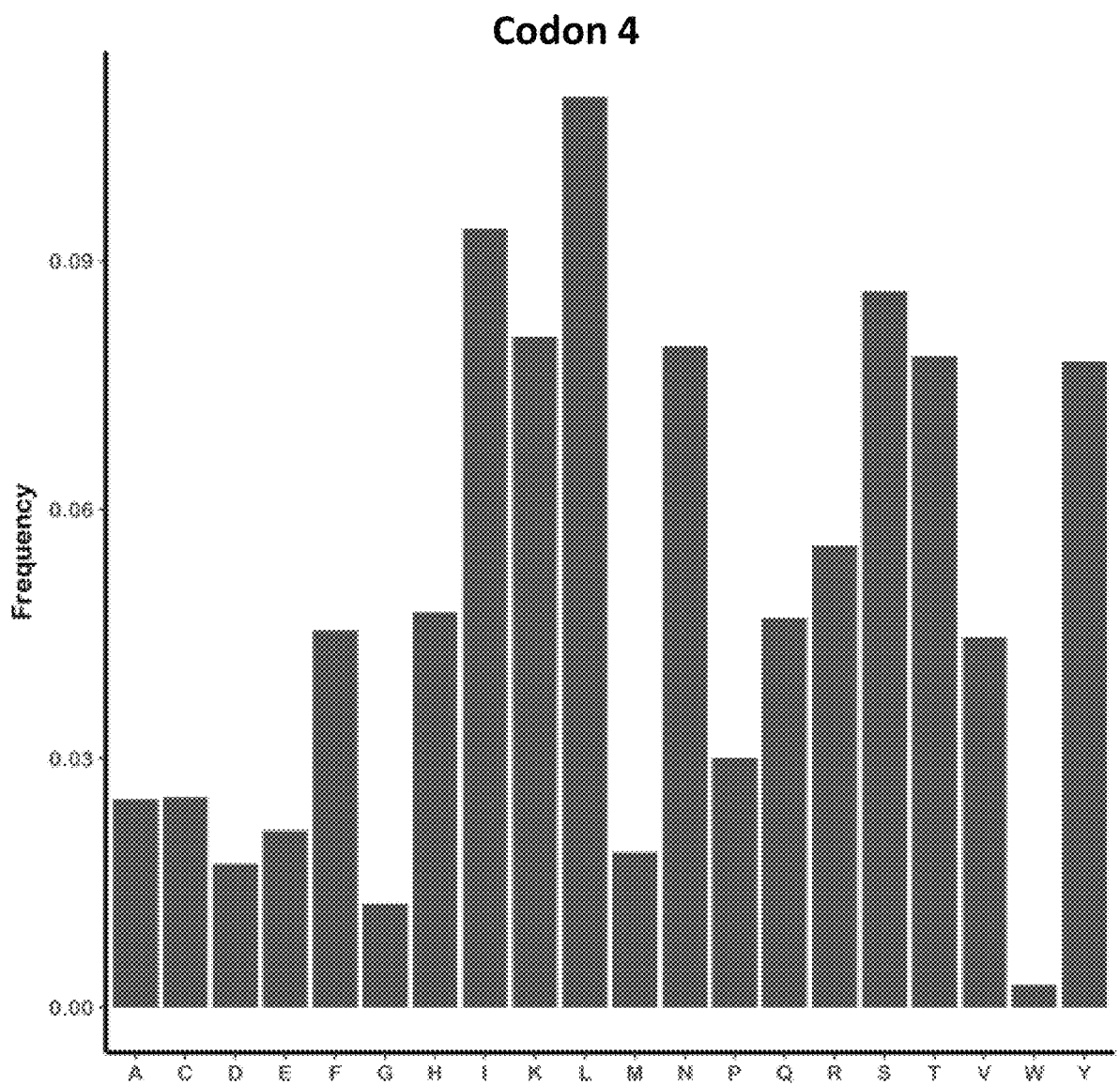
Figure 8F:
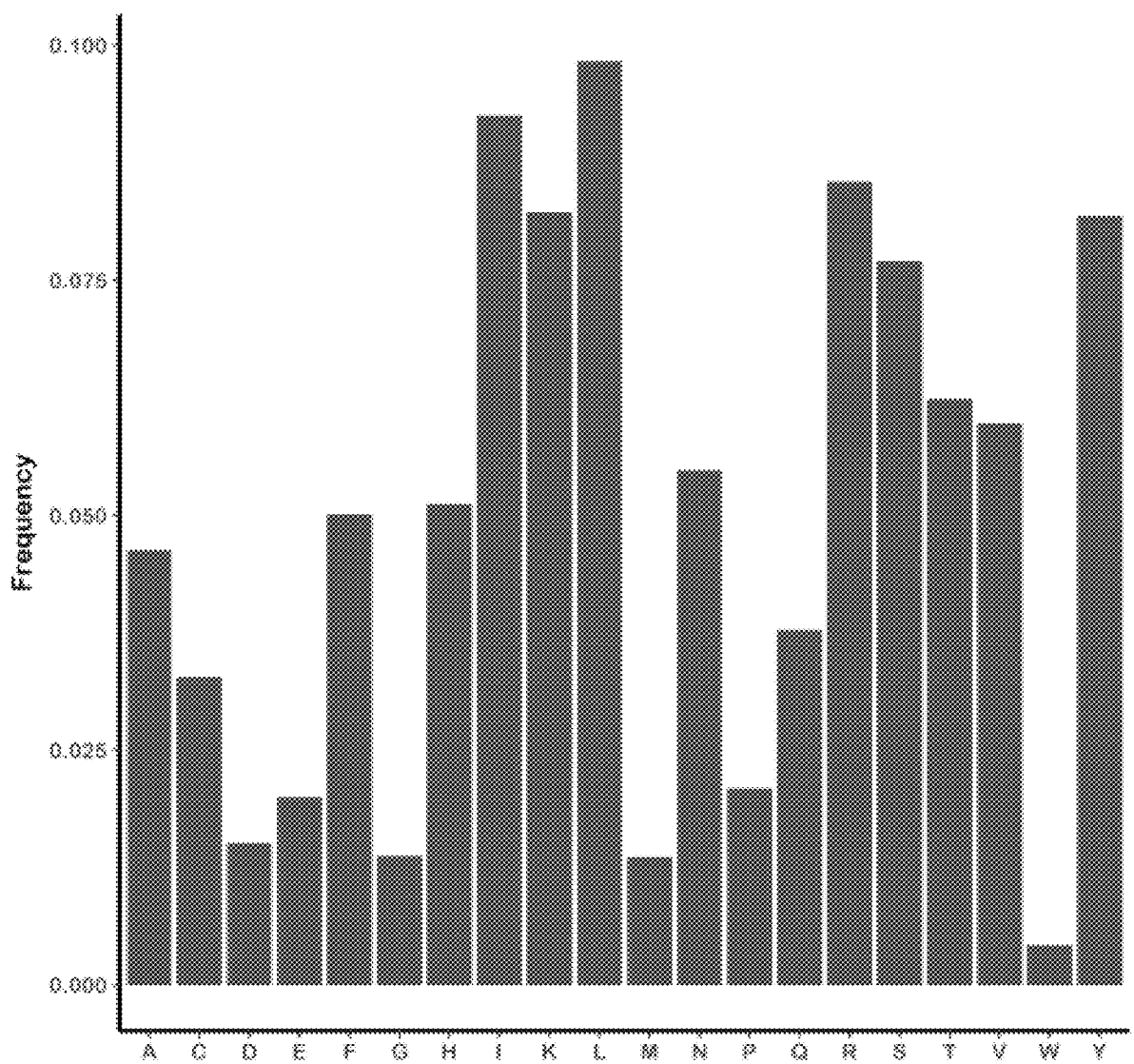
Figure 9A:
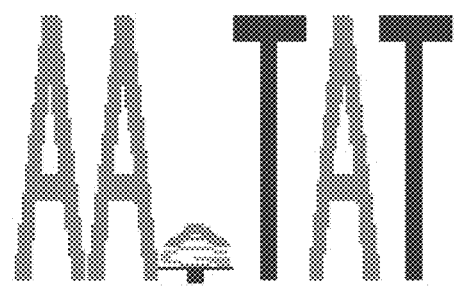
FIG. 9A, FIG. 9B, FIG. 9C, FIG. 9D, FIG. 9E, and FIG. 9F show that the motifs AADTAT and AAVATT each increase translation efficiency. A MEME analysis of RNA/DNA sequences of high expressing EGFP variants identified two motifs, AADTAT (FIG. 9A) and AAVATT (FIG. 9D). Briefly, the analysis was done on the complete library set of 230,000 sequences and their GFP scores using R package motif RG and MEME. Sequences with GFP score above 4 ("high expressing") were selected with a background of all sequences with GFP score 3 and below.
Figure 9B:
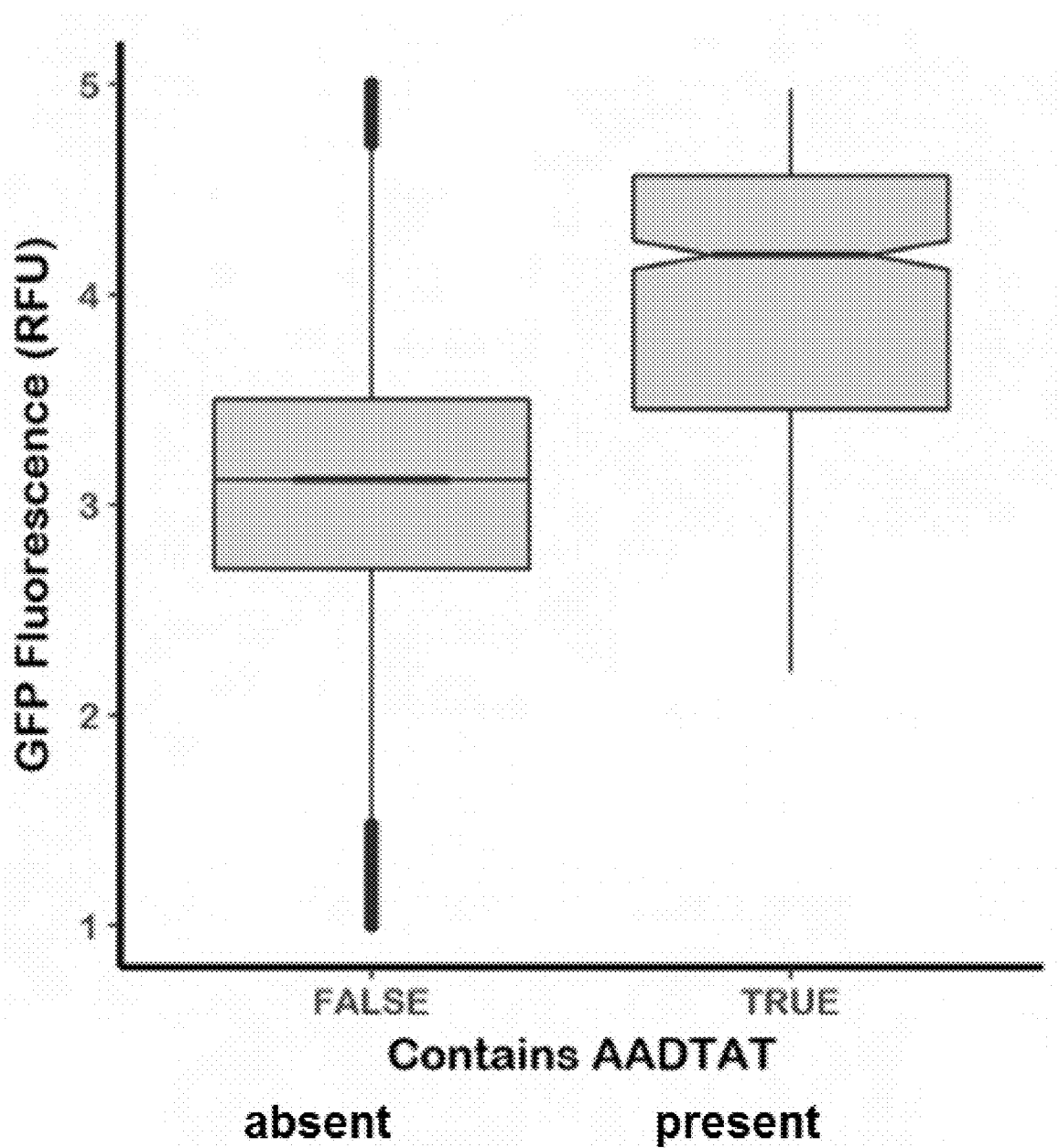
Figure 9C:
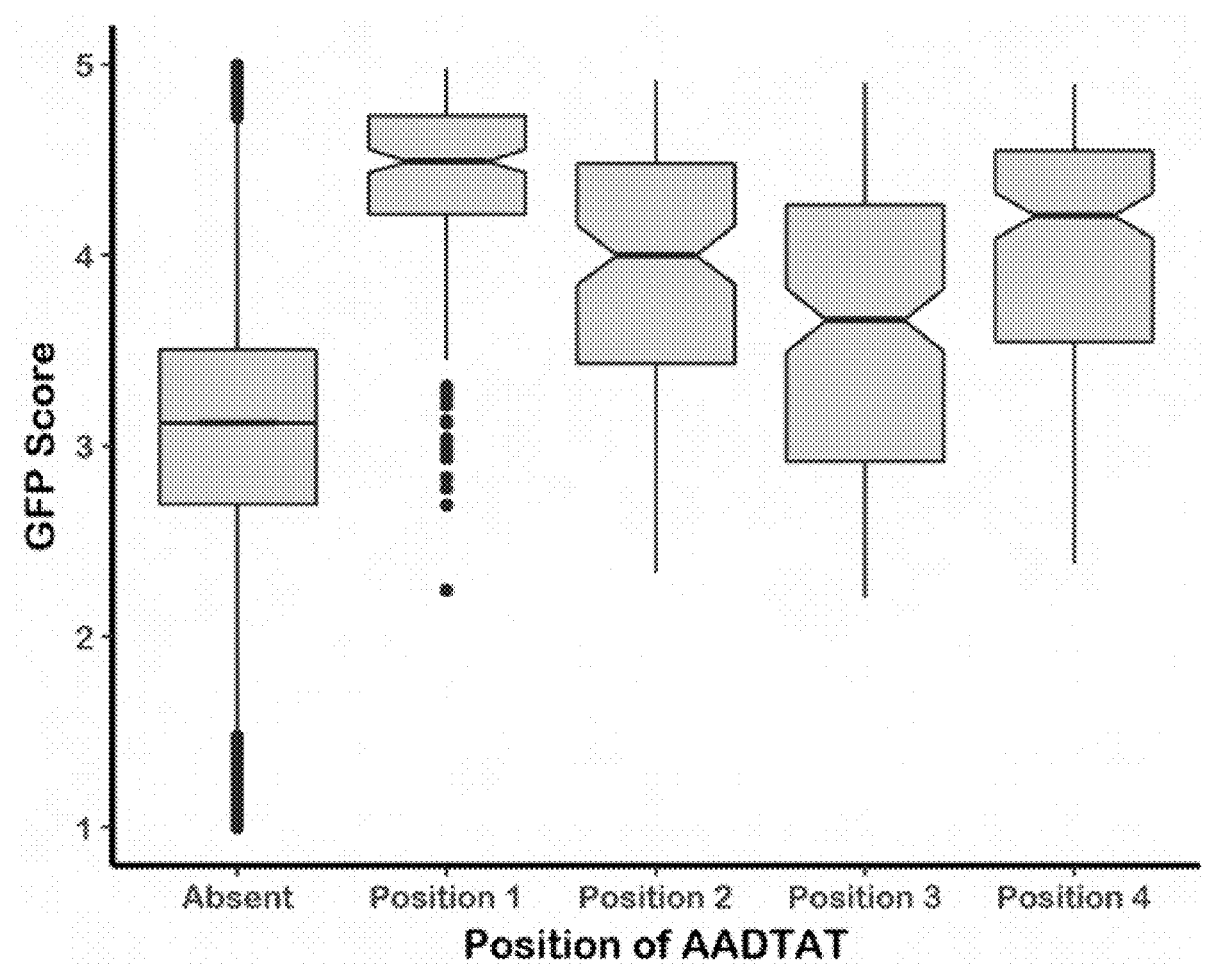
Figure 9D:
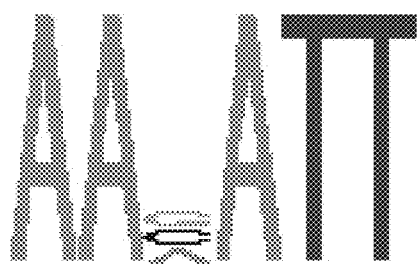
Figure 9E:
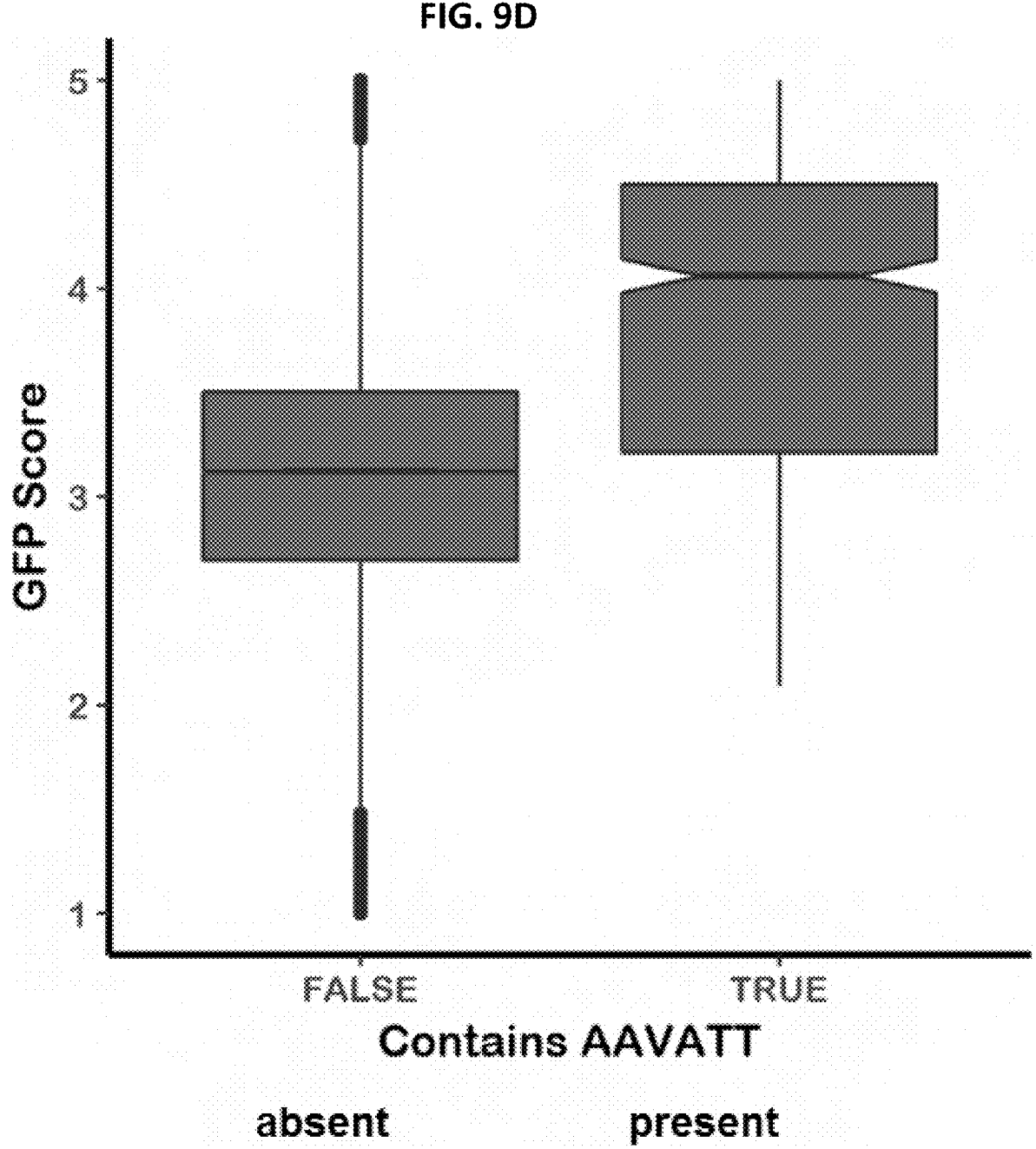
Figure 9F:
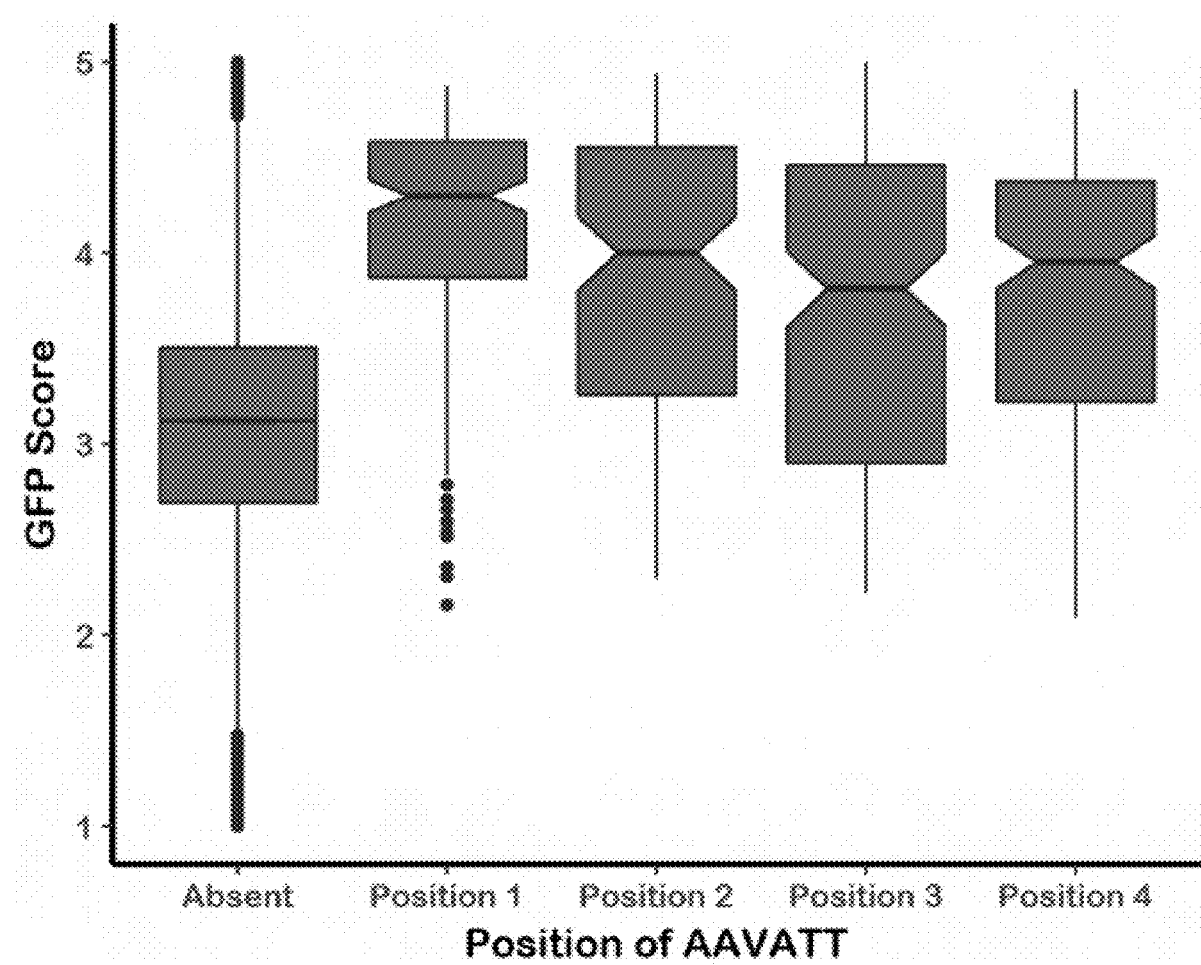
Figure 10A:
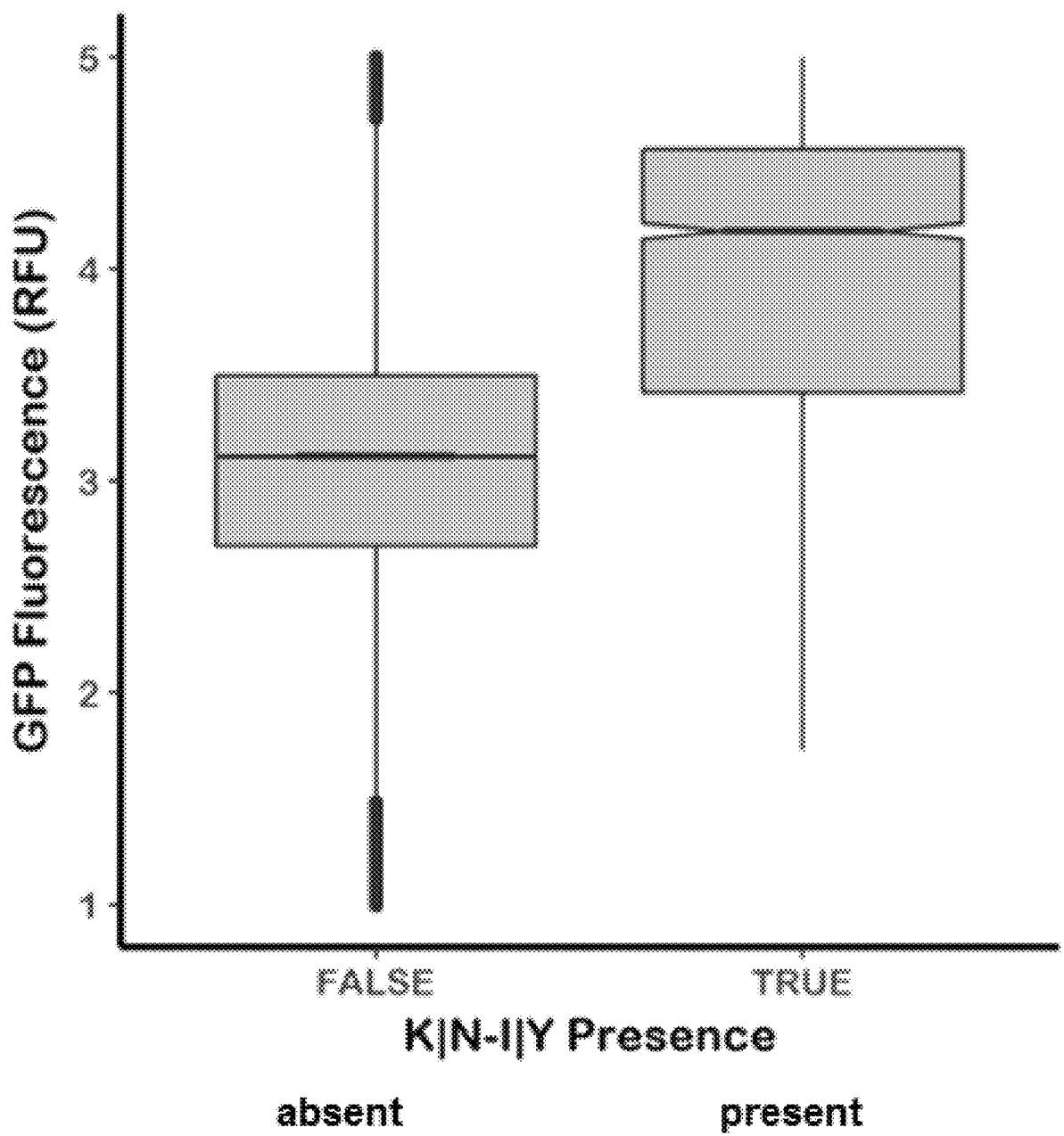
FIG. 10A, FIG. 10B, FIG. 10C, and FIG. 10D show that the motifs AADTAT and AAVATT each increase translation efficiency.
Figure 10B:
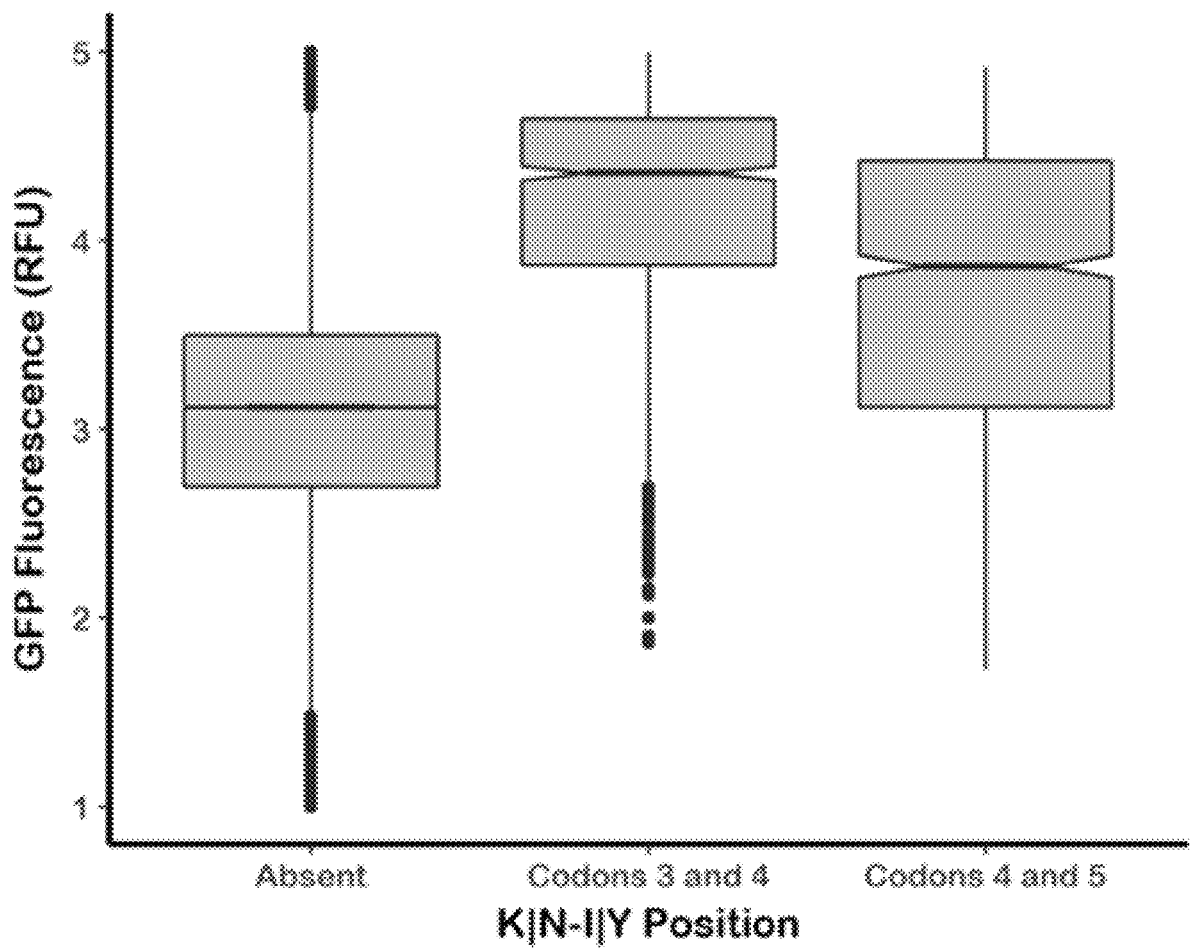
Figure 10C:
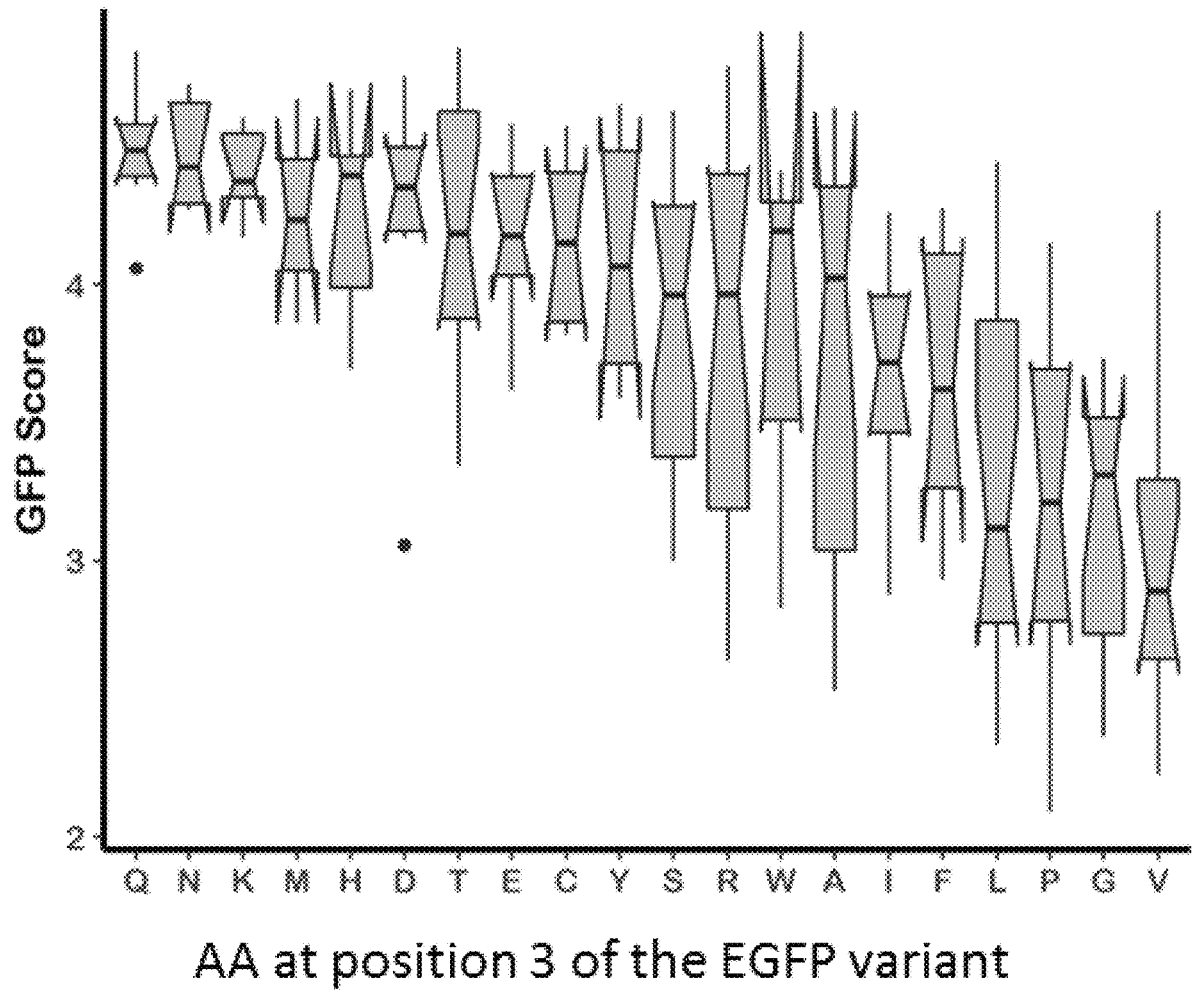
Figure 10D:
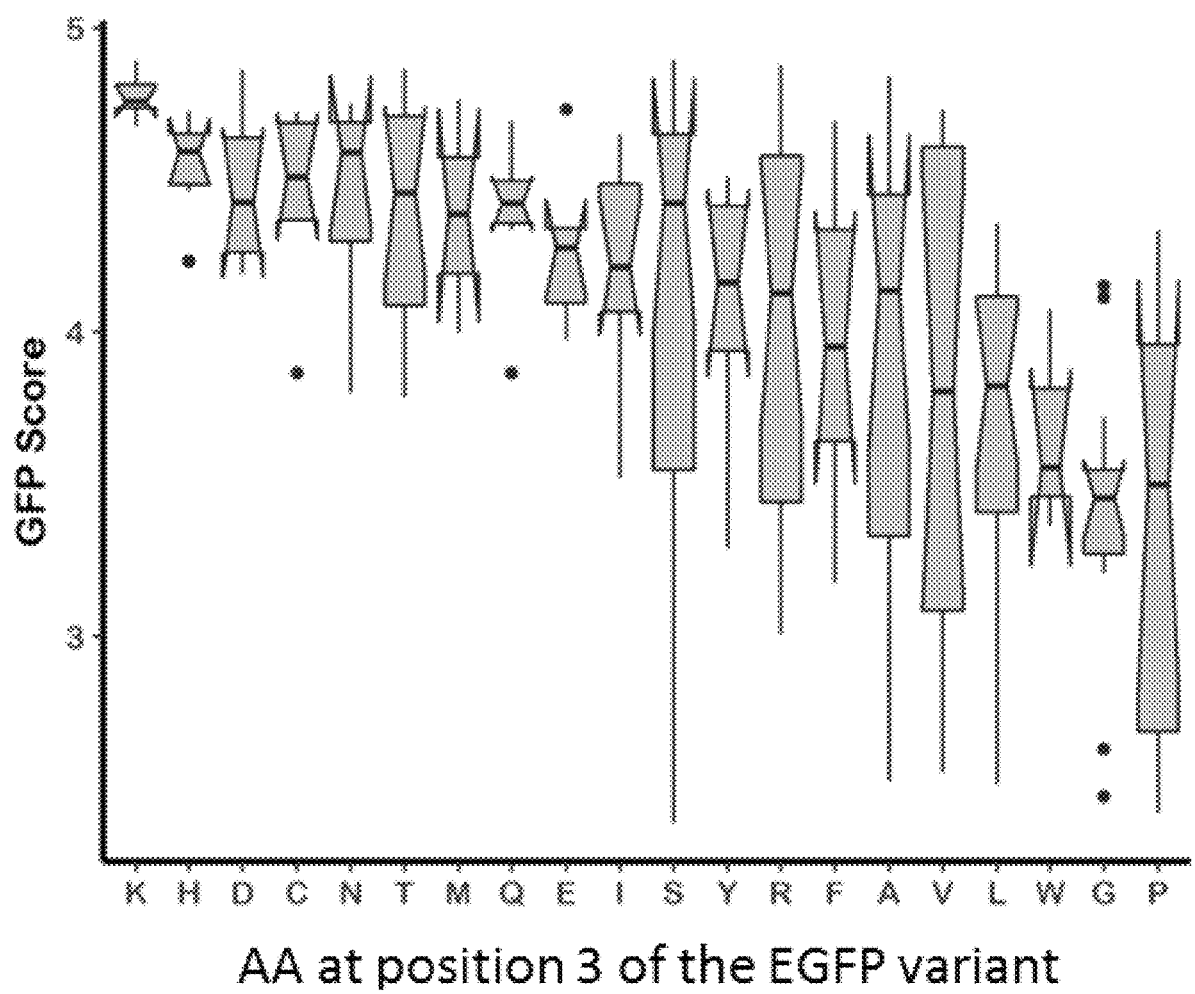
Figure 11A:
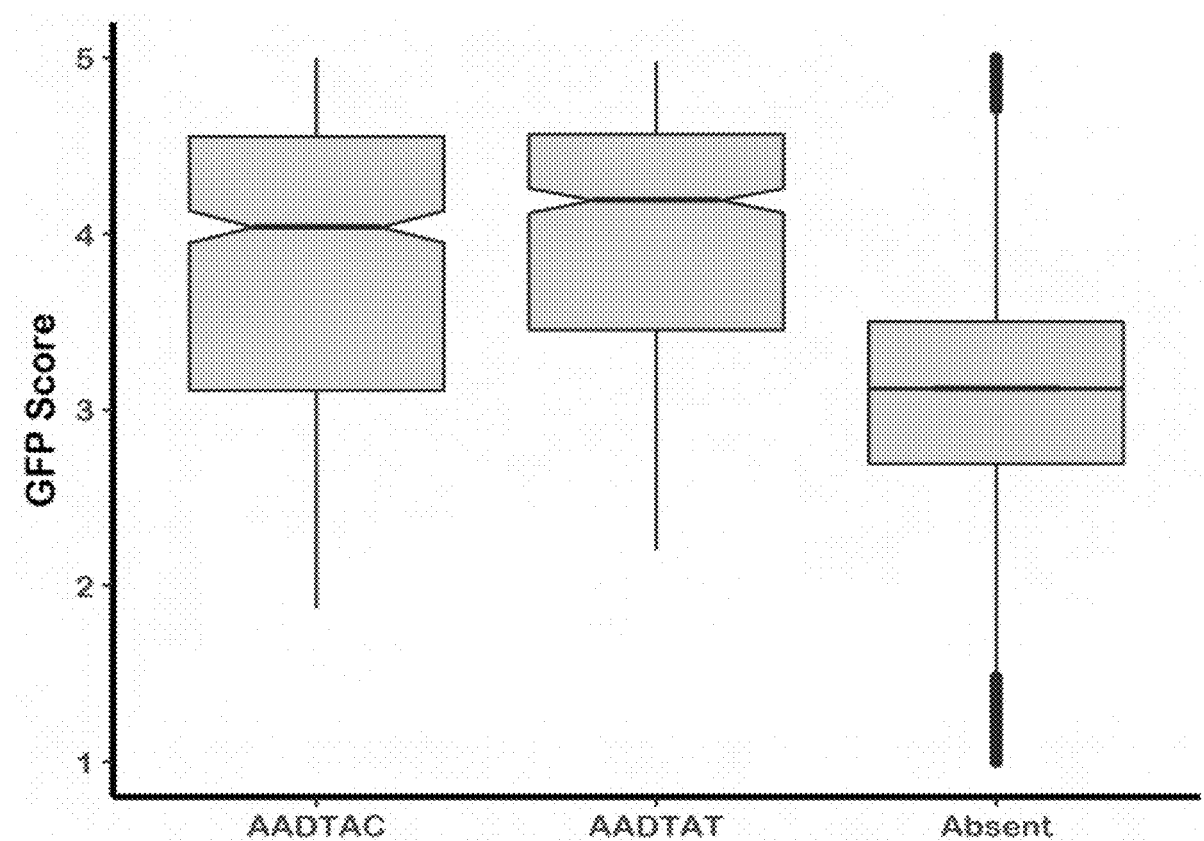
FIG. 11A, FIG. 11B, and FIG. 11C show the influence of tRNA:mRNA pairs on the GFP score.
Figure 11B:
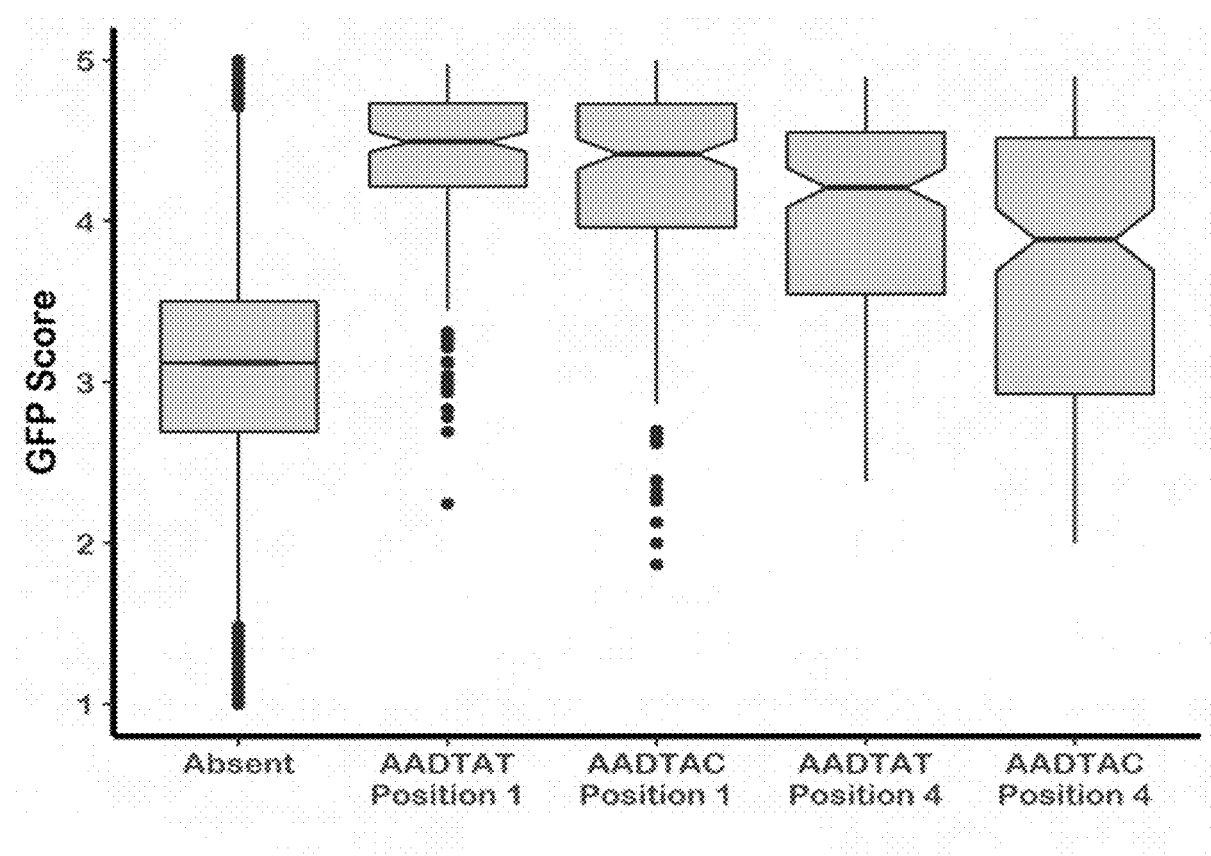
Figure 11C:
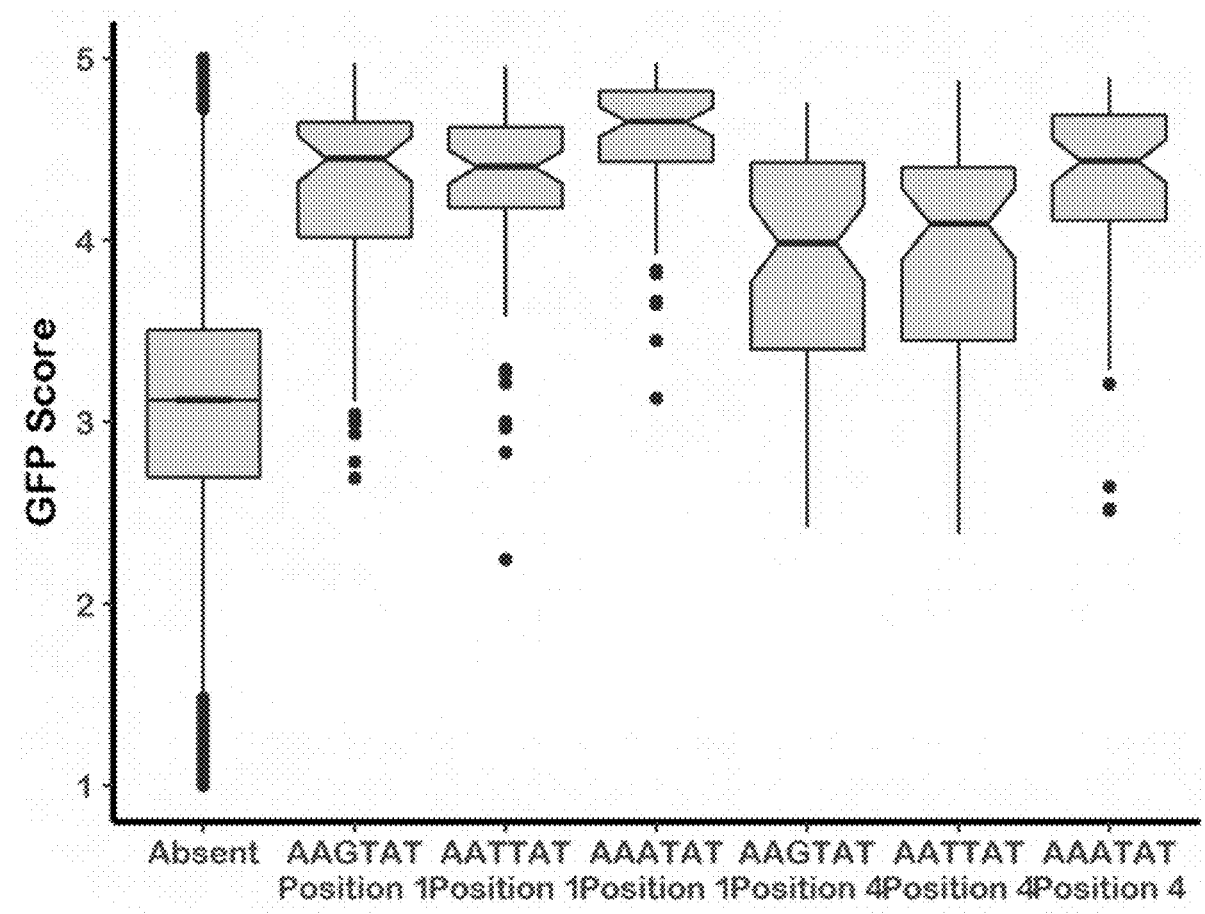
Figure 12A:
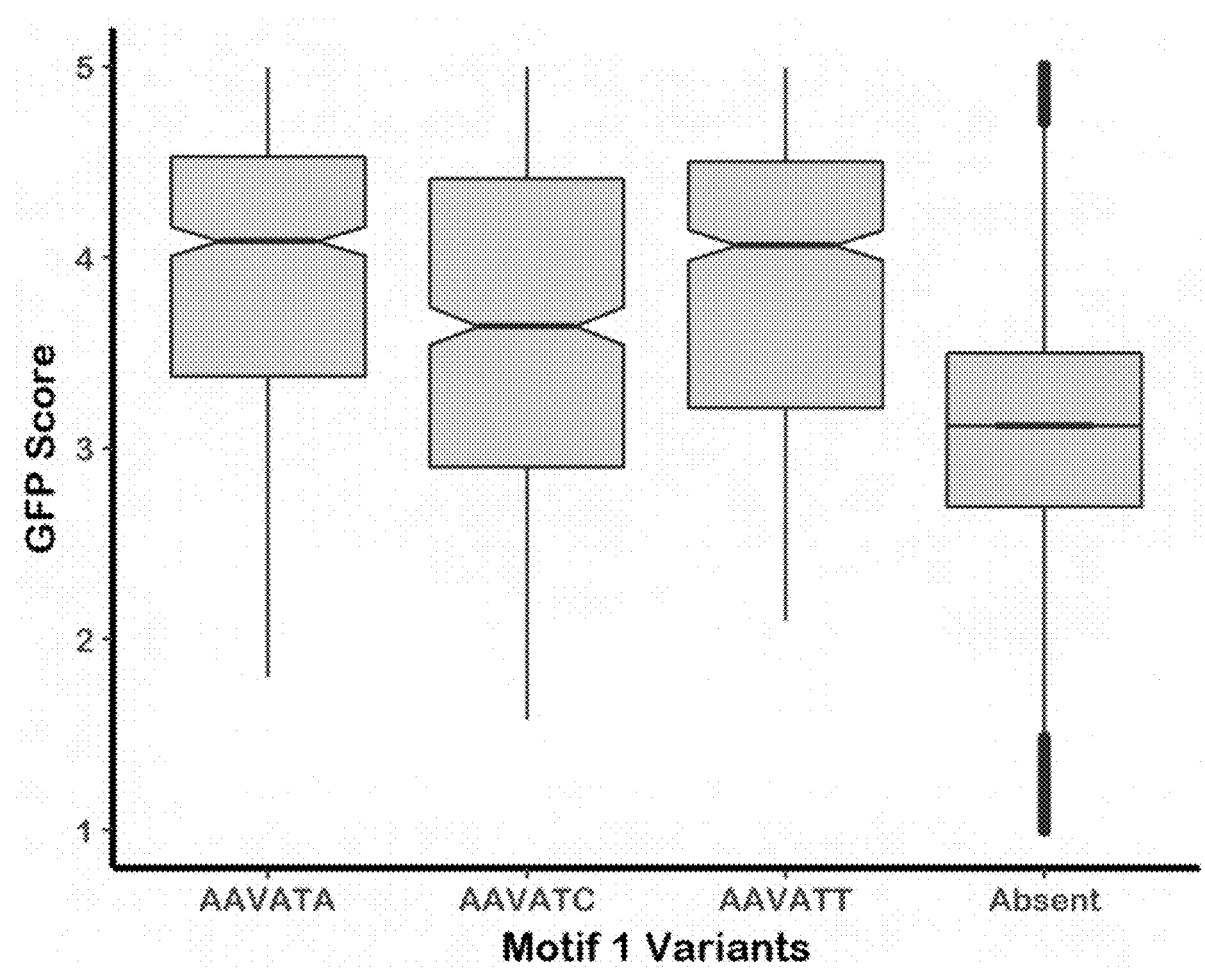
FIG. 12A and FIG. 12B graphically depict the influence of Ile tRNA:mRNA pairs on the distribution of GFP scores for 9nt sequences with the AAVATT motif.
Figure 12B:
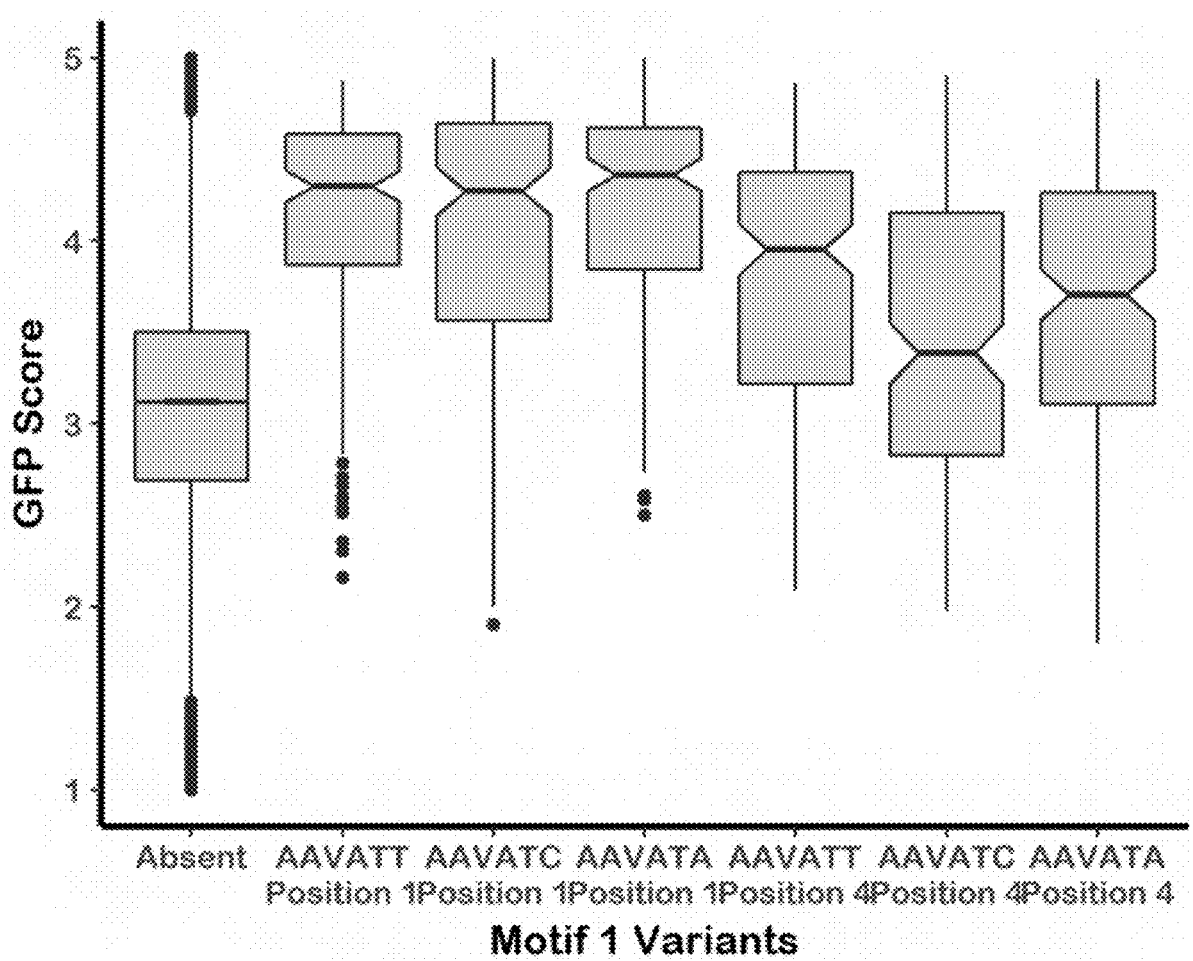
Figure 14:
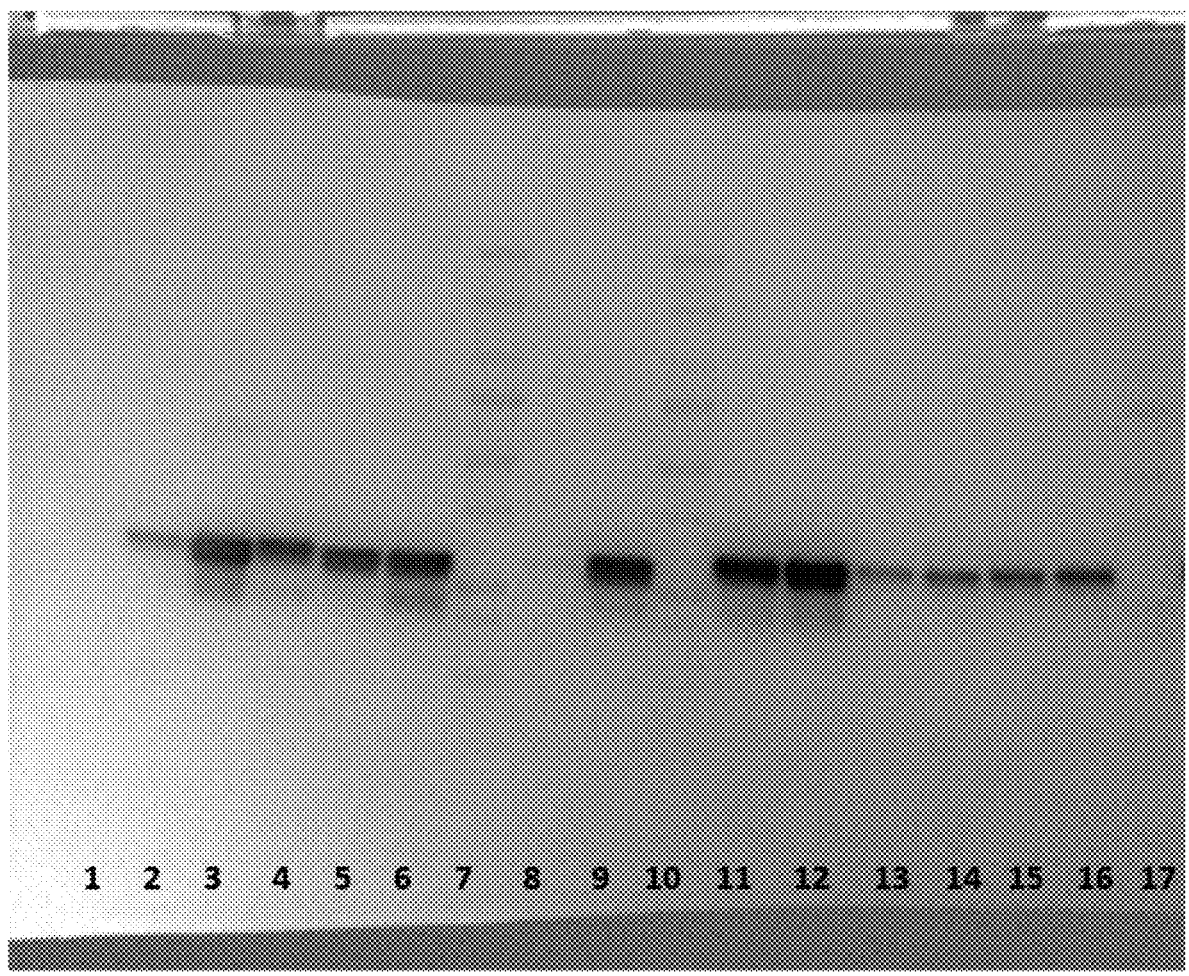
FIG. 14 is an image of a western blot from an in vitro transcription-translation reaction using the NEB PURE system. All lanes contain 10% of the in vitro protein synthesis reaction. GFP antibody was used to assess expression of EGFP protein from each clone. 100 ng of DNA from a PCR reaction was used as template for each protein synthesis reaction. Samples were incubated for 3 hours at 37° C. and reaction was stopped by addition of 2×SDS sample buffer and incubation of samples for 5 minutes at 95° C. Lane 1 is a control without DNA; lane 2 is wild type EGFP; lane 3 is an EGFP variant with the AADTAT motif in position 1; lane 4 is an EGFP variant with AADTAT motif in position 2; lane 5 is an EGFP variant with the AADTAT motif in position 3; lane 6 is an EGFP variant with the AADTAT motif in position 4; lane 7 is a marker; lane 8 is a random low expressing clone from Bin 1; lane 9 is a random high expressing clone from Bin 5; lane 10 is a marker; lane 11 is an EGFP variant with the amino acid sequence IGKHHHHH (SEQ ID NO: 12) inserted between amino acids 2 and 3 of WT EGFP; lane 12 is an EGFP variant with the amino acid sequence KFSHHHHH (SEQ ID NO: 13) inserted between amino acids 2 and 3 of WT EGFP; lane 13 is an EGFP variant with the amino acid sequence TVGHHHHH (SEQ ID NO: 14) inserted between amino acids 2 and 3 of WT EGFP; lane 14 is an EGFP variant with the amino acid sequence HHHHHIGK (SEQ ID NO: 15) inserted between amino acids 2 and 3 of WT EGFP; lane 15 is an EGFP variant with the amino acid sequence HHHHHKFS (SEQ ID NO: 16) inserted between amino acids 2 and 3 of WT EGFP; lane 16 is an EGFP variant with the amino acid sequence HHHHHTVG (SEQ ID NO: 17) inserted between amino acids 2 and 3 of WT EGFP; lane 17 is marker.

E. coli cells with a complete library in single (low) copy pBAD vector were grown from a frozen stock for 2 hours at 37° C. in LB media. Cells were centrifuged at 3000×g for 5 minutes and induced with LB media containing 0.5 L-Arabinose for 2 hours at 37° C. Cells were centrifuged at 3000×g for 5 minutes and re-suspended in media used for FACS sorting. Clones were separated by FACS into five groups, or "bins," based on the relative EGFP levels (RFU) expressed, as compared to non-induced library and non-transfected DH5α E. coli cells as baseline and cells expressing wild type EGFP sequence (RFU approximately 300 units) as median value The average RFU value for Bin #1 was 20; the average RFU value for Bin #2 was 120; the average RFU value for Bin #3 was 600; the average RFU value for Bin #4 was 3600; and the average RFU value for Bin #5 was 12,0000 (FIG. 4A). Each colony has one plasmid and each bin was sequenced independently to get a distribution of the 9 nt sequences comprising each bin. FIG. 4B depicts graphically the distribution of the 9 nt sequences in each bin. A GFP score was also calculated for each of 9 nt sequences as follows: Score=(Reads_bin_1/total_reads*1)+(Reads_bin_2/total_reads*2)+(Reads_bin_3/total_reads*3)+(Reads_bin_4/total_reads*4)+(Reads_bin_5/total_reads*5). Or for each clone (Reads_in_column D/reads_in_column_J*1)+(Reads_in_column E/reads_in_column_J*2)+ . . . +(Reads_in_column H/reads_in_column_J*5)=Score. As such is weighted score for each BIN. Wild type EGFP sequence, with a RFU value of about 300 units and a GFP Score of 2.3, falls within Bin 2. Additional characteristics of the library are illustrated in FIG. 5.

As further detailed in Tables A-C, changes in the polynucleotide sequence encoding codons 3, 4 and 5 ramp are responsible for at least a 3-4 order of magnitude difference in protein abundance. The observed difference is not dependent on tRNA abundance, efficiency of translation initiation, or overall mRNA structure (FIG. 6). Surprisingly, it was discovered that translation efficiency is regulated by composition of the amino acid sequence and to a much lower extent on the local mRNA structure (FIG. 7-12). Single-molecule measurements of translation kinetics indicate substantial pausing of ribosome on the $4^{th}$ or $5^{th}$ amino acid for distinct amino acid compositions within the short translational ramp.

Example 2

Experiments were performed to test the library for positional and amino acid bias using in vitro and in vivo experiments, and data are shown in FIG. 13-17.

For figures showing data from in vivo E. coli expression with low copy plasmids, western blot analysis was done on equal number of cells (measured by OD600 nm) using antibodies for either GFP (JL-8 Living Colors, Clontech), penta-His (Qiagen) or other specific antibodies. Cells were grown to optical density value of 0.3 (OD600 nm) and induced with 0.5% L-Arabinose. After 3 hours of induction each cell culture was measured at OD600 and normalized to lowest optical density culture. The same number of cells, based on optical density, was centrifuged and re-suspended in equal amount (100 ul) of 2×SDS sample buffer, boiled at 95° C. for 5 minutes and 10% of each sample was used for western blot analysis. Western blot analysis represents one of at least three biological replicates.

Figure 15:
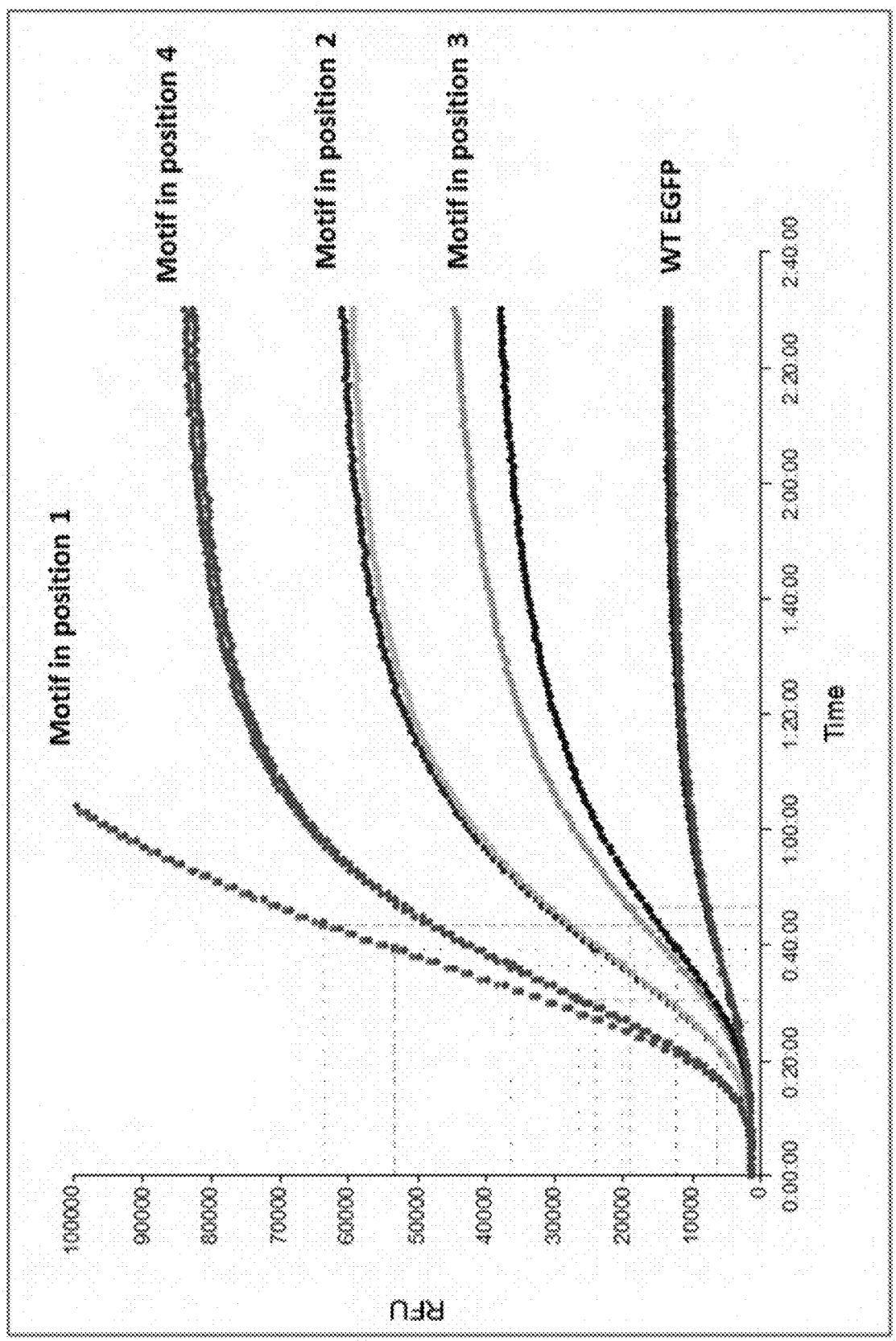
FIG. 15 graphically shows the EGFP fluorescence data from the in vitro transcription-translation reaction of FIG. 14 for WT EGFP and variants of AADTAT motif in different positions. Synthesis of EGFP in the reaction was followed by fluorescence of EGFP at Ex 488 nm/Em 525 nm in the plate reader. Each reaction was done in duplicate. The fluorescence recorded for AADTAT motif in position 1 goes out of range of the instrument at the 1 hour and 10 minute mark. Constructs tested in this particular experiment had a Lys as the $3^{rd}$ amino acid (position 1) and the $4^{th}$ amino acid (position 4).
Figure 16:
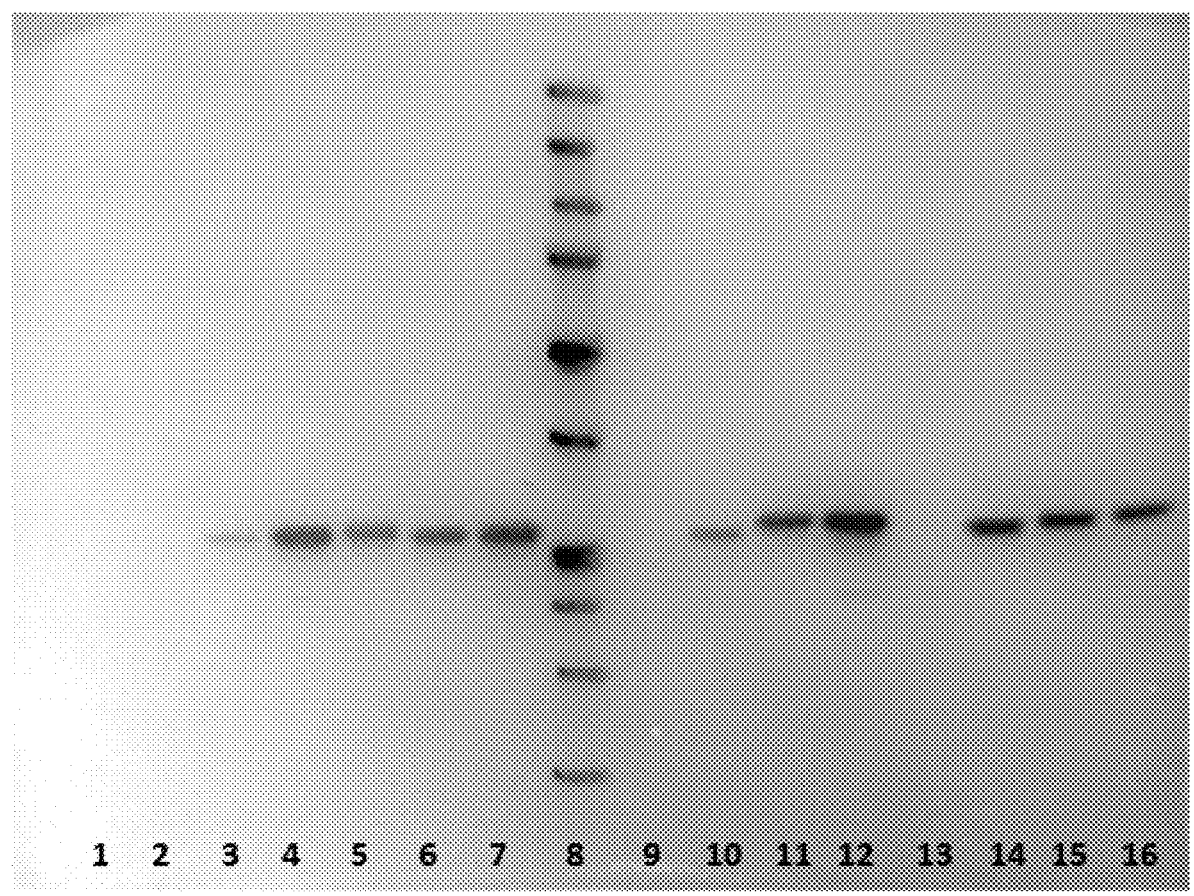
FIG. 16 is an image of a western blot from in vivo expression of EGFP variants in E. coli BL21 cells. Samples were obtained from 10% of the equal amount of cells 3 hours after induction with 0.5 Arabinose in LB medium. Lane 1 is non-induced wildtype EGFP; lane 2 is a non-induced EGFP variant with the AADTAT motif in position 1; lane 3 is an induced wildtype EGFP; lane 4 is an induced EGFP variant with AADTAT motif in position 1; lane 5 is an induced EGFP variant with AADTAT motif in position 5; lane 6 is an induced EGFP variant with the AADTAT motif in position 3; lane 7 is an induced EGFP variant with the AADTAT motif in position 4; lane 8 is a marker; lane 9 is a non-induced EGFP variant with the amino acid sequence IGKHHHHH (SEQ ID NO: 12) inserted between amino acids 2 and 3 of WT EGFP; lane 10 is an induced EGFP variant with the amino acid sequence TVGHHHHH (SEQ ID NO: 14) inserted between amino acids 2 and 3 of WT EGFP; lane 11 is an induced EGFP variant with the amino acid sequence IGKHHHHH (SEQ ID NO: 12) inserted between amino acids 2 and 3 of WT EGFP; lane 12 is an induced EGFP variant with the amino acid sequence KFSHHHHH (SEQ ID NO: 13) inserted between amino acids 2 and 3 of WT EGFP; lane 13 is a non-induced EGFP variant with the amino acid sequence HHHHHKFS (SEQ ID NO: 16) inserted between amino acids 2 and 3 of WT EGFP; lane 14 is an induced EGFP variant with the amino acid sequence HHHHHTVG (SEQ ID NO: 17) inserted between amino acids 2 and 3 of WT EGFP; lane 15 is an induced EGFP variant with the amino acid sequence HHHHHIGK (SEQ ID NO: 15) inserted between amino acids 2 and 3 of WT EGFP; and lane 16 is an induced EGFP variant with the amino acid sequence HHHHHKFS (SEQ ID NO: 16) inserted between amino acids 2 and 3 of WT EGFP.
Figure 17:
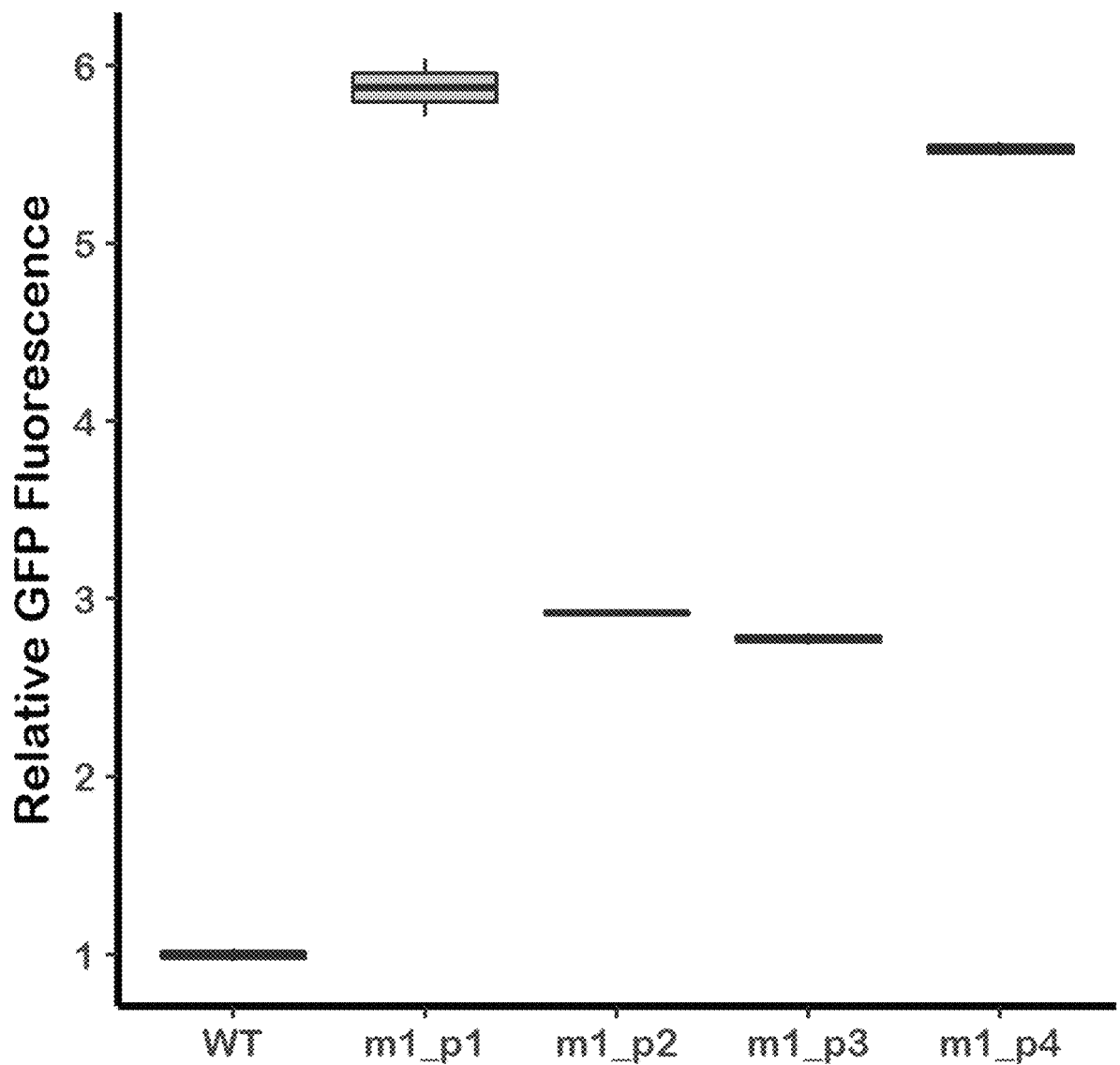
FIG. 17 graphically depicts the relative GFP fluorescence (y-axis) for E. coli BL21 cells expressing either WT EGFP (WT) or various EGFP variants: m1_p1=is a variant with the AADTAT motif in position 1; m1_p2=is a variant with the AADTAT motif in position 2; m1_p3=is a variant with the AADTAT motif in position 3; m1_p4=is a variant with the AADTAT motif in position 4. Fluorescence was measured at Ex 488 nm/Em 525 nm in plate reader at 3 hours after induction. RFU are normalized to wild type EGFP.

For the fluorescent measurements, three aliquots of 200 ul of each culture were measured in the plate reader for the previously noted emission and excitation wavelengths of fluorescence proteins. OD600 was measured in the same sample in the plate reader independently and fluorescence is normalized to number of the E. coli cells in the sample. Each measurement was done with three independent colonies coming from freshly transformed cells with purified and sequenced pBAD plasmids. Fluorescence levels were normalized to wild type EGFP expression. In vitro experiments are done using NEB PURE system by standard protocol. See, for example, www.neb.com/-/media/catalog/datacards-or-manuals/manuale6800.pdf. Briefly, 100 ng of purified T7 promoter containing PCR products for each variant was added to reaction mixture and reaction was kept at 37° C. for at least 2 hours. In FIG. 15, fluorescence of EGFP WT and the EGFP variants was monitored in the plate reader over the course of in vitro synthesis by recording fluorescence reading in 1 minute intervals. Background levels of fluorescence were subtracted and each graph is plotted from two independent repeats.

Example 3

Figure 18:
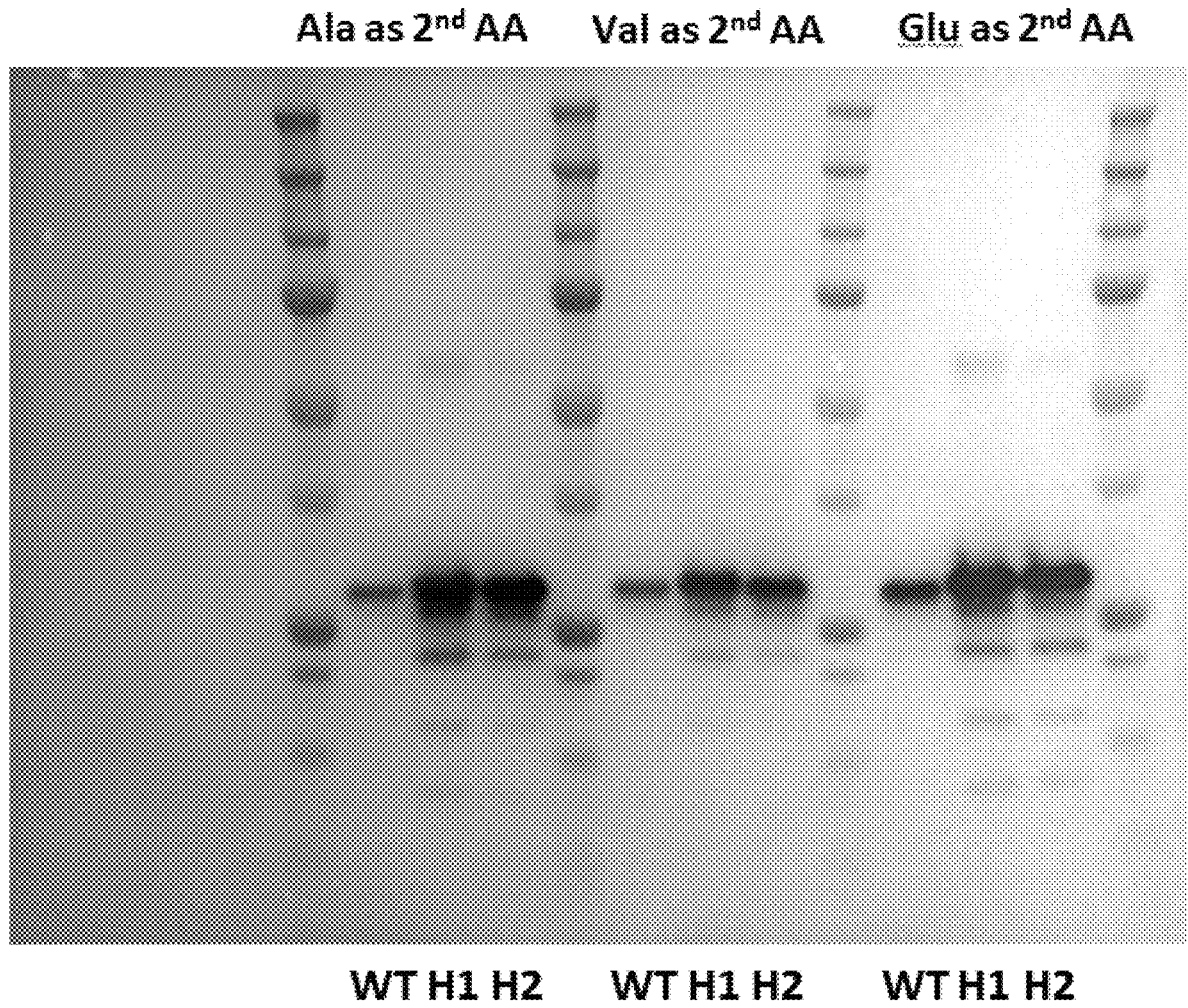
FIG. 18 is an image of a western blot from an experiment testing the influence of the $2^{nd}$ amino acid on expression of WT EGFP and two high expression EGFP variants, clones H1 and H2, in E. coli BL21 cells. WT EGFP has valine (Val) as the second amino acid and serine (Ser) as the third amino acid. In clone H1, the amino acid sequence "NCT" is inserted after the $2^{nd}$ amino acid of WT EGFP. In clone H2, the amino acid sequence "LQI" is inserted after the $2^{nd}$ amino acid of WT EGFP. Variants of WT, H1 and H2 with Ala and Glu as the amino acids in the $2^{nd}$ position were then tested. Samples were obtained from 10% of the equal amount of cells 3 hours after induction with 0.5 Arabinose in LB medium. While the identity of the $2^{nd}$ amino acid affects the overall level of EGFP (attributable to the N-terminal rule), H1 and H2 keep the same ratio to WT EGFP expression. This indicates the increase in translation efficiency observed in H1 and H2 is independent of $2^{nd}$ amino acid rule.

In this example, experiments were performed to test the influence of the $2^{nd}$ amino acid on expression of WT EGFP and two high expression EGFP variants, clones H1 and H2. in E. coli BL21 cells. WT EGFP has valine (Val) as the second amino acid and serine (Ser) as the third amino acid. In clone H1, the amino acid sequence "NCT" is inserted after the $2^{nd}$ amino acid of WT EGFP. In clone H2, the amino acid sequence "LQI" is inserted after the $2^{nd}$ amino acid of WT EGFP. Variants of WT, H1 and H2 with Ala and Glu as the amino acids in the $2^{nd}$ position were then generated and tested as in previous experiments. Samples were obtained from 10% of the equal amount of cells 3 hours after induction with 0.5 Arabinose in LB medium. While the identity of the $2^{nd}$ amino acid affects the overall level of EGFP (attributable to the N-terminal rule), H1 and H2 keep the same ratio to WT EGFP expression (FIG. 18). This indicates the increase in translation efficiency observed in H1 and H2 is independent of $2^{nd}$ amino acid rule.

Example 4

Figure 19:
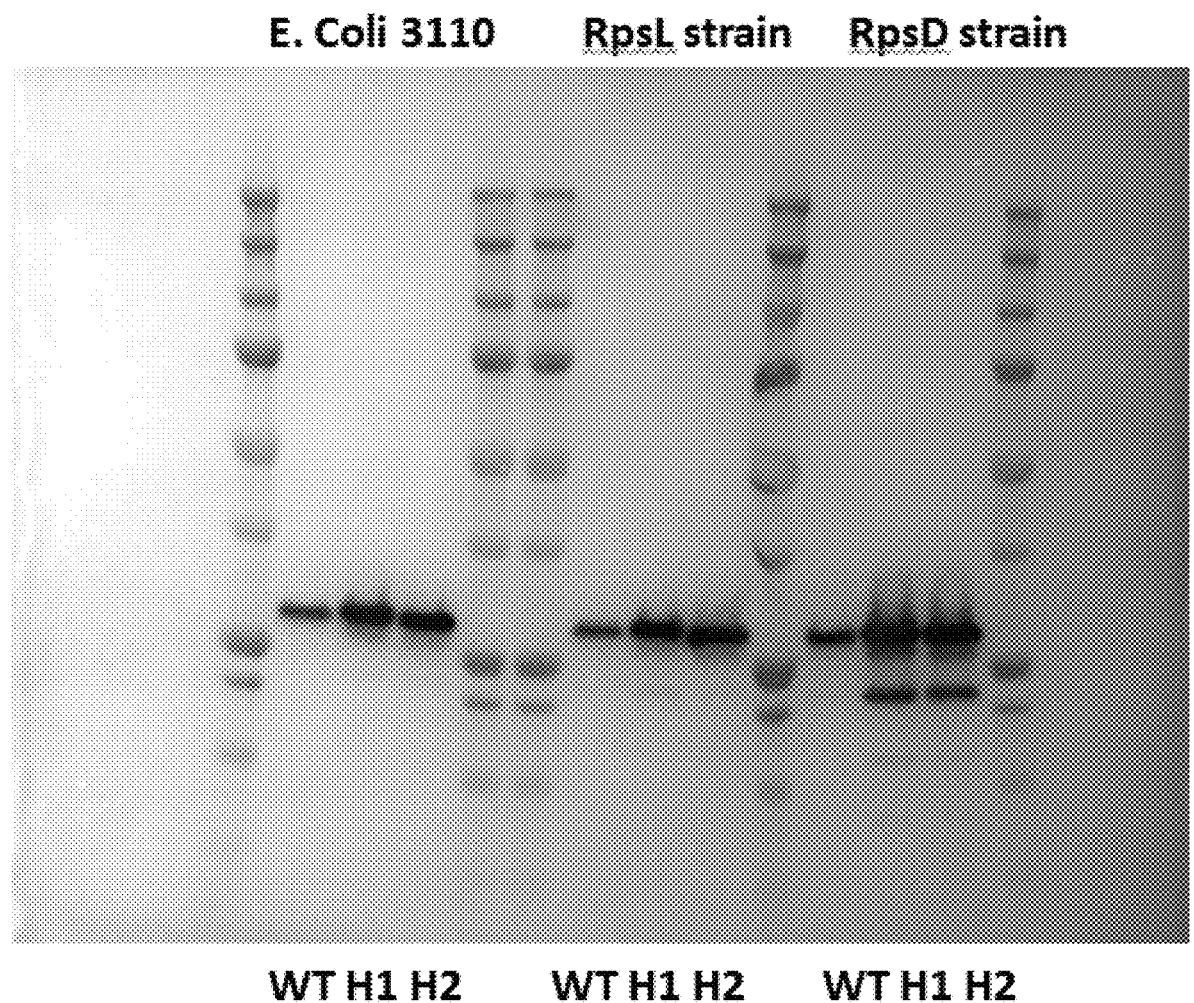
FIG. 19 is an image of a western blot from an experiment testing the influence of ribosomal differences on the expression of WT EGFP and two high expression EGFP variants, clones H1 and H2, in E. coli. E. coli W3110 is a derivative of E. coli K-12 that has a minimal number of mutations in the genome. rpsL and rpsD are strains displaying hyper-accurate (restrictive) and ribosomal ambiguity (increased number of translational error rates), respectively. Samples were obtained from 10% of the equal amount of cells 3 hours after induction with 0.5 Arabinose in LB medium. As was seen in FIG. 18, the ratio of between the two high expressing clones (H1 and H2) to WT EGFP is maintained in different E. coli strains. This indicates the increase in translation efficiency observed in H1 and H2 is independent of the E. coli strain.

In this example, experiments were performed to test the influence of ribosomal differences on the expression of WT EGFP and two high expression EGFP variants, clones H1 and H2, in E. coli. E. coli W3110 is a derivative of E. coli K-12 that has a minimal number of mutations in the genome. rpsL and rpsD are strains displaying hyper-accurate (restrictive) and ribosomal ambiguity (increased number of translational error rates), respectively. Samples were obtained from 10% of the equal amount of cells 3 hours after induction with 0.5 Arabinose in LB medium. The ratio of between the two high expressing clones (H1 and H2) to WT EGFP is maintained in different *E. coli* strains (FIG. 19). This indicates the increase in translation efficiency observed in H1 and H2 is independent of the *E. coli* strain.

Example 5

Figure 20A:
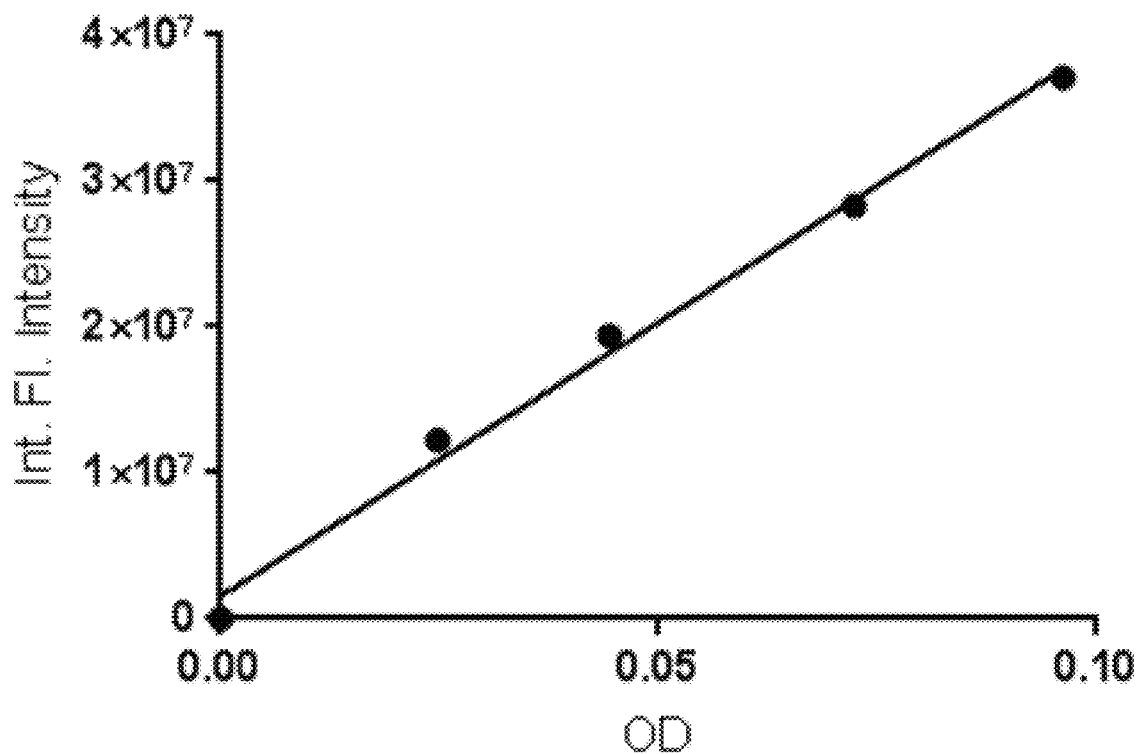
FIG. 20A, FIG. 20B, and FIG. 20C are graphs showing the same spectral properties for WT EGFP and a high expressing EGFP variant with the amino acid sequence "KFS" inserted after the $2^{nd}$ amino acid of WT EGFP. Measurement of the fluorescence intensity of Fluorescein standard (FIG. 20A) compared to purified WT EGFP (FIG. 20B) and the high expressing EGFP variant (FIG. 20C). Samples were diluted at the same levels and integrated fluorescence intensity was measured. The same quantum efficiency of the fluorophore (Q) is calculated for WT EGFP (Q=0.95*(3.6/3.76)*0.81=0.71) and the high expressing variant (Q=0.95*(3.55/3.76)*0.81=0.72), where Q=Q_R (Grad/Grad_R)($n^2/n^2$_R).
Figure 20B:
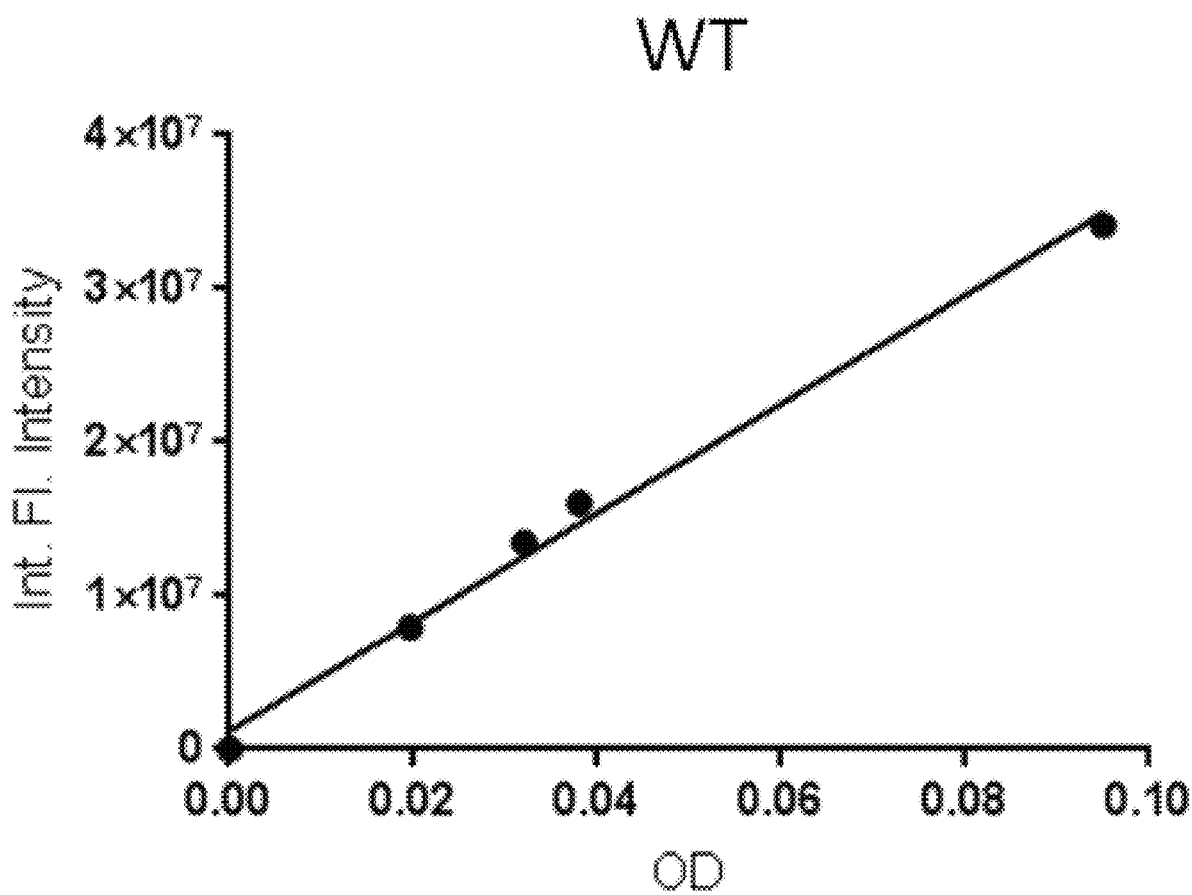
Figure 20C:
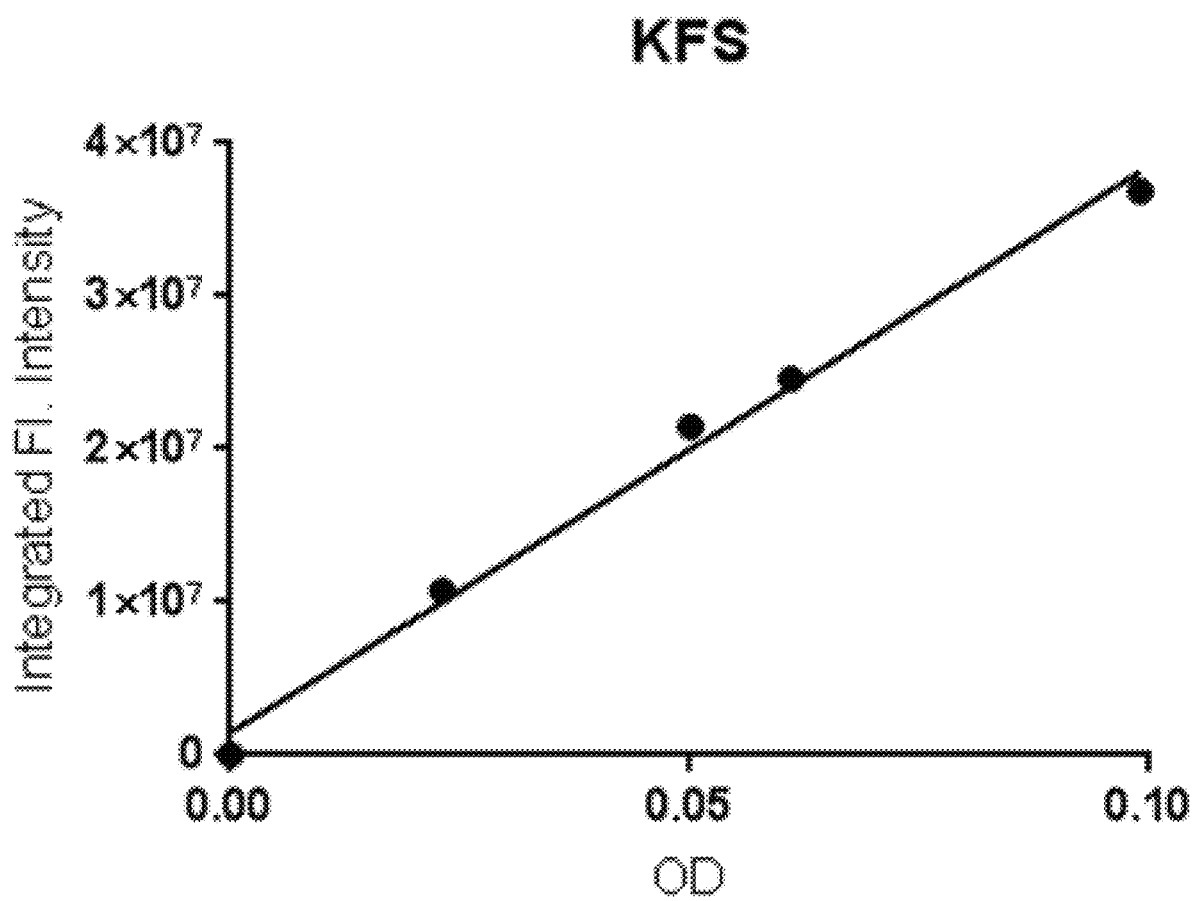
Figure 21:
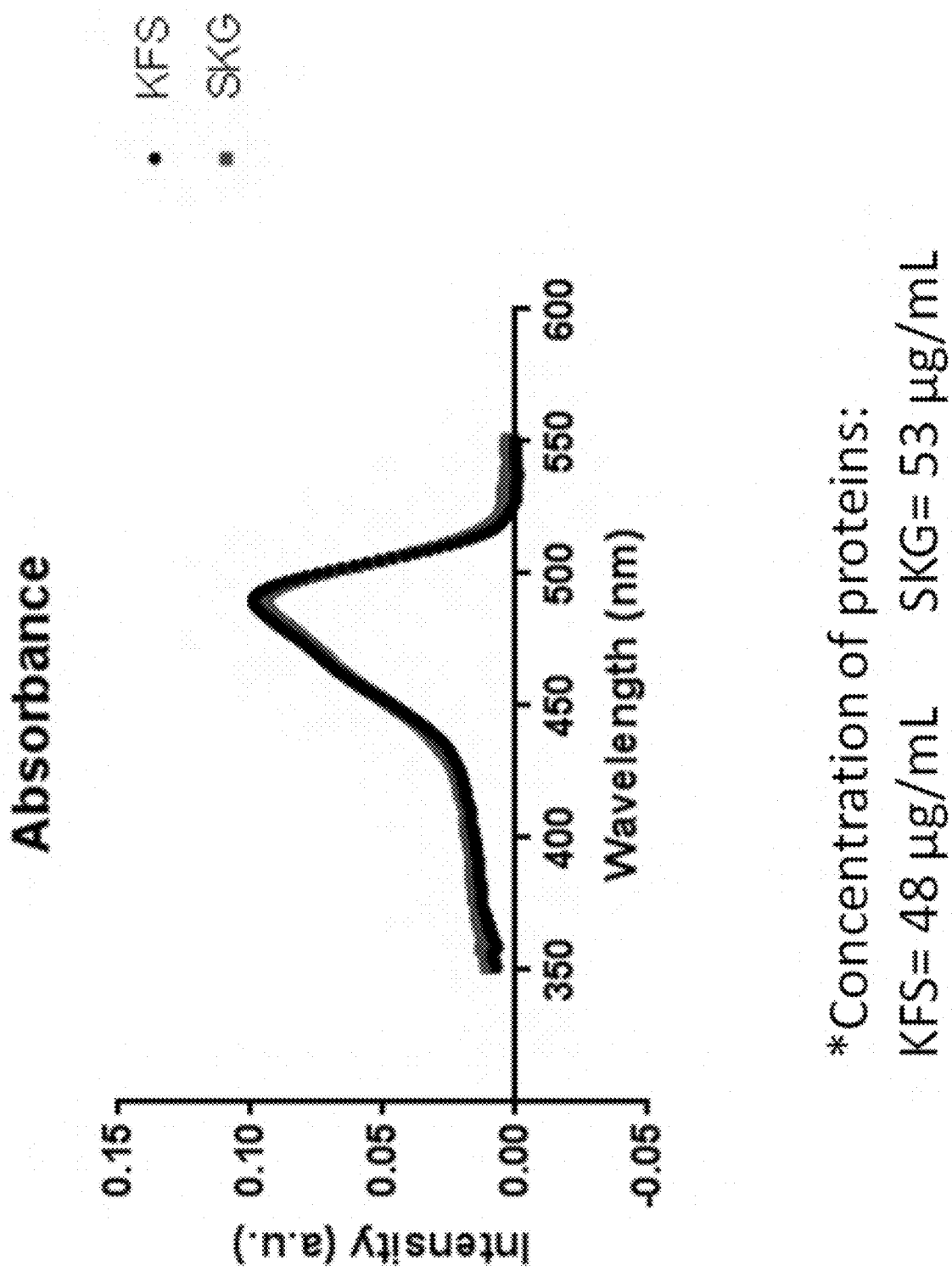
FIG. 21 is a graph depicting the absorbance spectra WT EGFP ("SKG") and a high expressing EGFP variant with the amino acid sequence "KFS" inserted after the 2$^{nd}$ amino acid of WT EGFP ("KFS"). The figure shows there is no difference between the two proteins.

In this example, experiments were performed to determine if the EGFP variants have different spectral properties than WT EGFP. Fluorescence intensity was measured for fluorescein standard and compared to purified WT EGFP and a high expressing EGFP variant with the amino acid sequence "KFS" inserted after the $2^{nd}$ amino acid of WT EGFP. Samples were diluted at the same levels and integrated fluorescence intensity was measured. The same quantum efficiency of the fluorophore (Q) is calculated for WT EGFP (Q=0.95*(3.6/3.76)*0.81=0.71) and the high expressing variant (Q=0.95*(3.55/3.76)*0.81=0.72), where Q=Q_R (Grad/Grad_R)($n^2/n^2\_R$). No differences were observed between WT EGFP and the EGFP variant (FIG. 20 and FIG. 21).

Example 6

To determine if the improvements in translation efficiency were specific to EGFP, the polynucleotide sequences encoding other proteins were similarly modified and the level of translation was measured.

Figure 22:
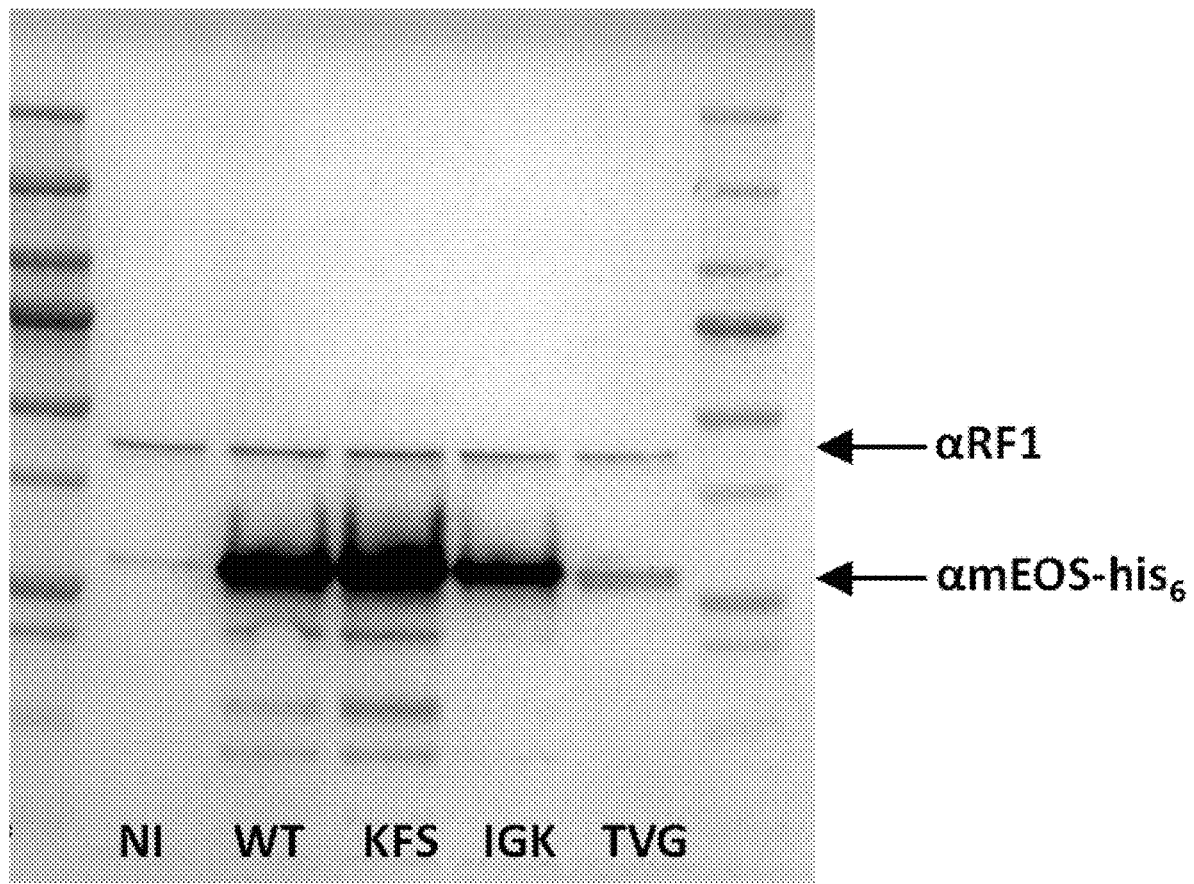
FIG. 22 is an image of a Western blot of E. coli release factor 1 (RF1) and mEOS2. Samples were obtained from 10% of the equal amount of E. coli BL21 cells 3 hours after induction with 0.5 Arabinose in LB medium expressing a his-tagged wild type mEOS2 (WT) or an mEOS2 variant with the amino acid sequence KFS, IGK, or TVG inserted between amino acids 2 and 3 of WT mEOS2. "NI" is the non-induced control. E. coli release factor 1 (RF1) is used for normalization. This figure shows improvements in translation efficiency are not dependent on the protein of interest.
Figure 23A:
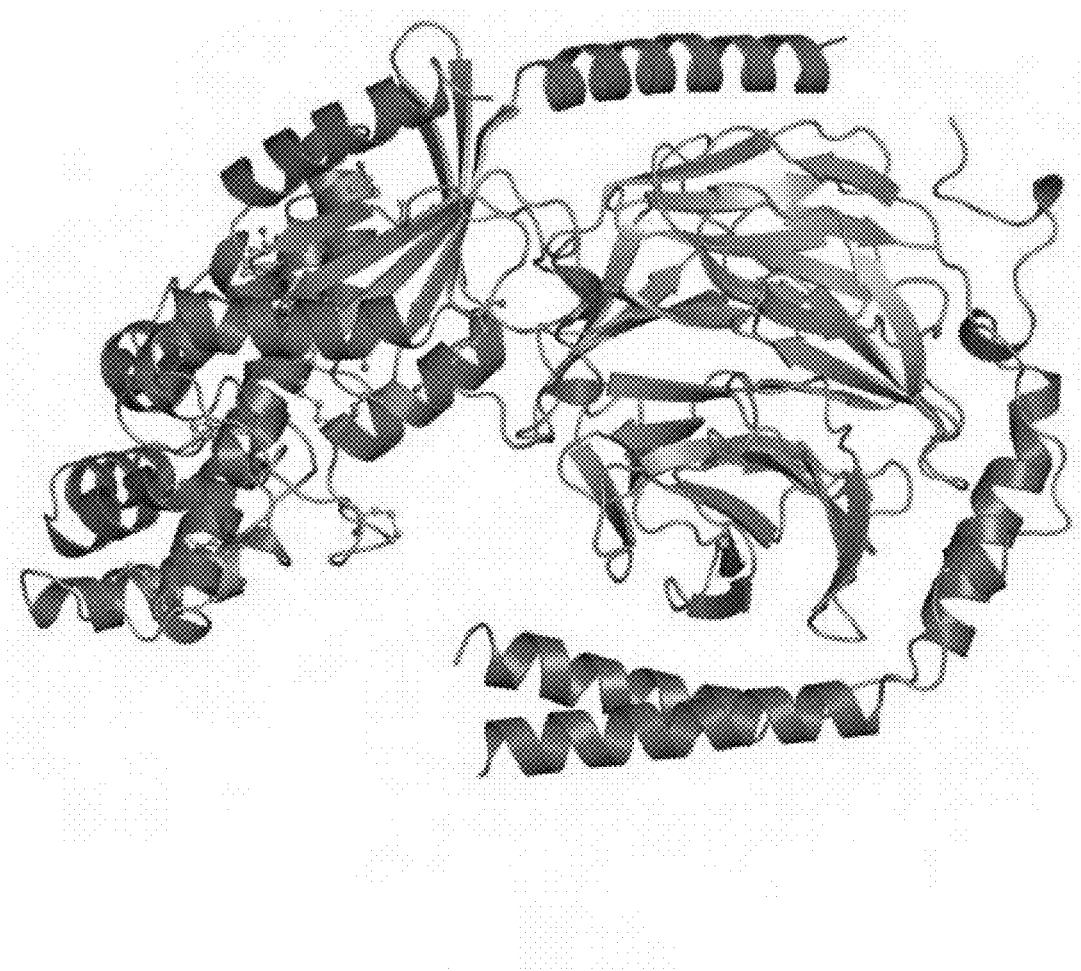
FIG. 23A-D provide further evidence that high expressing motifs can be used with different proteins of interest and plasmid vector sequences.
Figure 23B:
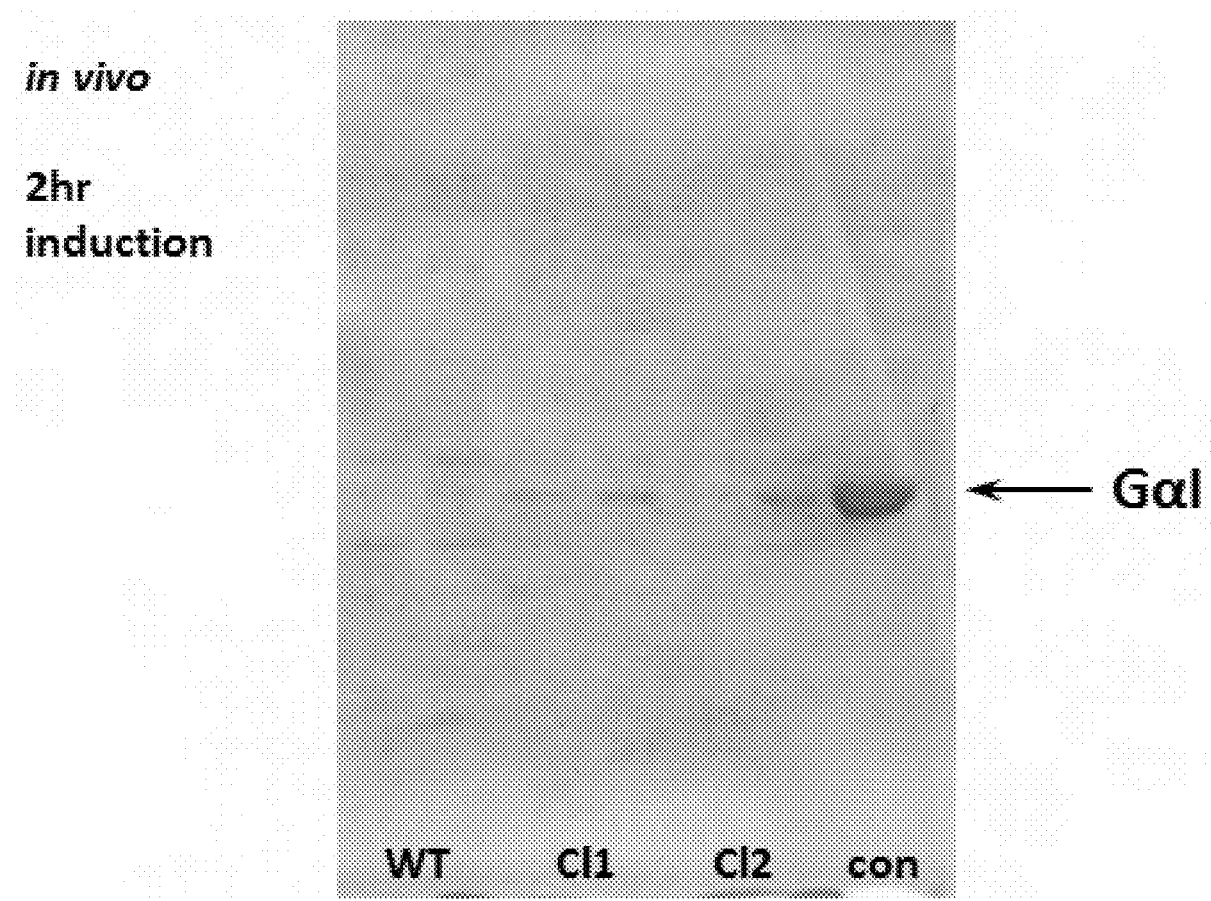
Figure 23C:
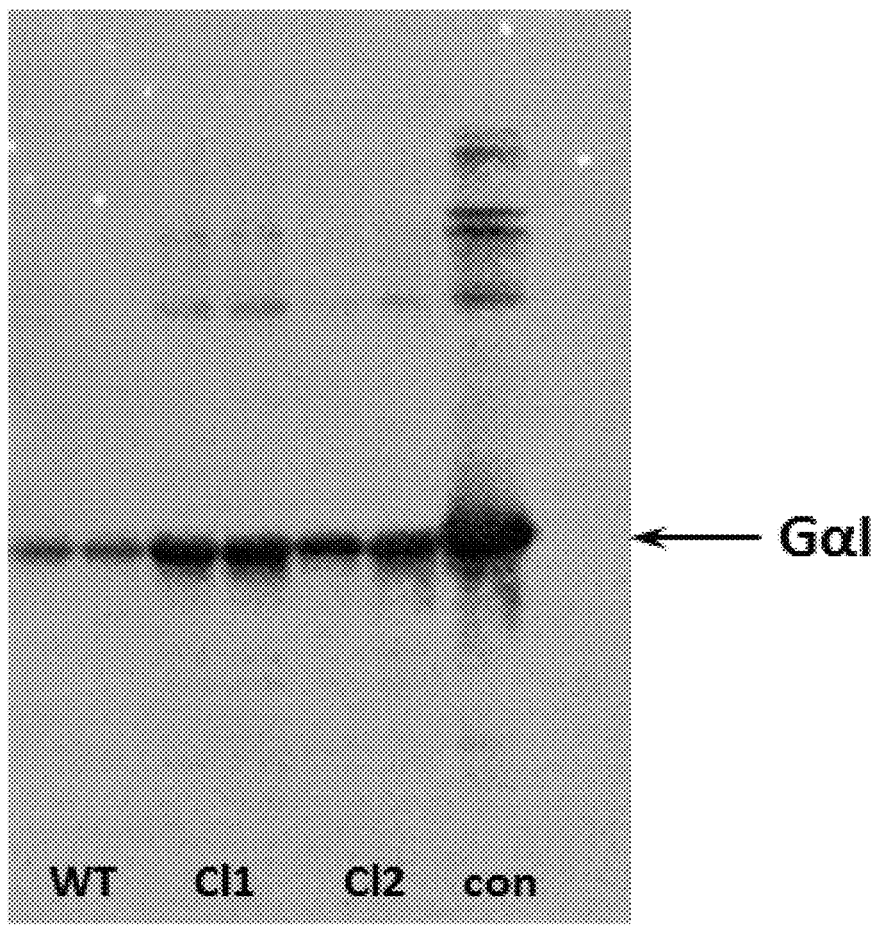
Figure 23D:
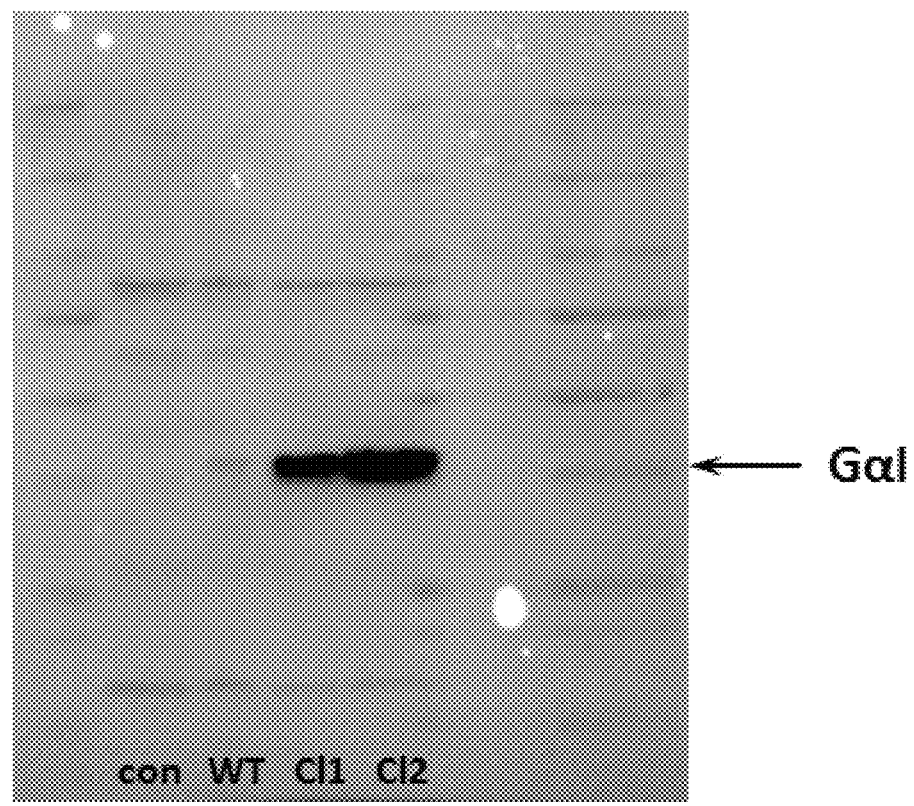

*E. coli* BL21 cells expressing a his-tagged wild type mEOS2 (WT) or an mEOS2 variant with the amino acid sequence KFS, IGK, or TVG inserted between amino acids 2 and 3 of WT mEOS2 were generated. Protein expression was induced with 0.5% Arabinose, with non-induced (NI) cells as a control. *E. coli* release factor 1 (RF1) is used for normalization. As shown in FIG. 22, improvements in translation efficiency are not dependent on the protein of interest. Similar results were also obtained when the protein of interest was human G-alpha inhibitory (Gαi) protein and expression occurred in *E. coli* or using an in vitro transcription/translation system (FIG. 23).

Example 7

Figure 24:
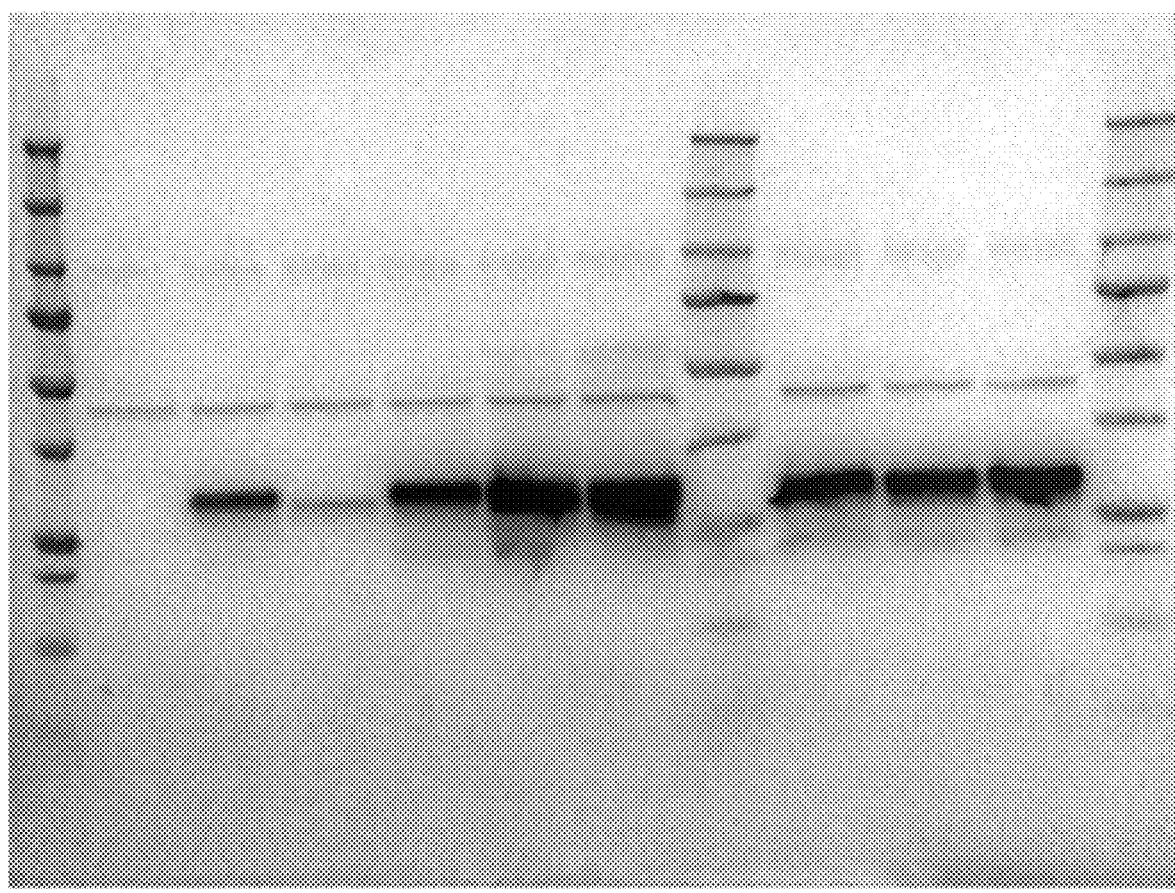
FIG. 24 is an image of a western blot from in vitro transcription-translation reactions using NEB PURE system and with a new 5' untranslated region adapted for single molecule FRET analysis. Specifically, the sequence 5-G-GGCAACCTAAAACTTACACACCCGGTAAGGAA-ATAACC-3' (SEQ ID NO: 18) was introduced in front of the start (ATG) codon in pet16b vector (Novagen) using XbaI and NcoI restriction sites. All lanes contain 10% of the in vitro protein synthesis reaction. GFP antibody was used to assess expression of EGFP protein from each clone. 100 ng of DNA from a PCR reaction was used as template for each reaction. Samples were incubated for 3 hours at 37° C. and reaction was stopped by addition of 2×SDS sample buffer and incubation of samples for 5 minutes at 95° C. Lane 1 is a control without DNA (CON); lane 2 is wild type EGFP (WT); lane 3 is an EGFP variant with the amino acid sequence TVG inserted between amino acids 2 and 3 of WT EGFP; lane 4 is an EGFP variant with the amino acid sequence IGK inserted between amino acids 2 and 3 of WT EGFP; lane 5 is an EGFP variant with the amino acid sequence KFS inserted between amino acids 2 and 3 of WT EGFP; lane 6 is an EGFP variant with the amino acid sequence KIH (Motif AAVATT (KI)) inserted between amino acids 2 and 3 of WT EGFP; lane 7 is a marker; lane 8 is an WT EGFP variant with a 6×His tag inserted between amino acids 2 and 3; lane 9 is an EGFP variant with the amino acid sequence HHHHHHTVG (SEQ ID NO: 19) inserted between amino acids 2 and 3 of WT EGFP; lane 10 is an EGFP variant with the amino acid sequence HHHHH-KIH (SEQ ID NO: 20) inserted between amino acids 2 and 3 of WT EGFP; lane 11 is marker. These data indicate that improvements in translation efficiency are independent of the upstream sequence.

In this example, experiments were performed to test the influence of the 5' untranslated region on the expression of WT EGFP and various EGFP variants. As shown in FIG. 24, improvements in translation efficiency are independent of the upstream sequence.

Example 8

To determine if the improvements in translation efficiency were specific to *E. coli*, experiments were performed in human and yeast cells.

Figure 25:
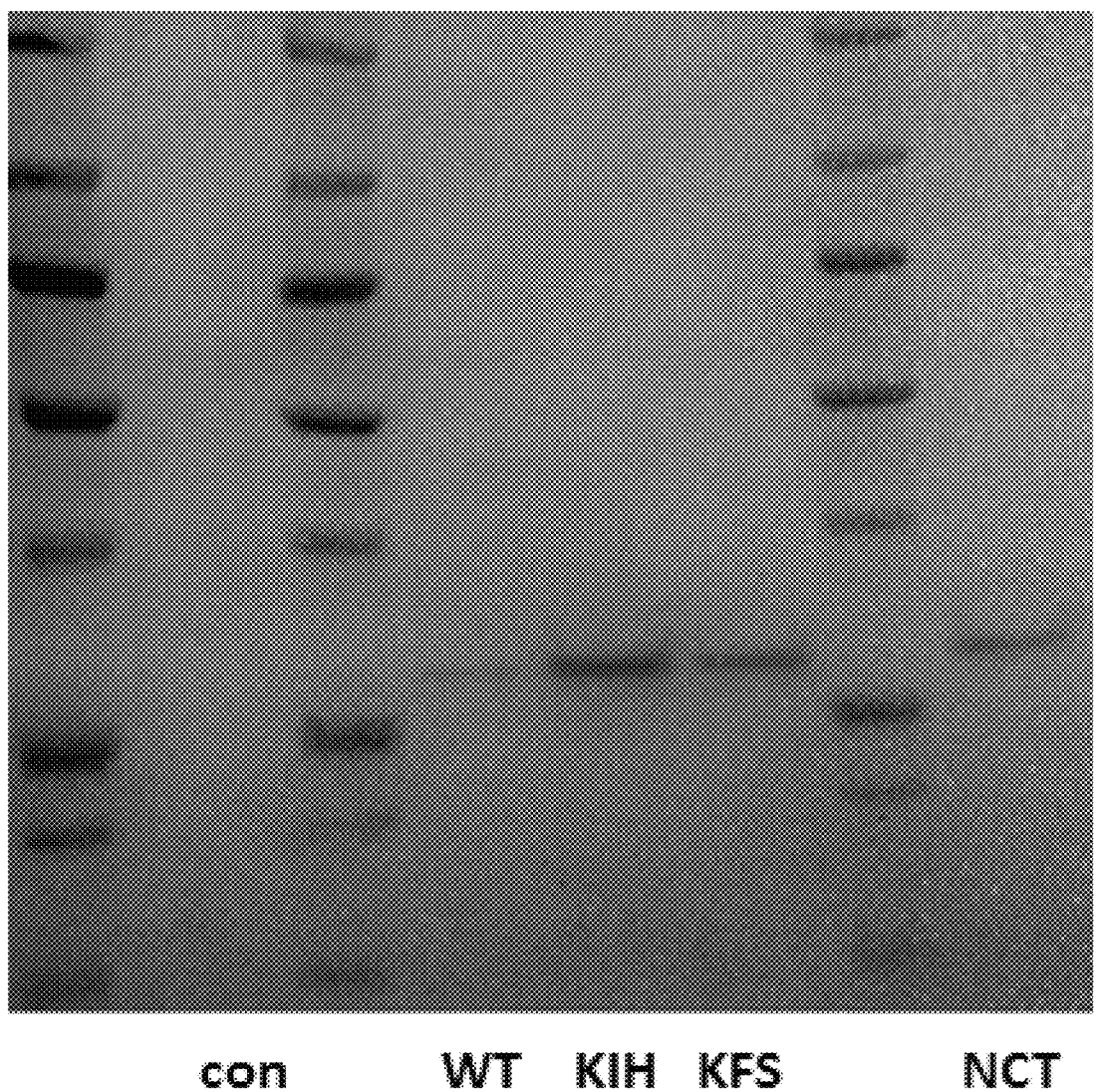
FIG. 25 is an image of a western blot. To express WT EGFP and three high expressing EGFP variants in human neo-natal dermal fibroblasts, 5' TOP (a short 5' untranslated region called the 5'-terminal oligopyrimidine sequence) constructs encoding WT and three higher expressing EGFP variants were in vitro transcribed using MMessage Machine (Ambion) mRNA synthesis kit and then m7GpppG capped. 2 ug of the mRNAs were electroporated in the same amount of human neo-natal dermal fibroblasts (HDFs, primary cells). Cells were collected 6 hours after, lysed in 2×SDS sample buffer and analyzed by western blot using α-GFP antibody. CON=non-electroporated cells; WT=wild type EGFP; KIH=an EGFP variant with the amino acid sequence KIH inserted between amino acids 2 and 3 of WT EGFP; KFS=an EGFP variant with the amino acid sequence KFS inserted between amino acids 2 and 3 of WT EGFP; NCT=and an EGFP variant with the amino acid sequence NCT inserted between amino acids 2 and 3 of WT EGFP. These data indicate that improvements in translation efficiency can be obtained in human cells as well.

FIG. 25 is an image of a western blot. To express WT EGFP and three high expressing EGFP variants in human neo-natal dermal fibroblasts, 5' TOP (a short 5' untranslated region called the 5'-terminal oligopyrimidine sequence) constructs encoding WT and three higher expressing EGFP variants were in vitro transcribed using MMessage Machine (Ambion) mRNA synthesis kit and then m7GpppG capped. 2 ug of the mRNAs were electroporated in the same amount of human neo-natal dermal fibroblasts (HDFs, primary cells). Cells were collected 6 hours after, lysed in 2×SDS sample buffer and analyzed by western blot using α-GFP antibody. CON=non-electroporated cells; WT=wild type EGFP; KIH=an EGFP variant with the amino acid sequence KIH inserted between amino acids 2 and 3 of WT EGFP; KFS=an EGFP variant with the amino acid sequence KFS inserted between amino acids 2 and 3 of WT EGFP; NCT=and an EGFP variant with the amino acid sequence NCT inserted between amino acids 2 and 3 of WT EGFP. These data indicate that improvements in translation efficiency can be obtained in human cells as well.

Figure 26A:
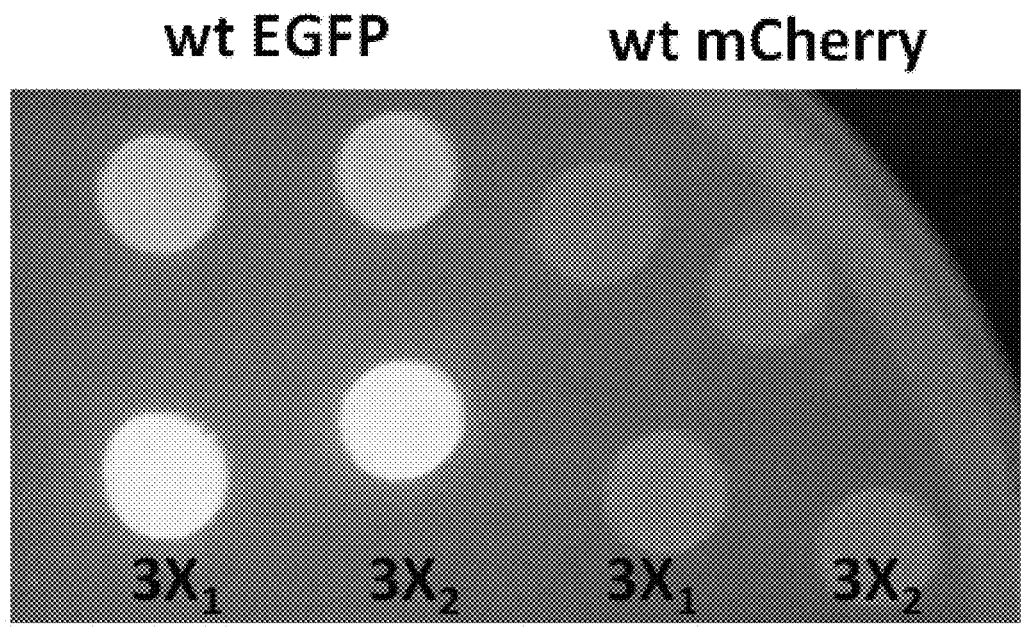
FIG. 26A, FIG. 26B, FIG. 26C, and FIG. 26D are images showing that introduction of high expressing sequence variants into different fluorescent proteins increases expression of these proteins in both bacteria and yeast. Briefly, the amino acid sequences NCT ("3$X_1$") and LQI ("3$X_2$") were inserted between amino acids 2 and 3 of WT EGFP, WT mCherry and WT mCardinal.
Figure 26B:
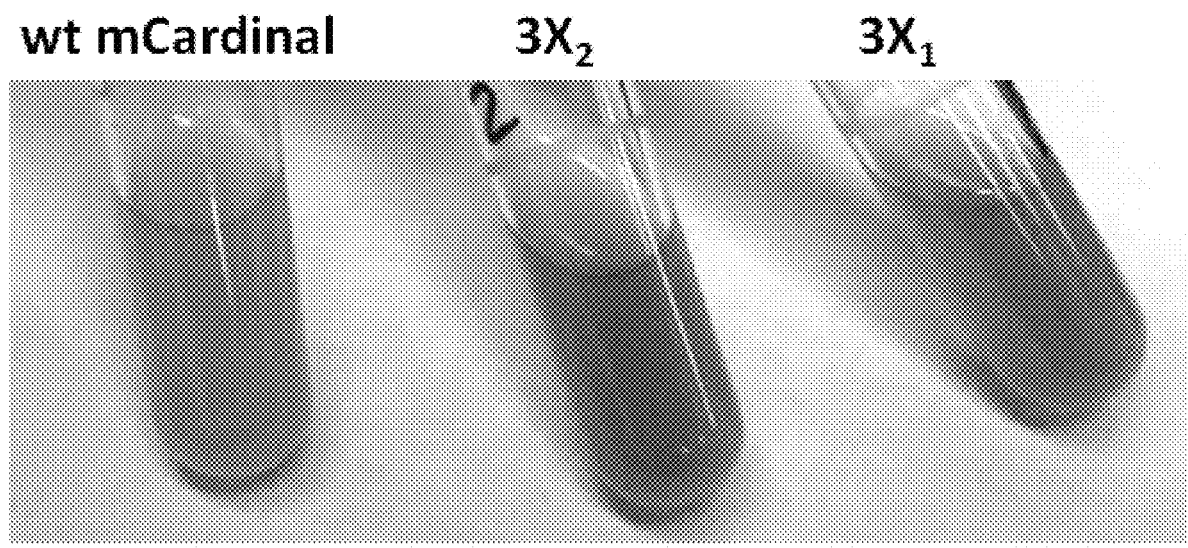
Figure 26C:
Figure 26D:
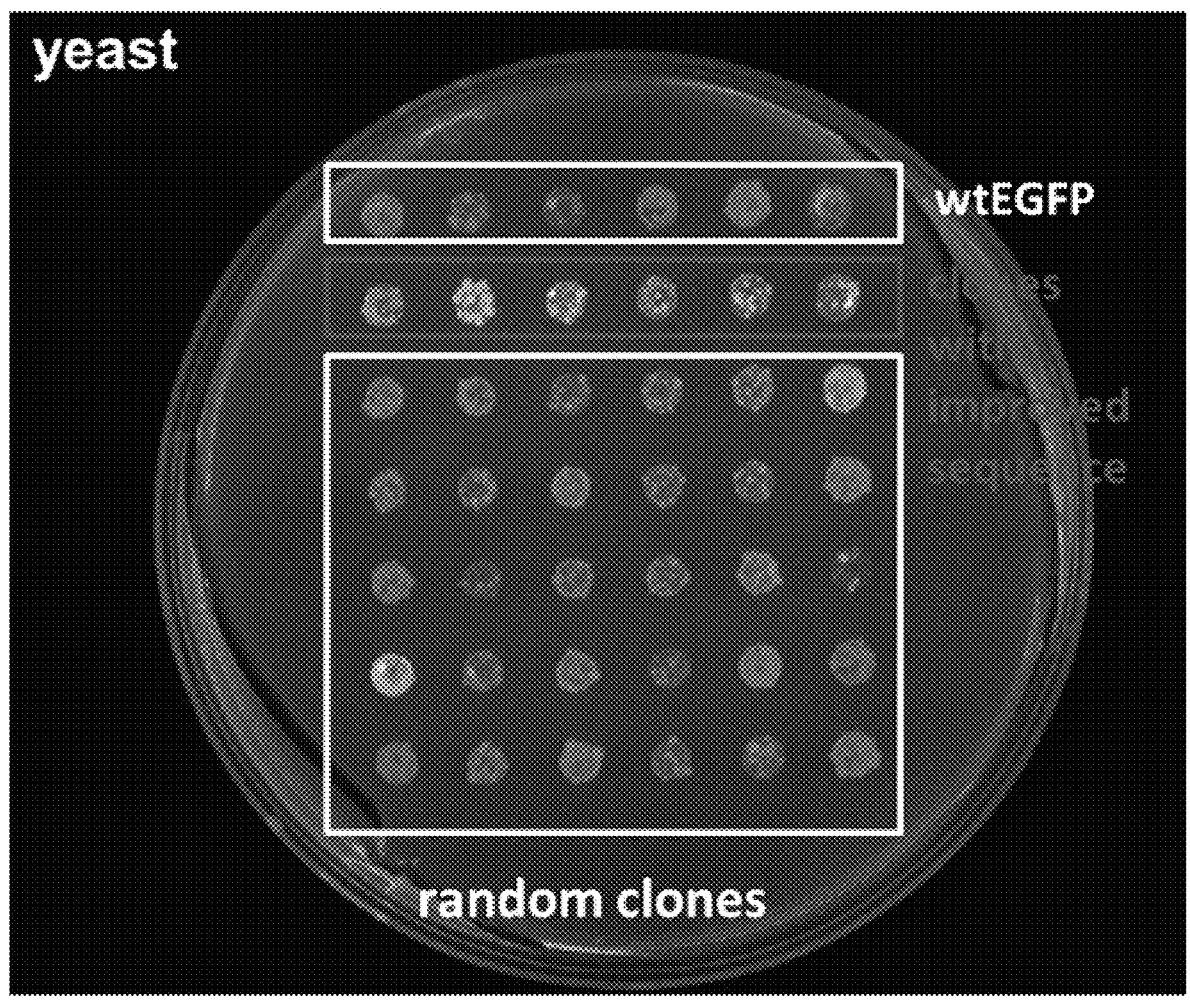
Figure 27:
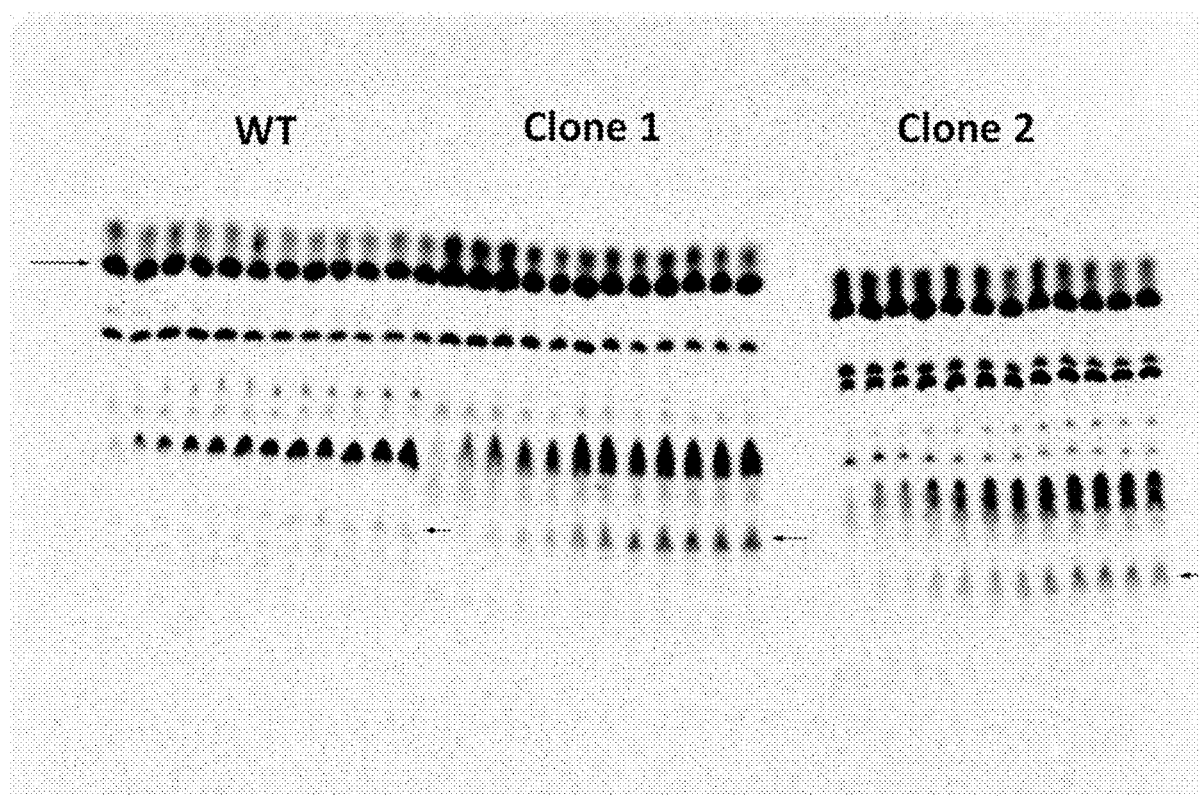
FIG. 27 is an image of thin layer chromatography of P32-labeled peptides after in vitro translation of WT (EGFP) and two high expressing EGFP variants. Clone 1 is an EGFP variant with the amino acid sequence KYH inserted after the second amino acid of WT EGFP. Clone 2 is an EGFP variant with the amino acid sequence YKH inserted after the second amino acid of WT EGFP. Short mRNAs were pelleted with purified E. coli ribosomes as initiation complexes and time points at 1, 5, 10, 20, 30, 45, 60, 90, 120, 180, 240, 300 seconds. The arrow on the left side indicates starting position for formylated P32 labeled methionine. While the arrow on the right side indicates labeled full length product. These data indicates a pause or stall in WT sequence which does not result in synthesis of the full product. Sequences for two clones were inserted between amino acids 2 and 3 of WT EGFP derived sequence.

FIG. 26A-D are images showing that introduction of high expressing sequence variants into different fluorescent proteins increases expression of these proteins in both bacteria and yeast. Briefly, the amino acid sequences NCT ("$3X_1$") and LQI ("$3X_2$") were inserted between amino acids 2 and 3 of WT EGFP, WT mCherry and WT mCardinal. In FIG. 26A, drops of the same amount of *E. coli* BL21 cells expressing the EGFP variants, the mCherry variants, or WT were plated on 0.2% Arabinose LB agar plates and exposed to blue light after overnight growth. In FIG. 26B, overnight cultures of mCardinal variants induced with 0.2% arabinose in LB media at the daylight indicating higher expression of high expressing variants by absorbance of the blue light from daylight spectra. FIG. 27C and FIG. 27C are images of *E. coli* and *S. cerevisiae* colonies expressing WT EGFP or an EGFP variant with additional amino acids inserted between 2nd and 3rd amino acid in EGFP sequence. EGFP sequence variants from pet16b vector expressed in *E. coli* were digested using NcoI and XhoI restriction enzymes and cloned into pGAL418 vector for expression in *S. cerevisiae*. *S. cerevisiae* and *E. coli* cultures were grown in minimal media and 5 ul of the log phase culture was spotted on agar plates with 0.5% inducer compound, galactose or arabinose for *S. cerevisiae* or *E. coli*, respectively. Plates were incubated overnight for *S. cerevisiae* at 30° C. and *E. coli* at 37° C. Clones that show higher expression in *E. coli* show a similar trend of expression in *S. cerevisiae*.

Example 9

In this example, SM FRET experiments were performed to investigate the mechanism responsible for the changes in protein translation efficiency. The data in FIG. 27-30 show that stalling of translation depends on the identity of codons 3-5. Moreover, it is believed that the stalling or "pause" observed between codons 3 and 4, as well as between codons 4 and 5, reduces ribosome processivity but does not affect the translation rate.

The invention claimed is:

1. A method of increasing the level of expression of a protein, the method comprising:
inserting a polynucleotide sequence into a nucleic acid sequence encoding a first protein of interest to produce a modified nucleic acid sequence encoding a second protein, wherein the nucleic acid encoding the first protein of interest comprises a coding region encoding the first protein of interest, wherein the coding region comprises a first, a second, a third, a fourth and a fifth codon in consecutive order, wherein the first codon is located at a 5'-most end of the coding region, and wherein
(a) the polynucleotide sequence is inserted between the second and third codons of the coding region and the polynucleotide sequence is selected from AAT, AAC, AAATAT, AAATAC, AACTAT, AACTAC, AAGTAT, AAGTAC, AATTAT, AATTAC, AAAT-ATTAT, AAATACTAT, AACTATTAT, AACTAC-TAT, AAGTATTAT, AAGTACTAT, AATTATTAT, AATTACTAT, AAATATTAC, AAATACTAC, AAC-TATTAC, AACTACTAC, AAGTATTAC, AAGTACTAC, AATTATTAC, or AATTACTAC;
(b) the polynucleotide sequence is inserted between the third and fourth codons of the coding region and the polynucleotide sequence is selected from AAT, AAC, TAT, TAC, ATT, ATC, ATA, TTA, CTT, AAATAT, AAATAC, AACTAT, AACTAC, AAGTAT, AAGTAC, AATTAT, or AATTAC;
(c) the polynucleotide sequence is inserted between the fourth and fifth codons of the coding region and the polynucleotide sequence is selected from TAT, TAC, ATA, ATC, ATT, AGA, TTA, CTT, or CTA;
and expressing the modified nucleic acid sequence in a cell or in a cell-free transcription/translation system thereby increasing the amount of second protein translated as compared to the amount of first protein translated, wherein the polynucleotide sequence does not encode a stop codon recognizable by the cell or the cell-free system.

2. The method of claim 1, wherein the polynucleotide sequence does not encode a methionine when read in frame.

3. The method of claim 1, wherein the first protein and the second protein have the same amino acid sequence.

4. The method of claim 1, wherein the first protein and the second protein have a different amino acid sequence.

* * * * *